US012516298B2

(12) United States Patent
Abeliovich et al.

(10) Patent No.: US 12,516,298 B2
(45) Date of Patent: Jan. 6, 2026

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US); Li Chin Wong, New York, NY (US); Hsuan-Ni Lin, New York, NY (US); Franz Hefti, New York, NY (US)

(73) Assignee: PREVAIL THERAPEUTICS, INC., Indianapolis, IN (US)

( * ) Notice: Subject to any disclaimer, the term of this patent is extended or adjusted under 35 U.S.C. 154(b) by 0 days.

(21) Appl. No.: 18/646,957

(22) Filed: Apr. 26, 2024

(65) Prior Publication Data

US 2024/0287471 A1 Aug. 29, 2024

Related U.S. Application Data

(62) Division of application No. 16/846,065, filed on Apr. 10, 2020, now Pat. No. 11,999,974.

(60) Provisional application No. 62/988,665, filed on Mar. 12, 2020, provisional application No. 62/960,471, filed on Jan. 13, 2020, provisional application No. 62/954,089, filed on Dec. 27, 2019, provisional application No. 62/934,450, filed on Nov. 12, 2019, provisional application No. 62/831,846, filed on Apr. 10, 2019.

(51) Int. Cl.

| | |
|---|---|
| ***C12N 7/00*** | (2006.01) |
| ***A61K 48/00*** | (2006.01) |
| ***A61P 25/28*** | (2006.01) |
| ***C07K 14/435*** | (2006.01) |
| ***C12N 9/02*** | (2006.01) |
| ***G01N 33/68*** | (2006.01) |

(52) U.S. Cl.

CPC ............ *C12N 7/00* (2013.01); *A61K 48/0075* (2013.01); *A61K 48/0083* (2013.01); *A61P 25/28* (2018.01); *C07K 14/435* (2013.01); *C12N 9/0071* (2013.01); *C12Y 114/18001* (2013.01); *G01N 33/6803* (2013.01); *C12N 2750/14132* (2013.01); *C12N 2750/14133* (2013.01); *C12N 2750/14143* (2013.01); *G01N 2333/435* (2013.01)

(58) Field of Classification Search

CPC ............ C12N 7/00; C12N 2750/14132; A61K 48/0083; A61K 48/005

See application file for complete search history.

(56) References Cited

U.S. PATENT DOCUMENTS

| | | | |
|---|---|---|---|
| 6,538,119 | B2 | 3/2003 | Billing-Medel et al. |
| 7,452,716 | B2 | 11/2008 | Yew |
| 8,486,635 | B2 | 7/2013 | Hutton et al. |
| 9,034,836 | B2 | 5/2015 | Dodge et al. |
| 9,486,541 | B2 | 11/2016 | Hutton et al. |
| 10,689,625 | B2 | 6/2020 | Abeliovich et al. |
| 11,655,460 | B2 | 5/2023 | Abeliovich et al. |
| 11,661,585 | B2 | 5/2023 | Abeliovich et al. |
| 11,999,974 | B2 | 6/2024 | Abeliovich et al. |
| 2003/0133924 | A1 | 7/2003 | Canfield |
| 2006/0292117 | A1 | 12/2006 | Loiler et al. |
| 2008/0003204 | A1 | 1/2008 | Flotte et al. |
| 2013/0287736 | A1 | 10/2013 | Passini et al. |
| 2015/0284472 | A1 | 10/2015 | Sardi et al. |
| 2017/0246263 | A1 | 8/2017 | Concino et al. |
| 2018/0147300 | A1 | 5/2018 | Park et al. |
| 2019/0282662 | A1 | 9/2019 | Kay et al. |
| 2019/0328906 | A1 | 10/2019 | Chen Plotkin et al. |
| 2019/0388507 | A1 | 12/2019 | Kay |
| 2020/0231970 | A1 | 7/2020 | Abeliovich et al. |
| 2020/0308554 | A1 | 10/2020 | Abeliovich et al. |
| 2020/0318115 | A1 | 10/2020 | Abeliovich et al. |
| 2020/0332265 | A1 | 10/2020 | Abeliovich et al. |
| 2020/0338148 | A1 | 10/2020 | Abeliovich et al. |
| 2021/0317474 | A1 | 10/2021 | Kaspar et al. |
| 2021/0332385 | A1 | 10/2021 | Abeliovich et al. |
| 2023/0287358 | A1 | 9/2023 | Abeliovich |
| 2023/0346979 | A1 | 11/2023 | Abeliovich et al. |

FOREIGN PATENT DOCUMENTS

| | | | |
|---|---|---|---|
| EP | 2687223 | A1 | 1/2014 |
| WO | WO-0183692 | A2 | 11/2001 |
| WO | WO-2009079399 | A2 | 6/2009 |
| WO | WO-2009120978 | A2 | 10/2009 |
| WO | WO-2014071282 | A1 | 5/2014 |
| WO | WO-2014186579 | A1 | 11/2014 |
| WO | WO-2016081927 | A2 | 5/2016 |
| WO | WO-2017136202 | A1 | 8/2017 |
| WO | WO-2019070891 | A1 | 4/2019 |
| WO | WO-2019070893 | A1 | 4/2019 |
| WO | WO-2019070894 | A1 | 4/2019 |
| WO | WO-2019084068 | A1 | 5/2019 |
| WO | WO-2020210615 | A1 | 10/2020 |

OTHER PUBLICATIONS

Amado, D. A. et al., "AAV-Mediated Progranulin Delivery to a Mouse Model of Progranulin Deficiency Causes T Cell-Mediated Toxicity." Molecular Therapy, 27(2):465-478 (2019).

(Continued)

*Primary Examiner* — Olga N Chernyshev
(74) *Attorney, Agent, or Firm* — Brian C. Cholewa

(57) ABSTRACT

The disclosure relates to compositions and methods for treatment of diseases associated with aberrant lysosomal function, such as fronto-temporal dementia (FTD). The disclosure also provides expression constructs comprising a transgene encoding progranulin or a portion thereof. The disclosure provides methods of treating FTD by administering such expression constructs to a subject in need thereof.

9 Claims, 83 Drawing Sheets

Specification includes a Sequence Listing.

(56) References Cited

OTHER PUBLICATIONS

Anderson, et al., "Human pathology in NCL." Biochim Biophys Acta. Nov. 2013;1832(11): 1807-26.
Arrant, et al., "Progranulin Gene Therapy Improves Lysosomal Dysfunction and Microglial Pathology Associated with Frontotemporal Dementia and Neuronal Ceroid Lipofuscinosis." J. Neurosci. Feb. 28, 2018; 38(9): 2341-2358.
[Author Unknown] G0345 pFBAAVCAGmcsBgHpA Viral Vector Core updated Feb. 22, 2017 [retrieved from the internet on Jun. 10, 2022], 7 pages.
[Author Unknown] "Optimization of use frequency of codons for high level expression of a plant-derived fatty acid desaturase in mammalian cells". Mem. School. B. O. S. T. Kinki University, 2008, No. 22, pp. 33-41.
Bond, et al., "Use of model organisms for the study of neuronal ceroid lipofuscinosis." Biochim Biophys Acta. Nov. 2013; 1832(11): 1842-65.
Button, et al., "Power failure: why small sample size undermines the reliability of neuroscience." Nat Rev Neurosci. May 2013; 14(5): 365-76. Epub Apr. 10, 2013.
Cenik, B. et al. "Suberoylanilide Hydroxamic Acid (Vorinostat) Up-regulates Progranulin Transcription." The Journal of Biological Chemistry, May 6, 2011, 286(18):16101-16108.
Choi, et al., "Optimization of AAV expression cassettes to improve packaging capacity and transgene expression in neurons." Molecular Brain, 2014, 7(17): 1-10.
Ciesielska, et al., "Cerebral infusion of AAV9 vector-encoding non-self proteins can elicit cell-mediated immune responses." Mol Ther. Jan. 2013;2 1(1): 158-66.
Database Accession No. BDA66566, "Adeno-associated virus—2 (AAV2) ITR S-sequence, Seq ID 3." Jul. 14, 2016, http://ibis.internal.epo.org/exam/dbfetch.jsp?id=GSN:BDA66566, 1 page.
Database Accession No. Q14108, "Lysosome membrane protein II." Nov. 1, 1997, https://www.uniprot.org/Q14108.txt, pp. 1-10.
Supplemental European Search Report mailed Jul. 2, 2021 in connection with Application No. 18864729.1, 12 pages.
Fath, S. et al., "Multiparameter RNA and Codon Optimization: A Standardized Tool to Assess and Enhance Autologous Mammalian Gene Expression." PLoS ONE, Mar. 3, 2011, 6(3): e17596:1-14.
François, et al. "The Cellular TATA Binding Protein Is Required for Rep-Dependent Replication of a Minimal Adeno-Associated Virus Type 2 p5 Element." Journal of Virology, Sep. 2005; 79(17): 11082-94.
Ge et al., "Optimization of eGFP expression using a modified baculovirus expression system." J Biotechnol. Mar. 10, 2014;173: 41-6.
GenBank Accession No. AAA60303.1 "Prosaposin [*Homo sapiens*]" Jan. 9, 1995 [online], 2 pages.
GenBank Accession No. AAC37547.1 "cathepsin B [*Homo sapiens*]" Apr. 7, 1994 [online], 1 page.
GenBank Accession No. AAF69824.1 "triggering receptor expressed on myeloid cells 2 [*Homo sapiens*]" May 23, 2000 [online], 1 page.
GenBank Accession No. AAH01503.1 "Prosaposin [*Homo sapiens*]" Aug. 4, 2008 [online], 2 pages.
GenBank Accession No. AAH02585.1 "RAB7, member RAS oncogene family-like 1 [*Homo sapiens*]" Jul. 15, 2006 [online], 3 pages.
GenBank Accession No. AAH04275.1 "Prosaposin [*Homo sapiens*]" Aug. 4, 2008 [online], 2 pages.
GenBank Accession No. AAH07612.1 "Prosaposin [*Homo sapiens*]" Aug. 4, 2008 [online], 2 pages.
GenBank Accession No. AAH10240.1 "Cathepsin B [*Homo sapiens*]" Jul. 15, 2006 [online], 2 pages.
GenBank Accession No. AAH25415.1 "Gtp cyclohydrolase 1 [*Homo sapiens*]" Aug. 7, 2008 [online], 2 pages.
GenBank Accession No. AAH29804.1 "Interleukin 34 [*Homo sapiens*]" Jun. 9, 2008 [online], 2 pages.
GenBank Accession No. AAH95408.1 "Cathepsin B [*Homo sapiens*]" Jul. 17, 2006 [online], 2 pages.
GenBank Accession No. AAP36904.1 "*Homo sapiens* glucosidase, beta; acid (includes glucosylceramidase), partial [synthetic construct]" Jul. 25, 2016 [online], 1 page.
GenBank Accession No. BT008212.1 "Synthetic construct *Homo sapiens* glucosidase, beta; acid (includes glucosylceramidase) mRNA, partial cds" Jul. 25, 2016 [online], 2 pages.
GenBank Accession No. EAW68726.1 "sphingomyelin phosphodiesterase 1, acid lysosomal (acid sphingomyelinase), isoform CRA_a [*Homo sapiens*]" Mar. 23, 2015 [online], 2 pages.
GenBank Accession No. EAW68727.1 "sphingomyelin phosphodiesterase 1, acid lysosomal (acid sphingomyelinase), isoform CRA_b [*Homo sapiens*]" Mar. 23, 2015 [online], 2 pages.
GenBank Accession No. EAW68728.1 "sphingomyelin phosphodiesterase 1, acid lysosomal (acid sphingomyelinase), isoform CRA_c [*Homo sapiens*]" Mar. 23, 2015 [online], 2 pages.
GenBank Accession No. EAW68729.1 "sphingomyelin phosphodiesterase 1, acid lysosomal (acid sphingomyelinase), isoform CRA_d [*Homo sapiens*]" Mar. 23, 2015 [online], 2 pages.
GenBank Accession No. EAW81359.1 "galactosylceramidase, isoform CRA_a [*Homo sapiens*]" Mar. 23, 2015 [online], 2 pages.
GenBank Accession No. EAW81360.1 "galactosylceramidase, isoform CRA_b [*Homo sapiens*]" Mar. 23, 2015 [online], 2 pages.
GenBank Accession No. EAW81362.1 "galactosylceramidase, isoform CRA_c [*Homo sapiens*]" Mar. 23, 2015 [online], 3 pages.
GenBank Accession No. NP_000144.2 "galactocerebrosidase isoform a precursor [*Homo sapiens*]" Sep. 26, 2019 [online], 3 pages.
GenBank Accession No. NP_000148.2 "lysosomal acid glucosylceramidase isoform 1 precursor [*Homo sapiens*]" Jan. 8, 2020 [online], 3 pages.
GenBank Accession No. NP_000152.1 "GTP cyclohydrolase 1 isoform 1 [*Homo sapiens*]" Dec. 30, 2019 [online], 3 pages.
GenBank Accession No. NP_000534.3 "sphingomyelin phosphodiesterase isoform 1 precursor [*Homo sapiens*]" Jan. 13, 2020 [online], 4 pages.
GenBank Accession No. NP_001005742.1 "lysosomal acid glucosylceramidase isoform 1 precursor [*Homo sapiens*]" Nov. 11, 2019 [online], 3 pages.
GenBank Accession No. NP_001165282.1 "lysosomal acid glucosylceramidase isoform 2 [*Homo sapiens*]" Nov. 11, 2019 [online], 3 pages.
GenBank Accession No. NP_001165283.1 "lysosomal acid glucosylceramidase isoform 3 [*Homo sapiens*]" Nov. 11, 2019 [online], 3 pages.
GenBank Accession No. NP_001191184.1 "lysosome membrane protein 2 isoform 2 precursor [*Homo sapiens*]" Jan. 4, 2020 [online], 3 pages.
GenBank Accession No. NP_001317589.1 "non-lysosomal glucosylceramidase isoform 2 [*Homo sapiens*]" Aug. 7, 2019 [online], 3 pages.
GenBank Accession No. NP_001899.1 "cathepsin B isoform 1 preproprotein [*Homo sapiens*]" Jan. 27, 2020 [online], 3 pages.
GenBank Accession No. NP_002078.1 "progranulin precursor [*Homo sapiens*]" Jan. 21, 2020 [online], 3 pages.
GenBank Accession No. NP_002087.1 "general transcription factor IIF, polypeptide 1, 74kDa [*Homo sapiens*]" Jun. 3, 2007 [online], 2 pages.
GenBank Accession No. NP_002769.1 "prosaposin isoform a preproprotein [*Homo sapiens*]" Sep. 27, 2019 [online], 4 pages.
GenBank Accession No. NP_003920.1 "ras-related protein Rab-7L1 isoform 1 [*Homo sapiens*]" Dec. 31, 2019 [online], 4 pages.
GenBank Accession No. NP_005497.1 "lysosome membrane protein 2 isoform 1 precursor [*Homo sapiens*]" Jan. 1, 2020 [online], 4 pages.
GenBank Accession No. NP_060676.2 "vacuolar protein sorting-associated protein 35 [*Homo sapiens*]" Oct. 11, 2019 [online], 3 pages.
GenBank Accession No. NP_060844.2 "transmembrane protein 106B [*Homo sapiens*]" Jul. 28, 2019 [online], 3 pages.
GenBank Accession No. NP_061838.1 "triggering receptor expressed on myeloid cells 2 precursor isoform 1 precursor [*Homo sapiens*]" Feb. 2, 2020 [online], 3 pages.

(56) References Cited

OTHER PUBLICATIONS

GenBank Accession No. NP_065995.1 "non-lysosomal glucosylceramidase isoform 1 [*Homo sapiens*]" Aug. 22, 2019 [online], 3 pages.

GenBank Accession No. NP_689669.2 "interleukin-34 isoform 1 precursor [*Homo sapiens*]" Dec. 25, 2019 [online], 3 pages.

Gorski, "One reason mouse studies often don't translate to humans very well". Science-Based Medicine.org. Aug. 26, 2019. pp. 1-1. Retrieved from https://sciencebasedmedicine.org/one-reason-mouse-studies-often-dont-translate-to-humans-very-well/, Feb. 10, 2023, 11 pages.

Gotz, et al. "Animal models for Alzheimer's disease and frontotemporal dementia: a perspective." ASN Neuro. Nov. 9, 2009; 1(4): e00019, 14 pages.

Heckman, L. et al. "Preclinical development of PR006, a gene therapy for the treatment of frontotemporal dementia with progranulin mutations." Alzheimer's & Dementia, Dec. 7, 2020, 16(Suppl. 2):e043632, 2 pages.

Huang, et al., "Targeting Visceral Fat by Intraperitoneal Delivery of Novel AAV Serotype Vector Restricting Off-Target Transduction in Liver." Molecular Therapy: Methods & Clinical Development, Sep. 2017, 6: 68-78.

Jian, et al., "Association Between Progranulin and Gaucher Disease." EBioMedicine, 2016, 11:127-137.

Lu et al. "Complete correction of hemophilia A with adeno-associated viral vectors containing a full-size expression cassette." Hum. Gene. Ther., Jun. 2008, 19(6):648-54.

Mayo Clinic, Frontotemporal Dementia—Diagnosis and treatment. Retrieved from https://www.mayoclinic.org/diseases-conditions/frontotemporal-dementia/diagnosis-treatment/drc-2035-474#:-:text= here's%20currently%20no%20cure%20or,the%20symptoms%20of%20frontotemporal%20dementia on Feb. 10, 2023, 7 pages.

NCBI Reference Sequence: "*Homo sapiens* granulin precursor (GRN), mRNA," NCBI Reference Sequence: NM_002087.3, Feb. 24, 2019, 5 pages.

Renaud-Gabardos, et al., "Internal ribosome entry site-based vectors for combined gene therapy," IRES-based vectors for the gene therapy, World Journal of Experimental Medicine, Feb. 20, 2015, 5(1): 11-20.

Rothaug, et al., "LIMP-2 expression is critical for β-glucocerebrosidase activity and α-synuclein clearance." PNAS, Oct. 28, 2014, 111(43): 15573-15578.

Samaranch, et al., "AAV9-mediated expression of a non-self protein in nonhuman primate central nervous system triggers widespread neuroinflammation driven by antigen-presenting cell transduction." Mol Ther. Feb. 2014; 22(2): 329-337.

Savy, et al., "Impact of Inverted Terminal Repeat Integrity on rAAV8 Production Using the Baculovirus/Sf9 Cells System." Human Gene Therapy Methods, 2017, 28(5): 277-289.

Sikora, J. et al., "Neurolysosomal pathology in human prosaposin deficiency suggests essential neurotrophic function of prosaposin." Acta Neuropathological, Feb. 2007, 113(2): 163-75.

Tamargo, et al., "The role of saposin C in Gaucher disease." Molecular Genetics and Metabolism, Apr. 29, 2012, 106: 257-263.

Valdez, C. et al. "Progranulin-mediated deficiency of cathepsin D results in FTD and NCL-like phenotypes in neurons derived from FTD patients." Human Molecular Genetics, Dec. 15, 2017, 26(24):4861-4872.

Wang, et al., "Enhancing Transgene Expression from Recombinant AAV8 Vectors in Different Tissues Using Woodchuck Hepatitis Virus Post-Transcriptional Regulatory Element." Int. J. Med. Sci., 2016, 13: 286-291.

Xu, et al., "Extracellular progranulin protects cortical neurons from toxic insults by activating survival signaling." Neurobiol Aging., Dec. 2011; 32(12): 2326.e5-16.

Yu, et al., "The spectrum of mutations in progranulin: a collaborative study screening 545 cases of neurodegeneration." Arch Neurol. Feb. 2010; 67(2): 161-70.

U.S. Appl. No. 18/298,529, filed Apr. 11, 2023.

U.S. Appl. No. 18/041,199, filed Feb. 9, 2023.

Arrant et al. "Restoring neuronal progranulin reverses deficits in a mouse model of frontotemporal dementia," Brain, May 1, 2017, 140(5):1477-1465.

Saraiva, J. et al., "Gene therapy for the CNS using AAVs: The impact of systemic delivery by AAV9," Journal of Controlled Release, 241:94-109 (2016); doi: 10.1016/j.jconrel.2016.09.011. Epub Sep. 13, 2016.

Zhou, X. et al., "Lysosomal processing of progranulin," Molecular Neurodegeneration, 12:62 (2017); doi: 10.1186/s13024-017-0205-9, 6 pages.

PrevailVector_FP1_JetLong_GBA1_bGH_JetLong_SCARB2_SV40L_4464nt
11,420 bp

PrevailVector_LT7s_JetLong_mRNAiaSyn_RAB7L1-T2A-GBA1_WPRE_bGH_3984nt
10940 bp

PrevailVector_FP12_CMVe_CBA_GBA1_bGH_JetLong_IL34_SV401_4503nt
11,459 bp updated_38.GRN_PW aligned both VM and P (1)

10,870 bp updated_PrevailVector_LT2s_JetLong_mRNAiaSYn_PSAP-FgsgT2A-GBA1_bGH_4374nt_aligned
11,292 bp

| PR006A dose | Total vg | vg / g brain |
|---|---|---|
| single | $9.7 \times 10^{10}$ | $2.4 \times 10^{11}$ |

| PR006A dose | Total vg | vg / g brain |
|---|---|---|
| Low | $1.1 \times 10^9$ | $2.7 \times 10^9$ |
| Medium | $1.1 \times 10^{10}$ | $2.7 \times 10^{10}$ |
| High | $1.1 \times 10^{11}$ | $2.7 \times 10^{11}$ |

SEQUENCE LISTING

```
Sequence total quantity: 91
SEQ ID NO: 1           moltype = DNA  length = 10697
FEATURE                Location/Qualifiers
misc_feature           1..10697
                       note = Synthetic polynucleotide
source                 1..10697
                       mol_type = other DNA
                       organism = synthetic construct
SEQUENCE: 1
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
cctagttatt aatagtaatc aattacgggg tcattagttc atagcccata tatggagttc  360
cgcgttacat aacttacggt aaatggcccg cctggctgac cgcccaacga cccccgccca  420
ttgacgtcaa taatgacgta tgttcccata gtaacgccaa tagggacttt ccattgacgt  480
caatgggtgg actatttacg gtaaactgcc cacttggcag tacatcaagt gtatcatatg  540
ccaagtacgc cccctattga cgtcaatgac ggtaaatggc ccgcctggca ttatgcccag  600
tacatgacct tatgggactt tcctacttgg cagtacatct acgtattagt catcgctatt  660
accatggtcg aggtgagccc cacgttctgc ttcactctcc ccatctcccc cccctcccca  720
cccccaattt tgtatttatt tattttttaa ttattttgtg cagcgatggg ggcggggggg  780
gggggggggc gcgcgccagg cggggcgggg cggggcgagg ggcggggcgg ggcgaggcgg  840
agaggtgcgg cggcagccaa tcagagcggc gcgctccgaa agtttccttt tatggcgagg  900
cggcggcggc ggcggcccta taaaaagcga agcgcgcggc gggcgggagt cgctgcgacg  960
ctgccttcgc cccgtgcccc gctccgccgc cgcctcgcgc cgcccgcccc ggctctgact  1020
gaccgcgtta ctcccacagg tgagcgggcg ggacggccct tctcctccgg gctgtaatta  1080
gcgcttggtt taatgacggc ttgttttctg tggctgcgtg aaagccttga ggggctccgg  1140
gagctagagc ctctgctaac catgttcatg ccttcttctt tttcctacag ctcctgggca  1200
acgtgctggt tattgtgctg tctcatcatt ttggcaaaga attcctcgaa gatccgaagg  1260
```

-continued

```
gaaagtcttc cacgactgtg ggatccgttc gaagatatca ccggttgagc caccatggaa  1320
ttcagcagcc ccagcagaga ggaatgcccc aagcctctga gccgggtgtc aatcatggcc  1380
ggatctctga caggactgct gctgcttcag gccgtgtctt gggcttctgg cgctagacct  1440
tgcatcccca agagcttcgg ctacagcagc gtcgtgtgcg tgtgcaatgc cacctactgc  1500
gacagcttcg accctcctac ctttcctgct ctgggcacct tcagcagata cgagagcacc  1560
agatccggca gacggatgga actgagcatg ggacccatcc aggccaatca cacaggcact  1620
ggcctgctgc tgacactgca gcctgagcag aaattccaga aagtgaaagg cttcggcgga  1680
gccatgacag atgccgccgc tctgaatatc ctggctctgt ctccaccagc tcagaacctg  1740
ctgctcaaga gctacttcag cgaggaaggc atcggctaca acatcatcag agtgcccatg  1800
gccagctgcg acttcagcat caggacctac acctacgccg acacacccga cgatttccag  1860
ctgcacaact tcagcctgcc tgaagaggac accaagctga agatccctct gatccacaga  1920
gccctgcagc tggcacaaag acccgtgtca ctgctggcct ctccatggac atctcccacc  1980
tggctgaaaa caaatggcgc cgtgaatggc aagggcagcc tgaaaggcca acctggcgac  2040
atctaccacc agacctgggc cagatacttc gtgaagttcc tggacgccta tgccgagcac  2100
aagctgcagt tttgggccgt gacagccgag aacgaacctt ctgctggact gctgagcggc  2160
taccccttc agtgcctggg ctttacaccc gagcaccagc gggactttat cgcccgtgat  2220
ctgggaccca cactggccaa tagcacccac cataatgtgc ggctgctgat gctggacgac  2280
cagagactgc ttctgcccca ctgggctaaa gtggtgctga cagatcctga ggccgccaaa  2340
tacgtgcacg gaatcgccgt gcactggtat ctggactttc tggcccctgc caaggccaca  2400
ctgggagaga cacacagact gttccccaac accatgctgt tcgccagcga agcctgtgtg  2460
ggcagcaagt tttgggaaca gagcgtgcgg ctcggcagct gggatagagg catgcagtac  2520
agccacagca tcatcaccaa cctgctgtac cacgtcgtcg gctggaccga ctggaatctg  2580
gccctgaatc ctgaaggcgg ccctaactgg gtccgaaact tcgtggacag ccccatcatc  2640
gtggacatca ccaaggacac cttctacaag cagcccatgt tctaccacct gggacacttc  2700
agcaagttca tccccgaggg ctctcagcgc gttggactgg tggcttccca gaagaacgat  2760
ctggacgccg tggctctgat gcaccctgat ggatctgctg tggtggtggt cctgaaccgc  2820
agcagcaaag atgtgcccct gaccatcaag gatcccgccg tgggattcct ggaaacaatc  2880
agccctggct actccatcca cacctacctg tggcgtagac agtgacaatt gttaattaag  2940
tttaaaccct cgaggccgca agcttatcga taatcaacct ctggattaca aaatttgtga  3000
aagattgact ggtattctta actatgttgc tccttttacg ctatgtggat acgctgcttt  3060
aatgcctttg tatcatgcta ttgcttcccg tatggctttc attttctcct ccttgtataa  3120
atcctggttg ctgtctcttt atgaggagtt gtggcccgtt gtcaggcaac gtggcgtggt  3180
gtgcactgtg tttgctgacg caacccccac tggttggggc attgccacca cctgtcagct  3240
cctttccggg actttcgctt tccccctccc tattgccacg gcggaactca tcgccgcctg  3300
ccttgcccgc tgctggacag gggctcggct gttgggcact gacaattccg tggtgttgtc  3360
ggggaaatca tcgtcctttc cttggctgct cgcctgtgtt gccacctgga ttctgcgcgg  3420
gacgtccttc tgctacgtcc cttcggccct caatccagcg gaccttcctt cccgcggcct  3480
gctgccggct ctgcggcctc ttccgcgtct tcgccttcgc cctcagacga gtcggatctc  3540
cctttgggcc gcctccccgc atcgataccg tcgactagag ctcgctgatc agcctcgact  3600
gtgccttcta gttgccagcc atctgttgtt tgcccctccc ccgtgccttc cttgaccctg  3660
gaaggtgcca ctcccactgt cctttcctaa taaaatgagg aaattgcatc gcattgtctg  3720
agtaggtgtc attctattct ggggggtggg gtggggcagg acagcaaggg ggaggattgg  3780
gaagacaata gcaggcatgc tggggagaga tccacgataa caaacagctt ttttggggtg  3840
aacatattga ctgaattccc tgcaggttgg ccactccctc tctgcgcgct cgctcgctca  3900
ctgaggccgc ccgggcaaag cccgggcgtc gggcgacctt tggtcgcccg gcctcagtga  3960
gcgagcgagc gcgcagagag ggagtggcca actccatcac taggggttcc tgcggccgct  4020
cgtacggtct cgaggaattc ctgcaggata acttgccaac ctcattctaa aatgtatata  4080
gaagcccaaa agacaataac aaaaatattc ttgtagaaca aaatgggaaa gaatgttcca  4140
ctaaatatca agatttagag caaagcatga gatgtgtggg gatagacagt gaggctgata  4200
aaatagagta gagctcagaa acagacccat tgatatatgt aagtgaccta tgaaaaaaat  4260
atggcatttt acaatgggaa aatgatggtc tttttctttt ttagaaaaac agggaaatat  4320
atttatatgt aaaaaataaa agggaaccca tatgtcatac catacacaca aaaaaattcc  4380
agtgaattat aagtctaaat ggagaaggca aaactttaaa tcttttagaa aataatatag  4440
aagcatgcag accagcctgg ccaacatgat gaaaccctct ctactaataa taaaatcagt  4500
agaactactc aggactactt tgagtgggaa gtccttttct atgaagactt ctttggccaa  4560
aattaggctc taaatgcaag gagatagtgc atcatgcctg gctgcactta ctgataaatg  4620
atgttatcac catctttaac caaatgcaca ggaacaagtt atggtactga tgtgctggat  4680
tgagaaggag ctctacttcc ttgacaggac acatttgtat caacttaaaa aagcagattt  4740
ttgccagcag aactattcat tcagaggtag gaaacttaga atagatgatg tcactgatta  4800
gcatggcttc cccatctcca cagctgcttc ccacccaggt tgcccacagt tgagtttgtc  4860
cagtgctcag ggctgcccac tctcagtaag aagccccaca ccagcccctc tccaaatatg  4920
ttggctgttc cttccattaa agtgacccca ctttagagca gcaagtggat ttctgtttct  4980
tacagttcag gaaggaggag tcagctgtga gaacctggag cctgagatgc ttctaagtcc  5040
cactgctact ggggtcaggg aagccagact ccagcatcag cagtcaggag cactaagccc  5100
ttgccaacat cctgtttctc agagaaactg cttccattat aatggttgtc cttttttaag  5160
ctatcaagcc aaacaaccag tgtctaccat tattctcatc acctgaagcc aagggttcta  5220
gcaaaagtca agctgtcttg taatggttga tgtgcctcca gcttctgtct tcagtcactc  5280
cactcttagc ctgctctgaa tcaactctga ccacagttcc ctggagcccc tgccacctgc  5340
tgcccctgcc accttctcca tctgcagtgc tgtgcagcct tctgcactct tgcagagcta  5400
ataggtggag acttgaagga agaggaggaa agtttctcat aatagccttg ctgcaagctc  5460
aaatgggagg tgggcactgt gcccaggagc cttggagcaa aggctgtgcc caacctctga  5520
ctgcatccag gtttggtctt gacagagata agaagccctg gcttttggag ccaaaatcta  5580
ggtcagactt aggcaggatt ctcaaagttt atcagcagaa catgaggcag aagacccttt  5640
ctgctccagc ttcttcaggc tcaaccttca tcagaataga tagaaagaga ggctgtgagg  5700
gttcttaaaa cagaagcaaa tctgactcag agaataaaca acctcctagt aaactacagc  5760
ttagacagag catctggtgg tgagtgtgct cagtgtccta ctcaactgtc tggtatcagc  5820
cctcatgagg acttctcttc tttccctcat agacctccat ctctgttttc cttagcctgc  5880
agaaatctgg atggctattc acagaatgcc tgtgctttca gagttgcatt ttttctctgg  5940
tattctggtt caagcatttg aaggtaggaa aggttctcca agtgcaagaa agccagccct  6000
```

```
gagcctcaac tgcctggcta gtgtggtcag taggatgcaa aggctgttga atgccacaag  6060
gccaaacttt aacctgtgta ccacaagcct agcagcagag gcagctctgc tcactggaac  6120
tctctgtctt ctttctcctg agccttttct tttcctgagt tttctagctc tcctcaacct  6180
tacctctgcc ctacccagga caaacccaag agccactgtt tctgtgatgt cctctccagc  6240
cctaattagg catcatgact tcagcctgac cttccatgct cagaagcagt gctaatccac  6300
ttcagatgag ctgctctatg caacacaggc agagcctaca aacctttgca ccagagccct  6360
ccacatatca gtgtttgttc atactcactt caacagcaaa tgtgactgct gagattaaga  6420
ttttacacaa gatggtctgt aatttcacag ttagttttat cccattaggt atgaaagaat  6480
tagcataatt ccccttaaac atgaatgaat cttagatttt ttaataaata gttttggaag  6540
taaagacaga gacatcagga gcacaaggaa tagcctgaga ggacaaacag aacaagaaag  6600
agtctggaaa tacacaggat gttcttggcc tcctcaaagc aagtgcaagc agatagtacc  6660
agcagcccca ggctatcaga gcccagtgaa gagaagtacc atgaaagcca cagctctaac  6720
caccctgttc cagagtgaca gacagtcccc aagacaagcc agcctgagcc agagagagaa  6780
ctgcaagaga aagtttctaa tttaggttct gttagattca gacaagtgca ggtcatcctc  6840
tctccacagc tactcacctc tccagcctaa caaagcctgc agtccacact ccaaccctgg  6900
tgtctcacct cctagcctct cccaacatcc tgctctctga ccatcttctg catctctcat  6960
ctcaccatct cccactgtct acagcctact cttgcaacta ccatctcatt ttctgacatc  7020
ctgtctacat cttctgccat actctgccat ctaccatacc acctcttacc atctaccaca  7080
ccatctttta tctccatccc tctcagaagc ctccaagctg aatcctgctt tatgtgttca  7140
tctcagcccc tgcatggaaa gctgacccca gaggcagaac tattcccaga gagcttggcc  7200
aagaaaaaca aaactaccag cctggccagg ctcaggagta gtaagctgca gtgtctgttg  7260
tgttctagct tcaacagctg caggagttcc actctcaaat gctccacatt tctcacatcc  7320
tcctgattct ggtcactacc catcttcaaa gaacagaata tctcacatca gcatactgtg  7380
aaggactagt catgggtgca gctgctcaga gctgcaaagt cattctggat ggtggagagc  7440
ttacaaacat ttcatgatgc tcccccccgct ctgatggctg gagcccaatc cctacacaga  7500
ctcctgctgt atgtgtttc ctttcactct gagccacagc cagagggcag gcattcagtc  7560
tcctcttcag gctggggctg gggcactgag aactcaccca acaccttgct ctcactcctt  7620
ctgcaaaaca agaaaagagct ttgtgctgca gtagccatga agaatgaaag gaaggcttta  7680
actaaaaaat gtcagagatt attttcaacc ccttactgtg gatcaccagc aaggaggaaa  7740
cacaacacag agacattttt tcccctcaaa ttatcaaaag aatcactgca tttgttaaag  7800
agagcaactg aatcaggaag cagagttttg aacatatcag aagttaggaa tctgcatcag  7860
agacaaatgc agtcatggtt gtttgctgca taccagccct aatcattaga agcctcatgg  7920
acttcaaaca tcattccctc tgacaagatg ctctagccta actccatgag ataaaataaa  7980
tctgcctttc agagccaaag aagagtccac cagcttcttc tcagtgtgaa caagagctcc  8040
agtcaggtta gtcagtccag tgcagtagag gagaccagtc tgcatcctct aattttcaaa  8100
ggcaagaaga tttgtttacc ctggacacca ggcacaagtg aggtcacaga gctcttagat  8160
atgcagtcct catgagtgag gagactaaag cgcatgccat caagacttca gtgtagagaa  8220
aacctccaaa aaagcctcct cactacttct ggaatagctc agaggccgag gcggcctcgg  8280
cctctgcata aataaaaaaa attagtcagc catggggcgg agaatgggcg gaactgggcg  8340
gagttagggg cgggatgggc ggagttaggg gcgggactat ggttgctgac taattgagat  8400
gcatgctttg catacttctg cctgctgggg agcctgggga ctttccacac ctggttgctg  8460
actaattgag atgcatgctt tgcatacttc tgcctgctgg ggagcctggg gactttccac  8520
accctaactg acacacattc cacagctgca ttaatgaatc ggccaacgcg cggggagagg  8580
cggtttgcgt attgggcgct cttccgcttc ctcgctcact gactcgctgc gctcggtcgt  8640
tcggctgcgg cgagcggtat cagctcactc aaaggcggta atacggttat ccacagaatc  8700
aggggataac gcaggaaaga acatgtgagc aaaaggccag caaaaggcca ggaaccgtaa  8760
aaaggccgcg ttgctggcgt ttttccatag gctccgcccc cctgacgagc atcacaaaaa  8820
tcgacgctca agtcagaggt ggcgaaaccc gacaggacta taaagatacc aggcgtttcc  8880
ccctggaagc tccctcgtgc gctctcctgt tccgaccctg ccgcttaccg gatacctgtc  8940
cgcctttctc ccttcgggaa gcgtggcgct ttctcatagc tcacgctgta ggtatctcag  9000
ttcggtgtag gtcgttcgct ccaagctggg ctgtgtgcac gaaccccccg ttcagcccga  9060
ccgctgcgcc ttatccggta actatcgtct tgagtccaac ccggtaagac acgacttatc  9120
gccactggca gcagccactg gtaacaggat tagcagagcg aggtatgtag gcggtgctac  9180
agagttcttg aagtggtggc ctaactacgg ctacactaga agaacagtat ttggtatctg  9240
cgctctgctg aagccagtta ccttcggaaa aagagttggt agctcttgat ccggcaaaca  9300
aaccaccgct ggtagcggtg gtttttttgt ttgcaagcag cagattacgc gcagaaaaaa  9360
aggatctcaa gaagatcctt tgatcttttc tacggggtct gacgctcagt ggaacgaaaa  9420
ctcacgttaa gggattttgg tcatgagatt atcaaaaagg atcttcacct agatcctttt  9480
aaattaaaaa tgaagtttta aatcaatcta aagtatatat gagtaaactt ggtctgacag  9540
ttaccaatgc ttaatcagtg aggcacctat ctcagcgatc tgtctatttc gttcatccat  9600
agttgcctga ctcctgcaaa ccacgttgtg tctcaaaatc tctgatgtta cattgcacaa  9660
gataaaaata tatcatcatg aacaataaaa ctgtctgctt acataaacag taatacaagg  9720
ggtgttatga gccatattca acgggaaacg tcttgctcga ggccgcgatt aaattccaac  9780
atggatgctg atttatatgg gtataaatgg gctcgcgata atgtcgggca atcaggtgcg  9840
acaatctatc gattgtatgg gaagcccgat gcgccagagt tgtttctgaa acatggcaaa  9900
ggtagcgttg ccaatgatgt tacagatgag atggtcagac taaactggct gacggaattt  9960
atgcctcttc cgaccatcaa gcattttatc cgtactcctg atgatgcatg gttactcacc  10020
actgcgatcc ccgggaaaac agcattccag gtattagaag aatatcctga ttcaggtgaa  10080
aatattgttg atgcgctggc agtgttcctg cgccggttgc attcgattcc tgtttgtaat  10140
tgtcctttta acagcgatcg cgtatttcgt ctcgctcagg cgcaatcacg aatgaataac  10200
ggtttggttg atgcgagtga ttttgatgac gagcgtaatg gctggcctgt tgaacaagtc  10260
tggaaagaaa tgcataagct tttgccattc tcaccggatt cagtcgtcac tcatggtgat  10320
ttctcacttg ataaccttat ttttgacgag gggaaattaa taggttgtat tgatgttgga  10380
cgagtcggaa tcgcagaccg ataccaggat cttgccatcc tatggaactg cctcggtgag  10440
ttttctcctt cattacagaa acggcttttt caaaaatatg gtattgataa tcctgatatg  10500
aataaattgc agtttcattt gatgctcgat gagtttttct aagggcggcc tgccaccata  10560
cccacgccga aacaagcgct catgagcccg aagtggcgag cccgatcttc cccatcggtg  10620
atgtcggcga tataggcgcc agcaaccgca cctgtggcgc cggtgatgag ggcgcgccaa  10680
gtcgacgtcc ggcagtc                                                 10697
```

```
SEQ ID NO: 2            moltype = DNA  length = 11355
FEATURE                 Location/Qualifiers
misc_feature            1..11355
                        note = Synthetic polynucleotide
source                  1..11355
                        mol_type = other DNA
                        organism = synthetic construct
SEQUENCE: 2
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catgggccgc tgctgcttct acaccgccgg  660
caccctgagc ctgctgctgc tggtgaccag cgtgaccctg ctggtggccc gcgtgttcca  720
gaaggccgtg gaccagagca tcgagaagaa gatcgtgctg cgcaacggca ccgaggcctt  780
cgacagctgg gagaagcccc ccctgcccgt gtacacccag ttctacttct tcaacgtgac  840
caaccccgag gagatcctgc gcggcgagac cccccgcgtg gaggaggtgg gcccctacac  900
ctaccgcgag ctgcgcaaca aggccaacat ccagttcggc gacaacggca ccaccatcag  960
cgccgtgagc aacaaggcct acgtgttcga gcgcgaccag agcgtgggcg accccaagat  1020
cgacctgatc cgcaccctga acatccccgt gctgaccgtg atcgagtgga gccaggtgca  1080
cttcctgcgc gagatcatcg aggccatgct gaaggcctac cagcagaagc tgttcgtgac  1140
ccacaccgtg gacgagctgc tgtggggcta caaggacgag atcctgagcc tgatccacgt  1200
gttccgcccc gacatcagcc cctacttcgg cctgttctac gagaagaacg gcaccaacga  1260
cggcgactac gtgttcctga ccggcgagga cagctacctg aacttcacca agatcgtgga  1320
gtggaacggc aagaccagcc tggactggtg gatcaccgac aagtgcaaca tgatcaacgg  1380
caccgacggc gacagcttcc acccccctgat caccaaggac gaggtgctgt acgtgttccc  1440
cagcgacttc tgccgcagcg tgtacatcac cttcagcgac tacgagagcg tgcagggcct  1500
gcccgccttc cgctacaagg tgcccgccga gatcctggcc aacaccagcg acaacgccgg  1560
cttctgcatc cccgagggca actgcctggg cagcggcgtg ctgaacgtga gcatctgcaa  1620
gaacggcgcc cccatcatca tgagcttccc ccacttctac caggccgacg agcgcttcgt  1680
gagcgccatc gagggcatgc accccaacca ggaggaccac gagaccttcg tggacatcaa  1740
cccccctgacc ggcatcatcc tgaaggccgc caagcgcttc cagatcaaca tctacgtgaa  1800
gaagctggac gacttcgtgg agaccggcga catccgcacc atggtgttcc ccgtgatgta  1860
cctgaacgag agcgtgcaca tcgacaagga gaccgccagc cgcctgaaga gcatgatcaa  1920
caccaccctg atcatcacca acatccccta catcatcatg gccctgggcg tgttcttcgg  1980
cctggtgttc acctggctgg cctgcaaggg ccagggcagc atggacgagg gcaccgccga  2040
cgagcgcgcc cccctgatcc gcacctgatt gtggccgaac cgccgaactc agaggccggc  2100
cccagaaaac ccgagcgagt agggggcggc gcgcaggagg gaggagaact gggggcgcgg  2160
gaggctggtg ggtgtggggg gtggagatgt agaagatgtg acgccgcggc ccggcgggtg  2220
ccagattagc ggacgcggtg cccgcggttg caacgggatc ccgggcgctg cagcttggga  2280
ggcggctctc cccaggcggc gtccgcggag acacccatcc gtgaacccca ggtcccgggc  2340
cgccggctcg ccgcgcacca ggggccggcg gacagaagag cggccgagcg gctcgaggct  2400
gggggaccgc gggcgcggcc gcgcgctgcc gggcgggagg ctggggggcc ggggccgggg  2460
ccgtgccccg gagcgggtcg gaggccgggg ccggggccgg gggacggcgg ctccccgcgc  2520
ggctccagcg gctcggggat cccggccggg ccccgcaggg accatgatgg aattcagcag  2580
ccccagcaga gaggaatgcc ccaagcctct gagccgggtg tcaatcatgg ccggatctct  2640
gacaggactg ctgctgcttc aggccgtgtc ttgggcttct ggcgctagac cttgcatccc  2700
caagagcttc ggctacagca gcgtcgtgtg cgtgtgcaat gccacctact gcgacagctt  2760
cgaccctcct acctttcctg ctctgggcac cttcagcaga tacgagagca ccagatccgg  2820
cagacggatg gaactgagca tggacccat ccaggccaat cacacaggca ctggcctgct  2880
gctgacactg cagcctgagc agaaattcca gaaagtgaaa ggcttcggcg gagccatgac  2940
agatgccgcc gctctgaata tcctggctct gtctccacca gctcagaacc tgctgctcaa  3000
gagctacttc agcgaggaag gcatcggcta caacatcatc agagtgccca tggccagctg  3060
cgacttcagc atcaggacct acacctacgc cgacacaccc gacgatttcc agctgcacaa  3120
cttcagcctg cctgaagagg acaccaagct gaagatccct ctgatccaca gagccctgca  3180
gctggcacaa agacccgtgt cactgctggc ctctccatgg acatctccca cctggctgaa  3240
aacaaatggc gccgtgaatg gcaagggcag cctgaaaggc caacctggcg acatctacca  3300
ccagacctgg gccagatact tcgtgaagtt cctggacgcc tatgccgagc acaagctgca  3360
gttttgggcc gtgacagccg agaacgaacc ttctgctgga ctgctgagcg gctacccctt  3420
tcagtgcctg ggctttacac ccgagcacca gcgggacttt atcgcccgtg atctgggacc  3480
cacactggcc aatagcaccc accataatgt gcggctgctg atgctggacg accagagact  3540
gcttctgccc cactgggcta aagtggtgct gacagatcct gaggccgcca aatacgtgca  3600
cggaatcgcc gtgcactggt atctggactt tctggcccct gccaaggcca cactgggaga  3660
gacacacaga ctgttcccca acaccatgct gttcgccagc gaagcctgtg tgggcagcaa  3720
gttttgggaa cagagcgtgc ggctcggcag ctgggataga ggcatgcagt acagccacag  3780
catcatcacc aacctgctgt accacgtcgt cggctggacc gactggaatc tggccctgaa  3840
tcctgaaggc ggccctaact gggtccgaaa cttcgtggac agccccatca tcgtggacat  3900
caccaaggac accttctaca agcagcccat gttctaccac ctgggacact tcagcaagtt  3960
catccccgag ggctctcagc gcgttggact ggtggcttcc cagaagaacg atctggacgc  4020
cgtggctctg atgcaccctg atggatctgc tgtggtggtg gtcctgaacc gcagcagcaa  4080
agatgtgccc ctgaccatca aggatcccgc cgtgggattc ctggaaacaa tcagccctgg  4140
ctactccatc cacacctacc tgtggcgtag acagtgacaa ttgttaatta agtttaaacc  4200
```

```
ctcgaggccg caagccgcat cgataccgtc gactagagct cgctgatcag cctcgactgt  4260
gccttctagt tgccagccat ctgttgtttg cccctccccc gtgccttcct tgaccctgga  4320
aggtgccact cccactgtcc tttcctaata aaatgaggaa attgcatcgc attgtctgag  4380
taggtgtcat tctattctgg ggggtggggt ggggcaggac agcaaggggg aggattggga  4440
agacaatagc aggcatgctg gggagagatc cacgataaca aacagctttt ttggggtgaa  4500
catattgact gaattccctg caggttggcc actccctctc tgcgcgctcg ctcgctcact  4560
gaggccgccc gggcaaagcc cgggcgtcgg gcgacctttg gtcgcccggc ctcagtgagc  4620
gagcgagcgc gcagagaggg agtggccaac tccatcacta ggggttcctg cggccgctcg  4680
tacggtctcg aggaattcct gcaggataac ttgccaacct cattctaaaa tgtatataga  4740
agcccaaaag acaataacaa aaatattctt gtagaacaaa atgggaaaga atgttccact  4800
aaatatcaag atttagagca aagcatgaga tgtgtgggga tagacagtga ggctgataaa  4860
atagagtaga gctcagaaac agacccattg atatatgtaa gtgacctatg aaaaaaatat  4920
ggcattttac aatgggaaaa tgatggtctt tttctttttt agaaaaacag ggaaatatat  4980
ttatatgtaa aaaataaaag ggaacccata tgtcatacca tacacacaaa aaaattccag  5040
tgaattataa gtctaaatgg agaaggcaaa actttaaatc ttttagaaaa taatatagaa  5100
gcatgcagac cagcctggcc aacatgatga aaccctctct actaataata aaatcagtag  5160
aactactcag gactactttg agtgggaagt ccttttctat gaagacttct ttggccaaaa  5220
ttaggctcta aatgcaagga gatagtgcat catgcctggc tgcacttact gataaatgat  5280
gttatcacca tctttaacca aatgcacagg aacaagttat ggtactgatg tgctggattg  5340
agaaggagct ctacttcctt gacaggacac atttgtatca acttaaaaaa gcagattttt  5400
gccagcagaa ctattcattc agaggtagga aacttagaat agatgatgtc actgattagc  5460
atggcttccc catctccaca gctgcttccc acccaggttg cccacagttg agtttgtcca  5520
gtgctcaggg ctgcccactc tcagtaagaa gccccacacc agcccctctc caaatatgtt  5580
ggctgttcct tccattaaag tgaccccact ttagagcagc aagtggattt ctgtttctta  5640
cagttcagga aggaggagtc agctgtgaga acctggagcc tgagatgctt ctaagtccca  5700
ctgctactgg ggtcagggaa gccagactcc agcatcagca gtcaggagca ctaagccctt  5760
gccaacatcc tgtttctcag agaaactgct tccattataa tggttgtcct tttttaagct  5820
atcaagccaa acaaccagtg tctaccatta ttctcatcac ctgaagccaa gggttctagc  5880
aaaagtcaag ctgtcttgta atggttgatg tgcctccagc ttctgtcttc agtcactcca  5940
ctcttagcct gctctgaatc aactctgacc acagttccct ggagcccctg ccacctgctg  6000
cccctgccac cttctccatc tgcagtgctg tgcagccttc tgcactcttg cagagctaat  6060
aggtggagac ttgaaggaag aggaggaaag tttctcataa tagccttgct gcaagctcaa  6120
atgggaggtg ggcactgtgc ccaggagcct tggagcaaag gctgtgccca acctctgact  6180
gcatccaggt ttggtcttga cagagataag aagccctggc ttttggagcc aaaatctagg  6240
tcagacttag gcaggattct caaagtttat cagcagaaca tgaggcagaa gacccttttct  6300
gctccagctt cttcaggctc aaccttcatc agaatagata gaaagagagg ctgtgagggt  6360
tcttaaaaca gaagcaaatc tgactcagag aataaacaac ctcctagtaa actacagctt  6420
agacagagca tctggtggtg agtgtgctca gtgtcctact caactgtctg gtatcagccc  6480
tcatgaggac ttctcttctt tccctcatag acctccatct ctgttttcct tagcctgcag  6540
aaatctggat ggctattcac agaatgcctg tgctttcaga gttgcatttt ttctctggta  6600
ttctggttca agcatttgaa ggtaggaaag gttctccaag tgcaagaaag ccagccctga  6660
gcctcaactg cctggctagt gtggtcagta ggatgcaaag gctgttgaat gccacaaggc  6720
caaactttaa cctgtgtacc acaagcctag cagcagaggc agctctgctc actggaactc  6780
tctgtcttct ttctcctgag ccttttcttt tcctgagttt tctagctctc ctcaacctta  6840
cctctgccct acccaggaca aacccaagag ccactgtttc tgtgatgtcc tctccagccc  6900
taattaggca tcatgacttc agcctgacct tccatgctca gaagcagtgc taatccactt  6960
cagatgagct gctctatgca acacaggcag agcctacaaa cctttgcacc agagccctcc  7020
acatatcagt gtttgttcat actcacttca acagcaaatg tgactgctga gattaagatt  7080
ttacacaaga tggtctgtaa tttcacagtt agttttatcc cattaggtat gaaagaatta  7140
gcataattcc ccttaaacat gaatgaatct tagatttttt aataaatagt tttggaagta  7200
aagacagaga catcaggagc acaaggaata gcctgagagg acaaacagaa caagaaagag  7260
tctggaaata cacaggatgt tcttggcctc ctcaaagcaa gtgcaagcag atagtaccag  7320
cagccccagg ctatcagagc ccagtgaaga gaagtaccat gaaagccaca gctctaacca  7380
ccctgttcca gagtgacaga cagtccccaa gacaagccag cctgagccag agagagaact  7440
gcaagagaaa gtttctaatt taggttctgt tagattcaga caagtgcagg tcatcctctc  7500
tccacagcta ctcacctctc cagcctaaca aagcctgcag tccacactcc aaccctggtg  7560
tctcacctcc tagcctctcc caacatcctg ctctctgacc atcttctgca tctctcatct  7620
caccatctcc cactgtctac agcctactct tgcaactacc atctcatttt ctgacatcct  7680
gtctacatct tctgccatac tctgccatct accataccac ctcttaccat ctaccacacc  7740
atcttttatc tccatccctc tcagaagcct ccaagctgaa tcctgcttta tgtgttcatc  7800
tcagcccctg catggaaagc tgaccccaga ggcagaacta ttcccagaga gcttggccaa  7860
gaaaaacaaa actaccagcc tggccaggct caggagtagt aagctgcagt gtctgttgtg  7920
ttctagcttc aacagctgca ggagttccac tctcaaatgc tccacatttc tcacatcctc  7980
ctgattctgg tcactaccca tcttcaaaga acagaatatc tcacatcagc atactgtgaa  8040
ggactagtca tgggtgcagc tgctcagagc tgcaaagtca ttctggatgg tggagagctt  8100
acaaacattt catgatgctc cccccgctct gatggctgga gcccaatccc tacacagact  8160
cctgctgtat gtgttttcct ttcactctga gccacagcca gagggcaggc attcagtctc  8220
ctcttcaggc tggggctggg gcactgagaa ctcacccaac accttgctct cactccttct  8280
gcaaaacaag aaagagcttt gtgctgcagt agccatgaag aatgaaagga aggctttaac  8340
taaaaaatgt cagagattat tttcaacccc ttactgtgga tcaccagcaa ggaggaaaca  8400
caacacagag acattttttc ccctcaaatt atcaaaagaa tcactgcatt tgttaaagag  8460
agcaactgaa tcaggaagca gagttttgaa catatcagaa gttaggaatc tgcatcagag  8520
acaaatgcag tcatggttgt ttgctgcata ccagccctaa tcattagaag cctcatggac  8580
ttcaaacatc attccctctg acaagatgct ctagcctaac tccatgagat aaaataaatc  8640
tgcctttcag agccaaagaa gagtccacca gcttcttctc agtgtgaaca agagctccag  8700
tcaggttagt cagtccagtg cagtagagga gaccagtctg catcctctaa ttttcaaagg  8760
caagaagatt tgtttaccct ggacaccagg cacaagtgag gtcacagagc tcttagatat  8820
gcagtcctca tgagtgagga gactaaagcg catgccatca agacttcagt gtagagaaaa  8880
cctccaaaaa agcctcctca ctacttctgg aatagctcag aggccgaggc ggcctcggcc  8940
```

```
tctgcataaa taaaaaaaat tagtcagcca tggggcggag aatgggcgga actgggcgga  9000
gttaggggcg ggatgggcgg agttaggggc gggactatgg ttgctgacta attgagatgc  9060
atgctttgca tacttctgcc tgctggggag cctggggact ttccacacct ggttgctgac  9120
taattgagat gcatgctttg catacttctg cctgctgggg agcctgggga ctttccacac  9180
cctaactgac acacattcca cagctgcatt aatgaatcgg ccaacgcgcg gggagaggcg  9240
gtttgcgtat tgggcgctct tccgcttcct cgctcactga ctcgctgcgc tcggtcgttc  9300
ggctgcggcg agcggtatca gctcactcaa aggcggtaat acggttatcc acagaatcag  9360
gggataacgc aggaaagaac atgtgagcaa aaggccagca aaaggccagg aaccgtaaaa  9420
aggccgcgtt gctggcgttt ttccataggc tccgcccccc tgacgagcat cacaaaaatc  9480
gacgctcaag tcagaggtgg cgaaacccga caggactata aagataccag gcgtttcccc  9540
ctggaagctc cctcgtgcgc tctcctgttc cgaccctgcc gcttaccgga tacctgtccg  9600
cctttctccc ttcgggaagc gtggcgcttt ctcatagctc acgctgtagg tatctcagtt  9660
cggtgtaggt cgttcgctcc aagctgggct gtgtgcacga accccccgtt cagcccgacc  9720
gctgcgcctt atccggtaac tatcgtcttg agtccaaccc ggtaagacac gacttatcgc  9780
cactggcagc agccactggt aacaggatta gcagagcgag gtatgtaggc ggtgctacag  9840
agttcttgaa gtggtggcct aactacggct acactagaag aacagtattt ggtatctgcg  9900
ctctgctgaa gccagttacc ttcggaaaaa gagttggtag ctcttgatcc ggcaaacaaa  9960
ccaccgctgg tagcggtggt ttttttgttt gcaagcagca gattacgcgc agaaaaaaag  10020
gatctcaaga agatcctttg atcttttcta cggggtctga cgctcagtgg aacgaaaact  10080
cacgttaagg gattttggtc atgagattat caaaaaggat cttcacctag atccttttaa  10140
attaaaaatg aagttttaaa tcaatctaaa gtatatatga gtaaacttgg tctgacagtt  10200
accaatgctt aatcagtgag gcacctatct cagcgatctg tctatttcgt tcatccatag  10260
ttgcctgact cctgcaaacc acgttgtgtc tcaaaatctc tgatgttaca ttgcacaaga  10320
taaaaatata tcatcatgaa caataaaact gtctgcttac ataaacagta atacaagggg  10380
tgttatgagc catattcaac gggaaacgtc ttgctcgagg ccgcgattaa attccaacat  10440
ggatgctgat ttatatgggt ataaatgggc tcgcgataat gtcgggcaat caggtgcgac  10500
aatctatcga ttgtatggga agcccgatgc gccagagttg tttctgaaac atggcaaagg  10560
tagcgttgcc aatgatgtta cagatgagat ggtcagacta aactggctga cggaatttat  10620
gcctcttccg accatcaagc attttatccg tactcctgat gatgcatggt tactcaccac  10680
tgcgatcccc gggaaaacag cattccaggt attagaagaa tatcctgatt caggtgaaaa  10740
tattgttgat gcgctggcag tgttcctgcg ccggttgcat tcgattcctg tttgtaattg  10800
tccttttaac agcgatcgcg tatttcgtct cgctcaggcg caatcacgaa tgaataacgg  10860
tttggttgat gcgagtgatt ttgatgacga gcgtaatggc tggcctgttg aacaagtctg  10920
gaaagaaatg cataagcttt tgccattctc accggattca gtcgtcactc atggtgattt  10980
ctcacttgat aaccttattt ttgacgaggg gaaattaata ggttgtattg atgttggacg  11040
agtcggaatc gcagaccgat accaggatct tgccatccta tggaactgcc tcggtgagtt  11100
ttctccttca ttacagaaac ggctttttca aaaatatggt attgataatc ctgatatgaa  11160
taaattgcag tttcatttga tgctcgatga gtttttctaa gggcggcctg ccaccatacc  11220
cacgccgaaa caagcgctca tgagcccgaa gtggcgagcc cgatcttccc catcggtgat  11280
gtcggcgata taggcgccag caaccgcacc tgtggcgccg gtgatgaggg cgcgccaagt  11340
cgacgtccgg cagtc                                                   11355
```

```
SEQ ID NO: 3            moltype = DNA  length = 11420
FEATURE                 Location/Qualifiers
misc_feature            1..11420
                        note = Synthetic polynucleotide
source                  1..11420
                        mol_type = other DNA
                        organism = synthetic construct
SEQUENCE: 3
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catggaattc agcagcccca gcagagagga  660
atgccccaag cctctgagcc gggtgtcaat catggccgga tctctgacag gactgctgct  720
gcttcaggcc gtgtcttggg cttctggcgc tagaccttgc atccccaaga gcttcggcta  780
cagcagcgtc gtgtgcgtgt gcaatgccac ctactgcgac agcttcgacc ctcctacctt  840
tcctgctctg ggcaccttca gcagatacga gagcaccaga tccggcagac ggatggaact  900
gagcatggga cccatccagg ccaatcacac aggcactggc ctgctgctga cactgcagcc  960
tgagcagaaa ttccagaaag tgaaaggctt cggcggagcc atgacagatg ccgccgctct  1020
gaatatcctg gctctgtctc caccagctca gaacctgctg ctcaagagct acttcagcga  1080
ggaaggcatc ggctacaaca tcatcagagt gcccatggcc agctgcgact tcagcatcag  1140
gacctacacc tacgccgaca caccegacga tttccagctg cacaacttca gcctgcctga  1200
agaggacacc aagctgaaga tccctctgat ccacagagcc ctgcagctgg cacaaagacc  1260
cgtgtcactg ctggcctctc catggacatc tcccacctgg ctgaaaacaa atggcgccgt  1320
gaatggcaag ggcagcctga aaggccaacc tggcgacatc taccaccaga cctgggccag  1380
atacttcgtg aagttcctgg acgcctatgc cgagcacaag ctgcagtttt gggccgtgac  1440
agccgagaac gaaccttctg ctggactgct gagcggctac ccctttcagt gcctgggctt  1500
tacacccgag caccagcggg actttatcgc ccgtgatctg ggacccacac tggccaatag  1560
cacccaccat aatgtgcggc tgctgatgct ggacgaccag agactgcttc tgccccactg  1620
ggctaaagtg gtgctgacag atcctgaggc cgccaaatac gtgcacggaa tcgccgtgca  1680
ctggtatctg gactttctgg cccctgccaa ggccacactg ggagagacac acagactgtt  1740
```

-continued

```
ccccaacacc atgctgttcg ccagcgaagc ctgtgtgggc agcaagtttt gggaacagag  1800
cgtgcggctc ggcagctggg atagaggcat gcagtacagc cacagcatca tcaccaacct  1860
gctgtaccac gtcgtcggct ggaccgactg gaatctggcc ctgaatcctg aaggcggccc  1920
taactgggtc cgaaacttcg tggacagccc catcatcgtg gacatcacca aggacacctt  1980
ctacaagcag cccatgttct accacctggg acacttcagc aagttcatcc ccgagggctc  2040
tcagcgcgtt ggactggtgg cttcccagaa gaacgatctg gacgccgtgg ctctgatgca  2100
ccctgatgga tctgctgtgg tggtggtcct gaaccgcagc agcaaagatg tgcccctgac  2160
catcaaggat cccgccgtgg gattcctgga aacaatcagc cctggctact ccatccacac  2220
ctacctgtgg cgtagacagt gacaattgtt aattaagttt catcgatacc gtcgactaga  2280
gctcgctgat cagcctcgac tgtgccttct agttgccagc catctgttgt ttgcccctcc  2340
cccgtgcctt ccttgaccct ggaaggtgcc actcccactg tcctttccta ataaaatgag  2400
gaaattgcat cgcattgtct gagtaggtgt cattctattc tggggggtgg ggtggggcag  2460
gacagcaagg gggaggattg ggaagacaat agcaggcatg ctggggagag atccacgata  2520
acaaacagct tttttggggg ggcggagtta gggcggagcc aatcagcgtg cgccgttccg  2580
aaagttgcct tttatggctg ggcggagaat gggcggtgaa cgccgatgat tatataagga  2640
cgcgccgggt gtggcacagc tagttccgtc gcagccggga tttgggtcgc ggttcttgtt  2700
tgtggatccc tgtgatcgtc acttggtaag tcactgactg tctatgcctg ggaaagggtg  2760
ggcaggagat ggggcagtgc aggaaaagtg gcactatgaa ccctgcagcc ctaggaatgc  2820
atctagacaa ttgtactaac cttcttctct ttcctctcct gacagtccgg aaagccacca  2880
tgggccgctg ctgcttctac accgccggca ccctgagcct gctgctgctg gtgaccagcg  2940
tgaccctgct ggtggcccgc gtgttccaga aggccgtgga ccagagcatc gagaagaaga  3000
tcgtgctgcg caacggcacc gaggccttcg acagctggga gaagcccccc ctgcccgtgt  3060
acacccagtt ctacttcttc aacgtgacca accccgagga gatcctgcgc ggcgagaccc  3120
cccgcgtgga ggaggtgggc ccctacacct accgcgagct gcgcaacaag gccaacatcc  3180
agttcggcga caacggcacc accatcagcg ccgtgagcaa caaggcctac gtgttcgagc  3240
gcgaccagag cgtgggcgac cccaagatcg acctgatccg caccctgaac atccccgtgc  3300
tgaccgtgat cgagtggagc caggtgcact tcctgcgcga gatcatcgag gccatgctga  3360
aggcctacca gcagaagctg ttcgtgaccc acaccgtgga cgagctgctg tggggctaca  3420
aggacgagat cctgagcctg atccacgtgt tccgccccga catcagcccc tacttcggcc  3480
tgttctacga gaagaacggc accaacgacg gcgactacgt gttcctgacc ggcgaggaca  3540
gctacctgaa cttcaccaag atcgtggagt ggaacggcaa gaccagcctg gactggtgga  3600
tcaccgacaa gtgcaacatg atcaacggca ccgacggcga cagcttccac cccctgatca  3660
ccaaggacga ggtgctgtac gtgttcccca gcgacttctg ccgcagcgtg tacatcacct  3720
tcagcgacta cgagagcgtg cagggcctgc ccgccttccg ctacaaggtg cccgccgaga  3780
tcctggccaa caccagcgac aacgccggct tctgcatccc cgagggcaac tgcctgggca  3840
gcggcgtgct gaacgtgagc atctgcaaga acggcgcccc catcatcatg agcttccccc  3900
acttctacca ggccgacgag cgcttcgtga gcgccatcga gggcatgcac cccaaccagg  3960
aggaccacga gaccttcgtg gacatcaacc ccctgaccgg catcatcctg aaggccgcca  4020
agcgcttcca gatcaacatc tacgtgaaga agctggacga cttcgtggag accggcgaca  4080
tccgcaccat ggtgttcccc gtgatgtacc tgaacgagag cgtgcacatc gacaaggaga  4140
ccgccagccg cctgaagagc atgatcaaca ccaccctgat catcaccaac atcccctaca  4200
tcatcatggc cctgggcgtg ttcttcggcc tggtgttcac ctggctggcc tgcaagggcc  4260
agggcagcat ggacgagggc accgccgacg agcgcgcccc cctgatccgc acctgaccca  4320
ggggactcaa tcagcctcga agacatgata agatacattg atgagtttgg acaaaccaca  4380
acaagaatgc agtgaaaaaa atgctttatt tgtgaaattt gtgatgctat tgctttattt  4440
gtaaccatta taagctgcaa taaacaagtt aacaacaaca attgcattca ttttatgttt  4500
caggttcagg gggagatgtg ggaggttttt taaagcaagt aaaacctcta caaatgtggt  4560
atgaacatat tgactgaatt ccctgcaggt tggccactcc ctctctgcgc gctcgctcgc  4620
tcactgaggc cgcccgggca aagcccgggc gtcgggcgac ctttggtcgc ccggcctcag  4680
tgagcgagcg agcgcgcaga gagggagtgg ccaactccat cactaggggt tcctgcggcc  4740
gctcgtacgg tctcgaggaa ttcctgcagg ataacttgcc aacctcattc taaaatgtat  4800
atagaagccc aaaagacaat aacaaaaata ttcttgtaga acaaaatggg aaagaatgtt  4860
ccactaaata tcaagattta gagcaaagca tgagatgtgt ggggatagac agtgaggctg  4920
ataaaataga gtagagctca gaaacagacc cattgatata tgtaagtgac ctatgaaaaa  4980
aatatggcat tttacaatgg gaaaatgatg gtctttttct tttttagaaa aacagggaaa  5040
tatatttata tgtaaaaaat aaaagggaac ccatatgtca taccatacac acaaaaaaat  5100
tccagtgaat tataagtcta aatggagaag gcaaaacttt aaatctttta gaaaataata  5160
tagaagcatg cagaccagcc tggccaacat gatgaaaccc tctctactaa taataaaatc  5220
agtagaacta ctcaggacta ctttgagtgg gaagtccttt tctatgaaga cttctttggc  5280
caaaattagg ctctaaatgc aaggagatag tgcatcatgc ctggctgcac ttactgataa  5340
atgatgttat caccatcttt aaccaaatgc acaggaacaa gttatggtac tgatgtgctg  5400
gattgagaag gagctctact tccttgacag gacacatttg tatcaactta aaaaagcaga  5460
tttttgccag cagaactatt cattcagagg taggaaactt agaatagatg atgtcactga  5520
ttagcatggc ttccccatct ccacagctgc ttcccaccca ggttgcccac agttgagttt  5580
gtccagtgct cagggctgcc cactctcagt aagaagcccc acaccagccc ctctccaaat  5640
atgttggctg ttccttccat taaagtgacc ccactttaga gcagcaagtg gatttctgtt  5700
tcttacagtt caggaaggag gagtcagctg tgagaacctg gagcctgaga tgcttctaag  5760
tcccactgct actggggtca gggaagccag actccagcat cagcagtcag gagcactaag  5820
cccttgccaa catcctgttt ctcagagaaa ctgcttccat tataatggtt gtcctttttt  5880
aagctatcaa gccaaacaac cagtgtctac cattattctc atcacctgaa gccaagggtt  5940
ctagcaaaag tcaagctgtc ttgtaatggt tgatgtgcct ccagcttctg tcttcagtca  6000
ctccactctt agcctgctct gaatcaactc tgaccacagt tccctggagc ccctgccacc  6060
tgctgcccct gccaccttct ccatctgcag tgctgtgcag ccttctgcac tcttgcagag  6120
ctaataggtg gagacttgaa ggaagaggag gaaagtttct cataatagcc ttgctgcaag  6180
ctcaaatggg aggtgggcac tgtgcccagg agccttggag caaaggctgt gcccaacctc  6240
tgactgcatc caggtttggt cttgacagag ataagaagcc ctggcttttg gagccaaaat  6300
ctaggtcaga cttaggcagg attctcaaag tttatcagca gaacatgagg cagaagaccc  6360
tttctgctcc agcttcttca ggctcaacct tcatcagaat agatagaaag agaggctgtg  6420
agggttctta aaacagaagc aaatctgact cagagaataa acaacctcct agtaaactac  6480
```

```
agcttagaca gagcatctgg tggtgagtgt gctcagtgtc ctactcaact gtctggtatc  6540
agccctcatg aggacttctc ttctttccct catagacctc catctctgtt ttccttagcc  6600
tgcagaaatc tggatggcta ttcacagaat gcctgtgctt tcagagttgc attttttctc  6660
tggtattctg gttcaagcat ttgaaggtag gaaaggttct ccaagtgcaa gaaagccagc  6720
cctgagcctc aactgcctgg ctagtgtggt cagtaggatg caaaggctgt tgaatgccac  6780
aaggccaaac tttaacctgt gtaccacaag cctagcagca gaggcagctc tgctcactgg  6840
aactctctgt cttctttctc ctgagccttt tcttttcctg agttttctag ctctcctcaa  6900
ccttacctct gccctaccca ggacaaaccc aagagccact gtttctgtga tgtcctctcc  6960
agccctaatt aggcatcatg acttcagcct gaccttccat gctcagaagc agtgctaatc  7020
cacttcagat gagctgctct atgcaacaca ggcagagcct acaaaccttt gcaccagagc  7080
cctccacata tcagtgtttg ttcatactca cttcaacagc aaatgtgact gctgagatta  7140
agattttaca caagatggtc tgtaatttca cagttagttt tatcccatta ggtatgaaag  7200
aattagcata attcccctta aacatgaatg aatcttagat tttttaataa atagttttgg  7260
aagtaaagac agagacatca ggagcacaag gaatagcctg agaggacaaa cagaacaaga  7320
aagagtctgg aaatacacag gatgttcttg gcctcctcaa agcaagtgca agcagatagt  7380
accagcagcc ccaggctatc agagcccagt gaagagaagt accatgaaag ccacagctct  7440
aaccaccctg ttccagagtg acagacagtc cccaagacaa gccagcctga gccagagaga  7500
gaactgcaag agaaagtttc taatttaggt tctgttagat tcagacaagt gcaggtcatc  7560
ctctctccac agctactcac ctctccagcc taacaaagcc tgcagtccac actccaaccc  7620
tggtgtctca cctcctagcc tctcccaaca tcctgctctc tgaccatctt ctgcatctct  7680
catctcacca tctcccactg tctacagcct actcttgcaa ctaccatctc atttctgac  7740
atcctgtcta catcttctgc catactctgc catctaccat accacctctt accatctacc  7800
acaccatctt ttatctccat ccctctcaga agcctccaag ctgaatcctg ctttatgtgt  7860
tcatctcagc ccctgcatgg aaagctgacc ccagaggcag aactattccc agagagcttg  7920
gccaagaaaa acaaaactac cagcctggcc aggctcagga gtagtaagct gcagtgtctg  7980
ttgtgttcta gcttcaacag ctgcaggagt tccactctca aatgctccac atttctcaca  8040
tcctcctgat tctggtcact acccatcttc aaagaacaga atatctcaca tcagcatact  8100
gtgaaggact agtcatgggt gcagctgctc agagctgcaa agtcattctg gatggtggag  8160
agcttacaaa catttcatga tgctccccc gctctgatgg ctggagccca atccctacac  8220
agactcctgc tgtatgtgtt ttcctttcac tctgagccac agccagaggg caggcattca  8280
gtctcctctt caggctgggg ctggggcact gagaactcac ccaacacctt gctctcactc  8340
cttctgcaaa acaagaaaga gctttgtgct gcagtagcca tgaagaatga aaggaaggct  8400
ttaactaaaa aatgtcagag attattttca accccttact gtggatcacc agcaaggagg  8460
aaacacaaca cagagacatt ttttcccctc aaattatcaa aagaatcact gcatttgtta  8520
aagagagcaa ctgaatcagg aagcagagtt ttgaacatat cagaagttag gaatctgcat  8580
cagagacaaa tgcagtcatg gttgtttgct gcataccagc cctaatcatt agaagcctca  8640
tggacttcaa acatcattcc ctctgacaag atgctctagc ctaactccat gagataaaat  8700
aaatctgcct ttcagagcca aagaagagtc caccagcttc ttctcagtgt gaacaagagc  8760
tccagtcagg ttagtcagtc cagtgcagta gaggagacca gtctgcatcc tctaattttc  8820
aaaggcaaga agatttgttt accctggaca ccaggcacaa gtgaggtcac agagctctta  8880
gatatgcagt cctcatgagt gaggagacta aagcgcatgc catcaagact tcagtgtaga  8940
gaaaacctcc aaaaaagcct cctcactact tctggaatag ctcagaggcc gaggcggcct  9000
cggcctctgc ataaataaaa aaaattagtc agccatgggg cggagaatgg gcggaactgg  9060
gcggagttag gggcgggatg ggcggagtta ggggcgggac tatggttgct gactaattga  9120
gatgcatgct ttgcatactt ctgcctgctg gggagcctgg ggactttcca cacctggttg  9180
ctgactaatt gagatgcatg ctttgcatac ttctgcctgc tggggagcct ggggactttc  9240
cacaccctaa ctgacacaca ttccacagct gcattaatga atcggccaac gcgcggggag  9300
aggcggtttg cgtattgggc gctcttccgc ttcctcgctc actgactcgc tgcgctcggt  9360
cgttcggctg cggcgagcgg tatcagctca ctcaaaggcg gtaatacggt tatccacaga  9420
atcaggggat aacgcaggaa agaacatgtg agcaaaaggc cagcaaaagg ccaggaaccg  9480
taaaaaggcc gcgttgctgg cgtttttcca taggctccgc ccccctgacg agcatcacaa  9540
aaatcgacgc tcaagtcaga ggtggcgaaa cccgacagga ctataaagat accaggcgtt  9600
tccccctgga agctccctcg tgcgctctcc tgttccgacc ctgccgctta ccggatacct  9660
gtccgccttt ctcccttcgg gaagcgtggc gctttctcat agctcacgct gtaggtatct  9720
cagttcggtg taggtcgttc gctccaagct gggctgtgtg cacgaacccc ccgttcagcc  9780
cgaccgctgc gccttatccg gtaactatcg tcttgagtcc aacccggtaa gacacgactt  9840
atcgccactg gcagcagcca ctggtaacag gattagcaga gcgaggtatg taggcggtgc  9900
tacagagttc ttgaagtggt ggcctaacta cggctacact agaagaacag tatttggtat  9960
ctgcgctctg ctgaagccag ttaccttcgg aaaaagagtt ggtagctctt gatccggcaa  10020
acaaaccacc gctggtagcg gtggtttttt tgtttgcaag cagcagatta cgcgcagaaa  10080
aaaaggatct caagaagatc ctttgatctt ttctacgggg tctgacgctc agtggaacga  10140
aaactcacgt taagggattt tggtcatgag attatcaaaa aggatcttca cctagatcct  10200
tttaaattaa aaatgaagtt ttaaatcaat ctaaagtata tatgagtaaa cttggtctga  10260
cagttaccaa tgcttaatca gtgaggcacc tatctcagcg atctgtctat ttcgttcatc  10320
catagttgcc tgactcctgc aaaccacgtt gtgtctcaaa atctctgatg ttacattgca  10380
caagataaaa atatatcatc atgaacaata aaactgtctg cttacataaa cagtaataca  10440
aggggtgtta tgagccatat tcaacgggaa acgtcttgct cgaggccgcg attaaattcc  10500
aacatggatg ctgatttata tgggtataaa tgggctcgcg ataatgtcgg gcaatcaggt  10560
gcgacaatct atcgattgta tgggaagccc gatgcgccag agttgtttct gaaacatggc  10620
aaaggtagcg ttgccaatga tgttacagat gagatggtca gactaaactg gctgacggaa  10680
tttatgcctc ttccgaccat caagcatttt atccgtactc ctgatgatgc atggttactc  10740
accactgcga tccccgggaa aacagcattc caggtattag aagaatatcc tgattcaggt  10800
gaaaatattg ttgatgcgct ggcagtgttc ctgcgccggt tgcattcgat tcctgtttgt  10860
aattgtcctt ttaacagcga tcgcgtattt cgtctcgctc aggcgcaatc acgaatgaat  10920
aacggtttgg ttgatgcgag tgattttgat gacgagcgta atggctggcc tgttgaacaa  10980
gtctggaaag aaatgcataa gcttttgcca ttctcaccgg attcagtcgt cactcatggt  11040
gatttctcac ttgataacct tatttttgac gaggggaaat taataggttg tattgatgtt  11100
ggacgagtcg gaatcgcaga ccgataccag gatcttgcca tcctatggaa ctgcctcggt  11160
gagttttctc cttcattaca gaaacggctt tttcaaaaat atggtattga taatcctgat  11220
```

```
atgaataaat tgcagtttca tttgatgctc gatgagtttt tctaagggcg gcctgccacc  11280
atacccacgc cgaaacaagc gctcatgagc ccgaagtggc gagcccgatc ttccccatcg  11340
gtgatgtcgg cgatataggc gccagcaacc gcacctgtgg cgccggtgat gagggcgcgc  11400
caagtcgacg tccggcagtc                                             11420

SEQ ID NO: 4            moltype = DNA  length = 11171
FEATURE                 Location/Qualifiers
misc_feature            1..11171
                        note = Synthetic polynucleotide
source                  1..11171
                        mol_type = other DNA
                        organism = synthetic construct
SEQUENCE: 4
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttctttttttg  780
tatcttttgt gtttcctaga aaacatctca gtcaccaccg cagccctagg aatgcatcta  840
gacaattgta ctaaccttct tctctttcct ctcctgacag tccggaaagc caccatgggc  900
cgctgctgct tctacaccgc cggcaccctg agcctgctgc tgctggtgac cagcgtgacc  960
ctgctggtgg cccgcgtgtt ccagaaggcc gtggaccaga gcatcgagaa gaagatcgtg  1020
ctgcgcaacg gcaccgaggc cttcgacagc tgggagaagc ccccccctgcc cgtgtacacc  1080
cagttctact tcttcaacgt gaccaacccc gaggagatcc tgcgcggcga gaccccccgc  1140
gtggaggagg tgggccccta cacctaccgc gagctgcgca acaaggccaa catccagttc  1200
ggcgacaacg gcaccaccat cagcgccgtg agcaacaagg cctacgtgtt cgagcgcgac  1260
cagagcgtgg gcgaccccaa gatcgacctg atccgcaccc tgaacatccc cgtgctgacc  1320
gtgatcgagt ggagccaggt gcacttcctg cgcgagatca tcgaggccat gctgaaggcc  1380
taccagcaga agctgttcgt gacccacacc gtggacgagc tgctgtgggg ctacaaggac  1440
gagatcctga gcctgatcca cgtgttccgc cccgacatca gcccctactt cggcctgttc  1500
tacgagaaga acggcaccaa cgacggcgac tacgtgttcc tgaccggcga ggacagctac  1560
ctgaacttca ccaagatcgt ggagtggaac ggcaagacca gcctggactg gtggatcacc  1620
gacaagtgca acatgatcaa cggcaccgac ggcgacagct tccacccccct gatcaccaag  1680
gacgaggtgc tgtacgtgtt ccccagcgac ttctgccgca gcgtgtacat caccttcagc  1740
gactacgaga gcgtgcaggg cctgcccgcc ttccgctaca aggtgcccgc cgagatcctg  1800
gccaacacca gcgacaacgc cggcttctgc atccccgagg gcaactgcct gggcagcggc  1860
gtgctgaacg tgagcatctg caagaacggc gcccccatca tcatgagctt cccccacttc  1920
taccaggccg acgagcgctt cgtgagcgcc atcgagggca tgcaccccaa ccaggaggac  1980
cacgagacct tcgtggacat caacccccctg accggcatca tcctgaaggc cgccaagcgc  2040
ttccagatca acatctacgt gaagaagctg gacgacttcg tggagaccgg cgacatccgc  2100
accatggtgt tccccgtgat gtacctgaac gagagcgtgc acatcgacaa ggagaccgcc  2160
agccgcctga agagcatgat caacaccacc ctgatcatca ccaacatccc ctacatcatc  2220
atggccctgg gcgtgttctt cggcctggtg ttcacctggc tggcctgcaa gggccagggc  2280
agcatggacg agggcaccgc cgacgagcgc gcccccctga tccgcaccga gggcagagga  2340
agtcttctga catgcggaga cgtggaagag aatcccggcc ctatggaatt cagcagcccc  2400
agcagagagg aatgccccaa gcctctgagc cgggtgtcaa tcatggccgg atctctgaca  2460
ggactgctgc tgcttcaggc cgtgtcttgg gcttctggcg ctagaccttg catccccaag  2520
agcttcggct acagcagcgt cgtgtgcgtg tgcaatgcca cctactgcga cagcttcgac  2580
cctcctacct ttcctgctct gggcaccttc agcagatacg agagcaccag atccggcaga  2640
cggatggaac tgagcatggg acccatccag gccaatcaca caggcactgg cctgctgctg  2700
acactgcagc ctgagcagaa attccagaaa gtgaaaggct tcggcggagc catgacagat  2760
gccgccgctc tgaatatcct ggctctgtct ccaccagctc agaacctgct gctcaagagc  2820
tacttcagcg aggaaggcat cggctacaac atcatcagag tgcccatggc cagctgcgac  2880
ttcagcatca ggacctacac ctacgccgac acacccgacg atttccagct gcacaacttc  2940
agcctgcctg aagaggacac caagctgaag atccctctga tccacagagc cctgcagctg  3000
gcacaaagac ccgtgtcact gctggcctct ccatggacat ctcccacctg gctgaaaaca  3060
aatggcgccg tgaatggcaa gggcagcctg aaaggccaac ctggcgacat ctaccaccag  3120
acctgggcca gatacttcgt gaagttcctg gacgcctatg ccgagcacaa gctgcagttt  3180
tgggccgtga cagccgagaa cgaaccttct gctggactgc tgagcggcta cccctttcag  3240
tgcctgggct ttacacccga gcaccagcgg gactttatcg cccgtgatct gggacccaca  3300
ctggccaata gcacccacca taatgtgcgg ctgctgatgc tggacgacca gagactgctt  3360
ctgccccact gggctaaagt ggtgctgaca gatcctgagg ccgccaaata cgtgcacgga  3420
atcgccgtgc actggtatct ggactttctg gcccctgcca aggccacact gggagagaca  3480
cacagactgt tccccaacac catgctgttc gccagcgaag cctgtgtggg cagcaagttt  3540
tgggaacaga gcgtgcggct cggcagctgg gatagaggca tgcagtacag ccacagcatc  3600
atcaccaacc tgctgtacca cgtcgtcggc tggaccgact ggaatctggc cctgaatcct  3660
gaaggcggcc ctaactgggt ccgaaacttc gtggacagcc ccatcatcgt ggacatcacc  3720
aaggacacct tctacaagca gcccatgttc taccacctgg gacacttcag caagttcatc  3780
cccgagggct ctcagcgcgt tggactggtg gcttcccaga agaacgatct ggacgccgtg  3840
gctctgatgc accctgatgg atctgctgtg gtggtggtcc tgaaccgcag cagcaaagat  3900
gtgcccctga ccatcaagga tcccgccgtg ggattcctgg aaacaatcag ccctggctac  3960
```

```
tccatccaca cctacctgtg gcgtagacag tgacaattgt taattaagtt taaaccctcg  4020
aggccgcaag ccgcatcgat accgtcgact agagctcgct gatcagcctc gactgtgcct  4080
tctagttgcc agccatctgt tgtttgcccc tcccccgtgc cttccttgac cctggaaggt  4140
gccactccca ctgtcctttc ctaataaaat gaggaaattg catcgcattg tctgagtagg  4200
tgtcattcta ttctgggggg tggggtgggg caggacagca agggggagga ttgggaagac  4260
aatagcaggc atgctgggga gagatccacg ataacaaaca gctttttgg ggtgaacata  4320
ttgactgaat tccctgcagg ttggccactc cctctctgcg cgctcgctcg ctcactgagg  4380
ccgcccgggc aaagcccggg cgtcgggcga cctttggtcg cccggcctca gtgagcgagc  4440
gagcgcgcag agagggagtg gccaactcca tcactagggg ttcctgcggc cgctcgtacg  4500
gtctcgagga attcctgcag gataacttgc caacctcatt ctaaaatgta tatagaagcc  4560
caaaagacaa taacaaaaat attcttgtag aacaaaatgg gaaagaatgt tccactaaat  4620
atcaagattt agagcaaagc atgagatgtg tggggataga cagtgaggct gataaaatag  4680
agtagagctc agaaacagac ccattgatat atgtaagtga cctatgaaaa aaatatggca  4740
ttttacaatg ggaaaatgat ggtctttttc tttttagaa aaacagggaa atatatttat  4800
atgtaaaaaa taaaagggaa cccatatgtc ataccataca cacaaaaaaa ttccagtgaa  4860
ttataagtct aaatggagaa ggcaaaactt taaatctttt agaaaataat atagaagcat  4920
gcagaccagc ctggccaaca tgatgaaacc ctctctacta ataataaaat cagtagaact  4980
actcaggact actttgagtg ggaagtcctt ttctatgaag acttctttgg ccaaaattag  5040
gctctaaatg caaggagata gtgcatcatg cctggctgca cttactgata aatgatgtta  5100
tcaccatctt taaccaaatg cacaggaaca agttatggta ctgatgtgct ggattgagaa  5160
ggagctctac ttccttgaca ggacacattt gtatcaactt aaaaaagcag atttttgcca  5220
gcagaactat tcattcagag gtaggaaact tagaatagat gatgtcactg attagcatgg  5280
cttccccatc tccacagctg cttcccaccc aggttgccca cagttgagtt tgtccagtgc  5340
tcagggctgc ccactctcag taagaagccc cacaccagcc cctctccaaa tatgttggct  5400
gttccttcca ttaaagtgac cccactttag agcagcaagt ggatttctgt ttcttacagt  5460
tcaggaagga ggagtcagct gtgagaacct ggagcctgag atgcttctaa gtcccactgc  5520
tactggggtc agggaagcca gactccagca tcagcagtca ggagcactaa gcccttgcca  5580
acatcctgtt tctcagagaa actgcttcca ttataatggt tgtccttttt taagctatca  5640
agccaaacaa ccagtgtcta ccattattct catcacctga agccaagggt tctagcaaaa  5700
gtcaagctgt cttgtaatgg ttgatgtgcc tccagcttct gtcttcagtc actccactct  5760
tagcctgctc tgaatcaact ctgaccacag ttccctggag cccctgccac ctgctgcccc  5820
tgccaccttc tccatctgca gtgctgtgca gccttctgca ctcttgcaga gctaataggt  5880
ggagacttga aggaagagga ggaaagtttc tcataatagc cttgctgcaa gctcaaatgg  5940
gaggtgggca ctgtgcccag gagccttgga gcaaaggctg tgcccaacct ctgactgcat  6000
ccaggtttgg tcttgacaga gataagaagc cctggctttt ggagccaaaa tctaggtcag  6060
acttaggcag gattctcaaa gtttatcagc agaacatgag gcagaagacc ctttctgctc  6120
cagcttcttc aggctcaacc ttcatcagaa tagatagaaa gagaggctgt gagggttctt  6180
aaaacagaag caaatctgac tcagagaata aacaacctcc tagtaaacta cagcttagac  6240
agagcatctg gtggtgagtg tgctcagtgt cctactcaac tgtctggtat cagccctcat  6300
gaggacttct cttctttccc tcatagacct ccatctctgt tttccttagc ctgcagaaat  6360
ctggatggct attcacagaa tgcctgtgct ttcagagttg catttttttct ctggtattct  6420
ggttcaagca tttgaaggta ggaaaggttc tccaagtgca agaaagccag ccctgagcct  6480
caactgcctg gctagtgtgg tcagtaggat gcaaaggctg ttgaatgcca caaggccaaa  6540
ctttaacctg tgtaccacaa gcctagcagc agaggcagct ctgctcactg gaactctctg  6600
tcttctttct cctgagcctt ttcttttcct gagttttcta gctctcctca accttacctc  6660
tgccctaccc aggacaaacc caagagccac tgtttctgtg atgtcctctc cagccctaat  6720
taggcatcat gacttcagcc tgaccttcca tgctcagaag cagtgctaat ccacttcaga  6780
tgagctgctc tatgcaacac aggcagagcc tacaaacctt tgcaccagag ccctccacat  6840
atcagtgttt gttcatactc acttcaacag caaatgtgac tgctgagatt aagattttac  6900
acaagatggt ctgtaatttc acagttagtt ttatcccatt aggtatgaaa gaattagcat  6960
aattcccctt aaacatgaat gaatcttaga ttttttaata aatagttttg gaagtaaaga  7020
cagagacatc aggagcacaa ggaatagcct gagaggacaa acagaacaag aaagagtctg  7080
gaaatacaca ggatgttctt ggcctcctca aagcaagtgc aagcagatag taccagcagc  7140
cccaggctat cagagcccag tgaagagaag taccatgaaa gccacagctc taaccaccct  7200
gttccagagt gacagacagt ccccaagaca agccagcctg agccagagag agaactgcaa  7260
gagaaagttt ctaatttagg ttctgttaga ttcagacaag tgcaggtcat cctctctcca  7320
cagctactca cctctccagc ctaacaaagc ctgcagtcca cactccaacc ctggtgtctc  7380
acctcctagc ctctcccaac atcctgctct ctgaccatct tctgcatctc tcatctcacc  7440
atctcccact gtctacagcc tactcttgca actaccatct catttctga catcctgtct  7500
acatcttctg ccatactctg ccatctacca taccacctct taccatctac cacaccatct  7560
tttatctcca tccctctcag aagcctccaa gctgaatcct gctttatgtg ttcatctcag  7620
cccctgcatg gaaagctgac cccagaggca gaactattcc cagagagctt ggccaagaaa  7680
aacaaaacta ccagcctggc caggctcagg agtagtaagc tgcagtgtct gttgtgttct  7740
agcttcaaca gctgcaggag ttccactctc aaatgctcca catttctcac atcctcctga  7800
ttctggtcac tacccatctt caaagaacag aatatctcac atcagcatac tgtgaaggac  7860
tagtcatggg tgcagctgct cagagctgca aagtcattct ggatggtgga gagcttacaa  7920
acatttcatg atgctccccc cgctctgatg gctggagccc aatccctaca cagactcctg  7980
ctgtatgtgt tttcctttca ctctgagcca cagccagagg gcaggcattc agtctcctct  8040
tcaggctggg gctggggcac tgagaactca cccaacacct tgctctcact ccttctgcaa  8100
aacaagaaag agctttgtgc tgcagtagcc atgaagaatg aaaggaaggc tttaactaaa  8160
aaatgtcaga gattattttc aacccettac tgtggatcac cagcaaggag gaaacacaac  8220
acagagacat tttttcccct caaattatca aaagaatcac tgcatttgtt aaagagagca  8280
actgaatcag gaagcagagt tttgaacata tcagaagtta ggaatctgca tcagagacaa  8340
atgcagtcat ggttgtttgc tgcataccag ccctaatcat tagaagcctc atggacttca  8400
aacatcattc cctctgacaa gatgctctag cctaactcca tgagataaaa taaatctgcc  8460
tttcagagcc aaagaagagt ccaccagctt cttctcagtg tgaacaagag ctccagtcag  8520
gttagtcagt ccagtgcagt agaggagacc agtctgcatc ctctaatttt caaaggcaag  8580
aagatttgtt taccctggac accaggcaca agtgaggtca cagagctctt agatatgcag  8640
tcctcatgag tgaggagact aaagcgcatg ccatcaagac ttcagtgtag agaaaacctc  8700
```

```
caaaaaagcc tcctcactac ttctggaata gctcagaggc cgaggcggcc tcggcctctg  8760
cataaataaa aaaaattagt cagccatggg gcggagaatg ggcggaactg ggcggagtta  8820
ggggcgggat gggcggagtt aggggcggga ctatggttgc tgactaattg agatgcatgc  8880
tttgcatact tctgcctgct ggggagcctg gggactttcc acacctggtt gctgactaat  8940
tgagatgcat gctttgcata cttctgcctg ctggggagcc tggggacttt ccacacccta  9000
actgacacac attccacagc tgcattaatg aatcggccaa cgcgcgggga gaggcggttt  9060
gcgtattggg cgctcttccg cttcctcgct cactgactcg ctgcgctcgg tcgttcggct  9120
gcggcgagcg gtatcagctc actcaaaggc ggtaatacgg ttatccacag aatcagggga  9180
taacgcagga aagaacatgt gagcaaaagg ccagcaaaag gccaggaacc gtaaaaaggc  9240
cgcgttgctg gcgtttttcc ataggctccg cccccctgac gagcatcaca aaaatcgacg  9300
ctcaagtcag aggtggcgaa acccgacagg actataaaga taccaggcgt ttccccctgg  9360
aagctccctc gtgcgctctc ctgttccgac cctgccgctt accggatacc tgtccgcctt  9420
tctcccttcg ggaagcgtgg cgctttctca tagctcacgc tgtaggtatc tcagttcggt  9480
gtaggtcgtt cgctccaagc tgggctgtgt gcacgaaccc cccgttcagc ccgaccgctg  9540
cgccttatcc ggtaactatc gtcttgagtc caacccggta agacacgact tatcgccact  9600
ggcagcagcc actggtaaca ggattagcag agcgaggtat gtaggcggtg ctacagagtt  9660
cttgaagtgg tggcctaact acggctacac tagaagaaca gtatttggta tctgcgctct  9720
gctgaagcca gttaccttcg gaaaaagagt tggtagctct tgatccggca aacaaaccac  9780
cgctggtagc ggtggttttt ttgtttgcaa gcagcagatt acgcgcagaa aaaaaggatc  9840
tcaagaagat cctttgatct tttctacggg gtctgacgct cagtggaacg aaaactcacg  9900
ttaagggatt ttggtcatga gattatcaaa aaggatcttc acctagatcc ttttaaatta  9960
aaaatgaagt tttaaatcaa tctaaagtat atatgagtaa acttggtctg acagttacca  10020
atgcttaatc agtgaggcac ctatctcagc gatctgtcta tttcgttcat ccatagttgc  10080
ctgactcctg caaaccacgt tgtgtctcaa aatctctgat gttacattgc acaagataaa  10140
aatatatcat catgaacaat aaaactgtct gcttacataa acagtaatac aaggggtgtt  10200
atgagccata ttcaacggga aacgtcttgc tcgaggccgc gattaaattc caacatggat  10260
gctgatttat atgggtataa atgggctcgc gataatgtcg ggcaatcagg tgcgacaatc  10320
tatcgattgt atgggaagcc cgatgcgcca gagttgtttc tgaaacatgg caaaggtagc  10380
gttgccaatg atgttacaga tgagatggtc agactaaact ggctgacgga atttatgcct  10440
cttccgacca tcaagcattt tatccgtact cctgatgatg catggttact caccactgcg  10500
atccccggga aaacagcatt ccaggtatta gaagaatatc ctgattcagg tgaaaatatt  10560
gttgatgcgc tggcagtgtt cctgcgccgg ttgcattcga ttcctgtttg taattgtcct  10620
tttaacagcg atcgcgtatt tcgtctcgct caggcgcaat cacgaatgaa taacggtttg  10680
gttgatgcga gtgattttga tgacgagcgt aatggctggc ctgttgaaca agtctggaaa  10740
gaaatgcata agcttttgcc attctcaccg gattcagtcg tcactcatgg tgatttctca  10800
cttgataacc ttatttttga cgaggggaaa ttaataggtt gtattgatgt tggacgagtc  10860
ggaatcgcag accgatacca ggatcttgcc atcctatgga actgcctcgg tgagttttct  10920
ccttcattac agaaacggct ttttcaaaaa tatggtattg ataatcctga tatgaataaa  10980
ttgcagtttc atttgatgct cgatgagttt ttctaagggc ggcctgccac catacccacg  11040
ccgaaacaag cgctcatgag cccgaagtgg cgagcccgat cttccccatc ggtgatgtcg  11100
gcgatatagg cgccagcaac cgcacctgtg gcgccggtga tgagggcgcg ccaagtcgac  11160
gtccggcagt c                                                        11171
```

```
SEQ ID NO: 5           moltype = DNA  length = 11309
FEATURE                Location/Qualifiers
misc_feature           1..11309
                       note = Synthetic polynucleotide
source                 1..11309
                       mol_type = other DNA
                       organism = synthetic construct
SEQUENCE: 5
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gagggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agccccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatgtac  900
gccctgttcc tgctggccag cctgctgggc gccgccctgg ccggccccgt gctgggcctg  960
aaggagtgca cccgcggcag cgccgtgtgg tgccagaacg tgaagaccgc cagcgactgc  1020
ggcgccgtga agcactgcct gcagaccgtg tggaacaagc ccaccgtgaa gagcctgccc  1080
tgcgacatct gcaaggacgt ggtgaccgcc gccggcgaca tgctgaagga caacgccacc  1140
gaggaggaga tcctggtgta cctggagaag acctgcgact ggctgcccaa gcccaacatg  1200
agcgccagct gcaaggagat cgtggacagc tacctgcccg tgatcctgga catcatcaag  1260
ggcgagatga gccgccccgg cgaggtgtgc agcgccctga acctgtgcga gagcctgcag  1320
aagcacctgg ccgagctgaa ccaccagaag cagctggaga gcaacaagat ccccgagctg  1380
gacatgaccg aggtggtggc cccctttcatg gccaacatcc ccctgctgct gtacccccag  1440
gacggccccc gcagcaagcc ccagcccaag gacaacggcg acgtgtgcca ggactgcatc  1500
cagatggtga ccgacatcca gaccgccgtg cgcaccaaca gcaccttcgt gcaggccctg  1560
gtggagcacg tgaaggagga gtgcgaccgc ctgggccccg gcatggccga catctgcaag  1620
aactacatca gccagtacag cgagatcgcc atccagatga tgatgcacat gcagcccaag  1680
```

```
gagatctgcg ccctggtggg cttctgcgac gaggtgaagg agatgcccat gcagaccctg  1740
gtgcccgcca aggtggccag caagaacgtg atccccgccc tggagctggt ggagcccatc  1800
aagaagcacg aggtgcccgc caagagcgac gtgtactgcg aggtgtgcga gttcctggtg  1860
aaggaggtga ccaagctgat cgacaacaac aagaccgaga aggagatcct ggacgccttc  1920
gacaagatgt gcagcaagct gcccaagagc ctgagcgagg agtgccagga ggtggtggac  1980
acctacggca gcagcatcct gagcatcctg ctggaggagg tgagccccga gctggtgtgc  2040
agcatgctgc acctgtgcag cggcacccgc ctgcccgccc tgaccgtgca cgtgacccag  2100
cccaaggacg gcggcttctg cgaggtgtgc aagaagctgg tgggctacct ggaccgcaac  2160
ctggagaaga acagcaccaa gcaggagatc ctggccgccc tggagaaggg ctgcagcttc  2220
ctgcccgacc cctaccagaa gcagtgcgac cagttcgtgg ccgagtacga gcccgtgctg  2280
atcgagatcc tggtggaggt gatggacccc agcttcgtgt gcctgaagat cggcgcctgc  2340
cccagcgccc acaagcccct gctgggcacc gagaagtgca tctggggccc cagctactgg  2400
tgccagaaca ccgagaccgc cgcccagtgc aacgccgtgg agcactgcaa gcgccacgtg  2460
tggaacgagg gcagaggaag tcttctgaca tgcggagacg tggaagagaa tcccggccct  2520
atggaattca gcagccccag cagagaggaa tgccccaagc ctctgagccg ggtgtcaatc  2580
atggccggat ctctgacagg actgctgctg cttcaggccg tgtcttgggc ttctggcgct  2640
agaccttgca tccccaagag cttcggctac agcagcgtcg tgtgcgtgtg caatgccacc  2700
tactgcgaca gcttcgaccc tcctaccttt cctgctctgg gcaccttcag cagatacgag  2760
agcaccagat ccggcagacg gatggaactg agcatgggac ccatccaggc caatcacaca  2820
ggcactggcc tgctgctgac actgcagcct gagcagaaat tccagaaagt gaaaggcttc  2880
ggcggagcca tgacagatgc cgccgctctg aatatcctgg ctctgtctcc accagctcag  2940
aacctgctgc tcaagagcta cttcagcgag gaaggcatcg gctacaacat catcagagtg  3000
cccatggcca gctgcgactt cagcatcagg acctacacct acgccgacac acccgacgat  3060
ttccagctgc acaacttcag cctgcctgaa gaggacacca agctgaagat ccctctgatc  3120
cacagagccc tgcagctggc acaaagaccc gtgtcactgc tggcctctcc atggacatct  3180
cccacctggc tgaaaacaaa tggcgccgtg aatggcaagg gcagcctgaa aggccaacct  3240
ggcgacatct accaccagac ctgggccaga tacttcgtga agttcctgga cgcctatgcc  3300
gagcacaagc tgcagttttg ggccgtgaca gccgagaacg aaccttctgc tggactgctg  3360
agcggctacc cctttcagtg cctgggcttt acacccgagc accagcggga ctttatcgcc  3420
cgtgatctgg gacccacact ggccaatagc acccaccata atgtgcggct gctgatgctg  3480
gacgaccaga gactgcttct gccccactgg gctaaagtgg tgctgacaga tcctgaggcc  3540
gccaaatacg tgcacggaat cgccgtgcac tggtatctgg actttctggc ccctgccaag  3600
gccacactgg gagagacaca cagactgttc cccaacacca tgctgttcgc cagcgaagcc  3660
tgtgtgggca gcaagttttg ggaacagagc gtgcggctcg gcagctggga tagaggcatg  3720
cagtacagcc acagcatcat caccaacctg ctgtaccacg tcgtcggctg gaccgactgg  3780
aatctggccc tgaatcctga aggcggccct aactgggtcc gaaacttcgt ggacagcccc  3840
atcatcgtgg acatcaccaa ggacaccttc tacaagcagc ccatgttcta ccacctggga  3900
cacttcagca agttcatccc cgagggctct cagcgcgttg gactggtggc ttcccagaag  3960
aacgatctgg acgccgtggc tctgatgcac cctgatggat ctgctgtggt ggtggtcctg  4020
aaccgcagca gcaaagatgt gcccctgacc atcaaggatc ccgccgtggg attcctggaa  4080
acaatcagcc ctggctactc catccacacc tacctgtggc gtagacagtg acaattgtta  4140
attaagttta aaccctcgag gccgcaagcc gcatcgatac cgtcgactag agctcgctga  4200
tcagcctcga ctgtgccttc tagttgccag ccatctgttg tttgcccctc ccccgtgcct  4260
tccttgaccc tggaaggtgc cactcccact gtcctttcct aataaaatga ggaaattgca  4320
tcgcattgtc tgagtaggtg tcattctatt ctggggggtg gggtggggca ggacagcaag  4380
ggggaggatt gggaagacaa tagcaggcat gctggggaga gatccacgat aacaaacagc  4440
tttttggggg tgaacatatt gactgaattc cctgcaggtt ggccactccc tctctgcgcg  4500
ctcgctcgct cactgaggcc gcccgggcaa agcccgggcg tcgggcgacc tttggtcgcc  4560
cggcctcagt gagcgagcga gcgcgcagag agggagtggc caactccatc actaggggtt  4620
cctgcggccg ctcgtacggt ctcgaggaat tcctgcagga taacttgcca acctcattct  4680
aaaatgtata tagaagccca aaagacaata acaaaaatat tcttgtagaa caaaatggga  4740
aagaatgttc cactaaatat caagatttag agcaaagcat gagatgtgtg gggatagaca  4800
gtgaggctga taaaatagag tagagctcag aaacagaccc attgatatat gtaagtgacc  4860
tatgaaaaaa atatggcatt ttacaatggg aaaatgatgg tctttttctt ttttagaaaa  4920
acagggaaat atatttatat gtaaaaaata aaagggaacc catatgtcat accatacaca  4980
caaaaaaatt ccagtgaatt ataagtctaa atggagaagg caaaacttta aatcttttag  5040
aaaataatat agaagcatgc agaccagcct ggccaacatg atgaaaccct ctctactaat  5100
aataaaatca gtagaactac tcaggactac tttgagtggg aagtcctttt ctatgaagac  5160
ttctttggcc aaaattaggc tctaaatgca aggagatagt gcatcatgcc tggctgcact  5220
tactgataaa tgatgttatc accatcttta accaaatgca caggaacaag ttatggtact  5280
gatgtgctgg attgagaagg agctctactt ccttgacagg acacatttgt atcaacttaa  5340
aaaagcagat ttttgccagc agaactattc attcagaggt aggaaactta gaatagatga  5400
tgtcactgat tagcatggct tccccatctc cacagctgct tcccacccag gttgcccaca  5460
gttgagtttg tccagtgctc agggctgccc actctcagta agaagcccca caccagcccc  5520
tctccaaata tgttggctgt tccttccatt aaagtgaccc cactttagag cagcaagtgg  5580
atttctgttt cttacagttc aggaaggagg agtcagctgt gagaacctgg agcctgagat  5640
gcttctaagt cccactgcta ctggggtcag ggaagccaga ctccagcatc agcagtcagg  5700
agcactaagc ccttgccaac atcctgtttc tcagagaaac tgcttccatt ataatggttg  5760
tcctttttta agctatcaag ccaaacaacc agtgtctacc attattctca tcacctgaag  5820
ccaagggttc tagcaaaagt caagctgtct tgtaatggtt gatgtgcctc cagcttctgt  5880
cttcagtcac tccactctta gcctgctctg aatcaactct gaccacagtt ccctggagcc  5940
cctgccacct gctgcccctg ccaccttctc catctgcagt gctgtgcagc cttctgcact  6000
cttgcagagc taataggtgg agacttgaag gaagaggagg aaagtttctc ataatagcct  6060
tgctgcaagc tcaaatggga ggtgggcact gtgcccagga gccttggagc aaaggctgtg  6120
cccaacctct gactgcatcc aggtttggtc ttgacagaga taagaagccc tggcttttgg  6180
agccaaaatc taggtcagac ttaggcagga ttctcaaagt ttatcagcag aacatgaggc  6240
agaagaccct ttctgctcca gcttcttcag gctcaacctt catcagaata gatagaaaga  6300
gaggctgtga gggttcttaa aacagaagca aatctgactc agagaataaa caacctccta  6360
gtaaactaca gcttagacag agcatctggt ggtgagtgtg ctcagtgtcc tactcaactg  6420
```

-continued

```
tctggtatca gccctcatga ggacttctct tctttccctc atagacctcc atctctgttt  6480
tccttagcct gcagaaatct ggatggctat tcacagaatg cctgtgcttt cagagttgca  6540
ttttttctct ggtattctgg ttcaagcatt tgaaggtagg aaaggttctc caagtgcaag  6600
aaagccagcc ctgagcctca actgcctggc tagtgtggtc agtaggatgc aaaggctgtt  6660
gaatgccaca aggccaaact ttaacctgtg taccacaagc ctagcagcag aggcagctct  6720
gctcactgga actctctgtc ttctttctcc tgagcctttt cttttcctga gttttctagc  6780
tctcctcaac cttacctctg ccctacccag gacaaaccca agagccactg tttctgtgat  6840
gtcctctcca gccctaatta ggcatcatga cttcagcctg accttccatg ctcagaagca  6900
gtgctaatcc acttcagatg agctgctcta tgcaacacag gcagagccta caaacctttg  6960
caccagagcc ctccacatat cagtgtttgt tcatactcac ttcaacagca aatgtgactg  7020
ctgagattaa gattttacac aagatggtct gtaatttcac agttagtttt atcccattag  7080
gtatgaaaga attagcataa ttcccettaa acatgaatga atcttagatt ttttaataaa  7140
tagttttgga agtaaagaca gagacatcag gagcacaagg aatagcctga gaggacaaac  7200
agaacaagaa agagtctgga aatacacagg atgttcttgg cctcctcaaa gcaagtgcaa  7260
gcagatagta ccagcagccc caggctatca gagcccagtg aagagaagta ccatgaaagc  7320
cacagctcta accaccctgt tccagagtga cagacagtcc ccaagacaag ccagcctgag  7380
ccagagagag aactgcaaga gaaagtttct aatttaggtt ctgttagatt cagacaagtg  7440
caggtcatcc tctctccaca gctactcacc tctccagcct aacaaagcct gcagtccaca  7500
ctccaaccct ggtgtctcac ctcctagcct ctcccaacat cctgctctct gaccatcttc  7560
tgcatctctc atctcaccat ctcccactgt ctacagccta ctcttgcaac taccatctca  7620
ttttctgaca tcctgtctac atcttctgcc atactctgcc atctaccata ccacctctta  7680
ccatctacca caccatcttt tatctccatc cctctcagaa gcctccaagc tgaatcctgc  7740
tttatgtgtt catctcagcc cctgcatgga aagctgaccc cagaggcaga actattccca  7800
gagagcttgg ccaagaaaaa caaaactacc agcctggcca ggctcaggag tagtaagctg  7860
cagtgtctgt tgtgttctag cttcaacagc tgcaggagtt ccactctcaa atgctcccaca  7920
tttctcacat cctcctgatt ctggtcacta cccatcttca aagaacagaa tatctcacat  7980
cagcatactg tgaaggacta gtcatgggtg cagctgctca gagctgcaaa gtcattctgg  8040
atggtggaga gcttacaaac atttcatgat gctccccccg ctctgatggc tggagcccaa  8100
tccctacaca gactcctgct gtatgtgttt tcctttcact ctgagccaca gccagagggc  8160
aggcattcag tctcctcttc aggctggggc tggggcactg agaactcacc caacaccttg  8220
ctctcactcc ttctgcaaaa caagaaagag ctttgtgctg cagtagccat gaagaatgaa  8280
aggaaggctt taactaaaaa atgtcagaga ttattttcaa cccccttactg tggatcacca  8340
gcaaggagga aacacaacac agagacattt tttccccctca aattatcaaa agaatcactg  8400
catttgttaa agagagcaac tgaatcagga agcagagttt tgaacatatc agaagttagg  8460
aatctgcatc agagacaaat gcagtcatgg ttgtttgctg cataccagcc ctaatcatta  8520
gaagcctcat ggacttcaaa catcattccc tctgacaaga tgctctagcc taactccatg  8580
agataaaata aatctgcctt tcagagccaa agaagagtcc accagcttct tctcagtgtg  8640
aacaagagct ccagtcaggt tagtcagtcc agtgcagtag aggagaccag tctgcatcct  8700
ctaattttca aaggcaagaa gatttgttta ccctggacac caggcacaag tgaggtcaca  8760
gagctcttag atatgcagtc ctcatgagtg aggagactaa agcgcatgcc atcaagactt  8820
cagtgtagag aaaacctcca aaaaagcctc ctcactactt ctggaatagc tcagaggccg  8880
aggcggcctc ggcctctgca taaataaaaa aaattagtca gccatggggc ggagaatggg  8940
cggaactggg cggagttagg ggcgggatgg gcggagttag gggcgggact atggttgctg  9000
actaattgag atgcatgctt tgcatacttc tgcctgctgg ggagcctggg gactttccac  9060
acctggttgc tgactaattg agatgcatgc tttgcatact tctgcctgct ggggagcctg  9120
gggactttcc acaccctaac tgacacacat tccacagctg cattaatgaa tcggccaacg  9180
cgcggggaga ggcggtttgc gtattgggcg ctcttccgct tcctcgctca ctgactcgct  9240
gcgctcggtc gttcggctgc ggcgagcggt atcagctcac tcaaaggcgg taatacggtt  9300
atccacagaa tcaggggata acgcaggaaa gaacatgtga gcaaaaggcc agcaaaaggc  9360
caggaaccgt aaaaaggccg cgttgctggc gtttttccat aggctccgcc cccctgacga  9420
gcatcacaaa aatcgacgct caagtcagag gtggcgaaac ccgacaggac tataaagata  9480
ccaggcgttt ccccctggaa gctccctcgt gcgctctcct gttccgaccc tgccgcttac  9540
cggatacctg tccgcctttc tcccttcggg aagcgtggcg ctttctcata gctcacgctg  9600
taggtatctc agttcggtgt aggtcgttcg ctccaagctg ggctgtgtgc acgaaccccc  9660
cgttcagccc gaccgctgcg ccttatccgg taactatcgt cttgagtcca acccggtaag  9720
acacgactta tcgccactgg cagcagccac tggtaacagg attagcagag cgaggtatgt  9780
aggcggtgct acagagttct tgaagtggtg gcctaactac ggctacacta gaagaacagt  9840
atttggtatc tgcgctctgc tgaagccagt taccttcgga aaaagagttg gtagctcttg  9900
atccggcaaa caaaccaccg ctggtagcgg tggttttttt gtttgcaagc agcagattac  9960
gcgcagaaaa aaaggatctc aagaagatcc tttgatcttt tctacggggt ctgacgctca  10020
gtggaacgaa aactcacgtt aagggatttt ggtcatgaga ttatcaaaaa ggatcttcac  10080
ctagatcctt ttaaattaaa aatgaagttt taaatcaatc taaagtatat atgagtaaac  10140
ttggtctgac agttaccaat gcttaatcag tgaggcacct atctcagcga tctgtctatt  10200
tcgttcatcc atagttgcct gactcctgca aaccacgttg tgtctcaaaa tctctgatgt  10260
tacattgcac aagataaaaa tatatcatca tgaacaataa aactgtctgc ttacataaac  10320
agtaatacaa ggggtgttat gagccatatt caacgggaaa cgtcttgctc gaggccgcga  10380
ttaaattcca acatggatgc tgatttatat gggtataaat gggctcgcga taatgtcggg  10440
caatcaggtg cgacaatcta tcgattgtat gggaagcccg atgcgccaga gttgtttctg  10500
aaacatggca aaggtagcgt tgccaatgat gttacagatg agatggtcag actaaactgg  10560
ctgacggaat ttatgcctct tccgaccatc aagcatttta tccgtactcc tgatgatgca  10620
tggttactca ccactgcgat ccccgggaaa acagcattcc aggtattaga agaatatcct  10680
gattcaggtg aaaatattgt tgatgcgctg gcagtgttcc tgcgccggtt gcattcgatt  10740
cctgtttgta attgtccttt taacagcgat cgcgtatttc gtctcgctca ggcgcaatca  10800
cgaatgaata acggtttggt tgatgcgagt gattttgatg acgagcgtaa tggctggcct  10860
gttgaacaag tctggaaaga aatgcataag cttttgccat tctcaccgga ttcagtcgtc  10920
actcatggtg atttctcact tgataacctt atttttgacg aggggaaatt aataggttgt  10980
attgatgttg gacgagtcgg aatcgcagac cgataccagg atcttgccat cctatggaac  11040
tgcctcggtg agttttctcc ttcattacag aaacggcttt ttcaaaaata tggtattgat  11100
aatcctgata tgaataaatt gcagtttcat ttgatgctcg atgagttttt ctaagggcgg  11160
```

```
cctgccacca tacccacgcc gaaacaagcg ctcatgagcc cgaagtggcg agcccgatct  11220
tccccatcgg tgatgtcggc gatataggcg ccagcaaccg cacctgtggc gccggtgatg  11280
agggcgcgcc aagtcgacgt ccggcagtc                                    11309

SEQ ID NO: 6            moltype = DNA  length = 11293
FEATURE                 Location/Qualifiers
misc_feature            1..11293
                        note = Synthetic polynucleotide
source                  1..11293
                        mol_type = other DNA
                        organism = synthetic construct
SEQUENCE: 6
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catgtacgcc ctgttcctgc tggccagcct  660
gctgggcgcc gccctggccg gccccgtgct gggcctgaag gagtgcaccc gcggcagcgc  720
cgtgtggtgc cagaacgtga agaccgccag cgactgcggc gccgtgaagc actgcctgca  780
gaccgtgtgg aacaagccca ccgtgaagag cctgccctgc gacatctgca aggacgtggt  840
gaccgccgcc ggcgacatgc tgaaggacaa cgccaccgag gaggagatcc tggtgtacct  900
ggagaagacc tgcgactggc tgcccaagcc caacatgagc gccagctgca aggagatcgt  960
ggacagctac ctgcccgtga tcctggacat catcaagggc gagatgagcc gccccggcga  1020
ggtgtgcagc gccctgaacc tgtgcgagag cctgcagaag cacctggccg agctgaacca  1080
ccagaagcag ctggagagca acaagatccc cgagctggac atgaccgagg tggtggcccc  1140
cttcatggcc aacatccccc tgctgctgta cccccaggac ggcccccgca gcaagcccca  1200
gcccaaggac aacggcgacg tgtgccagga ctgcatccag atggtgaccg acatccagac  1260
cgccgtgcgc accaacagca ccttcgtgca ggccctggtg gagcacgtga aggaggagtg  1320
cgaccgcctg ggccccggca tggccgacat ctgcaagaac tacatcagcc agtacagcga  1380
gatcgccatc cagatgatga tgcacatgca gcccaaggag atctgcgccc tggtgggctt  1440
ctgcgacgag gtgaaggaga tgcccatgca gaccctggtg cccgccaagg tggccagcaa  1500
gaacgtgatc cccgccctgg agctggtgga gcccatcaag aagcacgagg tgcccgccaa  1560
gagcgacgtg tactgcgagg tgtgcgagtt cctggtgaag gaggtgacca agctgatcga  1620
caacaacaag accgagaagg agatcctgga cgccttcgac aagatgtgca gcaagctgcc  1680
caagagcctg agcgaggagt gccaggaggt ggtggacacc tacggcagca gcatcctgag  1740
catcctgctg gaggaggtga gccccgagct ggtgtgcagc atgctgcacc tgtgcagcgg  1800
cacccgcctg cccgccctga ccgtgcacgt gacccagccc aaggacggcg gcttctgcga  1860
ggtgtgcaag aagctggtgg gctacctgga ccgcaacctg gagaagaaca gcaccaagca  1920
ggagatcctg gccgccctgg agaagggctg cagcttcctg cccgacccct accagaagca  1980
gtgcgaccag ttcgtggccg agtacgagcc cgtgctgatc gagatcctgg tggaggtgat  2040
ggaccccagc ttcgtgtgcc tgaagatcgg cgcctgcccc agcgcccaca agcccctgct  2100
gggcaccgag aagtgcatct ggggccccag ctactggtgc cagaacaccg agaccgccgc  2160
ccagtgcaac gccgtggagc actgcaagcg ccacgtgtgg aactgattgt ggccgaaccg  2220
ccgaactcag aggccggccc cagaaaaccc gagcgagtag ggggcggcgc gcaggaggga  2280
ggagaactgg gggcgcggga ggctggtggg tgtgggggt ggagatgtag aagatgtgac  2340
gccgcggccc ggcgggtgcc agattagcgg acgcggtgcc cgcggttgca acgggatccc  2400
gggcgctgca gcttgggagg cggctctccc caggcggcgt ccgcggagac acccatccgt  2460
gaaccccagg tcccgggccg ccggctcgcc gcgcaccagg ggccggcgga cagaagagcg  2520
gccgagcggc tcgaggctgg gggaccgcgg gcgcggccgc gcgctgccgg gcgggaggct  2580
gggggccgg ggccggggcc gtgccccgga gcgggtcgga ggccggggcc ggggccgggg  2640
gacggcggct ccccgcgcgg ctccagcggc tcggggatcc cggccgggcc ccgcagggac  2700
catgatggaa ttcagcagcc ccagcagaga ggaatgcccc aagcctctga gccgggtgtc  2760
aatcatggcc ggatctctga caggactgct gctgcttcag gccgtgtctt gggcttctgg  2820
cgctagacct tgcatcccca agagcttcgg ctacagcagc gtcgtgtgcg tgtgcaatgc  2880
cacctactgc gacagcttcg accctcctac ctttcctgct ctgggcacct tcagcagata  2940
cgagagcacc agatccggca gacggatgga actgagcatg ggacccatcc aggccaatca  3000
cacaggcact ggcctgctgc tgacactgca gcctgagcag aaattccaga aagtgaaagg  3060
cttcggcgga gccatgacag atgccgccgc tctgaatatc ctggctctgt ctccaccagc  3120
tcagaacctg ctgctcaaga gctacttcag cgaggaaggc atcggctaca acatcatcag  3180
agtgcccatg gccagctgcg acttcagcat caggacctac acctacgccg acacacccga  3240
cgatttccag ctgcacaact tcagcctgcc tgaagaggac accaagctga agatccctct  3300
gatccacaga gccctgcagc tggcacaaag acccgtgtca ctgctggcct ctccatggac  3360
atctcccacc tggctgaaaa caaatggcgc cgtgaatggc aagggcagcc tgaaaggcca  3420
acctggcgac atctaccacc agacctgggc cagatacttc gtgaagttcc tggacgccta  3480
tgccgagcac aagctgcagt tttgggccgt gacagccgag aacgaacctt ctgctggact  3540
gctgagcggc taccccttc agtgcctggg ctttacaccc gagcaccagc gggactttat  3600
cgcccgtgat ctgggaccca cactggccaa tagcacccac cataatgtgc ggctgctgat  3660
gctggacgac cagagactgc ttctgcccca ctgggctaaa gtggtgctga cagatcctga  3720
ggccgccaaa tacgtgcacg gaatcgccgt gcactggtat ctggactttc tggcccctgc  3780
caaggccaca ctgggagaga cacacagact gttccccaac accatgctgt tcgccagcga  3840
agcctgtgtg ggcagcaagt tttgggaaca gagcgtgcgg ctcggcagct gggatagagg  3900
catgcagtac agccacagca tcatcaccaa cctgctgtac cacgtcgtcg gctggaccga  3960
ctggaatctg gccctgaatc ctgaaggcgg ccctaactgg gtccgaaact tcgtggacag  4020
```

```
ccccatcatc gtggacatca ccaaggacac cttctacaag cagcccatgt tctaccacct  4080
gggacacttc agcaagttca tccccgaggg ctctcagcgc gttggactgg tggcttccca  4140
gaagaacgat ctggacgccg tggctctgat gcaccctgat ggatctgctg tggtggtggt  4200
cctgaaccgc agcagcaaag atgtgcccct gaccatcaag gatcccgccg tgggattcct  4260
ggaaacaatc agccctggct actccatcca cacctacctg tggcgtagac agtgacaatt  4320
gttaattaag tttaaaccct cgaggccgca agcaataaaa tatctttatt ttcattacat  4380
ctgtgtgttg gttttttgtg tggagatcca cgataacaaa cagctttttt ggggtgaaca  4440
tattgactga attccctgca ggttggccac tccctctctg cgcgctcgct cgctcactga  4500
ggccgcccgg gcaaagcccg ggcgtcgggc gacctttggt cgcccggcct cagtgagcga  4560
gcgagcgcgc agagagggag tggccaactc catcactagg ggttcctgcg gccgctcgta  4620
cggtctcgag gaattcctgc aggataactt gccaacctca ttctaaaatg tatatagaag  4680
cccaaaagac aataacaaaa atattcttgt agaacaaaat gggaaagaat gttccactaa  4740
atatcaagat ttagagcaaa gcatgagatg tgtggggata gacagtgagg ctgataaaat  4800
agagtagagc tcagaaacag acccattgat atatgtaagt gacctatgaa aaaaatatgg  4860
cattttacaa tgggaaaatg atggtctttt tctttttag aaaaacaggg aaatatattt  4920
atatgtaaaa aataaaaggg aacccatatg tcataccata cacacaaaaa aattccagtg  4980
aattataagt ctaaatggag aaggcaaaac tttaaatctt ttagaaaata atatagaagc  5040
atgcagacca gcctggccaa catgatgaaa ccctctctac taataataaa atcagtagaa  5100
ctactcagga ctactttgag tgggaagtcc ttttctatga agacttcttt ggccaaaatt  5160
aggctctaaa tgcaaggaga tagtgcatca tgcctggctg cacttactga taaatgatgt  5220
tatcaccatc tttaaccaaa tgcacaggaa caagttatgg tactgatgtg ctggattgag  5280
aaggagctct acttccttga caggacacat ttgtatcaac ttaaaaaagc agatttttgc  5340
cagcagaact attcattcag aggtaggaaa cttagaatag atgatgtcac tgattagcat  5400
ggcttcccca tctccacagc tgcttcccac ccaggttgcc cacagttgag tttgtccagt  5460
gctcagggct gcccactctc agtaagaagc cccacaccag cccctctcca aatatgttgg  5520
ctgttccttc cattaaagtg accccacttt agagcagcaa gtggatttct gtttcttaca  5580
gttcaggaag gaggagtcag ctgtgagaac ctggagcctg agatgcttct aagtcccact  5640
gctactgggg tcagggaagc cagactccag catcagcagt caggagcact aagcccttgc  5700
caacatcctg tttctcagag aaactgcttc cattataatg gttgtccttt tttaagctat  5760
caagccaaac aaccagtgtc taccattatt ctcatcacct gaagccaagg gttctagcaa  5820
aagtcaagct gtcttgtaat ggttgatgtg cctccagctt ctgtcttcag tcactccact  5880
cttagcctgc tctgaatcaa ctctgaccac agttccctgg agcccctgcc acctgctgcc  5940
cctgccacct tctccatctg cagtgctgtg cagccttctg cactcttgca gagctaatag  6000
gtggagactt gaaggaagag gaggaaagtt tctcataata gccttgctgc aagctcaaat  6060
gggaggtggg cactgtgccc aggagccttg gagcaaaggc tgtgcccaac ctctgactgc  6120
atccaggttt ggtcttgaca gagataagaa gccctggctt ttggagccaa aatctaggtc  6180
agacttaggc aggattctca aagtttatca gcagaacatg aggcagaaga ccctttctgc  6240
tccagcttct tcaggctcaa ccttcatcag aatagataga aagagaggct gtgagggttc  6300
ttaaaacaga agcaaatctg actcagagaa taaacaacct cctagtaaac tacagcttag  6360
acagagcatc tggtggtgag tgtgctcagt gtcctactca actgtctggt atcagccctc  6420
atgaggactt ctcttctttc cctcatagac ctccatctct gttttcctta gcctgcagaa  6480
atctggatgg ctattcacag aatgcctgtg ctttcagagt tgcatttttt ctctggtatt  6540
ctggttcaag catttgaagg taggaaaggt tctccaagtg caagaaagcc agccctgagc  6600
ctcaactgcc tggctagtgt ggtcagtagg atgcaaaggc tgttgaatgc cacaaggcca  6660
aactttaacc tgtgtaccac aagcctagca gcagaggcag ctctgctcac tggaactctc  6720
tgtcttcttt ctcctgagcc ttttcttttc ctgagtttc tagctctcct caaccttacc  6780
tctgccctac ccaggacaaa cccaagagcc actgtttctg tgatgtcctc tccagcccta  6840
attaggcatc atgacttcag cctgaccttc catgctcaga agcagtgcta atccacttca  6900
gatgagctgc tctatgcaac acaggcagag cctacaaacc tttgcaccag agccctccac  6960
atatcagtgt ttgttcatac tcacttcaac agcaaatgtg actgctgaga ttaagatttt  7020
acacaagatg gtctgtaatt tcacagttag ttttatccca ttaggtatga aagaattagc  7080
ataattcccc ttaaacatga atgaatctta gatttttaa taaatagttt tggaagtaaa  7140
gacagagaca tcaggagcac aaggaatagc ctgagaggac aaacagaaca agaaagagtc  7200
tggaaataca caggatgttc ttggcctcct caaagcaagt gcaagcagat agtaccagca  7260
gccccaggct atcagagccc agtgaagaga agtaccatga aagccacagc tctaaccacc  7320
ctgttccaga gtgacagaca gtccccaaga caagccagcc tgagccagag agagaactgc  7380
aagagaaagt ttctaattta ggttctgtta gattcagaca agtgcaggtc atcctctctc  7440
cacagctact cacctctcca gcctaacaaa gcctgcagtc cacactccaa ccctggtgtc  7500
tcacctccta gcctctccca acatcctgct ctctgaccat cttctgcatc tctcatctca  7560
ccatctccca ctgtctacag cctactcttg caactaccat ctcattttct gacatcctgt  7620
ctacatcttc tgccatactc tgccatctac cataccacct cttaccatct accacaccat  7680
cttttatctc catccctctc agaagcctcc aagctgaatc ctgctttatg tgttcatctc  7740
agcccctgca tggaaagctg accccagagg cagaactatt cccagagagc ttggccaaga  7800
aaaacaaaac taccagcctg gccaggctca ggagtagtaa gctgcagtgt ctgttgtgtt  7860
ctagcttcaa cagctgcagg agttccactc tcaaatgctc cacatttctc acatcctcct  7920
gattctggtc actacccatc ttcaaagaac agaatatctc acatcagcat actgtgaagg  7980
actagtcatg ggtgcagctg ctcagagctg caaagtcatt ctggatggtg gagagcttac  8040
aaacatttca tgatgctccc cccgctctga tggctggagc ccaatcccta cacagactcc  8100
tgctgtatgt gttttccttt cactctgagc cacagccaga gggcaggcat tcagtctcct  8160
cttcaggctg gggctggggc actgagaact cacccaacac cttgctctca ctccttctgc  8220
aaaacaagaa agagctttgt gctgcagtag ccatgaagaa tgaaaggaag gctttaacta  8280
aaaaatgtca gagattattt tcaacccctt actgtggatc accagcaagg aggaaacaca  8340
acacagagac attttttccc ctcaaattat caaaagaatc actgcatttg ttaaagagag  8400
caactgaatc aggaagcaga gttttgaaca tatcagaagt taggaatctg catcagagac  8460
aaatgcagtc atggttgttt gctgcatacc agccctaatc attagaagcc tcatggactt  8520
caaacatcat tccctctgac aagatgctct agcctaactc catgagataa aataaatctg  8580
cctttcagag ccaaagaaga gtccaccagc ttcttctcag tgtgaacaag agctccagtc  8640
aggttagtca gtccagtgca gtagaggaga ccagtctgca tcctctaatt ttcaaaggca  8700
agaagatttg tttaccctgg acaccaggca caagtgaggt cacagagctc ttagatatgc  8760
```

```
agtcctcatg agtgaggaga ctaaagcgca tgccatcaag acttcagtgt agagaaaacc  8820
tccaaaaaag cctcctcact acttctggaa tagctcagag gccgaggcgg cctcggcctc  8880
tgcataaata aaaaaaatta gtcagccatg gggcggagaa tgggcggaac tgggcggagt  8940
taggggcggg atgggcggag ttaggggcgg gactatggtt gctgactaat tgagatgcat  9000
gctttgcata cttctgcctg ctggggagcc tggggacttt ccacacctgg ttgctgacta  9060
attgagatgc atgctttgca tacttctgcc tgctggggag cctggggact ttccacaccc  9120
taactgacac acattccaca gctgcattaa tgaatcggcc aacgcgcggg gagaggcggt  9180
ttgcgtattg ggcgctcttc cgcttcctcg ctcactgact cgctgcgctc ggtcgttcgg  9240
ctgcggcgag cggtatcagc tcactcaaag gcggtaatac ggttatccac agaatcaggg  9300
gataacgcag gaaagaacat gtgagcaaaa ggccagcaaa aggccaggaa ccgtaaaaag  9360
gccgcgttgc tggcgttttt ccataggctc cgcccccctg acgagcatca caaaaatcga  9420
cgctcaagtc agaggtggcg aaacccgaca ggactataaa gataccaggc gtttccccct  9480
ggaagctccc tcgtgcgctc tcctgttccg accctgccgc ttaccggata cctgtccgcc  9540
tttctccctt cgggaagcgt ggcgctttct catagctcac gctgtaggta tctcagttcg  9600
gtgtaggtcg ttcgctccaa gctgggctgt gtgcacgaac cccccgttca gcccgaccgc  9660
tgcgccttat ccggtaacta tcgtcttgag tccaacccgg taagacacga cttatcgcca  9720
ctggcagcag ccactggtaa caggattagc agagcgaggt atgtaggcgg tgctacagag  9780
ttcttgaagt ggtggcctaa ctacggctac actagaagaa cagtatttgg tatctgcgct  9840
ctgctgaagc cagttacctt cggaaaaaga gttggtagct cttgatccgg caaacaaacc  9900
accgctggta gcggtggttt ttttgtttgc aagcagcaga ttacgcgcag aaaaaaagga  9960
tctcaagaag atcctttgat cttttctacg gggtctgacg ctcagtggaa cgaaaactca  10020
cgttaaggga ttttggtcat gagattatca aaaaggatct tcacctagat ccttttaaat  10080
taaaaatgaa gttttaaatc aatctaaagt atatatgagt aaacttggtc tgacagttac  10140
caatgcttaa tcagtgaggc acctatctca gcgatctgtc tatttcgttc atccatagtt  10200
gcctgactcc tgcaaaccac gttgtgtctc aaaatctctg atgttacatt gcacaagata  10260
aaaatatatc atcatgaaca ataaaactgt ctgcttacat aaacagtaat acaaggggtg  10320
ttatgagcca tattcaacgg gaaacgtctt gctcgaggcc gcgattaaat tccaacatgg  10380
atgctgattt atatgggtat aaatgggctc gcgataatgt cgggcaatca ggtgcgacaa  10440
tctatcgatt gtatgggaag cccgatgcgc cagagttgtt tctgaaacat ggcaaaggta  10500
gcgttgccaa tgatgttaca gatgagatgg tcagactaaa ctggctgacg gaatttatgc  10560
ctcttccgac catcaagcat tttatccgta ctcctgatga tgcatggtta ctcaccactg  10620
cgatccccgg gaaaacagca ttccaggtat tagaagaata tcctgattca ggtgaaaata  10680
ttgttgatgc gctggcagtg ttcctgcgcc ggttgcattc gattcctgtt tgtaattgtc  10740
cttttaacag cgatcgcgta tttcgtctcg ctcaggcgca atcacgaatg aataacggtt  10800
tggttgatgc gagtgatttt gatgacgagc gtaatggctg gcctgttgaa caagtctgga  10860
aagaaatgca taagcttttg ccattctcac cggattcagt cgtcactcat ggtgatttct  10920
cacttgataa ccttattttt gacgagggga aattaatagg ttgtattgat gttggacgag  10980
tcggaatcgc agaccgatac caggatcttg ccatcctatg gaactgcctc ggtgagtttt  11040
ctccttcatt acagaaacgg ctttttcaaa aatatggtat tgataatcct gatatgaata  11100
aattgcagtt tcatttgatg ctcgatgagt ttttctaagg gcggcctgcc accataccca  11160
cgccgaaaca agcgctcatg agcccgaagt ggcgagcccg atcttcccca tcggtgatgt  11220
cggcgatata ggcgccagca accgcacctg tggcgccggt gatgagggcg cgccaagtcg  11280
acgtccggca gtc                                                     11293

SEQ ID NO: 7           moltype = DNA  length = 10700
FEATURE                Location/Qualifiers
misc_feature           1..10700
                       note = Synthetic polynucleotide
source                 1..10700
                       mol_type = other DNA
                       organism = synthetic construct
SEQUENCE: 7
ttggccactc cctctctgcg cgctcgctcg ctcactgagg ccgcccgggc aaagcccggg  60
cgtcgggcga cctttggtcg cccggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttaat tattttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
tgccttcgcc ccgtgccccg ctccgccgcc gcctcgcgcc gcccgccccg gctctgactg  1020
accgcgttac tcccacaggt gagcgggcgg gacggccctt ctcctccggg ctgtaattag  1080
cgcttggttt aatgacggct tgtttctttt ctgtggctgc gtgaaagcct tgaggggctc  1140
cgggagctag agcctctgct aaccatgttc atgccttctt ctttttccta cagctcctgg  1200
gcaacgtgct ggttattgtg ctgtctcatc attttggcaa agaattcctc gaagatccga  1260
agggaaagtc ttccacgact gtgggatccg ttcgaagata tcaccggttg agccaccatg  1320
gaattcagca gccccagcag agaggaatgc cccaagcctc tgagccgggt gtcaatcatg  1380
gccggatctc tgacaggact gctgctgctt caggccgtgt cttgggcttc tggcgctaga  1440
ccttgcatcc ccaagagctt cggctacagc agcgtcgtgt gcgtgtgcaa tgccacctac  1500
tgcgacagct tcgaccctcc taccttteet gctctgggca ccttcagcag atacgagagc  1560
accagatccg gcagacggat ggaactgagc atggacccca tccaggccaa tcacacaggc  1620
```

-continued

```
actggcctgc tgctgacact gcagcctgag cagaaattcc agaaagtgaa aggcttcggc  1680
ggagccatga cagatgccgc cgctctgaat atcctggctc tgtctccacc agctcagaac  1740
ctgctgctca agagctactt cagcgaggaa ggcatcggct acaacatcat cagagtgccc  1800
atggccagct gcgacttcag catcaggacc tacacctacg ccgacacacc cgacgatttc  1860
cagctgcaca acttcagcct gcctgaagag gacaccaagc tgaagatccc tctgatccac  1920
agagccctgc agctggcaca aagacccgtg tcactgctgg cctctccatg gacatctccc  1980
acctggctga aaacaaatgg cgccgtgaat ggcaagggca gcctgaaagg ccaacctggc  2040
gacatctacc accagacctg ggccagatac ttcgtgaagt tcctggacgc ctatgccgag  2100
cacaagctgc agttttgggc cgtgacagcc gagaacgaac cttctgctgg actgctgagc  2160
ggctacccct ttcagtgcct gggctttaca cccgagcacc agcgggactt tatcgcccgt  2220
gatctgggac ccacactggc caatagcacc caccataatg tgcggctgct gatgctggac  2280
gaccagagac tgcttctgcc ccactgggct aaagtggtgc tgacagatcc tgaggccgcc  2340
aaatacgtgc acggaatcgc cgtgcactgg tatctggact ttctggcccc tgccaaggcc  2400
acactgggag agacacacag actgttcccc aacaccatgc tgttcgccag cgaagcctgt  2460
gtgggcagca agttttggga acagagcgtg cggctcggca gctgggatag aggcatgcag  2520
tacagccaca gcatcatcac caacctgctg taccacgtcg tcggctggac cgactggaat  2580
ctggccctga atcctgaagg cggccctaac tgggtccgaa acttcgtgga cagccccatc  2640
atcgtggaca tcaccaagga caccttctac aagcagccca tgttctacca cctgggacac  2700
ttcagcaagt tcatccccga gggctctcag cgcgttggac tggtggcttc ccagaagaac  2760
gatctggacg ccgtggctct gatgcaccct gatggatctg ctgtggtggt ggtcctgaac  2820
cgcagcagca aagatgtgcc cctgaccatc aaggatcccg ccgtgggatt cctggaaaca  2880
atcagccctg gctactccat ccacacctac ctgtggcgta gacagtgaca attgttaatt  2940
aagtttaaac cctcgaggcc gcaagcttat cgataatcaa cctctggatt acaaaatttg  3000
tgaaagattg actggtattc ttaactatgt tgctcctttt acgctatgtg gatacgctgc  3060
tttaatgcct ttgtatcatg ctattgcttc ccgtatggct ttcattttct cctccttgta  3120
taaatcctgg ttgctgtctc tttatgagga gttgtggccc gttgtcaggc aacgtggcgt  3180
ggtgtgcact gtgtttgctg acgcaacccc cactggttgg ggcattgcca ccacctgtca  3240
gctcctttcc gggactttcg ctttccccct ccctattgcc acggcggaac tcatcgccgc  3300
ctgccttgcc cgctgctgga caggggctcg gctgttgggc actgacaatt ccgtggtgtt  3360
gtcggggaaa tcatcgtcct ttccttggct gctcgcctgt gttgccacct ggattctgcg  3420
cgggacgtcc ttctgctacg tcccttcggc cctcaatcca gcggaccttc cttcccgcgg  3480
cctgctgccg gctctgcggc ctcttccgcg tcttcgcctt cgccctcaga cgagtcggat  3540
ctccctttgg gccgcctccc cgcatcgata ccgtcgacta gagctcgctg atcagcctcg  3600
actgtgcctt ctagttgcca gccatctgtt gtttgcccct cccccgtgcc ttccttgacc  3660
ctggaaggtg ccactcccac tgtcctttcc taataaaatg aggaaattgc atcgcattgt  3720
ctgagtaggt gtcattctat tctggggggt ggggtggggc aggacagcaa gggggaggat  3780
tgggaagaca atagcaggca tgctggggag agatccacga taacaaacag ctttttgggg  3840
gtgaacatat tgactgaatt ccctgcaggt tggccactcc ctctctgcgc gctcgctcgc  3900
tcactgaggc cgcccgggca aagcccgggc gtcgggcgac ctttggtcgc ccggcctcag  3960
tgagcgagcg agcgcgcaga gagggagtgg ccaactccat cactaggggt tcctgcggcc  4020
gctcgtacgg tctcgaggaa ttcctgcagg ataacttgcc aacctcattc taaaatgtat  4080
atagaagccc aaaagacaat aacaaaaata ttcttgtaga acaaaatggg aaagaatgtt  4140
ccactaaata tcaagattta gagcaaagca tgagatgtgt ggggatagac agtgaggctg  4200
ataaaataga gtagagctca gaaacagacc cattgatata tgtaagtgac ctatgaaaaa  4260
aaatatggca tttacaatgg gaaaatgatg gtctttttct tttttagaaa aacagggaaa  4320
tatatttata tgtaaaaaat aaaagggaac ccatatgtca taccatacac acaaaaaaat  4380
tccagtgaat tataagtcta aatggagaag gcaaaacttt aaatctttta gaaaataata  4440
tagaagcatg cagaccagcc tggccaacat gatgaaaccc tctctactaa taataaaatc  4500
agtagaacta ctcaggacta ctttgagtgg gaagtccttt tctatgaaga cttctttggc  4560
caaaattagg ctctaaatgc aaggagatag tgcatcatgc ctggctgcac ttactgataa  4620
atgatgttat caccatcttt aaccaaatgc acaggaacaa gttatggtac tgatgtgctg  4680
gattgagaag gagctctact tccttgacag gacacatttg tatcaactta aaaaagcaga  4740
tttttgccag cagaactatt cattcagagg taggaaactt agaatagatg atgtcactga  4800
ttagcatggc ttccccatct ccacagctgc ttcccaccca ggttgcccac agttgagttt  4860
gtccagtgct cagggctgcc cactctcagt aagaagcccc acaccagccc ctctccaaat  4920
atgttggctg ttccttccat taaagtgacc ccactttaga gcagcaagtg gatttctgtt  4980
tcttacagtt caggaaggag gagtcagctg tgagaacctg gagcctgaga tgcttctaag  5040
tcccactgct actggggtca gggaagccag actccagcat cagcagtcag gagcactaag  5100
cccttgccaa catcctgttt ctcagagaaa ctgcttccat tataatggtt gtcctttttt  5160
aagctatcaa gccaaacaac cagtgtctac cattattctc atcacctgaa gccaagggtt  5220
ctagcaaaag tcaagctgtc ttgtaatggt tgatgtgcct ccagcttctg tcttcagtca  5280
ctccactctt agcctgctct gaatcaactc tgaccacagt tccctggagc ccctgccacc  5340
tgctgcccct gccaccttct ccatctgcag tgctgtgcag ccttctgcac tcttgcagag  5400
ctaataggtg gagacttgaa ggaagaggag gaaagtttct cataatagcc ttgctgcaag  5460
ctcaaatggg aggtgggcac tgtgcccagg agccttggag caaaggctgt gcccaacctc  5520
tgactgcatc caggtttggt cttgacagag ataagaagcc ctggcttttg gagccaaaat  5580
ctaggtcaga cttaggcagg attctcaaag tttatcagca gaacatgagg cagaagaccc  5640
tttctgctcc agcttcttca ggctcaacct tcatcagaat agatagaaag agaggctgtg  5700
agggttctta aaacagaagc aaatctgact cagagaataa acaacctcct agtaaactac  5760
agcttagaca gagcatctgg tggtgagtgt gctcagtgtc ctactcaact gtctggtatc  5820
agccctcatg aggacttctc ttctttccct catagacctc catctctgtt ttccttagcc  5880
tgcagaaatc tggatggcta ttcacagaat gcctgtgctt tcagagttgc atttttctc  5940
tggtattctg gttcaagcat ttgaaggtag gaaaggttct ccaagtgcaa gaaagccagc  6000
cctgagcctc aactgcctgg ctagtgtggt cagtaggatg caaaggctgt tgaatgccac  6060
aaggccaaac tttaacctgt gtaccacaag cctagcagca gaggcagctc tgctcactgg  6120
aactctctgt cttctttctc ctgagccttt tcttttcctg agttttctag ctctcctcaa  6180
ccttacctct gccctaccca ggacaaaccc aagagccact gtttctgtga tgtcctctcc  6240
agccctaatt aggcatcatg acttcagcct gaccttccat gctcagaagc agtgctaatc  6300
cacttcagat gagctgctct atgcaacaca ggcagagcct acaaaccttt gcaccagagc  6360
```

```
cctccacata tcagtgtttg ttcatactca cttcaacagc aaatgtgact gctgagatta  6420
agattttaca caagatggtc tgtaatttca cagttagttt tatcccatta ggtatgaaag  6480
aattagcata attcccctta aacatgaatg aatcttagat tttttaataa atagttttgg  6540
aagtaaagac agagacatca ggagcacaag gaatagcctg agaggacaaa cagaacaaga  6600
aagagtctgg aaatacacag gatgttcttg gcctcctcaa agcaagtgca agcagatagt  6660
accagcagcc ccaggctatc agagcccagt gaagagaagt accatgaaag ccacagctct  6720
aaccaccctg ttccagagtg acagacagtc cccaagacaa gccagcctga gccagagaga  6780
gaactgcaag agaaagtttc taatttaggt tctgttagat tcagacaagt gcaggtcatc  6840
ctctctccac agctactcac ctctccagcc taacaaagcc tgcagtccac actccaaccc  6900
tggtgtctca cctcctagcc tctcccaaca tcctgctctc tgaccatctt ctgcatctct  6960
catctcacca tctcccactg tctacagcct actcttgcaa ctaccatctc attttctgac  7020
atcctgtcta catcttctgc catactctgc catctaccat accacctctt accatctacc  7080
acaccatctt ttatctccat ccctctcaga agcctccaag ctgaatcctg ctttatgtgt  7140
tcatctcagc ccctgcatgg aaagctgacc ccagaggcag aactattccc agagagcttg  7200
gccaagaaaa acaaaactac cagcctggcc aggctcagga gtagtaagct gcagtgtctg  7260
ttgtgttcta gcttcaacag ctgcaggagt tccactctca aatgctccac atttctcaca  7320
tcctcctgat tctggtcact acccatcttc aaagaacaga atatctcaca tcagcatact  7380
gtgaaggact agtcatgggt gcagctgctc agagctgcaa agtcattctg gatggtggag  7440
agcttacaaa catttcatga tgctccccc gctctgatgg ctggagccca atccctacac  7500
agactcctgc tgtatgtgtt ttcctttcac tctgagccac agccagaggg caggcattca  7560
gtctcctctt caggctgggg ctggggcact gagaactcac ccaacacctt gctctcactc  7620
cttctgcaaa acaagaaaga gctttgtgct gcagtagcca tgaagaatga aaggaaggct  7680
ttaactaaaa aatgtcagag attattttca acccccttact gtggatcacc agcaaggagg  7740
aaacacaaca cagagacatt ttttccccctc aaattatcaa aagaatcact gcatttgtta  7800
aagagagcaa ctgaatcagg aagcagagtt ttgaacatat cagaagttag gaatctgcat  7860
cagagacaaa tgcagtcatg gttgtttgct gcataccagc cctaatcatt agaagcctca  7920
tggacttcaa acatcattcc ctctgacaag atgctctagc ctaactccat gagataaaat  7980
aaatctgcct ttcagagcca aagaagagtc caccagcttc ttctcagtgt gaacaagagc  8040
tccagtcagg ttagtcagtc cagtgcagta gaggagacca gtctgcatcc tctaattttc  8100
aaaggcaaga agatttgttt accctggaca ccaggcacaa gtgaggtcac agagctctta  8160
gatatgcagt cctcatgagt gaggagacta aagcgcatgc catcaagact tcagtgtaga  8220
gaaaacctcc aaaaaagcct cctcactact tctggaatag ctcagaggcc gaggcggcct  8280
cggcctctgc ataaataaaa aaaattagtc agccatgggg cggagaatgg gcggaactgg  8340
gcggagttag gggcgggatg ggcggagtta ggggcgggac tatggttgct gactaattga  8400
gatgcatgct ttgcatactt ctgcctgctg gggagcctgg ggactttcca cacctggttg  8460
ctgactaatt gagatgcatg ctttgcatac ttctgcctgc tggggagcct ggggactttc  8520
cacaccctaa ctgacacaca ttccacagct gcattaatga atcggccaac gcgcggggag  8580
aggcggtttg cgtattgggc gctcttccgc ttcctcgctc actgactcgc tgcgctcggt  8640
cgttcggctg cggcgagcgg tatcagctca ctcaaaggcg gtaatacggt tatccacaga  8700
atcaggggat aacgcaggaa agaacatgtg agcaaaaggc cagcaaaagg ccaggaaccg  8760
taaaaaggcc gcgttgctgg cgtttttcca taggctccgc ccccctgacg agcatcacaa  8820
aaatcgacgc tcaagtcaga ggtggcgaaa cccgacagga ctataaagat accaggcgtt  8880
tccccctgga agctccctcg tgcgctctcc tgttccgacc ctgccgctta ccggatacct  8940
gtccgccttt ctcccttcgg gaagcgtggc gctttctcat agctcacgct gtaggtatct  9000
cagttcggtg taggtcgttc gctccaagct gggctgtgtg cacgaacccc ccgttcagcc  9060
cgaccgctgc gccttatccg gtaactatcg tcttgagtcc aacccggtaa gacacgactt  9120
atcgccactg gcagcagcca ctggtaacag gattagcaga gcgaggtatg taggcggtgc  9180
tacagagttc ttgaagtggt ggcctaacta cggctacact agaagaacag tatttggtat  9240
ctgcgctctg ctgaagccag ttaccttcgg aaaaagagtt ggtagctctt gatccggcaa  9300
acaaaccacc gctggtagcg gtggtttttt tgtttgcaag cagcagatta cgcgcagaaa  9360
aaaaggatct caagaagatc ctttgatctt ttctacgggg tctgacgctc agtggaacga  9420
aaactcacgt taagggattt tggtcatgag attatcaaaa aggatcttca cctagatcct  9480
tttaaattaa aaatgaagtt ttaaatcaat ctaaagtata tatgagtaaa cttggtctga  9540
cagttaccaa tgcttaatca gtgaggcacc tatctcagcg atctgtctat ttcgttcatc  9600
catagttgcc tgactcctgc aaaccacgtt gtgtctcaaa atctctgatg ttacattgca  9660
caagataaaa atatatcatc atgaacaata aaactgtctg cttacataaa cagtaataca  9720
aggggtgtta tgagccatat tcaacgggaa acgtcttgct cgaggccgcg attaaattcc  9780
aacatggatg ctgatttata tgggtataaa tgggctcgcg ataatgtcgg gcaatcaggt  9840
gcgacaatct atcgattgta tgggaagccc gatgcgccag agttgtttct gaaacatggc  9900
aaaggtagcg ttgccaatga tgttacagat gagatggtca gactaaactg gctgacggaa  9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
caagtcgacg tccggcagtc                                              10700
```

```
SEQ ID NO: 8            moltype = DNA  length = 10700
FEATURE                 Location/Qualifiers
misc_feature            1..10700
                        note = Synthetic polynucleotide
source                  1..10700
```

```
                         mol_type = other DNA
                         organism = synthetic construct
SEQUENCE: 8
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactatt agatctgatg gccgcgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttttaat tattttgtgc agcgatgggg gcgggggggg  780
gggggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
tgccttcgcc ccgtgccccg ctccgccgcc gcctcgcgcc gcccgccccg gctctgactg  1020
accgcgttac tcccacaggt gagcgggcgg gacggccctt ctcctccggg ctgtaattag  1080
cgcttggttt aatgacggct tgtttctttt ctgtggctgc gtgaaagcct tgaggggctc  1140
cgggagctag agcctctgct aaccatgttc atgccttctt cttttcccta cagctcctgg  1200
gcaacgtgct ggttattgtg ctgtctcatc attttggcaa agaattcctc gaagatccga  1260
agggaaagtc ttccacgact gtgggatccg ttcgaagata tcaccggttg agccaccatg  1320
gaattcagca gccccagcag agaggaatgc cccaagcctc tgagccgggt gtcaatcatg  1380
gccggatctc tgacaggact gctgctgctt caggccgtgt cttgggcttc tggcgctaga  1440
ccttgcatcc ccaagagctt cggctacagc agcgtcgtgt gcgtgtgcaa tgccacctac  1500
tgcgacagct tcgaccctcc taccttttcct gctctgggca ccttcagcag atacgagagc  1560
accagatccg gcagacggat ggaactgagc atgggaccca tccaggccaa tcacacaggc  1620
actggcctgc tgctgacact gcagcctgag cagaaattcc agaaagtgaa aggcttcggc  1680
ggagccatga cagatgccgc cgctctgaat atcctggctc tgtctccacc agctcagaac  1740
ctgctgctca agagctactt cagcgaggaa ggcatcggct acaacatcat cagagtgccc  1800
atggccagct gcgacttcag catcaggacc tacacctacg ccgacacacc cgacgatttc  1860
cagctgcaca acttcagcct gcctgaagag gacaccaagc tgaagatccc tctgatccac  1920
agagccctgc agctggcaca aagacccgtg tcactgctgg cctctccatg gacatctccc  1980
acctggctga aaacaaatgg cgccgtgaat ggcaagggca gcctgaaagg ccaacctggc  2040
gacatctacc accagacctg ggccagatac ttcgtgaagt tcctggacgc ctatgccgag  2100
cacaagctgc agttttgggc cgtgacagcc gagaacgaac cttctgctgg actgctgagc  2160
ggctacccct ttcagtgcct gggctttaca cccgagcacc agcgggactt tatcgcccgt  2220
gatctgggac ccacactggc caatagcacc caccataatg tgcggctgct gatgctggac  2280
gaccagagac tgcttctgcc ccactgggct aaagtggtgc tgacagatcc tgaggccgcc  2340
aaatacgtgc acggaatcgc cgtgcactgg tatctggact ttctggcccc tgccaaggcc  2400
acactgggag agacacacag actgttcccc aacaccatgc tgttcgccag cgaagcctgt  2460
gtgggcagca agttttggga acagagcgtg cggctcggca gctgggatag aggcatgcag  2520
tacagccaca gcatcatcac caacctgctg taccacgtcg tcggctggac cgactggaat  2580
ctggccctga atcctgaagg cggccctaac tgggtccgaa acttcgtgga cagccccatc  2640
atcgtggaca tcaccaagga caccttctac aagcagccca tgttctacca cctgggacac  2700
ttcagcaagt tcatccccga gggctctcag cgcgttggac tggtggcttc ccagaagaac  2760
gatctggacg ccgtggctct gatgcaccct gatggatctg ctgtggtggt ggtcctgaac  2820
cgcagcagca aagatgtgcc cctgaccatc aaggatcccg ccgtgggatt cctggaaaca  2880
atcagccctg gctactccat ccacacctac ctgtggcgta gacagtgaca attgttaatt  2940
aagtttaaac cctcgaggcc gcaagcttat cgataatcaa cctctggatt acaaaatttg  3000
tgaaagattg actggtattc ttaactatgt tgctcctttt acgctatgtg gatacgctgc  3060
tttaatgcct ttgtatcatg ctattgcttc ccgtatggct ttcattttct cctccttgta  3120
taaatcctgg ttgctgtctc tttatgagga gttgtggccc gttgtcaggc aacgtggcgt  3180
ggtgtgcact gtgtttgctg acgcaacccc cactggttgg ggcattgcca ccacctgtca  3240
gctcctttcc gggactttcg ctttccccct ccctattgcc acggcggaac tcatcgccgc  3300
ctgccttgcc cgctgctgga caggggctcg gctgttgggc actgacaatt ccgtggtgtt  3360
gtcggggaaa tcatcgtcct ttccttggct gctcgcctgt gttgccacct ggattctgcg  3420
cgggacgtcc ttctgctacg tcccttcggc cctcaatcca gcggaccttc cttcccgcgg  3480
cctgctgccg gctctgcggc ctcttccgcg tcttcgcctt cgccctcaga cgagtcggat  3540
ctccctttgg gccgcctccc cgcatcgata ccgtcgacta gagctcgctg atcagcctcg  3600
actgtgcctt ctagttgcca gccatctgtt gtttgcccct cccccgtgcc ttccttgacc  3660
ctggaaggtg ccactcccac tgtcctttcc taataaaatg aggaaattgc atcgcattgt  3720
ctgagtaggt gtcattctat tctggggggt ggggtggggc aggacagcaa gggggaggat  3780
tgggaagaca atagcaggca tgctggggag agatccacga taacaaacag cttttttggg  3840
gtgaacatat tgactgaatt ccctgcaggt tggccactcc ctctctgcgc gctcgctcgc  3900
tcactgaggc cgcccgggca aagcccgggc gtcgggcgac ctttggtcgc ccggcctcag  3960
tgagcgagcg agcgcgcaga gagggagtgg ccaactccat cactaggggt tcctgcggcc  4020
gctcgtacgg tctcgaggaa ttcctgcagg ataacttgcc aacctcattc taaaatgtat  4080
atagaagccc aaaagacaat aacaaaaata ttcttgtaga acaaaatggg aaagaatgtt  4140
ccactaaata tcaagattta gagcaaagca tgagatgtgt ggggatagac agtgaggctg  4200
ataaaataga gtagagctca gaaacagacc cattgatata tgtaagtgac ctatgaaaaa  4260
aatatggcat tttacaatgg gaaaatgatg gtcttttttct tttttagaaa aacagggaaa  4320
tatatttata tgtaaaaaat aaaagggaac ccatatgtca taccatacac acaaaaaaat  4380
tccagtgaat tataagtcta aatggagaag gcaaaacttt aaatctttta gaaaataata  4440
tagaagcatg cagaccagcc tggccaacat gatgaaaccc tctctactaa taataaaatc  4500
agtagaacta ctcaggacta ctttgagtgg gaagtccttt tctatgaaga cttctttggc  4560
```

-continued

```
caaaattagg ctctaaatgc aaggagatag tgcatcatgc ctggctgcac ttactgataa  4620
atgatgttat caccatcttt aaccaaatgc acaggaacaa gttatggtac tgatgtgctg  4680
gattgagaag gagctctact tccttgacag gacacatttg tatcaactta aaaaagcaga  4740
tttttgccag cagaactatt cattcagagg taggaaactt agaatagatg atgtcactga  4800
ttagcatggc ttccccatct ccacagctgc ttcccaccca ggttgcccac agttgagttt  4860
gtccagtgct cagggctgcc cactctcagt aagaagcccc acaccagccc ctctccaaat  4920
atgttggctg ttccttccat taaagtgacc ccactttaga gcagcaagtg gatttctgtt  4980
tcttacagtt caggaaggag gagtcagctg tgagaacctg gagcctgaga tgcttctaag  5040
tcccactgct actggggtca gggaagccag actccagcat cagcagtcag gagcactaag  5100
cccttgccaa catcctgttt ctcagagaaa ctgcttccat tataatggtt gtcctttttt  5160
aagctatcaa gccaaacaac cagtgtctac cattattctc atcacctgaa gccaagggtt  5220
ctagcaaaag tcaagctgtc ttgtaatggt tgatgtgcct ccagcttctg tcttcagtca  5280
ctccactctt agcctgctct gaatcaactc tgaccacagt tccctggagc ccctgccacc  5340
tgctgcccct gccaccttct ccatctgcag tgctgtgcag ccttctgcac tcttgcagag  5400
ctaataggtg gagacttgaa ggaagaggag gaaagtttct cataatagcc ttgctgcaag  5460
ctcaaatggg aggtgggcac tgtgcccagg agccttggag caaaggctgt gcccaacctc  5520
tgactgcatc caggtttggt cttgacagag ataagaagcc ctggcttttg gagccaaaat  5580
ctaggtcaga cttaggcagg attctcaaag tttatcagca gaacatgagg cagaagaccc  5640
tttctgctcc agcttcttca ggctcaacct tcatcagaat agatagaaag agaggctgtg  5700
agggttctta aaacagaagc aaatctgact cagagaataa acaacctcct agtaaactac  5760
agcttagaca gagcatctgg tggtgagtgt gctcagtgtc ctactcaact gtctggtatc  5820
agccctcatg aggacttctc ttctttccct catagacctc catctctgtt ttccttagcc  5880
tgcagaaatc tggatggcta ttcacagaat gcctgtgctt tcagagttgc attttttctc  5940
tggtattctg gttcaagcat ttgaaggtag gaaaggttct ccaagtgcaa gaaagccagc  6000
cctgagcctc aactgcctgg ctagtgtggt cagtaggatg caaaggctgt tgaatgccac  6060
aaggccaaac tttaacctgt gtaccacaag cctagcagca gaggcagctc tgctcactgg  6120
aactctctgt cttctttctc ctgagccttt tcttttcctg agttttctag ctctcctcaa  6180
ccttacctct gccctaccca ggacaaaccc aagagccact gtttctgtga tgtcctctcc  6240
agccctaatt aggcatcatg acttcagcct gaccttccat gctcagaagc agtgctaatc  6300
cacttcagat gagctgctct atgcaacaca ggcagagcct acaaaccttt gcaccagagc  6360
cctccacata tcagtgtttg ttcatactca cttcaacagc aaatgtgact gctgagatta  6420
agattttaca caagatggtc tgtaatttca cagttagttt tatcccatta ggtatgaaag  6480
aattagcata attcccctta aacatgaatg aatcttagat tttttaataa atagttttgg  6540
aagtaaagac agagacatca ggagcacaag gaatagcctg agaggacaaa cagaacaaga  6600
aagagtctgg aaatacacag gatgttcttg gcctcctcaa agcaagtgca agcagatagt  6660
accagcagcc ccaggctatc agagcccagt gaagagaagt accatgaaag ccacagctct  6720
aaccaccctg ttccagagtg acagacagtc cccaagacaa gccagcctga gccagagaga  6780
gaactgcaag agaaagtttc taatttaggt tctgttagat tcagacaagt gcaggtcatc  6840
ctctctccac agctactcac ctctccagcc taacaaagcc tgcagtccac actccaaccc  6900
tggtgtctca cctcctagcc tctcccaaca tcctgctctc tgaccatctt ctgcatctct  6960
catctcacca tctcccactg tctacagcct actcttgcaa ctaccatctc attttctgac  7020
atcctgtcta catcttctgc catactctgc catctaccat accacctctt accatctacc  7080
acaccatctt ttatctccat ccctctcaga agcctccaag ctgaatcctg ctttatgtgt  7140
tcatctcagc ccctgcatgg aaagctgacc ccagaggcag aactattccc agagagcttg  7200
gccaagaaaa acaaaactac cagcctggcc aggctcagga gtagtaagct gcagtgtctg  7260
ttgtgttcta gcttcaacag ctgcaggagt tccactctca aatgctccac atttctcaca  7320
tcctcctgat tctggtcact acccatcttc aaagaacaga atatctcaca tcagcatact  7380
gtgaaggact agtcatgggt gcagctgctc agagctgcaa agtcattctg gatggtggag  7440
agcttacaaa catttcatga tgctccccc gctctgatgg ctggagccca atccctacac  7500
agactcctgc tgtatgtgtt ttcctttcac tctgagccac agccagaggg caggcattca  7560
gtctcctctt caggctgggg ctggggcact gagaactcac ccaacacctt gctctcactc  7620
cttctgcaaa acaagaaaga gctttgtgct gcagtagcca tgaagaatga aaggaaggct  7680
ttaactaaaa aatgtcagag attattttca accccttact gtggatcacc agcaaggagg  7740
aaacacaaca cagagacatt ttttcccctc aaattatcaa aagaatcact gcatttgtta  7800
aagagagcaa ctgaatcagg aagcagagtt ttgaacatat cagaagttag gaatctgcat  7860
cagagacaaa tgcagtcatg gttgtttgct gcataccagc cctaatcatt agaagcctca  7920
tggacttcaa acatcattcc ctctgacaag atgctctagc ctaactccat gagataaaat  7980
aaatctgcct ttcagagcca aagaagagtc caccagcttc ttctcagtgt gaacaagagc  8040
tccagtcagg ttagtcagtc cagtgcagta gaggagacca gtctgcatcc tctaattttc  8100
aaaggcaaga agatttgttt accctggaca ccaggcacaa gtgaggtcac agagctctta  8160
gatatgcagt cctcatgagt gaggagacta aagcgcatgc catcaagact tcagtgtaga  8220
gaaaacctcc aaaaaaagcct cctcactact tctggaatag ctcagaggcc gaggcggcct  8280
cggcctctgc ataaataaaa aaaattagtc agccatgggg cggagaatgg gcggaactgg  8340
gcggagttag gggcgggatg ggcggagtta ggggcgggac tatggttgct gactaattga  8400
gatgcatgct ttgcatactt ctgcctgctg gggagcctgg ggactttcca cacctggttg  8460
ctgactaatt gagatgcatg ctttgcatac ttctgcctgc tggggagcct ggggactttc  8520
cacaccctaa ctgacacaca ttccacagct gcattaatga atcggccaac gcgcggggag  8580
aggcggtttg cgtattgggc gctcttccgc ttcctcgctc actgactcgc tgcgctcggt  8640
cgttcggctg cggcgagcgg tatcagctca ctcaaaggcg gtaatacggt tatccacaga  8700
atcaggggat aacgcaggaa agaacatgtg agcaaaaggc cagcaaaagg ccaggaaccg  8760
taaaaaggcc gcgttgctgg cgtttttcca taggctccgc ccccctgacg agcatcacaa  8820
aaatcgacgc tcaagtcaga ggtggcgaaa cccgacagga ctataaagat accaggcgtt  8880
tccccctgga agctccctcg tgcgctctcc tgttccgacc ctgccgctta ccggatacct  8940
gtccgccttt ctcccttcgg gaagcgtggc gctttctcat agctcacgct gtaggtatct  9000
cagttcggtg taggtcgttc gctccaagct gggctgtgtg cacgaacccc ccgttcagcc  9060
cgaccgctgc gccttatccg gtaactatcg tcttgagtcc aacccggtaa gacacgactt  9120
atcgccactg gcagcagcca ctggtaacag gattagcaga gcgaggtatg taggcggtgc  9180
tacagagttc ttgaagtggt ggcctaacta cggctacact agaagaacag tatttggtat  9240
ctgcgctctg ctgaagccag ttaccttcgg aaaaagagtt ggtagctctt gatccggcaa  9300
```

```
acaaaccacc gctggtagcg gtggtttttt tgtttgcaag cagcagatta cgcgcagaaa  9360
aaaaggatct caagaagatc ctttgatctt ttctacgggg tctgacgctc agtggaacga  9420
aaactcacgt taagggattt tggtcatgag attatcaaaa aggatcttca cctagatcct  9480
tttaaattaa aaatgaagtt ttaaatcaat ctaaagtata tatgagtaaa cttggtctga  9540
cagttaccaa tgcttaatca gtgaggcacc tatctcagcg atctgtctat ttcgttcatc  9600
catagttgcc tgactcctgc aaaccacgtt gtgtctcaaa atctctgatg ttacattgca  9660
caagataaaa atatatcatc atgaacaata aaactgtctg cttacataaa cagtaataca  9720
aggggtgtta tgagccatat tcaacgggaa acgtcttgct cgaggccgcg attaaattcc  9780
aacatggatg ctgatttata tgggtataaa tgggctcgcg ataatgtcgg gcaatcaggt  9840
gcgacaatct atcgattgta tgggaagccc gatgcgccag agttgtttct gaaacatggc  9900
aaaggtagcg ttgccaatga tgttacagat gagatggtca gactaaactg gctgacggaa  9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
caagtcgacg tccggcagtc                                             10700

SEQ ID NO: 9            moltype = DNA  length = 10700
FEATURE                 Location/Qualifiers
misc_feature            1..10700
                        note = Synthetic polynucleotide
source                  1..10700
                        mol_type = other DNA
                        organism = synthetic construct
SEQUENCE: 9
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttttaat tattttgtgc agcgatgggg gcgggggggg  780
gggggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
tgccttcgcc ccgtgccccg ctccgccgcc gcctcgcgcc gcccgccccg gctctgactg  1020
accgcgttac tcccacaggt gagcgggcgg gacggccctt ctcctccggg ctgtaattag  1080
cgcttggttt aatgacggct tgtttctttt ctgtggctgc gtgaaagcct tgaggggctc  1140
cgggagctag agcctctgct aaccatgttc atgccttctt ctttttccta cagctcctgg  1200
gcaacgtgct ggttattgtg ctgtctcatc attttggcaa agaattcctc gaagatccga  1260
agggaaagtc ttccacgact gtgggatccg ttcgaagata tcaccggttg agccaccatg  1320
gaattcagca gccccagcag agaggaatgc cccaagcctc tgagccgggt gtcaatcatg  1380
gccggatctc tgacaggact gctgctgctt caggccgtgt cttgggcttc tggcgctaga  1440
ccttgcatcc ccaagagctt cggctacagc agcgtcgtgt gcgtgtgcaa tgccacctac  1500
tgcgacagct tcgaccctcc tacctttcct gctctgggca ccttcagcag atacgagagc  1560
accagatccg gcagacggat ggaactgagc atgggaccca tccaggccaa tcacacaggc  1620
actggcctgc tgctgacact gcagcctgag cagaaattcc agaaagtgaa aggcttcggc  1680
ggagccatga cagatgccgc cgctctgaat atcctggctc tgtctccacc agctcagaac  1740
ctgctgctca agagctactt cagcgaggaa ggcatcggct acaacatcat cagagtgccc  1800
atggccagct gcgacttcag catcaggacc tacacctacg ccgacacacc cgacgatttc  1860
cagctgcaca acttcagcct gcctgaagag gacaccaagc tgaagatccc tctgatccac  1920
agagccctgc agctggcaca aagacccgtg tcactgctgg cctctccatg gacatctccc  1980
acctggctga aaacaaatgg cgccgtgaat ggcaagggca gcctgaaagg ccaacctggc  2040
gacatctacc accagacctg ggccagatac ttcgtgaagt tcctggacgc ctatgccgag  2100
cacaagctgc agttttgggc cgtgacagcc gagaacgaac cttctgctgg actgctgagc  2160
ggctacccct ttcagtgcct gggctttaca cccgagcacc agcgggactt tatcgcccgt  2220
gatctgggac ccacactggc caatagcacc caccataatg tgcggctgct gatgctggac  2280
gaccagagac tgcttctgcc ccactgggct aaagtggtgc tgacagatcc tgaggccgcc  2340
aaatacgtgc acggaatcgc cgtgcactgg tatctggact ttctggcccc tgccaaggcc  2400
acactgggag agacacacag actgttcccc aacaccatgc tgttcgccag cgaagcctgt  2460
gtgggcagca agttttggga acagagcgtg cggctcggca gctgggatag aggcatgcag  2520
tacagccaca gcatcatcac caacctgctg taccacgtcg tcggctggac cgactggaat  2580
ctggccctga atcctgaagg cggccctaac tgggtccgaa acttcgtgga cagccccatc  2640
atcgtggaca tcaccaagga caccttctac aagcagccca tgttctacca cctgggacac  2700
ttcagcaagt tcatccccga gggctctcag cgcgttggac tggtggcttc ccagaagaac  2760
```

```
gatctggacg ccgtggctct gatgcaccct gatggatctg ctgtggtggt ggtcctgaac  2820
cgcagcagca aagatgtgcc cctgaccatc aaggatcccg ccgtgggatt cctggaaaca  2880
atcagccctg gctactccat ccacacctac ctgtggcgta gacagtgaca attgttaatt  2940
aagtttaaac cctcgaggcc gcaagcttat cgataatcaa cctctggatt acaaaatttg  3000
tgaaagattg actggtattc ttaactatgt tgctcctttt acgctatgtg gatacgctgc  3060
tttaatgcct ttgtatcatg ctattgcttc ccgtatggct ttcattttct cctccttgta  3120
taaatcctgg ttgctgtctc tttatgagga gttgtggccc gttgtcaggc aacgtggcgt  3180
ggtgtgcact gtgtttgctg acgcaacccc cactggttgg ggcattgcca ccacctgtca  3240
gctcctttcc gggactttcg ctttccccct ccctattgcc acggcggaac tcatcgccgc  3300
ctgccttgcc cgctgctgga caggggctcg gctgttgggc actgacaatt ccgtggtgtt  3360
gtcggggaaa tcatcgtcct ttccttggct gctcgcctgt gttgccacct ggattctgcg  3420
cgggacgtcc ttctgctacg tcccttcggc cctcaatcca gcggaccttc cttcccgcgg  3480
cctgctgccg gctctgcggc ctcttccgcg tcttcgcctt cgccctcaga cgagtcggat  3540
ctccctttgg gccgcctccc cgcatcgata ccgtcgacta gagctcgctg atcagcctcg  3600
actgtgcctt ctagttgcca gccatctgtt gtttgcccct cccccgtgcc ttccttgacc  3660
ctggaaggtg ccactcccac tgtcctttcc taataaaatg aggaaattgc atcgcattgt  3720
ctgagtaggt gtcattctat tctggggggt ggggtggggc aggacagcaa gggggaggat  3780
tgggaagaca atagcaggca tgctggggag agatccacga taacaaacag ctttttgggg  3840
gtgaacatat tgactgaatt ccctgcaggt tggccactcc ctctctgcgc gctcgctcgc  3900
tcactgaggc cgcccgggca aagcccgggc gtcgggcgac ctttggtcgc ccggcctcag  3960
tgagcgagcg agcgcgcaga gagggagtgg ccaactccat cactaggggt tcctgcggcc  4020
gctcgtacgg tctcgaggaa ttcctgcagg ataacttgcc aacctcattc taaaatgtat  4080
atagaagccc aaaagacaat aacaaaaata ttcttgtaga acaaaatggg aaagaatgtt  4140
ccactaaata tcaagattta gagcaaagca tgagatgtgt ggggatagac agtgaggctg  4200
ataaaataga gtagagctca gaaacagacc cattgatata tgtaagtgac ctatgaaaaa  4260
aatatggcat tttacaatgg gaaaatgatg gtctttttct tttttagaaa aacagggaaa  4320
tatatttata tgtaaaaaat aaaagggaac ccatatgtca taccatacac acaaaaaaat  4380
tccagtgaat tataagtcta aatggagaag gcaaaacttt aaatctttta gaaaataata  4440
tagaagcatg cagaccagcc tggccaacat gatgaaaccc tctctactaa taataaaatc  4500
agtagaacta ctcaggacta ctttgagtgg gaagtccttt tctatgaaga cttctttggc  4560
caaaattagg ctctaaatgc aaggagatag tgcatcatgc ctggctgcac ttactgataa  4620
atgatgttat caccatcttt aaccaaatgc acaggaacaa gttatggtac tgatgtgctg  4680
gattgagaag gagctctact tccttgacag gacacatttg tatcaactta aaaaagcaga  4740
tttttgccag cagaactatt cattcagagg taggaaactt agaatagatg atgtcactga  4800
ttagcatggc ttccccatct ccacagctgc ttcccaccca ggttgcccac agttgagttt  4860
gtccagtgct cagggctgcc cactctcagt aagaagcccc acaccagccc ctctccaaat  4920
atgttggctg ttccttccat taaagtgacc ccactttaga gcagcaagtg gatttctgtt  4980
tcttacagtt caggaaggag gagtcagctg tgagaacctg gagcctgaga tgcttctaag  5040
tcccactgct actggggtca gggaagccag actccagcat cagcagtcag gagcactaag  5100
cccttgccaa catcctgttt ctcagagaaa ctgcttccat tataatggtt gtcctttttt  5160
aagctatcaa gccaaacaac cagtgtctac cattattctc atcacctgaa gccaagggtt  5220
ctagcaaaag tcaagctgtc ttgtaatggt tgatgtgcct ccagcttctg tcttcagtca  5280
ctccactctt agcctgctct gaatcaactc tgaccacagt tccctggagc ccctgccacc  5340
tgctgcccct gccaccttct ccatctgcag tgctgtgcag ccttctgcac tcttgcagag  5400
ctaataggtg gagacttgaa ggaagaggag gaaagtttct cataatagcc ttgctgcaag  5460
ctcaaatggg aggtgggcac tgtgcccagg agccttggag caaaggctgt gcccaacctc  5520
tgactgcatc caggtttggt cttgacagag ataagaagcc ctggcttttg gagccaaaat  5580
ctaggtcaga cttaggcagg attctcaaag tttatcagca gaacatgagg cagaagaccc  5640
tttctgctcc agcttcttca ggctcaacct tcatcagaat agatagaaag agaggctgtg  5700
agggttctta aaacagaagc aaatctgact cagagaataa acaacctcct agtaaactac  5760
agcttagaca gagcatctgg tggtgagtgt gctcagtgtc ctactcaact gtctggtatc  5820
agccctcatg aggacttctc ttctttccct catagacctc catctctgtt ttccttagcc  5880
tgcagaaatc tggatggcta ttcacagaat gcctgtgctt tcagagttgc atttttctc  5940
tggtattctg gttcaagcat ttgaaggtag gaaaggttct ccaagtgcaa gaaagccagc  6000
cctgagcctc aactgcctgg ctagtgtggt cagtaggatg caaaggctgt tgaatgccac  6060
aaggccaaac tttaacctgt gtaccacaag cctagcagca gaggcagctc tgctcactgg  6120
aactctctgt cttctttctc ctgagccttt tcttttcctg agttttctag ctctcctcaa  6180
ccttacctct gccctaccca ggacaaaccc aagagccact gtttctgtga tgtcctctcc  6240
agccctaatt aggcatcatg acttcagcct gaccttccat gctcagaagc agtgctaatc  6300
cacttcagat gagctgctct atgcaacaca ggcagagcct acaaaccttt gcaccagagc  6360
cctccacata tcagtgtttg ttcatactca cttcaacagc aaatgtgact gctgagatta  6420
agatttaca caagatggtc tgtaatttca cagttagttt tatcccatta ggtatgaaag  6480
aattagcata attcccctta aacatgaatg aatcttagat tttttaataa atagttttgg  6540
aagtaaagac agagacatca ggagcacaag gaatagcctg agaggacaaa cagaacaaga  6600
aagagtctgg aaatacacag gatgttcttg gcctcctcaa agcaagtgca agcagatagt  6660
accagcagcc ccaggctatc agagcccagt gaagagaagt accatgaaag ccacagctct  6720
aaccaccctg ttccagagtg acagacagtc cccaagacaa gccagcctga gccagagaga  6780
gaactgcaag agaaagtttc taatttaggt tctgttagat tcagacaagt gcaggtcatc  6840
ctctctccac agctactcac ctctccagcc taacaaagcc tgcagtccac actccaaccc  6900
tggtgtctca cctcctagcc tctcccaaca tcctgctctc tgaccatctt ctgcatctct  6960
catctcacca tctcccactg tctacagcct actcttgcaa ctaccatctc attttctgac  7020
atcctgtcta catcttctgc catactctgc catctaccat accacctctt accatctacc  7080
acaccatctt ttatctccat ccctctcaga agcctccaag ctgaatcctg ctttatgtgt  7140
tcatctcagc ccctgcatgg aaagctgacc ccagaggcag aactattccc agagagcttg  7200
gccaagaaaa acaaaactac cagcctggcc aggctcagga gtagtaagct gcagtgtctg  7260
ttgtgttcta gcttcaacag ctgcaggagt tccactctca aatgctccac atttctcaca  7320
tcctcctgat tctggtcact acccatcttc aaagaacaga atatctcaca tcagcatact  7380
gtgaaggact agtcatgggt gcagctgctc agagctgcaa agtcattctg gatggtggag  7440
agcttacaaa catttcatga tgctcccccc gctctgatgg ctggagccca atccctacac  7500
```

```
agactcctgc tgtatgtgtt ttcctttcac tctgagccac agccagaggg caggcattca  7560
gtctcctctt caggctgggg ctggggcact gagaactcac ccaacacctt gctctcactc  7620
cttctgcaaa acaagaaaga gctttgtgct gcagtagcca tgaagaatga aaggaaggct  7680
ttaactaaaa aatgtcagag attattttca acccccttact gtggatcacc agcaaggagg  7740
aaacacaaca cagagacatt ttttcccctc aaattatcaa aagaatcact gcatttgtta  7800
aagagagcaa ctgaatcagg aagcagagtt ttgaacatat cagaagttag gaatctgcat  7860
cagagacaaa tgcagtcatg gttgtttgct gcataccagc cctaatcatt agaagcctca  7920
tggacttcaa acatcattcc ctctgacaag atgctctagc ctaactccat gagataaaat  7980
aaatctgcct ttcagagcca aagaagagtc caccagcttc ttctcagtgt gaacaagagc  8040
tccagtcagg ttagtcagtc cagtgcagta gaggagacca gtctgcatcc tctaattttc  8100
aaaggcaaga agatttgttt accctggaca ccaggcacaa gtgaggtcac agagctctta  8160
gatatgcagt cctcatgagt gaggagacta aagcgcatgc catcaagact tcagtgtaga  8220
gaaaacctcc aaaaaagcct cctcactact tctggaatag ctcagaggcc gaggcggcct  8280
cggcctctgc ataaataaaa aaaattagtc agccatgggg cggagaatgg gcggaactgg  8340
gcggagttag gggcgggatg ggcggagtta ggggcgggac tatggttgct gactaattga  8400
gatgcatgct ttgcatactt ctgcctgctg gggagcctgg ggactttcca cacctggttg  8460
ctgactaatt gagatgcatg ctttgcatac ttctgcctgc tggggagcct ggggactttc  8520
cacaccctaa ctgacacaca ttccacagct gcattaatga atcggccaac gcgcggggag  8580
aggcggtttg cgtattgggc gctcttccgc ttcctcgctc actgactcgc tgcgctcggt  8640
cgttcggctg cggcgagcgg tatcagctca ctcaaaggcg gtaatacggt tatccacaga  8700
atcaggggat aacgcaggaa agaacatgtg agcaaaaggc cagcaaaagg ccaggaaccg  8760
taaaaaggcc gcgttgctgg cgtttttcca taggctccgc ccccctgacg agcatcacaa  8820
aaatcgacgc tcaagtcaga ggtggcgaaa cccgacagga ctataaagat accaggcgtt  8880
tccccctgga agctccctcg tgcgctctcc tgttccgacc ctgccgctta ccggatacct  8940
gtccgccttt ctcccttcgg gaagcgtggc gctttctcat agctcacgct gtaggtatct  9000
cagttcggtg taggtcgttc gctccaagct gggctgtgtg cacgaacccc ccgttcagcc  9060
cgaccgctgc gccttatccg gtaactatcg tcttgagtcc aacccggtaa gacacgactt  9120
atcgccactg gcagcagcca ctggtaacag gattagcaga gcgaggtatg taggcggtgc  9180
tacagagttc ttgaagtggt ggcctaacta cggctacact agaagaacag tatttggtat  9240
ctgcgctctg ctgaagccag ttaccttcgg aaaaagagtt ggtagctctt gatccggcaa  9300
acaaaccacc gctggtagcg gtggtttttt tgtttgcaag cagcagatta cgcgcagaaa  9360
aaaaggatct caagaagatc ctttgatctt ttctacgggg tctgacgctc agtggaacga  9420
aaactcacgt taagggattt tggtcatgag attatcaaaa aggatcttca cctagatcct  9480
tttaaattaa aaatgaagtt ttaaatcaat ctaaagtata tatgagtaaa cttggtctga  9540
cagttaccaa tgcttaatca gtgaggcacc tatctcagcg atctgtctat ttcgttcatc  9600
catagttgcc tgactcctgc aaaccacgtt gtgtctcaaa atctctgatg ttacattgca  9660
caagataaaa atatatcatc atgaacaata aaactgtctg cttacataaa cagtaataca  9720
aggggtgtta tgagccatat tcaacgggaa acgtcttgct cgaggccgcg attaaattcc  9780
aacatggatg ctgatttata tgggtataaa tgggctcgcg ataatgtcgg gcaatcaggt  9840
gcgacaatct atcgattgta tgggaagccc gatgcgccag agttgtttct gaaacatggc  9900
aaaggtagcg ttgccaatga tgttacagat gagatggtca gactaaactg gctgacggaa  9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
caagtcgacg tccggcagtc                                             10700
```

```
SEQ ID NO: 10          moltype = DNA  length = 10700
FEATURE                Location/Qualifiers
misc_feature           1..10700
                       note = Synthetic polynucleotide
source                 1..10700
                       mol_type = other DNA
                       organism = synthetic construct
SEQUENCE: 10
ttggccactc cctctctgcg cgctcgctcg ctcactgagg ccgcccgggc aaagcccggg  60
cgtcgggcga cctttggtcg cccggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttaat tattttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
```

```
tgccttcgcc ccgtgccccg ctccgccgcc gcctcgcgcc gcccgccccg gctctgactg  1020
accgcgttac tcccacaggt gagcgggcgg gacggccctt ctcctccggg ctgtaattag  1080
cgcttggttt aatgacggct tgtttctttt ctgtggctgc gtgaaagcct tgaggggctc  1140
cgggagctag agcctctgct aaccatgttc atgccttctt ctttttccta cagctcctgg  1200
gcaacgtgct ggttattgtg ctgtctcatc attttggcaa agaattcctc gaagatccga  1260
agggaaagtc ttccacgact gtgggatccg ttcgaagata tcaccggttg agccaccatg  1320
gaattcagca gccccagcag agaggaatgc cccaagcctc tgagccgggt gtcaatcatg  1380
gccggatctc tgacaggact gctgctgctt caggccgtgt cttgggcttc tggcgctaga  1440
ccttgcatcc ccaagagctt cggctacagc agcgtcgtgt gcgtgtgcaa tgccacctac  1500
tgcgacagct tcgaccctcc tacctttcct gctctgggca ccttcagcag atacgagagc  1560
accagatccg gcagacggat ggaactgagc atgggaccca tccaggccaa tcacacaggc  1620
actggcctgc tgctgacact gcagcctgag cagaaattcc agaaagtgaa aggcttcggc  1680
ggagccatga cagatgccgc cgctctgaat atcctggctc tgtctccacc agctcagaac  1740
ctgctgctca agagctactt cagcgaggaa ggcatcggct acaacatcat cagagtgccc  1800
atggccagct gcgacttcag catcaggacc tacacctacg ccgacacacc cgacgatttc  1860
cagctgcaca acttcagcct gcctgaagag gacaccaagc tgaagatccc tctgatccac  1920
agagccctgc agctggcaca aagacccgtg tcactgctgg cctctccatg gacatctccc  1980
acctggctga aaacaaatgg cgccgtgaat ggcaagggca gcctgaaagg ccaacctggc  2040
gacatctacc accagacctg ggccagatac ttcgtgaagt tcctggacgc ctatgccgag  2100
cacaagctgc agttttgggc cgtgacagcc gagaacgaac cttctgctgg actgctgagc  2160
ggctacccct ttcagtgcct gggctttaca cccgagcacc agcgggactt tatcgcccgt  2220
gatctgggac ccacactggc caatagcacc caccataatg tgcggctgct gatgctggac  2280
gaccagagac tgcttctgcc ccactgggct aaagtggtgc tgacagatcc tgaggccgcc  2340
aaatacgtgc acggaatcgc cgtgcactgg tatctggact ttctggcccc tgccaaggcc  2400
acactgggag agacacacag actgttcccc aacaccatgc tgttcgccag cgaagcctgt  2460
gtgggcagca agttttggga acagagcgtg cggctcggca gctgggatag aggcatgcag  2520
tacagccaca gcatcatcac caacctgctg taccacgtcg tcggctggac cgactggaat  2580
ctggccctga atcctgaagg cggccctaac tgggtccgaa acttcgtgga cagccccatc  2640
atcgtggaca tcaccaagga caccttctac aagcagccca tgttctacca cctgggacac  2700
ttcagcaagt tcatccccga gggctctcag cgcgttggac tggtggcttc ccagaagaac  2760
gatctggacg ccgtggctct gatgcaccct gatggatctg ctgtggtggt ggtcctgaac  2820
cgcagcagca aagatgtgcc cctgaccatc aaggatcccg ccgtgggatt cctggaaaca  2880
atcagccctg gctactccat ccacacctac ctgtggcgta gacagtgaca attgttaatt  2940
aagtttaaac cctcgaggcc gcaagcttat cgataatcaa cctctggatt acaaaatttg  3000
tgaaagattg actggtattc ttaactatgt tgctcctttt acgctatgtg gatacgctgc  3060
tttaatgcct ttgtatcatg ctattgcttc ccgtatggct ttcattttct cctccttgta  3120
taaatcctgg ttgctgtctc tttatgagga gttgtggccc gttgtcaggc aacgtggcgt  3180
ggtgtgcact gtgtttgctg acgcaacccc cactggttgg ggcattgcca ccacctgtca  3240
gctcctttcc gggactttcg ctttccccct ccctattgcc acggcggaac tcatcgccgc  3300
ctgccttgcc cgctgctgga caggggctcg gctgttgggc actgacaatt ccgtggtgtt  3360
gtcggggaaa tcatcgtcct ttccttggct gctcgcctgt gttgccacct ggattctgcg  3420
cgggacgtcc ttctgctacg tcccttcggc cctcaatcca gcggaccttc cttcccgcgg  3480
cctgctgccg gctctgcggc ctcttccgcg tcttcgcctt cgccctcaga cgagtcggat  3540
ctccctttgg gccgcctccc cgcatcgata ccgtcgacta gagctcgctg atcagcctcg  3600
actgtgcctt ctagttgcca gccatctgtt gtttgcccct cccccgtgcc ttccttgacc  3660
ctggaaggtg ccactcccac tgtcctttcc taataaaatg aggaaattgc atcgcattgt  3720
ctgagtaggt gtcattctat tctggggggt ggggtggggc aggacagcaa gggggaggat  3780
tgggaagaca atagcaggca tgctggggag agatccacga taacaaacag ctttttttggg  3840
gtgaacatat tgactgaatt ccctgcagga ggaaccccta gtgatggagt tggccactcc  3900
ctctctgcgc gctcgctcgc tcactgaggc cgcccgggca aagcccgggc gtcgggcgac  3960
ctttggtcgc ccggcctcag tgagcgagcg agcgcgcaga gagggagtgg ccaagcggcc  4020
gctcgtacgg tctcgaggaa ttcctgcagg ataacttgcc aacctcattc taaaatgtat  4080
atagaagccc aaaagacaat aacaaaaata ttcttgtaga acaaaatggg aaagaatgtt  4140
ccactaaata tcaagattta gagcaaagca tgagatgtgt ggggatagac agtgaggctg  4200
ataaaataga gtagagctca gaaacagacc cattgatata tgtaagtgac ctatgaaaaa  4260
aatatggcat tttacaatgg gaaaatgatg gtctttttct tttttagaaa aacagggaaa  4320
tatatttata tgtaaaaaat aaaagggaac ccatatgtca taccatacac acaaaaaaat  4380
tccagtgaat tataagtcta aatggagaag gcaaaacttt aaatctttta gaaaataata  4440
tagaagcatg cagaccagcc tggccaacat gatgaaaccc tctctactaa taataaaatc  4500
agtagaacta ctcaggacta ctttgagtgg gaagtccttt tctatgaaga cttctttggc  4560
caaaattagg ctctaaatgc aaggagatag tgcatcatgc ctggctgcac ttactgataa  4620
atgatgttat caccatcttt aaccaaatgc acaggaacaa gttatggtac tgatgtgctg  4680
gattgagaag gagctctact tccttgacag gacacatttg tatcaactta aaaaagcaga  4740
tttttgccag cagaactatt cattcagagg taggaaactt agaatagatg atgtcactga  4800
ttagcatggc ttccccatct ccacagctgc ttcccaccca ggttgcccac agttgagttt  4860
gtccagtgct cagggctgcc cactctcagt aagaagcccc acaccagccc ctctccaaat  4920
atgttggctg ttccttccat taaagtgacc ccactttaga gcagcaagtg gatttctgtt  4980
tcttacagtt caggaaggag gagtcagctg tgagaacctg gagcctgaga tgcttctaag  5040
tcccactgct actggggtca gggaagccag actccagcat cagcagtcag gagcactaag  5100
cccttgccaa catcctgttt ctcagagaaa ctgcttccat tataatggtt gtcctttttt  5160
aagctatcaa gccaaacaac cagtgtctac cattattctc atcacctgaa gccaagggtt  5220
ctagcaaaag tcaagctgtc ttgtaatggt tgatgtgcct ccagcttctg tcttcagtca  5280
ctccactctt agcctgctct gaatcaactc tgaccacagt tccctggagc ccctgccacc  5340
tgctgcccct gccaccttct ccatctgcag tgctgtgcag ccttctgcac tcttgcagag  5400
ctaataggtg gagacttgaa ggaagaggag gaaagtttct cataatagcc ttgctgcaag  5460
ctcaaatggg aggtgggcac tgtgcccagg agccttggag caaaggctgt gcccaacctc  5520
tgactgcatc caggtttggt cttgacagag ataagaagcc ctggcttttg gagccaaaat  5580
ctaggtcaga cttaggcagg attctcaaag tttatcagca gaacatgagg cagaagaccc  5640
tttctgctcc agcttcttca ggctcaacct tcatcagaat agatagaaag agaggctgtg  5700
```

-continued

```
agggttctta aaacagaagc aaatctgact cagagaataa acaacctcct agtaaactac  5760
agcttagaca gagcatctgg tggtgagtgt gctcagtgtc ctactcaact gtctggtatc  5820
agccctcatg aggacttctc ttctttccct catagacctc catctctgtt ttccttagcc  5880
tgcagaaatc tggatggcta ttcacagaat gcctgtgctt tcagagttgc attttttctc  5940
tggtattctg gttcaagcat ttgaaggtag gaaaggttct ccaagtgcaa gaaagccagc  6000
cctgagcctc aactgcctgg ctagtgtggt cagtaggatg caaaggctgt tgaatgccac  6060
aaggccaaac tttaacctgt gtaccacaag cctagcagca gaggcagctc tgctcactgg  6120
aactctctgt cttctttctc ctgagccttt tcttttcctg agttttctag ctctcctcaa  6180
ccttacctct gccctaccca ggacaaaccc aagagccact gtttctgtga tgtcctctcc  6240
agccctaatt aggcatcatg acttcagcct gaccttccat gctcagaagc agtgctaatc  6300
cacttcagat gagctgctct atgcaacaca ggcagagcct acaaaccttt gcaccagagc  6360
cctccacata tcagtgtttg ttcatactca cttcaacagc aaatgtgact gctgagatta  6420
agattttaca caagatggtc tgtaatttca cagttagttt tatcccatta ggtatgaaag  6480
aattagcata attcccctta aacatgaatg aatcttagat tttttaataa atagttttgg  6540
aagtaaagac agagacatca ggagcacaag gaatagcctg agaggacaaa cagaacaaga  6600
aagagtctgg aaatacacag gatgttcttg gcctcctcaa agcaagtgca agcagatagt  6660
accagcagcc ccaggctatc agagcccagt gaagagaagt accatgaaag ccacagctct  6720
aaccaccctg ttccagagtg acagacagtc cccaagacaa gccagcctga gccagagaga  6780
gaactgcaag agaaagtttc taatttaggt tctgttagat tcagacaagt gcaggtcatc  6840
ctctctccac agctactcac ctctccagcc taacaaagcc tgcagtccac actccaaccc  6900
tggtgtctca cctcctagcc tctcccaaca tcctgctctc tgaccatctt ctgcatctct  6960
catctcacca tctcccactg tctacagcct actcttgcaa ctaccatctc attttctgac  7020
atcctgtcta catcttctgc catactctgc catctaccat accacctctt accatctacc  7080
acaccatctt ttatctccat ccctctcaga agcctccaag ctgaatcctg ctttatgtgt  7140
tcatctcagc ccctgcatgg aaagctgacc ccagaggcag aactattccc agagagcttg  7200
gccaagaaaa acaaaactac cagcctggcc aggctcagga gtagtaagct gcagtgtctg  7260
ttgtgttcta gcttcaacag ctgcaggagt tccactctca aatgctccac atttctcaca  7320
tcctcctgat tctggtcact acccatcttc aaagaacaga atatctcaca tcagcatact  7380
gtgaaggact agtcatgggt gcagctgctc agagctgcaa agtcattctg gatggtggag  7440
agcttacaaa catttcatga tgctcccccc gctctgatgg ctggagccca atccctacac  7500
agactcctgc tgtatgtgtt ttcctttcac tctgagccac agccagaggg caggcattca  7560
gtctcctctt caggctgggg ctggggcact gagaactcac ccaacacctt gctctcactc  7620
cttctgcaaa acaagaaaga gctttgtgct gcagtagcca tgaagaatga aaggaaggct  7680
ttaactaaaa aatgtcagag attattttca accccttact gtggatcacc agcaaggagg  7740
aaacacaaca cagagacatt ttttcccctc aaattatcaa aagaatcact gcatttgtta  7800
aagagagcaa ctgaatcagg aagcagagtt ttgaacatat cagaagttag gaatctgcat  7860
cagagacaaa tgcagtcatg gttgtttgct gcataccagc cctaatcatt agaagcctca  7920
tggacttcaa acatcattcc ctctgacaag atgctctagc ctaactccat gagataaaat  7980
aaatctgcct ttcagagcca aagaagagtc caccagcttc ttctcagtgt gaacaagagc  8040
tccagtcagg ttagtcagtc cagtgcagta gaggagacca gtctgcatcc tctaattttc  8100
aaaggcaaga agatttgttt accctggaca ccaggcacaa gtgaggtcac agagctctta  8160
gatatgcagt cctcatgagt gaggagacta aagcgcatgc catcaagact tcagtgtaga  8220
gaaaacctcc aaaaaagcct cctcactact tctggaatag ctcagaggcc gaggcggcct  8280
cggcctctgc ataaataaaa aaaattagtc agccatgggg cggagaatgg gcggaactgg  8340
gcggagttag gggcgggatg ggcggagtta ggggcgggac tatggttgct gactaattga  8400
gatgcatgct ttgcatactt ctgcctgctg gggagcctgg ggactttcca cacctggttg  8460
ctgactaatt gagatgcatg ctttgcatac ttctgcctgc tggggagcct ggggactttc  8520
cacaccctaa ctgacacaca ttccacagct gcattaatga atcggccaac gcgcggggag  8580
aggcggtttg cgtattgggc gctcttccgc ttcctcgctc actgactcgc tgcgctcggt  8640
cgttcggctg cggcgagcgg tatcagctca ctcaaaggcg gtaatacggt tatccacaga  8700
atcaggggat aacgcaggaa agaacatgtg agcaaaaggc cagcaaaagg ccaggaaccg  8760
taaaaaggcc gcgttgctgg cgtttttcca taggctccgc ccccctgacg agcatcacaa  8820
aaatcgacgc tcaagtcaga ggtggcgaaa cccgacagga ctataaagat accaggcgtt  8880
tccccctgga agctccctcg tgcgctctcc tgttccgacc ctgccgctta ccggatacct  8940
gtccgccttt ctcccttcgg gaagcgtggc gctttctcat agctcacgct gtaggtatct  9000
cagttcggtg taggtcgttc gctccaagct gggctgtgtg cacgaacccc ccgttcagcc  9060
cgaccgctgc gccttatccg gtaactatcg tcttgagtcc aacccggtaa gacacgactt  9120
atcgccactg gcagcagcca ctggtaacag gattagcaga gcgaggtatg taggcggtgc  9180
tacagagttc ttgaagtggt ggcctaacta cggctacact agaagaacag tatttggtat  9240
ctgcgctctg ctgaagccag ttaccttcgg aaaaagagtt ggtagctctt gatccggcaa  9300
acaaaccacc gctggtagcg gtggtttttt tgtttgcaag cagcagatta cgcgcagaaa  9360
aaaaggatct caagaagatc ctttgatctt ttctacgggg tctgacgctc agtggaacga  9420
aaactcacgt taagggattt tggtcatgag attatcaaaa aggatcttca cctagatcct  9480
tttaaattaa aaatgaagtt ttaaatcaat ctaaagtata tatgagtaaa cttggtctga  9540
cagttaccaa tgcttaatca gtgaggcacc tatctcagcg atctgtctat ttcgttcatc  9600
catagttgcc tgactcctgc aaaccacgtt gtgtctcaaa atctctgatg ttacattgca  9660
caagataaaa atatatcatc atgaacaata aaactgtctg cttacataaa cagtaataca  9720
aggggtgtta tgagccatat tcaacgggaa acgtcttgct cgaggccgcg attaaattcc  9780
aacatggatg ctgatttata tgggtataaa tgggctcgcg ataatgtcgg gcaatcaggt  9840
gcgacaatct atcgattgta tgggaagccc gatgcgccag agttgtttct gaaacatggc  9900
aaaggtagcg ttgccaatga tgttacagat gagatggtca gactaaactg gctgacggaa  9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
```

```
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
caagtcgacg tccggcagtc                                              10700

SEQ ID NO: 11          moltype = DNA  length = 11188
FEATURE                Location/Qualifiers
misc_feature           1..11188
                       note = Synthetic polynucleotide
source                 1..11188
                       mol_type = other DNA
                       organism = synthetic construct
SEQUENCE: 11
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactatt agatctgatg gccgcgctag ctctgggtat ttaagcccga gtgagcacgc  180
agggtctcca ttttgaagcg ggaggttacg cgttcgtcga ctactagtgg gtaccagagc  240
gtggtgactg agatgttttc taggaaacac aaaagataca aaaaagaaca cgtggaagga  300
tagccaaaaa ggggggctgc cccccatttcc tgcaccccgc tgcgatggct ggcaccattt  360
ggaagacttc gagatacact gttgagcgca gtaagacaac agtgtatctc gaagtcttcc  420
agatggggcc agccggtcca ctctgtatcc aggccagttc tgcaaggcgt tcgaggacca  480
ccccccctccc ctcgccacca gggtggtctc atacagaact tataagattc ccaaatccaa  540
agacatttca cgtttatggt gatttcccag aacacatagc gacatgcaaa tattgcaggg  600
cgccactccc ctgtccctca cagccatctt cctgccaggg cgcacgcgcg ctgggtgttc  660
ccgcctagtg acactgggcc cgcgattcct tggagcgggt tgatgacgtc agcgtttccc  720
atggtgaatc cctaggttct agaaccggtg acgtctccca tggtgaagct tggatctgaa  780
ttcggtacct agttattaat agtaatcaat tacggggtca ttagttcata gcccatatat  840
ggagttccgc gttacataac ttacggtaaa tggcccgcct ggctgaccgc ccaacgaccc  900
ccgcccattg acgtcaataa tgacgtatgt tcccatagta acgccaatag ggactttcca  960
ttgacgtcaa tgggtggagt atttacggta aactgcccac ttggcagtac atcaagtgta  1020
tcatatgcca agtacgcccc ctattgacgt caatgacggt aaatggcccg cctggcatta  1080
tgcccagtac atgaccttat gggactttcc tacttggcag tacatctacg tattagtcat  1140
cgctattacc atggtcgagg tgagccccac gttctgcttc actctcccca tctccccccc  1200
ctccccaccc ccaattttgt atttatttat tttttaatta ttttgtgcag cgatgggggc  1260
gggggggggg gggggcgcgc cgccaggcgg ggcggggcgg ggcgaggggc ggggcggggc  1320
gaggcggaga ggtgcggcgg cagccaatca gagcggcgcg ctccgaaagt ttccttttat  1380
ggcgaggcgg cggcggcggc ggccctataa aaagcgaagc gcgcggcggg cgggagtcgc  1440
tgcgacgctg ccttcgcccc gtgccccgct ccgccgccgc ctcgcgccgc ccgccccggc  1500
tctgactgac cgcgttactc ccacaggtga gcgggcggga cggcccttct cctccgggct  1560
gtaattagcg cttggtttaa tgacggcttg tttcttttct gtggctgcgt gaaagccttg  1620
aggggctccg ggagctagag cctctgctaa ccatgttcat gccttcttct ttttcctaca  1680
gctcctgggc aacgtgctgg ttattgtgct gtctcatcat tttggcaaag aattcctcga  1740
agatccgaag ggaaagtctt ccacgactgt gggatccgtt cgaagatatc accggttgag  1800
ccaccatgga attcagcagc cccagcagag aggaatgccc caagcctctg agccgggtgt  1860
caatcatggc cggatctctg acaggactgc tgctgcttca ggccgtgtct tgggcttctg  1920
gcgctagacc ttgcatcccc aagagcttcg gctacagcag cgtcgtgtgc gtgtgcaatg  1980
ccacctactg cgacagcttc gaccctccta cctttcctgc tctgggcacc ttcagcagat  2040
acgagagcac cagatccggc agacggatgg aactgagcat gggacccatc caggccaatc  2100
acacaggcac tggcctgctg ctgacactgc agcctgagca gaaattccag aaagtgaaag  2160
gcttcggcgg agccatgaca gatgccgccg ctctgaatat cctggctctg tctccaccag  2220
ctcagaacct gctgctcaag agctacttca gcgaggaagg catcggctac aacatcatca  2280
gagtgcccat ggccagctgc gacttcagca tcaggaccta cacctacgcc gacacacccg  2340
acgatttcca gctgcacaac ttcagcctgc ctgaagagga caccaagctg aagatccctc  2400
tgatccacag agccctgcag ctggcacaaa gacccgtgtc actgctggcc tctccatgga  2460
catctcccac ctggctgaaa acaaatggcg ccgtgaatgg caagggcagc ctgaaaggcc  2520
aacctggcga catctaccac cagacctggg ccagatactt cgtgaagttc ctggacgcct  2580
atgccgagca caagctgcag ttttgggccg tgacagccga gaacgaacct tctgctggac  2640
tgctgagcgg ctacccccttt cagtgcctgg gctttacacc cgagcaccag cgggacttta  2700
tcgcccgtga tctgggaccc acactggcca atagcaccca ccataatgtg cggctgctga  2760
tgctggacga ccagagactg cttctgcccc actgggctaa agtggtgctg acagatcctg  2820
aggccgccaa atacgtgcac ggaatcgccg tgcactggta tctggacttt ctggcccctg  2880
ccaaggccac actgggagag acacacagac tgttccccaa caccatgctg ttcgccagcg  2940
aagcctgtgt gggcagcaag ttttgggaac agagcgtgcg gctcggcagc tgggatagag  3000
gcatgcagta cagccacagc atcatcacca acctgctgta ccacgtcgtc ggctggaccg  3060
actggaatct ggccctgaat cctgaaggcg gccctaactg ggtccgaaac ttcgtggaca  3120
gccccatcat cgtggacatc accaaggaca ccttctacaa gcagcccatg ttctaccacc  3180
tgggacactt cagcaagttc atccccgagg gctctcagcg cgttggactg gtggcttccc  3240
agaagaacga tctggacgcc gtggctctga tgcaccctga tggatctgct gtggtggtgg  3300
tcctgaaccg cagcagcaaa gatgtgcccc tgaccatcaa ggatcccgcc gtgggattcc  3360
tggaaacaat cagccctggc tactccatcc acacctacct gtggcgtaga cagtgacaat  3420
tgttaattaa gtttaaaccc tcgaggccgc aagcttatcg ataatcaacc tctggattac  3480
aaaatttgtg aaagattgac tggtattctt aactatgttg ctccttttac gctatgtgga  3540
tacgctgctt taatgccttt gtatcatgct attgcttccc gtatggcttt cattttctcc  3600
tccttgtata aatcctggtt gctgtctctt tatgaggagt tgtggcccgt tgtcaggcaa  3660
cgtggcgtgg tgtgcactgt gtttgctgac gcaacccccca ctggttgggg cattgccacc  3720
acctgtcagc tcctttccgg gactttcgct ttcccccctcc ctattgccac ggcggaactc  3780
atcgccgcct gccttgcccg ctgctggaca ggggctcggc tgttgggcac tgacaattcc  3840
gtggtgttgt cggggaaatc atcgtccttt ccttggctgc tcgcctgtgt tgccacctgg  3900
```

-continued attctgcgcg ggacgtcctt ctgctacgtc ccttcggccc tcaatccagc ggaccttcct 3960
tcccgcggcc tgctgccggc tctgcggcct cttccgcgtc ttcgccttcg ccctcagacg 4020
agtcggatct ccctttgggc cgcctccccg catcgatacc gtcgactaga gctcgctgat 4080
cagcctcgac tgtgccttct agttgccagc catctgttgt ttgcccctcc cccgtgcctt 4140
ccttgaccct ggaaggtgcc actcccactg tcctttccta ataaaatgag gaaattgcat 4200
cgcattgtct gagtaggtgt cattctattc tggggggtgg ggtggggcag gacagcaagg 4260
gggaggattg ggaagacaat agcaggcatg ctggggagag atccacgata acaaacagct 4320
tttttggggt gaacatattg actgaattcc ctgcaggttg gccactccct ctctgcgcgc 4380
tcgctcgctc actgaggccg cccgggcaaa gcccgggcgt cgggcgacct ttggtcgccc 4440
ggcctcagtg agcgagcgag cgcgcagaga gggagtggcc aactccatca ctaggggttc 4500
ctgcggccgc tcgtacggtc tcgaggaatt cctgcaggat aacttgccaa cctcattcta 4560
aaatgtatat agaagcccaa aagacaataa caaaaatatt cttgtagaac aaaatgggaa 4620
agaatgttcc actaaatatc aagatttaga gcaaagcatg agatgtgtgg ggatagacag 4680
tgaggctgat aaaatagagt agagctcaga aacagaccca ttgatatatg taagtgacct 4740
atgaaaaaaa tatggcattt tacaatggga aaatgatggt ctttttcttt tttagaaaaa 4800
cagggaaata tatttatatg taaaaaataa aagggaaccc atatgtcata ccatacacac 4860
aaaaaaattc cagtgaatta taagtctaaa tggagaaggc aaaactttaa atcttttaga 4920
aaataatata gaagcatgca gaccagcctg gccaacatga tgaaaccctc tctactaata 4980
ataaaatcag tagaactact caggactact ttgagtggga agtccttttc tatgaagact 5040
tctttggcca aaattaggct ctaaatgcaa ggagatagtg catcatgcct ggctgcactt 5100
actgataaat gatgttatca ccatctttaa ccaaatgcac aggaacaagt tatggtactg 5160
atgtgctgga ttgagaagga gctctacttc cttgacagga cacatttgta tcaacttaaa 5220
aaagcagatt tttgccagca gaactattca ttcagaggta ggaaacttag aatagatgat 5280
gtcactgatt agcatggctt ccccatctcc acagctgctt cccacccagg ttgcccacag 5340
ttgagtttgt ccagtgctca gggctgccca ctctcagtaa gaagccccac accagcccct 5400
ctccaaatat gttggctgtt ccttccatta aagtgacccc actttagagc agcaagtgga 5460
tttctgtttc ttacagttca ggaaggagga gtcagctgtg agaacctgga gcctgagatg 5520
cttctaagtc ccactgctac tggggtcagg gaagccagac tccagcatca gcagtcagga 5580
gcactaagcc cttgccaaca tcctgtttct cagagaaact gcttccatta taatggttgt 5640
cctttttttaa gctatcaagc caaacaacca gtgtctacca ttattctcat cacctgaagc 5700
caagggttct agcaaaagtc aagctgtctt gtaatggttg atgtgcctcc agcttctgtc 5760
ttcagtcact ccactcttag cctgctctga atcaactctg accacagttc cctggagccc 5820
ctgccacctg ctgcccctgc caccttctcc atctgcagtg ctgtgcagcc ttctgcactc 5880
ttgcagagct aataggtgga gacttgaagg aagaggagga aagtttctca taatagcctt 5940
gctgcaagct caaatgggag gtgggcactg tgcccaggag ccttggagca aaggctgtgc 6000
ccaacctctg actgcatcca ggtttggtct tgacagagat aagaagccct ggcttttgga 6060
gccaaaatct aggtcagact taggcaggat tctcaaagtt tatcagcaga acatgaggca 6120
gaagaccctt tctgctccag cttcttcagg ctcaaccttc atcagaatag atagaaagag 6180
aggctgtgag ggttcttaaa acagaagcaa atctgactca gagaataaac aacctcctag 6240
taaactacag cttagacaga gcatctggtg gtgagtgtgc tcagtgtcct actcaactgt 6300
ctggtatcag ccctcatgag gacttctctt ctttccctca tagacctcca tctctgtttt 6360
ccttagcctg cagaaatctg gatggctatt cacagaatgc ctgtgctttc agagttgcat 6420
tttttctctg gtattctggt tcaagcattt gaaggtagga aaggttctcc aagtgcaaga 6480
aagccagccc tgagcctcaa ctgcctggct agtgtggtca gtaggatgca aaggctgttg 6540
aatgccacaa ggccaaactt taacctgtgt accacaagcc tagcagcaga ggcagctctg 6600
ctcactggaa ctctctgtct tctttctcct gagccttttc ttttcctgag ttttctagct 6660
ctcctcaacc ttacctctgc cctacccagg acaaacccaa gagccactgt ttctgtgatg 6720
tcctctccag ccctaattag gcatcatgac ttcagcctga ccttccatgc tcagaagcag 6780
tgctaatcca cttcagatga gctgctctat gcaacacagg cagagcctac aaacctttgc 6840
accagagccc tccacatatc agtgtttgtt catactcact tcaacagcaa atgtgactgc 6900
tgagattaag attttacaca agatggtctg taatttcaca gttagtttta tcccattagg 6960
tatgaaagaa ttagcataat tccccttaaa catgaatgaa tcttagattt tttaataaat 7020
agttttggaa gtaaagacag agacatcagg agcacaagga atagcctgag aggacaaaca 7080
gaacaagaaa gagtctggaa atacacagga tgttcttggc ctcctcaaag caagtgcaag 7140
cagatagtac cagcagcccc aggctatcag agcccagtga agagaagtac catgaaagcc 7200
acagctctaa ccaccctgtt ccagagtgac agacagtccc caagacaagc cagcctgagc 7260
cagagagaga actgcaagag aaagtttcta atttaggttc tgttagattc agacaagtgc 7320
aggtcatcct ctctccacag ctactcacct ctccagccta acaaagcctg cagtccacac 7380
tccaaccctg gtgtctcacc tcctagcctc tcccaacatc ctgctctctg accatcttct 7440
gcatctctca tctcaccatc tcccactgtc tacagcctac tcttgcaact accatctcat 7500
tttctgacat cctgtctaca tcttctgcca tactctgcca tctaccatac cacctcttac 7560
catctaccac accatctttt atctccatcc ctctcagaag cctccaagct gaatcctgct 7620
ttatgtgttc atctcagccc ctgcatggaa agctgacccc agaggcagaa ctattcccag 7680
agagcttggc caagaaaaac aaaactacca gcctggccag gctcaggagt agtaagctgc 7740
agtgtctgtt gtgttctagc ttcaacagct gcaggagttc cactctcaaa tgctccacat 7800
ttctcacatc ctcctgattc tggtcactac ccatcttcaa agaacagaat atctcacatc 7860
agcatactgt gaaggactag tcatgggtgc agctgctcag agctgcaaag tcattctgga 7920
tggtggagag cttacaaaca tttcatgatg ctccccccgc tctgatggct ggagcccaat 7980
ccctacacag actcctgctg tatgtgtttt cctttcactc tgagccacag ccagagggca 8040
ggcattcagt ctcctcttca ggctggggct ggggcactga gaactcaccc aacaccttgc 8100
tctcactcct tctgcaaaac aagaaagagc tttgtgctgc agtagccatg aagaatgaaa 8160
ggaaggcttt aactaaaaaa tgtcagagat tattttcaac cccttactgt ggatcaccag 8220
caaggaggaa acacaacaca gagacatttt ttcccctcaa attatcaaaa gaatcactgc 8280
atttgttaaa gagagcaact gaatcaggaa gcagagtttt gaacatatca gaagttagga 8340
atctgcatca gagacaaatg cagtcatggt tgtttgctgc ataccagccc taatcattag 8400
aagcctcatg gacttcaaac atcattccct ctgacaagat gctctagcct aactccatga 8460
gataaaataa atctgccttt cagagccaaa gaagagtcca ccagcttctt ctcagtgtga 8520
acaagagctc cagtcaggtt agtcagtcca gtgcagtaga ggagaccagt ctgcatcctc 8580
taattttcaa aggcaagaag atttgtttac cctggacacc aggcacaagt gaggtcacag 8640

```
agctcttaga tatgcagtcc tcatgagtga ggagactaaa gcgcatgcca tcaagacttc  8700
agtgtagaga aaacctccaa aaaagcctcc tcactacttc tggaatagct cagaggccga  8760
ggcggcctcg gcctctgcat aaataaaaaa aattagtcag ccatggggcg gagaatgggc  8820
ggaactgggc ggagttaggg gcgggatggg cggagttagg ggcgggacta tggttgctga  8880
ctaattgaga tgcatgcttt gcatacttct gcctgctggg gagcctgggg actttccaca  8940
cctggttgct gactaattga gatgcatgct ttgcatactt ctgcctgctg gggagcctgg  9000
ggactttcca caccctaact gacacacatt ccacagctgc attaatgaat cggccaacgc  9060
gcggggagag gcggtttgcg tattgggcgc tcttccgctt cctcgctcac tgactcgctg  9120
cgctcggtcg ttcggctgcg gcgagcggta tcagctcact caaaggcggt aatacggtta  9180
tccacagaat caggggataa cgcaggaaag aacatgtgag caaaaggcca gcaaaaggcc  9240
aggaaccgta aaaaggccgc gttgctggcg tttttccata ggctccgccc ccctgacgag  9300
catcacaaaa atcgacgctc aagtcagagg tggcgaaacc cgacaggact ataaagatac  9360
caggcgtttc cccctggaag ctccctcgtg cgctctcctg ttccgaccct gccgcttacc  9420
ggatacctgt ccgcctttct cccttcggga agcgtggcgc tttctcatag ctcacgctgt  9480
aggtatctca gttcggtgta ggtcgttcgc tccaagctgg gctgtgtgca cgaacccccc  9540
gttcagcccg accgctgcgc cttatccggt aactatcgtc ttgagtccaa cccggtaaga  9600
cacgacttat cgccactggc agcagccact ggtaacagga ttagcagagc gaggtatgta  9660
ggcggtgcta cagagttctt gaagtggtgg cctaactacg gctacactag aagaacagta  9720
tttggtatct gcgctctgct gaagccagtt accttcggaa aaagagttgg tagctcttga  9780
tccggcaaac aaaccaccgc tggtagcggt ggtttttttg tttgcaagca gcagattacg  9840
cgcagaaaaa aaggatctca agaagatcct ttgatctttt ctacggggtc tgacgctcag  9900
tggaacgaaa actcacgtta agggattttg gtcatgagat tatcaaaaag gatcttcacc  9960
tagatccttt taaattaaaa atgaagtttt aaatcaatct aaagtatata tgagtaaact  10020
tggtctgaca gttaccaatg cttaatcagt gaggcaccta tctcagcgat ctgtctattt  10080
cgttcatcca tagttgcctg actcctgcaa accacgttgt gtctcaaaat ctctgatgtt  10140
acattgcaca agataaaaat atatcatcat gaacaataaa actgtctgct tacataaaca  10200
gtaatacaag gggtgttatg agccatattc aacgggaaac gtcttgctcg aggccgcgat  10260
taaattccaa catggatgct gatttatatg ggtataaatg ggctcgcgat aatgtcgggc  10320
aatcaggtgc gacaatctat cgattgtatg ggaagcccga tgcgccagag ttgtttctga  10380
aacatggcaa aggtagcgtt gccaatgatg ttacagatga gatggtcaga ctaaactggc  10440
tgacggaatt tatgcctctt ccgaccatca agcattttat ccgtactcct gatgatgcat  10500
ggttactcac cactgcgatc cccgggaaaa cagcattcca ggtattagaa gaatatcctg  10560
attcaggtga aaatattgtt gatgcgctgg cagtgttcct gcgccggttg cattcgattc  10620
ctgtttgtaa ttgtcctttt aacagcgatc gcgtatttcg tctcgctcag gcgcaatcac  10680
gaatgaataa cggtttggtt gatgcgagtg attttgatga cgagcgtaat ggctggcctg  10740
ttgaacaagt ctggaaagaa atgcataagc ttttgccatt ctcaccggat tcagtcgtca  10800
ctcatggtga tttctcactt gataacctta tttttgacga ggggaaatta ataggttgta  10860
ttgatgttgg acgagtcgga atcgcagacc gataccagga tcttgccatc ctatggaact  10920
gcctcggtga gttttctcct tcattacaga aacggctttt tcaaaaatat ggtattgata  10980
atcctgatat gaataaattg cagtttcatt tgatgctcga tgagtttttc taagggcggc  11040
ctgccaccat acccacgccg aaacaagcgc tcatgagccc gaagtggcga gcccgatctt  11100
ccccatcggt gatgtcggcg atataggcgc cagcaaccgc acctgtggcg ccggtgatga  11160
gggcgcgcca agtcgacgtc cggcagtc                                    11188

SEQ ID NO: 12          moltype = DNA  length = 11187
FEATURE                Location/Qualifiers
misc_feature           1..11187
                       note = Synthetic polynucleotide
source                 1..11187
                       mol_type = other DNA
                       organism = synthetic construct
SEQUENCE: 12
ctagaaccgg tgacgtctcc catggtgaag cttggatctg aattcggtac ctagttataa  60
tagtaatcaa ttacggggtc attagttcat agcccatata tggagttccg cgttacataa  120
cttacggtaa atggcccgcc tggctgaccg cccaacgacc cccgcccatt gacgtcaata  180
atgacgtatg ttcccatagt aacgccaata gggactttcc attgacgtca atgggtggag  240
tatttacggt aaactgccca cttggcagta catcaagtgt atcatatgcc aagtacgccc  300
cctattgacg tcaatgacgg taaatggccc gcctggcatt atgcccagta catgacctta  360
tgggactttc ctacttggca gtacatctac gtattagtca tcgctattac catggtcgag  420
gtgagcccca cgttctgctt cactctcccc atctcccccc cctccccacc cccaattttg  480
tatttattta tttttaatt attttgtgca gcgatggggg cgggggggg ggggggcgc  540
gcgccaggcg gggcggggcg gggcgagggg cggggcgggg cgaggcggag aggtgcggcg  600
gcagccaatc agagcggcgc gctccgaaag tttcctttta tggcgaggcg gcggcggcgg  660
cggccctata aaaagcgaag cgcgcggcgg gcgggagtcg ctgcgacgct gccttcgccc  720
cgtgccccgc tccgccgccg cctcgcgccg cccgccccgg ctctgactga ccgcgttact  780
cccacaggtg agcgggcggg acggcccttc tcctccgggc tgtaattagc gcttggttta  840
atgacggctt gtttcttttc tgtggctgcg tgaaagcctt gaggggctcc gggagctaga  900
gcctctgcta accatgttca tgccttcttc tttttcctac agctcctggg caacgtgctg  960
gttattgtgc tgtctcatca ttttggcaaa gaattcctcg aagatccgaa gggaaagtct  1020
tccacgactg tgggatccgt tcgaagatat caccggttga gccaccatgg aattcagcag  1080
ccccagcaga gaggaatgcc ccaagcctct gagccgggtg tcaatcatgg ccggatctct  1140
gacaggactg ctgctgcttc aggccgtgtc ttgggcttct ggcgctagac cttgcatccc  1200
caagagcttc ggctacagca gcgtcgtgtg cgtgtgcaat gccacctact gcgacagctt  1260
cgaccctcct acctttcctg ctctgggcac cttcagcaga tacgagagca ccagatccgg  1320
cagacggatg gaactgagca tgggacccat ccaggccaat cacacaggca ctggcctgct  1380
gctgacactg cagcctgagc agaaattcca gaaagtgaaa ggcttcggcg gagccatgac  1440
agatgccgcc gctctgaata tcctggctct gtctccacca gctcagaacc tgctgctcaa  1500
gagctacttc agcgaggaag gcatcggcta caacatcatc agagtgccca tggccagctg  1560
cgacttcagc atcaggacct acacctacgc cgacacaccc gacgatttcc agctgcacaa  1620
```

-continued

```
cttcagcctg cctgaagagg acaccaagct gaagatccct ctgatccaca gagccctgca  1680
gctggcacaa agacccgtgt cactgctggc ctctccatgg acatctccca cctggctgaa  1740
aacaaatggc gccgtgaatg gcaagggcag cctgaaaggc caacctggcg acatctacca  1800
ccagacctgg gccagatact tcgtgaagtt cctggacgcc tatgccgagc acaagctgca  1860
gttttgggcc gtgacagccg agaacgaacc ttctgctgga ctgctgagcg gctacccctt  1920
tcagtgcctg ggctttacac ccgagcacca gcgggacttt atcgcccgtg atctgggacc  1980
cacactggcc aatagcaccc accataatgt gcggctgctg atgctggacg accagagact  2040
gcttctgccc cactgggcta aagtggtgct gacagatcct gaggccgcca aatacgtgca  2100
cggaatcgcc gtgcactggt atctggactt tctggcccct gccaaggcca cactgggaga  2160
gacacacaga ctgttcccca acaccatgct gttcgccagc gaagcctgtg tgggcagcaa  2220
gttttgggaa cagagcgtgc ggctcggcag ctgggataga ggcatgcagt acagccacag  2280
catcatcacc aacctgctgt accacgtcgt cggctggacc gactggaatc tggccctgaa  2340
tcctgaaggc ggccctaact gggtccgaaa cttcgtggac agccccatca tcgtggacat  2400
caccaaggac accttctaca agcagcccat gttctaccac ctgggacact tcagcaagtt  2460
catccccgag ggctctcagc gcgttggact ggtggcttcc cagaagaacg atctggacgc  2520
cgtggctctg atgcaccctg atggatctgc tgtggtggtg gtcctgaacc gcagcagcaa  2580
agatgtgccc ctgaccatca aggatcccgc cgtgggattc ctggaaacaa tcagccctgg  2640
ctactccatc cacacctacc tgtggcgtag acagtgacaa ttgttaatta agtttaaacc  2700
ctcgaggccg caagcttatc gataatcaac ctctggatta caaaatttgt gaaagattga  2760
ctggtattct taactatgtt gctcctttta cgctatgtgg atacgctgct ttaatgcctt  2820
tgtatcatgc tattgcttcc cgtatggctt tcattttctc ctccttgtat aaatcctggt  2880
tgctgtctct ttatgaggag ttgtggcccg ttgtcaggca acgtggcgtg gtgtgcactg  2940
tgtttgctga cgcaaccccc actggttggg gcattgccac cacctgtcag ctcctttccg  3000
ggactttcgc tttccccctc cctattgcca cggcggaact catcgccgcc tgccttgccc  3060
gctgctggac aggggctcgg ctgttgggca ctgacaattc cgtggtgttg tcggggaaat  3120
catcgtcctt tccttggctg ctcgcctgtg ttgccacctg gattctgcgc gggacgtcct  3180
tctgctacgt cccttcggcc ctcaatccag cggaccttcc ttcccgcggc ctgctgccgg  3240
ctctgcggcc tcttccgcgt cttcgccttc gccctcagac gagtcggatc tccctttggg  3300
ccgcctcccc gcatcgatac cgtcgactag agctcgctga tcagcctcga ctgtgccttc  3360
tagttgccag ccatctgttg tttgcccctc ccccgtgcct tccttgaccc tggaaggtgc  3420
cactcccact gtcctttcct aataaaatga ggaaattgca tcgcattgtc tgagtaggtg  3480
tcattctatt ctggggggtg gggtggggca ggacagcaag ggggaggatt gggaagacaa  3540
tagcaggcat gctggggaga gatccacgat aacaaacagc tttttggggg tgaacatatt  3600
gactgaattc cctgcaggtt ggccactccc tctctgcgcg ctcgctcgct cactgaggcc  3660
gcccgggcaa agcccgggcg tcgggcgacc tttggtcgcc cggcctcagt gagcgagcga  3720
gcgcgcagag agggagtggc caactccatc actaggggtt cctgcggccg ctcgtacggt  3780
ctcgaggaat tcctgcagga taacttgcca acctcattct aaaatgtata tagaagccca  3840
aaagacaata acaaaaatat tcttgtagaa caaaatggga aagaatgttc cactaaatat  3900
caagatttag agcaaagcat gagatgtgtg gggatagaca gtgaggctga taaaatagag  3960
tagagctcag aaacagaccc attgatatat gtaagtgacc tatgaaaaaa atatggcatt  4020
ttacaatggg aaaatgatgg tctttttctt ttttagaaaa acagggaaat atatttatat  4080
gtaaaaaata aaagggaacc catatgtcat accatacaca caaaaaaatt ccagtgaatt  4140
ataagtctaa atggagaagg caaaacttta aatcttttag aaaataatat agaagcatgc  4200
agaccagcct ggccaacatg atgaaaccct ctctactaat aataaaatca gtagaactac  4260
tcaggactac tttgagtggg aagtcctttt ctatgaagac ttctttggcc aaaattaggc  4320
tctaaatgca aggagatagt gcatcatgcc tggctgcact tactgataaa tgatgttatc  4380
accatcttta accaaatgca caggaacaag ttatggtact gatgtgctgg attgagaagg  4440
agctctactt ccttgacagg acacatttgt atcaacttaa aaaagcagat ttttgccagc  4500
agaactattc attcagaggt aggaaactta gaatagatga tgtcactgat tagcatggct  4560
tccccatctc cacagctgct tcccacccag gttgcccaca gttgagtttg tccagtgctc  4620
agggctgccc actctcagta agaagcccca caccagcccc tctccaaata tgttggctgt  4680
tccttccatt aaagtgaccc cactttagag cagcaagtgg atttctgttt cttacagttc  4740
aggaaggagg agtcagctgt gagaacctgg agcctgagat gcttctaagt cccactgcta  4800
ctggggtcag ggaagccaga ctccagcatc agcagtcagg agcactaagc ccttgccaac  4860
atcctgtttc tcagagaaac tgcttccatt ataatggttg tcctttttta agctatcaag  4920
ccaaacaacc agtgtctacc attattctca tcacctgaag ccaagggttc tagcaaaagt  4980
caagctgtct tgtaatggtt gatgtgcctc cagcttctgt cttcagtcac tccactctta  5040
gcctgctctg aatcaactct gaccacagtt ccctggagcc cctgccacct gctgcccctg  5100
ccaccttctc catctgcagt gctgtgcagc cttctgcact cttgcagagc taataggtgg  5160
agacttgaag gaagaggagg aaagtttctc ataatagcct tgctgcaagc tcaaatggga  5220
ggtgggcact gtgcccagga gccttggagc aaaggctgtg cccaacctct gactgcatcc  5280
aggtttggtc ttgacagaga taagaagccc tggcttttgg agccaaaatc taggtcagac  5340
ttaggcagga ttctcaaagt ttatcagcag aacatgaggc agaagaccct ttctgctcca  5400
gcttcttcag gctcaacctt catcagaata gatagaaaga gaggctgtga gggttcttaa  5460
aacagaagca aatctgactc agagaataaa caacctccta gtaaactaca gcttagacag  5520
agcatctggt ggtgagtgtg ctcagtgtcc tactcaactg tctggtatca gccctcatga  5580
ggacttctct tctttccctc atagacctcc atctctgttt tccttagcct gcagaaatct  5640
ggatggctat tcacagaatg cctgtgcttt cagagttgca ttttttctct ggtattctgg  5700
ttcaagcatt tgaaggtagg aaaggttctc caagtgcaag aaagccagcc ctgagcctca  5760
actgcctggc tagtgtggtc agtaggatgc aaaggctgtt gaatgccaca aggccaaact  5820
ttaacctgtg taccacaagc ctagcagcag aggcagctct gctcactgga actctctgtc  5880
ttctttctcc tgagcctttt cttttcctga gttttctagc tctcctcaac cttacctctg  5940
ccctacccag gacaaaccca agagccactg tttctgtgat gtcctctcca gccctaatta  6000
ggcatcatga cttcagcctg accttccatg ctcagaagca gtgctaatcc acttcagatg  6060
agctgctcta tgcaacacag gcagagccta caaacctttg caccagagcc ctccacatat  6120
cagtgtttgt tcatactcac ttcaacagca aatgtgactg ctgagattaa gattttacac  6180
aagatggtct gtaatttcac agttagtttt atcccattag gtatgaaaga attagcataa  6240
ttccccttaa acatgaatga atcttagatt ttttaataaa tagttttgga agtaaagaca  6300
gagacatcag gagcacaagg aatagcctga gaggacaaac agaacaagaa agagtctgga  6360
```

-continued

```
aatacacagg atgttcttgg cctcctcaaa gcaagtgcaa gcagatagta ccagcagccc  6420
caggctatca gagcccagtg aagagaagta ccatgaaagc cacagctcta accaccctgt  6480
tccagagtga cagacagtcc ccaagacaag ccagcctgag ccagagagag aactgcaaga  6540
gaaagtttct aatttaggtt ctgttagatt cagacaagtg caggtcatcc tctctccaca  6600
gctactcacc tctccagcct aacaaagcct gcagtccaca ctccaaccct ggtgtctcac  6660
ctcctagcct ctcccaacat cctgctctct gaccatcttc tgcatctctc atctcaccat  6720
ctcccactgt ctacagccta ctcttgcaac taccatctca ttttctgaca tcctgtctac  6780
atcttctgcc atactctgcc atctaccata ccacctctta ccatctacca caccatcttt  6840
tatctccatc cctctcagaa gcctccaagc tgaatcctgc tttatgtgtt catctcagcc  6900
cctgcatgga aagctgaccc cagaggcaga actattccca gagagcttgg ccaagaaaaa  6960
caaaactacc agcctggcca ggctcaggag tagtaagctg cagtgtctgt tgtgttctag  7020
cttcaacagc tgcaggagtt ccactctcaa atgctccaca tttctcacat cctcctgatt  7080
ctggtcacta cccatcttca aagaacagaa tatctcacat cagcatactg tgaaggacta  7140
gtcatgggtg cagctgctca gagctgcaaa gtcattctgg atggtggaga gcttacaaac  7200
atttcatgat gctccccccg ctctgatggc tggagcccaa tccctacaca gactcctgct  7260
gtatgtgttt tcctttcact ctgagccaca gccagagggc aggcattcag tctcctcttc  7320
aggctggggc tggggcactg agaactcacc caacaccttg ctctcactcc ttctgcaaaa  7380
caagaaagag ctttgtgctg cagtagccat gaagaatgaa aggaaggctt taactaaaaa  7440
atgtcagaga ttattttcaa cccccttactg tggatcacca gcaaggagga aacacaacac  7500
agagacattt tttcccctca aattatcaaa agaatcactg catttgttaa agagagcaac  7560
tgaatcagga agcagagttt tgaacatatc agaagttagg aatctgcatc agagacaaat  7620
gcagtcatgg ttgtttgctg cataccagcc ctaatcatta gaagcctcat ggacttcaaa  7680
catcattccc tctgacaaga tgctctagcc taactccatg agataaaata aatctgcctt  7740
tcagagccaa agaagagtcc accagcttct tctcagtgtg aacaagagct ccagtcaggt  7800
tagtcagtcc agtgcagtag aggagaccag tctgcatcct ctaattttca aaggcaagaa  7860
gatttgttta ccctggacac caggcacaag tgaggtcaca gagctcttag atatgcagtc  7920
ctcatgagtg aggagactaa agcgcatgcc atcaagactt cagtgtagag aaaacctcca  7980
aaaaagcctc ctcactactt ctggaatagc tcagaggccg aggcggcctc ggcctctgca  8040
taaataaaaa aaattagtca gccatggggc ggagaatggg cggaactggg cggagttagg  8100
ggcgggatgg gcggagttag gggcgggact atggttgctg actaattgag atgcatgctt  8160
tgcatacttc tgcctgctgg ggagcctggg gactttccac acctggttgc tgactaattg  8220
agatgcatgc tttgcatact tctgcctgct ggggagcctg gggactttcc acaccctaac  8280
tgacacacat tccacagctg cattaatgaa tcggccaacg cgcggggaga ggcggtttgc  8340
gtattgggcg ctcttccgct tcctcgctca ctgactcgct gcgctcggtc gttcggctgc  8400
ggcgagcggt atcagctcac tcaaaggcgg taatacggtt atccacagaa tcaggggata  8460
acgcaggaaa gaacatgtga gcaaaaggcc agcaaaaggc caggaaccgt aaaaaggccg  8520
cgttgctggc gtttttccat aggctccgcc cccctgacga gcatcacaaa aatcgacgct  8580
caagtcagag gtggcgaaac ccgacaggac tataaagata ccaggcgttt ccccctggaa  8640
gctccctcgt gcgctctcct gttccgaccc tgccgcttac cggatacctg tccgcctttc  8700
tcccttcggg aagcgtggcg ctttctcata gctcacgctg taggtatctc agttcggtgt  8760
aggtcgttcg ctccaagctg ggctgtgtgc acgaaccccc cgttcagccc gaccgctgcg  8820
ccttatccgg taactatcgt cttgagtcca acccggtaag acacgactta tcgccactgg  8880
cagcagccac tggtaacagg attagcagag cgaggtatgt aggcggtgct acagagttct  8940
tgaagtggtg gcctaactac ggctacacta gaagaacagt atttggtatc tgcgctctgc  9000
tgaagccagt taccttcgga aaaagagttg gtagctcttg atccggcaaa caaaccaccg  9060
ctggtagcgg tggttttttt gtttgcaagc agcagattac gcgcagaaaa aaaggatctc  9120
aagaagatcc tttgatcttt tctacggggt ctgacgctca gtggaacgaa aactcacgtt  9180
aagggatttt ggtcatgaga ttatcaaaaa ggatcttcac ctagatcctt ttaaattaaa  9240
aatgaagttt taaatcaatc taaagtatat atgagtaaac ttggtctgac agttaccaat  9300
gcttaatcag tgaggcacct atctcagcga tctgtctatt tcgttcatcc atagttgcct  9360
gactcctgca aaccacgttg tgtctcaaaa tctctgatgt tacattgcac aagataaaaa  9420
tatatcatca tgaacaataa aactgtctgc ttacataaac agtaatacaa ggggtgttat  9480
gagccatatt caacgggaaa cgtcttgctc gaggccgcga ttaaattcca acatggatgc  9540
tgatttatat gggtataaat gggctcgcga taatgtcggg caatcaggtg cgacaatcta  9600
tcgattgtat gggaagcccg atgcgccaga gttgtttctg aaacatggca aaggtagcgt  9660
tgccaatgat gttacagatg agatggtcag actaaactgg ctgacggaat ttatgcctct  9720
tccgaccatc aagcatttta tccgtactcc tgatgatgca tggttactca ccactgcgat  9780
ccccgggaaa acagcattcc aggtattaga agaatatcct gattcaggtg aaaatattgt  9840
tgatgcgctg gcagtgttcc tgcgccggtt gcattcgatt cctgtttgta attgtccttt  9900
taacagcgat cgcgtatttc gtctcgctca ggcgcaatca cgaatgaata acggtttggt  9960
tgatgcgagt gattttgatg acgagcgtaa tggctggcct gttgaacaag tctggaaaga  10020
aatgcataag cttttgccat tctcaccgga ttcagtcgtc actcatggtg atttctcact  10080
tgataacctt atttttgacg aggggaaatt aataggttgt attgatgttg gacgagtcgg  10140
aatcgcagac cgataccagg atcttgccat cctatggaac tgcctcggtg agttttctcc  10200
ttcattacag aaacggcttt ttcaaaaata tggtattgat aatcctgata tgaataaatt  10260
gcagtttcat ttgatgctcg atgagttttt ctaagggcgg cctgccacca tacccacgcc  10320
gaaacaagcg ctcatgagcc cgaagtggcg agcccgatct tccccatcgg tgatgtcggc  10380
gatataggcg ccagcaaccg cacctgtggc gccggtgatg agggcgcgcc aagtcgacgt  10440
ccggcagtct tggccactcc ctctctgcgc gctcgctcgc tcactgaggc cgggcgacca  10500
aaggtcgccc gacgcccggg ctttgcccgg gcggcctcag tgagcgagcg agcgcgcaga  10560
gagggagtgg ccaactccat cactaggggt tcctgctagc tctgggtatt taagcccgag  10620
tgagcacgca gggtctccat tttgaagcgg gaggttacgc gttcgtcgac tactagtggg  10680
taccagagcg tggtgactga gatgttttct aggaaacaca aaagatacaa aaaagaacac  10740
gtggaaggat agccaaaaag gggggctgcc cccatttcct gcaccccgct gcgatggctg  10800
gcaccatttg gaagacttcg agatacactg ttgagcgcag taagacaaca gtgtatctcg  10860
aagtcttcca gatggggcca gccggtccac tctgtatcca ggccagttct gcaaggcgtt  10920
cgaggaccac ccccctcccc tcgccaccag ggtggtctca tacagaactt ataagattcc  10980
caaatccaaa gacatttcac gtttatggtg atttcccaga acacatagcg acatgcaaat  11040
attgcagggc gccactcccc tgtccctcac agccatcttc ctgccagggc gcacgcgcgc  11100
```

```
tgggtgttcc cgcctagtga cactgggccc gcgattcctt ggagcgggtt gatgacgtca  11160
gcgtttccca tggtgaatcc ctaggtt                                      11187

SEQ ID NO: 13          moltype = DNA  length = 10960
FEATURE                Location/Qualifiers
misc_feature           1..10960
                       note = Synthetic polynucleotide
source                 1..10960
                       mol_type = other DNA
                       organism = synthetic construct
SEQUENCE: 13
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
cctagttatt aatagtaatc aattacgggg tcattagttc atagcccata tatggagttc  360
cgcgttacat aacttacggt aaatggcccg cctggctgac cgcccaacga cccccgccca  420
ttgacgtcaa taatgacgta tgttcccata gtaacgccaa tagggacttt ccattgacgt  480
caatgggtgg actatttacg gtaaactgcc cacttggcag tacatcaagt gtatcatatg  540
ccaagtacgc cccctattga cgtcaatgac ggtaaatggc ccgcctggca ttatgcccag  600
tacatgacct tatgggactt tcctacttgg cagtacatct acgtattagt catcgctatt  660
accatggtcg aggtgagccc cacgttctgc ttcactctcc ccatctcccc cccctcccca  720
cccccaattt tgtatttatt tattttttaa ttattttgtg cagcgatggg ggcggggggg  780
gggggggggc gcgcgccagg cggggcgggg cggggcgagg ggcggggcgg ggcgaggcgg  840
agaggtgcgg cggcagccaa tcagagcggc gcgctccgaa agtttccttt tatggcgagg  900
cggcggcggc ggcggcccta taaaaagcga agcgcgcggc gggcgggagt cgctgcgacg  960
ctgccttcgc cccgtgcccc gctccgccgc cgcctcgcgc cgcccgcccc ggctctgact  1020
gaccgcgtta ctcccacagg tgagcgggcg ggacggccct tctcctccgg gctgtaatta  1080
gcgcttggtt taatgacggc ttgtcctggt ggcgaggggga gggggggtggt cctcgaacgc  1140
cttgcagaac tggcctggat acagagtgga ccggctggcc ccatctggaa gacttcgaga  1200
tacactgttg tcttactgcg ctcaacagtg tatctcgaag tcttccaaat ggtgccagcc  1260
atcgcagcgg ggtgcaggaa atgggggcag cccccctttt tggctatcct tccacgtgtt  1320
ctttttgta tcttttgtgt ttcctagaaa acatctcagt caccaccttt ctgtggctgc  1380
gtgaaagcct tgaggggctc cgggagctag agcctctgct aaccatgttc atgccttctt  1440
ctttttccta cagctcctgg gcaacgtgct ggttattgtg ctgtctcatc attttggcaa  1500
agaattcctc gaagatccga agggaaagtc ttccacgact gtgggatccg ttcgaagata  1560
tcaccggttg agccaccatg gaattcagca gccccagcag agaggaatgc cccaagcctc  1620
tgagccgggt gtcaatcatg gccggatctc tgacaggact gctgctgctt caggccgtgt  1680
cttgggcttc tggcgctaga ccttgcatcc ccaagagctt cggctacagc agcgtcgtgt  1740
gcgtgtgcaa tgccacctac tgcgacagct tcgaccctcc tacctttcct gctctgggca  1800
ccttcagcag atacgagagc accagatccg gcagacggat ggaactgagc atggacccca  1860
tccaggccaa tcacacaggc actggcctgc tgctgacact gcagcctgag cagaaattcc  1920
agaaagtgaa aggcttcggc ggagccatga cagatgccgc cgctctgaat atcctggctc  1980
tgtctccacc agctcagaac ctgctgctca agagctactt cagcgaggaa ggcatcggct  2040
acaacatcat cagagtgccc atggccagct gcgacttcag catcaggacc tacacctacg  2100
ccgacacacc cgacgatttc cagctgcaca acttcagcct gcctgaagag gacaccaagc  2160
tgaagatccc tctgatccac agagccctgc agctggcaca aagacccgtg tcactgctgg  2220
cctctccatg gacatctccc acctggctga aaacaaatgg cgccgtgaat ggcaagggca  2280
gcctgaaagg ccaacctggc gacatctacc accagacctg ggccagatac ttcgtgaagt  2340
tcctggacgc ctatgccgag cacaagctgc agttttgggc cgtgacagcc gagaacgaac  2400
cttctgctgg actgctgagc ggctacccct ttcagtgcct gggctttaca cccgagcacc  2460
agcgggactt tatcgcccgt gatctgggac ccacactggc caatagcacc caccataatg  2520
tgcggctgct gatgctggac gaccagagac tgcttctgcc ccactgggct aaagtggtgc  2580
tgacagatcc tgaggccgcc aaatacgtgc acggaatcgc cgtgcactgg tatctggact  2640
ttctggcccc tgccaaggcc acactgggag agacacacag actgttcccc aacaccatgc  2700
tgttcgccag cgaagcctgt gtgggcagca agttttggga acagagcgtg cggctcggca  2760
gctgggatag aggcatgcag tacagccaca gcatcatcac caacctgctg taccacgtcg  2820
tcggctggac cgactggaat ctggccctga atcctgaagg cggccctaac tgggtccgaa  2880
acttcgtgga cagccccatc atcgtggaca tcaccaagga caccttctac aagcagccca  2940
tgttctacca cctgggacac ttcagcaagt tcatccccga gggctctcag cgcgttggac  3000
tggtggcttc ccagaagaac gatctggacg ccgtggctct gatgcaccct gatggatctg  3060
ctgtggtggt ggtcctgaac cgcagcagca aagatgtgcc cctgaccatc aaggatcccg  3120
ccgtgggatt cctggaaaca atcagccctg gctactccat ccacacctac ctgtggcgta  3180
gacagtgaca attgttaatt aagtttaaac cctcgaggcc gcaagcttat cgataatcaa  3240
cctctggatt acaaaatttg tgaaagattg actggtattc ttaactatgt tgctcctttt  3300
acgctatgtg gatacgctgc tttaatgcct ttgtatcatg ctattgcttc ccgtatggct  3360
ttcattttct cctccttgta taaatcctgg ttgctgtctc tttatgagga gttgtggccc  3420
gttgtcaggc aacgtggcgt ggtgtgcact gtgtttgctg acgcaacccc cactggttgg  3480
ggcattgcca ccacctgtca gctcctttcc gggactttcg ctttccccct ccctattgcc  3540
acggcggaac tcatcgccgc ctgccttgcc cgctgctgga caggggctcg gctgttgggc  3600
actgacaatt ccgtggtgtt gtcggggaaa tcatcgtcct ttccttggct gctcgcctgt  3660
gttgccacct ggattctgcg cgggacgtcc ttctgctacg tcccttcggc cctcaatcca  3720
gcggaccttc cttcccgcgg cctgctgccg gctctgcggc ctcttccgcg tcttcgcctt  3780
cgccctcaga cgagtcggat ctccctttgg gccgcctccc cgcatcgata ccgtcgacta  3840
gagctcgctg atcagcctcg actgtgcctt ctagttgcca gccatctgtt gtttgcccct  3900
cccccgtgcc ttccttgacc ctggaaggtg ccactcccac tgtcctttcc taataaaatg  3960
aggaaattgc atcgcattgt ctgagtaggt gtcattctat tctggggggt ggggtggggc  4020
aggacagcaa gggggaggat tgggaagaca atagcaggca tgctggggag agatccacga  4080
```

```
taacaaacag ctttttttggg gtgaacatat tgactgaatt ccctgcaggt tggccactcc  4140
ctctctgcgc gctcgctcgc tcactgaggc cgcccgggca aagcccgggc gtcgggcgac  4200
ctttggtcgc ccggcctcag tgagcgagcg agcgcgcaga gagggagtgg ccaactccat  4260
cactaggggt tcctgcggcc gctcgtacgg tctcgaggaa ttcctgcagg ataacttgcc  4320
aacctcattc taaaatgtat atagaagccc aaaagacaat aacaaaaata ttcttgtaga  4380
acaaaatggg aaagaatgtt ccactaaata tcaagattta gagcaaagca tgagatgtgt  4440
ggggatagac agtgaggctg ataaaataga gtagagctca gaaacagacc cattgatata  4500
tgtaagtgac ctatgaaaaa aatatggcat tttacaatgg gaaaatgatg gtctttttct  4560
tttttagaaa aacagggaaa tatatttata tgtaaaaaat aaaagggaac ccatatgtca  4620
taccatacac acaaaaaaat tccagtgaat tataagtcta aatggagaag gcaaaacttt  4680
aaatctttta gaaaataata tagaagcatg cagaccagcc tggccaacat gatgaaaccc  4740
tctctactaa taataaaatc agtagaacta ctcaggacta ctttgagtgg gaagtccttt  4800
tctatgaaga cttctttggc caaaattagg ctctaaatgc aaggagatag tgcatcatgc  4860
ctggctgcac ttactgataa atgatgttat caccatcttt aaccaaatgc acaggaacaa  4920
gttatggtac tgatgtgctg gattgagaag gagctctact tccttgacag gacacatttg  4980
tatcaactta aaaaagcaga tttttgccag cagaactatt cattcagagg taggaaactt  5040
agaatagatg atgtcactga ttagcatggc ttccccatct ccacagctgc ttcccaccca  5100
ggttgcccac agttgagttt gtccagtgct cagggctgcc cactctcagt aagaagcccc  5160
acaccagccc ctctccaaat atgttggctg ttccttccat taaagtgacc ccactttaga  5220
gcagcaagtg gatttctgtt tcttacagtt caggaaggag gagtcagctg tgagaacctg  5280
gagcctgaga tgcttctaag tcccactgct actggggtca gggaagccag actccagcat  5340
cagcagtcag gagcactaag cccttgccaa catcctgttt ctcagagaaa ctgcttccat  5400
tataatggtt gtcctttttt aagctatcaa gccaaacaac cagtgtctac cattattctc  5460
atcacctgaa gccaagggtt ctagcaaaag tcaagctgtc ttgtaatggt tgatgtgcct  5520
ccagcttctg tcttcagtca ctccactctt agcctgctct gaatcaactc tgaccacagt  5580
tccctggagc ccctgccacc tgctgcccct gccaccttct ccatctgcag tgctgtgcag  5640
ccttctgcac tcttgcagag ctaataggtg gagacttgaa ggaagaggag gaaagtttct  5700
cataatagcc ttgctgcaag ctcaaatggg aggtgggcac tgtgcccagg agccttggag  5760
caaaggctgt gcccaacctc tgactgcatc caggtttggt cttgacagag ataagaagcc  5820
ctggcttttg gagccaaaat ctaggtcaga cttaggcagg attctcaaag tttatcagca  5880
gaacatgagg cagaagaccc tttctgctcc agcttcttca ggctcaacct tcatcagaat  5940
agatagaaag agaggctgtg agggttctta aaacagaagc aaatctgact cagagaataa  6000
acaacctcct agtaaactac agcttagaca gagcatctgg tggtgagtgt gctcagtgtc  6060
ctactcaact gtctggtatc agccctcatg aggacttctc ttctttccct catagacctc  6120
catctctgtt ttccttagcc tgcagaaatc tggatggcta ttcacagaat gcctgtgctt  6180
tcagagttgc atttttctc tggtattctg gttcaagcat ttgaaggtag gaaaggttct  6240
ccaagtgcaa gaaagccagc cctgagcctc aactgcctgg ctagtgtggt cagtaggatg  6300
caaaggctgt tgaatgccac aaggccaaac tttaacctgt gtaccacaag cctagcagca  6360
gaggcagctc tgctcactgg aactctctgt cttctttctc ctgagccttt tcttttcctg  6420
agttttctag ctctcctcaa ccttacctct gccctaccca ggacaaaccc aagagccact  6480
gtttctgtga tgtcctctcc agccctaatt aggcatcatg acttcagcct gaccttccat  6540
gctcagaagc agtgctaatc cacttcagat gagctgctct atgcaacaca ggcagagcct  6600
acaaaccttt gcaccagagc cctccacata tcagtgtttg ttcatactca cttcaacagc  6660
aaatgtgact gctgagatta agattttaca caagatggtc tgtaatttca cagttagttt  6720
tatcccatta ggtatgaaag aattagcata attcccctta aacatgaatg aatcttagat  6780
tttttaataa atagttttgg aagtaaagac agagacatca ggagcacaag gaatagcctg  6840
agaggacaaa cagaacaaga aagagtctgg aaatacacag gatgttcttg gcctcctcaa  6900
agcaagtgca agcagatagt accagcagcc ccaggctatc agagcccagt gaagagaagt  6960
accatgaaag ccacagctct aaccaccctg ttccagagtg acagacagtc cccaagacaa  7020
gccagcctga gccagagaga gaactgcaag agaaagtttc taatttaggt tctgttagat  7080
tcagacaagt gcaggtcatc ctctctccac agctactcac ctctccagcc taacaaagcc  7140
tgcagtccac actccaaccc tggtgtctca cctcctagcc tctcccaaca tcctgctctc  7200
tgaccatctt ctgcatctct catctcacca tctcccactg tctacagcct actcttgcaa  7260
ctaccatctc attttctgac atcctgtcta catcttctgc catactctgc catctaccat  7320
accacctctt accatctacc acaccatctt ttatctccat ccctctcaga agcctccaag  7380
ctgaatcctg ctttatgtgt tcatctcagc ccctgcatgg aaagctgacc ccagaggcag  7440
aactattccc agagagcttg gccaagaaaa acaaaactac cagcctggcc aggctcagga  7500
gtagtaagct gcagtgtctg ttgtgttcta gcttcaacag ctgcaggagt tccactctca  7560
aatgctccac atttctcaca tcctcctgat tctggtcact acccatcttc aaagaacaga  7620
atatctcaca tcagcatact gtgaaggact agtcatgggt gcagctgctc agagctgcaa  7680
agtcattctg gatggtggag agcttacaaa catttcatga tgctcccccc gctctgatgg  7740
ctggagccca atccctacac agactcctgc tgtatgtgtt ttcctttcac tctgagccac  7800
agccagaggg caggcattca gtctcctctt caggctgggg ctggggcact gagaactcac  7860
ccaacacctt gctctcactc cttctgcaaa acaagaaaga gctttgtgct gcagtagcca  7920
tgaagaatga aaggaaggct ttaactaaaa aatgtcagag attattttca accccttact  7980
gtggatcacc agcaaggagg aaacacaaca cagagacatt ttttccccctc aaattatcaa  8040
aagaatcact gcatttgtta aagagagcaa ctgaatcagg aagcagagtt ttgaacatat  8100
cagaagttag gaatctgcat cagagacaaa tgcagtcatg gttgtttgct gcataccagc  8160
cctaatcatt agaagcctca tggacttcaa acatcattcc ctctgacaag atgctctagc  8220
ctaactccat gagataaaat aaatctgcct ttcagagcca aagaagagtc caccagcttc  8280
ttctcagtgt gaacaagagc tccagtcagg ttagtcagtc cagtgcagta gaggagacca  8340
gtctgcatcc tctaattttc aaaggcaaga agatttgttt accctggaca ccaggcacaa  8400
gtgaggtcac agagctctta gatatgcagt cctcatgagt gaggagacta aagcgcatgc  8460
catcaagact tcagtgtaga gaaaacctcc aaaaaagcct cctcactact tctggaatag  8520
ctcagaggcc gaggcggcct cggcctctgc ataaataaaa aaaattagtc agccatgggg  8580
cggagaatgg gcggaactgg gcggagttag gggcgggatg ggcggagtta ggggcgggac  8640
tatggttgct gactaattga gatgcatgct ttgcatactt ctgcctgctg gggagcctgg  8700
ggactttcca cacctggttg ctgactaatt gagatgcatg ctttgcatac ttctgcctgc  8760
tggggagcct ggggactttc cacaccctaa ctgacacaca ttccacagct gcattaatga  8820
```

-continued

```
atcggccaac gcgcggggag aggcggtttg cgtattgggc gctcttccgc ttcctcgctc  8880
actgactcgc tgcgctcggt cgttcggctg cggcgagcgg tatcagctca ctcaaaggcg  8940
gtaatacggt tatccacaga atcaggggat aacgcaggaa agaacatgtg agcaaaaggc  9000
cagcaaaagg ccaggaaccg taaaaaggcc gcgttgctgg cgtttttcca taggctccgc  9060
cccccctgacg agcatcacaa aaatcgacgc tcaagtcaga ggtggcgaaa cccgacagga  9120
ctataaagat accaggcgtt tccccctgga agctccctcg tgcgctctcc tgttccgacc  9180
ctgccgctta ccggatacct gtccgccttt ctcccttcgg gaagcgtggc gctttctcat  9240
agctcacgct gtaggtatct cagttcggtg taggtcgttc gctccaagct gggctgtgtg  9300
cacgaacccc ccgttcagcc cgaccgctgc gccttatccg gtaactatcg tcttgagtcc  9360
aacccggtaa gacacgactt atcgccactg gcagcagcca ctggtaacag gattagcaga  9420
gcgaggtatg taggcggtgc tacagagttc ttgaagtggt ggcctaacta cggctacact  9480
agaagaacag tatttggtat ctgcgctctg ctgaagccag ttaccttcgg aaaaagagtt  9540
ggtagctctt gatccggcaa acaaaccacc gctggtagcg gtggtttttt tgtttgcaag  9600
cagcagatta cgcgcagaaa aaaaggatct caagaagatc ctttgatctt ttctacgggg  9660
tctgacgctc agtggaacga aaactcacgt taagggattt tggtcatgag attatcaaaa  9720
aggatcttca cctagatcct tttaaattaa aaatgaagtt ttaaatcaat ctaaagtata  9780
tatgagtaaa cttggtctga cagttaccaa tgcttaatca gtgaggcacc tatctcagcg  9840
atctgtctat ttcgttcatc catagttgcc tgactcctgc aaaccacgtt gtgtctcaaa  9900
atctctgatg ttacattgca caagataaaa atatatcatc atgaacaata aaactgtctg  9960
cttacataaa cagtaataca aggggtgtta tgagccatat tcaacgggaa acgtcttgct  10020
cgaggccgcg attaaattcc aacatggatg ctgatttata tgggtataaa tgggctcgcg  10080
ataatgtcgg gcaatcaggt gcgacaatct atcgattgta tgggaagccc gatgcgccag  10140
agttgtttct gaaacatggc aaaggtagcg ttgccaatga tgttacagat gagatggtca  10200
gactaaactg gctgacggaa tttatgcctc ttccgaccat caagcatttt atccgtactc  10260
ctgatgatgc atggttactc accactgcga tccccgggaa aacagcattc caggtattag  10320
aagaatatcc tgattcaggt gaaaatattg ttgatgcgct ggcagtgttc ctgcgccggt  10380
tgcattcgat tcctgtttgt aattgtcctt ttaacagcga tcgcgtattt cgtctcgctc  10440
aggcgcaatc acgaatgaat aacggtttgg ttgatgcgag tgattttgat gacgagcgta  10500
atggctggcc tgttgaacaa gtctggaaag aaatgcataa gcttttgcca ttctcaccgg  10560
attcagtcgt cactcatggt gatttctcac ttgataacct tatttttgac gaggggaaat  10620
taataggttg tattgatgtt ggacgagtcg gaatcgcaga ccgataccag gatcttgcca  10680
tcctatggaa ctgcctcggt gagttttctc cttcattaca gaaacggctt tttcaaaaat  10740
atggtattga taatcctgat atgaataaat tgcagtttca tttgatgctc gatgagtttt  10800
tctaagggcg gcctgccacc atacccacgc cgaaacaagc gctcatgagc ccgaagtggc  10860
gagcccgatc ttccccatcg gtgatgtcgg cgatataggc gccagcaacc gcacctgtgg  10920
cgccggtgat gagggcgcgc caagtcgacg tccggcagtc                       10960

SEQ ID NO: 14          moltype = AA  length = 536
FEATURE                Location/Qualifiers
source                 1..536
                       mol_type = protein
                       organism = Homo sapiens
SEQUENCE: 14
MEFSSPSREE CPKPLSRVSI MAGSLTGLLL LQAVSWASGA RPCIPKSFGY SSVVCVCNAT  60
YCDSFDPPTF PALGTFSRYE STRSGRRMEL SMGPIQANHT GTGLLLTLQP EQKFQKVKGF  120
GGAMTDAAAL NILALSPPAQ NLLLKSYFSE EGIGYNIIRV PMASCDFSIR TYTYADTPDD  180
FQLHNFSLPE EDTKLKIPLI HRALQLAQRP VSLLASPWTS PTWLKTNGAV NGKGSLKGQP  240
GDIYHQTWAR YFVKFLDAYA EHKLQFWAVT AENEPSAGLL SGYPFQCLGF TPEHQRDFIA  300
RDLGPTLANS THHNVRLLML DDQRLLLPHW AKVVLTDPEA AKYVHGIAVH WYLDFLAPAK  360
ATLGETHRLF PNTMLFASEA CVGSKFWEQS VRLGSWDRGM QYSHSIITNL LYHVVGWTDW  420
NLALNPEGGP NWVRNFVDSP IIVDITKDTF YKQPMFYHLG HFSKFIPEGS QRVGLVASQK  480
NDLDAVALMH PDGSAVVVVL NRSSKDVPLT IKDPAVGFLE TISPGYSIHT YLWRRQ      536

SEQ ID NO: 15          moltype = DNA  length = 1608
FEATURE                Location/Qualifiers
source                 1..1608
                       mol_type = other DNA
                       organism = Homo sapiens
SEQUENCE: 15
atggaattca gcagccccag cagagaggaa tgccccaagc ctctgagccg ggtgtcaatc  60
atggccggat ctctgacagg actgctgctg cttcaggccg tgtcttgggc ttctggcgct  120
agaccttgca tccccaagag cttcggctac agcagcgtcg tgtgcgtgtg caatgccacc  180
tactgcgaca gcttcgaccc tcctaccttt cctgctctgg gcaccttcag cagatacgag  240
agcaccagat ccggcagacg gatggaactg agcatgggac ccatccaggc caatcacaca  300
ggcactggcc tgctgctgac actgcagcct gagcagaaat tccagaaagt gaaaggcttc  360
ggcggagcca tgacagatgc cgccgctctg aatatcctgg ctctgtctcc accagctcag  420
aacctgctgc tcaagagcta cttcagcgag gaaggcatcg gctacaacat catcagagtg  480
cccatggcca gctgcgactt cagcatcagg acctacacct acgccgacac acccgacgat  540
ttccagctgc acaacttcag cctgcctgaa gaggacacca agctgaagat ccctctgatc  600
cacagagccc tgcagctggc acaaagaccc gtgtcactgc tggcctctcc atggacatct  660
cccacctggc tgaaaacaaa tggcgccgtg aatggcaagg gcagcctgaa aggccaacct  720
ggcgacatct accaccagac ctgggccaga tacttcgtga agttcctgga cgcctatgcc  780
gagcacaagc tgcagttttg ggccgtgaca gccgagaacg aaccttctgc tggactgctg  840
agcggctacc cctttcagtg cctgggcttt acacccgagc accagcggga ctttatcgcc  900
cgtgatctgg gacccacact ggccaatagc acccaccata atgtgcggct gctgatgctg  960
gacgaccaga gactgcttct gccccactgg gctaaagtgg tgctgacaga tcctgaggcc  1020
gccaaatacg tgcacggaat cgccgtgcac tggtatctgg actttctggc ccctgccaag  1080
gccacactgg gagagacaca cagactgttc cccaacacca tgctgttcgc cagcgaagcc  1140
tgtgtgggca gcaagttttg ggaacagagc gtgcggctcg gcagctggga tagaggcatg  1200
```

```
cagtacagcc acagcatcat caccaacctg ctgtaccacg tcgtcggctg gaccgactgg  1260
aatctggccc tgaatcctga aggcggccct aactgggtcc gaaacttcgt ggacagcccc  1320
atcatcgtgg acatcaccaa ggacaccttc tacaagcagc ccatgttcta ccacctggga  1380
cacttcagca agttcatccc cgagggctct cagcgcgttg gactggtggc ttcccagaag  1440
aacgatctgg acgccgtggc tctgatgcac cctgatggat ctgctgtggt ggtggtcctg  1500
aaccgcagca gcaaagatgt gcccctgacc atcaaggatc ccgccgtggg attcctggaa  1560
acaatcagcc ctggctactc catccacacc tacctgtggc gtagacag             1608

SEQ ID NO: 16           moltype = AA  length = 524
FEATURE                 Location/Qualifiers
source                  1..524
                        mol_type = protein
                        organism = Homo sapiens
SEQUENCE: 16
MYALFLLASL LGAALAGPVL GLKECTRGSA VWCQNVKTAS DCGAVKHCLQ TVWNKPTVKS  60
LPCDICKDVV TAAGDMLKDN ATEEEILVYL EKTCDWLPKP NMSASCKEIV DSYLPVILDI  120
IKGEMSRPGE VCSALNLCES LQKHLAELNH QKQLESNKIP ELDMTEVVAP FMANIPLLLY  180
PQDGPRSKPQ PKDNGDVCQD CIQMVTDIQT AVRTNSTFVQ ALVEHVKEEC DRLGPGMADI  240
CKNYISQYSE IAIQMMMHMQ PKEICALVGF CDEVKEMPMQ TLVPAKVASK NVIPALELVE  300
PIKKHEVPAK SDVYCEVCEF LVKEVTKLID NNKTEKEILD AFDKMCSKLP KSLSEECQEV  360
VDTYGSSILS ILLEEVSPEL VCSMLHLCSG TRLPALTVHV TQPKDGGFCE VCKKLVGYLD  420
RNLEKNSTKQ EILAALEKGC SFLPDPYQKQ CDQFVAEYEP VLIEILVEVM DPSFVCLKIG  480
ACPSAHKPLL GTEKCIWGPS YWCQNTETAA QCNAVEHCKR HVWN                  524

SEQ ID NO: 17           moltype = DNA  length = 1572
FEATURE                 Location/Qualifiers
source                  1..1572
                        mol_type = other DNA
                        organism = Homo sapiens
SEQUENCE: 17
atgtacgccc tgttcctgct ggccagcctg ctgggcgccg ccctggccgg ccccgtgctg  60
ggcctgaagg agtgcacccg cggcagcgcc gtgtggtgcc agaacgtgaa gaccgccagc  120
gactgcggcg ccgtgaagca ctgcctgcag accgtgtgga acaagcccac cgtgaagagc  180
ctgccctgcg acatctgcaa ggacgtggtg accgccgccg gcgacatgct gaaggacaac  240
gccaccgagg aggagatcct ggtgtacctg gagaagacct gcgactggct gcccaagccc  300
aacatgagcg ccagctgcaa ggagatcgtg gacagctacc tgcccgtgat cctggacatc  360
atcaagggcg agatgagccg ccccggcgag gtgtgcagcg ccctgaacct gtgcgagagc  420
ctgcagaagc acctggccga gctgaaccac cagaagcagc tggagagcaa caagatcccc  480
gagctggaca tgaccgaggt ggtggccccc ttcatggcca acatccccct gctgctgtac  540
ccccaggacg gcccccgcag caagccccag cccaaggaca acggcgacgt gtgccaggac  600
tgcatccaga tggtgaccga catccagacc gccgtgcgca ccaacagcac cttcgtgcag  660
gccctggtgg agcacgtgaa ggaggagtgc gaccgcctgg gccccggcat ggccgacatc  720
tgcaagaact acatcagcca gtacagcgag atcgccatcc agatgatgat gcacatgcag  780
cccaaggaga tctgcgccct ggtgggcttc tgcgacgagg tgaaggagat gcccatgcag  840
accctggtgc ccgccaaggt ggccagcaag aacgtgatcc ccgccctgga gctggtggag  900
cccatcaaga agcacgaggt gcccgccaag agcgacgtgt actgcgaggt gtgcgagttc  960
ctggtgaagg aggtgaccaa gctgatcgac aacaacaaga ccgagaagga gatcctggac  1020
gccttcgaca agatgtgcag caagctgccc aagagcctga gcgaggagtg ccaggaggtg  1080
gtggacacct acggcagcag catcctgagc atcctgctgg aggaggtgag ccccgagctg  1140
gtgtgcagca tgctgcacct gtgcagcggc acccgcctgc ccgccctgac cgtgcacgtg  1200
acccagccca aggacggcgg cttctgcgag gtgtgcaaga agctggtggg ctacctggac  1260
cgcaacctgg agaagaacag caccaagcag gagatcctgg ccgccctgga gaagggctgc  1320
agcttcctgc ccgaccccta ccagaagcag tgcgaccagt tcgtggccga gtacgagccc  1380
gtgctgatcg agatcctggt ggaggtgatg gaccccagct tcgtgtgcct gaagatcggc  1440
gcctgcccca gcgcccacaa gcccctgctg ggcaccgaga agtgcatctg gggccccagc  1500
tactggtgcc agaacaccga gaccgccgcc cagtgcaacg ccgtggagca ctgcaagcgc  1560
cacgtgtgga ac                                                    1572

SEQ ID NO: 18           moltype = AA  length = 478
FEATURE                 Location/Qualifiers
source                  1..478
                        mol_type = protein
                        organism = Homo sapiens
SEQUENCE: 18
MGRCCFYTAG TLSLLLLVTS VTLLVARVFQ KAVDQSIEKK IVLRNGTEAF DSWEKPPLPV  60
YTQFYFFNVT NPEEILRGET PRVEEVGPYT YRELRNKANI QFGDNGTTIS AVSNKAYVFE  120
RDQSVGDPKI DLIRTLNIPV LTVIEWSQVH FLREIIEAML KAYQQKLFVT HTVDELLWGY  180
KDEILSLIHV FRPDISPYFG LFYEKNGTND GDYVFLTGED SYLNFTKIVE WNGKTSLDWW  240
ITDKCNMING TDGDSFHPLI TKDEVLYVFP SDFCRSVYIT FSDYESVQGL PAFRYKVPAE  300
ILANTSDNAG FCIPEGNCLG SGVLNVSICK NGAPIIMSFP HFYQADERFV SAIEGMHPNQ  360
EDHETFVDIN PLTGIILKAA KRFQINIYVK KLDDFVETGD IRTMVFPVMY LNESVHIDKE  420
TASRLKSMIN TTLIITNIPY IIMALGVFFG LVFTWLACKG QGSMDEGTAD ERAPLIRT    478

SEQ ID NO: 19           moltype = DNA  length = 1434
FEATURE                 Location/Qualifiers
source                  1..1434
                        mol_type = other DNA
                        organism = Homo sapiens
SEQUENCE: 19
```

```
atgggccgct gctgcttcta caccgccggc accctgagcc tgctgctgct ggtgaccagc  60
gtgaccctgc tggtggcccg cgtgttccag aaggccgtgg accagagcat cgagaagaag  120
atcgtgctgc gcaacggcac cgaggccttc gacagctggg agaagccccc cctgcccgtg  180
tacacccagt tctacttctt caacgtgacc aaccccgagg agatcctgcg cggcgagacc  240
ccccgcgtgg aggaggtggg cccctacacc taccgcgagc tgcgcaacaa ggccaacatc  300
cagttcggcg acaacggcac caccatcagc gccgtgagca acaaggccta cgtgttcgag  360
cgcgaccaga gcgtgggcga ccccaagatc gacctgatcc gcaccctgaa catccccgtg  420
ctgaccgtga tcgagtggag ccaggtgcac ttcctgcgcg agatcatcga ggccatgctg  480
aaggcctacc agcagaagct gttcgtgacc cacaccgtgg acgagctgct gtggggctac  540
aaggacgaga tcctgagcct gatccacgtg ttccgccccg acatcagccc ctacttcggc  600
ctgttctacg agaagaacgg caccaacgac ggcgactacg tgttcctgac cggcgaggac  660
agctacctga acttcaccaa gatcgtggag tggaacggca agaccagcct ggactggtgg  720
atcaccgaca agtgcaacat gatcaacggc accgacggcg acagcttcca cccccctgatc  780
accaaggacg aggtgctgta cgtgttcccc agcgacttct gccgcagcgt gtacatcacc  840
ttcagcgact acgagagcgt gcagggcctg cccgccttcc gctacaaggt gcccgccgag  900
atcctggcca acaccagcga caacgccggc ttctgcatcc ccgagggcaa ctgcctgggc  960
agcggcgtgc tgaacgtgag catctgcaag aacggcgccc ccatcatcat gagcttcccc  1020
cacttctacc aggccgacga gcgcttcgtg agcgccatcg agggcatgca ccccaaccag  1080
gaggaccacg agaccttcgt ggacatcaac cccctgaccg gcatcatcct gaaggccgcc  1140
aagcgcttcc agatcaacat ctacgtgaag aagctggacg acttcgtgga gaccggcgac  1200
atccgcacca tggtgttccc cgtgatgtac ctgaacgaga gcgtgcacat cgacaaggag  1260
accgccagcc gcctgaagag catgatcaac accaccctga tcatcaccaa catcccctac  1320
atcatcatgg ccctgggcgt gttcttcggc ctggtgttca cctggctggc ctgcaagggc  1380
cagggcagca tggacgaggg caccgccgac gagcgcgccc ccctgatccg cacc        1434
```

```
SEQ ID NO: 20          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 20
tggaagactt cgagatacac tgt                                          23

SEQ ID NO: 21          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 21
acagtgtatc tcgaagtctt cca                                          23

SEQ ID NO: 22          moltype = DNA  length = 21
FEATURE                Location/Qualifiers
misc_feature           1..21
                       note = Synthetic polynucleotide
source                 1..21
                       mol_type = other DNA
                       organism = synthetic construct
SEQUENCE: 22
tttagaaata agtggtagtc a                                            21

SEQ ID NO: 23          moltype = DNA  length = 21
FEATURE                Location/Qualifiers
misc_feature           1..21
                       note = Synthetic polynucleotide
source                 1..21
                       mol_type = other DNA
                       organism = synthetic construct
SEQUENCE: 23
tgactaccac ttatttctaa a                                            21

SEQ ID NO: 24          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 24
agggtatcaa gactacgaa                                               19

SEQ ID NO: 25          moltype = DNA  length = 19
FEATURE                Location/Qualifiers
misc_feature           1..19
                       note = Synthetic polynucleotide
```

```
source                  1..19
                        mol_type = other DNA
                        organism = synthetic construct
SEQUENCE: 25
ttcgtagtct tgataccct                                              19

SEQ ID NO: 26           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 26
tattagatct gatggccgc                                              19

SEQ ID NO: 27           moltype = DNA  length = 20
FEATURE                 Location/Qualifiers
misc_feature            1..20
                        note = Synthetic polynucleotide
source                  1..20
                        mol_type = other DNA
                        organism = synthetic construct
SEQUENCE: 27
ctccatcact aggggttcct                                             20

SEQ ID NO: 28           moltype = DNA  length = 60
FEATURE                 Location/Qualifiers
misc_feature            1..60
                        note = Synthetic polynucleotide
source                  1..60
                        mol_type = other DNA
                        organism = synthetic construct
SEQUENCE: 28
agctctgggt atttaagccc gagtgagcac gcagggtctc cattttgaag cgggaggtta  60

SEQ ID NO: 29           moltype = DNA  length = 145
FEATURE                 Location/Qualifiers
misc_feature            1..145
                        note = AAV2 ITR
source                  1..145
                        mol_type = genomic DNA
                        organism = unidentified
SEQUENCE: 29
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag agagggagtg gccaa                                        145

SEQ ID NO: 30           moltype = AA  length = 927
FEATURE                 Location/Qualifiers
source                  1..927
                        mol_type = protein
                        organism = Homo sapiens
SEQUENCE: 30
MGTQDPGNMG TGVPASEQIS CAKEDPQVYC PEETGGTKDV QVTDCKSPED SRPPKETDCC  60
NPEDSGQLMV SYEGKAMGYQ VPPFGWRICL AHEFTEKRKP FQANNVSLSN MIKHIGMGLR  120
YLQWWYRKTH VEKKTPFIDM INSVPLRQIY GCPLGGIGGG TITRGWRGQF CRWQLNPGMY  180
QHRTVIADQF TVCLRREGQT VYQQVLSLER PSVLRSWNWG LCGYFAFYHA LYPRAWTVYQ  240
LPGQNVTLTC RQITPILPHD YQDSSLPVGV FVWDVENEGD EALDVSIMFS MRNGLGGGDD  300
APGGLWNEPF CLERSGETVR GLLLHHPTLP NPYTMAVAAR VTAATTVTHI TAFDPDSTGQ  360
QVWQDLLQDG QLDSPTGQST PTQKGVGIAG AVCVSSKLRP RGQCRLEFSL AWDMPRIMFG  420
AKGQVHYRRY TRFFGQDGDA APALSHYALC RYAEWEERIS AWQSPVLDDR SLPAWYKSAL  480
FNELYFLADG GTVWLEVLED SLPEELGRNM CHLRPTLRDY GRFGYLEGQE YRMYNTYDVH  540
FYASFALIML WPKLELSLQY DMALATLRED LTRRRYLMSG VMAPVKRRNV IPHDIGDPDD  600
EPWLRVNAYL IHDTADWKDL NLKFVLQVYR DYYLTGDQNF LKDMWPVCLA VMESEMKFDK  660
DHDGLIENGG YADQTYDGWV TTGPSAYCGG LWLAAVAVMV QMAALCGAQD IQDKFSSILS  720
RGQEAYERLL WNGRYYNYDS SSRPQSRSVM SDQCAGQWFL KACGLGEGDT EVFPTQHVVR  780
ALQTIFELNV QAFAGGAMGA VNGMQPHGVP DKSSVQSDEV WVGVVYGLAA TMIQEGLTWE  840
GFQTAEGCYR TVWERLGLAF QTPEAYCQQR VFRSLAYMRP LSIWAMQLAL QQQQHKKASW  900
PKVKQGTGLR TGPMFGPKEA MANLSPE                                      927

SEQ ID NO: 31           moltype = DNA  length = 2781
FEATURE                 Location/Qualifiers
source                  1..2781
                        mol_type = other DNA
                        organism = Homo sapiens
SEQUENCE: 31
atgggcaccc aggaccccgg caacatgggc accggcgtgc ccgccagcga gcagatcagc  60
tgcgccaagg aggaccccca ggtgtactgc cccgaggaga ccggcggcac caaggacgtg  120
```

```
caggtgaccg actgcaagag ccccgaggac agccgccccc ccaaggagac cgactgctgc  180
aaccccgagg acagcggcca gctgatggtg agctacgagg gcaaggccat gggctaccag  240
gtgccccccct tcggctggcg catctgcctg gcccacgagt tcaccgagaa gcgcaagccc  300
ttccaggcca acaacgtgag cctgagcaac atgatcaagc acatcggcat gggcctgcgc  360
tacctgcagt ggtggtaccg caagacccac gtggagaaga agacccctt catcgacatg  420
atcaacagcg tgcccctgcg ccagatctac ggctgccccc tgggcggcat cggcggcggc  480
accatcaccc gcggctggcg cggccagttc tgccgctggc agctgaaccc cggcatgtac  540
cagcaccgca ccgtgatcgc cgaccagttc accgtgtgcc tgcgccgcga gggccagacc  600
gtgtaccagc aggtgctgag cctggagcgc cccagcgtgc tgcgcagctg gaactggggc  660
ctgtgcggct acttcgcctt ctaccacgcc ctgtaccccc gcgcctggac cgtgtaccag  720
ctgcccggcc agaacgtgac cctgacctgc cgccagatca cccccatcct gccccacgac  780
taccaggaca gcagcctgcc cgtgggcgtg ttcgtgtggg acgtggagaa cgagggcgac  840
gaggccctgg acgtgagcat catgttcagc atgcgcaacg gcctgggcgg cggcgacgac  900
gcccccggcg gcctgtggaa cgagcccttc tgcctggagc gcagcggcga gaccgtgcgc  960
ggcctgctgc tgcaccaccc caccctgccc aacccctaca ccatggccgt ggccgcccgc  1020
gtgaccgccg ccaccaccgt gacccacatc accgccttcg accccgacag caccggccag  1080
caggtgtggc aggacctgct gcaggacggc cagctggaca gccccaccgg ccagagcacc  1140
cccacccaga agggcgtggg catcgccggc gccgtgtgcg tgagcagcaa gctgcgcccc  1200
cgcggccagt gccgcctgga gttcagcctg gcctgggaca tgccccgcat catgttcggc  1260
gccaagggcc aggtgcacta ccgccgctac acccgcttct tcggccagga cggcgacgcc  1320
gcccccgccc tgagccacta cgccctgtgc cgctacgccg agtgggagga gcgcatcagc  1380
gcctggcaga gccccgtgct ggacgaccgc agcctgcccg cctggtacaa gagcgccctg  1440
ttcaacgagc tgtacttcct ggccgacggc ggcaccgtgt ggctggaggt gctggaggac  1500
agcctgcccg aggagctggg ccgcaacatg tgccacctgc gccccaccct gcgcgactac  1560
ggccgcttcg gctacctgga gggccaggag taccgcatgt acaacaccta cgacgtgcac  1620
ttctacgcca gcttcgccct gatcatgctg tggcccaagc tggagctgag cctgcagtac  1680
gacatggccc tggccaccct gcgcgaggac ctgacccgcc gccgctacct gatgagcggc  1740
gtgatggccc ccgtgaagcg ccgcaacgtg atcccccacg acatcggcga ccccgacgac  1800
gagccctggc tgcgcgtgaa cgcctacctg atccacgaca ccgccgactg gaaggacctg  1860
aacctgaagt tcgtgctgca ggtgtaccgc gactactacc tgaccggcga ccagaacttc  1920
ctgaaggaca tgtggcccgt gtgcctggcc gtgatggaga gcgagatgaa gttcgacaag  1980
gaccacgacg gcctgatcga gaacggcggc tacgccgacc agacctacga cggctgggtg  2040
accaccggcc ccagcgccta ctgcggcggc ctgtggctgg ccgccgtggc cgtgatggtg  2100
cagatggccg ccctgtgcgg cgcccaggac atccaggaca agttcagcag catcctgagc  2160
cgcggccagg aggcctacga gcgcctgctg tggaacggcc gctactacaa ctacgacagc  2220
agcagccgcc cccagagccg cagcgtgatg agcgaccagt gcgccggcca gtggttcctg  2280
aaggcctgcg gcctgggcga gggcgacacc gaggtgttcc ccacccagca cgtggtgcgc  2340
gccctgcaga ccatcttcga gctgaacgtg caggccttcg ccggcggcgc catgggcgcc  2400
gtgaacggca tgcagcccca cggcgtgccc gacaagagca gcgtgcagag cgacgaggtg  2460
tgggtgggcg tggtgtacgg cctggccgcc accatgatcc aggagggcct gacctgggag  2520
ggcttccaga ccgccgaggg ctgctaccgc accgtgtggg agcgcctggg cctggccttc  2580
cagacccccg aggcctactg ccagcagcgc gtgttccgca gcctggccta catgcgcccc  2640
ctgagcatct gggccatgca gctggccctg cagcagcagc agcacaagaa ggccagctgg  2700
cccaaggtga agcagggcac cggcctgcgc accggcccca tgttcggccc caaggaggcc  2760
atggccaacc tgagccccga g                                          2781
```

```
SEQ ID NO: 32           moltype = DNA  length = 11264
FEATURE                 Location/Qualifiers
misc_feature            1..11264
                        note = Synthetic polynucleotide
source                  1..11264
                        mol_type = other DNA
                        organism = synthetic construct
SEQUENCE: 32
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agtaagtcac  300
tgactgtcta tgcctgggaa agggtgggca ggagatgggg cagtgcagga aaagtggcac  360
tatgaaccct cctggtggcg aggggagggg ggtggtcctc gaacgccttg cagaactggc  420
ctggatacag agtggaccgg ctggccccat ctggaagact tcgagataca ctgttgtctt  480
actgcgctca acagtgtatc tcgaagtctt ccaaatggtg ccagccatcg cagcggggtg  540
caggaaatgg gggcagcccc cctttttggc tatccttcca cgtgttcttt tttgtatctt  600
ttgtgtttcc tagaaaacat ctcagtcacc accgcagccc taggaatgca tctagacaat  660
tgtactaacc ttcttctctt tcctctcctg acagtccgga aagccaccat gggcacccag  720
gaccccggca acatgggcac cggcgtgccc gccagcgagc agatcagctg cgccaaggag  780
gacccccagg tgtactgccc cgaggagacc ggcggcacca aggacgtgca ggtgaccgac  840
tgcaagagcc ccgaggacag ccgccccccc aaggagaccg actgctgcaa ccccgaggac  900
agcggccagc tgatggtgag ctacgagggc aaggccatgg gctaccaggt gcccccccttc  960
ggctggcgca tctgcctggc ccacgagttc accgagaagc gcaagccctt ccaggccaac  1020
aacgtgagcc tgagcaacat gatcaagcac atcggcatgg gcctgcgcta cctgcagtgg  1080
tggtaccgca agacccacgt ggagaagaag accccccttca tcgacatgat caacagcgtg  1140
cccctgcgcc agatctacgg ctgccccctg ggcggcatcg gcggcggcac catcacccgc  1200
ggctggcgcg gccagttctg ccgctggcag ctgaaccccg gcatgtacca gcaccgcacc  1260
gtgatcgccg accagttcac cgtgtgcctg cgccgcgagg gccagaccgt gtaccagcag  1320
gtgctgagcc tggagcgccc cagcgtgctg cgcagctgga actggggcct gtgcggctac  1380
ttcgccttct accacgccct gtacccccgc gcctggaccg tgtaccagct gcccggccag  1440
aacgtgaccc tgacctgccg ccagatcacc cccatcctgc cccacgacta ccaggacagc  1500
```

```
agcctgcccg tgggcgtgtt cgtgtgggac gtggagaacg agggcgacga ggccctggac  1560
gtgagcatca tgttcagcat gcgcaacggc ctgggcggcg gcgacgacgc ccccggcggc  1620
ctgtggaacg agcccttctg cctggagcgc agcggcgaga ccgtgcgcgg cctgctgctg  1680
caccacccca ccctgcccaa cccctacacc atggccgtgg ccgcccgcgt gaccgccgcc  1740
accaccgtga cccacatcac cgccttcgac cccgacagca ccggccagca ggtgtggcag  1800
gacctgctgc aggacggcca gctggacagc ccccaccggcc agagcacccc cacccagaag  1860
ggcgtgggca tcgccggcgc cgtgtgcgtg agcagcaagc tgcgcccccg cggccagtgc  1920
cgcctggagt tcagcctggc ctgggacatg ccccgcatca tgttcggcgc caagggccag  1980
gtgcactacc gccgctacac ccgcttcttc ggccaggacg gcgacgccgc ccccgccctg  2040
agccactacg ccctgtgccg ctacgccgag tgggaggagc gcatcagcgc ctggcagagc  2100
cccgtgctgg acgaccgcag cctgcccgcc tggtacaaga gcgccctgtt caacgagctg  2160
tacttcctgg ccgacggcgg caccgtgtgg ctggaggtgc tggaggacag cctgcccgag  2220
gagctgggcc gcaacatgtg ccacctgcgc cccaccctgc gcgactacgg ccgcttcggc  2280
tacctggagg gccaggagta ccgcatgtac aacacctacg acgtgcactt ctacgccagc  2340
ttcgccctga tcatgctgtg gcccaagctg gagctgagcc tgcagtacga catggccctg  2400
gccaccctgc gcgaggacct gacccgccgc cgctacctga tgagcggcgt gatggccccc  2460
gtgaagcgcc gcaacgtgat cccccacgac atcggcgacc ccgacgacga gccctggctg  2520
cgcgtgaacg cctacctgat ccacgacacc gccgactgga aggacctgaa cctgaagttc  2580
gtgctgcagg tgtaccgcga ctactacctg accggcgacc agaacttcct gaaggacatg  2640
tggcccgtgt gcctggccgt gatggagagc gagatgaagt tcgacaagga ccacgacggc  2700
ctgatcgaga acggcggcta cgccgaccag acctacgacg gctgggtgac caccggcccc  2760
agcgcctact gcggcggcct gtggctggcc gccgtggccg tgatggtgca gatggccgcc  2820
ctgtgcggcg cccaggacat ccaggacaag ttcagcagca tcctgagccg cggccaggag  2880
gcctacgagc gcctgctgtg gaacggccgc tactacaact acgacagcag cagccgcccc  2940
cagagccgca gcgtgatgag cgaccagtgc gccggccagt ggttcctgaa ggcctgcggc  3000
ctgggcgagg gcgacaccga ggtgttcccc acccagcacg tggtgcgcgc cctgcagacc  3060
atcttcgagc tgaacgtgca ggccttcgcc ggcggcgcca tgggcgccgt gaacggcatg  3120
cagcccccacg gcgtgcccga caagagcagc gtgcagagcg acgaggtgtg ggtgggcgtg  3180
gtgtacggcc tggccgccac catgatccag gagggcctga cctgggaggg cttccagacc  3240
gccgagggct gctaccgcac cgtgtgggag cgcctgggcc tggccttcca gacccccgag  3300
gcctactgcc agcagcgcgt gttccgcagc ctggcctaca tgcgccccct gagcatctgg  3360
gccatgcagc tggccctgca gcagcagcag cacaagaagg ccagctggcc caaggtgaag  3420
cagggcaccg gcctgcgcac cggcccccatg ttcggcccca aggaggccat ggccaacctg  3480
agccccgagt gacaattgtt aattaagttt aaaccctcga ggccgcaagc ttatcgataa  3540
tcaacctctg gattacaaaa tttgtgaaag attgactggt attcttaact atgttgctcc  3600
ttttacgcta tgtggatacg ctgctttaat gcctttgtat catgctattg cttcccgtat  3660
ggctttcatt ttctcctcct tgtataaatc ctggttgctg tctctttatg aggagttgtg  3720
gcccgttgtc aggcaacgtg gcgtggtgtg cactgtgttt gctgacgcaa cccccactgg  3780
ttggggcatt gccaccacct gtcagctcct ttccgggact ttcgctttcc ccctccctat  3840
tgccacggcg gaactcatcg ccgcctgcct tgcccgctgc tggacagggg ctcggctgtt  3900
gggcactgac aattccgtgg tgttgtcggg gaaatcatcg tcctttcctt ggctgctcgc  3960
ctgtgttgcc acctggattc tgcgcgggac gtccttctgc tacgtccctt cggccctcaa  4020
tccagcggac cttccttccc gcggcctgct gccggctctg cggcctcttc cgcgtcttcg  4080
ccttcgccct cagacgagtc ggatctccct ttgggccgcc tccccgcatc gataccgtcg  4140
actagagctc gctgatcagc ctcgactgtg ccttctagtt gccagccatc tgttgtttgc  4200
ccctcccccg tgccttcctt gaccctggaa ggtgccactc ccactgtcct ttcctaataa  4260
aatgaggaaa ttgcatcgca ttgtctgagt aggtgtcatt ctattctggg gggtggggtg  4320
gggcaggaca gcaaggggga ggattgggaa gacaatagca ggcatgctgg ggagagatcc  4380
acgataacaa acagcttttt tggggtgaac atattgactg aattccctgc aggttggcca  4440
ctccctctct gcgcgctcgc tcgctcactg aggccgcccg ggcaaagccc gggcgtcggg  4500
cgacctttgg tcgcccggcc tcagtgagcg agcgagcgcg cagagaggga gtggccaact  4560
ccatcactag gggttcctgc ggccgctcgt acggtctcga ggaattcctg caggataact  4620
tgccaacctc attctaaaat gtatatagaa gcccaaaaga caataacaaa aatattcttg  4680
tagaacaaaa tgggaaagaa tgttccacta aatatcaaga tttagagcaa agcatgagat  4740
gtgtggggat agacagtgag gctgataaaa tagagtagag ctcagaaaca gacccattga  4800
tatatgtaag tgacctatga aaaaaatatg gcattttaca atgggaaaat gatggtcttt  4860
ttctttttta gaaaaacagg gaaatatatt tatatgtaaa aaataaaagg gaacccatat  4920
gtcataccat acacacaaaa aaattccagt gaattataag tctaaatgga gaaggcaaaa  4980
ctttaaatct tttagaaaat aatatagaag catgcagacc agcctggcca acatgatgaa  5040
accctctcta ctaataataa aatcagtaga actactcagg actactttga gtgggaagtc  5100
cttttctatg aagacttctt tggccaaaat taggctctaa atgcaaggag atagtgcatc  5160
atgcctggct gcacttactg ataaatgatg ttatcaccat ctttaaccaa atgcacagga  5220
acaagttatg gtactgatgt gctggattga gaaggagctc tacttccttg acaggacaca  5280
tttgtatcaa cttaaaaaag cagatttttg ccagcagaac tattcattca gaggtaggaa  5340
acttagaata gatgatgtca ctgattagca tggcttcccc atctccacag ctgcttccca  5400
cccaggttgc ccacagttga gtttgtccag tgctcagggc tgcccactct cagtaagaag  5460
ccccacacca gcccctctcc aaatatgttg gctgttcctt ccattaaagt gaccccactt  5520
tagagcagca agtggatttc tgtttcttac agttcaggaa ggaggagtca gctgtgagaa  5580
cctggagcct gagatgcttc taagtcccac tgctactggg gtcagggaag ccagactcca  5640
gcatcagcag tcaggagcac taagcccttg ccaacatcct gtttctcaga gaaactgctt  5700
ccattataat ggttgtcctt ttttaagcta tcaagccaaa caaccagtgt ctaccattat  5760
tctcatcacc tgaagccaag ggttctagca aaagtcaagc tgtcttgtaa tggttgatgt  5820
gcctccagct tctgtcttca gtcactccac tcttagcctg ctctgaatca actctgacca  5880
cagttccctg gagcccctgc cacctgctgc ccctgccacc ttctccatct gcagtgctgt  5940
gcagccttct gcactcttgc agagctaata ggtggagact tgaaggaaga ggaggaaagt  6000
ttctcataat agccttgctg caagctcaaa tgggaggtgg gcactgtgcc caggagcctt  6060
ggagcaaagg ctgtgcccaa cctctgactg catccaggtt tggtcttgac agagataaga  6120
agccctggct tttggagcca aaatctaggt cagacttagg caggattctc aaagtttatc  6180
agcagaacat gaggcagaag accctttctg ctccagcttc ttcaggctca accttcatca  6240
```

```
gaatagatag aaagagaggc tgtgagggtt cttaaaacag aagcaaatct gactcagaga  6300
ataaacaacc tcctagtaaa ctacagctta gacagagcat ctggtggtga gtgtgctcag  6360
tgtcctactc aactgtctgg tatcagccct catgaggact tctcttcttt ccctcataga  6420
cctccatctc tgttttcctt agcctgcaga aatctggatg gctattcaca gaatgcctgt  6480
gctttcagag ttgcattttt tctctggtat tctggttcaa gcatttgaag gtaggaaagg  6540
ttctccaagt gcaagaaagc cagccctgag cctcaactgc ctggctagtg tggtcagtag  6600
gatgcaaagg ctgttgaatg ccacaaggcc aaactttaac ctgtgtacca caagcctagc  6660
agcagaggca gctctgctca ctggaactct ctgtcttctt tctcctgagc cttttctttt  6720
cctgagtttt ctagctctcc tcaaccttac ctctgcccta cccaggacaa acccaagagc  6780
cactgtttct gtgatgtcct ctccagccct aattaggcat catgacttca gcctgacctt  6840
ccatgctcag aagcagtgct aatccacttc agatgagctg ctctatgcaa cacaggcaga  6900
gcctacaaac ctttgcacca gagccctcca catatcagtg tttgttcata ctcacttcaa  6960
cagcaaatgt gactgctgag attaagattt tacacaagat ggtctgtaat ttcacagtta  7020
gttttatccc attaggtatg aaagaattag cataattccc cttaaacatg aatgaatctt  7080
agatttttta ataaatagtt ttggaagtaa agacagagac atcaggagca caaggaatag  7140
cctgagagga caaacagaac aagaaagagt ctggaaatac acaggatgtt cttggcctcc  7200
tcaaagcaag tgcaagcaga tagtaccagc agccccaggc tatcagagcc cagtgaagag  7260
aagtaccatg aaagccacag ctctaaccac cctgttccag agtgacagac agtccccaag  7320
acaagccagc ctgagccaga gagagaactg caagagaaag tttctaattt aggttctgtt  7380
agattcagac aagtgcaggt catcctctct ccacagctac tcacctctcc agcctaacaa  7440
agcctgcagt ccacactcca accctggtgt ctcacctcct agcctctccc aacatcctgc  7500
tctctgacca tcttctgcat ctctcatctc accatctccc actgtctaca gcctactctt  7560
gcaactacca tctcattttc tgacatcctg tctacatctt ctgccatact ctgccatcta  7620
ccataccacc tcttaccatc taccacacca tcttttatct ccatccctct cagaagcctc  7680
caagctgaat cctgctttat gtgttcatct cagcccctgc atggaaagct gaccccagag  7740
gcagaactat tcccagagag cttggccaag aaaaacaaaa ctaccagcct ggccaggctc  7800
aggagtagta agctgcagtg tctgttgtgt tctagcttca acagctgcag gagttccact  7860
ctcaaatgct ccacatttct cacatcctcc tgattctggt cactacccat cttcaaagaa  7920
cagaatatct cacatcagca tactgtgaag gactagtcat gggtgcagct gctcagagct  7980
gcaaagtcat tctggatggt ggagagctta caaacatttc atgatgctcc ccccgctctg  8040
atggctggag cccaatccct acacagactc ctgctgtatg tgttttcctt tcactctgag  8100
ccacagccag agggcaggca ttcagtctcc tcttcaggct ggggctgggg cactgagaac  8160
tcacccaaca ccttgctctc actccttctg caaaacaaga aagagctttg tgctgcagta  8220
gccatgaaga atgaaaggaa ggctttaact aaaaaatgtc agagattatt ttcaacccct  8280
tactgtggat caccagcaag gaggaaacac aacacagaga catttttttcc cctcaaatta  8340
tcaaaagaat cactgcattt gttaaagaga gcaactgaat caggaagcag agttttgaac  8400
atatcagaag ttaggaatct gcatcagaga caaatgcagt catggttgtt tgctgcatac  8460
cagccctaat cattagaagc ctcatggact tcaaacatca ttccctctga caagatgctc  8520
tagcctaact ccatgagata aaataaatct gcctttcaga gccaaagaag agtccaccag  8580
cttcttctca gtgtgaacaa gagctccagt caggttagtc agtccagtgc agtagaggag  8640
accagtctgc atcctctaat tttcaaaggc aagaagattt gtttaccctg gacaccaggc  8700
acaagtgagg tcacagagct cttagatatg cagtcctcat gagtgaggag actaaagcgc  8760
atgccatcaa gacttcagtg tagagaaaac ctccaaaaaa gcctcctcac tacttctgga  8820
atagctcaga ggccgaggcg gcctcggcct ctgcataaat aaaaaaaatt agtcagccat  8880
ggggcggaga atgggcggaa ctgggcggag ttaggggcgg gatgggcgga gttaggggcg  8940
ggactatggt tgctgactaa ttgagatgca tgctttgcat acttctgcct gctggggagc  9000
ctggggactt tccacacctg gttgctgact aattgagatg catgctttgc atacttctgc  9060
ctgctgggga gcctggggac tttccacacc ctaactgaca cacattccac agctgcatta  9120
atgaatcggc caacgcgcgg ggagaggcgg tttgcgtatt gggcgctctt ccgcttcctc  9180
gctcactgac tcgctgcgct cggtcgttcg gctgcggcga gcggtatcag ctcactcaaa  9240
ggcggtaata cggttatcca cagaatcagg ggataacgca ggaaagaaca tgtgagcaaa  9300
aggccagcaa aaggccagga accgtaaaaa ggccgcgttg ctggcgtttt tccataggct  9360
ccgcccccct gacgagcatc acaaaaatcg acgctcaagt cagaggtggc gaaacccgac  9420
aggactataa agataccagg cgtttccccc tggaagctcc ctcgtgcgct ctcctgttcc  9480
gaccctgccg cttaccggat acctgtccgc ctttctccct tcgggaagcg tggcgctttc  9540
tcatagctca cgctgtaggt atctcagttc ggtgtaggtc gttcgctcca agctgggctg  9600
tgtgcacgaa ccccccgttc agcccgaccg ctgcgcctta tccggtaact atcgtcttga  9660
gtccaacccg gtaagacacg acttatcgcc actggcagca gccactggta acaggattag  9720
cagagcgagg tatgtaggcg gtgctacaga gttcttgaag tggtggccta actacggcta  9780
cactagaaga acagtatttg gtatctgcgc tctgctgaag ccagttacct tcggaaaaag  9840
agttggtagc tcttgatccg gcaaacaaac caccgctggt agcggtggtt tttttgtttg  9900
caagcagcag attacgcgca gaaaaaaagg atctcaagaa gatcctttga tcttttctac  9960
ggggtctgac gctcagtgga acgaaaactc acgttaaggg attttggtca tgagattatc  10020
aaaaaggatc ttcacctaga tccttttaaa ttaaaaatga agttttaaat caatctaaag  10080
tatatatgag taaacttggt ctgacagtta ccaatgctta atcagtgagg cacctatctc  10140
agcgatctgt ctatttcgtt catccatagt tgcctgactc ctgcaaacca cgttgtgtct  10200
caaaatctct gatgttacat tgcacaagat aaaaatatat catcatgaac aataaaactg  10260
tctgcttaca taaacagtaa tacaaggggt gttatgagcc atattcaacg ggaaacgtct  10320
tgctcgaggc cgcgattaaa ttccaacatg gatgctgatt tatatgggta taaatgggct  10380
cgcgataatg tcgggcaatc aggtgcgaca atctatcgat tgtatgggaa gcccgatgcg  10440
ccagagttgt ttctgaaaca tggcaaaggt agcgttgcca atgatgttac agatgagatg  10500
gtcagactaa actggctgac ggaatttatg cctcttccga ccatcaagca ttttatccgt  10560
actcctgatg atgcatggtt actcaccact gcgatccccg ggaaaacagc attccaggta  10620
ttagaagaat atcctgattc aggtgaaaat attgttgatg cgctggcagt gttcctgcgc  10680
cggttgcatt cgattcctgt ttgtaattgt ccttttaaca gcgatcgcgt atttcgtctc  10740
gctcaggcgc aatcacgaat gaataacggt ttggttgatg cgagtgattt tgatgacgag  10800
cgtaatggct ggcctgttga acaagtctgg aaagaaatgc ataagctttt gccattctca  10860
ccggattcag tcgtcactca tggtgatttc tcacttgata accttatttt tgacgagggg  10920
aaattaatag gttgtattga tgttggacga gtcggaatcg cagaccgata ccaggatctt  10980
```

```
gccatcctat ggaactgcct cggtgagttt tctccttcat tacagaaacg gctttttcaa  11040
aaatatggta ttgataatcc tgatatgaat aaattgcagt ttcatttgat gctcgatgag  11100
tttttctaag ggcggcctgc caccataccc acgccgaaac aagcgctcat gagcccgaag  11160
tggcgagccc gatcttcccc atcggtgatg tcggcgatat aggcgccagc aaccgcacct  11220
gtggcgccgg tgatgagggc gcgccaagtc gacgtccggc agtc                   11264

SEQ ID NO: 33          moltype = AA  length = 685
FEATURE                Location/Qualifiers
REGION                 1..685
                       note = Synthetic polypeptide
source                 1..685
                       mol_type = protein
                       organism = synthetic construct
SEQUENCE: 33
MAEWLLSASW QRRAKAMTAA AGSAGRAAVP LLLCALLAPG GAYVLDDSDG LGREFDGIGA  60
VSGGGATSRL LVNYPEPYRS QILDYLFKPN FGASLHILKV EIGGDGQTTD GTEPSHMHYA  120
LDENYFRGYE WWLMKEAKKR NPNITLIGLP WSFPGWLGKG FDWPYVNLQL TAYYVVTWIV  180
GAKRYHDLDI DYIGIWNERS YNANYIKILR KMLNYQGLQR VKIIASDNLW ESISASMLLD  240
AELFKVVDVI GAHYPGTHSA KDAKLTGKKL WSSEDFSTLN SDMGAGCWGR ILNQNYINGY  300
MTSTIAWNLV ASYYEQLPYG RCGLMTAQEP WSGHYVVESP VWVSAHTTQF TQPGWYYLKT  360
VGHLEKGGSY VALTDGLGNL TIIIETMSHK HSKCIRPFLP YFNVSQQFAT FVLKGSFSEI  420
PELQVWYTKL GKTSERFLFK QLDSLWLLDS DGSFTLSLHE DELFTLTTLT TGRKGSYPLP  480
PKSQPFPSTY KDDFNVDYPF FSEAPNFADQ TGVFEYFTNI EDPGEHHFTL RQVLNQRPIT  540
WAADASNTIS IIGDYNWTNL TIKCDVYIET PDTGGVFIAG RVNKGGILIR SARGIFFWIF  600
ANGSYRVTGD LAGWIIYALG RVEVTAKKWY TLTLTIKGHF TSGMLNDKSL WTDIPVNFPK  660
NGWAAIGTHS FEFAQFDNFL VEATR                                        685

SEQ ID NO: 34          moltype = DNA  length = 2055
FEATURE                Location/Qualifiers
misc_feature           1..2055
                       note = Synthetic polynucleotide
source                 1..2055
                       mol_type = other DNA
                       organism = synthetic construct
SEQUENCE: 34
atggccgagt ggctgctgag cgccagctgg cagcgccgcg ccaaggccat gaccgccgcc  60
gccggcagcg ccggccgcgc cgccgtgccc ctgctgctgt gcgccctgct ggccccggc  120
ggcgcctacg tgctggacga cagcgacggc ctgggccgcg agttcgacgg catcggcgcc  180
gtgagcggcg gcggcgccac cagccgcctg ctggtgaact accccgagcc ctaccgcagc  240
cagatcctgg actacctgtt caagcccaac ttcggcgcca gcctgcacat cctgaaggtg  300
gagatcggcg gcgacggcca gaccaccgac ggcaccgagc ccagccacat gcactacgcc  360
ctggacgaga actacttccg cggctacgag tggtggctga tgaaggaggc caagaagcgc  420
aaccccaaca tcaccctgat cggcctgccc tggagcttcc ccggctggct gggcaagggc  480
ttcgactggc cctacgtgaa cctgcagctg accgcctact acgtggtgac ctggatcgtg  540
ggcgccaagc gctaccacga cctggacatc gactacatcg gcatctggaa cgagcgcagc  600
tacaacgcca actacatcaa gatcctgcgc aagatgctga actaccaggg cctgcagcgc  660
gtgaagatca tcgccagcga caacctgtgg gagagcatca gcgccagcat gctgctggac  720
gccgagctgt tcaaggtggt ggacgtgatc ggcgcccact accccggcac ccacagcgcc  780
aaggacgcca agctgaccgg caagaagctg tggagcagcg aggacttcag caccctgaac  840
agcgacatgg gcgccggctg ctggggccgc atcctgaacc agaactacat caacggctac  900
atgaccagca ccatcgcctg gaacctggtg gccagctact acgagcagct gccctacggc  960
cgctgcggcc tgatgaccgc ccaggagccc tggagcggcc actacgtggt ggagagcccc  1020
gtgtgggtga gcgcccacac cacccagttc acccagcccg gctggtacta cctgaagacc  1080
gtgggccacc tggagaaggg cggcagctac gtggccctga ccgacggcct gggcaacctg  1140
accatcatca tcgagaccat gagccacaag cacagcaagt gcatccgccc cttcctgccc  1200
tacttcaacg tgagccagca gttcgccacc ttcgtgctga agggcagctt cagcgagatc  1260
cccgagctgc aggtgtggta caccaagctg ggcaagacca gcgagcgctt cctgttcaag  1320
cagctggaca gcctgtggct gctggacagc gacggcagct tcaccctgag cctgcacgag  1380
gacgagctgt tcaccctgac caccctgacc accggccgca agggcagcta cccccctgccc  1440
cccaagagcc agcccttccc cagcacctac aaggacgact tcaacgtgga ctaccccttc  1500
ttcagcgagg cccccaactt cgccgaccag accggcgtgt tcgagtactt caccaacatc  1560
gaggaccccg gcgagcacca cttcaccctg cgccaggtgc tgaaccagcg ccccatcacc  1620
tgggccgccg acgccagcaa caccatcagc atcatcggcg actacaactg gaccaacctg  1680
accatcaagt gcgacgtgta catcgagacc cccgacaccg gcggcgtgtt catcgccggc  1740
cgcgtgaaca agggcggcat cctgatccgc agcgcccgcg gcatcttctt ctggatcttc  1800
gccaacggca gctaccgcgt gaccggcgac ctggccggct ggatcatcta cgccctgggc  1860
cgcgtggagg tgaccgccaa gaagtggtac accctgaccc tgaccatcaa gggccacttc  1920
accagcggca tgctgaacga caagagcctg tggaccgaca tccccgtgaa cttccccaag  1980
aacggctggg ccgccatcgg cacccacagc ttcgagttcg cccagttcga caacttcctg  2040
gtggaggcca cccgc                                                   2055

SEQ ID NO: 35          moltype = AA  length = 339
FEATURE                Location/Qualifiers
REGION                 1..339
                       note = Synthetic polypeptide
source                 1..339
                       mol_type = protein
                       organism = synthetic construct
SEQUENCE: 35
```

```
MWQLWASLCC LLVLANARSR PSFHPLSDEL VNYVNKRNTT WQAGHNFYNV DMSYLKRLCG  60
TFLGGPKPPQ RVMFTEDLKL PASFDAREQW PQCPTIKEIR DQGSCGSCWA FGAVEAISDR  120
ICIHTNAHVS VEVSAEDLLT CCGSMCGDGC NGGYPAEAWN FWTRKGLVSG GLYESHVGCR  180
PYSIPPCEHH VNGSRPPCTG EGDTPKCSKI CEPGYSPTYK QDKHYGYNSY SVSNSEKDIM  240
AEIYKNGPVE GAFSVYSDFL LYKSGVYQHV TGEMMGGHAI RILGWGVENG TPYWLVANSW  300
NTDWGDNGFF KILRGQDHCG IESEVVAGIP RTDQYWEKI                        339

SEQ ID NO: 36          moltype = DNA  length = 1017
FEATURE                Location/Qualifiers
misc_feature           1..1017
                       note = Synthetic polynucleotide
source                 1..1017
                       mol_type = other DNA
                       organism = synthetic construct
SEQUENCE: 36
atgtggcagc tgtgggccag cctgtgctgc ctgctggtgc tggccaacgc ccgcagccgc  60
cccagcttcc acccccctgag cgacgagctg gtgaactacg tgaacaagcg caacaccacc  120
tggcaggccg gccacaactt ctacaacgtg gacatgagct acctgaagcg cctgtgcggc  180
accttcctgg gcggccccaa gcccccccag cgcgtgatgt tcaccgagga cctgaagctg  240
cccgccagct tcgacgcccg cgagcagtgg ccccagtgcc ccaccatcaa ggagatccgc  300
gaccagggca gctgcggcag ctgctgggcc ttcggcgccg tggaggccat cagcgaccgc  360
atctgcatcc acaccaacgc ccacgtgagc gtggaggtga gcgccgagga cctgctgacc  420
tgctgcggca gcatgtgcgg cgacggctgc aacggcggct accccgccga ggcctggaac  480
ttctggaccc gcaagggcct ggtgagcggc ggcctgtacg agagccacgt gggctgccgc  540
ccctacagca tcccccctg cgagcaccac gtgaacggca gccgcccccc ctgcaccggc  600
gagggcgaca cccccaagtg cagcaagatc tgcgagcccg gctacagccc cacctacaag  660
caggacaagc actacggcta caacagctac agcgtgagca acagcgagaa ggacatcatg  720
gccgagatct acaagaacgg ccccgtggag ggcgccttca gcgtgtacag cgacttcctg  780
ctgtacaaga gcggcgtgta ccagcacgtg accggcgaga tgatgggcgg ccacgccatc  840
cgcatcctgg gctggggcgt ggagaacggc accccctact ggctggtggc caacagctgg  900
aacaccgact ggggcgacaa cggcttcttc aagatcctgc gcggccagga ccactgcggc  960
atcgagagcg aggtggtggc cggcatcccc cgcaccgacc agtactggga gaagatc     1017

SEQ ID NO: 37          moltype = AA  length = 631
FEATURE                Location/Qualifiers
REGION                 1..631
                       note = Synthetic polypeptide
source                 1..631
                       mol_type = protein
                       organism = synthetic construct
SEQUENCE: 37
MPRYGASLRQ SCPRSGREQG QDGTAGAPGL LWMGLVLALA LALALALALS DSRVLWAPAE  60
AHPLSPQGHP ARLHRIVPRL RDVFGWGNLT CPICKGLFTA INLGLKKEPN VARVGSVAIK  120
LCNLLKIAPP AVCQSIVHLF EDDMVEVWRR SVLSPSEACG LLLGSTCGHW DIFSSWNISL  180
PTVPKPPPKP PSPPAPGAPV SRILFLTDLH WDHDYLEGTD PDCADPLCCR RGSGLPPASR  240
PGAGYWGEYS KCDLPLRTLE SLLSGLGPAG PFDMVYWTGD IPAHDVWHQT RQDQLRALTT  300
VTALVRKFLG PVPVYPAVGN HESTPVNSFP PPFIEGNHSS RWLYEAMAKA WEPWLPAEAL  360
RTLRIGGFYA LSPYPGLRLI SLNMNFCSRE NFWLLINSTD PAGQLQWLVG ELQAAEDRGD  420
KVHIIGHIPP GHCLKSWSWN YYRIVARYEN TLAAQFFGHT HVDEFEVFYD EETLSRPLAV  480
AFLAPSATTY IGLNPGYRVY QIDGNYSGSS HVVLDHETYI LNLTQANIPG AIPHWQLLYR  540
ARETYGLPNT LPTAWHNLVY RMRGDMQLFQ TFWFLYHKGH PPSEPCGTPC RLATLCAQLS  600
ARADSPALCR HLMPDGSLPE AQSLWPRPLF C                                631

SEQ ID NO: 38          moltype = DNA  length = 1896
FEATURE                Location/Qualifiers
misc_feature           1..1896
                       note = Synthetic polynucleotide
source                 1..1896
                       mol_type = other DNA
                       organism = synthetic construct
SEQUENCE: 38
atgccccgct acggcgccag cctgcgccag agctgccccc gcagcggccg cgagcagggc  60
caggacggca ccgccggcgc ccccggcctg ctgtggatgg gcctggtgct ggccctggcc  120
ctggccctgg ccctggccct ggccctgagc gacagccgcg tgctgtgggc ccccgccgag  180
gcccacccccc tgagccccca gggccacccc gcccgcctgc accgcatcgt gccccgcctg  240
cgcgacgtgt tcggctgggg caacctgacc tgccccatct gcaagggcct gttcaccgcc  300
atcaacctgg gcctgaagaa ggagcccaac gtggcccgcg tgggcagcgt ggccatcaag  360
ctgtgcaacc tgctgaagat cgcccccccc gccgtgtgcc agagcatcgt gcacctgttc  420
gaggacgaca tggtggaggt gtggcgccgc agcgtgctga gccccagcga ggcctgcggc  480
ctgctgctgg gcagcacctg cggccactgg gacatcttca gcagctggaa catcagcctg  540
cccaccgtgc ccaagccccc ccccaagccc cccagccccc ccgcccccgg cgcccccgtg  600
agccgcatcc tgttcctgac cgacctgcac tgggaccacg actacctgga gggcaccgac  660
cccgactgcg ccgacccccct gtgctgccgc cgcggcagcg gcctgccccc cgccagccgc  720
cccggcgccg gctactgggg cgagtacagc aagtgcgacc tgcccctgcg caccctggag  780
agcctgctga gcggcctggg ccccgccggc cccttcgaca tggtgtactg gaccggcgac  840
atccccgccc acgacgtgtg gcaccagacc cgccaggacc agctgcgcgc cctgaccacc  900
gtgaccgccc tggtgcgcaa gttcctgggc cccgtgcccg tgtaccccgc cgtgggcaac  960
cacgagagca cccccgtgaa cagcttcccc ccccccttca tcgagggcaa ccacagcagc  1020
cgctggctgt acgaggccat ggccaaggcc tgggagccct ggctgcccgc cgaggccctg  1080
```

```
cgcaccctgc gcatcggcgg cttctacgcc ctgagcccct accccggcct gcgcctgatc  1140
agcctgaaca tgaacttctg cagccgcgag aacttctggc tgctgatcaa cagcaccgac  1200
cccgccggcc agctgcagtg gctggtgggc gagctgcagg ccgccgagga ccgcggcgac  1260
aaggtgcaca tcatcggcca catccccccc ggccactgcc tgaagagctg gagctggaac  1320
tactaccgca tcgtggcccg ctacgagaac accctggccg cccagttctt cggccacacc  1380
cacgtggacg agttcgaggt gttctacgac gaggagaccc tgagccgccc cctggccgtg  1440
gccttcctgg cccccagcgc caccacctac atcggcctga accccggcta ccgcgtgtac  1500
cagatcgacg gcaactacag cggcagcagc cacgtggtgc tggaccacga gacctacatc  1560
ctgaacctga cccaggccaa catccccggc gccatccccc actggcagct gctgtaccgc  1620
gcccgcgaga cctacggcct gcccaacacc ctgcccaccg cctggcacaa cctggtgtac  1680
cgcatgcgcg gcgacatgca gctgttccag accttctggt tcctgtacca caagggccac  1740
ccccccagcg agccctgcgg cacccccctgc cgcctggcca ccctgtgcgc ccagctgagc  1800
gcccgcgccg acagccccgc cctgtgccgc cacctgatgc ccgacggcag cctgcccgag  1860
gcccagagcc tgtggccccg ccccctgttc tgctaa                            1896
```

```
SEQ ID NO: 39          moltype = DNA  length = 11329
FEATURE                Location/Qualifiers
misc_feature           1..11329
                       note = Synthetic polynucleotide
source                 1..11329
                       mol_type = other DNA
                       organism = synthetic construct
SEQUENCE: 39
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atgggggcagt gcaggaaaag  540
tggcactatg aaccctgcag ccctaggaat gcatctagac aattgtacta accttcttct  600
ctttcctctc ctgacagtcc ggaaagccac catggaattc agcagcccca gcagagagga  660
atgccccaag cctctgagcc gggtgtcaat catggccgga tctctgacag gactgctgct  720
gcttcaggcc gtgtcttggg cttctggcgc tagaccttgc atccccaaga gcttcggcta  780
cagcagcgtc gtgtgcgtgt gcaatgccac ctactgcgac agcttcgacc ctcctacctt  840
tcctgctctg ggcaccttca gcagatacga gagcaccaga tccggcagac ggatggaact  900
gagcatggga cccatccagg ccaatcacac aggcactggc ctgctgctga cactgcagcc  960
tgagcagaaa ttccagaaag tgaaaggctt cggcggagcc atgacagatg ccgccgctct  1020
gaatatcctg gctctgtctc caccagctca gaacctgctg ctcaagagct acttcagcga  1080
ggaaggcatc ggctacaaca tcatcagagt gcccatggcc agctgcgact tcagcatcag  1140
gacctacacc tacgccgaca cacccgacga tttccagctg cacaacttca gcctgcctga  1200
agaggacacc aagctgaaga tccctctgat ccacagagcc ctgcagctgg cacaaagacc  1260
cgtgtcactg ctggcctctc catggacatc tcccacctgg ctgaaaacaa atggcgccgt  1320
gaatggcaag ggcagcctga aaggccaacc tggcgacatc taccaccaga cctgggccag  1380
atacttcgtg aagttcctgg acgcctatgc cgagcacaag ctgcagtttt gggccgtgac  1440
agccgagaac gaaccttctg ctggactgct gagcggctac ccctttcagt gcctgggctt  1500
tacacccgag caccagcggg actttatcgc ccgtgatctg ggacccacac tggccaatag  1560
cacccaccat aatgtgcggc tgctgatgct ggacgaccag agactgcttc tgccccactg  1620
ggctaaagtg gtgctgacag atcctgaggc cgccaaatac gtgcacggaa tcgccgtgca  1680
ctggtatctg gactttctgg cccctgccaa ggccacactg ggagagagcac acagactgtt  1740
ccccaacacc atgctgttcg ccagcgaagc ctgtgtgggc agcaagtttt gggaacagag  1800
cgtgcggctc ggcagctggg atagaggcat gcagtacagc cacagcatca tcaccaacct  1860
gctgtaccac gtcgtcggct ggaccgactg gaatctggcc ctgaatcctg aaggcggccc  1920
taactgggtc cgaaacttcg tggacagccc catcatcgtg gacatcacca aggacacctt  1980
ctacaagcag cccatgttct accacctggg acacttcagc aagttcatcc ccgagggctc  2040
tcagcgcgtt ggactggtgg cttcccagaa gaacgatctg gacgccgtgg ctctgatgca  2100
ccctgatgga tctgctgtgg tggtggtcct gaaccgcagc agcaaagatg tgcccctgac  2160
catcaaggat cccgccgtgg gattcctgga aacaatcagc cctggctact ccatccacac  2220
ctacctgtgg cgtagacagg agggcagagg aagtcttctg acatgcggag acgtggaaga  2280
gaatcccggc cctatggccg agtggctgct gagcgccagc tggcagcgcc gcgccaaggc  2340
catgaccgcc gccgccggca gcgccggccg cgccgccgtg cccctgctgc tgtgcgccct  2400
gctggccccc ggcggcgcct acgtgctgga cgacagcgac ggcctgggcc gcgagttcga  2460
cggcatcggc gccgtgagcg gcggcggcgc caccagccgc ctgctggtga actaccccga  2520
gccctaccgc agccagatcc tggactacct gttcaagccc aacttcggcg ccagcctgca  2580
catcctgaag gtggagatcg gcggcgacgg ccagaccacc gacggcaccg agcccagcca  2640
catgcactac gccctggacg agaactactt ccgcggctac gagtggtggc tgatgaagga  2700
ggccaagaag cgcaacccca acatcaccct gatcggcctg ccctggagct tccccggctg  2760
gctgggcaag ggcttcgact ggccctacgt gaacctgcag ctgaccgcct actacgtggt  2820
gacctggatc gtgggcgcca agcgctacca cgacctggac atcgactaca tcggcatctg  2880
gaacgagcgc agctacaacg ccaactacat caagatcctg cgcaagatgc tgaactacca  2940
gggcctgcag cgcgtgaaga tcatcgccag cgacaacctg tgggagagca tcagcgccag  3000
catgctgctg gacgccgagc tgttcaaggt ggtggacgtg atcggcgccc actaccccgg  3060
cacccacagc gccaaggacg ccaagctgac cggcaagaag ctgtggagca gcgaggactt  3120
cagcaccctg aacagcgaca tgggcgccgg ctgctggggc cgcatcctga accagaacta  3180
catcaacggc tacatgacca gcaccatcgc ctggaacctg gtggccagct actacgagca  3240
gctgccctac ggccgctgcg gcctgatgac cgcccaggag ccctggagcg gccactacgt  3300
ggtggagagc cccgtgtggg tgagcgccca caccacccag ttcacccagc ccggctggta  3360
```

-continued

```
ctacctgaag accgtgggcc acctggagaa gggcggcagc tacgtggccc tgaccgacgg  3420
cctgggcaac ctgaccatca tcatcgagac catgagccac aagcacagca agtgcatccg  3480
ccccttcctg ccctacttca acgtgagcca gcagttcgcc accttcgtgc tgaagggcag  3540
cttcagcgag atccccgagc tgcaggtgtg gtacaccaag ctgggcaaga ccagcgagcg  3600
cttcctgttc aagcagctgg acagcctgtg gctgctggac agcgacggca gcttcaccct  3660
gagcctgcac gaggacgagc tgttcaccct gaccaccctg accaccggcc gcaagggcag  3720
ctacccccctg ccccccaaga gccagccctt ccccagcacc tacaaggacg acttcaacgt  3780
ggactacccc ttcttcagcg aggcccccaa cttcgccgac cagaccggcg tgttcgagta  3840
cttcaccaac atcgaggacc ccggcgagca ccacttcacc ctgcgccagg tgctgaacca  3900
gcgccccatc acctgggccg ccgacgccag caacaccatc agcatcatcg gcgactacaa  3960
ctggaccaac ctgaccatca agtgcgacgt gtacatcgag acccccgaca ccggcggcgt  4020
gttcatcgcc ggccgcgtga acaagggcgg catcctgatc cgcagcgccc gcggcatctt  4080
cttctggatc ttcgccaacg gcagctaccg cgtgaccggc gacctggccg gctggatcat  4140
ctacgccctg ggccgcgtgg aggtgaccgc caagaagtgg tacaccctga ccctgaccat  4200
caagggccac ttcaccagcg gcatgctgaa cgacaagagc ctgtggaccg acatccccgt  4260
gaacttcccc aagaacggct gggccgccat cggcacccac agcttcgagt tcgcccagtt  4320
cgacaacttc ctggtggagg ccacccgctg acaattgtta attaagttta aaccctcgag  4380
gccgcaagca ataaaatatc tttattttca ttacatctgt gtgttggttt tttgtgtgga  4440
gatccacgat aacaaacagc tttttggggg tgaacatatt gactgaattc cctgcaggtt  4500
ggccactccc tctctgcgcg ctcgctcgct cactgaggcc gcccgggcaa agcccgggcg  4560
tcgggcgacc tttggtcgcc cggcctcagt gagcgagcga gcgcgcagag agggagtggc  4620
caactccatc actaggggtt cctgcggccg ctcgtacggt ctcgaggaat tcctgcagga  4680
taacttgcca acctcattct aaaatgtata tagaagccca aaagacaata acaaaaatat  4740
tcttgtagaa caaaatggga aagaatgttc cactaaatat caagatttag agcaaagcat  4800
gagatgtgtg gggatagaca gtgaggctga taaaatagag tagagctcag aaacagaccc  4860
attgatatat gtaagtgacc tatgaaaaaa atatggcatt ttacaatggg aaaatgatgg  4920
tctttttctt ttttagaaaa acagggaaat atatttatat gtaaaaaata aaagggaacc  4980
catatgtcat accatacaca caaaaaaatt ccagtgaatt ataagtctaa atggagaagg  5040
caaaacttta aatcttttag aaaataatat agaagcatgc agaccagcct ggccaacatg  5100
atgaaaccct ctctactaat aataaaatca gtagaactac tcaggactac tttgagtggg  5160
aagtcctttt ctatgaagac ttctttggcc aaaattaggc tctaaatgca aggagatagt  5220
gcatcatgcc tggctgcact tactgataaa tgatgttatc accatcttta accaaatgca  5280
caggaacaag ttatggtact gatgtgctgg attgagaagg agctctactt ccttgacagg  5340
acacatttgt atcaacttaa aaaagcagat ttttgccagc agaactattc attcagaggt  5400
aggaaactta gaatagatga tgtcactgat tagcatggct tccccatctc cacagctgct  5460
tcccacccag gttgcccaca gttgagtttg tccagtgctc agggctgccc actctcagta  5520
agaagcccca caccagcccc tctccaaata tgttggctgt tccttccatt aaagtgaccc  5580
cactttagag cagcaagtgg atttctgttt cttacagttc aggaaggagg agtcagctgt  5640
gagaacctgg agcctgagat gcttctaagt cccactgcta ctggggtcag ggaagccaga  5700
ctccagcatc agcagtcagg agcactaagc ccttgccaac atcctgtttc tcagagaaac  5760
tgcttccatt ataatggttg tcctttttta agctatcaag ccaaacaacc agtgtctacc  5820
attattctca tcacctgaag ccaagggttc tagcaaaagt caagctgtct tgtaatggtt  5880
gatgtgcctc cagcttctgt cttcagtcac tccactctta gcctgctctg aatcaactct  5940
gaccacagtt ccctggagcc cctgccacct gctgcccctg ccaccttctc catctgcagt  6000
gctgtgcagc cttctgcact cttgcagagc taataggtgg agacttgaag gaagaggagg  6060
aaagtttctc ataatagcct tgctgcaagc tcaaatggga ggtgggcact gtgcccagga  6120
gccttggagc aaaggctgtg cccaacctct gactgcatcc aggtttggtc ttgacagaga  6180
taagaagccc tggcttttgg agccaaaatc taggtcagac ttaggcagga ttctcaaagt  6240
ttatcagcag aacatgaggc agaagaccct ttctgctcca gcttcttcag gctcaacctt  6300
catcagaata gatagaaaga gaggctgtga gggttcttaa aacagaagca aatctgactc  6360
agagaataaa caacctccta gtaaactaca gcttagacag agcatctggt ggtgagtgtg  6420
ctcagtgtcc tactcaactg tctggtatca gccctcatga ggacttctct tctttccctc  6480
atagacctcc atctctgttt tccttagcct gcagaaatct ggatggctat tcacagaatg  6540
cctgtgcttt cagagttgca tttttctct ggtattctgg ttcaagcatt tgaaggtagg  6600
aaaggttctc caagtgcaag aaagccagcc ctgagcctca actgcctggc tagtgtggtc  6660
agtaggatgc aaaggctgtt gaatgccaca aggccaaact ttaacctgtg taccacaagc  6720
ctagcagcag aggcagctct gctcactgga actctctgtc ttctttctcc tgagcctttt  6780
cttttcctga gttttctagc tctcctcaac cttacctctg ccctacccag gacaaaccca  6840
agagccactg tttctgtgat gtcctctcca gccctaatta ggcatcatga cttcagcctg  6900
accttccatg ctcagaagca gtgctaatcc acttcagatg agctgctcta tgcaacacag  6960
gcagagccta caaacctttg caccagagcc ctccacatat cagtgtttgt tcatactcac  7020
ttcaacagca aatgtgactg ctgagattaa gattttacac aagatggtct gtaatttcac  7080
agttagtttt atcccattag gtatgaaaga attagcataa ttccccttaa acatgaatga  7140
atcttagatt ttttaataaa tagttttgga agtaaagaca gagacatcag gagcacaagg  7200
aatagcctga gaggacaaac agaacaagaa agagtctgga aatacacagg atgttcttgg  7260
cctcctcaaa gcaagtgcaa gcagatagta ccagcagccc caggctatca gagcccagtg  7320
aagagaagta ccatgaaagc cacagctcta accaccctgt tccagagtga cagacagtcc  7380
ccaagacaag ccagcctgag ccagagagag aactgcaaga gaaagtttct aatttaggtt  7440
ctgttagatt cagacaagtg caggtcatcc tctctccaca gctactcacc tctccagcct  7500
aacaaagcct gcagtccaca ctccaaccct ggtgtctcac ctcctagcct ctcccaacat  7560
cctgctctct gaccatcttc tgcatctctc atctcaccat ctcccactgt ctacagccta  7620
ctcttgcaac taccatctca ttttctgaca tcctgtctac atcttctgcc atactctgcc  7680
atctaccata ccacctctta ccatctacca caccatcttt tatctccatc cctctcagaa  7740
gcctccaagc tgaatcctgc tttatgtgtt catctcagcc cctgcatgga aagctgaccc  7800
cagaggcaga actattccca gagagcttgg ccaagaaaaa caaaactacc agcctggcca  7860
ggctcaggag tagtaagctg cagtgtctgt tgtgttctag cttcaacagc tgcaggagtt  7920
ccactctcaa atgctccaca tttctcacat cctcctgatt ctggtcacta cccatcttca  7980
aagaacagaa tatctcacat cagcatactg tgaaggacta gtcatgggtg cagctgctca  8040
gagctgcaaa gtcattctgg atggtggaga gcttacaaac atttcatgat gctcccccg  8100
```

```
ctctgatggc tggagcccaa tccctacaca gactcctgct gtatgtgttt tcctttcact  8160
ctgagccaca gccagagggc aggcattcag tctcctcttc aggctggggc tggggcactg  8220
agaactcacc caacaccttg ctctcactcc ttctgcaaaa caagaaagag ctttgtgctg  8280
cagtagccat gaagaatgaa aggaaggctt taactaaaaa atgtcagaga ttattttcaa  8340
ccccttactg tggatcacca gcaaggagga aacacaacac agagacattt tttcccctca  8400
aattatcaaa agaatcactg catttgttaa agagagcaac tgaatcagga agcagagttt  8460
tgaacatatc agaagttagg aatctgcatc agagacaaat gcagtcatgg ttgtttgctg  8520
cataccagcc ctaatcatta gaagcctcat ggacttcaaa catcattccc tctgacaaga  8580
tgctctagcc taactccatg agataaaata aatctgcctt tcagagccaa agaagagtcc  8640
accagcttct tctcagtgtg aacaagagct ccagtcaggt tagtcagtcc agtgcagtag  8700
aggagaccag tctgcatcct ctaattttca aaggcaagaa gatttgttta ccctggacac  8760
caggcacaag tgaggtcaca gagctcttag atatgcagtc ctcatgagtg aggagactaa  8820
agcgcatgcc atcaagactt cagtgtagag aaaacctcca aaaaagcctc ctcactactt  8880
ctggaatagc tcagaggccg aggcggcctc ggcctctgca taaataaaaa aaattagtca  8940
gccatggggc ggagaatggg cggaactggg cggagttagg ggcgggatgg gcggagttag  9000
gggcgggact atggttgctg actaattgag atgcatgctt tgcatacttc tgcctgctgg  9060
ggagcctggg gactttccac acctggttgc tgactaattg agatgcatgc tttgcatact  9120
tctgcctgct ggggagcctg gggactttcc acaccctaac tgacacacat tccacagctg  9180
cattaatgaa tcggccaacg cgcggggaga ggcggtttgc gtattgggcg ctcttccgct  9240
tcctcgctca ctgactcgct gcgctcggtc gttcggctgc ggcgagcggt atcagctcac  9300
tcaaaggcgg taatacggtt atccacagaa tcaggggata acgcaggaaa gaacatgtga  9360
gcaaaaggcc agcaaaaggc caggaaccgt aaaaaggccg cgttgctggc gtttttccat  9420
aggctccgcc cccctgacga gcatcacaaa aatcgacgct caagtcagag gtggcgaaac  9480
ccgacaggac tataaagata ccaggcgttt ccccctggaa gctccctcgt gcgctctcct  9540
gttccgaccc tgccgcttac cggatacctg tccgcctttc tcccttcggg aagcgtggcg  9600
ctttctcata gctcacgctg taggtatctc agttcggtgt aggtcgttcg ctccaagctg  9660
ggctgtgtgc acgaaccccc cgttcagccc gaccgctgcg ccttatccgg taactatcgt  9720
cttgagtcca acccggtaag acacgactta tcgccactgg cagcagccac tggtaacagg  9780
attagcagag cgaggtatgt aggcggtgct acagagttct tgaagtggtg gcctaactac  9840
ggctacacta gaagaacagt atttggtatc tgcgctctgc tgaagccagt taccttcgga  9900
aaaagagttg gtagctcttg atccggcaaa caaaccaccg ctggtagcgg tggttttttt  9960
gtttgcaagc agcagattac gcgcagaaaa aaaggatctc aagaagatcc tttgatcttt  10020
tctacggggt ctgacgctca gtggaacgaa aactcacgtt aagggatttt ggtcatgaga  10080
ttatcaaaaa ggatcttcac ctagatcctt ttaaattaaa aatgaagttt taaatcaatc  10140
taaagtatat atgagtaaac ttggtctgac agttaccaat gcttaatcag tgaggcacct  10200
atctcagcga tctgtctatt tcgttcatcc atagttgcct gactcctgca aaccacgttg  10260
tgtctcaaaa tctctgatgt tacattgcac aagataaaaa tatatcatca tgaacaataa  10320
aactgtctgc ttacataaac agtaatacaa ggggtgttat gagccatatt caacgggaaa  10380
cgtcttgctc gaggccgcga ttaaattcca acatggatgc tgatttatat gggtataaat  10440
gggctcgcga taatgtcggg caatcaggtg cgacaatcta tcgattgtat gggaagcccg  10500
atgcgccaga gttgtttctg aaacatggca aaggtagcgt tgccaatgat gttacagatg  10560
agatggtcag actaaactgg ctgacggaat ttatgcctct tccgaccatc aagcatttta  10620
tccgtactcc tgatgatgca tggttactca ccactgcgat ccccgggaaa acagcattcc  10680
aggtattaga agaatatcct gattcaggtg aaaatattgt tgatgcgctg gcagtgttcc  10740
tgcgccggtt gcattcgatt cctgtttgta attgtccttt taacagcgat cgcgtatttc  10800
gtctcgctca ggcgcaatca cgaatgaata acggtttggt tgatgcgagt gattttgatg  10860
acgagcgtaa tggctggcct gttgaacaag tctggaaaga aatgcataag cttttgccat  10920
tctcaccgga ttcagtcgtc actcatggtg atttctcact tgataacctt atttttgacg  10980
aggggaaatt aataggttgt attgatgttg gacgagtcgg aatcgcagac cgataccagg  11040
atcttgccat cctatggaac tgcctcggtg agttttctcc ttcattacag aaacggcttt  11100
ttcaaaaata tggtattgat aatcctgata tgaataaatt gcagtttcat ttgatgctcg  11160
atgagttttt ctaagggcgg cctgccacca tacccacgcc gaaacaagcg ctcatgagcc  11220
cgaagtggcg agcccgatct tccccatcgg tgatgtcggc gatataggcg ccagcaaccg  11280
cacctgtggc gccggtgatg agggcgcgcc aagtcgacgt ccggcagtc             11329
```

```
SEQ ID NO: 40          moltype = DNA  length = 11776
FEATURE                Location/Qualifiers
misc_feature           1..11776
                       note = Synthetic polynucleotide
source                 1..11776
                       mol_type = other DNA
                       organism = synthetic construct
SEQUENCE: 40
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catggccgag tggctgctga gcgccagctg  660
gcagcgccgc gccaaggcca tgaccgccgc cgccggcagc gccggccgcg ccgccgtgcc  720
cctgctgctg tgcgccctgc tggcccccgg cggcgcctac gtgctggacg acagcgacgg  780
cctgggccgc gagttcgacg gcatcggcgc cgtgagcggc ggcggcgcca ccagccgcct  840
gctggtgaac taccccgagc cctaccgcag ccagatcctg gactacctgt tcaagcccaa  900
cttcggcgcc agcctgcaca tcctgaaggt ggagatcggc ggcgacggcc agaccaccga  960
```

-continued

```
cggcaccgag cccagccaca tgcactacgc cctggacgag aactacttcc gcggctacga  1020
gtggtggctg atgaaggagg ccaagaagcg caaccccaac atcaccctga tcggcctgcc  1080
ctggagcttc cccggctggc tgggcaaggg cttcgactgg ccctacgtga acctgcagct  1140
gaccgcctac tacgtggtga cctggatcgt gggcgccaag cgctaccacg acctggacat  1200
cgactacatc ggcatctgga acgagcgcag ctacaacgcc aactacatca agatcctgcg  1260
caagatgctg aactaccagg gcctgcagcg cgtgaagatc atcgccagcg acaacctgtg  1320
ggagagcatc agcgccagca tgctgctgga cgccgagctg ttcaaggtgg tggacgtgat  1380
cggcgcccac taccccggca cccacagcgc caaggacgcc aagctgaccg gcaagaagct  1440
gtggagcagc gaggacttca gcaccctgaa cagcgacatg ggcgccggct gctggggccg  1500
catcctgaac cagaactaca tcaacggcta catgaccagc accatcgcct ggaacctggt  1560
ggccagctac tacgagcagc tgccctacgg ccgctgcggc ctgatgaccg cccaggagcc  1620
ctggagcggc cactacgtgg tggagagccc cgtgtgggtg agcgcccaca ccacccagtt  1680
cacccagccc ggctggtact acctgaagac cgtgggccac ctggagaagg gcggcagcta  1740
cgtggccctg accgacggcc tgggcaacct gaccatcatc atcgagacca tgagccacaa  1800
gcacagcaag tgcatccgcc ccttcctgcc ctacttcaac gtgagccagc agttcgccac  1860
cttcgtgctg aagggcagct tcagcgagat ccccgagctg caggtgtggt acaccaagct  1920
gggcaagacc agcgagcgct tcctgttcaa gcagctggac agcctgtggc tgctggacag  1980
cgacggcagc ttcaccctga gcctgcacga ggacgagctg ttcaccctga ccaccctgac  2040
caccggccgc aagggcagct acccccctgcc ccccaagagc cagcccttcc ccagcaccta  2100
caaggacgac ttcaacgtgg actacccctt cttcagcgag gcccccaact tcgccgacca  2160
gaccggcgtg ttcgagtact tcaccaacat cgaggacccc ggcgagcacc acttcaccct  2220
gcgccaggtg ctgaaccagc gccccatcac ctgggccgcc gacgccagca acaccatcag  2280
catcatcggc gactacaact ggaccaacct gaccatcaag tgcgacgtgt acatcgagac  2340
ccccgacacc ggcggcgtgt tcatcgccgg ccgcgtgaac aagggcggca tcctgatccg  2400
cagcgcccgc ggcatcttct tctggatctt cgccaacggc agctaccgcg tgaccggcga  2460
cctggccggc tggatcatct acgccctggg ccgcgtggag gtgaccgcca agaagtggta  2520
caccctgacc ctgaccatca agggccactt caccagcggc atgctgaacg acaagagcct  2580
gtggaccgac atccccgtga acttccccaa gaacggctgg gccgccatcg gcacccacag  2640
cttcgagttc gcccagttcg acaacttcct ggtggaggcc acccgctgat tgtggccgaa  2700
ccgccgaact cagaggccgg ccccagaaaa cccgagcgag taggggggcgg cgcgcaggag  2760
ggaggagaac tgggggcgcg ggaggctggt gggtgtgggg ggtggagatg tagaagatgt  2820
gacgccgcgg cccggcgggt gccagattag cggacgcggt gcccgcggtt gcaacgggat  2880
cccgggcgct gcagcttggg aggcggctct ccccaggcgg cgtccgcgga gacacccatc  2940
cgtgaacccc aggtcccggg ccgccggctc gccgcgcacc aggggccggc ggacagaaga  3000
gcggccgagc ggctcgaggc tgggggaccg cgggcgcggc cgcgcgctgc cgggcgggag  3060
gctggggggc cggggccggg gccgtgcccc ggagcgggtc ggaggccggg gccggggccg  3120
ggggacggcg gctccccgcg cggctccagc ggctcgggga tcccggccgg gccccgcagg  3180
gaccatgatg gaattcagca gccccagcag agaggaatgc cccaagcctc tgagccgggt  3240
gtcaatcatg gccggatctc tgacaggact gctgctgctt caggccgtgt cttgggcttc  3300
tggcgctaga ccttgcatcc ccaagagctt cggctacagc agcgtcgtgt gcgtgtgcaa  3360
tgccacctac tgcgacagct tcgaccctcc tacctttcct gctctgggca ccttcagcag  3420
atacgagagc accagatccg gcagacggat ggaactgagc atgggaccca tccaggccaa  3480
tcacacaggc actggcctgc tgctgacact gcagcctgag cagaaattcc agaaagtgaa  3540
aggcttcggc ggagccatga cagatgccgc cgctctgaat atcctggctc tgtctccacc  3600
agctcagaac ctgctgctca agagctactt cagcgaggaa ggcatcggct acaacatcat  3660
cagagtgccc atggccagct gcgacttcag catcaggacc tacacctacg ccgacacacc  3720
cgacgatttc cagctgcaca acttcagcct gcctgaagag gacaccaagc tgaagatccc  3780
tctgatccac agagccctgc agctggcaca aagacccgtg tcactgctgg cctctccatg  3840
gacatctccc acctggctga aaacaaatgg cgccgtgaat ggcaagggca gcctgaaagg  3900
ccaacctggc gacatctacc accagacctg ggccagatac ttcgtgaagt tcctggacgc  3960
ctatgccgag cacaagctgc agttttgggc cgtgacagcc gagaacgaac cttctgctgg  4020
actgctgagc ggctacccct ttcagtgcct gggctttaca cccgagcacc agcgggactt  4080
tatcgcccgt gatctgggac ccacactggc caatagcacc caccataatg tgcggctgct  4140
gatgctggac gaccagagac tgcttctgcc ccactgggct aaagtggtgc tgacagatcc  4200
tgaggccgcc aaatacgtgc acggaatcgc cgtgcactgg tatctggact ttctggcccc  4260
tgccaaggcc acactgggag agacacacag actgttcccc aacaccatgc tgttcgccag  4320
cgaagcctgt gtgggcagca agttttggga acagagcgtg cggctcggca gctgggatag  4380
aggcatgcag tacagccaca gcatcatcac caacctgctg taccacgtcg tcggctggac  4440
cgactggaat ctggccctga atcctgaagg cggccctaac tgggtccgaa acttcgtgga  4500
cagccccatc atcgtggaca tcaccaagga caccttctac aagcagccca tgttctacca  4560
cctgggacac ttcagcaagt tcatccccga gggctctcag cgcgttggac tggtggcttc  4620
ccagaagaac gatctggacg ccgtggctct gatgcaccct gatggatctg ctgtggtggt  4680
ggtcctgaac cgcagcagca aagatgtgcc cctgaccatc aaggatcccg ccgtgggatt  4740
cctggaaaca atcagccctg gctactccat ccacacctac ctgtggcgta gacagtgaca  4800
attgttaatt aagtttaaac cctcgaggcc gcaagcaata aaatatcttt attttcatta  4860
catctgtgtg ttggtttttt gtgtggagat ccacgataac aaacagcttt tttggggtga  4920
acatattgac tgaattccct gcaggttggc cactccctct ctgcgcgctc gctcgctcac  4980
tgaggccgcc cgggcaaagc ccgggcgtcg ggcgaccttt ggtcgcccgg cctcagtgag  5040
cgagcgagcg cgcagagagg gagtggccaa ctccatcact aggggttcct gcggccgctc  5100
gtacggtctc gaggaattcc tgcaggataa cttgccaacc tcattctaaa atgtatatag  5160
aagcccaaaa gacaataaca aaaatattct tgtagaacaa aatgggaaag aatgttccac  5220
taaatatcaa gatttagagc aaagcatgag atgtgtgggg atagacagtg aggctgataa  5280
aatagagtag agctcagaaa cagacccatt gatatatgta agtgacctat gaaaaaaata  5340
tggcatttta caatgggaaa atgatggtct ttttcttttt tagaaaaaca gggaaatata  5400
tttatatgta aaaaataaaa gggaacccat atgtcatacc atacacacaa aaaaattcca  5460
gtgaattata agtctaaatg gagaaggcaa aactttaaat cttttagaaa ataatataga  5520
agcatgcaga ccagcctggc caacatgatg aaaccctctc tactaataat aaaatcagta  5580
gaactactca ggactacttt gagtgggaag tccttttcta tgaagacttc tttggccaaa  5640
attaggctct aaatgcaagg agatagtgca tcatgcctgg ctgcacttac tgataaatga  5700
```

-continued

```
tgttatcacc atctttaacc aaatgcacag gaacaagtta tggtactgat gtgctggatt  5760
gagaaggagc tctacttcct tgacaggaca catttgtatc aacttaaaaa agcagatttt  5820
tgccagcaga actattcatt cagaggtagg aaacttagaa tagatgatgt cactgattag  5880
catggcttcc ccatctccac agctgcttcc cacccaggtt gcccacagtt gagtttgtcc  5940
agtgctcagg gctgcccact ctcagtaaga agccccacac cagcccctct ccaaatatgt  6000
tggctgttcc ttccattaaa gtgaccccac tttagagcag caagtggatt tctgtttctt  6060
acagttcagg aaggaggagt cagctgtgag aacctggagc ctgagatgct tctaagtccc  6120
actgctactg gggtcaggga agccagactc cagcatcagc agtcaggagc actaagccct  6180
tgccaacatc ctgtttctca gagaaactgc ttccattata atggttgtcc ttttttaagc  6240
tatcaagcca aacaaccagt gtctaccatt attctcatca cctgaagcca agggttctag  6300
caaaagtcaa gctgtcttgt aatggttgat gtgcctccag cttctgtctt cagtcactcc  6360
actcttagcc tgctctgaat caactctgac cacagttccc tggagcccct gccacctgct  6420
gcccctgcca ccttctccat ctgcagtgct gtgcagcctt ctgcactctt gcagagctaa  6480
taggtggaga cttgaaggaa gaggaggaaa gtttctcata atagccttgc tgcaagctca  6540
aatgggaggt gggcactgtg cccaggagcc ttggagcaaa ggctgtgccc aacctctgac  6600
tgcatccagg tttggtcttg acagagataa gaagccctgg cttttggagc caaaatctag  6660
gtcagactta ggcaggattc tcaaagttta tcagcagaac atgaggcaga agaccctttc  6720
tgctccagct tcttcaggct caaccttcat cagaatagat agaaagagag gctgtgaggg  6780
ttcttaaaac agaagcaaat ctgactcaga gaataaacaa cctcctagta aactacagct  6840
tagacagagc atctggtggt gagtgtgctc agtgtcctac tcaactgtct ggtatcagcc  6900
ctcatgagga cttctcttct ttccctcata gacctccatc tctgttttcc ttagcctgca  6960
gaaatctgga tggctattca cagaatgcct gtgctttcag agttgcattt tttctctggt  7020
attctggttc aagcatttga aggtaggaaa ggttctccaa gtgcaagaaa gccagccctg  7080
agcctcaact gcctggctag tgtggtcagt aggatgcaaa ggctgttgaa tgccacaagg  7140
ccaaacttta acctgtgtac cacaagccta gcagcagagg cagctctgct cactggaact  7200
ctctgtcttc tttctcctga gccttttctt ttcctgagtt ttctagctct cctcaacctt  7260
acctctgccc tacccaggac aaacccaaga gccactgttt ctgtgatgtc ctctccagcc  7320
ctaattaggc atcatgactt cagcctgacc ttccatgctc agaagcagtg ctaatccact  7380
tcagatgagc tgctctatgc aacacaggca gagcctacaa acctttgcac cagagccctc  7440
cacatatcag tgtttgttca tactcacttc aacagcaaat gtgactgctg agattaagat  7500
tttacacaag atggtctgta atttcacagt tagttttatc ccattaggta tgaaagaatt  7560
agcataattc cccttaaaca tgaatgaatc ttagattttt taataaatag ttttggaagt  7620
aaagacagag acatcaggag cacaaggaat agcctgagag gacaaacaga acaagaaaga  7680
gtctggaaat acacaggatg ttcttggcct cctcaaagca agtgcaagca gatagtacca  7740
gcagccccag gctatcagag cccagtgaag agaagtacca tgaaagccac agctctaacc  7800
accctgttcc agagtgacag acagtcccca agacaagcca gcctgagcca gagagagaac  7860
tgcaagagaa agtttctaat ttaggttctg ttagattcag acaagtgcag gtcatcctct  7920
ctccacagct actcacctct ccagcctaac aaagcctgca gtccacactc caaccctggt  7980
gtctcacctc ctagcctctc ccaacatcct gctctctgac catcttctgc atctctcatc  8040
tcaccatctc ccactgtcta cagcctactc ttgcaactac catctcattt tctgacatcc  8100
tgtctacatc ttctgccata ctctgccatc taccatacca cctcttacca tctaccacac  8160
catcttttat ctccatccct ctcagaagcc tccaagctga atcctgcttt atgtgttcat  8220
ctcagcccct gcatggaaag ctgaccccag aggcagaact attcccagag agcttggcca  8280
agaaaaacaa aactaccagc ctggccaggc tcaggagtag taagctgcag tgtctgttgt  8340
gttctagctt caacagctgc aggagttcca ctctcaaatg ctccacattt ctcacatcct  8400
cctgattctg gtcactaccc atcttcaaag aacagaatat ctcacatcag catactgtga  8460
aggactagtc atgggtgcag ctgctcagag ctgcaaagtc attctggatg gtggagagct  8520
tacaaacatt tcatgatgct ccccccgctc tgatggctgg agcccaatcc ctacacagac  8580
tcctgctgta tgtgttttcc tttcactctg agccacagcc agagggcagg cattcagtct  8640
cctcttcagg ctggggctgg ggcactgaga actcacccaa caccttgctc tcactccttc  8700
tgcaaaaacaa gaaagagctt tgtgctgcag tagccatgaa gaatgaaagg aaggctttaa  8760
ctaaaaaatg tcagagatta ttttcaaccc cttactgtgg atcaccagca aggaggaaac  8820
acaacacaga gacatttttt cccctcaaat tatcaaaaga atcactgcat ttgttaaaga  8880
gagcaactga atcaggaagc agagttttga acatatcaga agttaggaat ctgcatcaga  8940
gacaaatgca gtcatggttg tttgctgcat accagcccta atcattagaa gcctcatgga  9000
cttcaaacat cattccctct gacaagatgc tctagcctaa ctccatgaga taaaataaat  9060
ctgcctttca gagccaaaga agagtccacc agcttcttct cagtgtgaac aagagctcca  9120
gtcaggttag tcagtccagt gcagtagagg agaccagtct gcatcctcta attttcaaag  9180
gcaagaagat ttgtttaccc tggacaccag gcacaagtga ggtcacagag ctcttagata  9240
tgcagtcctc atgagtgagg agactaaagc gcatgccatc aagacttcag tgtagagaaa  9300
acctccaaaa aagcctcctc actacttctg gaatagctca gaggccgagg cggcctcggc  9360
ctctgcataa ataaaaaaaa ttagtcagcc atggggcgga gaatgggcgg aactgggcgg  9420
agttagggc gggatgggcg gagttagggg cgggactatg gttgctgact aattgagatg  9480
catgctttgc atacttctgc ctgctgggga gcctggggac tttccacacc tggttgctga  9540
ctaattgaga tgcatgcttt gcatacttct gcctgctggg gagcctgggg actttccaca  9600
ccctaactga cacacattcc acagctgcat taatgaatcg gccaacgcgc ggggagaggc  9660
ggtttgcgta ttgggcgctc ttccgcttcc tcgctcactg actcgctgcg ctcggtcgtt  9720
cggctgcggc gagcggtatc agctcactca aaggcggtaa tacggttatc cacagaatca  9780
ggggataacg caggaaagaa catgtgagca aaaggccagc aaaaggccag gaaccgtaaa  9840
aaggccgcgt tgctggcgtt tttccatagg ctccgccccc ctgacgagca tcacaaaaat  9900
cgacgctcaa gtcagaggtg gcgaaacccg acaggactat aaagatacca ggcgtttccc  9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
```

```
ggatctcaag aagatccttt gatcttttct acggggtctg acgctcagtg gaacgaaaac  10500
tcacgttaag ggattttggt catgagatta tcaaaaagga tcttcaccta gatcctttta  10560
aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tcctgcaaac cacgttgtgt ctcaaaatct ctgatgttac attgcacaag  10740
ataaaaatat atcatcatga acaataaaac tgtctgctta cataaacagt aatacaaggg  10800
gtgttatgag ccatattcaa cgggaaacgt cttgctcgag gccgcgatta aattccaaca  10860
tggatgctga tttatatggg tataaatggg ctcgcgataa tgtcgggcaa tcaggtgcga  10920
caatctatcg attgtatggg aagcccgatg cgccagagtt gtttctgaaa catggcaaag  10980
gtagcgttgc caatgatgtt acagatgaga tggtcagact aaactggctg acggaattta  11040
tgcctcttcc gaccatcaag cattttatcc gtactcctga tgatgcatgg ttactcacca  11100
ctgcgatccc cgggaaaaca gcattccagg tattagaaga atatcctgat tcaggtgaaa  11160
atattgttga tgcgctggca gtgttcctgc gccggttgca ttcgattcct gtttgtaatt  11220
gtccttttaa cagcgatcgc gtatttcgtc tcgctcaggc gcaatcacga atgaataacg  11280
gtttggttga tgcgagtgat tttgatgacg agcgtaatgg ctggcctgtt gaacaagtct  11340
ggaaagaaat gcataagctt ttgccattct caccggattc agtcgtcact catggtgatt  11400
tctcacttga taaccttatt tttgacgagg ggaaattaat aggttgtatt gatgttggac  11460
gagtcggaat cgcagaccga taccaggatc ttgccatcct atggaactgc ctcggtgagt  11520
tttctccttc attacagaaa cggctttttc aaaaatatgg tattgataat cctgatatga  11580
ataaattgca gtttcatttg atgctcgatg agtttttcta agggcggcct gccaccatac  11640
ccacgccgaa acaagcgctc atgagcccga agtggcgagc ccgatcttcc ccatcggtga  11700
tgtcggcgat ataggcgcca gcaaccgcac ctgtggcgcc ggtgatgagg gcgcgccaag  11760
tcgacgtccg gcagtc                                                  11776
```

```
SEQ ID NO: 41          moltype = DNA  length = 11348
FEATURE                Location/Qualifiers
misc_feature           1..11348
                       note = Synthetic polynucleotide
source                 1..11348
                       mol_type = other DNA
                       organism = synthetic construct
SEQUENCE: 41
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatgtgg  900
cagctgtggg ccagcctgtg ctgcctgctg gtgctggcca acgcccgcag ccgccccagc  960
ttccaccccc tgagcgacga gctggtgaac tacgtgaaca agcgcaacac cacctggcag  1020
gccggccaca acttctacaa cgtggacatg agctacctga agcgcctgtg cggcaccttc  1080
ctgggcggcc ccaagccccc ccagcgcgtg atgttcaccg aggacctgaa gctgcccgcc  1140
agcttcgacg cccgcgagca gtggccccag tgccccacca tcaaggagat ccgcgaccag  1200
ggcagctgcg gcagctgctg ggccttcggc gccgtggagg ccatcagcga ccgcatctgc  1260
atccacacca acgcccacgt gagcgtggag gtgagcgccg aggacctgct gacctgctgc  1320
ggcagcatgt gcggcgacgg ctgcaacggc ggctaccccg ccgaggcctg gaacttctgg  1380
acccgcaagg gcctggtgag cggcggcctg tacgagagcc acgtgggctg ccgcccctac  1440
agcatccccc cctgcgagca ccacgtgaac ggcagccgcc cccctgcac cggcgagggc  1500
gacaccccca agtgcagcaa gatctgcgag cccggctaca gccccaccta caagcaggac  1560
aagcactacg gctacaacag ctacagcgtg agcaacagcg agaaggacat catggccgag  1620
atctacaaga acggccccgt ggagggcgcc ttcagcgtgt acagcgactt cctgctgtac  1680
aagagcggcg tgtaccagca cgtgaccggc gagatgatgg gcggccacgc catccgcatc  1740
ctgggctggg gcgtggagaa cggcaccccc tactggctgg tggccaacag ctggaacacc  1800
gactggggcg acaacggctt cttcaagatc ctgcgcggcc aggaccactg cggcatcgag  1860
agcgaggtgg tggccggcat cccccgcacc gaccagtact gggagaagat cgagggcaga  1920
ggaagtcttc tgacatgcgg agacgtggaa gagaatcccg gccctatgga attcagcagc  1980
cccagcagag aggaatgccc caagcctctg agccgggtgt caatcatggc cggatctctg  2040
acaggactgc tgctgcttca ggccgtgtct tgggcttctg gcgctagacc ttgcatcccc  2100
aagagcttcg gctacagcag cgtcgtgtgc gtgtgcaatg ccacctactg cgacagcttc  2160
gaccctccta ccttttcctgc tctgggcacc ttcagcagat acgagagcac cagatccggc  2220
agacggatgg aactgagcat gggacccatc caggccaatc acacaggcac tggcctgctg  2280
ctgacactgc agcctgagca gaaattccag aaagtgaaag gcttcggcgg agccatgaca  2340
gatgccgccg ctctgaatat cctggctctg tctccaccag ctcagaacct gctgctcaag  2400
agctacttca gcgaggaagg catcggctac aacatcatca gagtgcccat ggccagctgc  2460
gacttcagca tcaggaccta cacctacgcc gacacacccg acgatttcca gctgcacaac  2520
ttcagcctgc ctgaagagga caccaagctg aagatccctc tgatccacag agccctgcag  2580
ctggcacaaa gacccgtgtc actgctggcc tctccatgga catctcccac ctggctgaaa  2640
acaaatggcg ccgtgaatgg caagggcagc ctgaaaggcc aacctggcga catctaccac  2700
cagacctggg ccagatactt cgtgaagttc ctggacgcct atgccgagca caagctgcag  2760
ttttgggccg tgacagccga gaacgaacct tctgctggac tgctgagcgg ctacccctt  2820
```

```
cagtgcctgg gctttacacc cgagcaccag cgggacttta tcgcccgtga tctgggaccc  2880
acactggcca atagcaccca ccataatgtg cggctgctga tgctggacga ccagagactg  2940
cttctgcccc actgggctaa agtggtgctg acagatcctg aggccgccaa atacgtgcac  3000
ggaatcgccg tgcactggta tctggacttt ctggcccctg ccaaggccac actgggagag  3060
acacacagac tgttccccaa caccatgctg ttcgccagcg aagcctgtgt gggcagcaag  3120
ttttgggaac agagcgtgcg gctcggcagc tgggatagag gcatgcagta cagccacagc  3180
atcatcacca acctgctgta ccacgtcgtc ggctggaccg actggaatct ggccctgaat  3240
cctgaaggcg gccctaactg ggtccgaaac ttcgtggaca gccccatcat cgtggacatc  3300
accaaggaca ccttctacaa gcagcccatg ttctaccacc tgggacactt cagcaagttc  3360
atccccgagg gctctcagcg cgttggactg gtggcttccc agaagaacga tctggacgcc  3420
gtggctctga tgcaccctga tggatctgct gtggtggtgg tcctgaaccg cagcagcaaa  3480
gatgtgcccc tgaccatcaa ggatcccgcc gtgggattcc tggaaacaat cagccctggc  3540
tactccatcc acacctacct gtggcgtaga cagtgacaat tgttaattaa gtttaaaccc  3600
tcgaggccgc aagcttatcg ataatcaacc tctggattac aaaatttgtg aaagattgac  3660
tggtattctt aactatgttg ctccttttac gctatgtgga tacgctgctt taatgccttt  3720
gtatcatgct attgcttccc gtatggcttt cattttctcc tccttgtata aatcctggtt  3780
gctgtctctt tatgaggagt tgtggcccgt tgtcaggcaa cgtggcgtgg tgtgcactgt  3840
gtttgctgac gcaaccccca ctggttgggg cattgccacc acctgtcagc tcctttccgg  3900
gactttcgct ttccccctcc ctattgccac ggcggaactc atcgccgcct gccttgcccg  3960
ctgctggaca ggggctcggc tgttgggcac tgacaattcc gtggtgttgt cggggaaatc  4020
atcgtccttt ccttggctgc tcgcctgtgt tgccacctgg attctgcgcg ggacgtcctt  4080
ctgctacgtc ccttcggccc tcaatccagc ggaccttcct tcccgcggcc tgctgccggc  4140
tctgcggcct cttccgcgtc ttcgccttcg ccctcagacg agtcggatct ccctttgggc  4200
cgcctccccg catcgatacc gtcgactaga gctcgctgat cagcctcgac tgtgccttct  4260
agttgccagc catctgttgt ttgcccctcc cccgtgcctt ccttgaccct ggaaggtgcc  4320
actcccactg tcctttccta ataaaatgag gaaattgcat cgcattgtct gagtaggtgt  4380
cattctattc tggggggtgg ggtggggcag gacagcaagg gggaggattg ggaagacaat  4440
agcaggcatg ctggggagag atccacgata acaaacagct tttttggggt gaacatattg  4500
actgaattcc ctgcaggttg gccactccct ctctgcgcgc tcgctcgctc actgaggccg  4560
cccgggcaaa gcccgggcgt cgggcgacct ttggtcgccc ggcctcagtg agcgagcgag  4620
cgcgcagaga gggagtggcc aactccatca ctaggggttc ctgcggccgc tcgtacggtc  4680
tcgaggaatt cctgcaggat aacttgccaa cctcattcta aaatgtatat agaagcccaa  4740
aagacaataa caaaaatatt cttgtagaac aaaatgggaa agaatgttcc actaaatatc  4800
aagatttaga gcaaagcatg agatgtgtgg ggatagacag tgaggctgat aaaatagagt  4860
agagctcaga aacagaccca ttgatatatg taagtgacct atgaaaaaaa tatggcattt  4920
tacaatggga aaatgatggt ctttttcttt tttagaaaaa cagggaaata tatttatatg  4980
taaaaaataa aagggaaccc atatgtcata ccatacacac aaaaaaattc cagtgaatta  5040
taagtctaaa tggagaaggc aaaactttaa atcttttaga aaataatata gaagcatgca  5100
gaccagcctg gccaacatga tgaaaccctc tctactaata ataaaatcag tagaactact  5160
caggactact ttgagtggga agtccttttc tatgaagact tctttggcca aaattaggct  5220
ctaaatgcaa ggagatagtg catcatgcct ggctgcactt actgataaat gatgttatca  5280
ccatctttaa ccaaatgcac aggaacaagt tatggtactg atgtgctgga ttgagaagga  5340
gctctacttc cttgacagga cacatttgta tcaacttaaa aaagcagatt tttgccagca  5400
gaactattca ttcagaggta ggaaacttag aatagatgat gtcactgatt agcatggctt  5460
ccccatctcc acagctgctt cccacccagg ttgcccacag ttgagtttgt ccagtgctca  5520
gggctgccca ctctcagtaa gaagccccac accagcccct ctccaaatat gttggctgtt  5580
ccttccatta aagtgacccc actttagagc agcaagtgga tttctgtttc ttacagttca  5640
ggaaggagga gtcagctgtg agaacctgga gcctgagatg cttctaagtc ccactgctac  5700
tggggtcagg gaagccagac tccagcatca gcagtcagga gcactaagcc cttgccaaca  5760
tcctgtttct cagagaaact gcttccatta taatggttgt cctttttaa gctatcaagc  5820
caaacaacca gtgtctacca ttattctcat cacctgaagc caagggttct agcaaaagtc  5880
aagctgtctt gtaatggttg atgtgcctcc agcttctgtc ttcagtcact ccactcttag  5940
cctgctctga atcaactctg accacagttc cctggagccc ctgccacctg ctgcccctgc  6000
caccttctcc atctgcagtg ctgtgcagcc ttctgcactc ttgcagagct aataggtgga  6060
gacttgaagg aagaggagga aagtttctca taatagcctt gctgcaagct caaatgggag  6120
gtgggcactg tgcccaggag ccttggagca aaggctgtgc ccaacctctg actgcatcca  6180
ggtttggtct tgacagagat aagaagccct ggcttttgga gccaaaatct aggtcagact  6240
taggcaggat tctcaaagtt tatcagcaga acatgaggca gaagaccctt tctgctccag  6300
cttcttcagg ctcaaccttc atcagaatag atagaaagag aggctgtgag ggttcttaaa  6360
acagaagcaa atctgactca gagaataaac aacctcctag taaactacag cttagacaga  6420
gcatctggtg gtgagtgtgc tcagtgtcct actcaactgt ctggtatcag ccctcatgag  6480
gacttctctt ctttccctca tagacctcca tctctgtttt ccttagcctg cagaaatctg  6540
gatggctatt cacagaatgc ctgtgctttc agagttgcat tttttctctg gtattctggt  6600
tcaagcattt gaaggtagga aaggttctcc aagtgcaaga aagccagccc tgagcctcaa  6660
ctgcctggct agtgtggtca gtaggatgca aaggctgttg aatgccacaa ggccaaactt  6720
taacctgtgt accacaagcc tagcagcaga ggcagctctg ctcactggaa ctctctgtct  6780
tctttctcct gagccttttc ttttcctgag ttttctagct ctcctcaacc ttacctctgc  6840
cctacccagg acaaacccaa gagccactgt ttctgtgatg tcctctccag ccctaattag  6900
gcatcatgac ttcagcctga ccttccatgc tcagaagcag tgctaatcca cttcagatga  6960
gctgctctat gcaacacagg cagagcctac aaacctttgc accagagccc tccacatatc  7020
agtgtttgtt catactcact tcaacagcaa atgtgactgc tgagattaag attttacaca  7080
agatggtctg taatttcaca gttagtttta tcccattagg tatgaaagaa ttagcataat  7140
tccccttaaa catgaatgaa tcttagattt tttaataaat agttttggaa gtaaagacag  7200
agacatcagg agcacaagga atagcctgag aggacaaaca gaacaagaaa gagtctggaa  7260
atacacagga tgttcttggc ctcctcaaag caagtgcaag cagatagtac cagcagcccc  7320
aggctatcag agcccagtga agagaagtac catgaaagcc acagctctaa ccaccctgtt  7380
ccagagtgac agacagtccc caagacaagc cagcctgagc cagagagaga actgcaagag  7440
aaagtttcta atttaggttc tgttagattc agacaagtgc aggtcatcct ctctccacag  7500
ctactcacct ctccagccta acaaagcctg cagtccacac tccaaccctg gtgtctcacc  7560
```

```
tcctagcctc tcccaacatc ctgctctctg accatcttct gcatctctca tctcaccatc  7620
tcccactgtc tacagcctac tcttgcaact accatctcat tttctgacat cctgtctaca  7680
tcttctgcca tactctgcca tctaccatac cacctcttac catctaccac accatctttt  7740
atctccatcc ctctcagaag cctccaagct gaatcctgct ttatgtgttc atctcagccc  7800
ctgcatggaa agctgacccc agaggcagaa ctattcccag agagcttggc caagaaaaac  7860
aaaactacca gcctggccag gctcaggagt agtaagctgc agtgtctgtt gtgttctagc  7920
ttcaacagct gcaggagttc cactctcaaa tgctccacat ttctcacatc ctcctgattc  7980
tggtcactac ccatcttcaa agaacagaat atctcacatc agcatactgt gaaggactag  8040
tcatgggtgc agctgctcag agctgcaaag tcattctgga tggtggagag cttacaaaca  8100
tttcatgatg ctccccccgc tctgatggct ggagcccaat ccctacacag actcctgctg  8160
tatgtgtttt cctttcactc tgagccacag ccagagggca ggcattcagt ctcctcttca  8220
ggctggggct ggggcactga gaactcaccc aacaccttgc tctcactcct tctgcaaaac  8280
aagaaagagc tttgtgctgc agtagccatg aagaatgaaa ggaaggcttt aactaaaaaa  8340
tgtcagagat tattttcaac cccttactgt ggatcaccag caaggaggaa acacaacaca  8400
gagacatttt ttcccctcaa attatcaaaa gaatcactgc atttgttaaa gagagcaact  8460
gaatcaggaa gcagagtttt gaacatatca gaagttagga atctgcatca gagacaaatg  8520
cagtcatggt tgtttgctgc ataccagccc taatcattag aagcctcatg gacttcaaac  8580
atcattccct ctgacaagat gctctagcct aactccatga gataaaataa atctgccttt  8640
cagagccaaa gaagagtcca ccagcttctt ctcagtgtga acaagagctc cagtcaggtt  8700
agtcagtcca gtgcagtaga ggagaccagt ctgcatcctc taattttcaa aggcaagaag  8760
atttgtttac cctggacacc aggcacaagt gaggtcacag agctcttaga tatgcagtcc  8820
tcatgagtga ggagactaaa gcgcatgcca tcaagacttc agtgtagaga aaacctccaa  8880
aaaagcctcc tcactacttc tggaatagct cagaggccga ggcggcctcg gcctctgcat  8940
aaataaaaaa aattagtcag ccatggggcg gagaatgggc ggaactgggc ggagttaggg  9000
gcgggatggg cggagttagg ggcgggacta tggttgctga ctaattgaga tgcatgcttt  9060
gcatacttct gcctgctggg gagcctgggg actttccaca cctggttgct gactaattga  9120
gatgcatgct ttgcatactt ctgcctgctg gggagcctgg ggactttcca caccctaact  9180
gacacacatt ccacagctgc attaatgaat cggccaacgc gcggggagag gcggtttgcg  9240
tattgggcgc tcttccgctt cctcgctcac tgactcgctg cgctcggtcg ttcggctgcg  9300
gcgagcggta tcagctcact caaaggcggt aatacggtta tccacagaat caggggataa  9360
cgcaggaaag aacatgtgag caaaaggcca gcaaaaggcc aggaaccgta aaaaggccgc  9420
gttgctggcg tttttccata ggctccgccc ccctgacgag catcacaaaa atcgacgctc  9480
aagtcagagg tggcgaaacc cgacaggact ataaagatac caggcgtttc cccctggaag  9540
ctccctcgtg cgctctcctg ttccgaccct gccgcttacc ggatacctgt ccgcctttct  9600
cccttcggga agcgtggcgc tttctcatag ctcacgctgt aggtatctca gttcggtgta  9660
ggtcgttcgc tccaagctgg gctgtgtgca cgaacccccc gttcagcccg accgctgcgc  9720
cttatccggt aactatcgtc ttgagtccaa cccggtaaga cacgacttat cgccactggc  9780
agcagccact ggtaacagga ttagcagagc gaggtatgta ggcggtgcta cagagttctt  9840
gaagtggtgg cctaactacg gctacactag aagaacagta tttggtatct gcgctctgct  9900
gaagccagtt accttcggaa aaagagttgg tagctcttga tccggcaaac aaaccaccgc  9960
tggtagcggt ggtttttttg tttgcaagca gcagattacg cgcagaaaaa aaggatctca  10020
agaagatcct ttgatctttt ctacggggtc tgacgctcag tggaacgaaa actcacgtta  10080
agggattttg gtcatgagat tatcaaaaag gatcttcacc tagatccttt taaattaaaa  10140
atgaagtttt aaatcaatct aaagtatata tgagtaaact tggtctgaca gttaccaatg  10200
cttaatcagt gaggcaccta tctcagcgat ctgtctattt cgttcatcca tagttgcctg  10260
actcctgcaa accacgttgt gtctcaaaat ctctgatgtt acattgcaca agataaaaat  10320
atatcatcat gaacaataaa actgtctgct tacataaaca gtaatacaag gggtgttatg  10380
agccatattc aacgggaaac gtcttgctcg aggccgcgat taaattccaa catggatgct  10440
gatttatatg ggtataaatg ggctcgcgat aatgtcgggc aatcaggtgc gacaatctat  10500
cgattgtatg ggaagcccga tgcgccagag ttgtttctga aacatggcaa aggtagcgtt  10560
gccaatgatg ttacagatga gatggtcaga ctaaactggc tgacggaatt tatgcctctt  10620
ccgaccatca agcattttat ccgtactcct gatgatgcat ggttactcac cactgcgatc  10680
cccgggaaaa cagcattcca ggtattagaa gaatatcctg attcaggtga aaatattgtt  10740
gatgcgctgg cagtgttcct gcgccggttg cattcgattc ctgtttgtaa ttgtcctttt  10800
aacagcgatc gcgtatttcg tctcgctcag gcgcaatcac gaatgaataa cggtttggtt  10860
gatgcgagtg attttgatga cgagcgtaat ggctggcctg ttgaacaagt ctggaaagaa  10920
atgcataagc ttttgccatt ctcaccggat tcagtcgtca ctcatggtga tttctcactt  10980
gataacctta tttttgacga ggggaaatta ataggttgta ttgatgttgg acgagtcgga  11040
atcgcagacc gataccagga tcttgccatc ctatggaact gcctcggtga gttttctcct  11100
tcattacaga aacggctttt tcaaaaatat ggtattgata atcctgatat gaataaattg  11160
cagtttcatt tgatgctcga tgagtttttc taagggcggc ctgccaccat acccacgccg  11220
aaacaagcgc tcatgagccc gaagtggcga gcccgatctt ccccatcggt gatgtcggcg  11280
atataggcgc cagcaaccgc acctgtggcg ccggtgatga gggcgcgcca agtcgacgtc  11340
cggcagtc                                                           11348
```

```
SEQ ID NO: 42           moltype = DNA  length = 11433
FEATURE                 Location/Qualifiers
misc_feature            1..11433
                        note = Synthetic polynucleotide
source                  1..11433
                        mol_type = other DNA
                        organism = synthetic construct
SEQUENCE: 42
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
```

```
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatggaa  900
ttcagcagcc ccagcagaga ggaatgcccc aagcctctga gccgggtgtc aatcatggcc  960
ggatctctga caggactgct gctgcttcag gccgtgtctt gggcttctgg cgctagacct  1020
tgcatcccca agagcttcgg ctacagcagc gtcgtgtgcg tgtgcaatgc cacctactgc  1080
gacagcttcg accctcctac ctttcctgct ctgggcacct tcagcagata cgagagcacc  1140
agatccggca gacggatgga actgagcatg ggacccatcc aggccaatca cacaggcact  1200
ggcctgctgc tgacactgca gcctgagcag aaattccaga aagtgaaagg cttcggcgga  1260
gccatgacag atgccgccgc tctgaatatc ctggctctgt ctccaccagc tcagaacctg  1320
ctgctcaaga gctacttcag cgaggaaggc atcggctaca acatcatcag agtgcccatg  1380
gccagctgcg acttcagcat caggacctac acctacgccg acacacccga cgatttccag  1440
ctgcacaact tcagcctgcc tgaagaggac accaagctga agatccctct gatccacaga  1500
gccctgcagc tggcacaaag acccgtgtca ctgctggcct ctccatggac atctcccacc  1560
tggctgaaaa caaatggcgc cgtgaatggc aagggcagcc tgaaaggcca acctggcgac  1620
atctaccacc agacctgggc cagatacttc gtgaagttcc tggacgccta tgccgagcac  1680
aagctgcagt tttgggccgt gacagccgag aacgaacctt ctgctggact gctgagcggc  1740
taccccttc agtgcctggg ctttacaccc gagcaccagc gggactttat cgcccgtgat  1800
ctgggaccca cactggccaa tagcacccac cataatgtgc ggctgctgat gctggacgac  1860
cagagactgc ttctgcccca ctgggctaaa gtggtgctga cagatcctga ggccgccaaa  1920
tacgtgcacg gaatcgccgt gcactggtat ctggactttc tggcccctgc caaggccaca  1980
ctgggagaga cacacagact gttccccaac accatgctgt tcgccagcga agcctgtgtg  2040
ggcagcaagt tttgggaaca gagcgtgcgg ctcggcagct gggatagagg catgcagtac  2100
agccacagca tcatcaccaa cctgctgtac cacgtcgtcg gctggaccga ctggaatctg  2160
gccctgaatc ctgaaggcgg ccctaactgg gtccgaaact tcgtggacag ccccatcatc  2220
gtggacatca ccaaggacac cttctacaag cagcccatgt tctaccacct gggacacttc  2280
agcaagttca tccccgaggg ctctcagcgc gttggactgg tggcttccca gaagaacgat  2340
ctggacgccg tggctctgat gcaccctgat ggatctgctg tggtggtggt cctgaaccgc  2400
agcagcaaag atgtgcccct gaccatcaag gatcccgccg tgggattcct ggaaacaatc  2460
agccctggct actccatcca cacctacctg tggcgtagac aggagggcag aggaagtctt  2520
ctgacatgcg gagacgtgga agagaatccc ggccctatgc cccgctacgg cgccagcctg  2580
cgccagagct gcccccgcag cggccgcgag cagggccagg acggcaccgc cggcgccccc  2640
ggcctgctgt ggatgggcct ggtgctggcc ctggccctgg ccctggccct ggccctggcc  2700
ctgagcgaca gccgcgtgct gtgggccccc gccgaggccc acccccctgag cccccagggc  2760
caccccgccc gcctgcaccg catcgtgccc cgcctgcgcg acgtgttcgg ctggggcaac  2820
ctgacctgcc ccatctgcaa gggcctgttc accgccatca acctgggcct gaagaaggag  2880
cccaacgtgg cccgcgtggg cagcgtggcc atcaagctgt gcaacctgct gaagatcgcc  2940
ccccccgccg tgtgccagag catcgtgcac ctgttcgagg acgacatggt ggaggtgtgg  3000
cgccgcagcg tgctgagccc cagcgaggcc tgcggcctgc tgctgggcag cacctgcggc  3060
cactgggaca tcttcagcag ctggaacatc agcctgccca ccgtgcccaa gccccccccc  3120
aagcccccca gcccccccgc ccccggcgcc cccgtgagcc gcatcctgtt cctgaccgac  3180
ctgcactggg accacgacta cctggagggc accgaccccg actgcgccga cccccctgtgc  3240
tgccgccgcg gcagcggcct gccccccgcc agccgccccg gcgccggcta ctggggcgag  3300
tacagcaagt gcgacctgcc cctgcgcacc ctggagagcc tgctgagcgg cctgggcccc  3360
gccggcccct tcgacatggt gtactggacc ggcgacatcc ccgcccacga cgtgtggcac  3420
cagacccgcc aggaccagct gcgcgccctg accaccgtga ccgccctggt gcgcaagttc  3480
ctgggccccg tgcccgtgta ccccgccgtg ggcaaccacg agagcacccc cgtgaacagc  3540
ttcccccccc ccttcatcga gggcaaccac agcagccgct ggctgtacga ggccatggcc  3600
aaggcctggg agccctggct gcccgccgag gccctgcgca ccctgcgcat cggcggcttc  3660
tacgccctga gcccctaccc cggcctgcgc ctgatcagcc tgaacatgaa cttctgcagc  3720
cgcgagaact tctggctgct gatcaacagc accgaccccg ccggccagct gcagtggctg  3780
gtgggcgagc tgcaggccgc cgaggaccgc ggcgacaagg tgcacatcat cggccacatc  3840
ccccccggcc actgcctgaa gagctggagc tggaactact accgcatcgt ggcccgctac  3900
gagaacaccc tggccgccca gttcttcggc cacacccacg tggacgagtt cgaggtgttc  3960
tacgacgagg agaccctgag ccgcccccctg gccgtggcct tcctggcccc cagcgccacc  4020
acctacatcg gcctgaaccc cggctaccgc gtgtaccaga tcgacggcaa ctacagcggc  4080
agcagccacg tggtgctgga ccacgagacc tacatcctga acctgaccca ggccaacatc  4140
cccggcgcca tcccccactg gcagctgctg taccgcgccc gcgagaccta cggcctgccc  4200
aacaccctgc ccaccgcctg gcacaacctg gtgtaccgca tgcgcggcga catgcagctg  4260
ttccagacct tctggttcct gtaccacaag ggccaccccc ccagcgagcc ctgcggcacc  4320
ccctgccgcc tggccaccct gtgcgcccag ctgagcgccc gcgccgacag ccccgccctg  4380
tgccgccacc tgatgcccga cggcagcctg cccgaggccc agagcctgtg gccccgcccc  4440
ctgttctgct aatgacaatt gttaattaag tttaaaccct cgaggccgca agcaataaaa  4500
tatctttatt ttcattacat ctgtgtgttg gtttttttgtg tggagatcca cgataacaaa  4560
cagcttttttt ggggtgaaca tattgactga attccctgca ggttggccac tccctctctg  4620
cgcgctcgct cgctcactga ggccgcccgg gcaaagcccg ggcgtcgggc gacctttggt  4680
cgcccggcct cagtgagcga gcgagcgcgc agagagggag tggccaactc catcactagg  4740
ggttcctgcg gccgctcgta cggtctcgag gaattcctgc aggataactt gccaacctca  4800
ttctaaaatg tatatagaag cccaaaagac aataacaaaa atattcttgt agaacaaaat  4860
gggaaagaat gttccactaa atatcaagat ttagagcaaa gcatgagatg tgtggggata  4920
gacagtgagg ctgataaaat agagtagagc tcagaaacag acccattgat atatgtaagt  4980
gacctatgaa aaaaatatgg cattttacaa tgggaaaatg atggtctttt tctttttag  5040
aaaaacaggg aaatatattt atatgtaaaa aataaaaggg aacccatatg tcataccata  5100
```

```
cacacaaaaa aattccagtg aattataagt ctaaatggag aaggcaaaac tttaaatctt  5160
ttagaaaata atatagaagc atgcagacca gcctggccaa catgatgaaa ccctctctac  5220
taataataaa atcagtagaa ctactcagga ctactttgag tgggaagtcc ttttctatga  5280
agacttcttt ggccaaaatt aggctctaaa tgcaaggaga tagtgcatca tgcctggctg  5340
cacttactga taaatgatgt tatcaccatc tttaaccaaa tgcacaggaa caagttatgg  5400
tactgatgtg ctggattgag aaggagctct acttccttga caggacacat ttgtatcaac  5460
ttaaaaaagc agatttttgc cagcagaact attcattcag aggtaggaaa cttagaatag  5520
atgatgtcac tgattagcat ggcttcccca tctccacagc tgcttcccac ccaggttgcc  5580
cacagttgag tttgtccagt gctcagggct gcccactctc agtaagaagc cccacaccag  5640
cccctctcca aatatgttgg ctgttccttc cattaaagtg accccacttt agagcagcaa  5700
gtggatttct gtttcttaca gttcaggaag gaggagtcag ctgtgagaac ctggagcctg  5760
agatgcttct aagtcccact gctactgggg tcagggaagc cagactccag catcagcagt  5820
caggagcact aagcccttgc caacatcctg tttctcagag aaactgcttc cattataatg  5880
gttgtccttt tttaagctat caagccaaac aaccagtgtc taccattatt ctcatcacct  5940
gaagccaagg gttctagcaa aagtcaagct gtcttgtaat ggttgatgtg cctccagctt  6000
ctgtcttcag tcactccact cttagcctgc tctgaatcaa ctctgaccac agttccctgg  6060
agcccctgcc acctgctgcc cctgccacct tctccatctg cagtgctgtg cagccttctg  6120
cactcttgca gagctaatag gtggagactt gaaggaagag gaggaaagtt tctcataata  6180
gccttgctgc aagctcaaat gggaggtggg cactgtgccc aggagccttg gagcaaaggc  6240
tgtgcccaac ctctgactgc atccaggttt ggtcttgaca gagataagaa gccctggctt  6300
ttggagccaa aatctaggtc agacttaggc aggattctca aagtttatca gcagaacatg  6360
aggcagaaga ccctttctgc tccagcttct tcaggctcaa ccttcatcag aatagataga  6420
aagagaggct gtgagggttc ttaaaacaga agcaaatctg actcagagaa taaacaacct  6480
cctagtaaac tacagcttag acagagcatc tggtggtgag tgtgctcagt gtcctactca  6540
actgtctggt atcagccctc atgaggactt ctcttctttc cctcatagac ctccatctct  6600
gttttcctta gcctgcagaa atctggatgg ctattcacag aatgcctgtg ctttcagagt  6660
tgcatttttt ctctggtatt ctggttcaag catttgaagg taggaaaggt tctccaagtg  6720
caagaaagcc agccctgagc ctcaactgcc tggctagtgt ggtcagtagg atgcaaaggc  6780
tgttgaatgc cacaaggcca aactttaacc tgtgtaccac aagcctagca gcagaggcag  6840
ctctgctcac tggaactctc tgtcttcttt ctcctgagcc ttttcttttc ctgagttttc  6900
tagctctcct caaccttacc tctgccctac ccaggacaaa cccaagagcc actgtttctg  6960
tgatgtcctc tccagcccta attaggcatc atgacttcag cctgaccttc catgctcaga  7020
agcagtgcta atccacttca gatgagctgc tctatgcaac acaggcagag cctacaaacc  7080
tttgcaccag agccctccac atatcagtgt ttgttcatac tcacttcaac agcaaatgtg  7140
actgctgaga ttaagatttt acacaagatg gtctgtaatt tcacagttag ttttatccca  7200
ttaggtatga aagaattagc ataattcccc ttaaacatga atgaatctta gatttttttaa 7260
taaatagttt tggaagtaaa gacagagaca tcaggagcac aaggaatagc ctgagaggac  7320
aaacagaaca agaaagagtc tggaaataca caggatgttc ttggcctcct caaagcaagt  7380
gcaagcagat agtaccagca gccccaggct atcagagccc agtgaagaga agtaccatga  7440
aagccacagc tctaaccacc ctgttccaga gtgacagaca gtccccaaga caagccagcc  7500
tgagccagag agagaactgc aagagaaagt ttctaattta ggttctgtta gattcagaca  7560
agtgcaggtc atcctctctc cacagctact cacctctcca gcctaacaaa gcctgcagtc  7620
cacactccaa ccctggtgtc tcacctccta gcctctccca acatcctgct ctctgaccat  7680
cttctgcatc tctcatctca ccatctccca ctgtctacag cctactcttg caactaccat  7740
ctcattttct gacatcctgt ctacatcttc tgccatactc tgccatctac cataccacct  7800
cttaccatct accacaccat cttttatctc catccctctc agaagcctcc aagctgaatc  7860
ctgctttatg tgttcatctc agcccctgca tggaaagctg accccagagg cagaactatt  7920
cccagagagc ttggccaaga aaaacaaaac taccagcctg gccaggctca ggagtagtaa  7980
gctgcagtgt ctgttgtgtt ctagcttcaa cagctgcagg agttccactc tcaaatgctc  8040
cacatttctc acatcctcct gattctggtc actacccatc ttcaaagaac agaatatctc  8100
acatcagcat actgtgaagg actagtcatg ggtgcagctg ctcagagctg caaagtcatt  8160
ctggatggtg gagagcttac aaacatttca tgatgctccc cccgctctga tggctggagc  8220
ccaatcccta cacagactcc tgctgtatgt gttttccttt cactctgagc cacagccaga  8280
gggcaggcat tcagtctcct cttcaggctg gggctggggc actgagaact cacccaacac  8340
cttgctctca ctccttctgc aaaacaagaa agagctttgt gctgcagtag ccatgaagaa  8400
tgaaaggaag gctttaacta aaaaatgtca gagattattt tcaacccctt actgtggatc  8460
accagcaagg aggaaacaca acacagagac atttttttccc ctcaaattat caaaagaatc 8520
actgcatttg ttaaagagag caactgaatc aggaagcaga gttttgaaca tatcagaagt  8580
taggaatctg catcagagac aaatgcagtc atggttgttt gctgcatacc agccctaatc  8640
attagaagcc tcatggactt caaacatcat tccctctgac aagatgctct agcctaactc  8700
catgagataa aataaatctg cctttcagag ccaaagaaga gtccaccagc ttcttctcag  8760
tgtgaacaag agctccagtc aggttagtca gtccagtgca gtagaggaga ccagtctgca  8820
tcctctaatt ttcaaaggca agaagatttg tttaccctgg acaccaggca caagtgaggt  8880
cacagagctc ttagatatgc agtcctcatg agtgaggaga ctaaagcgca tgccatcaag  8940
acttcagtgt agagaaaacc tccaaaaaag cctcctcact acttctggaa tagctcagag  9000
gccgaggcgg cctcggcctc tgcataaata aaaaaaatta gtcagccatg gggcggagaa  9060
tgggcggaac tgggcggagt taggggcggg atgggcggag ttaggggcgg gactatggtt  9120
gctgactaat tgagatgcat gctttgcata cttctgcctg ctggggagcc tggggacttt  9180
ccacacctgg ttgctgacta attgagatgc atgctttgca tacttctgcc tgctggggag  9240
cctggggact ttccacaccc taactgacac acattccaca gctgcattaa tgaatcggcc  9300
aacgcgcggg gagaggcggt ttgcgtattg ggcgctcttc cgcttcctcg ctcactgact  9360
cgctgcgctc ggtcgttcgg ctgcggcgag cggtatcagc tcactcaaag gcggtaatac  9420
ggttatccac agaatcaggg gataacgcag gaaagaacat gtgagcaaaa ggccagcaaa  9480
aggccaggaa ccgtaaaaag gccgcgttgc tggcgttttt ccataggctc cgcccccctg  9540
acgagcatca caaaaatcga cgctcaagtc agaggtggcg aaacccgaca ggactataaa  9600
gataccaggc gtttccccct ggaagctccc tcgtgcgctc tcctgttccg accctgccgc  9660
ttaccggata cctgtccgcc tttctccctt cgggaagcgt ggcgctttct catagctcac  9720
gctgtaggta tctcagttcg gtgtaggtcg ttcgctccaa gctgggctgt gtgcacgaac  9780
cccccgttca gcccgaccgc tgcgccttat ccggtaacta tcgtcttgag tccaacccgg  9840
```

```
taagacacga cttatcgcca ctggcagcag ccactggtaa caggattagc agagcgaggt  9900
atgtaggcgg tgctacagag ttcttgaagt ggtggcctaa ctacggctac actagaagaa  9960
cagtatttgg tatctgcgct ctgctgaagc cagttacctt cggaaaaaga gttggtagct  10020
cttgatccgg caaacaaacc accgctggta gcggtggttt ttttgtttgc aagcagcaga  10080
ttacgcgcag aaaaaaagga tctcaagaag atcctttgat cttttctacg gggtctgacg  10140
ctcagtggaa cgaaaactca cgttaaggga ttttggtcat gagattatca aaaaggatct  10200
tcacctagat ccttttaaat taaaaatgaa gttttaaatc aatctaaagt atatatgagt  10260
aaacttggtc tgacagttac caatgcttaa tcagtgaggc acctatctca gcgatctgtc  10320
tatttcgttc atccatagtt gcctgactcc tgcaaaccac gttgtgtctc aaaatctctg  10380
atgttacatt gcacaagata aaaatatatc atcatgaaca ataaaactgt ctgcttacat  10440
aaacagtaat acaaggggtg ttatgagcca tattcaacgg gaaacgtctt gctcgaggcc  10500
gcgattaaat tccaacatgg atgctgattt atatgggtat aaatgggctc gcgataatgt  10560
cgggcaatca ggtgcgacaa tctatcgatt gtatgggaag cccgatgcgc cagagttgtt  10620
tctgaaacat ggcaaaggta gcgttgccaa tgatgttaca gatgagatgg tcagactaaa  10680
ctggctgacg gaatttatgc ctcttccgac catcaagcat tttatccgta ctcctgatga  10740
tgcatggtta ctcaccactg cgatccccgg gaaaacagca ttccaggtat tagaagaata  10800
tcctgattca ggtgaaaata ttgttgatgc gctggcagtg ttcctgcgcc ggttgcattc  10860
gattcctgtt tgtaattgtc cttttaacag cgatcgcgta tttcgtctcg ctcaggcgca  10920
atcacgaatg aataacggtt tggttgatgc gagtgatttt gatgacgagc gtaatggctg  10980
gcctgttgaa caagtctgga aagaaatgca taagcttttg ccattctcac cggattcagt  11040
cgtcactcat ggtgatttct cacttgataa ccttattttt gacgagggga aattaatagg  11100
ttgtattgat gttggacgag tcggaatcgc agaccgatac caggatcttg ccatcctatg  11160
gaactgcctc ggtgagtttt ctccttcatt acagaaacgg ctttttcaaa aatatggtat  11220
tgataatcct gatatgaata aattgcagtt tcatttgatg ctcgatgagt ttttctaagg  11280
gcggcctgcc accataccca cgccgaaaca agcgctcatg agcccgaagt ggcgagcccg  11340
atcttcccca tcggtgatgt cggcgatata ggcgccagca accgcacctg tggcgccggt  11400
gatgagggcg cgccaagtcg acgtccggca gtc                              11433

SEQ ID NO: 43          moltype = DNA  length = 11776
FEATURE                Location/Qualifiers
misc_feature           1..11776
                       note = Synthetic polynucleotide
source                 1..11776
                       mol_type = other DNA
                       organism = synthetic construct
SEQUENCE: 43
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catggccgag tggctgctga gcgccagctg  660
gcagcgccgc gccaaggcca tgaccgccgc cgccggcagc gccggccgcg ccgccgtgcc  720
cctgctgctg tgcgccctgc tggcccccgg cggcgcctac gtgctggacg acagcgacgg  780
cctgggccgc gagttcgacg gcatcggcgc cgtgagcggc ggcggcgcca ccagccgcct  840
gctggtgaac taccccgagc cctaccgcag ccagatcctg gactacctgt tcaagcccaa  900
cttcggcgcc agcctgcaca tcctgaaggt ggagatcggc ggcgacggcc agaccaccga  960
cggcaccgag cccagccaca tgcactacgc cctggacgag aactacttcc gcggctacga  1020
gtggtggctg atgaaggagg ccaagaagcg caaccccaac atcaccctga tcggcctgcc  1080
ctggagcttc cccggctggc tgggcaaggg cttcgactgg ccctacgtga acctgcagct  1140
gaccgcctac tacgtggtga cctggatcgt gggcgccaag cgctaccacg acctggacat  1200
cgactacatc ggcatctgga acgagcgcag ctacaacgcc aactacatca agatcctgcg  1260
caagatgctg aactaccagg gcctgcagcg cgtgaagatc atcgccagcg acaacctgtg  1320
ggagagcatc agcgccagca tgctgctgga cgccgagctg ttcaaggtgg tggacgtgat  1380
cggcgcccac taccccggca cccacagcgc caaggacgcc aagctgaccg gcaagaagct  1440
gtggagcagc gaggacttca gcaccctgaa cagcgacatg ggcgccggct gctggggccg  1500
catcctgaac cagaactaca tcaacggcta catgaccagc accatcgcct ggaacctggt  1560
ggccagctac tacgagcagc tgccctacgg ccgctgcggc ctgatgaccg cccaggagcc  1620
ctggagcggc cactacgtgg tggagagccc cgtgtgggtg agcgcccaca ccacccagtt  1680
cacccagccc ggctggtact acctgaagac cgtgggccac ctggagaagg gcggcagcta  1740
cgtggccctg accgacggcc tgggcaacct gaccatcatc atcgagacca tgagccacaa  1800
gcacagcaag tgcatccgcc ccttcctgcc ctacttcaac gtgagccagc agttcgccac  1860
cttcgtgctg aagggcagct tcagcgagat ccccgagctg caggtgtggt acaccaagct  1920
gggcaagacc agcgagcgct tcctgttcaa gcagctggac agcctgtggc tgctggacag  1980
cgacggcagc ttcaccctga gcctgcacga ggacgagctg ttcaccctga ccaccctgac  2040
caccggccgc aagggcagct acccccctgcc ccccaagagc cagcccttcc ccagcaccta  2100
caaggacgac ttcaacgtgg actacccctt cttcagcgag gcccccaact tcgccgacca  2160
gaccggcgtg ttcgagtact tcaccaacat cgaggacccc ggcgagcacc acttcaccct  2220
gcgccaggtg ctgaaccagc gccccatcac ctgggccgcc gacgccagca acaccatcag  2280
catcatcggc gactacaact ggaccaacct gaccatcaag tgcgacgtgt acatcgagac  2340
ccccgacacc ggcggcgtgt tcatcgccgg ccgcgtgaac aagggcggca tcctgatccg  2400
cagcgcccgc ggcatcttct tctggatctt cgccaacggc agctaccgcg tgaccggcga  2460
cctggccggc tggatcatct acgccctggg ccgcgtggag gtgaccgcca agaagtggta  2520
caccctgacc ctgaccatca agggccactt caccagcggc atgctgaacg acaagagcct  2580
```

```
gtggaccgac atccccgtga acttccccaa gaacggctgg gccgccatcg gcacccacag  2640
cttcgagttc gcccagttcg acaacttcct ggtggaggcc acccgctgat tgtggccgaa  2700
ccgccgaact cagaggccgg ccccagaaaa cccgagcgag tagggggcgg cgcgcaggag  2760
ggaggagaac tgggggcgcg ggaggctggt gggtgtgggg ggtggagatg tagaagatgt  2820
gacgccgcgg cccggcgggt gccagattag cggacgcggt gcccgcggtt gcaacgggat  2880
cccgggcgct gcagcttggg aggcggctct ccccaggcgg cgtccgcgga gacacccatc  2940
cgtgaacccc aggtcccggg ccgccggctc gccgcgcacc aggggccggc ggacagaaga  3000
gcggccgagc ggctcgaggc tgggggaccg cgggcgcggc cgcgcgctgc cgggcgggag  3060
gctgggggc cggggccggg gccgtgcccc ggagcgggtc ggaggccggg gccggggccg  3120
ggggacggcg gctccccgcg cggctccagc ggctcgggga tcccggccgg gccccgcagg  3180
gaccatgatg gaattcagca gccccagcag agaggaatgc cccaagcctc tgagccgggt  3240
gtcaatcatg gccggatctc tgacaggact gctgctgctt caggccgtgt cttgggcttc  3300
tggcgctaga ccttgcatcc ccaagagctt cggctacagc agcgtcgtgt gcgtgtgcaa  3360
tgccacctac tgcgacagct tcgaccctcc tacctttcct gctctgggca ccttcagcag  3420
atacgagagc accagatccg gcagacggat ggaactgagc atgggaccca tccaggccaa  3480
tcacacaggc actggcctgc tgctgacact gcagcctgag cagaaattcc agaaagtgaa  3540
aggcttcggc ggagccatga cagatgccgc cgctctgaat atcctggctc tgtctccacc  3600
agctcagaac ctgctgctca agagctactt cagcgaggaa ggcatcggct acaacatcat  3660
cagagtgccc atggccagct gcgacttcag catcaggacc tacacctacg ccgacacacc  3720
cgacgatttc cagctgcaca acttcagcct gcctgaagag gacaccaagc tgaagatccc  3780
tctgatccac agagccctgc agctggcaca aagacccgtg tcactgctgg cctctccatg  3840
gacatctccc acctggctga aaacaaatgg cgccgtgaat ggcaagggca gcctgaaagg  3900
ccaacctggc gacatctacc accagacctg ggccagatac ttcgtgaagt tcctggacgc  3960
ctatgccgag cacaagctgc agttttgggc cgtgacagcc gagaacgaac cttctgctgg  4020
actgctgagc ggctacccct ttcagtgcct gggctttaca cccgagcacc agcgggactt  4080
tatcgcccgt gatctgggac ccacactggc caatagcacc caccataatg tgcggctgct  4140
gatgctggac gaccagagac tgcttctgcc ccactgggct aaagtggtgc tgacagatcc  4200
tgaggccgcc aaatacgtgc acggaatcgc cgtgcactgg tatctggact ttctggcccc  4260
tgccaaggcc acactgggag agacacacag actgttcccc aacaccatgc tgttcgccag  4320
cgaagcctgt gtgggcagca agttttggga acagagcgtg cggctcggca gctgggatag  4380
aggcatgcag tacagccaca gcatcatcac caacctgctg taccacgtcg tcggctggac  4440
cgactggaat ctggccctga atcctgaagg cggccctaac tgggtccgaa acttcgtgga  4500
cagccccatc atcgtggaca tcaccaagga caccttctac aagcagccca tgttctacca  4560
cctgggacac ttcagcaagt tcatccccga gggctctcag cgcgttggac tggtggcttc  4620
ccagaagaac gatctggacg ccgtggctct gatgcaccct gatggatctg ctgtggtggt  4680
ggtcctgaac cgcagcagca aagatgtgcc cctgaccatc aaggatcccg ccgtgggatt  4740
cctggaaaca atcagccctg gctactccat ccacacctac ctgtggcgta gacagtgaca  4800
attgttaatt aagtttaaac cctcgaggcc gcaagcaata aaatatcttt attttcatta  4860
catctgtgtg ttggtttttt gtgtggagat ccacgataac aaacagcttt tttggggtga  4920
acatattgac tgaattccct gcaggttggc cactccctct ctgcgcgctc gctcgctcac  4980
tgaggccgcc cgggcaaagc ccgggcgtcg ggcgaccttt ggtcgcccgg cctcagtgag  5040
cgagcgagcg cgcagagagg gagtggccaa ctccatcact aggggttcct gcggccgctc  5100
gtacggtctc gaggaattcc tgcaggataa cttgccaacc tcattctaaa atgtatatag  5160
aagcccaaaa gacaataaca aaaatattct tgtagaacaa aatgggaaag aatgttccac  5220
taaatatcaa gatttagagc aaagcatgag atgtgtgggg atagacagtg aggctgataa  5280
aatagagtag agctcagaaa cagacccatt gatatatgta agtgacctat gaaaaaaata  5340
tggcatttta caatgggaaa atgatggtct tttctttttt tagaaaaaca gggaaatata  5400
tttatatgta aaaaataaaa gggaacccat atgtcatacc atacacacaa aaaaattcca  5460
gtgaattata agtctaaatg gagaaggcaa aactttaaat cttttagaaa ataatataga  5520
agcatgcaga ccagcctggc caacatgatg aaaccctctc tactaataat aaaatcagta  5580
gaactactca ggactacttt gagtgggaag tccttttcta tgaagacttc tttggccaaa  5640
attaggctct aaatgcaagg agatagtgca tcatgcctgg ctgcacttac tgataaatga  5700
tgttatcacc atctttaacc aaatgcacag gaacaagtta tggtactgat gtgctggatt  5760
gagaaggagc tctacttcct tgacaggaca catttgtatc aacttaaaaa agcagatttt  5820
tgccagcaga actattcatt cagaggtagg aaacttagaa tagatgatgt cactgattag  5880
catggcttcc ccatctccac agctgcttcc cacccaggtt gcccacagtt gagtttgtcc  5940
agtgctcagg gctgcccact ctcagtaaga agccccacac cagcccctct ccaaatatgt  6000
tggctgttcc ttccattaaa gtgaccccac tttagagcag caagtggatt tctgtttctt  6060
acagttcagg aaggaggagt cagctgtgag aacctggagc ctgagatgct tctaagtccc  6120
actgctactg gggtcaggga agccagactc cagcatcagc agtcaggagc actaagccct  6180
tgccaacatc ctgtttctca gagaaactgc ttccattata atggttgtcc tttttttaagc  6240
tatcaagcca aacaaccagt gtctaccatt attctcatca cctgaagcca agggttctag  6300
caaaagtcaa gctgtcttgt aatggttgat gtgcctccag cttctgtctt cagtcactcc  6360
actcttagcc tgctctgaat caactctgac cacagttccc tggagcccct gccacctgct  6420
gcccctgcca ccttctccat ctgcagtgct gtgcagcctt ctgcactctt gcagagctaa  6480
taggtggaga cttgaaggaa gaggaggaaa gtttctcata atagccttgc tgcaagctca  6540
aatgggaggt gggcactgtg cccaggagcc ttggagcaaa ggctgtgccc aacctctgac  6600
tgcatccagg tttggtcttg acagagataa gaagccctgg cttttggagc caaaatctag  6660
gtcagactta ggcaggattc tcaaagttta tcagcagaac atgaggcaga agaccctttc  6720
tgctccagct tcttcaggct caaccttcat cagaatagat agaaagagag gctgtgaggg  6780
ttcttaaaac agaagcaaat ctgactcaga gaataaacaa cctcctagta aactacagct  6840
tagacagagc atctggtggt gagtgtgctc agtgtcctac tcaactgtct ggtatcagcc  6900
ctcatgagga cttctcttct ttccctcata gacctccatc tctgttttcc ttagcctgca  6960
gaaatctgga tggctattca cagaatgcct gtgctttcag agttgcattt tttctctggt  7020
attctggttc aagcatttga aggtaggaaa ggttctccaa gtgcaagaaa gccagccctg  7080
agcctcaact gcctggctag tgtggtcagt aggatgcaaa ggctgttgaa tgccacaagg  7140
ccaaacttta acctgtgtac cacaagccta gcagcagagg cagctctgct cactggaact  7200
ctctgtcttc tttctcctga gccttttctt ttcctgagtt ttctagctct cctcaacctt  7260
acctctgccc tacccaggac aaacccaaga gccactgttt ctgtgatgtc ctctccagcc  7320
```

```
ctaattaggc atcatgactt cagcctgacc ttccatgctc agaagcagtg ctaatccact  7380
tcagatgagc tgctctatgc aacacaggca gagcctacaa acctttgcac cagagccctc  7440
cacatatcag tgtttgttca tactcacttc aacagcaaat gtgactgctg agattaagat  7500
tttacacaag atggtctgta atttcacagt tagttttatc ccattaggta tgaaagaatt  7560
agcataattc cccttaaaca tgaatgaatc ttagattttt taataaatag ttttggaagt  7620
aaagacagag acatcaggag cacaaggaat agcctgagag gacaaacaga acaagaaaga  7680
gtctggaaat acacaggatg ttcttggcct cctcaaagca agtgcaagca gatagtacca  7740
gcagccccag gctatcagag cccagtgaag agaagtacca tgaaagccac agctctaacc  7800
accctgttcc agagtgacag acagtcccca agacaagcca gcctgagcca gagagagaac  7860
tgcaagagaa agtttctaat ttaggttctg ttagattcag acaagtgcag gtcatcctct  7920
ctccacagct actcacctct ccagcctaac aaagcctgca gtccacactc caaccctggt  7980
gtctcacctc ctagcctctc ccaacatcct gctctctgac catcttctgc atctctcatc  8040
tcaccatctc ccactgtcta cagcctactc ttgcaactac catctcattt tctgacatcc  8100
tgtctacatc ttctgccata ctctgccatc taccatacca cctcttacca tctaccacac  8160
catcttttat ctccatccct ctcagaagcc tccaagctga atcctgcttt atgtgttcat  8220
ctcagcccct gcatggaaag ctgaccccag aggcagaact attcccagag agcttggcca  8280
agaaaaacaa aactaccagc ctggccaggc tcaggagtag taagctgcag tgtctgttgt  8340
gttctagctt caacagctgc aggagttcca ctctcaaatg ctccacattt ctcacatcct  8400
cctgattctg gtcactaccc atcttcaaag aacagaatat ctcacatcag catactgtga  8460
aggactagtc atgggtgcag ctgctcagag ctgcaaagtc attctggatg gtggagagct  8520
tacaaacatt tcatgatgct ccccccgctc tgatggctgg agcccaatcc ctacacagac  8580
tcctgctgta tgtgttttcc tttcactctg agccacagcc agagggcagg cattcagtct  8640
cctcttcagg ctggggctgg ggcactgaga actcacccaa caccttgctc tcactccttc  8700
tgcaaaacaa gaaagagctt tgtgctgcag tagccatgaa gaatgaaagg aaggctttaa  8760
ctaaaaaatg tcagagatta ttttcaaccc cttactgtgg atcaccagca aggaggaaac  8820
acaacacaga gacatttttt cccctcaaat tatcaaaaga atcactgcat ttgttaaaga  8880
gagcaactga atcaggaagc agagttttga acatatcaga agttaggaat ctgcatcaga  8940
gacaaatgca gtcatggttg tttgctgcat accagcccta atcattagaa gcctcatgga  9000
cttcaaacat cattccctct gacaagatgc tctagcctaa ctccatgaga taaaataaat  9060
ctgcctttca gagccaaaga agagtccacc agcttcttct cagtgtgaac aagagctcca  9120
gtcaggttag tcagtccagt gcagtagagg agaccagtct gcatcctcta attttcaaag  9180
gcaagaagat ttgtttaccc tggacaccag gcacaagtga ggtcacagag ctcttagata  9240
tgcagtcctc atgagtgagg agactaaagc gcatgccatc aagacttcag tgtagagaaa  9300
acctccaaaa aagcctcctc actacttctg gaatagctca gaggccgagg cggcctcggc  9360
ctctgcataa ataaaaaaaa ttagtcagcc atggggcgga gaatgggcgg aactgggcgg  9420
agttaggggc gggatgggcg gagttagggg cgggactatg gttgctgact aattgagatg  9480
catgctttgc atacttctgc ctgctgggga gcctggggac tttccacacc tggttgctga  9540
ctaattgaga tgcatgcttt gcatacttct gcctgctggg gagcctgggg actttccaca  9600
ccctaactga cacacattcc acagctgcat taatgaatcg gccaacgcgc ggggagaggc  9660
ggtttgcgta ttgggcgctc ttccgcttcc tcgctcactg actcgctgcg ctcggtcgtt  9720
cggctgcggc gagcggtatc agctcactca aaggcggtaa tacggttatc cacagaatca  9780
ggggataacg caggaaagaa catgtgagca aaaggccagc aaaaggccag gaaccgtaaa  9840
aaggccgcgt tgctggcgtt tttccatagg ctccgccccc ctgacgagca tcacaaaaat  9900
cgacgctcaa gtcagaggtg gcgaaacccg acaggactat aaagatacca ggcgtttccc  9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
ggatctcaag aagatccttt gatcttttct acggggtctg acgctcagtg gaacgaaaac  10500
tcacgttaag ggattttggt catgagatta tcaaaaagga tcttcaccta gatcctttta  10560
aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tcctgcaaac cacgttgtgt ctcaaaatct ctgatgttac attgcacaag  10740
ataaaaatat atcatcatga acaataaaac tgtctgctta cataaacagt aatacaaggg  10800
gtgttatgag ccatattcaa cgggaaacgt cttgctcgag gccgcgatta aattccaaca  10860
tggatgctga tttatatggg tataaatggg ctcgcgataa tgtcgggcaa tcaggtgcga  10920
caatctatcg attgtatggg aagcccgatg cgccagagtt gtttctgaaa catggcaaag  10980
gtagcgttgc caatgatgtt acagatgaga tggtcagact aaactggctg acggaattta  11040
tgcctcttcc gaccatcaag cattttatcc gtactcctga tgatgcatgg ttactcacca  11100
ctgcgatccc cgggaaaaca gcattccagg tattagaaga atatcctgat tcaggtgaaa  11160
atattgttga tgcgctggca gtgttcctgc gccggttgca ttcgattcct gtttgtaatt  11220
gtccttttaa cagcgatcgc gtatttcgtc tcgctcaggc gcaatcacga atgaataacg  11280
gtttggttga tgcgagtgat tttgatgacg agcgtaatgg ctggcctgtt gaacaagtct  11340
ggaaagaaat gcataagctt ttgccattct caccggattc agtcgtcact catggtgatt  11400
tctcacttga taaccttatt tttgacgagg ggaaattaat aggttgtatt gatgttggac  11460
gagtcggaat cgcagaccga taccaggatc ttgccatcct atggaactgc ctcggtgagt  11520
tttctccttc attacagaaa cggctttttc aaaaatatgg tattgataat cctgatatga  11580
ataaattgca gtttcatttg atgctcgatg agtttttcta agggcggcct gccaccatac  11640
ccacgccgaa acaagcgctc atgagcccga agtggcgagc ccgatcttcc ccatcggtga  11700
tgtcggcgat ataggcgcca gcaaccgcac ctgtggcgcc ggtgatgagg gcgcgccaag  11760
tcgacgtccg gcagtc                                                  11776

SEQ ID NO: 44          moltype = DNA  length = 11064
FEATURE                Location/Qualifiers
misc_feature           1..11064
```

```
                         note = Synthetic polynucleotide
source                   1..11064
                         mol_type = other DNA
                         organism = synthetic construct
SEQUENCE: 44
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catggaattc agcagcccca gcagagagga  660
atgccccaag cctctgagcc gggtgtcaat catggccgga tctctgacag gactgctgct  720
gcttcaggcc gtgtcttggg cttctggcgc tagaccttgc atccccaaga gcttcggcta  780
cagcagcgtc gtgtgcgtgt gcaatgccac ctactgcgac agcttcgacc ctcctacctt  840
tcctgctctg ggcaccttca gcagatacga gagcaccaga tccggcagac ggatggaact  900
gagcatggga cccatccagg ccaatcacac aggcactggc ctgctgctga cactgcagcc  960
tgagcagaaa ttccagaaag tgaaaggctt cggcggagcc atgacagatg ccgccgctct  1020
gaatatcctg gctctgtctc caccagctca gaacctgctg ctcaagagct acttcagcga  1080
ggaaggcatc ggctacaaca tcatcagagt gcccatggcc agctgcgact tcagcatcag  1140
gacctacacc tacgccgaca cacccgacga tttccagctg cacaacttca gcctgcctga  1200
agaggacacc aagctgaaga tccctctgat ccacagagcc ctgcagctgg cacaaagacc  1260
cgtgtcactg ctggcctctc catggacatc tcccacctgg ctgaaaacaa atggcgccgt  1320
gaatggcaag ggcagcctga aaggccaacc tggcgacatc taccaccaga cctgggccag  1380
atacttcgtg aagttcctgg acgcctatgc cgagcacaag ctgcagtttt gggccgtgac  1440
agccgagaac gaaccttctg ctggactgct gagcggctac ccctttcagt gcctgggctt  1500
tacacccgag caccagcggg actttatcgc ccgtgatctg ggacccacac tggccaatag  1560
cacccaccat aatgtgcggc tgctgatgct ggacgaccag agactgcttc tgccccactg  1620
ggctaaagtg gtgctgacag atcctgaggc cgccaaatac gtgcacggaa tcgccgtgca  1680
ctggtatctg gactttctgg cccctgccaa ggccacactg ggagagacac acagactgtt  1740
ccccaacacc atgctgttcg ccagcgaagc ctgtgtgggc agcaagtttt gggaacagag  1800
cgtgcggctc ggcagctggg atagaggcat gcagtacagc cacagcatca tcaccaacct  1860
gctgtaccac gtcgtcggct ggaccgactg gaatctggcc ctgaatcctg aaggcggccc  1920
taactgggtc cgaaacttcg tggacagccc catcatcgtg gacatcacca aggacacctt  1980
ctacaagcag cccatgttct accacctggg acacttcagc aagttcatcc ccgagggctc  2040
tcagcgcgtt ggactggtgg cttcccagaa gaacgatctg gacgccgtgg ctctgatgca  2100
ccctgatgga tctgctgtgg tggtggtcct gaaccgcagc agcaaagatg tgcccctgac  2160
catcaaggat cccgccgtgg gattcctgga aacaatcagc cctggctact ccatccacac  2220
ctacctgtgg cgtagacagt gacaattgtt aattaagttt aaaccctcga ggccgcaagc  2280
cgcatcgata ccgtcgacta gagctcgctg atcagcctcg actgtgcctt ctagttgcca  2340
gccatctgtt gtttgcccct cccccgtgcc ttccttgacc ctggaaggtg ccactcccac  2400
tgtcctttcc taataaaatg aggaaattgc atcgcattgt ctgagtaggt gtcattctat  2460
tctggggggt ggggtggggc aggacagcaa gggggaggat tgggaagaca atagcaggca  2520
tgctggggag agatccacga taacaaacag ctttttttggg ggggcggagt tagggcggag  2580
ccaatcagcg tgcgccgttc cgaaagttgc cttttatggc tgggcggaga atgggcggtg  2640
aacgccgatg attatataag gacgcgccgg gtgtggcaca gctagttccg tcgcagccgg  2700
gatttgggtc gcggttcttg tttgtggatc cctgtgatcg tcacttggta agtcactgac  2760
tgtctatgcc tgggaaaggg tgggcaggag atggggcagt gcaggaaaag tggcactatg  2820
aaccctgcag ccctaggaat gcatctagac aattgtacta accttcttct ctttcctctc  2880
ctgacagtcc ggaaagccac catgtggcag ctgtgggcca gcctgtgctg cctgctggtg  2940
ctggccaacg cccgcagccg ccccagcttc cacccccctga gcgacgagct ggtgaactac  3000
gtgaacaagc gcaacaccac ctggcaggcc ggccacaact tctacaacgt ggacatgagc  3060
tacctgaagc gcctgtgcgg caccttcctg ggcggcccca agcccccccca gcgcgtgatg  3120
ttcaccgagg acctgaagct gcccgccagc ttcgacgccc gcgagcagtg gccccagtgc  3180
cccaccatca aggagatccg cgaccagggc agctgcggca gctgctgggc cttcggcgcc  3240
gtggaggcca tcagcgaccg catctgcatc cacaccaacg cccacgtgag cgtggaggtg  3300
agcgccgagg acctgctgac ctgctgcggc agcatgtgcg gcgacggctg caacggcggc  3360
taccccgccg aggcctggaa cttctggacc cgcaagggcc tggtgagcgg cggcctgtac  3420
gagagccacg tgggctgccg cccctacagc atcccccccct gcgagcacca cgtgaacggc  3480
agccgcccccc cctgcaccgg cgagggcgac accccccaagt gcagcaagat ctgcgagccc  3540
ggctacagcc ccacctacaa gcaggacaag cactacggct acaacagcta cagcgtgagc  3600
aacagcgaga aggacatcat ggccgagatc tacaagaacg gccccgtgga gggcgccttc  3660
agcgtgtaca gcgacttcct gctgtacaag agcggcgtgt accagcacgt gaccggcgag  3720
atgatgggcg gccacgccat ccgcatcctg ggctggggcg tggagaacgg cacccccctac  3780
tggctggtgg ccaacagctg gaacaccgac tggggcgaca acggcttctt caagatcctg  3840
cgcggccagg accactgcgg catcgagagc gaggtggtgg ccggcatccc ccgcaccgac  3900
cagtactggg agaagatctg acccagggga ctcagcggcc gctcgagtct agagggcccg  3960
tttaaacccg ctgatcagcc tcgaagacat gataagatac attgatgagt ttggacaaac  4020
cacaacaaga atgcagtgaa aaaaatgctt tatttgtgaa atttgtgatg ctattgcttt  4080
atttgtaacc attataagct gcaataaaca agttaacaac aacaattgca ttcattttat  4140
gtttcaggtt cagggggaga tgtgggaggt tttttaaagc aagtaaaacc tctacaaatg  4200
tggtatgaac atattgactg aattccctgc aggttggcca ctccctctct gcgcgctcgc  4260
tcgctcactg aggccgcccg ggcaaagccc gggcgtcggg cgacctttgg tcgcccggcc  4320
tcagtgagcg agcgagcgcg cagagaggga gtggccaact ccatcactag gggttcctgc  4380
ggccgctcgt acggtctcga ggaattcctg caggataact tgccaacctc attctaaaat  4440
```

```
gtatatagaa gcccaaaaga caataacaaa aatattcttg tagaacaaaa tgggaaagaa  4500
tgttccacta aatatcaaga tttagagcaa agcatgagat gtgtggggat agacagtgag  4560
gctgataaaa tagagtagag ctcagaaaca gacccattga tatatgtaag tgacctatga  4620
aaaaaatatg gcattttaca atgggaaaat gatggtcttt ttcttttttta gaaaaacagg  4680
gaaatatatt tatatgtaaa aaataaaagg gaacccatat gtcataccat acacacaaaa  4740
aaattccagt gaattataag tctaaatgga gaaggcaaaa ctttaaatct tttagaaaat  4800
aatatagaag catgcagacc agcctggcca acatgatgaa accctctcta ctaataataa  4860
aatcagtaga actactcagg actactttga gtgggaagtc cttttctatg aagacttctt  4920
tggccaaaat taggctctaa atgcaaggag atagtgcatc atgcctggct gcacttactg  4980
ataaatgatg ttatcaccat ctttaaccaa atgcacagga acaagttatg gtactgatgt  5040
gctggattga gaaggagctc tacttccttg acaggacaca tttgtatcaa cttaaaaaag  5100
cagatttttg ccagcagaac tattcattca gaggtaggaa acttagaata gatgatgtca  5160
ctgattagca tggcttcccc atctccacag ctgcttccca cccaggttgc ccacagttga  5220
gtttgtccag tgctcagggc tgcccactct cagtaagaag ccccacacca gcccctctcc  5280
aaatatgttg gctgttcctt ccattaaagt gaccccactt tagagcagca agtggatttc  5340
tgtttcttac agttcaggaa ggaggagtca gctgtgagaa cctggagcct gagatgcttc  5400
taagtcccac tgctactggg gtcagggaag ccagactcca gcatcagcag tcaggagcac  5460
taagcccttg ccaacatcct gtttctcaga gaaactgctt ccattataat ggttgtcctt  5520
ttttaagcta tcaagccaaa caaccagtgt ctaccattat tctcatcacc tgaagccaag  5580
ggttctagca aaagtcaagc tgtcttgtaa tggttgatgt gcctccagct tctgtcttca  5640
gtcactccac tcttagcctg ctctgaatca actctgacca cagttccctg gagcccctgc  5700
cacctgctgc ccctgccacc ttctccatct gcagtgctgt gcagccttct gcactcttgc  5760
agagctaata ggtggagact tgaaggaaga ggaggaaagt ttctcataat agccttgctg  5820
caagctcaaa tgggaggtgg gcactgtgcc caggagcctt ggagcaaagg ctgtgcccaa  5880
cctctgactg catccaggtt tggtcttgac agagataaga agccctggct tttggagcca  5940
aaatctaggt cagacttagg caggattctc aaagtttatc agcagaacat gaggcagaag  6000
accctttctg ctccagcttc ttcaggctca accttcatca gaatagatag aaagagaggc  6060
tgtgagggtt cttaaaacag aagcaaatct gactcagaga ataaacaacc tcctagtaaa  6120
ctacagctta gacagagcat ctggtggtga gtgtgctcag tgtcctactc aactgtctgg  6180
tatcagccct catgaggact tctcttcttt ccctcataga cctccatctc tgtttttcctt  6240
agcctgcaga aatctggatg gctattcaca gaatgcctgt gctttcagag ttgcattttt  6300
tctctggtat tctggttcaa gcatttgaag gtaggaaagg ttctccaagt gcaagaaagc  6360
cagccctgag cctcaactgc ctggctagtg tggtcagtag gatgcaaagg ctgttgaatg  6420
ccacaaggcc aaactttaac ctgtgtacca caagcctagc agcagaggca gctctgctca  6480
ctggaactct ctgtcttctt tctcctgagc cttttctttt cctgagtttt ctagctctcc  6540
tcaaccttac ctctgcccta cccaggacaa acccaagagc cactgtttct gtgatgtcct  6600
ctccagccct aattaggcat catgacttca gcctgacctt ccatgctcag aagcagtgct  6660
aatccacttc agatgagctg ctctatgcaa cacaggcaga gcctacaaac ctttgcacca  6720
gagccctcca catatcagtg tttgttcata ctcacttcaa cagcaaatgt gactgctgag  6780
attaagattt tacacaagat ggtctgtaat ttcacagtta gttttatccc attaggtatg  6840
aaagaattag cataattccc cttaaacatg aatgaatctt agattttttta ataaatagtt  6900
ttggaagtaa agacagagac atcaggagca caaggaatag cctgagagga caaacagaac  6960
aagaaagagt ctggaaatac acaggatgtt cttggcctcc tcaaagcaag tgcaagcaga  7020
tagtaccagc agccccaggc tatcagagcc cagtgaagag aagtaccatg aaagccacag  7080
ctctaaccac cctgttccag agtgacagac agtccccaag acaagccagc ctgagccaga  7140
gagagaactg caagagaaag tttctaattt aggttctgtt agattcagac aagtgcaggt  7200
catcctctct ccacagctac tcacctctcc agcctaacaa agcctgcagt ccacactcca  7260
accctggtgt ctcacctcct agcctctccc aacatcctgc tctctgacca tcttctgcat  7320
ctctcatctc accatctccc actgtctaca gcctactctt gcaactacca tctcattttc  7380
tgacatcctg tctacatctt ctgccatact ctgccatcta ccataccacc tcttaccatc  7440
taccacacca tcttttatct ccatccctct cagaagcctc caagctgaat cctgctttat  7500
gtgttcatct cagcccctgc atggaaagct gaccccagag gcagaactat tcccagagag  7560
cttggccaag aaaaacaaaa ctaccagcct ggccaggctc aggagtagta agctgcagtg  7620
tctgttgtgt tctagcttca acagctgcag gagttccact ctcaaatgct ccacatttct  7680
cacatcctcc tgattctggt cactacccat cttcaaagaa cagaatatct cacatcagca  7740
tactgtgaag gactagtcat gggtgcagct gctcagagct gcaaagtcat tctggatggt  7800
ggagagctta caaacatttc atgatgctcc ccccgctctg atggctggag cccaatccct  7860
acacagactc ctgctgtatg tgttttcctt tcactctgag ccacagccag agggcaggca  7920
ttcagtctcc tcttcaggct ggggctgggg cactgagaac tcacccaaca ccttgctctc  7980
actccttctg caaaacaaga aagagctttg tgctgcagta gccatgaaga atgaaaggaa  8040
ggctttaact aaaaaatgtc agagattatt ttcaacccct tactgtggat caccagcaag  8100
gaggaaacac aacacagaga catttttttcc cctcaaatta tcaaaagaat cactgcattt  8160
gttaaagaga gcaactgaat caggaagcag agttttgaac atatcagaag ttaggaatct  8220
gcatcagaga caaatgcagt catggttgtt tgctgcatac cagccctaat cattagaagc  8280
ctcatggact tcaaacatca ttccctctga caagatgctc tagcctaact ccatgagata  8340
aaataaatct gcctttcaga gccaaagaag agtccaccag cttcttctca gtgtgaacaa  8400
gagctccagt caggttagtc agtccagtgc agtagaggag accagtctgc atcctctaat  8460
tttcaaaggc aagaagattt gtttaccctg gacaccaggc acaagtgagg tcacagagct  8520
cttagatatg cagtcctcat gagtgaggag actaaagcgc atgccatcaa gacttcagtg  8580
tagagaaaac ctccaaaaaa gcctcctcac tacttctgga atagctcaga ggccgaggcg  8640
gcctcggcct ctgcataaat aaaaaaaatt agtcagccat ggggcggaga atgggcggaa  8700
ctgggcggag ttaggggcgg gatgggcgga gttaggggcg ggactatggt tgctgactaa  8760
ttgagatgca tgctttgcat acttctgcct gctggggagc ctggggactt tccacacctg  8820
gttgctgact aattgagatg catgctttgc atacttctgc ctgctgggga gcctggggac  8880
tttccacacc ctaactgaca cacattccac agctgcatta atgaatcggc caacgcgcgg  8940
ggagaggcgg tttgcgtatt gggcgctctt ccgcttcctc gctcactgac tcgctgcgct  9000
cggtcgttcg gctgcggcga gcggtatcag ctcactcaaa ggcggtaata cggttatcca  9060
cagaatcagg ggataacgca ggaaagaaca tgtgagcaaa aggccagcaa aaggccagga  9120
accgtaaaaa ggccgcgttg ctggcgtttt tccataggct ccgcccccct gacgagcatc  9180
```

```
acaaaaatcg acgctcaagt cagaggtggc gaaacccgac aggactataa agataccagg  9240
cgtttccccc tggaagctcc ctcgtgcgct ctcctgttcc gaccctgccg cttaccggat  9300
acctgtccgc ctttctccct tcgggaagcg tggcgctttc tcatagctca cgctgtaggt  9360
atctcagttc ggtgtaggtc gttcgctcca agctgggctg tgtgcacgaa ccccccgttc  9420
agcccgaccg ctgcgcctta tccggtaact atcgtcttga gtccaacccg gtaagacacg  9480
acttatcgcc actggcagca gccactggta acaggattag cagagcgagg tatgtaggcg  9540
gtgctacaga gttcttgaag tggtggccta actacggcta cactagaaga acagtatttg  9600
gtatctgcgc tctgctgaag ccagttacct tcggaaaaag agttggtagc tcttgatccg  9660
gcaaacaaac caccgctggt agcggtggtt tttttgtttg caagcagcag attacgcgca  9720
gaaaaaaagg atctcaagaa gatcctttga tcttttctac ggggtctgac gctcagtgga  9780
acgaaaactc acgttaaggg attttggtca tgagattatc aaaaaggatc ttcacctaga  9840
tccttttaaa ttaaaaatga agttttaaat caatctaaag tatatatgag taaacttggt  9900
ctgacagtta ccaatgctta atcagtgagg cacctatctc agcgatctgt ctatttcgtt  9960
catccatagt tgcctgactc ctgcaaacca cgttgtgtct caaaatctct gatgttacat  10020
tgcacaagat aaaaatatat catcatgaac aataaaactg tctgcttaca taaacagtaa  10080
tacaaggggt gttatgagcc atattcaacg ggaaacgtct tgctcgaggc cgcgattaaa  10140
ttccaacatg gatgctgatt tatatgggta taaatgggct cgcgataatg tcgggcaatc  10200
aggtgcgaca atctatcgat tgtatgggaa gcccgatgcg ccagagttgt ttctgaaaca  10260
tggcaaaggt agcgttgcca atgatgttac agatgagatg gtcagactaa actggctgac  10320
ggaatttatg cctcttccga ccatcaagca ttttatccgt actcctgatg atgcatggtt  10380
actcaccact gcgatccccg ggaaaacagc attccaggta ttagaagaat atcctgattc  10440
aggtgaaaat attgttgatg cgctggcagt gttcctgcgc cggttgcatt cgattcctgt  10500
ttgtaattgt ccttttaaca gcgatcgcgt atttcgtctc gctcaggcgc aatcacgaat  10560
gaataacggt ttggttgatg cgagtgattt tgatgacgag cgtaatggct ggcctgttga  10620
acaagtctgg aaagaaatgc ataagctttt gccattctca ccggattcag tcgtcactca  10680
tggtgatttc tcacttgata accttatttt tgacgagggg aaattaatag gttgtattga  10740
tgttggacga gtcggaatcg cagaccgata ccaggatctt gccatcctat ggaactgcct  10800
cggtgagttt tctccttcat tacagaaacg gctttttcaa aaatatggta ttgataatcc  10860
tgatatgaat aaattgcagt ttcatttgat gctcgatgag tttttctaag ggcggcctgc  10920
caccataccc acgccgaaac aagcgctcat gagcccgaag tggcgagccc gatcttcccc  10980
atcggtgatg tcggcgatat aggcgccagc aaccgcacct gtggcgccgg tgatgagggc  11040
gcgccaagtc gacgtccggc agtc                                        11064

SEQ ID NO: 45          moltype = AA  length = 250
FEATURE                Location/Qualifiers
REGION                 1..250
                       note = Synthetic polypeptide
source                 1..250
                       mol_type = protein
                       organism = synthetic construct
SEQUENCE: 45
MEKGPVRAPA EKPRGARCSN GFPERDPPRP GPSRPAEKPP RPEAKSAQPA DGWKGERPRS  60
EEDNELNLPN LAAAYSSILS SLGENPQRQG LLKTPWRAAS AMQFFTKGYQ ETISDVLNDA  120
IFDEDHDEMV IVKDIDMFSM CEHHLVPFVG KVHIGYLPNK QVLGLSKLAR IVEIYSRRLQ  180
VQERLTKQIA VAITEALRPA GVGVVVEATH MCMVMRGVQK MNSKTVTSTM LGVFREDPKT  240
REEFLTLIRS                                                        250

SEQ ID NO: 46          moltype = DNA  length = 750
FEATURE                Location/Qualifiers
misc_feature           1..750
                       note = Synthetic polynucleotide
source                 1..750
                       mol_type = other DNA
                       organism = synthetic construct
SEQUENCE: 46
atggagaagg gccccgtgcg cgcccccgcc gagaagcccc gcggcgcccg ctgcagcaac  60
ggcttccccg agcgcgaccc cccccgcccc ggccccagcc gccccgccga gaagcccccc  120
cgccccgagg ccaagagcgc ccagcccgcc gacggctgga agggcgagcg cccccgcagc  180
gaggaggaca acgagctgaa cctgcccaac ctggccgccg cctacagcag catcctgagc  240
agcctgggcg agaaccccca gcgccagggc ctgctgaaga ccccctggcg cgccgccagc  300
gccatgcagt tcttcaccaa gggctaccag gagaccatca gcgacgtgct gaacgacgcc  360
atcttcgacg aggaccacga cgagatggtg atcgtgaagg acatcgacat gttcagcatg  420
tgcgagcacc acctggtgcc cttcgtgggc aaggtgcaca tcggctacct gcccaacaag  480
caggtgctgg gcctgagcaa gctggcccgc atcgtggaga tctacagccg ccgcctgcag  540
gtgcaggagc gcctgaccaa gcagatcgcc gtggccatca ccgaggccct gcgccccgcc  600
ggcgtgggcg tggtggtgga ggccacccac atgtgcatgg tgatgcgcgg cgtgcagaag  660
atgaacagca agaccgtgac cagcaccatg ctgggcgtgt tccgcgagga ccccaagacc  720
cgcgaggagt tcctgaccct gatccgcagc                                  750

SEQ ID NO: 47          moltype = AA  length = 203
FEATURE                Location/Qualifiers
REGION                 1..203
                       note = Synthetic polypeptide
source                 1..203
                       mol_type = protein
                       organism = synthetic construct
SEQUENCE: 47
MGSRDHLFKV LVVGDAAVGK TSLVQRYSQD SFSKHYKSTV GVDFALKVLQ WSDYEIVRLQ  60
LWDIAGQERF TSMTRLYYRD ASACVIMFDV TNATTFSNSQ RWKQDLDSKL TLPNGEPVPC  120
```

```
LLLANKCDLS PWAVSRDQID RFSKENGFTG WTETSVKENK NINEAMRVLI EKMMRNSTED  180
IMSLSTQGDY INLQTKSSSW SCC                                          203

SEQ ID NO: 48          moltype = DNA  length = 609
FEATURE                Location/Qualifiers
misc_feature           1..609
                       note = Synthetic polynucleotide
source                 1..609
                       mol_type = other DNA
                       organism = synthetic construct
SEQUENCE: 48
atgggcagcc gcgaccacct gttcaaggtg ctggtggtgg gcgacgccgc cgtgggcaag  60
accagcctgg tgcagcgcta cagccaggac agcttcagca agcactacaa gagcaccgtg  120
ggcgtggact tcgccctgaa ggtgctgcag tggagcgact acgagatcgt gcgcctgcag  180
ctgtgggaca tcgccggcca ggagcgcttc accagcatga cccgcctgta ctaccgcgac  240
gccagcgcct gcgtgatcat gttcgacgtg accaacgcca ccaccttcag caacagccag  300
cgctggaagc aggacctgga cagcaagctg accctgccca acggcgagcc cgtgccctgc  360
ctgctgctgg ccaacaagtg cgacctgagc cctgggccg tgagccgcga ccagatcgac  420
cgcttcagca aggagaacgg cttcaccggc tggaccgaga ccagcgtgaa ggagaacaag  480
aacatcaacg aggccatgcg cgtgctgatc gagaagatga tgcgcaacag caccgaggac  540
atcatgagcc tgagcaccca gggcgactac atcaacctgc agaccaagag cagcagctgg  600
agctgctgc                                                          609

SEQ ID NO: 49          moltype = AA  length = 796
FEATURE                Location/Qualifiers
REGION                 1..796
                       note = Synthetic polypeptide
source                 1..796
                       mol_type = protein
                       organism = synthetic construct
SEQUENCE: 49
MPTTQQSPQD EQEKLLDEAI QAVKVQSFQM KRCLDKNKLM DALKHASNML GELRTSMLSP  60
KSYYELYMAI SDELHYLEVY LTDEFAKGRK VADLYELVQY AGNIIPRLYL LITVGVVYVK  120
SFPQSRKDIL KDLVEMCRGV QHPLRGLFLR NYLLQCTRNI LPDEGEPTDE ETTGDISDSM  180
DFVLLNFAEM NKLWVRMQHQ GHSRDREKRE RERQELRILV GTNLVRLSQL EGVNVERYKQ  240
IVLTGILEQV VNCRDALAQE YLMECIIQVF PDEFHLQTLN PFLRACAELH QNVNVKNIII  300
ALIDRLALFA HREDGPGIPA DIKLFDIFSQ QVATVIQSRQ DMPSEDVVSL QVSLINLAMK  360
CYPDRVDYVD KVLETTVEIF NKLNLEHIAT SSAVSKELTR LLKIPVDTYN NILTVLKLKH  420
FHPLFEYFDY ESRKSMSCYV LSNVLDYNTE IVSQDQVDSI MNLVSTLIQD QPDQPVEDPD  480
PEDFADEQSL VGRFIHLLRS EDPDQQYLIL NTARKHFGAG GNQRIRFTLP PLVFAAYQLA  540
FRYKENSKVD DKWEKKCQKI FSFAHQTISA LIKAELAELP LRLFLQGALA AGEIGFENHE  600
TVAYEFMSQA FSLYEDEISD SKAQLAAITL IIGTFERMKC FSEENHEPLR TQCALAASKL  660
LKKPDQGRAV STCAHLFWSG RNTDKNGEEL HGGKRVMECL KKALKIANQC MDPSLQVQLF  720
IEILNRYIYF YEKENDAVTI QVLNQLIQKI REDLPNLESS EETEQINKHF HNTLEHLRLR  780
RESPESEGPI YEGLIL                                                  796

SEQ ID NO: 50          moltype = DNA  length = 2388
FEATURE                Location/Qualifiers
misc_feature           1..2388
                       note = Synthetic polynucleotide
source                 1..2388
                       mol_type = other DNA
                       organism = synthetic construct
SEQUENCE: 50
atgcccacca cccagcagag cccccaggac gagcaggaga agctgctgga cgaggccatc  60
caggccgtga aggtgcagag cttccagatg aagcgctgcc tggacaagaa caagctgatg  120
gacgccctga agcacgccag caacatgctg ggcgagctgc gcaccagcat gctgagcccc  180
aagagctact acgagctgta catggccatc agcgacgagc tgcactacct ggaggtgtac  240
ctgaccgacg agttcgccaa gggccgcaag gtggccgacc tgtacgagct ggtgcagtac  300
gccggcaaca tcatcccccg cctgtacctg ctgatcaccg tgggcgtggt gtacgtgaag  360
agcttccccc agagccgcaa ggacatcctg aaggacctgg tggagatgtg ccgcggcgtg  420
cagcaccccc tgcgcggcct gttcctgcgc aactacctgc tgcagtgcac ccgcaacatc  480
ctgcccgacg agggcgagcc caccgacgag gagaccaccg gcgacatcag cgacagcatg  540
gacttcgtgc tgctgaactt cgccgagatg aacaagctgt gggtgcgcat gcagcaccag  600
ggccacagcc gcgaccgcga gaagcgcgag cgcgagcgcc aggagctgcg catcctggtg  660
ggcaccaacc tggtgcgcct gagccagctg gagggcgtga acgtggagcg ctacaagcag  720
atcgtgctga ccggcatcct ggagcaggtg gtgaactgcc gcgacgccct ggcccaggag  780
tacctgatgg agtgcatcat ccaggtgttc cccgacgagt tccacctgca gaccctgaac  840
cccttcctgc gcgcctgcgc cgagctgcac cagaacgtga acgtgaagaa catcatcatc  900
gccctgatcg accgcctggc cctgttcgcc caccgcgagg acggccccgg catccccgcc  960
gacatcaagc tgttcgacat cttcagccag caggtggcca ccgtgatcca gagccgccag  1020
gacatgccca gcgaggacgt ggtgagcctg caggtgagcc tgatcaacct ggccatgaag  1080
tgctaccccg accgcgtgga ctacgtggac aaggtgctgg agaccaccgt ggagatcttc  1140
aacaagctga acctggagca catcgccacc agcagcgccg tgagcaagga gctgacccgc  1200
ctgctgaaga tccccgtgga cacctacaac aacatcctga ccgtgctgaa gctgaagcac  1260
ttccaccccc tgttcgagta cttcgactac gagagccgca agagcatgag ctgctacgtg  1320
ctgagcaacg tgctggacta caacaccgag atcgtgagcc aggaccaggt ggacagcatc  1380
atgaacctgg tgagcaccct gatccaggac cagcccgacc agcccgtgga ggaccccgac  1440
cccgaggact tcgccgacga gcagagcctg gtgggccgct tcatccacct gctgcgcagc  1500
```

```
gaggaccccg accagcagta cctgatcctg aacaccgccc gcaagcactt cggcgccggc  1560
ggcaaccagc gcatccgctt caccctgccc cccctggtgt tcgccgccta ccagctggcc  1620
ttccgctaca aggagaacag caaggtggac gacaagtggg agaagaagtg ccagaagatc  1680
ttcagcttcg cccaccagac catcagcgcc ctgatcaagg ccgagctggc cgagctgccc  1740
ctgcgcctgt tcctgcaggg cgccctggcc gccggcgaga tcggcttcga gaaccacgag  1800
accgtggcct acgagttcat gagccaggcc ttcagcctgt acgaggacga gatcagcgac  1860
agcaaggccc agctggccgc catcaccctg atcatcggca ccttcgagcg catgaagtgc  1920
ttcagcgagg agaaccacga gcccctgcgc acccagtgcg ccctggccgc cagcaagctg  1980
ctgaagaagc ccgaccaggg ccgcgccgtg agcacctgcg cccacctgtt ctggagcggc  2040
cgcaacaccg acaagaacgg cgaggagctg cacggcggca agcgcgtgat ggagtgcctg  2100
aagaaggccc tgaagatcgc caaccagtgc atggacccca gcctgcaggt gcagctgttc  2160
atcgagatcc tgaaccgcta catctacttc tacgagaagg agaacgacgc cgtgaccatc  2220
caggtgctga accagctgat ccagaagatc cgcgaggacc tgcccaacct ggagagcagc  2280
gaggagaccg agcagatcaa caagcacttc cacaacaccc tggagcacct gcgcctgcgc  2340
cgcgagagcc ccgagagcga gggccccatc tacgagggcc tgatcctg              2388

SEQ ID NO: 51          moltype = DNA  length = 11081
FEATURE                Location/Qualifiers
misc_feature           1..11081
                       note = Synthetic polynucleotide
source                 1..11081
                       mol_type = other DNA
                       organism = synthetic construct
SEQUENCE: 51
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agccccccctt tttggctatc cttccacgtg ttctttttttg  780
tatcttttgt gtttcctaga aaacatctca gtcaccaccg cagccctagg aatgcatcta  840
gacaattgta ctaaccttct tctctttcct ctcctgacag tccggaaagc caccatggaa  900
ttcagcagcc ccagcagaga ggaatgcccc aagcctctga gccgggtgtc aatcatggcc  960
ggatctctga caggactgct gctgcttcag gccgtgtctt gggcttctgg cgctagacct  1020
tgcatcccca agagcttcgg ctacagcagc gtcgtgtgcg tgtgcaatgc cacctactgc  1080
gacagcttcg accctcctac ctttcctgct ctgggcacct tcagcagata cgagagcacc  1140
agatccggca gacggatgga actgagcatg ggacccatcc aggccaatca cacaggcact  1200
ggcctgctgc tgacactgca gcctgagcag aaattccaga aagtgaaagg cttcggcgga  1260
gccatgacag atgccgccgc tctgaatatc ctggctctgt ctccaccagc tcagaacctg  1320
ctgctcaaga gctacttcag cgaggaaggc atcggctaca acatcatcag agtgcccatg  1380
gccagctgcg acttcagcat caggacctac acctacgccg acacacccga cgatttccag  1440
ctgcacaact tcagcctgcc tgaagaggac accaagctga agatccctct gatccacaga  1500
gccctgcagc tggcacaaag acccgtgtca ctgctggcct ctccatggac atctcccacc  1560
tggctgaaaa caaatggcgc cgtgaatggc aagggcagcc tgaaaggcca acctggcgac  1620
atctaccacc agacctgggc cagatacttc gtgaagttcc tggacgccta tgccgagcac  1680
aagctgcagt tttgggccgt gacagccgag aacgaacctt ctgctggact gctgagcggc  1740
taccccttttc agtgcctggg ctttacaccc gagcaccagc gggactttat cgcccgtgat  1800
ctgggaccca cactggccaa tagcacccac cataatgtgc ggctgctgat gctggacgac  1860
cagagactgc ttctgcccca ctgggctaaa gtggtgctga cagatcctga ggccgccaaa  1920
tacgtgcacg gaatcgccgt gcactggtat ctggactttc tggcccctgc caaggccaca  1980
ctgggagaga cacacagact gttccccaac accatgctgt tcgccagcga agcctgtgtg  2040
ggcagcaagt tttgggaaca gagcgtgcgg ctcggcagct gggatagagg catgcagtac  2100
agccacagca tcatcaccaa cctgctgtac cacgtcgtcg gctggaccga ctggaatctg  2160
gccctgaatc ctgaaggcgg ccctaactgg gtccgaaact tcgtggacag ccccatcatc  2220
gtggacatca ccaaggacac cttctacaag cagcccatgt tctaccacct gggacacttc  2280
agcaagttca tccccgaggg ctctcagcgc gttggactgg tggcttccca gaagaacgat  2340
ctggacgccg tggctctgat gcaccctgat ggatctgctg tggtggtggt cctgaaccgc  2400
agcagcaaag atgtgcccct gaccatcaag gatcccgccg tgggattcct ggaaacaatc  2460
agccctggct actccatcca cacctacctg tggcgtagac aggagggcag aggaagtctt  2520
ctgacatgcg gagacgtgga agagaatccc ggccctatgg agaagggccc cgtgcgcgcc  2580
cccgccgaga agccccgcgg cgcccgctgc agcaacggct tccccgagcg cgaccccccc  2640
cgccccggcc ccagccgccc cgccgagaag cccccccgcc ccgaggccaa gagcgcccag  2700
cccgccgacg gctggaaggg cgagcgcccc cgcagcgagg aggacaacga gctgaacctg  2760
cccaacctgg ccgccgccta cagcagcatc ctgagcagcc tgggcgagaa cccccagcgc  2820
cagggcctgc tgaagacccc ctggcgcgcc gccagcgcca tgcagttctt caccaagggc  2880
taccaggaga ccatcagcga cgtgctgaac gacgccatct tcgacgagga ccacgacgag  2940
atggtgatcg tgaaggacat cgacatgttc agcatgtgcg agcaccacct ggtgcccttc  3000
gtgggcaagg tgcacatcgg ctacctgccc aacaagcagg tgctgggcct gagcaagctg  3060
gcccgcatcg tggagatcta cagccgccgc ctgcaggtgc aggagcgcct gaccaagcag  3120
atcgccgtgg ccatcaccga ggccctgcgc cccgccggcg tgggcgtggt ggtggaggcc  3180
acccacatgt gcatggtgat gcgcggcgtg cagaagatga acagcaagac cgtgaccagc  3240
accatgctgg gcgtgttccg cgaggacccc aagacccgcg aggagttcct gaccctgatc  3300
```

```
cgcagctgac aattgttaat taagtttaaa ccctcgaggc cgcaagctta tcgataatca  3360
acctctggat tacaaaattt gtgaaagatt gactggtatt cttaactatg ttgctccttt  3420
tacgctatgt ggatacgctg ctttaatgcc tttgtatcat gctattgctt cccgtatggc  3480
tttcattttc tcctccttgt ataaatcctg gttgctgtct ctttatgagg agttgtggcc  3540
cgttgtcagg caacgtggcg tggtgtgcac tgtgtttgct gacgcaaccc ccactggttg  3600
gggcattgcc accacctgtc agctcctttc cgggactttc gctttccccc tccctattgc  3660
cacggcggaa ctcatcgccg cctgccttgc ccgctgctgg acaggggctc ggctgttggg  3720
cactgacaat tccgtggtgt tgtcggggaa atcatcgtcc tttccttggc tgctcgcctg  3780
tgttgccacc tggattctgc gcgggacgtc cttctgctac gtcccttcgg ccctcaatcc  3840
agcggacctt ccttcccgcg gcctgctgcc ggctctgcgg cctcttccgc gtcttcgcct  3900
tcgccctcag acgagtcgga tctccctttg ggccgcctcc ccgcatcgat accgtcgact  3960
agagctcgct gatcagcctc gactgtgcct tctagttgcc agccatctgt tgtttgcccc  4020
tcccccgtgc cttccttgac cctggaaggt gccactccca ctgtcctttc ctaataaaat  4080
gaggaaattg catcgcattg tctgagtagg tgtcattcta ttctgggggg tggggtgggg  4140
caggacagca agggggagga ttgggaagac aatagcaggc atgctgggga gagatccacg  4200
ataacaaaca gctttttttgg ggtgaacata ttgactgaat tccctgcagg ttggccactc  4260
cctctctgcg cgctcgctcg ctcactgagg ccgcccgggc aaagcccggg cgtcgggcga  4320
cctttggtcg cccggcctca gtgagcgagc gagcgcgcag agagggagtg gccaactcca  4380
tcactagggg ttcctgcggc cgctcgtacg gtctcgagga attcctgcag gataacttgc  4440
caacctcatt ctaaaatgta tatagaagcc caaaagacaa taacaaaaat attcttgtag  4500
aacaaaatgg gaaagaatgt tccactaaat atcaagattt agagcaaagc atgagatgtg  4560
tggggataga cagtgaggct gataaaatag agtagagctc agaaacagac ccattgatat  4620
atgtaagtga cctatgaaaa aaatatggca ttttacaatg ggaaaatgat ggtctttttc  4680
tttttagaa aaacagggaa atatatttat atgtaaaaaa taaaagggaa cccatatgtc  4740
ataccataca cacaaaaaaa ttccagtgaa ttataagtct aaatggagaa ggcaaaactt  4800
taaatctttt agaaaataat atagaagcat gcagaccagc ctggccaaca tgatgaaacc  4860
ctctctacta ataataaaat cagtagaact actcaggact actttgagtg ggaagtcctt  4920
ttctatgaag acttctttgg ccaaaattag gctctaaatg caaggagata gtgcatcatg  4980
cctggctgca cttactgata aatgatgtta tcaccatctt taaccaaatg cacaggaaca  5040
agttatggta ctgatgtgct ggattgagaa ggagctctac ttccttgaca ggacacattt  5100
gtatcaactt aaaaaagcag atttttgcca gcagaactat tcattcagag gtaggaaact  5160
tagaatagat gatgtcactg attagcatgg cttccccatc tccacagctg cttcccaccc  5220
aggttgccca cagttgagtt tgtccagtgc tcagggctgc ccactctcag taagaagccc  5280
cacaccagcc cctctccaaa tatgttggct gttccttcca ttaaagtgac cccactttag  5340
agcagcaagt ggatttctgt ttcttacagt tcaggaagga ggagtcagct gtgagaacct  5400
ggagcctgag atgcttctaa gtcccactgc tactggggtc agggaagcca gactccagca  5460
tcagcagtca ggagcactaa gcccttgcca acatcctgtt tctcagagaa actgcttcca  5520
ttataatggt tgtccttttt taagctatca agccaaacaa ccagtgtcta ccattattct  5580
catcacctga agccaagggt tctagcaaaa gtcaagctgt cttgtaatgg ttgatgtgcc  5640
tccagcttct gtcttcagtc actccactct tagcctgctc tgaatcaact ctgaccacag  5700
ttccctggag cccctgccac ctgctgcccc tgccaccttc tccatctgca gtgctgtgca  5760
gccttctgca ctcttgcaga gctaataggt ggagacttga aggaagagga ggaaagtttc  5820
tcataatagc cttgctgcaa gctcaaatgg gaggtgggca ctgtgcccag gagccttgga  5880
gcaaaggctg tgcccaacct ctgactgcat ccaggtttgg tcttgacaga gataagaagc  5940
cctggctttt ggagccaaaa tctaggtcag acttaggcag gattctcaaa gtttatcagc  6000
agaacatgag gcagaagacc ctttctgctc cagcttcttc aggctcaacc ttcatcagaa  6060
tagatagaaa gagaggctgt gagggttctt aaaacagaag caaatctgac tcagagaata  6120
aacaacctcc tagtaaacta cagcttagac agagcatctg gtggtgagtg tgctcagtgt  6180
cctactcaac tgtctggtat cagccctcat gaggacttct cttctttccc tcatagacct  6240
ccatctctgt tttccttagc ctgcagaaat ctggatggct attcacagaa tgcctgtgct  6300
ttcagagttg catttttttct ctggtattct ggttcaagca tttgaaggta ggaaaggttc  6360
tccaagtgca agaaagccag ccctgagcct caactgcctg gctagtgtgg tcagtaggat  6420
gcaaaggctg ttgaatgcca caaggccaaa ctttaacctg tgtaccacaa gcctagcagc  6480
agaggcagct ctgctcactg gaactctctg tcttctttct cctgagcctt ttcttttcct  6540
gagttttcta gctctcctca accttacctc tgccctaccc aggacaaacc caagagccac  6600
tgtttctgtg atgtcctctc cagccctaat taggcatcat gacttcagcc tgaccttcca  6660
tgctcagaag cagtgctaat ccacttcaga tgagctgctc tatgcaacac aggcagagcc  6720
tacaaacctt tgcaccagag ccctccacat atcagtgttt gttcatactc acttcaacag  6780
caaatgtgac tgctgagatt aagattttac acaagatggt ctgtaatttc acagttagtt  6840
ttatcccatt aggtatgaaa gaattagcat aattcccctt aaacatgaat gaatcttaga  6900
ttttttaata aatagttttg gaagtaaaga cagagacatc aggagcacaa ggaatagcct  6960
gagaggacaa acagaacaag aaagagtctg gaaatacaca ggatgttctt ggcctcctca  7020
aagcaagtgc aagcagatag taccagcagc cccaggctat cagagcccag tgaagagaag  7080
taccatgaaa gccacagctc taaccaccct gttccagagt gacagacagt ccccaagaca  7140
agccagcctg agccagagag agaactgcaa gagaaagttt ctaatttagg ttctgttaga  7200
ttcagacaag tgcaggtcat cctctctcca cagctactca cctctccagc ctaacaaagc  7260
ctgcagtcca cactccaacc ctggtgtctc acctcctagc ctctcccaac atcctgctct  7320
ctgaccatct tctgcatctc tcatctcacc atctcccact gtctacagcc tactcttgca  7380
actaccatct catttctgta catcctgtct acatcttctg ccatactctg ccatctacca  7440
taccacctct taccatctac cacaccatct tttatctcca tccctctcag aagcctccaa  7500
gctgaatcct gctttatgtg ttcatctcag cccctgcatg gaaagctgac cccagaggca  7560
gaactattcc cagagagctt ggccaagaaa aacaaaacta ccagcctggc caggctcagg  7620
agtagtaagc tgcagtgtct gttgtgttct agcttcaaca gctgcaggag ttccactctc  7680
aaatgctcca catttctcac atcctcctga ttctggtcac tacccatctt caaagaacag  7740
aatatctcac atcagcatac tgtgaaggac tagtcatggg tgcagctgct cagagctgca  7800
aagtcattct ggatggtgga gagcttacaa acatttcatg atgctccccc cgctctgatg  7860
gctggagccc aatccctaca cagactcctg ctgtatgtgt tttcctttca ctctgagcca  7920
cagccagagg gcaggcattc agtctcctct tcaggctggg gctggggcac tgagaactca  7980
cccaacacct tgctctcact ccttctgcaa aacaagaaag agctttgtgc tgcagtagcc  8040
```

```
atgaagaatg aaaggaaggc tttaactaaa aaatgtcaga gattattttc aaccccttac  8100
tgtggatcac cagcaaggag gaaacacaac acagagacat tttttcccct caaattatca  8160
aaagaatcac tgcatttgtt aaagagagca actgaatcag gaagcagagt tttgaacata  8220
tcagaagtta ggaatctgca tcagagacaa atgcagtcat ggttgtttgc tgcataccag  8280
ccctaatcat tagaagcctc atggacttca aacatcattc cctctgacaa gatgctctag  8340
cctaactcca tgagataaaa taaatctgcc tttcagagcc aaagaagagt ccaccagctt  8400
cttctcagtg tgaacaagag ctccagtcag gttagtcagt ccagtgcagt agaggagacc  8460
agtctgcatc ctctaatttt caaaggcaag aagatttgtt taccctggac accaggcaca  8520
agtgaggtca cagagctctt agatatgcag tcctcatgag tgaggagact aaagcgcatg  8580
ccatcaagac ttcagtgtag agaaaacctc caaaaaagcc tcctcactac ttctggaata  8640
gctcagaggc cgaggcggcc tcggcctctg cataaataaa aaaaattagt cagccatggg  8700
gcggagaatg ggcggaactg ggcggagtta ggggcgggat gggcggagtt aggggcggga  8760
ctatggttgc tgactaattg agatgcatgc tttgcatact tctgcctgct ggggagcctg  8820
gggactttcc acacctggtt gctgactaat tgagatgcat gctttgcata cttctgcctg  8880
ctggggagcc tggggacttt ccacacccta actgacacac attccacagc tgcattaatg  8940
aatcggccaa cgcgcgggga gaggcggttt gcgtattggg cgctcttccg cttcctcgct  9000
cactgactcg ctgcgctcgg tcgttcggct gcggcgagcg gtatcagctc actcaaaggc  9060
ggtaatacgg ttatccacag aatcagggga taacgcagga aagaacatgt gagcaaaagg  9120
ccagcaaaag gccaggaacc gtaaaaaggc cgcgttgctg gcgtttttcc ataggctccg  9180
cccccctgac gagcatcaca aaaatcgacg ctcaagtcag aggtggcgaa acccgacagg  9240
actataaaga taccaggcgt ttccccctgg aagctccctc gtgcgctctc ctgttccgac  9300
cctgccgctt accggatacc tgtccgcctt tctcccttcg ggaagcgtgg cgctttctca  9360
tagctcacgc tgtaggtatc tcagttcggt gtaggtcgtt cgctccaagc tgggctgtgt  9420
gcacgaaccc cccgttcagc ccgaccgctg cgccttatcc ggtaactatc gtcttgagtc  9480
caacccggta agacacgact tatcgccact ggcagcagcc actggtaaca ggattagcag  9540
agcgaggtat gtaggcggtg ctacagagtt cttgaagtgg tggcctaact acggctacac  9600
tagaagaaca gtatttggta tctgcgctct gctgaagcca gttaccttcg gaaaaagagt  9660
tggtagctct tgatccggca aacaaaccac cgctggtagc ggtggttttt ttgtttgcaa  9720
gcagcagatt acgcgcagaa aaaaaggatc tcaagaagat cctttgatct tttctacggg  9780
gtctgacgct cagtggaacg aaaactcacg ttaagggatt ttggtcatga gattatcaaa  9840
aaggatcttc acctagatcc ttttaaatta aaaatgaagt tttaaatcaa tctaaagtat  9900
atatgagtaa acttggtctg acagttacca atgcttaatc agtgaggcac ctatctcagc  9960
gatctgtcta tttcgttcat ccatagttgc ctgactcctg caaaccacgt tgtgtctcaa  10020
aatctctgat gttacattgc acaagataaa aatatatcat catgaacaat aaaactgtct  10080
gcttacataa acagtaatac aaggggtgtt atgagccata ttcaacggga aacgtcttgc  10140
tcgaggccgc gattaaattc caacatggat gctgatttat atgggtataa atgggctcgc  10200
gataatgtcg ggcaatcagg tgcgacaatc tatcgattgt atgggaagcc cgatgcgcca  10260
gagttgtttc tgaaacatgg caaaggtagc gttgccaatg atgttacaga tgagatggtc  10320
agactaaact ggctgacgga atttatgcct cttccgacca tcaagcattt tatccgtact  10380
cctgatgatg catggttact caccactgcg atccccggga aaacagcatt ccaggtatta  10440
gaagaatatc ctgattcagg tgaaaatatt gttgatgcgc tggcagtgtt cctgcgccgg  10500
ttgcattcga ttcctgtttg taattgtcct tttaacagcg atcgcgtatt tcgtctcgct  10560
caggcgcaat cacgaatgaa taacggtttg gttgatgcga gtgattttga tgacgagcgt  10620
aatggctggc ctgttgaaca agtctggaaa gaaatgcata agcttttgcc attctcaccg  10680
gattcagtcg tcactcatgg tgatttctca cttgataacc ttatttttga cgaggggaaa  10740
ttaataggtt gtattgatgt tggacgagtc ggaatcgcag accgatacca ggatcttgcc  10800
atcctatgga actgcctcgg tgagttttct ccttcattac agaaacggct ttttcaaaaa  10860
tatggtattg ataatcctga tatgaataaa ttgcagtttc atttgatgct cgatgagttt  10920
ttctaagggc ggcctgccac catacccacg ccgaaacaag cgctcatgag cccgaagtgg  10980
cgagcccgat cttccccatc ggtgatgtcg gcgatatagg cgccagcaac cgcacctgtg  11040
gcgccggtga tgagggcgcg ccaagtcgac gtccggcagt c                      11081
```

```
SEQ ID NO: 52           moltype = DNA  length = 10940
FEATURE                 Location/Qualifiers
misc_feature            1..10940
                        note = Synthetic polynucleotide
source                  1..10940
                        mol_type = other DNA
                        organism = synthetic construct
SEQUENCE: 52
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatgggc  900
agccgcgacc acctgttcaa ggtgctggtg gtgggcgacg ccgccgtggg caagaccagc  960
ctggtgcagc gctacagcca ggacagcttc agcaagcact acaagagcac cgtgggcgtg  1020
gacttcgccc tgaaggtgct gcagtggagc gactacgaga tcgtgcgcct gcagctgtgg  1080
gacatcgccg gccaggagcg cttcaccagc atgacccgcc tgtactaccg cgacgccagc  1140
```

```
gcctgcgtga tcatgttcga cgtgaccaac gccaccacct tcagcaacag ccagcgctgg  1200
aagcaggacc tggacagcaa gctgaccctg cccaacggcg agcccgtgcc ctgcctgctg  1260
ctggccaaca agtgcgacct gagcccctgg gccgtgagcc gcgaccagat cgaccgcttc  1320
agcaaggaga acggcttcac cggctggacc gagaccagcg tgaaggagaa caagaacatc  1380
aacgaggcca tgcgcgtgct gatcgagaag atgatgcgca acagcaccga ggacatcatg  1440
agcctgagca cccagggcga ctacatcaac ctgcagacca agagcagcag ctggagctgc  1500
tgcgagggca gaggaagtct tctgacatgc ggagacgtgg aagagaatcc cggccctatg  1560
gaattcagca gccccagcag agaggaatgc cccaagcctc tgagccgggt gtcaatcatg  1620
gccggatctc tgacaggact gctgctgctt caggccgtgt cttgggcttc tggcgctaga  1680
ccttgcatcc ccaagagctt cggctacagc agcgtcgtgt gcgtgtgcaa tgccacctac  1740
tgcgacagct tcgaccctcc tacctttcct gctctgggca ccttcagcag atacgagagc  1800
accagatccg gcagacggat ggaactgagc atgggaccca tccaggccaa tcacacaggc  1860
actggcctgc tgctgacact gcagcctgag cagaaattcc agaaagtgaa aggcttcggc  1920
ggagccatga cagatgccgc cgctctgaat atcctggctc tgtctccacc agctcagaac  1980
ctgctgctca agagctactt cagcgaggaa ggcatcggct acaacatcat cagagtgccc  2040
atggccagct gcgacttcag catcaggacc tacacctacg ccgacacacc cgacgatttc  2100
cagctgcaca acttcagcct gcctgaagag gacaccaagc tgaagatccc tctgatccac  2160
agagccctgc agctggcaca aagacccgtg tcactgctgg cctctccatg gacatctccc  2220
acctggctga aaacaaatgg cgccgtgaat ggcaagggca gcctgaaagg ccaacctggc  2280
gacatctacc accagacctg ggccagatac ttcgtgaagt tcctggacgc ctatgccgag  2340
cacaagctgc agttttgggc cgtgacagcc gagaacgaac cttctgctgg actgctgagc  2400
ggctacccct ttcagtgcct gggctttaca cccgagcacc agcgggactt tatcgcccgt  2460
gatctgggac ccacactggc caatagcacc caccataatg tgcggctgct gatgctggac  2520
gaccagagac tgcttctgcc ccactgggct aaagtggtgc tgacagatcc tgaggccgcc  2580
aaatacgtgc acggaatcgc cgtgcactgg tatctggact ttctggcccc tgccaaggcc  2640
acactgggag agacacacag actgttcccc aacaccatgc tgttcgccag cgaagcctgt  2700
gtgggcagca agttttggga acagagcgtg cggctcggca gctgggatag aggcatgcag  2760
tacagccaca gcatcatcac caacctgctg taccacgtcg tcggctggac cgactggaat  2820
ctggccctga atcctgaagg cggccctaac tgggtccgaa acttcgtgga cagccccatc  2880
atcgtggaca tcaccaagga caccttctac aagcagccca tgttctacca cctgggacac  2940
ttcagcaagt tcatccccga gggctctcag cgcgttggac tggtggcttc ccagaagaac  3000
gatctggacg ccgtggctct gatgcaccct gatggatctg ctgtggtggt ggtcctgaac  3060
cgcagcagca aagatgtgcc cctgaccatc aaggatcccg ccgtgggatt cctggaaaca  3120
atcagccctg gctactccat ccacacctac ctgtggcgta gacagtgaca attgttaatt  3180
aagtttaaac cctcgaggcc gcaagcttat cgataatcaa cctctggatt acaaaatttg  3240
tgaaagattg actggtattc ttaactatgt tgctcctttt acgctatgtg gatacgctgc  3300
tttaatgcct ttgtatcatg ctattgcttc ccgtatggct ttcattttct cctccttgta  3360
taaatcctgg ttgctgtctc tttatgagga gttgtggccc gttgtcaggc aacgtggcgt  3420
ggtgtgcact gtgtttgctg acgcaacccc cactggttgg ggcattgcca ccacctgtca  3480
gctcctttcc gggactttcg ctttccccct ccctattgcc acggcggaac tcatcgccgc  3540
ctgccttgcc cgctgctgga caggggctcg gctgttgggc actgacaatt ccgtggtgtt  3600
gtcggggaaa tcatcgtcct ttccttggct gctcgcctgt gttgccacct ggattctgcg  3660
cgggacgtcc ttctgctacg tcccttcggc cctcaatcca gcggaccttc cttcccgcgg  3720
cctgctgccg gctctgcggc ctcttccgcg tcttcgcctt cgccctcaga cgagtcggat  3780
ctccctttgg gccgcctccc cgcatcgata ccgtcgacta gagctcgctg atcagcctcg  3840
actgtgcctt ctagttgcca gccatctgtt gtttgcccct cccccgtgcc ttccttgacc  3900
ctggaaggtg ccactcccac tgtcctttcc taataaaatg aggaaattgc atcgcattgt  3960
ctgagtaggt gtcattctat tctggggggt ggggtggggc aggacagcaa gggggaggat  4020
tgggaagaca atagcaggca tgctggggag agatccacga taacaaacag ctttttttggg  4080
gtgaacatat tgactgaatt ccctgcaggt tggccactcc ctctctgcgc gctcgctcgc  4140
tcactgaggc cgcccgggca aagcccgggc gtcgggcgac ctttggtcgc ccggcctcag  4200
tgagcgagcg agcgcgcaga gagggagtgg ccaactccat cactaggggt tcctgcggcc  4260
gctcgtacgg tctcgaggaa ttcctgcagg ataacttgcc aacctcattc taaaatgtat  4320
atagaagccc aaaagacaat aacaaaaata ttcttgtaga acaaaatggg aaagaatgtt  4380
ccactaaata tcaagattta gagcaaagca tgagatgtgt ggggatagac agtgaggctg  4440
ataaaataga gtagagctca gaaacagacc cattgatata tgtaagtgac ctatgaaaaa  4500
aatatggcat tttacaatgg gaaaatgatg gtctttttct tttttagaaa aacagggaaa  4560
tatatttata tgtaaaaaat aaaagggaac ccatatgtca taccatacac acaaaaaaat  4620
tccagtgaat tataagtcta aatggagaag gcaaaacttt aaatctttta gaaaataata  4680
tagaagcatg cagaccagcc tggccaacat gatgaaaccc tctctactaa taataaaatc  4740
agtagaacta ctcaggacta ctttgagtgg gaagtccttt tctatgaaga cttctttggc  4800
caaaattagg ctctaaatgc aaggagatag tgcatcatgc ctggctgcac ttactgataa  4860
atgatgttat caccatcttt aaccaaatgc acaggaacaa gttatggtac tgatgtgctg  4920
gattgagaag gagctctact tccttgacag gacacatttg tatcaactta aaaaagcaga  4980
tttttgccag cagaactatt cattcagagg taggaaactt agaatagatg atgtcactga  5040
ttagcatggc ttccccatct ccacagctgc ttcccaccca ggttgcccac agttgagttt  5100
gtccagtgct cagggctgcc cactctcagt aagaagcccc acaccagccc ctctccaaat  5160
atgttggctg ttccttccat taaagtgacc ccactttaga gcagcaagtg gatttctgtt  5220
tcttacagtt caggaaggag gagtcagctg tgagaacctg gagcctgaga tgcttctaag  5280
tcccactgct actggggtca gggaagccag actccagcat cagcagtcag gagcactaag  5340
cccttgccaa catcctgttt ctcagagaaa ctgcttccat tataatggtt gtccttttttt  5400
aagctatcaa gccaaacaac cagtgtctac cattattctc atcacctgaa gccaagggtt  5460
ctagcaaaag tcaagctgtc ttgtaatggt tgatgtgcct ccagcttctg tcttcagtca  5520
ctccactctt agcctgctct gaatcaactc tgaccacagt tccctggagc ccctgccacc  5580
tgctgcccct gccaccttct ccatctgcag tgctgtgcag ccttctgcac tcttgcagag  5640
ctaataggtg gagacttgaa ggaagaggag gaaagtttct cataatagcc ttgctgcaag  5700
ctcaaatggg aggtgggcac tgtgcccagg agccttggag caaaggctgt gcccaacctc  5760
tgactgcatc caggtttggt cttgacagag ataagaagcc ctggcttttg gagccaaaat  5820
ctaggtcaga cttaggcagg attctcaaag tttatcagca gaacatgagg cagaagaccc  5880
```

-continued

```
tttctgctcc agcttcttca ggctcaacct tcatcagaat agatagaaag agaggctgtg  5940
agggttctta aaacagaagc aaatctgact cagagaataa acaacctcct agtaaactac  6000
agcttagaca gagcatctgg tggtgagtgt gctcagtgtc ctactcaact gtctggtatc  6060
agccctcatg aggacttctc ttctttccct catagacctc catctctgtt ttccttagcc  6120
tgcagaaatc tggatggcta ttcacagaat gcctgtgctt tcagagttgc attttttctc  6180
tggtattctg gttcaagcat ttgaaggtag gaaaggttct ccaagtgcaa gaaagccagc  6240
cctgagcctc aactgcctgg ctagtgtggt cagtaggatg caaaggctgt tgaatgccac  6300
aaggccaaac tttaacctgt gtaccacaag cctagcagca gaggcagctc tgctcactgg  6360
aactctctgt cttctttctc ctgagccttt tcttttcctg agttttctag ctctcctcaa  6420
ccttacctct gccctaccca ggacaaaccc aagagccact gtttctgtga tgtcctctcc  6480
agccctaatt aggcatcatg acttcagcct gaccttccat gctcagaagc agtgctaatc  6540
cacttcagat gagctgctct atgcaacaca ggcagagcct acaaaccttt gcaccagagc  6600
cctccacata tcagtgtttg ttcatactca cttcaacagc aaatgtgact gctgagatta  6660
agattttaca caagatggtc tgtaatttca cagttagttt tatcccatta ggtatgaaag  6720
aattagcata attcccctta aacatgaatg aatcttagat tttttaataa atagttttgg  6780
aagtaaagac agagacatca ggagcacaag gaatagcctg agaggacaaa cagaacaaga  6840
aagagtctgg aaatacacag gatgttcttg gcctcctcaa agcaagtgca agcagatagt  6900
accagcagcc ccaggctatc agagcccagt gaagagaagt accatgaaag ccacagctct  6960
aaccaccctg ttccagagtg acagacagtc cccaagacaa gccagcctga gccagagaga  7020
gaactgcaag agaaagtttc taatttaggt tctgttagat tcagacaagt gcaggtcatc  7080
ctctctccac agctactcac ctctccagcc taacaaagcc tgcagtccac actccaaccc  7140
tggtgtctca cctcctagcc tctcccaaca tcctgctctc tgaccatctt ctgcatctct  7200
catctcacca tctcccactg tctacagcct actcttgcaa ctaccatctc attttctgac  7260
atcctgtcta catcttctgc catactctgc catctaccat accacctctt accatctacc  7320
acaccatctt ttatctccat ccctctcaga agcctccaag ctgaatcctg ctttatgtgt  7380
tcatctcagc ccctgcatgg aaagctgacc ccagaggcag aactattccc agagagcttg  7440
gccaagaaaa acaaaactac cagcctggcc aggctcagga gtagtaagct gcagtgtctg  7500
ttgtgttcta gcttcaacag ctgcaggagt tccactctca aatgctccac atttctcaca  7560
tcctcctgat tctggtcact acccatcttc aaagaacaga atatctcaca tcagcatact  7620
gtgaaggact agtcatgggt gcagctgctc agagctgcaa agtcattctg gatggtggag  7680
agcttacaaa catttcatga tgctcccccc gctctgatgg ctggagccca atccctacac  7740
agactcctgc tgtatgtgtt ttcctttcac tctgagccac agccagaggg caggcattca  7800
gtctcctctt caggctgggg ctggggcact gagaactcac ccaacacctt gctctcactc  7860
cttctgcaaa acaagaaaga gctttgtgct gcagtagcca tgaagaatga aaggaaggct  7920
ttaactaaaa aatgtcagag attattttca accccttact gtggatcacc agcaaggagg  7980
aaacacaaca cagagacatt ttttcccctc aaattatcaa aagaatcact gcatttgtta  8040
aagagagcaa ctgaatcagg aagcagagtt ttgaacatat cagaagttag gaatctgcat  8100
cagagacaaa tgcagtcatg gttgtttgct gcataccagc cctaatcatt agaagcctca  8160
tggacttcaa acatcattcc ctctgacaag atgctctagc ctaactccat gagataaaat  8220
aaatctgcct ttcagagcca aagaagagtc caccagcttc ttctcagtgt gaacaagagc  8280
tccagtcagg ttagtcagtc cagtgcagta gaggagacca gtctgcatcc tctaattttc  8340
aaaggcaaga agatttgttt accctggaca ccaggcacaa gtgaggtcac agagctctta  8400
gatatgcagt cctcatgagt gaggagacta aagcgcatgc catcaagact tcagtgtaga  8460
gaaaacctcc aaaaaaagcct cctcactact tctggaatag ctcagaggcc gaggcggcct  8520
cggcctctgc ataaataaaa aaaattagtc agccatgggg cggagaatgg gcggaactgg  8580
gcggagttag gggcgggatg ggcggagtta ggggcgggac tatggttgct gactaattga  8640
gatgcatgct ttgcatactt ctgcctgctg gggagcctgg ggactttcca cacctggttg  8700
ctgactaatt gagatgcatg ctttgcatac ttctgcctgc tggggagcct ggggactttc  8760
cacaccctaa ctgacacaca ttccacagct gcattaatga atcggccaac gcgcggggag  8820
aggcggtttg cgtattgggc gctcttccgc ttcctcgctc actgactcgc tgcgctcggt  8880
cgttcggctg cggcgagcgg tatcagctca ctcaaaggcg gtaatacggt tatccacaga  8940
atcaggggat aacgcaggaa agaacatgtg agcaaaaggc cagcaaaagg ccaggaaccg  9000
taaaaaggcc gcgttgctgg cgtttttcca taggctccgc ccccctgacg agcatcacaa  9060
aaatcgacgc tcaagtcaga ggtggcgaaa cccgacagga ctataaagat accaggcgtt  9120
tccccctgga agctccctcg tgcgctctcc tgttccgacc ctgccgctta ccggatacct  9180
gtccgccttt ctcccttcgg gaagcgtggc gctttctcat agctcacgct gtaggtatct  9240
cagttcggtg taggtcgttc gctccaagct gggctgtgtg cacgaacccc ccgttcagcc  9300
cgaccgctgc gccttatccg gtaactatcg tcttgagtcc aacccggtaa gacacgactt  9360
atcgccactg gcagcagcca ctggtaacag gattagcaga gcgaggtatg taggcggtgc  9420
tacagagttc ttgaagtggt ggcctaacta cggctacact agaagaacag tatttggtat  9480
ctgcgctctg ctgaagccag ttaccttcgg aaaaagagtt ggtagctctt gatccggcaa  9540
acaaaccacc gctggtagcg gtggtttttt tgtttgcaag cagcagatta cgcgcagaaa  9600
aaaaggatct caagaagatc ctttgatctt ttctacgggg tctgacgctc agtggaacga  9660
aaactcacgt taagggattt tggtcatgag attatcaaaa aggatcttca cctagatcct  9720
tttaaattaa aaatgaagtt ttaaatcaat ctaaagtata tatgagtaaa cttggtctga  9780
cagttaccaa tgcttaatca gtgaggcacc tatctcagcg atctgtctat ttcgttcatc  9840
catagttgcc tgactcctgc aaaccacgtt gtgtctcaaa atctctgatg ttacattgca  9900
caagataaaa atatatcatc atgaacaata aaactgtctg cttacataaa cagtaataca  9960
aggggtgtta tgagccatat tcaacgggaa acgtcttgct cgaggccgcg attaaattcc  10020
aacatggatg ctgatttata tgggtataaa tgggctcgcg ataatgtcgg gcaatcaggt  10080
gcgacaatct atcgattgta tgggaagccc gatgcgccag agttgtttct gaaacatggc  10140
aaaggtagcg ttgccaatga tgttacagat gagatggtca gactaaactg gctgacggaa  10200
tttatgcctc ttccgaccat caagcatttt atccgtactc ctgatgatgc atggttactc  10260
accactgcga tccccgggaa aacagcattc caggtattag aagaatatcc tgattcaggt  10320
gaaaatattg ttgatgcgct ggcagtgttc ctgcgccggt tgcattcgat tcctgtttgt  10380
aattgtcctt ttaacagcga tcgcgtattt cgtctcgctc aggcgcaatc acgaatgaat  10440
aacggtttgg ttgatgcgag tgattttgat gacgagcgta atggctggcc tgttgaacaa  10500
gtctggaaag aaatgcataa gcttttgcca ttctcaccgg attcagtcgt cactcatggt  10560
gatttctcac ttgataacct tatttttgac gaggggaaat taataggttg tattgatgtt  10620
```

```
ggacgagtcg gaatcgcaga ccgataccag gatcttgcca tcctatggaa ctgcctcggt  10680
gagttttctc cttcattaca gaaacggctt tttcaaaaat atggtattga taatcctgat  10740
atgaataaat tgcagtttca tttgatgctc gatgagtttt tctaagggcg gcctgccacc  10800
atacccacgc cgaaacaagc gctcatgagc ccgaagtggc gagcccgatc ttccccatcg  10860
gtgatgtcgg cgatataggc gccagcaacc gcacctgtgg cgccggtgat gagggcgcgc  10920
caagtcgacg tccggcagtc                                             10940
```

```
SEQ ID NO: 53           moltype = DNA  length = 10934
FEATURE                 Location/Qualifiers
misc_feature            1..10934
                        note = Synthetic polynucleotide
source                  1..10934
                        mol_type = other DNA
                        organism = synthetic construct
SEQUENCE: 53
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gagggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatggaa  900
ttcagcagcc ccagcagaga ggaatgcccc aagcctctga gccgggtgtc aatcatggcc  960
ggatctctga caggactgct gctgcttcag gccgtgtctt gggcttctgg cgctagacct  1020
tgcatcccca agagcttcgg ctacagcagc gtcgtgtgcg tgtgcaatgc cacctactgc  1080
gacagcttcg accctcctac ctttcctgct ctgggcacct tcagcagata cgagagcacc  1140
agatccggca gacggatgga actgagcatg ggacccatcc aggccaatca cacaggcact  1200
ggcctgctgc tgacactgca gcctgagcag aaattccaga aagtgaaagg cttcggcgga  1260
gccatgacag atgccgccgc tctgaatatc ctggctctgt ctccaccagc tcagaacctg  1320
ctgctcaaga gctacttcag cgaggaaggc atcggctaca acatcatcag agtgcccatg  1380
gccagctgcg acttcagcat caggacctac acctacgccg acacacccga cgatttccag  1440
ctgcacaact tcagcctgcc tgaagaggac accaagctga agatccctct gatccacaga  1500
gccctgcagc tggcacaaag acccgtgtca ctgctggcct ctccatggac atctcccacc  1560
tggctgaaaa caaatggcgc cgtgaatggc aagggcagcc tgaaaggcca acctggcgac  1620
atctaccacc agacctgggc cagatacttc gtgaagttcc tggacgccta tgccgagcac  1680
aagctgcagt tttgggccgt gacagccgag aacgaacctt ctgctggact gctgagcggc  1740
tacccctttc agtgcctggg ctttacaccc gagcaccagc gggactttat cgcccgtgat  1800
ctgggaccca cactggccaa tagcacccac cataatgtgc ggctgctgat gctggacgac  1860
cagagactgc ttctgcccca ctgggctaaa gtggtgctga cagatcctga ggccgccaaa  1920
tacgtgcacg gaatcgccgt gcactggtat ctggactttc tggcccctgc caaggccaca  1980
ctgggagaga cacacagact gttccccaac accatgctgt tcgccagcga agcctgtgtg  2040
ggcagcaagt tttgggaaca gagcgtgcgg ctcggcagct gggatagagg catgcagtac  2100
agccacagca tcatcaccaa cctgctgtac cacgtcgtcg gctggaccga ctggaatctg  2160
gccctgaatc ctgaaggcgg ccctaactgg gtccgaaact tcgtggacag ccccatcatc  2220
gtggacatca ccaaggacac cttctacaag cagcccatgt tctaccacct gggacacttc  2280
agcaagttca tccccgaggg ctctcagcgc gttggactgg tggcttccca gaagaacgat  2340
ctggacgccg tggctctgat gcaccctgat ggatctgctg tggtggtggt cctgaaccgc  2400
agcagcaaag atgtgcccct gaccatcaag gatcccgccg tgggattcct ggaaacaatc  2460
agccctggct actccatcca cacctacctg tggcgtagac agtgattgtg gccgaaccgc  2520
cgaactcaga ggccggcccc agaaaacccg agcgagtagg gggcggcgcg caggagggag  2580
gagaactggg ggcgcgggag gctggtgggt gtgggggggtg gagatgtaga agatgtgacg  2640
ccgcggcccg gcgggtgcca gattagcgga cgcggtgccc gcggttgcaa cgggatcccg  2700
ggcgctgcag cttgggaggc ggctctcccc aggcggcgtc cgcggagaca cccatccgtg  2760
aaccccaggt cccgggccgc cggctcgccg cgcaccaggg gccggcggac agaagagcgg  2820
ccgagcggct cgaggctggg ggaccgcggg cgcggccgcg cgctgccggg cgggaggctg  2880
gggggccggg gccggggccg tgccccggag cgggtcggag gccggggccg gggccggggg  2940
acggcggctc cccgcgcggc tccagcggct cggggatccc ggccgggccc cgcagggacc  3000
atgatggaga agggccccgt gcgcgccccc gccgagaagc cccgcggcgc ccgctgcagc  3060
aacggcttcc ccgagcgcga cccccccgc cccggcccca gccgccccgc cgagaagccc  3120
ccccgccccg aggccaagag cgcccagccc gccgacggct ggaagggcga gcgcccccgc  3180
agcgaggagg acaacgagct gaacctgccc aacctggccg ccgcctacag cagcatcctg  3240
agcagcctgg gcgagaaccc ccagcgccag ggcctgctga agacccccctg gcgcgccgcc  3300
agcgccatgc agttcttcac caagggctac caggagacca tcagcgacgt gctgaacgac  3360
gccatcttcg acgaggacca cgacgagatg gtgatcgtga aggacatcga catgttcagc  3420
atgtgcgagc accacctggt gcccttcgtg ggcaaggtgc acatcggcta cctgcccaac  3480
aagcaggtgc tgggcctgag caagctggcc cgcatcgtgg agatctacag ccgccgcctg  3540
caggtgcagg agcgcctgac caagcagatc gccgtggcca tcaccgaggc cctgcgcccc  3600
gccggcgtgg gcgtggtggt ggaggccacc cacatgtgca tggtgatgcg cggcgtgcag  3660
aagatgaaca gcaagaccgt gaccagcacc atgctgggcg tgttccgcga ggaccccaag  3720
acccgcgagg agttcctgac cctgatccgc agctgacaat tgttaattaa gtttaaaccc  3780
tcgaggccgc aagccgcatc gataccgtcg actagagctc gctgatcagc ctcgactgtg  3840
```

```
ccttctagtt gccagccatc tgttgtttgc ccctcccccg tgccttcctt gaccctggaa  3900
ggtgccactc ccactgtcct ttcctaataa aatgaggaaa ttgcatcgca ttgtctgagt  3960
aggtgtcatt ctattctggg gggtggggtg gggcaggaca gcaaggggga ggattgggaa  4020
gacaatagca ggcatgctgg ggagagatcc acgataacaa acagcttttt tggggtgaac  4080
atattgactg aattccctgc aggttggcca ctccctctct gcgcgctcgc tcgctcactg  4140
aggccgcccg ggcaaagccc gggcgtcggg cgacctttgg tcgcccggcc tcagtgagcg  4200
agcgagcgcg cagagaggga gtggccaact ccatcactag gggttcctgc ggccgctcgt  4260
acggtctcga ggaattcctg caggataact tgccaacctc attctaaaat gtatatagaa  4320
gcccaaaaga caataacaaa aatattcttg tagaacaaaa tgggaaagaa tgttccacta  4380
aatatcaaga tttagagcaa agcatgagat gtgtggggat agacagtgag gctgataaaa  4440
tagagtagag ctcagaaaca gacccattga tatatgtaag tgacctatga aaaaaatatg  4500
gcattttaca atgggaaaat gatggtcttt ttcttttta gaaaaacagg gaaatatatt  4560
tatatgtaaa aaataaaagg gaacccatat gtcataccat acacacaaaa aaattccagt  4620
gaattataag tctaaatgga gaaggcaaaa ctttaaatct tttagaaaat aatatagaag  4680
catgcagacc agcctggcca acatgatgaa accctctcta ctaataataa aatcagtaga  4740
actactcagg actactttga gtgggaagtc cttttctatg aagacttctt tggccaaaat  4800
taggctctaa atgcaaggag atagtgcatc atgcctggct gcacttactg ataaatgatg  4860
ttatcaccat ctttaaccaa atgcacagga acaagttatg gtactgatgt gctggattga  4920
gaaggagctc tacttccttg acaggacaca tttgtatcaa cttaaaaaag cagatttttg  4980
ccagcagaac tattcattca gaggtaggaa acttagaata gatgatgtca ctgattagca  5040
tggcttcccc atctccacag ctgcttccca cccaggttgc ccacagttga gtttgtccag  5100
tgctcagggc tgcccactct cagtaagaag ccccacacca gcccctctcc aaatatgttg  5160
gctgttcctt ccattaaagt gaccccactt tagagcagca agtggatttc tgtttcttac  5220
agttcaggaa ggaggagtca gctgtgagaa cctggagcct gagatgcttc taagtcccac  5280
tgctactggg gtcagggaag ccagactcca gcatcagcag tcaggagcac taagcccttg  5340
ccaacatcct gtttctcaga gaaactgctt ccattataat ggttgtcctt ttttaagcta  5400
tcaagccaaa caaccagtgt ctaccattat tctcatcacc tgaagccaag ggttctagca  5460
aaagtcaagc tgtcttgtaa tggttgatgt gcctccagct tctgtcttca gtcactccac  5520
tcttagcctg ctctgaatca actctgacca cagttccctg gagcccctgc cacctgctgc  5580
ccctgccacc ttctccatct gcagtgctgt gcagccttct gcactcttgc agagctaata  5640
ggtggagact tgaaggaaga ggaggaaagt ttctcataat agccttgctg caagctcaaa  5700
tgggaggtgg gcactgtgcc caggagcctt ggagcaaagg ctgtgcccaa cctctgactg  5760
catccaggtt tggtcttgac agagataaga agccctggct tttggagcca aaatctaggt  5820
cagacttagg caggattctc aaagtttatc agcagaacat gaggcagaag accctttctg  5880
ctccagcttc ttcaggctca accttcatca gaatagatag aaagagaggc tgtgagggtt  5940
cttaaaacag aagcaaatct gactcagaga ataaacaacc tcctagtaaa ctacagctta  6000
gacagagcat ctggtggtga gtgtgctcag tgtcctactc aactgtctgg tatcagccct  6060
catgaggact tctcttcttt ccctcataga cctccatctc tgttttcctt agcctgcaga  6120
aatctggatg gctattcaca gaatgcctgt gctttcagag ttgcattttt tctctggtat  6180
tctggttcaa gcatttgaag gtaggaaagg ttctccaagt gcaagaaagc cagccctgag  6240
cctcaactgc ctggctagtg tggtcagtag gatgcaaagg ctgttgaatg ccacaaggcc  6300
aaactttaac ctgtgtacca caagcctagc agcagaggca gctctgctca ctggaactct  6360
ctgtcttctt tctcctgagc cttttctttt cctgagtttt ctagctctcc tcaaccttac  6420
ctctgcccta cccaggacaa acccaagagc cactgtttct gtgatgtcct ctccagccct  6480
aattaggcat catgacttca gcctgacctt ccatgctcag aagcagtgct aatccacttc  6540
agatgagctg ctctatgcaa cacaggcaga gcctacaaac ctttgcacca gagccctcca  6600
catatcagtg tttgttcata ctcacttcaa cagcaaatgt gactgctgag attaagattt  6660
tacacaagat ggtctgtaat ttcacagtta gttttatccc attaggtatg aaagaattag  6720
cataattccc cttaaacatg aatgaatctt agatttttta ataaatagtt ttggaagtaa  6780
agacagagac atcaggagca caaggaatag cctgagagga caaacagaac aagaaagagt  6840
ctggaaatac acaggatgtt cttggcctcc tcaaagcaag tgcaagcaga tagtaccagc  6900
agccccaggc tatcagagcc cagtgaagag aagtaccatg aaagccacag ctctaaccac  6960
cctgttccag agtgacagac agtccccaag acaagccagc ctgagccaga gagagaactg  7020
caagagaaag tttctaattt aggttctgtt agattcagac aagtgcaggt catcctctct  7080
ccacagctac tcacctctcc agcctaacaa agcctgcagt ccacactcca accctggtgt  7140
ctcacctcct agcctctccc aacatcctgc tctctgacca tcttctgcat ctctcatctc  7200
accatctccc actgtctaca gcctactctt gcaactacca tctcatttc tgacatcctg  7260
tctacatctt ctgccatact ctgccatcta ccataccacc tcttaccatc taccacacca  7320
tcttttatct ccatccctct cagaagcctc caagctgaat cctgctttat gtgttcatct  7380
cagcccctgc atggaaagct gaccccagag gcagaactat tcccagagag cttggccaag  7440
aaaaacaaaa ctaccagcct ggccaggctc aggagtagta agctgcagtg tctgttgtgt  7500
tctagcttca acagctgcag gagttccact ctcaaatgct ccacatttct cacatcctcc  7560
tgattctggt cactacccat cttcaaagaa cagaatatct cacatcagca tactgtgaag  7620
gactagtcat gggtgcagct gctcagagct gcaaagtcat tctggatggt ggagagctta  7680
caaacatttc atgatgctcc ccccgctctg atggctggag cccaatccct acacagactc  7740
ctgctgtatg tgttttcctt tcactctgag ccacagccag agggcaggca ttcagtctcc  7800
tcttcaggct ggggctgggg cactgagaac tcacccaaca ccttgctctc actccttctg  7860
caaaacaaga aagagctttg tgctgcagta gccatgaaga atgaaaggaa ggctttaact  7920
aaaaaatgtc agagattatt ttcaacccct tactgtggat caccagcaag gaggaaacac  7980
aacacagaga catttttttcc cctcaaatta tcaaaagaat cactgcattt gttaaagaga  8040
gcaactgaat caggaagcag agttttgaac atatcagaag ttaggaatct gcatcagaga  8100
caaatgcagt catggttgtt tgctgcatac cagccctaat cattagaagc ctcatggact  8160
tcaaacatca ttccctctga caagatgctc tagcctaact ccatgagata aaataaatct  8220
gcctttcaga gccaaagaag agtccaccag cttcttctca gtgtgaacaa gagctccagt  8280
caggttagtc agtccagtgc agtagaggag accagtctgc atcctctaat tttcaaaggc  8340
aagaagattt gtttaccctg gacaccaggc acaagtgagg tcacagagct cttagatatg  8400
cagtcctcat gagtgaggag actaaagcgc atgccatcaa gacttcagtg tagagaaaac  8460
ctccaaaaaa gcctcctcac tacttctgga atagctcaga ggccgaggcg gcctcggcct  8520
ctgcataaat aaaaaaaatt agtcagccat ggggcggaga atgggcggaa ctgggcggag  8580
```

```
ttaggggcgg gatgggcgga gttaggggcg ggactatggt tgctgactaa ttgagatgca  8640
tgctttgcat acttctgcct gctggggagc ctggggactt tccacacctg gttgctgact  8700
aattgagatg catgctttgc atacttctgc ctgctgggga gcctggggac tttccacacc  8760
ctaactgaca cacattccac agctgcatta atgaatcggc caacgcgcgg ggagaggcgg  8820
tttgcgtatt gggcgctctt ccgcttcctc gctcactgac tcgctgcgct cggtcgttcg  8880
gctgcggcga gcggtatcag ctcactcaaa ggcggtaata cggttatcca cagaatcagg  8940
ggataacgca ggaaagaaca tgtgagcaaa aggccagcaa aaggccagga accgtaaaaa  9000
ggccgcgttg ctggcgtttt tccataggct ccgcccccct gacgagcatc acaaaaatcg  9060
acgctcaagt cagaggtggc gaaacccgac aggactataa agataccagg cgtttccccc  9120
tggaagctcc ctcgtgcgct ctcctgttcc gaccctgccg cttaccggat acctgtccgc  9180
ctttctccct tcgggaagcg tggcgctttc tcatagctca cgctgtaggt atctcagttc  9240
ggtgtaggtc gttcgctcca agctgggctg tgtgcacgaa ccccccgttc agcccgaccg  9300
ctgcgcctta tccggtaact atcgtcttga gtccaacccg gtaagacacg acttatcgcc  9360
actggcagca gccactggta acaggattag cagagcgagg tatgtaggcg gtgctacaga  9420
gttcttgaag tggtggccta actacggcta cactagaaga acagtatttg gtatctgcgc  9480
tctgctgaag ccagttacct tcggaaaaag agttggtagc tcttgatccg gcaaacaaac  9540
caccgctggt agcggtggtt tttttgtttg caagcagcag attacgcgca gaaaaaaagg  9600
atctcaagaa gatcctttga tcttttctac ggggtctgac gctcagtgga acgaaaactc  9660
acgttaaggg attttggtca tgagattatc aaaaaggatc ttcacctaga tccttttaaa  9720
ttaaaaatga agttttaaat caatctaaag tatatatgag taaacttggt ctgacagtta  9780
ccaatgctta atcagtgagg cacctatctc agcgatctgt ctatttcgtt catccatagt  9840
tgcctgactc ctgcaaacca cgttgtgtct caaaatctct gatgttacat tgcacaagat  9900
aaaaatatat catcatgaac aataaaactg tctgcttaca taaacagtaa tacaaggggt  9960
gttatgagcc atattcaacg ggaaacgtct tgctcgaggc cgcgattaaa ttccaacatg  10020
gatgctgatt tatatgggta taaatgggct cgcgataatg tcgggcaatc aggtgcgaca  10080
atctatcgat tgtatgggaa gcccgatgcg ccagagttgt ttctgaaaca tggcaaaggt  10140
agcgttgcca atgatgttac agatgagatg gtcagactaa actggctgac ggaatttatg  10200
cctcttccga ccatcaagca ttttatccgt actcctgatg atgcatggtt actcaccact  10260
gcgatccccg ggaaaacagc attccaggta ttagaagaat atcctgattc aggtgaaaat  10320
attgttgatg cgctggcagt gttcctgcgc cggttgcatt cgattcctgt ttgtaattgt  10380
ccttttaaca gcgatcgcgt atttcgtctc gctcaggcgc aatcacgaat gaataacggt  10440
ttggttgatg cgagtgattt tgatgacgag cgtaatggct ggcctgttga acaagtctgg  10500
aaagaaatgc ataagctttt gccattctca ccggattcag tcgtcactca tggtgatttc  10560
tcacttgata accttatttt tgacgagggg aaattaatag gttgtattga tgttggacga  10620
gtcggaatcg cagaccgata ccaggatctt gccatcctat ggaactgcct cggtgagttt  10680
tctccttcat tacagaaacg gctttttcaa aaatatggta ttgataatcc tgatatgaat  10740
aaattgcagt ttcatttgat gctcgatgag tttttctaag ggcggcctgc caccataccc  10800
acgccgaaac aagcgctcat gagcccgaag tggcgagccc gatcttcccc atcggtgatg  10860
tcggcgatat aggcgccagc aaccgcacct gtggcgccgg tgatgagggc gcgccaagtc  10920
gacgtccggc agtc                                                   10934
```

```
SEQ ID NO: 54          moltype = DNA  length = 11138
FEATURE                Location/Qualifiers
misc_feature           1..11138
                       note = Synthetic polynucleotide
source                 1..11138
                       mol_type = other DNA
                       organism = synthetic construct
SEQUENCE: 54
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agtaagtcac  300
tgactgtcta tgcctgggaa agggtgggca ggagatgggg cagtgcagga aaagtggcac  360
tatgaaccct cctggtggcg aggggagggg ggtggtcctc gaacgccttg cagaactggc  420
ctggatacag agtggaccgg ctggccccat ctggaagact tcgagataca ctgttgtctt  480
actgcgctca acagtgtatc tcgaagtctt ccaaatggtg ccagccatcg cagcggggtg  540
caggaaatgg gggcagcccc cctttttggc tatccttcca cgtgttcttt tttgtatctt  600
ttgtgtttcc tagaaaacat ctcagtcacc accgtgatat cacaaggtcc cagggctggg  660
gtcagaaatt ctctcccgag ggaatgaagc cacaggagcc aagagcagga ggaccaaggc  720
cctggcgaag gccgtggcct cgttcaagta aaagatccta gtacagtgca ggtcccaatg  780
tgtactagga tcttttactt gaacggggac gccggcatcc gggctcagga ccccccctctc  840
tgccagaggc accaacacca gagttcacaa atcagtctcc tgccctttgc atgtagcaaa  900
gcagccctag gaatgcatct agacaattgt actaaccttc ttctctttcc tctcctgaca  960
gtccggaaag ccaccatgcc caccacccag cagagccccc aggacgagca ggagaagctg  1020
ctggacgagg ccatccaggc cgtgaaggtg cagagcttcc agatgaagcg ctgcctggac  1080
aagaacaagc tgatggacgc cctgaagcac gccagcaaca tgctgggcga gctgcgcacc  1140
agcatgctga gccccaagag ctactacgag ctgtacatgg ccatcagcga cgagctgcac  1200
tacctggagg tgtacctgac cgacgagttc gccaagggcc gcaaggtggc cgacctgtac  1260
gagctggtgc agtacgccgg caacatcatc ccccgcctgt acctgctgat caccgtgggc  1320
gtggtgtacg tgaagagctt cccccagagc cgcaaggaca tcctgaagga cctggtggag  1380
atgtgccgcg gcgtgcagca ccccctgcgc ggcctgttcc tgcgcaacta cctgctgcag  1440
tgcacccgca acatcctgcc cgacgagggc gagcccaccg acgaggagac caccggcgac  1500
atcagcgaca gcatggactt cgtgctgctg aacttcgccg agatgaacaa gctgtgggtg  1560
cgcatgcagc accagggcca cagccgcgac cgcgagaagc gcgagcgcga gcgccaggag  1620
ctgcgcatcc tggtgggcac caacctggtg cgcctgagcc agctggaggg cgtgaacgtg  1680
gagcgctaca agcagatcgt gctgaccggc atcctggagc aggtggtgaa ctgccgcgac  1740
gccctggccc aggagtacct gatggagtgc atcatccagg tgttccccga cgagttccac  1800
```

```
ctgcagaccc tgaacccctt cctgcgcgcc tgcgccgagc tgcaccagaa cgtgaacgtg  1860
aagaacatca tcatcgccct gatcgaccgc ctggccctgt tcgcccaccg cgaggacggc  1920
cccggcatcc ccgccgacat caagctgttc gacatcttca gccagcaggt ggccaccgtg  1980
atccagagcc gccaggacat gcccagcgag gacgtggtga gcctgcaggt gagcctgatc  2040
aacctggcca tgaagtgcta ccccgaccgc gtggactacg tggacaaggt gctggagacc  2100
accgtggaga tcttcaacaa gctgaacctg gagcacatcg ccaccagcag cgccgtgagc  2160
aaggagctga cccgcctgct gaagatcccc gtggacacct acaacaacat cctgaccgtg  2220
ctgaagctga agcacttcca cccccctgttc gagtacttcg actacgagag ccgcaagagc  2280
atgagctgct acgtgctgag caacgtgctg gactacaaca ccgagatcgt gagccaggac  2340
caggtggaca gcatcatgaa cctggtgagc accctgatcc aggaccagcc cgaccagccc  2400
gtggaggacc ccgaccccga ggacttcgcc gacgagcaga gcctggtggg ccgcttcatc  2460
cacctgctgc gcagcgagga ccccgaccag cagtacctga tcctgaacac cgcccgcaag  2520
cacttcggcg ccggcggcaa ccagcgcatc cgcttcaccc tgcccccccct ggtgttcgcc  2580
gcctaccagc tggccttccg ctacaaggag aacagcaagg tggacgacaa gtgggagaag  2640
aagtgccaga agatcttcag cttcgcccac cagaccatca gcgccctgat caaggccgag  2700
ctggccgagc tgcccctgcg cctgttcctg cagggcgccc tggccgccgg cgagatcggc  2760
ttcgagaacc acgagaccgt ggcctacgag ttcatgagcc aggccttcag cctgtacgag  2820
gacgagatca gcgacagcaa ggcccagctg gccgccatca ccctgatcat cggcaccttc  2880
gagcgcatga agtgcttcag cgaggagaac cacgagcccc tgcgcaccca gtgcgccctg  2940
gccgccagca agctgctgaa gaagcccgac cagggccgcg ccgtgagcac ctgcgcccac  3000
ctgttctgga gcggccgcaa caccgacaag aacggcgagg agctgcacgg cggcaagcgc  3060
gtgatggagt gcctgaagaa ggccctgaag atcgccaacc agtgcatgga ccccagcctg  3120
caggtgcagc tgttcatcga gatcctgaac cgctacatct acttctacga gaaggagaac  3180
gacgccgtga ccatccaggt gctgaaccag ctgatccaga agatccgcga ggacctgccc  3240
aacctggaga gcagcgagga gaccgagcag atcaacaagc acttccacaa caccctggag  3300
cacctgcgcc tgcgccgcga gagccccgag agcgagggcc ccatctacga gggcctgatc  3360
ctgtgacaat tgttaattaa gtttaaaccc tcgaggccgc aagcttatcg ataatcaacc  3420
tctggattac aaaatttgtg aaagattgac tggtattctt aactatgttg ctccttttac  3480
gctatgtgga tacgctgctt taatgccttt gtatcatgct attgcttccc gtatggcttt  3540
cattttctcc tccttgtata aatcctggtt gctgtctctt tatgaggagt tgtggcccgt  3600
tgtcaggcaa cgtggcgtgg tgtgcactgt gtttgctgac gcaaccccca ctggttgggg  3660
cattgccacc acctgtcagc tcctttccgg gactttcgct ttccccctcc ctattgccac  3720
ggcggaactc atcgccgcct gccttgcccg ctgctggaca ggggctcggc tgttgggcac  3780
tgacaattcc gtggtgttgt cggggaaatc atcgtccttt ccttggctgc tcgcctgtgt  3840
tgccacctgg attctgcgcg ggacgtcctt ctgctacgtc ccttcggccc tcaatccagc  3900
ggaccttcct tcccgcggcc tgctgccggc tctgcggcct cttccgcgtc ttcgccttcg  3960
ccctcagacg agtcggatct ccctttgggc cgcctccccg catcgatacc gtcgactaga  4020
gctcgctgat cagcctcgac tgtgccttct agttgccagc catctgttgt ttgcccctcc  4080
cccgtgcctt ccttgaccct ggaaggtgcc actcccactg tcctttccta ataaaatgag  4140
gaaattgcat cgcattgtct gagtaggtgt cattctattc tggggggtgg ggtggggcag  4200
gacagcaagg gggaggattg ggaagacaat agcaggcatg ctggggagag atccacgata  4260
acaaacagct tttttggggt gaacatattg actgaattcc ctgcaggttg gccactccct  4320
ctctgcgcgc tcgctcgctc actgaggccg cccgggcaaa gcccgggcgt cgggcgacct  4380
ttggtcgccc ggcctcagtg agcgagcgag cgcgcagaga gggagtggcc aactccatca  4440
ctaggggttc ctgcggccgc tcgtacggtc tcgaggaatt cctgcaggat aacttgccaa  4500
cctcattcta aaatgtatat agaagcccaa aagacaataa caaaaatatt cttgtagaac  4560
aaaatgggaa agaatgttcc actaaatatc aagatttaga gcaaagcatg agatgtgtgg  4620
ggatagacag tgaggctgat aaaatagagt agagctcaga aacagaccca ttgatatatg  4680
taagtgacct atgaaaaaaa tatggcattt tacaatggga aaatgatggt ctttttcttt  4740
tttagaaaaa cagggaaata tatttatatg taaaaaataa aagggaaccc atatgtcata  4800
ccatacacac aaaaaaattc cagtgaatta taagtctaaa tggagaaggc aaaactttaa  4860
atcttttaga aaataatata gaagcatgca gaccagcctg gccaacatga tgaaaccctc  4920
tctactaata ataaaatcag tagaactact caggactact ttgagtggga agtccttttc  4980
tatgaagact tctttggcca aaattaggct ctaaatgcaa ggagatagtg catcatgcct  5040
ggctgcactt actgataaat gatgttatca ccatctttaa ccaaatgcac aggaacaagt  5100
tatggtactg atgtgctgga ttgagaagga gctctacttc cttgacagga cacatttgta  5160
tcaacttaaa aaagcagatt tttgccagca gaactattca ttcagaggta ggaaacttag  5220
aatagatgat gtcactgatt agcatggctt ccccatctcc acagctgctt cccacccagg  5280
ttgcccacag ttgagtttgt ccagtgctca gggctgccca ctctcagtaa gaagccccac  5340
accagcccct ctccaaatat gttggctgtt ccttccatta aagtgacccc actttagagc  5400
agcaagtgga tttctgtttc ttacagttca ggaaggagga gtcagctgtg agaacctgga  5460
gcctgagatg cttctaagtc ccactgctac tggggtcagg gaagccagac tccagcatca  5520
gcagtcagga gcactaagcc cttgccaaca tcctgtttct cagagaaact gcttccatta  5580
taatggttgt cctttttaa gctatcaagc caaacaacca gtgtctacca ttattctcat  5640
cacctgaagc caagggttct agcaaaagtc aagctgtctt gtaatggttg atgtgcctcc  5700
agcttctgtc ttcagtcact ccactcttag cctgctctga atcaactctg accacagttc  5760
cctggagccc ctgccacctg ctgcccctgc caccttctcc atctgcagtg ctgtgcagcc  5820
ttctgcactc ttgcagagct aataggtgga gacttgaagg aagaggagga aagtttctca  5880
taatagcctt gctgcaagct caaatgggag gtgggcactg tgcccaggag ccttggagca  5940
aaggctgtgc ccaacctctg actgcatcca ggtttggtct tgacagagat aagaagccct  6000
ggcttttgga gccaaaatct aggtcagact taggcaggat tctcaaagtt tatcagcaga  6060
acatgaggca gaagaccctt tctgctccag cttcttcagg ctcaaccttc atcagaatag  6120
atagaaagag aggctgtgag ggttcttaaa acagaagcaa atctgactca gagaataaac  6180
aacctcctag taaactacag cttagacaga gcatctggtg gtgagtgtgc tcagtgtcct  6240
actcaactgt ctggtatcag ccctcatgag gacttctctt ctttccctca tagacctcca  6300
tctctgtttt ccttagcctg cagaaatctg gatggctatt cacagaatgc ctgtgctttc  6360
agagttgcat tttttctctg gtattctggt tcaagcattt gaaggtagga aaggttctcc  6420
aagtgcaaga aagccagccc tgagcctcaa ctgcctggct agtgtggtca gtaggatgca  6480
aaggctgttg aatgccacaa ggccaaactt taacctgtgt accacaagcc tagcagcaga  6540
```

```
ggcagctctg ctcactggaa ctctctgtct tctttctcct gagccttttc ttttcctgag  6600
ttttctagct ctcctcaacc ttacctctgc cctacccagg acaaacccaa gagccactgt  6660
ttctgtgatg tcctctccag ccctaattag gcatcatgac ttcagcctga ccttccatgc  6720
tcagaagcag tgctaatcca cttcagatga gctgctctat gcaacacagg cagagcctac  6780
aaacctttgc accagagccc tccacatatc agtgtttgtt catactcact tcaacagcaa  6840
atgtgactgc tgagattaag attttacaca agatggtctg taatttcaca gttagtttta  6900
tcccattagg tatgaaagaa ttagcataat tccccttaaa catgaatgaa tcttagattt  6960
tttaataaat agttttggaa gtaaagacag agacatcagg agcacaagga atagcctgag  7020
aggacaaaca gaacaagaaa gagtctggaa atacacagga tgttcttggc ctcctcaaag  7080
caagtgcaag cagatagtac cagcagcccc aggctatcag agcccagtga agagaagtac  7140
catgaaagcc acagctctaa ccaccctgtt ccagagtgac agacagtccc caagacaagc  7200
cagcctgagc cagagagaga actgcaagag aaagtttcta atttaggttc tgttagattc  7260
agacaagtgc aggtcatcct ctctccacag ctactcacct ctccagccta acaaagcctg  7320
cagtccacac tccaaccctg gtgtctcacc tcctagcctc tcccaacatc ctgctctctg  7380
accatcttct gcatctctca tctcaccatc tcccactgtc tacagcctac tcttgcaact  7440
accatctcat tttctgacat cctgtctaca tcttctgcca tactctgcca tctaccatac  7500
cacctcttac catctaccac accatctttt atctccatcc ctctcagaag cctccaagct  7560
gaatcctgct ttatgtgttc atctcagccc ctgcatggaa agctgacccc agaggcagaa  7620
ctattcccag agagcttggc caagaaaaac aaaactacca gcctggccag gctcaggagt  7680
agtaagctgc agtgtctgtt gtgttctagc ttcaacagct gcaggagttc cactctcaaa  7740
tgctccacat ttctcacatc ctcctgattc tggtcactac ccatcttcaa agaacagaat  7800
atctcacatc agcatactgt gaaggactag tcatgggtgc agctgctcag agctgcaaag  7860
tcattctgga tggtggagag cttacaaaca tttcatgatg ctccccccgc tctgatggct  7920
ggagcccaat ccctacacag actcctgctg tatgtgtttt cctttcactc tgagccacag  7980
ccagagggca ggcattcagt ctcctcttca ggctggggct ggggcactga gaactcaccc  8040
aacaccttgc tctcactcct tctgcaaaac aagaaagagc tttgtgctgc agtagccatg  8100
aagaatgaaa ggaaggcttt aactaaaaaa tgtcagagat tattttcaac cccttactgt  8160
ggatcaccag caaggaggaa acacaacaca gagacatttt ttcccctcaa attatcaaaa  8220
gaatcactgc atttgttaaa gagagcaact gaatcaggaa gcagagtttt gaacatatca  8280
gaagttagga atctgcatca gagacaaatg cagtcatggt tgtttgctgc ataccagccc  8340
taatcattag aagcctcatg gacttcaaac atcattccct ctgacaagat gctctagcct  8400
aactccatga gataaaataa atctgccttt cagagccaaa gaagagtcca ccagcttctt  8460
ctcagtgtga acaagagctc cagtcaggtt agtcagtcca gtgcagtaga ggagaccagt  8520
ctgcatcctc taattttcaa aggcaagaag atttgtttac cctggacacc aggcacaagt  8580
gaggtcacag agctcttaga tatgcagtcc tcatgagtga ggagactaaa gcgcatgcca  8640
tcaagacttc agtgtagaga aaacctccaa aaaagcctcc tcactacttc tggaatagct  8700
cagaggccga ggcggcctcg gcctctgcat aaataaaaaa aattagtcag ccatggggcg  8760
gagaatgggc ggaactgggc ggagttaggg gcgggatggg cggagttagg ggcgggacta  8820
tggttgctga ctaattgaga tgcatgcttt gcatacttct gcctgctggg gagcctgggg  8880
actttccaca cctggttgct gactaattga gatgcatgct ttgcatactt ctgcctgctg  8940
gggagcctgg ggactttcca caccctaact gacacacatt ccacagctgc attaatgaat  9000
cggccaacgc gcggggagag gcggtttgcg tattgggcgc tcttccgctt cctcgctcac  9060
tgactcgctg cgctcggtcg ttcggctgcg gcgagcggta tcagctcact caaaggcggt  9120
aatacggtta tccacagaat caggggataa cgcaggaaag aacatgtgag caaaaggcca  9180
gcaaaaggcc aggaaccgta aaaaggccgc gttgctggcg tttttccata ggctccgccc  9240
ccctgacgag catcacaaaa atcgacgctc aagtcagagg tggcgaaacc cgacaggact  9300
ataaagatac caggcgtttc cccctggaag ctccctcgtg cgctctcctg ttccgaccct  9360
gccgcttacc ggatacctgt ccgcctttct cccttcggga agcgtggcgc tttctcatag  9420
ctcacgctgt aggtatctca gttcggtgta ggtcgttcgc tccaagctgg gctgtgtgca  9480
cgaacccccc gttcagcccg accgctgcgc cttatccggt aactatcgtc ttgagtccaa  9540
cccggtaaga cacgacttat cgccactggc agcagccact ggtaacagga ttagcagagc  9600
gaggtatgta ggcggtgcta cagagttctt gaagtggtgg cctaactacg gctacactag  9660
aagaacagta tttggtatct gcgctctgct gaagccagtt accttcggaa aaagagttgg  9720
tagctcttga tccggcaaac aaaccaccgc tggtagcggt ggtttttttg tttgcaagca  9780
gcagattacg cgcagaaaaa aaggatctca agaagatcct ttgatctttt ctacggggtc  9840
tgacgctcag tggaacgaaa actcacgtta agggattttg gtcatgagat tatcaaaaag  9900
gatcttcacc tagatccttt taaattaaaa atgaagtttt aaatcaatct aaagtatata  9960
tgagtaaact tggtctgaca gttaccaatg cttaatcagt gaggcaccta tctcagcgat  10020
ctgtctattt cgttcatcca tagttgcctg actcctgcaa accacgttgt gtctcaaaat  10080
ctctgatgtt acattgcaca agataaaaat atatcatcat gaacaataaa actgtctgct  10140
tacataaaca gtaatacaag gggtgttatg agccatattc aacgggaaac gtcttgctcg  10200
aggccgcgat taaattccaa catggatgct gatttatatg ggtataaatg ggctcgcgat  10260
aatgtcgggc aatcaggtgc gacaatctat cgattgtatg ggaagcccga tgcgccagag  10320
ttgtttctga aacatggcaa aggtagcgtt gccaatgatg ttacagatga gatggtcaga  10380
ctaaactggc tgacggaatt tatgcctctt ccgaccatca agcattttat ccgtactcct  10440
gatgatgcat ggttactcac cactgcgatc cccgggaaaa cagcattcca ggtattagaa  10500
gaatatcctg attcaggtga aaatattgtt gatgcgctgg cagtgttcct gcgccggttg  10560
cattcgattc ctgtttgtaa ttgtcctttt aacagcgatc gcgtatttcg tctcgctcag  10620
gcgcaatcac gaatgaataa cggtttggtt gatgcgagtg attttgatga cgagcgtaat  10680
ggctggcctg ttgaacaagt ctggaaagaa atgcataagc ttttgccatt ctcaccggat  10740
tcagtcgtca ctcatggtga tttctcactt gataacctta tttttgacga ggggaaatta  10800
ataggttgta ttgatgttgg acgagtcgga atcgcagacc gataccagga tcttgccatc  10860
ctatggaact gcctcggtga gttttctcct tcattacaga aacggctttt tcaaaaatat  10920
ggtattgata atcctgatat gaataaattg cagtttcatt tgatgctcga tgagtttttc  10980
taagggcggc ctgccaccat acccacgccg aaacaagcgc tcatgagccc gaagtggcga  11040
gcccgatctt ccccatcggt gatgtcggcg atataggcgc cagcaaccgc acctgtggcg  11100
ccggtgatga gggcgcgcca agtcgacgtc cggcagtc                         11138
```

SEQ ID NO: 55 moltype = AA length = 242

```
FEATURE                 Location/Qualifiers
REGION                  1..242
                        note = Synthetic polypeptide
source                  1..242
                        mol_type = protein
                        organism = synthetic construct
SEQUENCE: 55
MPRGFTWLRY LGIFLGVALG NEPLEMWPLT QNEECTVTGF LRDKLQYRSR LQYMKHYFPI  60
NYKISVPYEG VFRIANVTRL QRAQVSEREL RYLWVLVSLS ATESVQDVLL EGHPSWKYLQ  120
EVETLLLNVQ QGLTDVEVSP KVESVLSLLN APGPNLKLVR PKALLDNCFR VMELLYCSCC  180
KQSSVLNWQD CEVPSPQSCS PEPSLQYAAT QLYPPPPWSP SSPPHSTGSV RPVRAQGEGL  240
LP                                                                242

SEQ ID NO: 56           moltype = DNA  length = 729
FEATURE                 Location/Qualifiers
misc_feature            1..729
                        note = Synthetic polynucleotide
source                  1..729
                        mol_type = other DNA
                        organism = synthetic construct
SEQUENCE: 56
atgccccgcg gcttcacctg gctgcgctac ctgggcatct tcctgggcgt ggccctgggc  60
aacgagcccc tggagatgtg gcccctgacc cagaacgagg agtgcaccgt gaccggcttc  120
ctgcgcgaca agctgcagta ccgcagccgc ctgcagtaca tgaagcacta cttccccatc  180
aactacaaga tcagcgtgcc ctacgagggc gtgttccgca tcgccaacgt gacccgcctg  240
cagcgcgccc aggtgagcga gcgcgagctg cgctacctgt gggtgctggt gagcctgagc  300
gccaccgaga gcgtgcagga cgtgctgctg gagggccacc ccagctggaa gtacctgcag  360
gaggtggaga ccctgctgct gaacgtgcag cagggcctga ccgacgtgga ggtgagcccc  420
aaggtggaga gcgtgctgag cctgctgaac gcccccggcc ccaacctgaa gctggtgcgc  480
cccaaggccc tgctggacaa ctgcttccgc gtgatggagc tgctgtactg cagctgctgc  540
aagcagagca gcgtgctgaa ctggcaggac tgcgaggtgc ccagccccca gagctgcagc  600
cccgagccca gcctgcagta cgccgccacc cagctgtacc cccccccccc ctggagcccc  660
agcagccccc cccacagcac cggcagcgtg cgccccgtgc gcgcccaggg cgagggcctg  720
ctgccctaa                                                         729

SEQ ID NO: 57           moltype = AA  length = 230
FEATURE                 Location/Qualifiers
REGION                  1..230
                        note = Synthetic polypeptide
source                  1..230
                        mol_type = protein
                        organism = synthetic construct
SEQUENCE: 57
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RSLLEGEIPF PPTSILLLLA  180
CIFLIKILAA SALWAAAWHG QKPGTHPPSE LDCGHDPGYQ LQTLPGLRDT            230

SEQ ID NO: 58           moltype = DNA  length = 690
FEATURE                 Location/Qualifiers
misc_feature            1..690
                        note = Synthetic polynucleotide
source                  1..690
                        mol_type = other DNA
                        organism = synthetic construct
SEQUENCE: 58
atggagcccc tgcgcctgct gatcctgctg ttcgtgaccg agctgagcgg cgcccacaac  60
accaccgtgt tccagggcgt ggccggccag agcctgcagg tgagctgccc ctacgacagc  120
atgaagcact ggggccgccg caaggcctgg tgccgccagc tgggcgagaa gggcccctgc  180
cagcgcgtgg tgagcaccca caacctgtgg ctgctgagct tcctgcgccg ctggaacggc  240
agcaccgcca tcaccgacga caccctgggc ggcaccctga ccatcaccct gcgcaacctg  300
cagccccacg acgccggcct gtaccagtgc cagagcctgc acggcagcga ggccgacacc  360
ctgcgcaagg tgctggtgga ggtgctggcc gacccccctgg accaccgcga cgccggcgac  420
ctgtggttcc ccggcgagag cgagagcttc gaggacgccc acgtggagca cagcatcagc  480
cgcagcctgc tggagggcga gatccccttc ccccccacca gcatcctgct gctgctggcc  540
tgcatcttcc tgatcaagat cctggccgcc agcgccctgt gggccgccgc ctggcacggc  600
cagaagcccg gcacccaccc ccccagcgag ctggactgcg gccacgaccc cggctaccag  660
ctgcagaccc tgcccggcct gcgcgacacc                                  690

SEQ ID NO: 59           moltype = DNA  length = 11060
FEATURE                 Location/Qualifiers
misc_feature            1..11060
                        note = Synthetic polynucleotide
source                  1..11060
                        mol_type = other DNA
                        organism = synthetic construct
SEQUENCE: 59
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
```

```
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gagggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatggaa  900
ttcagcagcc ccagcagaga ggaatgcccc aagcctctga gccgggtgtc aatcatggcc  960
ggatctctga caggactgct gctgcttcag gccgtgtctt gggcttctgg cgctagacct  1020
tgcatcccca agagcttcgg ctacagcagc gtcgtgtgcg tgtgcaatgc cacctactgc  1080
gacagcttcg accctcctac ctttcctgct ctgggcacct tcagcagata cgagagcacc  1140
agatccggca gacggatgga actgagcatg ggacccatcc aggccaatca cacaggcact  1200
ggcctgctgc tgacactgca gcctgagcag aaattccaga aagtgaaagg cttcggcgga  1260
gccatgacag atgccgccgc tctgaatatc ctggctctgt ctccaccagc tcagaacctg  1320
ctgctcaaga gctacttcag cgaggaaggc atcggctaca acatcatcag agtgcccatg  1380
gccagctgcg acttcagcat caggacctac acctacgccg acacacccga cgatttccag  1440
ctgcacaact tcagcctgcc tgaagaggac accaagctga agatccctct gatccacaga  1500
gccctgcagc tggcacaaag acccgtgtca ctgctggcct ctccatggac atctcccacc  1560
tggctgaaaa caaatggcgc cgtgaatggc aagggcagcc tgaaaggcca acctggcgac  1620
atctaccacc agacctgggc cagatacttc gtgaagttcc tggacgccta tgccgagcac  1680
aagctgcagt tttgggccgt gacagccgag aacgaacctt ctgctggact gctgagcggc  1740
taccccttc agtgcctggg ctttacaccc gagcaccagc gggactttat cgcccgtgat  1800
ctgggaccca cactggccaa tagcacccac cataatgtgc ggctgctgat gctggacgac  1860
cagagactgc ttctgcccca ctgggctaaa gtggtgctga cagatcctga ggccgccaaa  1920
tacgtgcacg gaatcgccgt gcactggtat ctggactttc tggcccctgc caaggccaca  1980
ctgggagaga cacacagact gttccccaac accatgctgt tcgccagcga agcctgtgtg  2040
ggcagcaagt tttgggaaca gagcgtgcgg ctcggcagct gggatagagg catgcagtac  2100
agccacagca tcatcaccaa cctgctgtac cacgtcgtcg gctggaccga ctggaatctg  2160
gccctgaatc ctgaaggcgg ccctaactgg gtccgaaact tcgtggacag ccccatcatc  2220
gtggacatca ccaaggacac cttctacaag cagcccatgt tctaccacct gggacacttc  2280
agcaagttca tccccgaggg ctctcagcgc gttggactgg tggcttccca gaagaacgat  2340
ctggacgccg tggctctgat gcaccctgat ggatctgctg tggtggtggt cctgaaccgc  2400
agcagcaaag atgtgcccct gaccatcaag gatcccgccg tgggattcct ggaaacaatc  2460
agccctggct actccatcca cacctacctg tggcgtagac aggagggcag aggaagtctt  2520
ctgacatgcg gagacgtgga agagaatccc ggccctatgc cccgcggctt cacctggctg  2580
cgctacctgg gcatcttcct gggcgtggcc ctgggcaacg agcccctgga gatgtggccc  2640
ctgacccaga acgaggagtg caccgtgacc ggcttcctgc gcgacaagct gcagtaccgc  2700
agccgcctgc agtacatgaa gcactacttc cccatcaact acaagatcag cgtgccctac  2760
gagggcgtgt tccgcatcgc caacgtgacc cgcctgcagc gcgcccaggt gagcgagcgc  2820
gagctgcgct acctgtgggt gctggtgagc ctgagcgcca ccgagagcgt gcaggacgtg  2880
ctgctggagg gccaccccag ctggaagtac ctgcaggagg tggagaccct gctgctgaac  2940
gtgcagcagg gcctgaccga cgtggaggtg agccccaagg tggagagcgt gctgagcctg  3000
ctgaacgccc ccggccccaa cctgaagctg gtgcgcccca aggccctgct ggacaactgc  3060
ttccgcgtga tggagctgct gtactgcagc tgctgcaagc agagcagcgt gctgaactgg  3120
caggactgcg aggtgcccag cccccagagc tgcagccccg agcccagcct gcagtacgcc  3180
gccacccagc tgtacccccc cccccctgg agccccagca gcccccccca cagcaccggc  3240
agcgtgcgcc ccgtgcgcgc ccagggcgag ggcctgctgc cctaatgaca attgttaatt  3300
aagtttaaac cctcgaggcc gcaagcttat cgataatcaa cctctggatt acaaaatttg  3360
tgaaagattg actggtattc ttaactatgt tgctcctttt acgctatgtg gatacgctgc  3420
tttaatgcct ttgtatcatg ctattgcttc ccgtatggct ttcattttct cctccttgta  3480
taaatcctgg ttgctgtctc tttatgagga gttgtggccc gttgtcaggc aacgtggcgt  3540
ggtgtgcact gtgtttgctg acgcaacccc cactggttgg ggcattgcca ccacctgtca  3600
gctcctttcc gggactttcg ctttccccct ccctattgcc acggcggaac tcatcgccgc  3660
ctgccttgcc cgctgctgga caggggctcg gctgttgggc actgacaatt ccgtggtgtt  3720
gtcggggaaa tcatcgtcct ttccttggct gctcgcctgt gttgccacct ggattctgcg  3780
cgggacgtcc ttctgctacg tcccttcggc cctcaatcca gcggaccttc cttcccgcgg  3840
cctgctgccg gctctgcggc ctcttccgcg tcttcgcctt cgccctcaga cgagtcggat  3900
ctccctttgg gccgcctccc cgcatcgata ccgtcgacta gagctcgctg atcagcctcg  3960
actgtgcctt ctagttgcca gccatctgtt gtttgcccct cccccgtgcc ttccttgacc  4020
ctggaaggtg ccactcccac tgtcctttcc taataaaatg aggaaattgc atcgcattgt  4080
ctgagtaggt gtcattctat tctggggggt ggggtggggc aggacagcaa gggggaggat  4140
tgggaagaca atagcaggca tgctggggag agatccacga taacaaacag cttttttggg  4200
gtgaacatat tgactgaatt ccctgcaggt tggccactcc ctctctgcgc gctcgctcgc  4260
tcactgaggc cgcccgggca aagcccgggc gtcgggcgac ctttggtcgc ccggcctcag  4320
tgagcgagcg agcgcgcaga gagggagtgg ccaactccat cactaggggt tcctgcggcc  4380
gctcgtacgg tctcgaggaa ttcctgcagg ataacttgcc aacctcattc taaaatgtat  4440
atagaagccc aaaagacaat aacaaaaata ttcttgtaga acaaaatggg aaagaatgtt  4500
ccactaaata tcaagattta gagcaaagca tgagatgtgt ggggatagac agtgaggctg  4560
ataaaataga gtagagctca gaaacagacc cattgatata tgtaagtgac ctatgaaaaa  4620
aatatggcat tttacaatgg gaaaatgatg gtctttttct tttttagaaa aacagggaaa  4680
tatatttata tgtaaaaaat aaaagggaac ccatatgtca taccatacac acaaaaaaat  4740
tccagtgaat tataagtcta aatggagaag gcaaaacttt aaatctttta gaaaataata  4800
tagaagcatg cagaccagcc tggccaacat gatgaaaccc tctctactaa taataaaatc  4860
```

```
agtagaacta ctcaggacta ctttgagtgg gaagtccttt tctatgaaga cttctttggc  4920
caaaattagg ctctaaatgc aaggagatag tgcatcatgc ctggctgcac ttactgataa  4980
atgatgttat caccatcttt aaccaaatgc acaggaacaa gttatggtac tgatgtgctg  5040
gattgagaag gagctctact tccttgacag gacacatttg tatcaactta aaaaagcaga  5100
tttttgccag cagaactatt cattcagagg taggaaactt agaatagatg atgtcactga  5160
ttagcatggc ttccccatct ccacagctgc ttcccaccca ggttgcccac agttgagttt  5220
gtccagtgct cagggctgcc cactctcagt aagaagcccc acaccagccc ctctccaaat  5280
atgttggctg ttccttccat taaagtgacc ccactttaga gcagcaagtg gatttctgtt  5340
tcttacagtt caggaaggag gagtcagctg tgagaacctg gagcctgaga tgcttctaag  5400
tcccactgct actggggtca gggaagccag actccagcat cagcagtcag gagcactaag  5460
cccttgccaa catcctgttt ctcagagaaa ctgcttccat tataatggtt gtcctttttt  5520
aagctatcaa gccaaacaac cagtgtctac cattattctc atcacctgaa gccaagggtt  5580
ctagcaaaag tcaagctgtc ttgtaatggt tgatgtgcct ccagcttctg tcttcagtca  5640
ctccactctt agcctgctct gaatcaactc tgaccacagt tccctggagc ccctgccacc  5700
tgctgcccct gccaccttct ccatctgcag tgctgtgcag ccttctgcac tcttgcagag  5760
ctaataggtg gagacttgaa ggaagaggag gaaagtttct cataatagcc ttgctgcaag  5820
ctcaaatggg aggtgggcac tgtgcccagg agccttggag caaaggctgt gcccaacctc  5880
tgactgcatc caggtttggt cttgacagag ataagaagcc ctggcttttg gagccaaaat  5940
ctaggtcaga cttaggcagg attctcaaag tttatcagca gaacatgagg cagaagaccc  6000
tttctgctcc agcttcttca ggctcaacct tcatcagaat agatagaaag agaggctgtg  6060
agggttctta aaacagaagc aaatctgact cagagaataa acaacctcct agtaaactac  6120
agcttagaca gagcatctgg tggtgagtgt gctcagtgtc ctactcaact gtctggtatc  6180
agccctcatg aggacttctc ttctttccct catagacctc catctctgtt ttccttagcc  6240
tgcagaaatc tggatggcta ttcacagaat gcctgtgctt tcagagttgc atttttcctc  6300
tggtattctg gttcaagcat ttgaaggtag gaaaggttct ccaagtgcaa gaaagccagc  6360
cctgagcctc aactgcctgg ctagtgtggt cagtaggatg caaaggctgt tgaatgccac  6420
aaggccaaac tttaacctgt gtaccacaag cctagcagca gaggcagctc tgctcactgg  6480
aactctctgt cttctttctc ctgagccttt tcttttcctg agttttctag ctctcctcaa  6540
ccttacctct gccctaccca ggacaaaccc aagagccact gtttctgtga tgtcctctcc  6600
agccctaatt aggcatcatg acttcagcct gaccttccat gctcagaagc agtgctaatc  6660
cacttcagat gagctgctct atgcaacaca ggcagagcct acaaaccttt gcaccagagc  6720
cctccacata tcagtgtttg ttcatactca cttcaacagc aaatgtgact gctgagatta  6780
agattttaca caagatggtc tgtaatttca cagttagttt tatcccatta ggtatgaaag  6840
aattagcata attcccctta aacatgaatg aatcttagat tttttaataa atagttttgg  6900
aagtaaagac agagacatca ggagcacaag gaatagcctg agaggacaaa cagaacaaga  6960
aagagtctgg aaatacacag gatgttcttg gcctcctcaa agcaagtgca agcagatagt  7020
accagcagcc ccaggctatc agagcccagt gaagagaagt accatgaaag ccacagctct  7080
aaccaccctg ttccagagtg acagacagtc cccaagacaa gccagcctga gccagagaga  7140
gaactgcaag agaaagtttc taatttaggt tctgttagat tcagacaagt gcaggtcatc  7200
ctctctccac agctactcac ctctccagcc taacaaagcc tgcagtccac actccaaccc  7260
tggtgtctca cctcctagcc tctcccaaca tcctgctctc tgaccatctt ctgcatctct  7320
catctcacca tctcccactg tctacagcct actcttgcaa ctaccatctc attttctgac  7380
atcctgtcta catcttctgc catactctgc catctaccat accacctctt accatctacc  7440
acaccatctt ttatctccat ccctctcaga agcctccaag ctgaatcctg ctttatgtgt  7500
tcatctcagc ccctgcatgg aaagctgacc ccagaggcag aactattccc agagagcttg  7560
gccaagaaaa acaaaactac cagcctggcc aggctcagga gtagtaagct gcagtgtctg  7620
ttgtgttcta gcttcaacag ctgcaggagt tccactctca aatgctccac atttctcaca  7680
tcctcctgat tctggtcact acccatcttc aaagaacaga atatctcaca tcagcatact  7740
gtgaaggact agtcatgggt gcagctgctc agagctgcaa agtcattctg gatggtggag  7800
agcttacaaa catttcatga tgctcccccc gctctgatgg ctggagccca atccctacac  7860
agactcctgc tgtatgtgtt ttcctttcac tctgagccac agccagaggg caggcattca  7920
gtctcctctt caggctgggg ctggggcact gagaactcac ccaacacctt gctctcactc  7980
cttctgcaaa acaagaaaga gctttgtgct gcagtagcca tgaagaatga aaggaaggct  8040
ttaactaaaa aatgtcagag attattttca accccttact gtggatcacc agcaaggagg  8100
aaacacaaca cagagacatt ttttccccctc aaattatcaa aagaatcact gcatttgtta  8160
aagagagcaa ctgaatcagg aagcagagtt ttgaacatat cagaagttag gaatctgcat  8220
cagagacaaa tgcagtcatg gttgtttgct gcataccagc cctaatcatt agaagcctca  8280
tggacttcaa acatcattcc ctctgacaag atgctctagc ctaactccat gagataaaat  8340
aaatctgcct ttcagagcca aagaagagtc caccagcttc ttctcagtgt gaacaagagc  8400
tccagtcagg ttagtcagtc cagtgcagta gaggagacca gtctgcatcc tctaattttc  8460
aaaggcaaga agatttgttt accctggaca ccaggcacaa gtgaggtcac agagctctta  8520
gatatgcagt cctcatgagt gaggagacta aagcgcatgc catcaagact tcagtgtaga  8580
gaaaacctcc aaaaaagcct cctcactact tctggaatag ctcagaggcc gaggcggcct  8640
cggcctctgc ataaataaaa aaaattagtc agccatgggg cggagaatgg gcggaactgg  8700
gcggagttag gggcgggatg ggcggagtta ggggcgggac tatggttgct gactaattga  8760
gatgcatgct ttgcatactt ctgcctgctg gggagcctgg ggactttcca cacctggttg  8820
ctgactaatt gagatgcatg ctttgcatac ttctgcctgc tggggagcct ggggactttc  8880
cacaccctaa ctgacacaca ttccacagct gcattaatga atcggccaac gcgcggggag  8940
aggcggtttg cgtattgggc gctcttccgc ttcctcgctc actgactcgc tgcgctcggt  9000
cgttcggctg cggcgagcgg tatcagctca ctcaaaggcg gtaatacggt tatccacaga  9060
atcaggggat aacgcaggaa agaacatgtg agcaaaaggc cagcaaaagg ccaggaaccg  9120
taaaaaggcc gcgttgctgg cgtttttcca taggctccgc ccccctgacg agcatcacaa  9180
aaatcgacgc tcaagtcaga ggtggcgaaa cccgacagga ctataaagat accaggcgtt  9240
tccccctgga agctccctcg tgcgctctcc tgttccgacc ctgccgctta ccggatacct  9300
gtccgccttt ctcccttcgg gaagcgtggc gctttctcat agctcacgct gtaggtatct  9360
cagttcggtg taggtcgttc gctccaagct gggctgtgtg cacgaacccc ccgttcagcc  9420
cgaccgctgc gccttatccg gtaactatcg tcttgagtcc aacccggtaa gacacgactt  9480
atcgccactg gcagcagcca ctggtaacag gattagcaga gcgaggtatg taggcggtgc  9540
tacagagttc ttgaagtggt ggcctaacta cggctacact agaagaacag tatttggtat  9600
```

```
ctgcgctctg ctgaagccag ttaccttcgg aaaaagagtt ggtagctctt gatccggcaa  9660
acaaaccacc gctggtagcg gtggtttttt tgtttgcaag cagcagatta cgcgcagaaa  9720
aaaaggatct caagaagatc ctttgatctt ttctacgggg tctgacgctc agtggaacga  9780
aaactcacgt taagggattt tggtcatgag attatcaaaa aggatcttca cctagatcct  9840
tttaaattaa aaatgaagtt ttaaatcaat ctaaagtata tatgagtaaa cttggtctga  9900
cagttaccaa tgcttaatca gtgaggcacc tatctcagcg atctgtctat ttcgttcatc  9960
catagttgcc tgactcctgc aaaccacgtt gtgtctcaaa atctctgatg ttacattgca  10020
caagataaaa atatatcatc atgaacaata aaactgtctg cttacataaa cagtaataca  10080
aggggtgtta tgagccatat tcaacgggaa acgtcttgct cgaggccgcg attaaattcc  10140
aacatggatg ctgatttata tgggtataaa tgggctcgcg ataatgtcgg gcaatcaggt  10200
gcgacaatct atcgattgta tgggaagccc gatgcgccag agttgtttct gaaacatggc  10260
aaaggtagcg ttgccaatga tgttacagat gagatggtca gactaaactg gctgacggaa  10320
tttatgcctc ttccgaccat caagcatttt atccgtactc ctgatgatgc atggttactc  10380
accactgcga tccccgggaa aacagcattc caggtattag aagaatatcc tgattcaggt  10440
gaaaatattg ttgatgcgct ggcagtgttc ctgcgccggt tgcattcgat tcctgtttgt  10500
aattgtcctt ttaacagcga tcgcgtattt cgtctcgctc aggcgcaatc acgaatgaat  10560
aacggtttgg ttgatgcgag tgattttgat gacgagcgta atggctggcc tgttgaacaa  10620
gtctggaaag aaatgcataa gcttttgcca ttctcaccgg attcagtcgt cactcatggt  10680
gatttctcac ttgataacct tatttttgac gaggggaaat taataggttg tattgatgtt  10740
ggacgagtcg gaatcgcaga ccgataccag gatcttgcca tcctatggaa ctgcctcggt  10800
gagttttctc cttcattaca gaaacggctt tttcaaaaat atggtattga taatcctgat  10860
atgaataaat tgcagtttca tttgatgctc gatgagtttt tctaagggcg gcctgccacc  10920
atacccacgc cgaaacaagc gctcatgagc ccgaagtggc gagcccgatc ttccccatcg  10980
gtgatgtcgg cgatataggc gccagcaacc gcacctgtgg cgccggtgat gagggcgcgc  11040
caagtcgacg tccggcagtc                                              11060
```

```
SEQ ID NO: 60          moltype = DNA  length = 10913
FEATURE                Location/Qualifiers
misc_feature           1..10913
                       note = Synthetic polynucleotide
source                 1..10913
                       mol_type = other DNA
                       organism = synthetic construct
SEQUENCE: 60
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agccccccctt tttggctatc cttccacgtg ttctttttg  780
tatcttttgt gtttcctaga aaacatctca gtcaccaccg cagccctagg aatgcatcta  840
gacaattgta ctaaccttct tctctttcct ctcctgacag tccggaaagc caccatggaa  900
ttcagcagcc ccagcagaga ggaatgcccc aagcctctga gccgggtgtc aatcatggcc  960
ggatctctga caggactgct gctgcttcag gccgtgtctt gggcttctgg cgctagacct  1020
tgcatcccca agagcttcgg ctacagcagc gtcgtgtgcg tgtgcaatgc cacctactgc  1080
gacagcttcg accctcctac ctttcctgct ctgggcacct tcagcagata cgagagcacc  1140
agatccggca gacggatgga actgagcatg ggacccatcc aggccaatca cacaggcact  1200
ggcctgctgc tgacactgca gcctgagcag aaattccaga aagtgaaagg cttcggcgga  1260
gccatgacag atgccgccgc tctgaatatc ctggctctgt ctccaccagc tcagaacctg  1320
ctgctcaaga gctacttcag cgaggaaggc atcggctaca acatcatcag agtgcccatg  1380
gccagctgcg acttcagcat caggacctac acctacgccg acacacccga cgatttccag  1440
ctgcacaact tcagcctgcc tgaagaggac accaagctga agatccctct gatccacaga  1500
gccctgcagc tggcacaaag acccgtgtca ctgctggcct ctccatggac atctcccacc  1560
tggctgaaaa caaatggcgc cgtgaatggc aagggcagcc tgaaaggcca acctggcgac  1620
atctaccacc agacctgggc cagatacttc gtgaagttcc tggacgccta tgccgagcac  1680
aagctgcagt tttgggccgt gacagccgag aacgaacctt ctgctggact gctgagcggc  1740
taccccttc agtgcctggg ctttacaccc gagcaccagc gggactttat cgcccgtgat  1800
ctgggaccca cactggccaa tagcacccac cataatgtgc ggctgctgat gctggacgac  1860
cagagactgc ttctgcccca ctgggctaaa gtggtgctga cagatcctga ggccgccaaa  1920
tacgtgcacg gaatcgccgt gcactggtat ctggactttc tggcccctgc caaggccaca  1980
ctgggagaga cacacagact gttccccaac accatgctgt tcgccagcga agcctgtgtg  2040
ggcagcaagt tttgggaaca gagcgtgcgg ctcggcagct gggatagagg catgcagtac  2100
agccacagca tcatcaccaa cctgctgtac cacgtcgtcg gctggaccga ctggaatctg  2160
gccctgaatc ctgaaggcgg ccctaactgg gtccgaaact tcgtggacag ccccatcatc  2220
gtggacatca ccaaggacac cttctacaag cagcccatgt tctaccacct gggacacttc  2280
agcaagttca tccccgaggg ctctcagcgc gttggactgg tggcttccca gaagaacgat  2340
ctggacgccg tggctctgat gcaccctgat ggatctgctg tggtggtggt cctgaaccgc  2400
agcagcaaag atgtgcccct gaccatcaag gatcccgccg tgggattcct ggaaacaatc  2460
agccctggct actccatcca cacctacctg tggcgtagac agtgattgtg gccgaaccgc  2520
cgaactcaga ggccggcccc agaaaacccg agcgagtagg gggcggcgcg caggagggag  2580
gagaactggg ggcgcgggag gctggtgggt gtggggggtg gagatgtaga agatgtgacg  2640
ccgcggcccg gcgggtgcca gattagcgga cgcggtgccc gcggttgcaa cgggatcccg  2700
```

```
ggcgctgcag cttgggaggc ggctctcccc aggcggcgtc cgcggagaca cccatccgtg  2760
aaccccaggt cccgggccgc cggctcgccg cgcaccaggg gccggcggac agaagagcgg  2820
ccgagcggct cgaggctggg ggaccgcggg cgcggccgcg cgctgccggg cgggaggctg  2880
gggggccggg gccggggccg tgccccggag cgggtcggag gccggggccg gggccggggg  2940
acggcggctc cccgcgcggc tccagcggct cggggatccc ggccgggccc cgcagggacc  3000
atgatgcccc gcggcttcac ctggctgcgc tacctgggca tcttcctggg cgtggccctg  3060
ggcaacgagc ccctggagat gtggcccctg acccagaacg aggagtgcac cgtgaccggc  3120
ttcctgcgcg acaagctgca gtaccgcagc cgcctgcagt acatgaagca ctacttcccc  3180
atcaactaca agatcagcgt gccctacgag ggcgtgttcc gcatcgccaa cgtgacccgc  3240
ctgcagcgcg cccaggtgag cgagcgcgag ctgcgctacc tgtgggtgct ggtgagcctg  3300
agcgccaccg agagcgtgca ggacgtgctg ctggagggcc accccagctg gaagtacctg  3360
caggaggtgg agaccctgct gctgaacgtg cagcagggcc tgaccgacgt ggaggtgagc  3420
cccaaggtgg agagcgtgct gagcctgctg aacgcccccg gccccaacct gaagctggtg  3480
cgccccaagg ccctgctgga caactgcttc cgcgtgatgg agctgctgta ctgcagctgc  3540
tgcaagcaga gcagcgtgct gaactggcag gactgcgagg tgcccagccc ccagagctgc  3600
agccccgagc ccagcctgca gtacgccgcc acccagctgt accccccccc cccctggagc  3660
cccagcagcc ccccccacag caccggcagc gtgcgccccg tgcgcgccca gggcgagggc  3720
ctgctgccct aatgacaatt gttaattaag tttaaaccct cgaggccgca agccgcatcg  3780
ataccgtcga ctagagctcg ctgatcagcc tcgactgtgc cttctagttg ccagccatct  3840
gttgtttgcc cctcccccgt gccttccttg accctggaag gtgccactcc cactgtcctt  3900
tcctaataaa atgaggaaat tgcatcgcat tgtctgagta ggtgtcattc tattctgggg  3960
ggtggggtgg ggcaggacag caagggggag gattgggaag acaatagcag gcatgctggg  4020
gagagatcca cgataacaaa cagctttttt ggggtgaaca tattgactga attccctgca  4080
ggttggccac tccctctctg cgcgctcgct cgctcactga ggccgcccgg gcaaagcccg  4140
ggcgtcgggc gacctttggt cgcccggcct cagtgagcga gcgagcgcgc agagagggag  4200
tggccaactc catcactagg ggttcctgcg gccgctcgta cggtctcgag gaattcctgc  4260
aggataactt gccaacctca ttctaaaatg tatatagaag cccaaaagac aataacaaaa  4320
atattcttgt agaacaaaat gggaaagaat gttccactaa atatcaagat ttagagcaaa  4380
gcatgagatg tgtggggata gacagtgagg ctgataaaat agagtagagc tcagaaacag  4440
acccattgat atatgtaagt gacctatgaa aaaaatatgg cattttacaa tgggaaaatg  4500
atggtctttt tctttttttag aaaaacaggg aaatatattt atatgtaaaa aataaaaggg  4560
aacccatatg tcataccata cacacaaaaa aattccagtg aattataagt ctaaatggag  4620
aaggcaaaac tttaaatctt ttagaaaata atatagaagc atgcagacca gcctggccaa  4680
catgatgaaa ccctctctac taataataaa atcagtagaa ctactcagga ctactttgag  4740
tgggaagtcc ttttctatga agacttcttt ggccaaaatt aggctctaaa tgcaaggaga  4800
tagtgcatca tgcctggctg cacttactga taaatgatgt tatcaccatc tttaaccaaa  4860
tgcacaggaa caagttatgg tactgatgtg ctggattgag aaggagctct acttccttga  4920
caggacacat ttgtatcaac ttaaaaaagc agatttttgc cagcagaact attcattcag  4980
aggtaggaaa cttagaatag atgatgtcac tgattagcat ggcttcccca tctccacagc  5040
tgcttcccac ccaggttgcc cacagttgag tttgtccagt gctcagggct gcccactctc  5100
agtaagaagc cccacaccag cccctctcca aatatgttgg ctgttccttc cattaaagtg  5160
accccacttt agagcagcaa gtggatttct gtttcttaca gttcaggaag gaggagtcag  5220
ctgtgagaac ctggagcctg agatgcttct aagtcccact gctactgggg tcagggaagc  5280
cagactccag catcagcagt caggagcact aagcccttgc caacatcctg tttctcagag  5340
aaactgcttc cattataatg gttgtccttt tttaagctat caagccaaac aaccagtgtc  5400
taccattatt ctcatcacct gaagccaagg gttctagcaa aagtcaagct gtcttgtaat  5460
ggttgatgtg cctccagctt ctgtcttcag tcactccact cttagcctgc tctgaatcaa  5520
ctctgaccac agttccctgg agcccctgcc acctgctgcc cctgccacct tctccatctg  5580
cagtgctgtg cagccttctg cactcttgca gagctaatag gtggagactt gaaggaagag  5640
gaggaaagtt tctcataata gccttgctgc aagctcaaat gggaggtggg cactgtgccc  5700
aggagccttg gagcaaaggc tgtgcccaac ctctgactgc atccaggttt ggtcttgaca  5760
gagataagaa gccctggctt ttggagccaa aatctaggtc agacttaggc aggattctca  5820
aagtttatca gcagaacatg aggcagaaga ccctttctgc tccagcttct tcaggctcaa  5880
ccttcatcag aatagataga aagagaggct gtgagggttc ttaaaacaga agcaaatctg  5940
actcagagaa taaacaacct cctagtaaac tacagcttag acagagcatc tggtggtgag  6000
tgtgctcagt gtcctactca actgtctggt atcagccctc atgaggactt ctcttctttc  6060
cctcatagac ctccatctct gtttccttta gcctgcagaa atctggatgg ctattcacag  6120
aatgcctgtg ctttcagagt tgcatttttt ctctggtatt ctggttcaag catttgaagg  6180
taggaaaggt tctccaagtg caagaaagcc agccctgagc ctcaactgcc tggctagtgt  6240
ggtcagtagg atgcaaaggc tgttgaatgc cacaaggcca aactttaacc tgtgtaccac  6300
aagcctagca gcagaggcag ctctgctcac tggaactctc tgtcttcttt ctcctgagcc  6360
ttttctttc ctgagttttc tagctctcct caaccttacc tctgccctac ccaggacaaa  6420
cccaagagcc actgtttctg tgatgtcctc tccagcccta attaggcatc atgacttcag  6480
cctgaccttc catgctcaga agcagtgcta atccacttca gatgagctgc tctatgcaac  6540
acaggcagag cctacaaacc tttgcaccag agccctccac atatcagtgt ttgttcatac  6600
tcacttcaac agcaaatgtg actgctgaga ttaagatttt acacaagatg gtctgtaatt  6660
tcacagttag ttttatccca ttaggtatga aagaattagc ataattcccc ttaaacatga  6720
atgaatctta gattttttaa taaatagttt tggaagtaaa gacagagaca tcaggagcac  6780
aaggaatagc ctgagaggac aaacagaaca agaaagagtc tggaaataca caggatgttc  6840
ttggcctcct caaagcaagt gcaagcagat agtaccagca gccccaggct atcagagccc  6900
agtgaagaga agtaccatga aagccacagc tctaaccacc ctgttccaga gtgacagaca  6960
gtccccaaga caagccagcc tgagccagag agagaactgc aagagaaagt ttctaattta  7020
ggttctgtta gattcagaca agtgcaggtc atcctctctc cacagctact cacctctcca  7080
gcctaacaaa gcctgcagtc cacactccaa ccctggtgtc tcacctccta gcctctccca  7140
acatcctgct ctctgaccat cttctgcatc tctcatctca ccatctccca ctgtctacag  7200
cctactcttg caactaccat ctcattttct gacatcctgt ctacatcttc tgccatactc  7260
tgccatctac cataccacct cttaccatct accacaccat cttttatctc catccctctc  7320
agaagcctcc aagctgaatc ctgctttatg tgttcatctc agcccctgca tggaaagctg  7380
accccagagg cagaactatt cccagagagc ttggccaaga aaaacaaaac taccagcctg  7440
```

```
gccaggctca ggagtagtaa gctgcagtgt ctgttgtgtt ctagcttcaa cagctgcagg  7500
agttccactc tcaaatgctc cacatttctc acatcctcct gattctggtc actacccatc  7560
ttcaaagaac agaatatctc acatcagcat actgtgaagg actagtcatg ggtgcagctg  7620
ctcagagctg caaagtcatt ctggatggtg gagagcttac aaacatttca tgatgctccc  7680
cccgctctga tggctggagc ccaatcccta cacagactcc tgctgtatgt gttttccttt  7740
cactctgagc cacagccaga gggcaggcat tcagtctcct cttcaggctg gggctggggc  7800
actgagaact cacccaacac cttgctctca ctccttctgc aaaacaagaa agagctttgt  7860
gctgcagtag ccatgaagaa tgaaaggaag gctttaacta aaaaatgtca gagattattt  7920
tcaacccctt actgtggatc accagcaagg aggaaacaca acacagagac attttttccc  7980
ctcaaattat caaaagaatc actgcatttg ttaaagagag caactgaatc aggaagcaga  8040
gttttgaaca tatcagaagt taggaatctg catcagagac aaatgcagtc atggttgttt  8100
gctgcatacc agccctaatc attagaagcc tcatggactt caaacatcat tccctctgac  8160
aagatgctct agcctaactc catgagataa aataaatctg cctttcagag ccaaagaaga  8220
gtccaccagc ttcttctcag tgtgaacaag agctccagtc aggttagtca gtccagtgca  8280
gtagaggaga ccagtctgca tcctctaatt ttcaaaggca agaagatttg tttaccctgg  8340
acaccaggca caagtgaggt cacagagctc ttagatatgc agtcctcatg agtgaggaga  8400
ctaaagcgca tgccatcaag acttcagtgt agagaaaacc tccaaaaaag cctcctcact  8460
acttctggaa tagctcagag gccgaggcgg cctcggcctc tgcataaata aaaaaaatta  8520
gtcagccatg gggcggagaa tgggcggaac tgggcggagt taggggcggg atgggcggag  8580
ttaggggcgg gactatggtt gctgactaat tgagatgcat gctttgcata cttctgcctg  8640
ctggggagcc tggggacttt ccacacctgg ttgctgacta attgagatgc atgctttgca  8700
tacttctgcc tgctggggag cctggggact ttccacaccc taactgacac acattccaca  8760
gctgcattaa tgaatcggcc aacgcgcggg gagaggcggt ttgcgtattg ggcgctcttc  8820
cgcttcctcg ctcactgact cgctgcgctc ggtcgttcgg ctgcggcgag cggtatcagc  8880
tcactcaaag gcggtaatac ggttatccac agaatcaggg gataacgcag gaaagaacat  8940
gtgagcaaaa ggccagcaaa aggccaggaa ccgtaaaaag gccgcgttgc tggcgttttt  9000
ccataggctc cgcccccctg acgagcatca caaaaatcga cgctcaagtc agaggtggcg  9060
aaacccgaca ggactataaa gataccaggc gtttccccct ggaagctccc tcgtgcgctc  9120
tcctgttccg accctgccgc ttaccggata cctgtccgcc tttctccctt cgggaagcgt  9180
ggcgctttct catagctcac gctgtaggta tctcagttcg gtgtaggtcg ttcgctccaa  9240
gctgggctgt gtgcacgaac cccccgttca gcccgaccgc tgcgccttat ccggtaacta  9300
tcgtcttgag tccaacccgg taagacacga cttatcgcca ctggcagcag ccactggtaa  9360
caggattagc agagcgaggt atgtaggcgg tgctacagag ttcttgaagt ggtggcctaa  9420
ctacggctac actagaagaa cagtatttgg tatctgcgct ctgctgaagc cagttacctt  9480
cggaaaaaga gttggtagct cttgatccgg caaacaaacc accgctggta gcggtggttt  9540
ttttgtttgc aagcagcaga ttacgcgcag aaaaaaagga tctcaagaag atcctttgat  9600
cttttctacg gggtctgacg ctcagtggaa cgaaaactca cgttaaggga ttttggtcat  9660
gagattatca aaaaggatct tcacctagat ccttttaaat taaaaatgaa gttttaaatc  9720
aatctaaagt atatatgagt aaacttggtc tgacagttac caatgcttaa tcagtgaggc  9780
acctatctca gcgatctgtc tatttcgttc atccatagtt gcctgactcc tgcaaaccac  9840
gttgtgtctc aaaatctctg atgttacatt gcacaagata aaaatatatc atcatgaaca  9900
ataaaactgt ctgcttacat aaacagtaat acaaggggtg ttatgagcca tattcaacgg  9960
gaaacgtctt gctcgaggcc gcgattaaat tccaacatgg atgctgattt atatgggtat  10020
aaatgggctc gcgataatgt cgggcaatca ggtgcgacaa tctatcgatt gtatgggaag  10080
cccgatgcgc cagagttgtt tctgaaacat ggcaaaggta gcgttgccaa tgatgttaca  10140
gatgagatgg tcagactaaa ctggctgacg gaatttatgc ctcttccgac catcaagcat  10200
tttatccgta ctcctgatga tgcatggtta ctcaccactg cgatccccgg gaaaacagca  10260
ttccaggtat tagaagaata tcctgattca ggtgaaaata ttgttgatgc gctggcagtg  10320
ttcctgcgcc ggttgcattc gattcctgtt tgtaattgtc cttttaacag cgatcgcgta  10380
tttcgtctcg ctcaggcgca atcacgaatg aataacggtt tggttgatgc gagtgatttt  10440
gatgacgagc gtaatggctg gcctgttgaa caagtctgga aagaaatgca taagcttttg  10500
ccattctcac cggattcagt cgtcactcat ggtgatttct cacttgataa ccttattttt  10560
gacgagggga aattaatagg ttgtattgat gttggacgag tcggaatcgc agaccgatac  10620
caggatcttg ccatcctatg gaactgcctc ggtgagtttt ctccttcatt acagaaacgg  10680
ctttttcaaa aatatggtat tgataatcct gatatgaata aattgcagtt tcatttgatg  10740
ctcgatgagt ttttctaagg gcggcctgcc accataccca cgccgaaaca agcgctcatg  10800
agcccgaagt ggcgagcccg atcttcccca tcggtgatgt cggcgatata ggcgccagca  10860
accgcacctg tggcgccggt gatgagggcg cgccaagtcg acgtccggca gtc         10913
```

```
SEQ ID NO: 61          moltype = DNA  length = 11209
FEATURE                Location/Qualifiers
misc_feature           1..11209
                       note = Synthetic polynucleotide
source                 1..11209
                       mol_type = other DNA
                       organism = synthetic construct
SEQUENCE: 61
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catggaattc agcagcccca gcagagagga  660
atgccccaag cctctgagcc gggtgtcaat catggccgga tctctgacag gactgctgct  720
```

-continued gcttcaggcc gtgtcttggg cttctggcgc tagaccttgc atccccaaga gcttcggcta 780
cagcagcgtc gtgtgcgtgt gcaatgccac ctactgcgac agcttcgacc ctcctacctt 840
tcctgctctg ggcaccttca gcagatacga gagcaccaga tccggcagac ggatggaact 900
gagcatggga cccatccagg ccaatcacac aggcactggc ctgctgctga cactgcagcc 960
tgagcagaaa ttccagaaag tgaaaggctt cggcggagcc atgacagatg ccgccgctct 1020
gaatatcctg gctctgtctc caccagctca gaacctgctg ctcaagagct acttcagcga 1080
ggaaggcatc ggctacaaca tcatcagagt gcccatggcc agctgcgact tcagcatcag 1140
gacctacacc tacgccgaca caccccgacga tttccagctg cacaacttca gcctgcctga 1200
agaggacacc aagctgaaga tccctctgat ccacagagcc ctgcagctgg cacaaagacc 1260
cgtgtcactg ctggcctctc catggacatc tcccacctgg ctgaaaacaa atggcgccgt 1320
gaatggcaag ggcagcctga aaggccaacc tggcgacatc taccaccaga cctgggccag 1380
atacttcgtg aagttcctgg acgcctatgc cgagcacaag ctgcagtttt gggccgtgac 1440
agccgagaac gaaccttctg ctggactgct gagcggctac ccctttcagt gcctgggctt 1500
tacacccgag caccagcggg actttatcgc ccgtgatctg ggacccacac tggccaatag 1560
cacccaccat aatgtgcggc tgctgatgct ggacgaccag agactgcttc tgccccactg 1620
ggctaaagtg gtgctgacag atcctgaggc cgccaaatac gtgcacggaa tcgccgtgca 1680
ctggtatctg gactttctgg cccctgccaa ggccacactg ggagagacac acagactgtt 1740
ccccaacacc atgctgttcg ccagcgaagc ctgtgtgggc agcaagtttt gggaacagag 1800
cgtgcggctc ggcagctggg atagaggcat gcagtacagc cacagcatca tcaccaacct 1860
gctgtaccac gtcgtcggct ggaccgactg gaatctggcc ctgaatcctg aaggcggccc 1920
taactgggtc cgaaacttcg tggacagccc catcatcgtg gacatcacca aggacacctt 1980
ctacaagcag cccatgttct accacctggg acacttcagc aagttcatcc ccgagggctc 2040
tcagcgcgtt ggactggtgg cttcccagaa gaacgatctg gacgccgtgg ctctgatgca 2100
ccctgatgga tctgctgtgg tggtggtcct gaaccgcagc agcaaagatg tgcccctgac 2160
catcaaggat cccgccgtgg gattcctgga aacaatcagc cctggctact ccatccacac 2220
ctacctgtgg cgtagacagt gacaattgtt aattaagttt aaaccctcga ggccgcaagc 2280
cgcatcgata ccgtcgacta gagctcgctg atcagcctcg actgtgcctt ctagttgcca 2340
gccatctgtt gtttgcccct cccccgtgcc ttccttgacc ctggaaggtg ccactcccac 2400
tgtcctttcc taataaaatg aggaaattgc atcgcattgt ctgagtaggt gtcattctat 2460
tctggggggt ggggtggggc aggacagcaa gggggaggat tgggaagaca atagcaggca 2520
tgctggggag agatccacga taacaaacag ctttttgggg ggatatcaaa ctgcctgttt 2580
gggcttctca tttcttacct ccccttccct ctcccacctg ctactgggtg catctctgct 2640
ccccccttcc ccagcagatg gttacctttg ggctgttgct ttcttgtcac catctgagtt 2700
ctcagacgct ggaaagccat gttctcggct ctgtgaatga caatgctgac tggagtgctg 2760
cccctctgta aagggctggg tgtggatggt cacaagcccc tcacatgcct cagccaagag 2820
gaagtagtac aggggtcagc ccagaggtcc aggggaaagg agtggaaacc gatttcccca 2880
ccaagggagg ggcctgtacc tcagctgttc ccatagctta cttgccacaa ctgccaagca 2940
agtttcgctg agtttgacac atggatccct gtggatcaac tgccctagga ctccgtttgc 3000
acccatgtga cactgttgac tttgccctga cgaagcaggg ccaacagtcc cctaacttaa 3060
ttacaaaaac taatgactaa gagagaggtg gctagagctg aggcccctga gtcaggctgt 3120
gggtgggatc atctccagta caggaagtga gactttcatt tcctcctttc caagagaggg 3180
ctgagggagc agggttgagc aactggtgca gacagcctag ctggactttg ggtgaggcgg 3240
ttcagccata tcgaattctg ctggggctac tggcaggtaa ggaggaagga ggctgagggg 3300
agggggcccc tgggagggag cctgccctgg gttgctaacc atctcctctc tgccaaaagt 3360
ccggaaagcc accatggagc ccctgcgcct gctgatcctg ctgttcgtga ccgagctgag 3420
cggcgcccac aacaccaccg tgttccaggg cgtggccggc cagagcctgc aggtgagctg 3480
cccctacgac agcatgaagc actggggccg ccgcaaggcc tggtgccgcc agctgggcga 3540
gaagggcccc tgccagcgcg tggtgagcac ccacaacctg tggctgctga gcttcctgcg 3600
ccgctggaac ggcagcaccg ccatcaccga cgacaccctg ggcggcaccc tgaccatcac 3660
cctgcgcaac ctgcagcccc acgacgccgg cctgtaccag tgccagagcc tgcacggcag 3720
cgaggccgac accctgcgca aggtgctggt ggaggtgctg gccgaccccc tggaccaccg 3780
cgacgccggc gacctgtggt tccccggcga gagcgagagc ttcgaggacg cccacgtgga 3840
gcacagcatc agccgcagcc tgctggaggg cgagatcccc ttccccccca ccagcatcct 3900
gctgctgctg gcctgcatct tcctgatcaa gatcctggcc gccagcgccc tgtgggccgc 3960
cgcctggcac ggccagaagc ccggcaccca cccccccagc gagctggact gcggccacga 4020
ccccggctac cagctgcaga ccctgcccgg cctgcgcgac acctgaccca ggggactcag 4080
cggccgctcg agtctagagg gcccgtttaa acccgctgat cagcctcgaa gacatgataa 4140
gatacattga tgagtttgga caaaccacaa caagaatgca gtgaaaaaaa tgctttattt 4200
gtgaaatttg tgatgctatt gctttatttg taaccattat aagctgcaat aaacaagtta 4260
acaacaacaa ttgcattcat tttatgtttc aggttcaggg ggagatgtgg gaggtttttt 4320
aaagcaagta aaacctctac aaatgtggta tgaacatatt gactgaattc cctgcaggtt 4380
ggccactccc tctctgcgcg ctcgctcgct cactgaggcc gcccgggcaa agcccgggcg 4440
tcgggcgacc tttggtcgcc cggcctcagt gagcgagcga gcgcgcagag agggagtggc 4500
caactccatc actaggggtt cctgcggccg ctcgtacggt ctcgaggaat tcctgcagga 4560
taacttgcca acctcattct aaaatgtata tagaagccca aaagacaata acaaaaatat 4620
tcttgtagaa caaaatggga aagaatgttc cactaaatat caagatttag agcaaagcat 4680
gagatgtgtg gggatagaca gtgaggctga taaaatagag tagagctcag aaacagaccc 4740
attgatatat gtaagtgacc tatgaaaaaa atatggcatt ttacaatggg aaaatgatgg 4800
tctttttctt ttttagaaaa acagggaaat atatttatat gtaaaaaata aaagggaacc 4860
catatgtcat accatacaca caaaaaaatt ccagtgaatt ataagtctaa atggagaagg 4920
caaaacttta aatcttttag aaaataatat agaagcatgc agaccagcct ggccaacatg 4980
atgaaaccct ctctactaat aataaaatca gtagaactac tcaggactac tttgagtggg 5040
aagtcctttt ctatgaagac ttctttggcc aaaattaggc tctaaatgca aggagatagt 5100
gcatcatgcc tggctgcact tactgataaa tgatgttatc accatcttta accaaatgca 5160
caggaacaag ttatggtact gatgtgctgg attgagaagg agctctactt ccttgacagg 5220
acacatttgt atcaacttaa aaaagcagat ttttgccagc agaactattc attcagaggt 5280
aggaaactta gaatagatga tgtcactgat tagcatggct tccccatctc cacagctgct 5340
tcccacccag gttgcccaca gttgagtttg tccagtgctc agggctgccc actctcagta 5400
agaagcccca caccagcccc tctccaaata tgttggctgt tccttccatt aaagtgaccc 5460

-continued

```
cactttagag cagcaagtgg atttctgttt cttacagttc aggaaggagg agtcagctgt  5520
gagaacctgg agcctgagat gcttctaagt cccactgcta ctggggtcag ggaagccaga  5580
ctccagcatc agcagtcagg agcactaagc ccttgccaac atcctgtttc tcagagaaac  5640
tgcttccatt ataatggttg tcctttttta agctatcaag ccaaacaacc agtgtctacc  5700
attattctca tcacctgaag ccaagggttc tagcaaaagt caagctgtct tgtaatggtt  5760
gatgtgcctc cagcttctgt cttcagtcac tccactctta gcctgctctg aatcaactct  5820
gaccacagtt ccctggagcc cctgccacct gctgcccctg ccaccttctc catctgcagt  5880
gctgtgcagc cttctgcact cttgcagagc taataggtgg agacttgaag gaagaggagg  5940
aaagtttctc ataatagcct tgctgcaagc tcaaatggga ggtgggcact gtgcccagga  6000
gccttggagc aaaggctgtg cccaacctct gactgcatcc aggtttggtc ttgacagaga  6060
taagaagccc tggcttttgg agccaaaatc taggtcagac ttaggcagga ttctcaaagt  6120
ttatcagcag aacatgaggc agaagaccct ttctgctcca gcttcttcag gctcaacctt  6180
catcagaata gatagaaaga gaggctgtga gggttcttaa aacagaagca aatctgactc  6240
agagaataaa caacctccta gtaaactaca gcttagacag agcatctggt ggtgagtgtg  6300
ctcagtgtcc tactcaactg tctggtatca gccctcatga ggacttctct tctttccctc  6360
atagacctcc atctctgttt tccttagcct gcagaaatct ggatggctat tcacagaatg  6420
cctgtgcttt cagagttgca ttttttctct ggtattctgg ttcaagcatt tgaaggtagg  6480
aaaggttctc caagtgcaag aaagccagcc ctgagcctca actgcctggc tagtgtggtc  6540
agtaggatgc aaaggctgtt gaatgccaca aggccaaact ttaacctgtg taccacaagc  6600
ctagcagcag aggcagctct gctcactgga actctctgtc ttctttctcc tgagcctttt  6660
cttttcctga gttttctagc tctcctcaac cttacctctg ccctacccag gacaaaccca  6720
agagccactg tttctgtgat gtcctctcca gccctaatta ggcatcatga cttcagcctg  6780
accttccatg ctcagaagca gtgctaatcc acttcagatg agctgctcta tgcaacacag  6840
gcagagccta caaacctttg caccagagcc ctccacatat cagtgtttgt tcatactcac  6900
ttcaacagca aatgtgactg ctgagattaa gattttacac aagatggtct gtaatttcac  6960
agttagtttt atcccattag gtatgaaaga attagcataa ttccccttaa acatgaatga  7020
atcttagatt ttttaataaa tagttttgga agtaaagaca gagacatcag gagcacaagg  7080
aatagcctga gaggacaaac agaacaagaa agagtctgga aatacacagg atgttcttgg  7140
cctcctcaaa gcaagtgcaa gcagatagta ccagcagccc caggctatca gagcccagtg  7200
aagagaagta ccatgaaagc cacagctcta accaccctgt tccagagtga cagacagtcc  7260
ccaagacaag ccagcctgag ccagagagag aactgcaaga gaaagtttct aatttaggtt  7320
ctgttagatt cagacaagtg caggtcatcc tctctccaca gctactcacc tctccagcct  7380
aacaaagcct gcagtccaca ctccaaccct ggtgtctcac ctcctagcct ctcccaacat  7440
cctgctctct gaccatcttc tgcatctctc atctcaccat ctcccactgt ctacagccta  7500
ctcttgcaac taccatctca ttttctgaca tcctgtctac atcttctgcc atactctgcc  7560
atctaccata ccacctctta ccatctacca caccatcttt tatctccatc cctctcagaa  7620
gcctccaagc tgaatcctgc tttatgtgtt catctcagcc cctgcatgga aagctgaccc  7680
cagaggcaga actattccca gagagcttgg ccaagaaaaa caaaactacc agcctggcca  7740
ggctcaggag tagtaagctg cagtgtctgt tgtgttctag cttcaacagc tgcaggagtt  7800
ccactctcaa atgctccaca tttctcacat cctcctgatt ctggtcacta cccatcttca  7860
aagaacagaa tatctcacat cagcatactg tgaaggacta gtcatgggtg cagctgctca  7920
gagctgcaaa gtcattctgg atggtggaga gcttacaaac atttcatgat gctccccccg  7980
ctctgatggc tggagcccaa tccctacaca gactcctgct gtatgtgttt tcctttcact  8040
ctgagccaca gccagagggc aggcattcag tctcctcttc aggctggggc tggggcactg  8100
agaactcacc caacaccttg ctctcactcc ttctgcaaaa caagaaagag ctttgtgctg  8160
cagtagccat gaagaatgaa aggaaggctt taactaaaaa atgtcagaga ttattttcaa  8220
ccccttactg tggatcacca gcaaggagga aacacaacac agagacattt tttcccctca  8280
aattatcaaa agaatcactg catttgttaa agagagcaac tgaatcagga agcagagttt  8340
tgaacatatc agaagttagg aatctgcatc agagacaaat gcagtcatgg ttgtttgctg  8400
cataccagcc ctaatcatta gaagcctcat ggacttcaaa catcattccc tctgacaaga  8460
tgctctagcc taactccatg agataaaata aatctgcctt tcagagccaa agaagagtcc  8520
accagcttct tctcagtgtg aacaagagct ccagtcaggt tagtcagtcc agtgcagtag  8580
aggagaccag tctgcatcct ctaattttca aaggcaagaa gatttgttta ccctggacac  8640
caggcacaag tgaggtcaca gagctcttag atatgcagtc ctcatgagtg aggagactaa  8700
agcgcatgcc atcaagactt cagtgtagag aaaacctcca aaaaagcctc ctcactactt  8760
ctggaatagc tcagaggccg aggcggcctc ggcctctgca taaataaaaa aaattagtca  8820
gccatggggc ggagaatggg cggaactggg cggagttagg ggcgggatgg gcggagttag  8880
gggcgggact atggttgctg actaattgag atgcatgctt tgcatacttc tgcctgctgg  8940
ggagcctggg gactttccac acctggttgc tgactaattg agatgcatgc tttgcatact  9000
tctgcctgct ggggagcctg gggactttcc acaccctaac tgacacacat tccacagctg  9060
cattaatgaa tcggccaacg cgcggggaga ggcggtttgc gtattgggcg ctcttccgct  9120
tcctcgctca ctgactcgct gcgctcggtc gttcggctgc ggcgagcggt atcagctcac  9180
tcaaaggcgg taatacggtt atccacagaa tcaggggata acgcaggaaa gaacatgtga  9240
gcaaaaggcc agcaaaaggc caggaaccgt aaaaaggccg cgttgctggc gtttttccat  9300
aggctccgcc cccctgacga gcatcacaaa aatcgacgct caagtcagag gtggcgaaac  9360
ccgacaggac tataaagata ccaggcgttt ccccctggaa gctccctcgt gcgctctcct  9420
gttccgaccc tgccgcttac cggatacctg tccgcctttc tcccttcggg aagcgtggcg  9480
ctttctcata gctcacgctg taggtatctc agttcggtgt aggtcgttcg ctccaagctg  9540
ggctgtgtgc acgaaccccc cgttcagccc gaccgctgcg ccttatccgg taactatcgt  9600
cttgagtcca acccggtaag acacgactta tcgccactgg cagcagccac tggtaacagg  9660
attagcagag cgaggtatgt aggcggtgct acagagttct tgaagtggtg gcctaactac  9720
ggctacacta gaagaacagt atttggtatc tgcgctctgc tgaagccagt taccttcgga  9780
aaaagagttg gtagctcttg atccggcaaa caaaccaccg ctggtagcgg tggttttttt  9840
gtttgcaagc agcagattac gcgcagaaaa aaaggatctc aagaagatcc tttgatcttt  9900
tctacggggt ctgacgctca gtggaacgaa aactcacgtt aagggatttt ggtcatgaga  9960
ttatcaaaaa ggatcttcac ctagatcctt ttaaattaaa aatgaagttt taaatcaatc  10020
taaagtatat atgagtaaac ttggtctgac agttaccaat gcttaatcag tgaggcacct  10080
atctcagcga tctgtctatt tcgttcatcc atagttgcct gactcctgca aaccacgttg  10140
tgtctcaaaa tctctgatgt tacattgcac aagataaaaa tatatcatca tgaacaataa  10200
```

```
aactgtctgc ttacataaac agtaatacaa ggggtgttat gagccatatt caacgggaaa  10260
cgtcttgctc gaggccgcga ttaaattcca acatggatgc tgatttatat gggtataaat  10320
gggctcgcga taatgtcggg caatcaggtg cgacaatcta tcgattgtat gggaagcccg  10380
atgcgccaga gttgtttctg aaacatggca aaggtagcgt tgccaatgat gttacagatg  10440
agatggtcag actaaactgg ctgacggaat ttatgcctct tccgaccatc aagcatttta  10500
tccgtactcc tgatgatgca tggttactca ccactgcgat ccccgggaaa acagcattcc  10560
aggtattaga agaatatcct gattcaggtg aaaatattgt tgatgcgctg gcagtgttcc  10620
tgcgccggtt gcattcgatt cctgtttgta attgtccttt taacagcgat cgcgtatttc  10680
gtctcgctca ggcgcaatca cgaatgaata acggtttggt tgatgcgagt gattttgatg  10740
acgagcgtaa tggctggcct gttgaacaag tctggaaaga aatgcataag cttttgccat  10800
tctcaccgga ttcagtcgtc actcatggtg atttctcact tgataacctt atttttgacg  10860
aggggaaatt aataggttgt attgatgttg gacgagtcgg aatcgcagac cgataccagg  10920
atcttgccat cctatggaac tgcctcggtg agttttctcc ttcattacag aaacggcttt  10980
ttcaaaaata tggtattgat aatcctgata tgaataaatt gcagtttcat ttgatgctcg  11040
atgagttttt ctaagggcgg cctgccacca tacccacgcc gaaacaagcg ctcatgagcc  11100
cgaagtggcg agcccgatct tccccatcgg tgatgtcggc gatataggcg ccagcaaccg  11160
cacctgtggc gccggtgatg agggcgcgcc aagtcgacgt ccggcagtc             11209
```

```
SEQ ID NO: 62          moltype = DNA  length = 11459
FEATURE                Location/Qualifiers
misc_feature           1..11459
                       note = Synthetic polynucleotide
source                 1..11459
                       mol_type = other DNA
                       organism = synthetic construct
SEQUENCE: 62
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
cctagttatt aatagtaatc aattacgggg tcattagttc atagcccata tatggagttc  360
cgcgttacat aacttacggt aaatggcccg cctggctgac cgcccaacga cccccgccca  420
ttgacgtcaa taatgacgta tgttcccata gtaacgccaa tagggacttt ccattgacgt  480
caatgggtgg actatttacg gtaaactgcc cacttggcag tacatcaagt gtatcatatg  540
ccaagtacgc cccctattga cgtcaatgac ggtaaatggc ccgcctggca ttatgcccag  600
tacatgacct tatgggactt tcctacttgg cagtacatct acgtattagt catcgctatt  660
accatggtcg aggtgagccc cacgttctgc ttcactctcc ccatctcccc cccctcccca  720
cccccaattt tgtatttatt tatttttttaa ttattttgtg cagcgatggg ggcggggggg  780
gggggggggc gcgcgccagg cggggcgggg cggggcgagg ggcggggcgg ggcgaggcgg  840
agaggtgcgg cggcagccaa tcagagcggc gcgctccgaa agtttccttt tatggcgagg  900
cggcggcggc ggcggcccta taaaaagcga agcgcgcggc gggcgggagt cgctgcgacg  960
ctgccttcgc cccgtgcccc gctccgccgc cgcctcgcgc cgcccgcccc ggctctgact  1020
gaccgcgtta ctcccacagg tgagcgggcg ggacggccct tctcctccgg gctgtaatta  1080
gcgcttggtt taatgacggc ttgtttcttg tggctgcgtg aaagccttga ggggctccgg  1140
gagctagagc ctctgctaac catgttcatg ccttcttctt tttcctacag ctcctgggca  1200
acgtgctggt tattgtgctg tctcatcatt ttggcaaaga attcctcgaa gatccgaagg  1260
gaaagtcttc cacgactgtg ggatccgttc gaagatatca ccggttgagc caccatggaa  1320
ttcagcagcc ccagcagaga ggaatgcccc aagcctctga gccgggtgtc aatcatggcc  1380
ggatctctga caggactgct gctgcttcag gccgtgtctt gggcttctgg cgctagacct  1440
tgcatcccca agagcttcgg ctacagcagc gtcgtgtgcg tgtgcaatgc cacctactgc  1500
gacagcttcg accctcctac ctttcctgct ctgggcacct tcagcagata cgagagcacc  1560
agatccggca gacggatgga actgagcatg ggacccatcc aggccaatca cacaggcact  1620
ggcctgctgc tgacactgca gcctgagcag aaattccaga aagtgaaagg cttcggcgga  1680
gccatgacag atgccgccgc tctgaatatc ctggctctgt ctccaccagc tcagaacctg  1740
ctgctcaaga gctacttcag cgaggaaggc atcggctaca acatcatcag agtgcccatg  1800
gccagctgcg acttcagcat caggacctac acctacgccg acacacccga cgatttccag  1860
ctgcacaact tcagcctgcc tgaagaggac accaagctga agatccctct gatccacaga  1920
gccctgcagc tggcacaaag acccgtgtca ctgctggcct ctccatggac atctcccacc  1980
tggctgaaaa caaatggcgc cgtgaatggc aagggcagcc tgaaaggcca acctggcgac  2040
atctaccacc agacctgggc cagatacttc gtgaagttcc tggacgccta tgccgagcac  2100
aagctgcagt tttgggccgt gacagccgag aacgaacctt ctgctggact gctgagcggc  2160
taccccttc agtgcctggg ctttacaccc gagcaccagc gggactttat cgcccgtgat  2220
ctgggaccca cactggccaa tagcacccac cataatgtgc ggctgctgat gctggacgac  2280
cagagactgc ttctgcccca ctgggctaaa gtggtgctga cagatcctga ggccgccaaa  2340
tacgtgcacg gaatcgccgt gcactggtat ctggactttc tggcccctgc caaggccaca  2400
ctgggagaga cacacagact gttccccaac accatgctgt tcgccagcga agcctgtgtg  2460
ggcagcaagt tttgggaaca gagcgtgcgg ctcggcagct gggatagagg catgcagtac  2520
agccacagca tcatcaccaa cctgctgtac cacgtcgtcg gctggaccga ctggaatctg  2580
gccctgaatc ctgaaggcgg ccctaactgg gtccgaaact tcgtggacag ccccatcatc  2640
gtggacatca ccaaggacac cttctacaag cagcccatgt tctaccacct gggacacttc  2700
agcaagttca tccccgaggg ctctcagcgc gttggactgg tggcttccca gaagaacgat  2760
ctggacgccg tggctctgat gcaccctgat ggatctgctg tggtggtggt cctgaaccgc  2820
agcagcaaag atgtgcccct gaccatcaag gatcccgccg tgggattcct ggaaacaatc  2880
agccctggct actccatcca cacctacctg tggcgtagac agtgacaatt gttaattaag  2940
tttaaaccct cgaggccgca agccgcatcg ataccgtcga ctagagctcg ctgatcagcc  3000
tcgactgtgc cttctagttg ccagccatct gttgtttgcc cctcccccgt gccttccttg  3060
accctggaag gtgccactcc cactgtcctt tcctaataaa atgaggaaat tgcatcgcat  3120
tgtctgagta ggtgtcattc tattctgggg ggtggggtgg ggcaggacag caagggggag  3180
```

```
gattgggaag acaatagcag gcatgctggg gagagatcca cgataacaaa cagctttttt  3240
gggggggcgg agttagggcg gagccaatca gcgtgcgccg ttccgaaagt tgccttttat  3300
ggctgggcgg agaatgggcg gtgaacgccg atgattatat aaggacgcgc cgggtgtggc  3360
acagctagtt ccgtcgcagc cgggatttgg gtcgcggttc ttgtttgtgg atccctgtga  3420
tcgtcacttg gtaagtcact gactgtctat gcctgggaaa gggtgggcag gagatggggc  3480
agtgcaggaa aagtggcact atgaaccctg cagccctagg aatgcatcta gacaattgta  3540
ctaaccttct tctctttcct ctcctgacag tccggaaagc caccatgccc cgcggcttca  3600
cctggctgcg ctacctgggc atcttcctgg gcgtggccct gggcaacgag cccctggaga  3660
tgtggcccct gacccagaac gaggagtgca ccgtgaccgg cttcctgcgc gacaagctgc  3720
agtaccgcag ccgcctgcag tacatgaagc actacttccc catcaactac aagatcagcg  3780
tgccctacga gggcgtgttc cgcatcgcca acgtgacccg cctgcagcgc gcccaggtga  3840
gcgagcgcga gctgcgctac ctgtgggtgc tggtgagcct gagcgccacc gagagcgtgc  3900
aggacgtgct gctggagggc caccccagct ggaagtacct gcaggaggtg gagaccctgc  3960
tgctgaacgt gcagcagggc ctgaccgacg tggaggtgag ccccaaggtg gagagcgtgc  4020
tgagcctgct gaacgccccc ggccccaacc tgaagctggt gcgccccaag gccctgctgg  4080
acaactgctt ccgcgtgatg gagctgctgt actgcagctg ctgcaagcag agcagcgtgc  4140
tgaactggca ggactgcgag gtgcccagcc cccagagctg cagccccgag cccagcctgc  4200
agtacgccgc cacccagctg tacccccccc cccccctggag ccccagcagc cccccccaca  4260
gcaccggcag cgtgcgcccc gtgcgcgccc agggcgaggg cctgctgccc taatgaccca  4320
ggggactcag cggccgctcg agtctagagg gcccgtttaa acccgctgat cagcctcgaa  4380
gacatgataa gatacattga tgagtttgga caaaccacaa caagaatgca gtgaaaaaaa  4440
tgctttattt gtgaaatttg tgatgctatt gctttatttg taaccattat aagctgcaat  4500
aaacaagtta acaacaacaa ttgcattcat tttatgtttc aggttcaggg ggagatgtgg  4560
gaggtttttt aaagcaagta aaacctctac aaatgtggta tgaacatatt gactgaattc  4620
cctgcaggtt ggccactccc tctctgcgcg ctcgctcgct cactgaggcc gcccgggcaa  4680
agcccgggcg tcgggcgacc tttggtcgcc cggcctcagt gagcgagcga gcgcgcagag  4740
agggagtggc caactccatc actaggggtt cctgcggccg ctcgtacggt ctcgaggaat  4800
tcctgcagga taacttgcca acctcattct aaaatgtata tagaagccca aaagacaata  4860
acaaaaatat tcttgtagaa caaaatggga aagaatgttc cactaaatat caagatttag  4920
agcaaagcat gagatgtgtg gggatagaca gtgaggctga taaaatagag tagagctcag  4980
aaacagaccc attgatatat gtaagtgacc tatgaaaaaa atatggcatt ttacaatggg  5040
aaaatgatgg tctttttctt ttttagaaaa acagggaaat atatttatat gtaaaaaata  5100
aaagggaacc catatgtcat accatacaca caaaaaaatt ccagtgaatt ataagtctaa  5160
atggagaagg caaaacttta aatcttttag aaaataatat agaagcatgc agaccagcct  5220
ggccaacatg atgaaaccct ctctactaat aataaaatca gtagaactac tcaggactac  5280
tttgagtggg aagtcctttt ctatgaagac ttctttggcc aaaattaggc tctaaatgca  5340
aggagatagt gcatcatgcc tggctgcact tactgataaa tgatgttatc accatcttta  5400
accaaatgca caggaacaag ttatggtact gatgtgctgg attgagaagg agctctactt  5460
ccttgacagg acacatttgt atcaacttaa aaaagcagat tttgccagc agaactattc  5520
attcagaggt aggaaactta gaatagatga tgtcactgat tagcatggct tccccatctc  5580
cacagctgct tcccacccag gttgcccaca gttgagtttg tccagtgctc agggctgccc  5640
actctcagta agaagcccca caccagcccc tctccaaata tgttggctgt tccttccatt  5700
aaagtgaccc cactttagag cagcaagtgg atttctgttt cttacagttc aggaaggagg  5760
agtcagctgt gagaacctgg agcctgagat gcttctaagt ccccactgcta ctggggtcag  5820
ggaagccaga ctccagcatc agcagtcagg agcactaagc ccttgccaac atcctgtttc  5880
tcagagaaac tgcttccatt ataatggttg tccttttttta agctatcaag ccaaacaacc  5940
agtgtctacc attattctca tcacctgaag ccaagggttc tagcaaaagt caagctgtct  6000
tgtaatggtt gatgtgcctc cagcttctgt cttcagtcac tccactctta gcctgctctg  6060
aatcaactct gaccacagtt ccctggagcc cctgccacct gctgcccctg ccaccttctc  6120
catctgcagt gctgtgcagc cttctgcact cttgcagagc taataggtgg agacttgaag  6180
gaagaggagg aaagtttctc ataatagcct tgctgcaagc tcaaatggga ggtgggcact  6240
gtgcccagga gccttggagc aaaggctgtg cccaacctct gactgcatcc aggtttggtc  6300
ttgacagaga taagaagccc tggcttttgg agccaaaatc taggtcagac ttaggcagga  6360
ttctcaaagt ttatcagcag aacatgaggc agaagaccct ttctgctcca gcttcttcag  6420
gctcaacctt catcagaata gatagaaaga gaggctgtga gggttcttaa aacagaagca  6480
aatctgactc agagaataaa caacctccta gtaaactaca gcttagacag agcatctggt  6540
ggtgagtgtg ctcagtgtcc tactcaactg tctggtatca gccctcatga ggacttctct  6600
tctttccctc atagacctcc atctctgttt tccttagcct gcagaaatct ggatggctat  6660
tcacagaatg cctgtgcttt cagagttgca tttttctctt ggtattctgg ttcaagcatt  6720
tgaaggtagg aaaggttctc caagtgcaag aaagccagcc ctgagcctca actgcctggc  6780
tagtgtggtc agtaggatgc aaaggctgtt gaatgccaca aggccaaact ttaacctgtg  6840
taccacaagc ctagcagcag aggcagctct gctcactgga actctctgtc ttctttctcc  6900
tgagcctttt cttttcctga gttttctagc tctcctcaac cttacctctg ccctacccag  6960
gacaaaccca agagccactg tttctgtgat gtcctctcca gccctaatta ggcatcatga  7020
cttcagcctg accttccatg ctcagaagca gtgctaatcc acttcagatg agctgctcta  7080
tgcaacacag gcagagccta caaacctttg caccagagcc ctccacatat cagtgtttgt  7140
tcatactcac ttcaacagca aatgtgactg ctgagattaa gattttacac aagatggtct  7200
gtaatttcac agttagtttt atcccattag gtatgaaaga attagcataa ttccccttaa  7260
acatgaatga atcttagatt ttttaataaa tagttttgga agtaaagaca gagacatcag  7320
gagcacaagg aatagcctga gaggacaaac agaacaagaa agagtctgga aatacacagg  7380
atgttcttgg cctcctcaaa gcaagtgcaa gcagatagta ccagcagccc caggctatca  7440
gagcccagtg aagagaagta ccatgaaagc cacagctcta accaccctgt tccagagtga  7500
cagacagtcc ccaagacaag ccagcctgag ccagagagag aactgcaaga gaaagtttct  7560
aatttaggtt ctgttagatt cagacaagtg caggtcatcc tctctccaca gctactcacc  7620
tctccagcct aacaaagcct gcagtccaca ctccaaccct ggtgtctcac ctcctagcct  7680
ctcccaacat cctgctctct gaccatcttc tgcatctctc atctcaccat ctcccactgt  7740
ctacagccta ctcttgcaac taccatctca ttttctgaca tcctgtctac atcttctgcc  7800
atactctgcc atctaccata ccacctctta ccatctacca caccatcttt tatctccatc  7860
cctctcagaa gcctccaagc tgaatcctgc tttatgtgtt catctcagcc cctgcatgga  7920
```

```
aagctgaccc cagaggcaga actattccca gagagcttgg ccaagaaaaa caaaactacc  7980
agcctggcca ggctcaggag tagtaagctg cagtgtctgt tgtgttctag cttcaacagc  8040
tgcaggagtt ccactctcaa atgctccaca tttctcacat cctcctgatt ctggtcacta  8100
cccatcttca aagaacagaa tatctcacat cagcatactg tgaaggacta gtcatgggtg  8160
cagctgctca gagctgcaaa gtcattctgg atggtggaga gcttacaaac atttcatgat  8220
gctcccccg ctctgatggc tggagcccaa tccctacaca gactcctgct gtatgtgttt  8280
tcctttcact ctgagccaca gccagagggc aggcattcag tctcctcttc aggctggggc  8340
tggggcactg agaactcacc caacaccttg ctctcactcc ttctgcaaaa caagaaagag  8400
ctttgtgctg cagtagccat gaagaatgaa aggaaggctt taactaaaaa atgtcagaga  8460
ttattttcaa ccccttactg tggatcacca gcaaggagga aacacaacac agagacattt  8520
tttcccctca aattatcaaa agaatcactg catttgttaa agagagcaac tgaatcagga  8580
agcagagttt tgaacatatc agaagttagg aatctgcatc agagacaaat gcagtcatgg  8640
ttgtttgctg cataccagcc ctaatcatta gaagcctcat ggacttcaaa catcattccc  8700
tctgacaaga tgctctagcc taactccatg agataaaata aatctgcctt tcagagccaa  8760
agaagagtcc accagcttct tctcagtgtg aacaagagct ccagtcaggt tagtcagtcc  8820
agtgcagtag aggagaccag tctgcatcct ctaattttca aaggcaagaa gatttgttta  8880
ccctggacac caggcacaag tgaggtcaca gagctcttag atatgcagtc ctcatgagtg  8940
aggagactaa agcgcatgcc atcaagactt cagtgtagag aaaacctcca aaaaagcctc  9000
ctcactactt ctggaatagc tcagaggccg aggcggcctc ggcctctgca taaataaaaa  9060
aaattagtca gccatggggc ggagaatggg cggaactggg cggagttagg ggcgggatgg  9120
gcggagttag gggcgggact atggttgctg actaattgag atgcatgctt tgcatacttc  9180
tgcctgctgg ggagcctggg gactttccac acctggttgc tgactaattg agatgcatgc  9240
tttgcatact tctgcctgct ggggagcctg gggactttcc acaccctaac tgacacacat  9300
tccacagctg cattaatgaa tcggccaacg cgcggggaga ggcggtttgc gtattgggcg  9360
ctcttccgct tcctcgctca ctgactcgct gcgctcggtc gttcggctgc ggcgagcggt  9420
atcagctcac tcaaaggcgg taatacggtt atccacagaa tcaggggata acgcaggaaa  9480
gaacatgtga gcaaaaggcc agcaaaaggc caggaaccgt aaaaaggccg cgttgctggc  9540
gtttttccat aggctccgcc cccctgacga gcatcacaaa aatcgacgct caagtcagag  9600
gtggcgaaac ccgacaggac tataaagata ccaggcgttt ccccctggaa gctccctcgt  9660
gcgctctcct gttccgaccc tgccgcttac cggatacctg tccgcctttc tcccttcggg  9720
aagcgtggcg ctttctcata gctcacgctg taggtatctc agttcggtgt aggtcgttcg  9780
ctccaagctg ggctgtgtgc acgaaccccc cgttcagccc gaccgctgcg ccttatccgg  9840
taactatcgt cttgagtcca acccggtaag acacgactta tcgccactgg cagcagccac  9900
tggtaacagg attagcagag cgaggtatgt aggcggtgct acagagttct tgaagtggtg  9960
gcctaactac ggctacacta gaagaacagt atttggtatc tgcgctctgc tgaagccagt  10020
taccttcgga aaaagagttg gtagctcttg atccggcaaa caaaccaccg ctggtagcgg  10080
tggttttttt gtttgcaagc agcagattac gcgcagaaaa aaaggatctc aagaagatcc  10140
tttgatcttt tctacggggt ctgacgctca gtggaacgaa aactcacgtt aagggatttt  10200
ggtcatgaga ttatcaaaaa ggatcttcac ctagatcctt ttaaattaaa aatgaagttt  10260
taaatcaatc taaagtatat atgagtaaac ttggtctgac agttaccaat gcttaatcag  10320
tgaggcacct atctcagcga tctgtctatt tcgttcatcc atagttgcct gactcctgca  10380
aaccacgttg tgtctcaaaa tctctgatgt tacattgcac aagataaaaa tatatcatca  10440
tgaacaataa aactgtctgc ttacataaac agtaatacaa ggggtgttat gagccatatt  10500
caacgggaaa cgtcttgctc gaggccgcga ttaaattcca acatggatgc tgatttatat  10560
gggtataaat gggctcgcga taatgtcggg caatcaggtg cgacaatcta tcgattgtat  10620
gggaagcccg atgcgccaga gttgtttctg aaacatggca aaggtagcgt tgccaatgat  10680
gttacagatg agatggtcag actaaactgg ctgacggaat ttatgcctct tccgaccatc  10740
aagcatttta tccgtactcc tgatgatgca tggttactca ccactgcgat ccccgggaaa  10800
acagcattcc aggtattaga agaatatcct gattcaggtg aaaatattgt tgatgcgctg  10860
gcagtgttcc tgcgccggtt gcattcgatt cctgtttgta attgtccttt taacagcgat  10920
cgcgtatttc gtctcgctca ggcgcaatca cgaatgaata acggtttggt tgatgcgagt  10980
gattttgatg acgagcgtaa tggctggcct gttgaacaag tctggaaaga aatgcataag  11040
cttttgccat tctcaccgga ttcagtcgtc actcatggtg atttctcact tgataacctt  11100
atttttgacg aggggaaatt aataggttgt attgatgttg gacgagtcgg aatcgcagac  11160
cgataccagg atcttgccat cctatggaac tgcctcggtg agttttctcc ttcattacag  11220
aaacggcttt ttcaaaaata tggtattgat aatcctgata tgaataaatt gcagtttcat  11280
ttgatgctcg atgagttttt ctaagggcgg cctgccacca tacccacgcc gaaacaagcg  11340
ctcatgagcc cgaagtggcg agcccgatct tccccatcgg tgatgtcggc gatataggcg  11400
ccagcaaccg cacctgtggc gccggtgatg agggcgcgcc aagtcgacgt ccggcagtc   11459
```

```
SEQ ID NO: 63          moltype = AA  length = 274
FEATURE                Location/Qualifiers
REGION                 1..274
                       note = Synthetic polypeptide
source                 1..274
                       mol_type = protein
                       organism = synthetic construct
SEQUENCE: 63
MGKSLSHLPL HSSKEDAYDG VTSENMRNGL VNSEVHNEDG RNGDVSQFPY VEFTGRDSVT  60
CPTCQGTGRI PRGQENQLVA LIPYSDQRLR PRRTKLYVMA SVFVCLLLSG LAVFFLFPRS  120
IDVKYIGVKS AYVSYDVQKR TIYLNITNTL NITNNNYYSV EVENITAQVQ FSKTVIGKAR  180
LNNITIIGPL DMKQIDYTVP TVIAEEMSYM YDFCTLISIK VHNIVLMMQV TVTTTYFGHS  240
EQISQERYQY VDCGRNTTYQ LGQSEYLNVL QPQQ                            274
```

```
SEQ ID NO: 64          moltype = DNA  length = 825
FEATURE                Location/Qualifiers
misc_feature           1..825
                       note = Synthetic polynucleotide
source                 1..825
```

```
                         mol_type = other DNA
                         organism = synthetic construct
SEQUENCE: 64
atgggcaaga gcctgagcca cctgccccctg cacagcagca aggaggacgc ctacgacggc  60
gtgaccagcg agaacatgcg caacggcctg gtgaacagcg aggtgcacaa cgaggacggc  120
cgcaacggcg acgtgagcca gttcccctac gtggagttca ccggccgcga cagcgtgacc  180
tgccccacct gccagggcac cggccgcatc ccccgcggcc aggagaacca gctggtggcc  240
ctgatcccct acagcgacca gcgcctgcgc ccccgccgca ccaagctgta cgtgatggcc  300
agcgtgttcg tgtgcctgct gctgagcggc ctggccgtgt tcttcctgtt cccccgcagc  360
atcgacgtga agtacatcgg cgtgaagagc gcctacgtga gctacgacgt gcagaagcgc  420
accatctacc tgaacatcac caacaccctg aacatcacca acaacaacta ctacagcgtg  480
gaggtggaga acatcaccgc ccaggtgcag ttcagcaaga ccgtgatcgg caaggcccgc  540
ctgaacaaca tcaccatcat cggccccctg gacatgaagc agatcgacta caccgtgccc  600
accgtgatcg ccgaggagat gagctacatg tacgacttct gcaccctgat cagcatcaag  660
gtgcacaaca tcgtgctgat gatgcaggtg accgtgacca ccacctactt cggccacagc  720
gagcagatca gccaggagcg ctaccagtac gtggactgcg gccgcaacac cacctaccag  780
ctgggccaga gcgagtacct gaacgtgctg cagccccagc agtaa                 825

SEQ ID NO: 65            moltype = DNA  length = 267
FEATURE                  Location/Qualifiers
misc_feature             1..267
                         note = Synthetic polynucleotide
source                   1..267
                         mol_type = other DNA
                         organism = synthetic construct
SEQUENCE: 65
gtgatatcac aaggtcccag ggctggggtc agaaattctc tcccgaggga atgaagccac  60
aggagccaag agcaggagga ccaaggccct ggcgaaggcc gtggcctcgt tcaagtaaaa  120
gatcctagta cagtgcaggt cccaatgtgt actaggatct tttacttgaa cggggacgcc  180
ggcatccggg ctcaggaccc ccctctctgc cagaggcacc aacaccagag ttcacaaatc  240
agtctcctgc cctttgcatg tagcaaa                                     267

SEQ ID NO: 66            moltype = DNA  length = 267
FEATURE                  Location/Qualifiers
misc_feature             1..267
                         note = Synthetic polynucleotide
source                   1..267
                         mol_type = other DNA
                         organism = synthetic construct
SEQUENCE: 66
tttgctacat gcaaagggca ggagactgat ttgtgaactc tggtgttggt gcctctggca  60
gagagggggg tcctgagccc ggatgccggc gtccccgttc aagtaaaaga tcctagtaca  120
cattgggacc tgcactgtac taggatcttt tacttgaacg aggccacggc cttcgccagg  180
gccttggtcc tcctgctctt ggctcctgtg gcttcattcc ctcgggagag aatttctgac  240
cccagccctg ggaccttgtg atatcac                                     267

SEQ ID NO: 67            moltype = AA  length = 593
FEATURE                  Location/Qualifiers
REGION                   1..593
                         note = Synthetic polypeptide
source                   1..593
                         mol_type = protein
                         organism = synthetic construct
SEQUENCE: 67
MWTLVSWVAL TAGLVAGTRC PDGQFCPVAC CLDPGGASYS CCRPLLDKWP TTLSRHLGGP  60
CQVDAHCSAG HSCIFTVSGT SSCCPFPEAV ACGDGHHCCP RGFHCSADGR SCFQRSGNNS  120
VGAIQCPDSQ FECPDFSTCC VMVDGSWGCC PMPQASCCED RVHCCPHGAF CDLVHTRCIT  180
PTGTHPLAKK LPAQRTNRAV ALSSSVMCPD ARSRCPDGST CCELPSGKYG CCPMPNATCC  240
SDHLHCCPQD TVCDLIQSKC LSKENATTDL LTKLPAHTVG DVKCDMEVSC PDGYTCCRLQ  300
SGAWGCCPFT QAVCCEDHIH CCPAGFTCDT QKGTCEQGPH QVPWMEKAPA HLSLPDPQAL  360
KRDVPCDNVS SCPSSDTCCQ LTSGEWGCCP IPEAVCCSDH QHCCPQGYTC VAEGQCQRGS  420
EIVAGLEKMP ARRASLSHPR DIGCDQHTSC PVGQTCCPSL GGSWACCQLP HAVCCEDRQH  480
CCPAGYTCNV KARSCEKEVV SAQPATFLAR SPHVGVKDVE CGEGHFCHDN QTCCRDNRQG  540
WACCPYRQGV CCADRRHCCP AGFRCAARGT KCLRREAPRW DAPLRDPALR QLL        593

SEQ ID NO: 68            moltype = DNA  length = 1779
FEATURE                  Location/Qualifiers
misc_feature             1..1779
                         note = Synthetic polynucleotide
source                   1..1779
                         mol_type = other DNA
                         organism = synthetic construct
SEQUENCE: 68
atgtggaccc tggtgagctg ggtggccctg accgccggcc tggtggccgg cacccgctgc  60
cccgacggcc agttctgccc cgtggcctgc tgcctggacc ccggcggcgc cagctacagc  120
tgctgccgcc ccctgctgga caagtggccc accaccctga gccgccacct gggcggcccc  180
tgccaggtgg acgcccactg cagcgccggc cacagctgca tcttcaccgt gagcggcacc  240
agcagctgct gccccttccc cgaggccgtg gcctgcggcg acggccacca ctgctgcccc  300
cgcggcttcc actgcagcgc cgacggccgc agctgcttcc agcgcagcgg caacaacagc  360
```

```
gtgggcgcca tccagtgccc cgacagccag ttcgagtgcc ccgacttcag cacctgctgc  420
gtgatggtgg acggcagctg ggctgctgc cccatgcccc aggccagctg ctgcgaggac  480
cgcgtgcact gctgccccca cggcgccttc tgcgacctgg tgcacacccg ctgcatcacc  540
cccaccggca cccacccccct ggccaagaag ctgcccgccc agcgcaccaa ccgcgccgtg  600
gccctgagca gcagcgtgat gtgccccgac gcccgcagcc gctgccccga cggcagcacc  660
tgctgcgagc tgcccagcgg caagtacggc tgctgcccca tgcccaacgc cacctgctgc  720
agcgaccacc tgcactgctg cccccaggac accgtgtgcg acctgatcca gagcaagtgc  780
ctgagcaagg agaacgccac caccgacctg ctgaccaagc tgcccgccca caccgtgggc  840
gacgtgaagt gcgacatgga ggtgagctgc cccgacggct acacctgctg ccgcctgcag  900
agcggcgcct ggggctgctg ccccttcacc caggccgtgt gctgcgagga ccacatccac  960
tgctgccccg ccggcttcac ctgcgacacc cagaagggca cctgcgagca gggcccccac  1020
caggtgccct ggatggagaa ggcccccgcc cacctgagcc tgcccgaccc ccaggccctg  1080
aagcgcgacg tgccctgcga caacgtgagc agctgcccca gcagcgacac ctgctgccag  1140
ctgaccagcg gcgagtgggg ctgctgcccc atccccgagg ccgtgtgctg cagcgaccac  1200
cagcactgct gcccccaggg ctacacctgc gtggccgagg gccagtgcca gcgcggcagc  1260
gagatcgtgg ccggcctgga gaagatgccc gcccgccgcg ccagcctgag ccacccccgc  1320
gacatcggct gcgaccagca caccagctgc cccgtgggcc agacctgctg ccccagcctg  1380
ggcggcagct gggcctgctg ccagctgccc cacgccgtgt gctgcgagga ccgccagcac  1440
tgctgccccg ccggctacac ctgcaacgtg aaggcccgca gctgcgagaa ggaggtggtg  1500
agcgcccagc ccgccacctt cctggcccgc agcccccacg tgggcgtgaa ggacgtggag  1560
tgcggcgagg gccacttctg ccacgacaac cagacctgct gccgcgacaa ccgccagggc  1620
tgggcctgct gcccctaccg ccagggcgtg tgctgcgccg accgccgcca ctgctgcccc  1680
gccggcttcc gctgcgccgc ccgcggcacc aagtgcctgc gccgcgaggc cccccgctgg  1740
gacgcccccc tgcgcgaccc cgccctgcgc cagctgctg                         1779
```

```
SEQ ID NO: 69          moltype = DNA  length = 10871
FEATURE                Location/Qualifiers
misc_feature           1..10871
                       note = Synthetic polynucleotide
source                 1..10871
                       mol_type = other DNA
                       organism = synthetic construct
SEQUENCE: 69
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttaat tattttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
tgccttcgcc ccgtgccccg ctccgccgcc gcctcgcgcc gcccgccccg gctctgactg  1020
accgcgttac tcccacaggt gagcgggcgg gacggccctt ctcctccggg ctgtaattag  1080
cgcttggttt aatgacggct tgtttctttt ctgtggctgc gtgaaagcct tgaggggctc  1140
cgggagctag agcctctgct aaccatgttc atgccttctt ctttttccta cagctcctgg  1200
gcaacgtgct ggttattgtg ctgtctcatc attttggcaa agaattcctc gaagatccga  1260
agggaaagtc ttccacgact gtgggatccg ttcgaagata tcaccggttg agccaccatg  1320
tggaccctgg tgagctgggt ggccctgacc gccggcctgg tggccggcac ccgctgcccc  1380
gacggccagt tctgccccgt ggcctgctgc ctggaccccg gcggcgccag ctacagctgc  1440
tgccgccccc tgctggacaa gtggcccacc accctgagcc gccacctggg cggcccctgc  1500
caggtggacg cccactgcag cgccggccac agctgcatct tcaccgtgag cggcaccagc  1560
agctgctgcc ccttccccga ggccgtggcc tgcggcgacg gccaccactg ctgcccccgc  1620
ggcttccact gcagcgccga cggccgcagc tgcttccagc gcagcggcaa caacagcgtg  1680
ggcgccatcc agtgccccga cagccagttc gagtgccccg acttcagcac ctgctgcgtg  1740
atggtggacg gcagctgggg ctgctgcccc atgccccagg ccagctgctg cgaggaccgc  1800
gtgcactgct gcccccacgg cgccttctgc gacctggtgc acacccgctg catcaccccc  1860
accggcaccc acccccctggc caagaagctg cccgcccagc gcaccaaccg cgccgtggcc  1920
ctgagcagca gcgtgatgtg ccccgacgcc cgcagccgct gccccgacgg cagcacctgc  1980
tgcgagctgc ccagcggcaa gtacggctgc tgccccatgc ccaacgccac ctgctgcagc  2040
gaccacctgc actgctgccc ccaggacacc gtgtgcgacc tgatccagag caagtgcctg  2100
agcaaggaga acgccaccac cgacctgctg accaagctgc ccgcccacac cgtgggcgac  2160
gtgaagtgcg acatggaggt gagctgcccc gacggctaca cctgctgccg cctgcagagc  2220
ggcgcctggg gctgctgccc cttcacccag gccgtgtgct gcgaggacca catccactgc  2280
tgccccgccg gcttcacctg cgacacccag aagggcacct gcgagcaggg cccccaccag  2340
gtgccctgga tggagaaggc cccgcccac ctgagcctgc ccgaccccca ggccctgaag  2400
cgcgacgtgc cctgcgacaa cgtgagcagc tgccccagca gcgacacctg ctgccagctg  2460
accagcggcg agtggggctg ctgccccatc cccgaggccg tgtgctgcag cgaccaccag  2520
cactgctgcc cccagggcta cacctgcgtg gccgagggcc agtgccagcg cggcagcgag  2580
atcgtggccg gcctggagaa gatgcccgcc cgccgcgcca gcctgagcca cccccgcgac  2640
atcggctgcg accagcacac cagctgcccc gtgggccaga cctgctgccc cagcctgggc  2700
ggcagctggg cctgctgcca gctgccccac gccgtgtgct gcgaggaccg ccagcactgc  2760
```

```
tgccccgccg gctacacctg caacgtgaag gcccgcagct gcgagaagga ggtggtgagc  2820
gcccagcccg ccaccttcct ggcccgcagc ccccacgtgg gcgtgaagga cgtggagtgc  2880
ggcgagggcc acttctgcca cgacaaccag acctgctgcc gcgacaaccg ccagggctgg  2940
gcctgctgcc cctaccgcca gggcgtgtgc tgcgccgacc gccgccactg ctgccccgcc  3000
ggcttccgct gcgccgcccg cggcaccaag tgcctgcgcc gcgaggcccc ccgctgggac  3060
gcccccctgc gcgaccccgc cctgcgccag ctgctgtgac aattgttaat taagtttaaa  3120
ccctcgaggc cgcaagctta tcgataatca acctctggat tacaaaattt gtgaaagatt  3180
gactggtatt cttaactatg ttgctccttt tacgctatgt ggatacgctg ctttaatgcc  3240
tttgtatcat gctattgctt cccgtatggc tttcattttc tcctccttgt ataaatcctg  3300
gttgctgtct ctttatgagg agttgtggcc cgttgtcagg caacgtggcg tggtgtgcac  3360
tgtgtttgct gacgcaaccc ccactggttg gggcattgcc accacctgtc agctcctttc  3420
cgggactttc gctttccccc tccctattgc cacggcggaa ctcatcgccg cctgccttgc  3480
ccgctgctgg acaggggctc ggctgttggg cactgacaat tccgtggtgt tgtcggggaa  3540
atcatcgtcc tttccttggc tgctcgcctg tgttgccacc tggattctgc gcgggacgtc  3600
cttctgctac gtcccttcgg ccctcaatcc agcggacctt ccttcccgcg gcctgctgcc  3660
ggctctgcgg cctcttccgc gtcttcgcct tcgccctcag acgagtcgga tctccctttg  3720
ggccgcctcc ccgcatcgat accgtcgact agagctcgct gatcagcctc gactgtgcct  3780
tctagttgcc agccatctgt tgtttgcccc tcccccgtgc cttccttgac cctggaaggt  3840
gccactccca ctgtcctttc ctaataaaat gaggaaattg catcgcattg tctgagtagg  3900
tgtcattcta ttctgggggg tggggtgggg caggacagca agggggagga ttgggaagac  3960
aatagcaggc atgctgggga gagatccacg ataacaaaca gctttttttgg ggtgaacata  4020
ttgactgaat tccctgcagg ttggccactc cctctctgcg cgctcgctcg ctcactgagg  4080
ccgcccgggc aaagcccggg cgtcgggcga cctttggtcg cccggcctca gtgagcgagc  4140
gagcgcgcag agagggagtg gccaactcca tcactagggg ttcctgcggc cgctcgtacg  4200
gtctcgagga attcctgcag gataacttgc caacctcatt ctaaaatgta tatagaagcc  4260
caaaagacaa taacaaaaat attcttgtag aacaaaatgg gaaagaatgt tccactaaat  4320
atcaagattt agagcaaagc atgagatgtg tggggataga cagtgaggct gataaaatag  4380
agtagagctc agaaacagac ccattgatat atgtaagtga cctatgaaaa aaatatggca  4440
ttttacaatg ggaaaatgat ggtctttttc tttttagaa aaacagggaa atatatttat  4500
atgtaaaaaa taaaagggaa cccatatgtc ataccataca cacaaaaaaa ttccagtgaa  4560
ttataagtct aaatggagaa ggcaaaactt taaatctttt agaaaataat atagaagcat  4620
gcagaccagc ctggccaaca tgatgaaacc ctctctacta ataataaaat cagtagaact  4680
actcaggact actttgagtg ggaagtcctt ttctatgaag acttctttgg ccaaaattag  4740
gctctaaatg caaggagata gtgcatcatg cctggctgca cttactgata aatgatgtta  4800
tcaccatctt taaccaaatg cacaggaaca agttatggta ctgatgtgct ggattgagaa  4860
ggagctctac ttccttgaca ggacacattt gtatcaactt aaaaaagcag atttttgcca  4920
gcagaactat tcattcagag gtaggaaact tagaatagat gatgtcactg attagcatgg  4980
cttccccatc tccacagctg cttcccaccc aggttgccca cagttgagtt tgtccagtgc  5040
tcagggctgc ccactctcag taagaagccc cacaccagcc cctctccaaa tatgttggct  5100
gttccttcca ttaaagtgac cccactttag agcagcaagt ggatttctgt ttcttacagt  5160
tcaggaagga ggagtcagct gtgagaacct ggagcctgag atgcttctaa gtcccactgc  5220
tactggggtc agggaagcca gactccagca tcagcagtca ggagcactaa gcccttgcca  5280
acatcctgtt tctcagagaa actgcttcca ttataatggt tgtccttttt taagctatca  5340
agccaaacaa ccagtgtcta ccattattct catcacctga agccaagggt tctagcaaaa  5400
gtcaagctgt cttgtaatgg ttgatgtgcc tccagcttct gtcttcagtc actccactct  5460
tagcctgctc tgaatcaact ctgaccacag ttccctggag cccctgccac ctgctgcccc  5520
tgccaccttc tccatctgca gtgctgtgca gccttctgca ctcttgcaga gctaataggt  5580
ggagacttga aggaagagga ggaaagtttc tcataatagc cttgctgcaa gctcaaatgg  5640
gaggtgggca ctgtgcccag gagccttgga gcaaaggctg tgcccaacct ctgactgcat  5700
ccaggtttgg tcttgacaga gataagaagc cctggctttt ggagccaaaa tctaggtcag  5760
acttaggcag gattctcaaa gtttatcagc agaacatgag gcagaagacc ctttctgctc  5820
cagcttcttc aggctcaacc ttcatcagaa tagatagaaa gagaggctgt gagggttctt  5880
aaaacagaag caaatctgac tcagagaata aacaacctcc tagtaaacta cagcttagac  5940
agagcatctg gtggtgagtg tgctcagtgt cctactcaac tgtctggtat cagccctcat  6000
gaggacttct cttctttccc tcatagacct ccatctctgt tttccttagc ctgcagaaat  6060
ctggatggct attcacagaa tgcctgtgct ttcagagttg catttttttct ctggtattct  6120
ggttcaagca tttgaaggta ggaaaggttc tccaagtgca agaaagccag ccctgagcct  6180
caactgcctg gctagtgtgg tcagtaggat gcaaaggctg ttgaatgcca caaggccaaa  6240
ctttaacctg tgtaccacaa gcctagcagc agaggcagct ctgctcactg gaactctctg  6300
tcttctttct cctgagcctt ttcttttcct gagttttcta gctctcctca accttacctc  6360
tgccctaccc aggacaaacc caagagccac tgtttctgtg atgtcctctc cagccctaat  6420
taggcatcat gacttcagcc tgaccttcca tgctcagaag cagtgctaat ccacttcaga  6480
tgagctgctc tatgcaacac aggcagagcc tacaaacctt tgcaccagag ccctccacat  6540
atcagtgttt gttcatactc acttcaacag caaatgtgac tgctgagatt aagattttac  6600
acaagatggt ctgtaatttc acagttagtt ttatcccatt aggtatgaaa gaattagcat  6660
aattcccctt aaacatgaat gaatcttaga ttttttaata aatagttttg gaagtaaaga  6720
cagagacatc aggagcacaa ggaatagcct gagaggacaa acagaacaag aaagagtctg  6780
gaaatacaca ggatgttctt ggcctcctca aagcaagtgc aagcagatag taccagcagc  6840
cccaggctat cagagcccag tgaagagaag taccatgaaa gccacagctc taaccaccct  6900
gttccagagt gacagacagt ccccaagaca agccagcctg agccagagag agaactgcaa  6960
gagaaagttt ctaatttagg ttctgttaga ttcagacaag tgcaggtcat cctctctcca  7020
cagctactca cctctccagc ctaacaaagc ctgcagtcca cactccaacc ctggtgtctc  7080
acctcctagc ctctcccaac atcctgctct ctgaccatct tctgcatctc tcatctcacc  7140
atctcccact gtctacagcc tactcttgca actaccatct cattttctga catcctgtct  7200
acatcttctg ccatactctg ccatctacca taccacctct taccatctac cacaccatct  7260
tttatctcca tccctctcag aagcctccaa gctgaatcct gctttatgtg ttcatctcag  7320
cccctgcatg gaaagctgac cccagaggca gaactattcc cagagagctt ggccaagaaa  7380
aacaaaacta ccagcctggc caggctcagg agtagtaagc tgcagtgtct gttgtgttct  7440
agcttcaaca gctgcaggag ttccactctc aaatgctcca catttctcac atcctcctga  7500
```

```
ttctggtcac tacccatctt caaagaacag aatatctcac atcagcatac tgtgaaggac  7560
tagtcatggg tgcagctgct cagagctgca aagtcattct ggatggtgga gagcttacaa  7620
acatttcatg atgctccccc cgctctgatg gctggagccc aatccctaca cagactcctg  7680
ctgtatgtgt tttcctttca ctctgagcca cagccagagg gcaggcattc agtctcctct  7740
tcaggctggg gctggggcac tgagaactca cccaacacct tgctctcact ccttctgcaa  7800
aacaagaaag agctttgtgc tgcagtagcc atgaagaatg aaaggaaggc tttaactaaa  7860
aaatgtcaga gattatttc aacccttac tgtggatcac cagcaaggag gaaacacaac  7920
acagagacat tttttcccct caaattatca aaagaatcac tgcatttgtt aaagagagca  7980
actgaatcag gaagcagagt tttgaacata tcagaagtta ggaatctgca tcagagacaa  8040
atgcagtcat ggttgtttgc tgcataccag ccctaatcat tagaagcctc atggacttca  8100
aacatcattc cctctgacaa gatgctctag cctaactcca tgagataaaa taaatctgcc  8160
tttcagagcc aaagaagagt ccaccagctt cttctcagtg tgaacaagag ctccagtcag  8220
gttagtcagt ccagtgcagt agaggagacc agtctgcatc ctctaatttt caaaggcaag  8280
aagatttgtt taccctggac accaggcaca agtgaggtca cagagctctt agatatgcag  8340
tcctcatgag tgaggagact aaagcgcatg ccatcaagac ttcagtgtag agaaaacctc  8400
caaaaaagcc tcctcactac ttctggaata gctcagaggc cgaggcggcc tcggcctctg  8460
cataaataaa aaaaattagt cagccatggg gcggagaatg ggcggaactg ggcggagtta  8520
ggggcgggat gggcggagtt aggggcggga ctatggttgc tgactaattg agatgcatgc  8580
tttgcatact tctgcctgct ggggagcctg gggactttcc acacctggtt gctgactaat  8640
tgagatgcat gctttgcata cttctgcctg ctggggagcc tggggacttt ccacacccta  8700
actgacacac attccacagc tgcattaatg aatcggccaa cgcgcgggga gaggcggttt  8760
gcgtattggg cgctcttccg cttcctcgct cactgactcg ctgcgctcgg tcgttcggct  8820
gcggcgagcg gtatcagctc actcaaaggc ggtaatacgg ttatccacag aatcagggga  8880
taacgcagga aagaacatgt gagcaaaagg ccagcaaaag gccaggaacc gtaaaaaggc  8940
cgcgttgctg gcgtttttcc ataggctccg cccccctgac gagcatcaca aaaatcgacg  9000
ctcaagtcag aggtggcgaa acccgacagg actataaaga taccaggcgt ttccccctgg  9060
aagctccctc gtgcgctctc ctgttccgac cctgccgctt accggatacc tgtccgcctt  9120
tctcccttcg ggaagcgtgg cgctttctca tagctcacgc tgtaggtatc tcagttcggt  9180
gtaggtcgtt cgctccaagc tgggctgtgt gcacgaaccc cccgttcagc ccgaccgctg  9240
cgccttatcc ggtaactatc gtcttgagtc caacccggta agacacgact tatcgccact  9300
ggcagcagcc actggtaaca ggattagcag agcgaggtat gtaggcggtg ctacagagtt  9360
cttgaagtgg tggcctaact acggctacac tagaagaaca gtatttggta tctgcgctct  9420
gctgaagcca gttaccttcg gaaaaagagt tggtagctct tgatccggca aacaaaccac  9480
cgctggtagc ggtggttttt ttgtttgcaa gcagcagatt acgcgcagaa aaaaaggatc  9540
tcaagaagat cctttgatct tttctacggg gtctgacgct cagtggaacg aaaactcacg  9600
ttaagggatt ttggtcatga gattatcaaa aaggatcttc acctagatcc ttttaaatta  9660
aaaatgaagt tttaaatcaa tctaaagtat atatgagtaa acttggtctg acagttacca  9720
atgcttaatc agtgaggcac ctatctcagc gatctgtcta tttcgttcat ccatagttgc  9780
ctgactcctg caaaccacgt tgtgtctcaa aatctctgat gttacattgc acaagataaa  9840
aatatatcat catgaacaat aaaactgtct gcttacataa acagtaatac aaggggtgtt  9900
atgagccata ttcaacggga aacgtcttgc tcgaggccgc gattaaattc caacatggat  9960
gctgatttat atgggtataa atgggctcgc gataatgtcg ggcaatcagg tgcgacaatc  10020
tatcgattgt atgggaagcc cgatgcgcca gagttgtttc tgaaacatgg caaaggtagc  10080
gttgccaatg atgttacaga tgagatggtc agactaaact ggctgacgga atttatgcct  10140
cttccgacca tcaagcattt tatccgtact cctgatgatg catggttact caccactgcg  10200
atccccggga aaacagcatt ccaggtatta gaagaatatc ctgattcagg tgaaaatatt  10260
gttgatgcgc tggcagtgtt cctgcgccgg ttgcattcga ttcctgtttg taattgtcct  10320
tttaacagcg atcgcgtatt tcgtctcgct caggcgcaat cacgaatgaa taacggtttg  10380
gttgatgcga gtgattttga tgacgagcgt aatggctggc ctgttgaaca agtctggaaa  10440
gaaatgcata agcttttgcc attctcaccg gattcagtcg tcactcatgg tgatttctca  10500
cttgataacc ttatttttga cgaggggaaa ttaataggtt gtattgatgt tggacgagtc  10560
ggaatcgcag accgatacca ggatcttgcc atcctatgga actgcctcgg tgagttttct  10620
ccttcattac agaaacggct ttttcaaaaa tatggtattg ataatcctga tatgaataaa  10680
ttgcagtttc atttgatgct cgatgagttt ttctaaggcg ggcctgccac catacccacg  10740
ccgaaacaag cgctcatgag cccgaagtgg cgagcccgat cttccccatc ggtgatgtcg  10800
gcgatatagg cgccagcaac cgcacctgtg gcgccggtga tgagggcgcg ccaagtcgac  10860
gtccggcagt c                                                       10871
```

```
SEQ ID NO: 70          moltype = DNA  length = 4151
FEATURE                Location/Qualifiers
misc_feature           1..4151
                       note = Synthetic polynucleotide
source                 1..4151
                       mol_type = other DNA
                       organism = synthetic construct
SEQUENCE: 70
gggaggttac gcgttcgtcg actactagtg ggtaccagag cgggcggagt tagggcggag  60
ccaatcagcg tgcgccgttc cgaaagttgc cttttatggc tgggcggaga atgggcggtg  120
aacgccgatg attatataag gacgcgccgg gtgtggcaca gctagttccg tcgcagccgg  180
gatttgggtc gcggttcttg tttgtggatc cctgtgatcg tcacttggta agtcactgac  240
tgtctatgcc tgggaaaggg tgggcaggag atggggcagt gcaggaaaag tggcactatg  300
aaccctgcag ccctaggaat gcatctagac aattgtacta accttcttct ctttcctctc  360
ctgacagtcc ggaaagccac catgtacgcc ctgttcctgc tggccagcct gctgggcgcc  420
gccctggccg gccccgtgct gggcctgaag gagtgcaccc gcggcagcgc cgtgtggtgc  480
cagaacgtga agaccgccag cgactgcggc gccgtgaagc actgcctgca gaccgtgtgg  540
aacaagccca ccgtgaagag cctgccctgc gacatctgca aggacgtggt gaccgccgcc  600
ggcgacatgc tgaaggacaa cgccaccgag gaggagatcc tggtgtacct ggagaagacc  660
tgcgactggc tgcccaagcc caacatgagc gccagctgca aggagatcgt ggacagctac  720
ctgcccgtga tcctggacat catcaagggc gagatgagcc gccccggcga ggtgtgcagc  780
```

```
gccctgaacc tgtgcgagag cctgcagaag cacctggccg agctgaacca ccagaagcag  840
ctggagagca acaagatccc cgagctggac atgaccgagg tggtggcccc cttcatggcc  900
aacatccccc tgctgctgta cccccaggac ggcccccgca gcaagcccca gcccaaggac  960
aacggcgacg tgtgccagga ctgcatccag atggtgaccg acatccagac cgccgtgcgc  1020
accaacagca ccttcgtgca ggccctggtg gagcacgtga aggaggagtg cgaccgcctg  1080
ggccccggca tggccgacat ctgcaagaac tacatcagcc agtacagcga gatcgccatc  1140
cagatgatga tgcacatgca gcccaaggag atctgcgccc tggtgggctt ctgcgacgag  1200
gtgaaggaga tgcccatgca gaccctggtg cccgccaagg tggccagcaa gaacgtgatc  1260
cccgccctgg agctggtgga gcccatcaag aagcacgagg tgcccgccaa gagcgacgtg  1320
tactgcgagg tgtgcgagtt cctggtgaag gaggtgacca agctgatcga caacaacaag  1380
accgagaagg agatcctgga cgccttcgac aagatgtgca gcaagctgcc caagagcctg  1440
agcgaggagt gccaggaggt ggtggacacc tacggcagca gcatcctgag catcctgctg  1500
gaggaggtga gccccgagct ggtgtgcagc atgctgcacc tgtgcagcgg cacccgcctg  1560
cccgccctga ccgtgcacgt gacccagccc aaggacggcg gcttctgcga ggtgtgcaag  1620
aagctggtgg gctacctgga ccgcaacctg gagaagaaca gcaccaagca ggagatcctg  1680
gccgccctgg agaagggctg cagcttcctg cccgacccct accagaagca gtgcgaccag  1740
ttcgtggccg agtacgagcc cgtgctgatc gagatcctgg tggaggtgat ggacccagc  1800
ttcgtgtgcc tgaagatcgg cgcctgcccc agcgcccaca agcccctgct gggcaccgag  1860
aagtgcatct ggggccccag ctactggtgc cagaacaccg agaccgccgc ccagtgcaac  1920
gccgtggagc actgcaagcg ccacgtgtgg aacagaagaa agagaggaag tggagagggc  1980
agaggaagtc ttctgacatg cggagacgtg gaagagaatc ccggccctat gtggaccctg  2040
gtgagctggg tggccctgac cgccggcctg gtggccggca cccgctgccc cgacggccag  2100
ttctgccccg tggcctgctg cctggacccc ggcggcgcca gctacagctg ctgccgcccc  2160
ctgctggaca agtggcccac caccctgagc cgccacctgg gcggcccctg ccaggtggac  2220
gcccactgca gcgccggcca cagctgcatc ttcaccgtga gcggcaccag cagctgctgc  2280
cccttccccg aggccgtggc ctgcggcgac ggccaccact gctgcccccg cggcttccac  2340
tgcagcgccg acggccgcag ctgcttccag cgcagcggca acaacagcgt gggcgccatc  2400
cagtgccccg acagccagtt cgagtgcccc gacttcagca cctgctgcgt gatggtggac  2460
ggcagctggg gctgctgccc catgccccag gccagctgct gcgaggaccg cgtgcactgc  2520
tgcccccacg gcgccttctg cgacctggtg cacacccgct gcatcacccc caccggcacc  2580
cacccccctgg ccaagaagct gcccgcccag cgcaccaacc gcgccgtggc cctgagcagc  2640
agcgtgatgt gccccgacgc ccgcagccgc tgccccgacg gcagcacctg ctgcgagctg  2700
cccagcggca agtacggctg ctgccccatg cccaacgcca cctgctgcag cgaccacctg  2760
cactgctgcc cccaggacac cgtgtgcgac ctgatccaga gcaagtgcct gagcaaggag  2820
aacgccacca ccgacctgct gaccaagctg cccgcccaca ccgtgggcga cgtgaagtgc  2880
gacatggagg tgagctgccc cgacggctac acctgctgcc gcctgcagag cggcgcctgg  2940
ggctgctgcc ccttcaccca ggccgtgtgc tgcgaggacc acatccactg ctgccccgcc  3000
ggcttcacct gcgacaccca gaagggcacc tgcgagcagg gcccccacca ggtgccctgg  3060
atggagaagg cccccgccca cctgagcctg cccgaccccc aggccctgaa gcgcgacgtg  3120
ccctgcgaca acgtgagcag ctgccccagc agcgacacct gctgccagct gaccagcggc  3180
gagtggggct gctgccccat ccccgaggcc gtgtgctgca gcgaccacca gcactgctgc  3240
ccccagggct acacctgcgt ggccgagggc cagtgccagc gcggcagcga gatcgtggcc  3300
ggcctggaga agatgcccgc ccgccgcgcc agcctgagcc acccccgcga catcggctgc  3360
gaccagcaca ccagctgccc cgtgggccag acctgctgcc ccagcctggg cggcagctgg  3420
gcctgctgcc agctgcccca cgccgtgtgc tgcgaggacc gccagcactg ctgccccgcc  3480
ggctacacct gcaacgtgaa ggcccgcagc tgcgagaagg aggtggtgag cgcccagccc  3540
gccaccttcc tggcccgcag cccccacgtg ggcgtgaagg acgtggagtg cggcgagggc  3600
cacttctgcc acgacaacca gacctgctgc cgcgacaacc gccagggctg ggcctgctgc  3660
ccctaccgcc agggcgtgtg ctgcgccgac cgccgccact gctgccccgc cggcttccgc  3720
tgcgccgccc gcggcaccaa gtgcctgcgc cgcgaggccc cccgctggga cgccccccctg  3780
cgcgaccccg ccctgcgcca gctgctgtga caattgttaa ttaagtttaa accctcgagg  3840
ccgcaagcaa taaaatatct ttattttcat tacatctgtg tgttggtttt ttgtgtgaca  3900
attgttaatt aagtttaaac gttcgaggcc gcaagcgaga tccacgataa caaacagctt  3960
ttttggggtg aacatattga ctgaattccc tgcaggttgg ccactccctc tctgcgcgct  4020
cgctcgctca ctgaggccgc ccgggcaaag cccgggcgtc gggcgacctt tggtcgcccg  4080
gcctcagtga gcgagcgagc gcgcagagag ggagtggcca actccatcac taggggttcc  4140
tgcggccgct c                                                       4151
```

```
SEQ ID NO: 71          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 71
aagagggtgt tctctatgta ggc                                          23

SEQ ID NO: 72          moltype = DNA  length = 22
FEATURE                Location/Qualifiers
misc_feature           1..22
                       note = Synthetic polynucleotide
source                 1..22
                       mol_type = other DNA
                       organism = synthetic construct
SEQUENCE: 72
gctcctccaa catttgtcac tt                                           22

SEQ ID NO: 73          moltype = DNA  length = 23
```

```
FEATURE                Location/Qualifiers
misc_feature           1..23
                       note = Synthetic polynucleotide
source                 1..23
                       mol_type = other DNA
                       organism = synthetic construct
SEQUENCE: 73
acacagtacc taccgttata gca                                           23

SEQ ID NO: 74          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 74
tgttgtcaca gtaacttgca tca                                           23

SEQ ID NO: 75          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 75
ctgggctaca ctgagcacc                                                19

SEQ ID NO: 76          moltype = DNA  length = 21
FEATURE                Location/Qualifiers
misc_feature           1..21
                       note = Synthetic polynucleotide
source                 1..21
                       mol_type = other DNA
                       organism = synthetic construct
SEQUENCE: 76
aagtggtcgt tgagggcaat g                                             21

SEQ ID NO: 77          moltype = DNA  length = 20
FEATURE                Location/Qualifiers
misc_feature           1..20
                       note = Synthetic polynucleotide
source                 1..20
                       mol_type = other DNA
                       organism = synthetic construct
SEQUENCE: 77
tattagatct gatggccgcg                                               20

SEQ ID NO: 78          moltype = DNA  length = 20
FEATURE                Location/Qualifiers
misc_feature           1..20
                       note = Synthetic polynucleotide
source                 1..20
                       mol_type = other DNA
                       organism = synthetic construct
SEQUENCE: 78
tccatcacta ggggttcctg                                               20

SEQ ID NO: 79          moltype = DNA  length = 4013
FEATURE                Location/Qualifiers
misc_feature           1..4013
                       note = Synthetic polynucleotide
source                 1..4013
                       mol_type = other DNA
                       organism = synthetic construct
SEQUENCE: 79
ttggccactc cctctctgcg cgctcgctcg ctcactgagg ccgcccgggc aaagcccggg  60
cgtcgggcga cctttggtcg cccggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
```

```
ccccaatttt gtatttattt attttttaat tattttgtgc agcgatgggg gcgggggggg  780
gggggggcgcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgg  1320
aattcagcag ccccagcaga gaggaatgcc ccaagcctct gagccgggtg tcaatcatgg  1380
ccggatctct gacaggactg ctgctgcttc aggccgtgtc ttgggcttct ggcgctagac  1440
cttgcatccc caagagcttc ggctacagca gcgtcgtgtg cgtgtgcaat gccacctact  1500
gcgacagctt cgaccctcct acctttcctg ctctgggcac cttcagcaga tacgagagca  1560
ccagatccgg cagacggatg gaactgagca tgggacccat ccaggccaat cacacaggca  1620
ctggcctgct gctgacactg cagcctgagc agaaattcca gaaagtgaaa ggcttcggcg  1680
gagccatgac agatgccgcc gctctgaata tcctggctct gtctccacca gctcagaacc  1740
tgctgctcaa gagctacttc agcgaggaag gcatcggcta caacatcatc agagtgccca  1800
tggccagctg cgacttcagc atcaggacct acacctacgc cgacacaccc gacgatttcc  1860
agctgcacaa cttcagcctg cctgaagagg acaccaagct gaagatccct ctgatccaca  1920
gagccctgca gctggcacaa agacccgtgt cactgctggc ctctccatgg acatctccca  1980
cctggctgaa aacaaatggc gccgtgaatg gcaagggcag cctgaaaggc caacctggcg  2040
acatctacca ccagacctgg gccagatact tcgtgaagtt cctggacgcc tatgccgagc  2100
acaagctgca gttttgggcc gtgacagccg agaacgaacc ttctgctgga ctgctgagcg  2160
gctacccctt tcagtgcctg ggctttacac ccgagcacca gcgggacttt atcgcccgtg  2220
atctgggacc cacactggcc aatagcaccc accataatgt gcggctgctg atgctggacg  2280
accagagact gcttctgccc cactgggcta aagtggtgct gacagatcct gaggccgcca  2340
aatacgtgca cggaatcgcc gtgcactggt atctggactt tctggcccct gccaaggcca  2400
cactgggaga gacacacaga ctgttcccca acaccatgct gttcgccagc gaagcctgtg  2460
tgggcagcaa gttttgggaa cagagcgtgc ggctcggcag ctgggataga ggcatgcagt  2520
acagccacag catcatcacc aacctgctgt accacgtcgt cggctggacc gactggaatc  2580
tggccctgaa tcctgaaggc ggccctaact gggtccgaaa cttcgtggac agccccatca  2640
tcgtggacat caccaaggac accttctaca agcagcccat gttctaccac ctgggacact  2700
tcagcaagtt catccccgag ggctctcagc gcgttggact ggtggcttcc cagaagaacg  2760
atctggacgc cgtggctctg atgcaccctg atggatctgc tgtggtggtg gtcctgaacc  2820
gcagcagcaa agatgtgccc ctgaccatca aggatcccgc cgtgggattc ctggaaacaa  2880
tcagccctgg ctactccatc cacacctacc tgtggcgtag acagtgacaa ttgttaatta  2940
agtttaaacc ctcgaggccg caagcttatc gataatcaac ctctggatta caaaatttgt  3000
gaaagattga ctggtattct taactatgtt gctcctttta cgctatgtgg atacgctgct  3060
ttaatgcctt tgtatcatgc tattgcttcc cgtatggctt tcattttctc ctccttgtat  3120
aaatcctggt tgctgtctct ttatgaggag ttgtggcccg ttgtcaggca acgtggcgtg  3180
gtgtgcactg tgtttgctga cgcaacccccc actggttggg gcattgccac cacctgtcag  3240
ctcctttccg ggactttcgc tttccccctc cctattgcca cggcggaact catcgccgcc  3300
tgccttgccc gctgctggac aggggctcgg ctgttgggca ctgacaattc cgtggtgttg  3360
tcggggaaat catcgtcctt tccttggctg ctcgcctgtg ttgccacctg gattctgcgc  3420
gggacgtcct tctgctacgt cccttcggcc ctcaatccag cggaccttcc ttcccgcggc  3480
ctgctgccgg ctctgcggcc tcttccgcgt cttcgccttc gccctcagac gagtcggatc  3540
tccctttggg ccgcctcccc gcatcgatac cgtcgactag agctcgctga tcagcctcga  3600
ctgtgccttc tagttgccag ccatctgttg tttgcccctc ccccgtgcct tccttgaccc  3660
tggaaggtgc cactcccact gtcctttcct aataaaatga ggaaattgca tcgcattgtc  3720
tgagtaggtg tcattctatt ctgggggggtg gggtggggca ggacagcaag ggggaggatt  3780
gggaagacaa tagcaggcat gctggggaga gatccacgat aacaaacagc tttttttgggg  3840
tgaacatatt gactgaattc cctgcaggtt ggccactccc tctctgcgcg ctcgctcgct  3900
cactgaggcc gcccgggcaa agcccgggcg tcgggcgacc tttggtcgcc cggcctcagt  3960
gagcgagcga gcgcgcagag agggagtggc caactccatc actaggggtt cct         4013

SEQ ID NO: 80           moltype = DNA  length = 4013
FEATURE                 Location/Qualifiers
misc_feature            1..4013
                        note = Synthetic polynucleotide
source                  1..4013
                        mol_type = other DNA
                        organism = synthetic construct
SEQUENCE: 80
ttggccactc cctctctgcg cgctcgctcg ctcactgagg ccgcccgggc aaagcccggg  60
cgtcgggcga cctttggtcg cccggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt attttttaat tattttgtgc agcgatgggg gcgggggggg  780
gggggggcgcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
```

```
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgg  1320
aattcagcag ccccagcaga gaggaatgcc ccaagcctct gagccgggtg tcaatcatgg  1380
ccggatctct gacaggactg ctgctgcttc aggccgtgtc ttgggcttct ggcgctagac  1440
cttgcatccc caagagcttc ggctacagca gcgtcgtgtg cgtgtgcaat gccacctact  1500
gcgacagctt cgaccctcct acctttcctg ctctgggcac cttcagcaga tacgagagca  1560
ccagatccgg cagacggatg gaactgagca tgggacccat ccaggccaat cacacaggca  1620
ctggcctgct gctgacactg cagcctgagc agaaattcca gaaagtgaaa ggcttcggcg  1680
gagccatgac agatgccgcc gctctgaata tcctggctct gtctccacca gctcagaacc  1740
tgctgctcaa gagctacttc agcgaggaag gcatcggcta caacatcatc agagtgccca  1800
tggccagctg cgacttcagc atcaggacct acacctacgc cgacacaccc gacgatttcc  1860
agctgcacaa cttcagcctg cctgaagagg acaccaagct gaagatccct ctgatccaca  1920
gagccctgca gctggcacaa agacccgtgt cactgctggc ctctccatgg acatctccca  1980
cctggctgaa aacaaatggc gccgtgaatg gcaagggcag cctgaaaggc caacctggcg  2040
acatctacca ccagacctgg gccagatact tcgtgaagtt cctggacgcc tatgccgagc  2100
acaagctgca gttttgggcc gtgacagccg agaacgaacc ttctgctgga ctgctgagcg  2160
gctacccctt tcagtgcctg ggctttacac ccgagcacca gcgggacttt atcgcccgtg  2220
atctgggacc cacactggcc aatagcaccc accataatgt gcggctgctg atgctggacg  2280
accagagact gcttctgccc cactgggcta aagtggtgct gacagatcct gaggccgcca  2340
aatacgtgca cggaatcgcc gtgcactggt atctggactt tctggcccct gccaaggcca  2400
cactgggaga gacacacaga ctgttcccca acaccatgct gttcgccagc gaagcctgtg  2460
tgggcagcaa gttttgggaa cagagcgtgc ggctcggcag ctgggataga ggcatgcagt  2520
acagccacag catcatcacc aacctgctgt accacgtcgt cggctggacc gactggaatc  2580
tggccctgaa tcctgaaggc ggccctaact gggtccgaaa cttcgtggac agccccatca  2640
tcgtggacat caccaaggac accttctaca agcagcccat gttctaccac ctgggacact  2700
tcagcaagtt catccccgag ggctctcagc gcgttggact ggtggcttcc cagaagaacg  2760
atctggacgc cgtggctctg atgcaccctg atggatctgc tgtggtggtg gtcctgaacc  2820
gcagcagcaa agatgtgccc ctgaccatca aggatcccgc cgtgggattc ctggaaacaa  2880
tcagccctgg ctactccatc cacacctacc tgtggcgtag acagtgacaa ttgttaatta  2940
agtttaaacc ctcgaggccg caagcttatc gataatcaac ctctggatta caaaatttgt  3000
gaaagattga ctggtattct taactatgtt gctcctttta cgctatgtgg atacgctgct  3060
ttaatgcctt tgtatcatgc tattgcttcc cgtatggctt tcattttctc ctccttgtat  3120
aaatcctggt tgctgtctct ttatgaggag ttgtggcccg ttgtcaggca acgtggcgtg  3180
gtgtgcactg tgtttgctga cgcaaccccc actggttggg gcattgccac cacctgtcag  3240
ctcctttccg ggactttcgc tttccccctc cctattgcca cggcggaact catcgccgcc  3300
tgccttgccc gctgctggac aggggctcgg ctgttgggca ctgacaattc cgtggtgttg  3360
tcggggaaat catcgtcctt tccttggctg ctcgcctgtg ttgccacctg gattctgcgc  3420
gggacgtcct tctgctacgt cccttcggcc ctcaatccag cggaccttcc ttcccgcggc  3480
ctgctgccgg ctctgcggcc tcttccgcgt cttcgccttc gccctcagac gagtcggatc  3540
tccctttggg ccgcctcccc gcatcgatac cgtcgactag agctcgctga tcagcctcga  3600
ctgtgccttc tagttgccag ccatctgttg tttgcccctc ccccgtgcct tccttgaccc  3660
tggaaggtgc cactcccact gtcctttcct aataaaatga ggaaattgca tcgcattgtc  3720
tgagtaggtg tcattctatt ctggggggtg gggtggggca ggacagcaag ggggaggatt  3780
gggaagacaa tagcaggcat gctggggaga gatccacgat aacaaacagc tttttggggg  3840
tgaacatatt gactgaattc cctgcaggtt ggccactccc tctctgcgcg ctcgctcgct  3900
cactgaggcc gcccgggcaa agcccgggcg tcgggcgacc tttggtcgcc cggcctcagt  3960
gagcgagcga gcgcgcagag agggagtggc caactccatc actaggggtt cct         4013

SEQ ID NO: 81          moltype = DNA  length = 4162
FEATURE                Location/Qualifiers
misc_feature           1..4162
                       note = Synthetic polynucleotide
source                 1..4162
                       mol_type = other DNA
                       organism = synthetic construct
SEQUENCE: 81
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
cccaatttt gtatttattt attttttaat tattttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
tgccttcgcc ccgtgccccg ctccgccgcc gcctcgcgcc gcccgccccg gctctgactg  1020
accgcgttac tcccacaggt gagcgggcgg gacggccctt ctcctcagcg ctgtaattag  1080
```

```
cgcttggttt aatgacggct tgttggaggc ttgctgaagg ctgtatgctg ttgtctttag  1140
aaataagtgg tagtcaagtg aagccacaga tgtgactacc acttatttct aaaaggacac  1200
aaggcctgtt actagcactc acatggaaca aatggccacc gtgggaggat gacaatttct  1260
gtggctgcgt gaaagccttg aggggctccg ggagctagag cctctgctaa ccatgttcat  1320
gccttcttct ttttcctaca gctcctgggc aacgtgctgg ttattgtgct gtctcatcat  1380
tttggcaaag aattcctcga agatccgaag ggaaagtctt ccacgactgt gggatccgtt  1440
cgaagatatc accggttgag ccaccatgga attcagcagc cccagcagag aggaatgccc  1500
caagcctctg agccgggtgt caatcatggc cggatctctg acaggactgc tgctgcttca  1560
ggccgtgtct tgggcttctg gcgctagacc ttgcatcccc aagagcttcg gctacagcag  1620
cgtcgtgtgc gtgtgcaatg ccacctactg cgacagcttc gaccctccta cctttcctgc  1680
tctgggcacc ttcagcagat acgagagcac cagatccggc agacggatgg aactgagcat  1740
gggacccatc caggccaatc acacaggcac tggcctgctg ctgacactgc agcctgagca  1800
gaaattccag aaagtgaaag gcttcggcgg agccatgaca gatgccgccg ctctgaatat  1860
cctggctctg tctccaccag ctcagaacct gctgctcaag agctacttca gcgaggaagg  1920
catcggctac aacatcatca gagtgcccat ggccagctgc gacttcagca tcaggaccta  1980
cacctacgcc gacacacccg acgatttcca gctgcacaac ttcagcctgc ctgaagagga  2040
caccaagctg aagatccctc tgatccacag agccctgcag ctggcacaaa gacccgtgtc  2100
actgctggcc tctccatgga catctcccac ctggctgaaa acaaatggcg ccgtgaatgg  2160
caagggcagc ctgaaaggcc aacctggcga catctaccac cagacctggg ccagatactt  2220
cgtgaagttc ctggacgcct atgccgagca caagctgcag ttttgggccg tgacagccga  2280
gaacgaacct tctgctggac tgctgagcgg ctaccccttt cagtgcctgg gctttacacc  2340
cgagcaccag cgggacttta tcgcccgtga tctgggaccc acactggcca atagcaccca  2400
ccataatgtg cggctgctga tgctggacga ccagagactg cttctgcccc actgggctaa  2460
agtggtgctg acagatcctg aggccgccaa atacgtgcac ggaatcgccg tgcactggta  2520
tctggacttt ctggcccctg ccaaggccac actgggagag acacacagac tgttccccaa  2580
caccatgctg ttcgccagcg aagcctgtgt gggcagcaag ttttgggaac agagcgtgcg  2640
gctcggcagc tgggatagag gcatgcagta cagccacagc atcatcacca acctgctgta  2700
ccacgtcgtc ggctggaccg actggaatct ggccctgaat cctgaaggcg gccctaactg  2760
ggtccgaaac ttcgtggaca gccccatcat cgtggacatc accaaggaca ccttctacaa  2820
gcagcccatg ttctaccacc tgggacactt cagcaagttc atccccgagg gctctcagcg  2880
cgttggactg gtggcttccc agaagaacga tctggacgcc gtggctctga tgcaccctga  2940
tggatctgct gtggtggtgg tcctgaaccg cagcagcaaa gatgtgcccc tgaccatcaa  3000
ggatcccgcc gtgggattcc tggaaacaat cagccctggc tactccatcc acacctacct  3060
gtggcgtaga cagtgacaat tgttaattaa gtttaaaccc tcgaggccgc aagcttatcg  3120
ataatcaacc tctggattac aaaatttgtg aaagattgac tggtattctt aactatgttg  3180
ctccttttac gctatgtgga tacgctgctt taatgccttt gtatcatgct attgcttccc  3240
gtatggcttt cattttctcc tccttgtata aatcctggtt gctgtctctt tatgaggagt  3300
tgtggcccgt tgtcaggcaa cgtggcgtgg tgtgcactgt gtttgctgac gcaaccccca  3360
ctggttgggg cattgccacc acctgtcagc tcctttccgg gactttcgct ttccccctcc  3420
ctattgccac ggcggaactc atcgccgcct gccttgcccg ctgctggaca ggggctcggc  3480
tgttgggcac tgacaattcc gtggtgttgt cggggaaatc atcgtccttt ccttggctgc  3540
tcgcctgtgt tgccacctgg attctgcgcg ggacgtcctt ctgctacgtc ccttcggccc  3600
tcaatccagc ggaccttcct tcccgcggcc tgctgccggc tctgcggcct cttccgcgtc  3660
ttcgccttcg ccctcagacg agtcggatct ccctttgggc cgcctccccg catcgatacc  3720
gtcgactaga gctcgctgat cagcctcgac tgtgccttct agttgccagc catctgttgt  3780
ttgcccctcc cccgtgcctt ccttgaccct ggaaggtgcc actcccactg tcctttccta  3840
ataaaatgag gaaattgcat cgcattgtct gagtaggtgt cattctattc tggggggtgg  3900
ggtggggcag gacagcaagg gggaggattg ggaagacaat agcaggcatg ctggggagag  3960
atccacgata acaaacagct tttttggggc ccacatgtac actgaattcc ctgcaggttg  4020
gccactccct ctctgcgcgc tcgctcgctc actgaggccg cccgggcaaa gcccgggcgt  4080
cgggcgacct ttggtcgccc ggcctcagtg agcgagcgag cgcgcagaga gggagtggcc  4140
aactccatca ctaggggttc ct                                            4162

SEQ ID NO: 82           moltype = DNA  length = 4184
FEATURE                 Location/Qualifiers
misc_feature            1..4184
                        note = Synthetic polynucleotide
source                  1..4184
                        mol_type = other DNA
                        organism = synthetic construct
SEQUENCE: 82
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttttaat tatttttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
```

```
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgt  1320
ggaccctggt gagctgggtg gccctgaccg ccggcctggt ggccggcacc cgctgccccg  1380
acggccagtt ctgccccgtg gcctgctgcc tggaccccgg cggcgccagc tacagctgct  1440
gccgcccccct gctggacaag tggcccacca ccctgagccg ccacctgggc ggcccctgcc  1500
aggtggacgc ccactgcagc gccggccaca gctgcatctt caccgtgagc ggcaccagca  1560
gctgctgccc cttccccgag gccgtggcct gcggcgacgg ccaccactgc tgccccgcg  1620
gcttccactg cagcgccgac ggccgcagct gcttccagcg cagcggcaac aacagcgtgg  1680
gcgccatcca gtgccccgac agccagttcg agtgccccga cttcagcacc tgctgcgtga  1740
tggtggacgg cagctggggc tgctgcccca tgccccaggc cagctgctgc gaggaccgcg  1800
tgcactgctg cccccacggc gccttctgcg acctggtgca cacccgctgc atcacccccca  1860
ccggcaccca ccccctggcc aagaagctgc ccgcccagcg caccaaccgc gccgtggccc  1920
tgagcagcag cgtgatgtgc cccgacgccc gcagccgctg ccccgacggc agcacctgct  1980
gcgagctgcc cagcggcaag tacggctgct gccccatgcc caacgccacc tgctgcagcg  2040
accacctgca ctgctgcccc caggacaccg tgtgcgacct gatccagagc aagtgcctga  2100
gcaaggagaa cgccaccacc gacctgctga ccaagctgcc cgcccacacc gtgggcgacg  2160
tgaagtgcga catggaggtg agctgccccg acggctacac ctgctgccgc ctgcagagcg  2220
gcgcctgggg ctgctgcccc ttcacccagg ccgtgtgctg cgaggaccac atccactgct  2280
gccccgccgg cttcacctgc gacacccaga agggcacctg cgagcagggc ccccaccagg  2340
tgccctggat ggagaaggcc cccgcccacc tgagcctgcc cgacccccag gccctgaagc  2400
gcgacgtgcc ctgcgacaac gtgagcagct gccccagcag cgacacctgc tgccagctga  2460
ccagcggcga gtggggctgc tgccccatcc ccgaggccgt gtgctgcagc gaccaccagc  2520
actgctgccc ccagggctac acctgcgtgg ccgagggcca gtgccagcgc ggcagcgaga  2580
tcgtggccgg cctggagaag atgcccgccc gccgcgccag cctgagccac ccccgcgaca  2640
tcggctgcga ccagcacacc agctgccccg tgggccagac ctgctgcccc agcctgggcg  2700
gcagctgggc ctgctgccag ctgccccacg ccgtgtgctg cgaggaccgc cagcactgct  2760
gccccgccgg ctacacctgc aacgtgaagg cccgcagctg cgagaaggag gtggtgagcg  2820
cccagcccgc caccttcctg gcccgcagcc cccacgtggg cgtgaaggac gtggagtgcg  2880
gcgagggcca cttctgccac gacaaccaga cctgctgccg cgacaaccgc cagggctggg  2940
cctgctgccc ctaccgccag ggcgtgtgct gcgccgaccg ccgccactgc tgccccgccg  3000
gcttccgctg cgccgcccgc ggcaccaagt gcctgcgccg cgaggccccc cgctgggacg  3060
ccccccctgcg cgaccccgcc ctgcgccagc tgctgtgaca attgttaatt aagtttaaac  3120
cctcgaggcc gcaagcttat cgataatcaa cctctggatt acaaaatttg tgaaagattg  3180
actggtattc ttaactatgt tgctcctttt acgctatgtg gatacgctgc tttaatgcct  3240
ttgtatcatg ctattgcttc ccgtatggct ttcattttct cctccttgta taaatcctgg  3300
ttgctgtctc tttatgagga gttgtggccc gttgtcaggc aacgtggcgt ggtgtgcact  3360
gtgtttgctg acgcaacccc cactggttgg ggcattgcca ccacctgtca gctcctttcc  3420
gggactttcg ctttccccct ccctattgcc acggcggaac tcatcgccgc ctgccttgcc  3480
cgctgctgga caggggctcg gctgttgggc actgacaatt ccgtggtgtt gtcggggaaa  3540
tcatcgtcct ttccttggct gctcgcctgt gttgccacct ggattctgcg cgggacgtcc  3600
ttctgctacg tcccttcggc cctcaatcca gcggaccttc cttcccgcgg cctgctgccg  3660
gctctgcggc ctcttccgcg tcttcgcctt cgccctcaga cgagtcggat ctccctttgg  3720
gccgcctccc cgcatcgata ccgtcgacta gagctcgctg atcagcctcg actgtgcctt  3780
ctagttgcca gccatctgtt gtttgcccct cccccgtgcc ttccttgacc ctggaaggtg  3840
ccactcccac tgtcctttcc taataaaatg aggaaattgc atcgcattgt ctgagtaggt  3900
gtcattctat tctggggggt ggggtggggc aggacagcaa gggggaggat tgggaagaca  3960
atagcaggca tgctggggag agatccacga taacaaacag cttttttggg gcccacatgt  4020
acactgaatt ccctgcaggt tggccactcc ctctctgcgc gctcgctcgc tcactgaggc  4080
cgcccgggca aagcccgggc gtcgggcgac ctttggtcgc ccggcctcag tgagcgagcg  4140
agcgcgcaga gagggagtgg ccaactccat cactaggggt tcct                  4184

SEQ ID NO: 83           moltype = DNA  length = 4184
FEATURE                 Location/Qualifiers
misc_feature            1..4184
                        note = Synthetic polynucleotide
source                  1..4184
                        mol_type = other DNA
                        organism = synthetic construct
SEQUENCE: 83
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttaat tattttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
```

```
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgt  1320
ggaccctggt gagctgggtg gccctgaccg ccggcctggt ggccggcacc cgctgccccg  1380
acggccagtt ctgccccgtg gcctgctgcc tggaccccgg cggcgccagc tacagctgct  1440
gccgccccct gctggacaag tggcccacca ccctgagccg ccacctgggc ggcccctgcc  1500
aggtggacgc ccactgcagc gccggccaca gctgcatctt caccgtgagc ggcaccagca  1560
gctgctgccc cttccccgag gccgtggcct gcggcgacgg ccaccactgc tgccccgcg   1620
gcttccactg cagcgccgac ggccgcagct gcttccagcg cagcggcaac aacagcgtgg  1680
gcgccatcca gtgccccgac agccagttcg agtgccccga cttcagcacc tgctgcgtga  1740
tggtggacgg cagctggggc tgctgcccca tgccccaggc cagctgctgc gaggaccgcg  1800
tgcactgctg cccccacggc gccttctgcg acctggtgca cacccgctgc atcaccccca  1860
ccggcaccca cccccctggcc aagaagctgc ccgcccagcg caccaaccgc gccgtggccc  1920
tgagcagcag cgtgatgtgc cccgacgccc gcagccgctg ccccgacggc agcacctgct  1980
gcgagctgcc cagcggcaag tacggctgct gccccatgcc caacgccacc tgctgcagcg  2040
accacctgca ctgctgcccc caggacaccg tgtgcgacct gatccagagc aagtgcctga  2100
gcaaggagaa cgccaccacc gacctgctga ccaagctgcc cgcccacacc gtgggcgacg  2160
tgaagtgcga catggaggtg agctgccccg acggctacac ctgctgccgc ctgcagagcg  2220
gcgcctgggg ctgctgcccc ttcacccagg ccgtgtgctg cgaggaccac atccactgct  2280
gccccgccgg cttcacctgc gacacccaga agggcacctg cgagcagggc ccccaccagg  2340
tgccctggat ggagaaggcc cccgcccacc tgagcctgcc cgacccccag gccctgaagc  2400
gcgacgtgcc ctgcgacaac gtgagcagct gccccagcag cgacacctgc tgccagctga  2460
ccagcggcga gtggggctgc tgccccatcc ccgaggccgt gtgctgcagc gaccaccagc  2520
actgctgccc ccagggctac acctgcgtgg ccgagggcca gtgccagcgc ggcagcgaga  2580
tcgtggccgg cctggagaag atgcccgccc gccgcgccag cctgagccac ccccgcgaca  2640
tcggctgcga ccagcacacc agctgccccg tgggccagac ctgctgcccc agcctgggcg  2700
gcagctgggc ctgctgccag ctgccccacg ccgtgtgctg cgaggaccgc cagcactgct  2760
gccccgccgg ctacacctgc aacgtgaagg cccgcagctg cgagaaggag gtggtgagcg  2820
cccagcccgc caccttcctg gcccgcagcc cccacgtggg cgtgaaggac gtggagtgcg  2880
gcgagggcca cttctgccac gacaaccaga cctgctgccg cgacaaccgc cagggctggg  2940
cctgctgccc ctaccgccag ggcgtgtgct gcgccgaccg ccgccactgc tgccccgccg  3000
gcttccgctg cgccgcccgc ggcaccaagt gcctgcgccg cgaggccccc cgctgggacg  3060
ccccctgcg cgaccccgcc ctgcgccagc tgctgtgaca attgttaatt aagtttaaac  3120
cctcgaggcc gcaagcttat cgataatcaa cctctggatt acaaaatttg tgaaagattg  3180
actggtattc ttaactatgt tgctcctttt acgctatgtg gatacgctgc tttaatgcct  3240
ttgtatcatg ctattgcttc ccgtatggct ttcattttct cctccttgta taaatcctgg  3300
ttgctgtctc tttatgagga gttgtggccc gttgtcaggc aacgtggcgt ggtgtgcact  3360
gtgtttgctg acgcaacccc cactggttgg ggcattgcca ccacctgtca gctcctttcc  3420
gggactttcg ctttccccct ccctattgcc acggcggaac tcatcgccgc ctgccttgcc  3480
cgctgctgga caggggctcg gctgttgggc actgacaatt ccgtggtgtt gtcggggaaa  3540
tcatcgtcct ttccttggct gctcgcctgt gttgccacct ggattctgcg cgggacgtcc  3600
ttctgctacg tcccttcggc cctcaatcca gcggaccttc cttcccgcgg cctgctgccg  3660
gctctgcggc ctcttccgcg tcttcgcctt cgccctcaga cgagtcggat ctccctttgg  3720
gccgcctccc cgcatcgata ccgtcgacta gagctcgctg atcagcctcg actgtgcctt  3780
ctagttgcca gccatctgtt gtttgcccct cccccgtgcc ttccttgacc ctggaaggtg  3840
ccactcccac tgtcctttcc taataaaatg aggaaattgc atcgcattgt ctgagtaggt  3900
gtcattctat tctggggggt ggggtggggc aggacagcaa gggggaggat tgggaagaca  3960
atagcaggca tgctggggag agatccacga taacaaacag cttttttggg gcccacatgt  4020
acactgaatt ccctgcaggt tggccactcc ctctctgcgc gctcgctcgc tcactgaggc  4080
cgcccgggca aagcccgggc gtcgggcgac ctttggtcgc ccggcctcag tgagcgagcg  4140
agcgcgcaga gagggagtgg ccaactccat cactaggggt tcct                    4184
```

```
SEQ ID NO: 84            moltype = DNA  length = 4578
FEATURE                  Location/Qualifiers
misc_feature             1..4578
                         note = Synthetic polynucleotide
source                   1..4578
                         mol_type = other DNA
                         organism = synthetic construct
SEQUENCE: 84
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
aaaaaaattg tcatcctccc acggtggcca tttgttccat gtgagtgcta gtaacaggcc  300
ttgtgtcctt tgtagactat ttgcacactg catctgtggc ttcactcagt gtgcaaatag  360
tctacaagac aacagcatac agccttcagc aagcctccag tggtctcata cagaacttat  420
aagattccca aatccaaaga catttcacgt ttatggtgat ttcccagaac acatagcgac  480
atgcaaatat tgcagggcgc cactcccctg tccctcacag ccatcttcct gccagggcgc  540
acgcgcgctg ggtgttcccg cctagtgaca ctgggcccgc gattccttgg agcgggttga  600
tgacgtcagc gtttcccatg gtgaagcttg gatctgatcc ctaggttcta gaaccggtga  660
cgtctcccat ggtgaagctt ggatctgaat tcggtaccta gttattaata gtaatcaatt  720
acggggtcat tagttcatag cccatatatg gagttccgcg ttacataact tacggtaaat  780
ggcccgcctg gctgaccgcc caacgacccc cgcccattga cgtcaataat gacgtatgtt  840
cccatagtaa cgccaatagg gactttccat tgacgtcaat gggtggagta tttacggtaa  900
actgcccact tggcagtaca tcaagtgtat catatgccaa gtacgccccc tattgacgtc  960
aatgacggta aatggcccgc ctggcattat gcccagtaca tgaccttatg ggactttcct  1020
acttggcagt acatctacgt attagtcatc gctattacca tggtcgaggt gagccccacg  1080
```

```
ttctgcttca ctctccccat ctcccccccc tccccacccc caattttgta tttatttatt  1140
ttttaattat tttgtgcagc gatgggggcg gggggggggg gggggcgcgc gccaggcggg  1200
gcggggcggg gcgaggggcg gggcggggcg aggcggagag gtgcggcggc agccaatcag  1260
agcggcgcgc tccgaaagtt tccttttatg gcgaggcggc ggcggcggcg gccctataaa  1320
aagcgaagcg cgcggcgggc gggagtcgct gcgacgctgc cttcgccccg tgccccgctc  1380
cgccgccgcc tcgcgccgcc cgccccggct ctgactgacc gcgttactcc cacaggtgag  1440
cgggcgggac ggcccttctc ctccgggctg taattagcgc ttggtttaat gacggcttgt  1500
tttctgtggc tgcgtgaaag ccttgagggg ctccgggagc tagagcctct gctaaccatg  1560
ttcatgcctt cttctttttc ctacagctcc tgggcaacgt gctggttatt gtgctgtctc  1620
atcattttgg caaagaattc ctcgaagatc cgaagggaaa gtcttccacg actgtgggat  1680
ccgttcgaag atatcaccgg ttgagccacc atgtggaccc tggtgagctg ggtggccctg  1740
accgccggcc tggtggccgg cacccgctgc cccgacggcc agttctgccc cgtggcctgc  1800
tgcctggacc ccggcggcgc cagctacagc tgctgccgcc ccctgctgga caagtggccc  1860
accaccctga gccgccacct gggcggcccc tgccaggtgg acgcccactg cagcgccggc  1920
cacagctgca tcttcaccgt gagcggcacc agcagctgct gccccttccc cgaggccgtg  1980
gcctgcggcg acggccacca ctgctgcccc cgcggcttcc actgcagcgc cgacggccgc  2040
agctgcttcc agcgcagcgg caacaacagc gtgggcgcca tccagtgccc cgacagccag  2100
ttcgagtgcc ccgacttcag cacctgctgc gtgatggtgg acggcagctg ggctgctgc  2160
cccatgcccc aggccagctg ctgcgaggac cgcgtgcact gctgccccca cggcgccttc  2220
tgcgacctgg tgcacacccg ctgcatcacc cccaccggca cccacccccct ggccaagaag  2280
ctgcccgccc agcgcaccaa ccgcgccgtg gccctgagca gcagcgtgat gtgccccgac  2340
gcccgcagcc gctgccccga cggcagcacc tgctgcgagc tgcccagcgg caagtacggc  2400
tgctgcccca tgcccaacgc cacctgctgc agcgaccacc tgcactgctg cccccaggac  2460
accgtgtgcg acctgatcca gagcaagtgc ctgagcaagg agaacgccac caccgacctg  2520
ctgaccaagc tgcccgccca caccgtgggc gacgtgaagt gcgacatgga ggtgagctgc  2580
cccgacggct acacctgctg ccgcctgcag agcggcgcct ggggctgctg ccccttcacc  2640
caggccgtgt gctgcgagga ccacatccac tgctgccccg ccggcttcac ctgcgacacc  2700
cagaagggca cctgcgagca gggcccccac caggtgccct ggatggagaa ggcccccgcc  2760
cacctgagcc tgcccgaccc ccaggccctg aagcgcgacg tgccctgcga caacgtgagc  2820
agctgcccca gcagcgacac ctgctgccag ctgaccagcg gcgagtgggg ctgctgcccc  2880
atccccgagg ccgtgtgctg cagcgaccac cagcactgct gcccccaggg ctacacctgc  2940
gtggccgagg gccagtgcca gcgcggcagc gagatcgtgg ccggcctgga gaagatgccc  3000
gcccgccgcg ccagcctgag ccacccccgc gacatcggct gcgaccagca caccagctgc  3060
cccgtgggcc agacctgctg ccccagcctg ggcggcagct gggcctgctg ccagctgccc  3120
cacgccgtgt gctgcgagga ccgccagcac tgctgccccg ccggctacac ctgcaacgtg  3180
aaggcccgca gctgcgagaa ggaggtggtg agcgcccagc ccgccacctt cctggcccgc  3240
agcccccacg tgggcgtgaa ggacgtggag tgcggcgagg gccacttctg ccacgacaac  3300
cagacctgct gccgcgacaa ccgccagggc tgggcctgct gcccctaccg ccagggcgtg  3360
tgctgcgccg accgccgcca ctgctgcccc gccggcttcc gctgcgccgc ccgcggcacc  3420
aagtgcctgc gccgcgaggc cccccgctgg gacgcccccc tgcgcgaccc cgccctgcgc  3480
cagctgctgt gacaattgtt aattaagttt aaaccctcga ggccgcaagc ttatcgataa  3540
tcaacctctg gattacaaaa tttgtgaaag attgactggt attcttaact atgttgctcc  3600
ttttacgcta tgtggatacg ctgctttaat gcctttgtat catgctattg cttcccgtat  3660
ggctttcatt ttctcctcct tgtataaatc ctggttgctg tctctttatg aggagttgtg  3720
gcccgttgtc aggcaacgtg gcgtggtgtg cactgtgttt gctgacgcaa cccccactgg  3780
ttggggcatt gccaccacct gtcagctcct ttccgggact ttcgctttcc ccctccctat  3840
tgccacggcg gaactcatcg ccgcctgcct tgcccgctgc tggacagggg ctcggctgtt  3900
gggcactgac aattccgtgg tgttgtcggg gaaatcatcg tcctttcctt ggctgctcgc  3960
ctgtgttgcc acctggattc tgcgcgggac gtccttctgc tacgtccctt cggccctcaa  4020
tccagcggac cttccttccc gcggcctgct gccggctctg cggcctcttc cgcgtcttcg  4080
ccttcgccct cagacgagtc ggatctccct ttgggccgcc tccccgcatc gataccgtcg  4140
actagagctc gctgatcagc ctcgactgtg ccttctagtt gccagccatc tgttgtttgc  4200
ccctcccccg tgccttcctt gaccctggaa ggtgccactc ccactgtcct ttcctaataa  4260
aatgaggaaa ttgcatcgca ttgtctgagt aggtgtcatt ctattctggg gggtggggtg  4320
gggcaggaca gcaaggggga ggattgggaa gacaatagca ggcatgctgg ggagagatcc  4380
acgataacaa acagcttttt tggggtgaac atattgactg aattccctgc aggttggcca  4440
ctccctctct gcgcgctcgc tcgctcactg aggccgcccg ggcaaagccc gggcgtcggg  4500
cgacctttgg tcgcccggcc tcagtgagcg agcgagcgcg cagagaggga gtggccaact  4560
ccatcactag gggttcct                                                4578

SEQ ID NO: 85          moltype = DNA  length = 4162
FEATURE                Location/Qualifiers
misc_feature           1..4162
                       note = Synthetic polynucleotide
source                 1..4162
                       mol_type = other DNA
                       organism = synthetic construct
SEQUENCE: 85
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
```

```
ccatggtcga ggtgagcccc acgttctgct tcactctccc catctccccc ccctccccac  720
ccccaatttt gtatttattt attttttaat tattttgtgc agcgatgggg gcgggggggg  780
gggggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgacgc  960
tgccttcgcc ccgtgccccg ctccgccgcc gcctcgcgcc gcccgccccg gctctgactg  1020
accgcgttac tcccacaggt gagcgggcgg gacggccctt ctcctcagcg ctgtaattag  1080
cgcttggttt aatgacggct tgttggaggc ttgctgaagg ctgtatgctg ttgtctttag  1140
aaataagtgg tagtcaagtg aagccacaga tgtgactacc acttatttct aaaaggacac  1200
aaggcctgtt actagcactc acatggaaca aatggccacc gtgggaggat gacaatttct  1260
gtggctgcgt gaaagccttg aggggctccg ggagctagag cctctgctaa ccatgttcat  1320
gccttcttct ttttcctaca gctcctgggc aacgtgctgg ttattgtgct gtctcatcat  1380
tttggcaaag aattcctcga agatccgaag ggaaagtctt ccacgactgt gggatccgtt  1440
cgaagatatc accggttgag ccaccatgga attcagcagc cccagcagag aggaatgccc  1500
caagcctctg agccgggtgt caatcatggc cggatctctg acaggactgc tgctgcttca  1560
ggccgtgtct tgggcttctg gcgctagacc ttgcatcccc aagagcttcg gctacagcag  1620
cgtcgtgtgc gtgtgcaatg ccacctactg cgacagcttc gaccctccta cctttcctgc  1680
tctgggcacc ttcagcagat acgagagcac cagatccggc agacggatgg aactgagcat  1740
gggacccatc caggccaatc acacaggcac tggcctgctg ctgacactgc agcctgagca  1800
gaaattccag aaagtgaaag gcttcggcgg agccatgaca gatgccgccg ctctgaatat  1860
cctggctctg tctccaccag ctcagaacct gctgctcaag agctacttca gcgaggaagg  1920
catcggctac aacatcatca gagtgcccat ggccagctgc gacttcagca tcaggaccta  1980
cacctacgcc gacacacccg acgatttcca gctgcacaac ttcagcctgc ctgaagagga  2040
caccaagctg aagatccctc tgatccacag agccctgcag ctggcacaaa gacccgtgtc  2100
actgctggcc tctccatgga catctcccac ctggctgaaa acaaatggcg ccgtgaatgg  2160
caagggcagc ctgaaaggcc aacctggcga catctaccac cagacctggg ccagatactt  2220
cgtgaagttc ctggacgcct atgccgagca caagctgcag ttttgggccg tgacagccga  2280
gaacgaacct tctgctggac tgctgagcgg ctacccccttt cagtgcctgg gctttacacc  2340
cgagcaccag cgggacttta tcgcccgtga tctgggaccc acactggcca atagcaccca  2400
ccataatgtg cggctgctga tgctggacga ccagagactg cttctgcccc actgggctaa  2460
agtggtgctg acagatcctg aggccgccaa atacgtgcac ggaatcgccg tgcactggta  2520
tctggacttt ctggcccctg ccaaggccac actgggagag acacacagac tgttccccaa  2580
caccatgctg ttcgccagcg aagcctgtgt gggcagcaag ttttgggaac agagcgtgcg  2640
gctcggcagc tgggatagag gcatgcagta cagccacagc atcatcacca acctgctgta  2700
ccacgtcgtc ggctggaccg actggaatct ggccctgaat cctgaaggcg gccctaactg  2760
ggtccgaaac ttcgtggaca gccccatcat cgtggacatc accaaggaca ccttctacaa  2820
gcagcccatg ttctaccacc tgggacactt cagcaagttc atccccgagg gctctcagcg  2880
cgttggactg gtggcttccc agaagaacga tctggacgcc gtggctctga tgcaccctga  2940
tggatctgct gtggtggtgg tcctgaaccg cagcagcaaa gatgtgcccc tgaccatcaa  3000
ggatcccgcc gtgggattcc tggaaacaat cagccctggc tactccatcc acacctacct  3060
gtggcgtaga cagtgacaat tgttaattaa gtttaaaccc tcgaggccgc aagcttatcg  3120
ataatcaacc tctggattac aaaatttgtg aaagattgac tggtattctt aactatgttg  3180
ctccttttac gctatgtgga tacgctgctt taatgccttt gtatcatgct attgcttccc  3240
gtatggcttt cattttctcc tccttgtata aatcctggtt gctgtctctt tatgaggagt  3300
tgtggcccgt tgtcaggcaa cgtggcgtgg tgtgcactgt gtttgctgac gcaaccccca  3360
ctggttgggg cattgccacc acctgtcagc tcctttccgg gactttcgct ttccccctcc  3420
ctattgccac ggcggaactc atcgccgcct gccttgcccg ctgctggaca ggggctcggc  3480
tgttgggcac tgacaattcc gtggtgttgt cggggaaatc atcgtccttt ccttggctgc  3540
tcgcctgtgt tgccacctgg attctgcgcg ggacgtcctt ctgctacgtc ccttcggccc  3600
tcaatccagc ggaccttcct tcccgcggcc tgctgccggc tctgcggcct cttccgcgtc  3660
ttcgccttcg ccctcagacg agtcggatct ccctttgggc cgcctccccg catcgatacc  3720
gtcgactaga gctcgctgat cagcctcgac tgtgccttct agttgccagc catctgttgt  3780
ttgcccctcc cccgtgcctt ccttgaccct ggaaggtgcc actcccactg tcctttccta  3840
ataaaatgag gaaattgcat cgcattgtct gagtaggtgt cattctattc tggggggtgg  3900
ggtggggcag gacagcaagg gggaggattg ggaagacaat agcaggcatg ctggggagag  3960
atccacgata acaaacagct tttttggggc ccacatgtac actgaattcc ctgcaggttg  4020
gccactccct ctctgcgcgc tcgctcgctc actgaggccg cccgggcaaa gcccgggcgt  4080
cgggcgacct ttggtcgccc ggcctcagtg agcgagcgag cgcgcagaga gggagtggcc  4140
aactccatca ctaggggttc ct                                            4162

SEQ ID NO: 86          moltype = DNA  length = 3977
FEATURE                Location/Qualifiers
misc_feature           1..3977
                       note = Synthetic polynucleotide
source                 1..3977
                       mol_type = other DNA
                       organism = synthetic construct
SEQUENCE: 86
ttggccactc cctctctgcg cgctcgctcg ctcactgagg ccgcccgggc aaagcccggg  60
cgtcgggcga cctttggtcg cccggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
```

```
ccatggtcga ggtgagcccc acgttctgct tcactctccc catctccccc ccctccccac  720
ccccaatttt gtatttattt atttttttaat tattttgtgc agcgatgggg gcgggggggg  780
gggggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgt  1320
acgccctgtt cctgctggcc agcctgctgg gcgccgccct ggccggcccc gtgctgggcc  1380
tgaaggagtg cacccgcggc agcgccgtgt ggtgccagaa cgtgaagacc gccagcgact  1440
gcggcgccgt gaagcactgc ctgcagaccg tgtggaacaa gcccaccgtg aagagcctgc  1500
cctgcgacat ctgcaaggac gtggtgaccg ccgccggcga catgctgaag gacaacgcca  1560
ccgaggagga gatcctggtg tacctggaga agacctgcga ctggctgccc aagcccaaca  1620
tgagcgccag ctgcaaggag atcgtggaca gctacctgcc cgtgatcctg gacatcatca  1680
agggcgagat gagccgcccc ggcgaggtgt gcagcgccct gaacctgtgc gagagcctgc  1740
agaagcacct ggccgagctg aaccaccaga agcagctgga gagcaacaag atccccgagc  1800
tggacatgac cgaggtggtg gccccettca tggccaacat cccccctgctg ctgtaccccc  1860
aggacggccc ccgcagcaag ccccagccca aggacaacgg cgacgtgtgc caggactgca  1920
tccagatggt gaccgacatc cagaccgccg tgcgcaccaa cagcaccttc gtgcaggccc  1980
tggtggagca cgtgaaggag gagtgcgacc gcctgggccc cggcatggcc gacatctgca  2040
agaactacat cagccagtac agcgagatcg ccatccagat gatgatgcac atgcagccca  2100
aggagatctg cgccctggtg ggcttctgcg acgaggtgaa ggagatgccc atgcagaccc  2160
tggtgcccgc caaggtggcc agcaagaacg tgatccccgc cctggagctg gtggagccca  2220
tcaagaagca cgaggtgccc gccaagagcg acgtgtactg cgaggtgtgc gagttcctgg  2280
tgaaggaggt gaccaagctg atcgacaaca acaagaccga gaaggagatc ctggacgcct  2340
tcgacaagat gtgcagcaag ctgcccaaga gcctgagcga ggagtgccag gaggtggtgg  2400
acacctacgg cagcagcatc ctgagcatcc tgctggagga ggtgagcccc gagctggtgt  2460
gcagcatgct gcacctgtgc agcggcaccc gcctgcccgc cctgaccgtg cacgtgaccc  2520
agcccaagga cggcggcttc tgcgaggtgt gcaagaagct ggtgggctac ctggaccgca  2580
acctggagaa gaacagcacc aagcaggaga tcctggccgc cctggagaag ggctgcagct  2640
tcctgcccga cccctaccag aagcagtgcg accagttcgt ggccgagtac gagcccgtgc  2700
tgatcgagat cctggtggag gtgatggacc ccagcttcgt gtgcctgaag atcggcgcct  2760
gccccagcgc ccacaagccc ctgctgggca ccgagaagtg catctggggc cccagctact  2820
ggtgccagaa caccgagacc gccgcccagt gcaacgccgt ggagcactgc aagcgccacg  2880
tgtggaactg acaattgtta attaagttta aaccctcgag gccgcaagct tatcgataat  2940
caacctctgg attacaaaat ttgtgaaaga ttgactggta ttcttaacta tgttgctcct  3000
tttacgctat gtggatacgc tgctttaatg cctttgtatc atgctattgc ttcccgtatg  3060
gctttcattt tctcctcctt gtataaatcc tggttgctgt ctctttatga ggagttgtgg  3120
cccgttgtca ggcaacgtgg cgtggtgtgc actgtgtttg ctgacgcaac ccccactggt  3180
tggggcattg ccaccacctg tcagctcctt tccgggactt tcgctttccc cctccctatt  3240
gccacggcgg aactcatcgc cgcctgcctt gcccgctgct ggacaggggc tcggctgttg  3300
ggcactgaca attccgtggt gttgtcgggg aaatcatcgt cctttccttg gctgctcgcc  3360
tgtgttgcca cctggattct gcgcgggacg tccttctgct acgtcccttc ggccctcaat  3420
ccagcggacc ttccttcccg cggcctgctg ccggctctgc ggcctcttcc gcgtcttcgc  3480
cttcgccctc agacgagtcg gatctccctt tgggccgcct ccccgcatcg ataccgtcga  3540
ctagagctcg ctgatcagcc tcgactgtgc cttctagttg ccagccatct gttgtttgcc  3600
cctcccccgt gccttccttg accctggaag gtgccactcc cactgtcctt tcctaataaa  3660
atgaggaaat tgcatcgcat tgtctgagta ggtgtcattc tattctgggg ggtggggtgg  3720
ggcaggacag caagggggag gattgggaag acaatagcag gcatgctggg gagagatcca  3780
cgataacaaa cagctttttt ggggcccaca tgtacactga attccctgca ggttggccac  3840
tccctctctg cgcgctcgct cgctcactga ggccgcccgg gcaaagcccg ggcgtcgggc  3900
gacctttggt cgcccggcct cagtgagcga gcgagcgcgc agagagggag tggccaactc  3960
catcactagg ggttcct                                                 3977

SEQ ID NO: 87           moltype = DNA  length = 4013
FEATURE                 Location/Qualifiers
misc_feature            1..4013
                        note = Synthetic polynucleotide
source                  1..4013
                        mol_type = other DNA
                        organism = synthetic construct
SEQUENCE: 87
ttggccactc cctctctgcg cgctcgctcg ctcactgagg ccgcccgggc aaagcccggg  60
cgtcgggcga cctttggtcg cccggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttttaat tattttgtgc agcgatgggg gcgggggggg  780
gggggggggcg cgcgccaggc ggggcggggc ggggcgaggg gcggggcggg gcgaggcgga  840
```

```
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgg  1320
aattcagcag ccccagcaga gaggaatgcc ccaagcctct gagccgggtg tcaatcatgg  1380
ccggatctct gacaggactg ctgctgcttc aggccgtgtc ttgggcttct ggcgctagac  1440
cttgcatccc caagagcttc ggctacagca gcgtcgtgtg cgtgtgcaat gccacctact  1500
gcgacagctt cgaccctcct acctttcctg ctctgggcac cttcagcaga tacgagagca  1560
ccagatccgg cagacggatg gaactgagca tgggacccat ccaggccaat cacacaggca  1620
ctggcctgct gctgacactg cagcctgagc agaaattcca gaaagtgaaa ggcttcggcg  1680
gagccatgac agatgccgcc gctctgaata tcctggctct gtctccacca gctcagaacc  1740
tgctgctcaa gagctacttc agcgaggaag gcatcggcta caacatcatc agagtgccca  1800
tggccagctg cgacttcagc atcaggacct acacctacgc cgacacaccc gacgatttcc  1860
agctgcacaa cttcagcctg cctgaagagg acaccaagct gaagatccct ctgatccaca  1920
gagccctgca gctggcacaa agacccgtgt cactgctggc ctctccatgg acatctccca  1980
cctggctgaa aacaaatggc gccgtgaatg gcaagggcag cctgaaaggc caacctggcg  2040
acatctacca ccagacctgg gccagatact tcgtgaagtt cctggacgcc tatgccgagc  2100
acaagctgca gtttgggccc gtgacagccg agaacgaacc ttctgctgga ctgctgagcg  2160
gctacccctt tcagtgcctg ggctttacac ccgagcacca gcgggacttt atcgcccgtg  2220
atctgggacc cacactggcc aatagcaccc accataatgt gcggctgctg atgctggacg  2280
accagagact gcttctgccc cactgggcta aagtggtgct gacagatcct gaggccgcca  2340
aatacgtgca cggaatcgcc gtgcactggt atctggactt tctggcccct gccaaggcca  2400
cactgggaga gacacacaga ctgttcccca acaccatgct gttcgccagc gaagcctgtg  2460
tgggcagcaa gttttgggaa cagagcgtgc ggctcggcag ctgggataga ggcatgcagt  2520
acagccacag catcatcacc aacctgctgt accacgtcgt cggctggacc gactggaatc  2580
tggccctgaa tcctgaaggc ggccctaact gggtccgaaa cttcgtggac agccccatca  2640
tcgtggacat caccaaggac accttctaca agcagcccat gttctaccac ctgggacact  2700
tcagcaagtt catccccgag ggctctcagc gcgttggact ggtggcttcc cagaagaacg  2760
atctggacgc cgtggctctg atgcaccctg atggatctgc tgtggtggtg gtcctgaacc  2820
gcagcagcaa agatgtgccc ctgaccatca aggatcccgc cgtgggattc ctggaaacaa  2880
tcagccctgg ctactccatc cacacctacc tgtggcgtag acagtgacaa ttgttaatta  2940
agtttaaacc ctcgaggccg caagcttatc gataatcaac ctctggatta caaaatttgt  3000
gaaagattga ctggtattct taactatgtt gctcctttta cgctatgtgg atacgctgct  3060
ttaatgcctt tgtatcatgc tattgcttcc cgtatggctt tcattttctc ctccttgtat  3120
aaatcctggt tgctgtctct ttatgaggag ttgtggcccg ttgtcaggca acgtggcgtg  3180
gtgtgcactg tgtttgctga cgcaaccccc actggttggg gcattgccac cacctgtcag  3240
ctcctttccg ggactttcgc tttccccctc cctattgcca cggcggaact catcgccgcc  3300
tgccttgccc gctgctggac aggggctcgg ctgttgggca ctgacaattc cgtggtgttg  3360
tcggggaaat catcgtcctt tccttggctg ctcgcctgtg ttgccacctg gattctgcgc  3420
gggacgtcct tctgctacgt cccttcggcc ctcaatccag cggaccttcc ttcccgcggc  3480
ctgctgccgg ctctgcggcc tcttccgcgt cttcgccttc gccctcagac gagtcggatc  3540
tccctttggg ccgcctcccc gcatcgatac cgtcgactag agctcgctga tcagcctcga  3600
ctgtgccttc tagttgccag ccatctgttg tttgcccctc ccccgtgcct tccttgaccc  3660
tggaaggtgc cactcccact gtcctttcct aataaaatga ggaaattgca tcgcattgtc  3720
tgagtaggtg tcattctatt ctggggggtg gggtggggca ggacagcaag ggggaggatt  3780
gggaagacaa tagcaggcat gctggggaga gatccacgat aacaaacagc tttttttgggg  3840
tgaacatatt gactgaattc cctgcaggtt ggccactccc tctctgcgcg ctcgctcgct  3900
cactgaggcc gcccgggcaa agcccgggcg tcgggcgacc tttggtcgcc cggcctcagt  3960
gagcgagcga gcgcgcagag agggagtggc caactccatc actaggggtt cct         4013

SEQ ID NO: 88           moltype = DNA  length = 4625
FEATURE                 Location/Qualifiers
misc_feature            1..4625
                        note = Synthetic polynucleotide
source                  1..4625
                        mol_type = other DNA
                        organism = synthetic construct
SEQUENCE: 88
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
tggcactatg aaccctgcag ccctaggaat gcatctagac aattgtacta accttcttct  600
ctttcctctc ctgacagtcc ggaaagccac catggaattc agcagcccca gcagagagga  660
atgccccaag cctctgagcc gggtgtcaat catggccgga tctctgacag gactgctgct  720
gcttcaggcc gtgtcttggg cttctggcgc tagaccttgc atccccaaga gcttcggcta  780
cagcagcgtc gtgtgcgtgt gcaatgccac ctactgcgac agcttcgacc ctcctacctt  840
tcctgctctg ggcaccttca gcagatacga gagcaccaga tccggcagac ggatggaact  900
gagcatggga cccatccagg ccaatcacac aggcactggc ctgctgctga cactgcagcc  960
tgagcagaaa ttccagaaag tgaaaggctt cggcggagcc atgacagatg ccgccgctct  1020
```

```
gaatatcctg gctctgtctc caccagctca gaacctgctg ctcaagagct acttcagcga  1080
ggaaggcatc ggctacaaca tcatcagagt gcccatggcc agctgcgact tcagcatcag  1140
gacctacacc tacgccgaca cacccgacga tttccagctg cacaacttca gcctgcctga  1200
agaggacacc aagctgaaga tccctctgat ccacagagcc ctgcagctgg cacaaagacc  1260
cgtgtcactg ctggcctctc catggacatc tcccacctgg ctgaaaacaa atggcgccgt  1320
gaatggcaag ggcagcctga aaggccaacc tggcgacatc taccaccaga cctgggccag  1380
atacttcgtg aagttcctgg acgcctatgc cgagcacaag ctgcagtttt gggccgtgac  1440
agccgagaac gaaccttctg ctggactgct gagcggctac ccctttcagt gcctgggctt  1500
tacacccgag caccagcggg actttatcgc ccgtgatctg ggacccacac tggccaatag  1560
cacccaccat aatgtgcggc tgctgatgct ggacgaccag agactgcttc tgccccactg  1620
ggctaaagtg gtgctgacag atcctgaggc cgccaaatac gtgcacggaa tcgccgtgca  1680
ctggtatctg gactttctgg cccctgccaa ggccacactg ggagagacac acagactgtt  1740
ccccaacacc atgctgttcg ccagcgaagc ctgtgtgggc agcaagtttt gggaacagag  1800
cgtgcggctc ggcagctggg atagaggcat gcagtacagc cacagcatca tcaccaacct  1860
gctgtaccac gtcgtcggct ggaccgactg gaatctggcc ctgaatcctg aaggcggccc  1920
taactgggtc cgaaacttcg tggacagccc catcatcgtg gacatcacca aggacacctt  1980
ctacaagcag cccatgttct accacctggg acacttcagc aagttcatcc ccgagggctc  2040
tcagcgcgtt ggactggtgg cttcccagaa gaacgatctg gacgccgtgg ctctgatgca  2100
ccctgatgga tctgctgtgg tggtggtcct gaaccgcagc agcaaagatg tgcccctgac  2160
catcaaggat cccgccgtgg gattcctgga aacaatcagc cctggctact ccatccacac  2220
ctacctgtgg cgtagacaga gaagaaagag aggaagtgga gagggcagag gaagtcttct  2280
gacatgcgga gacgtggaag agaatcccgg ccctatggcc gagtggctgc tgagcgccag  2340
ctggcagcgc cgcgccaagg ccatgaccgc cgccgccggc agcgccggcc gcgccgccgt  2400
gcccctgctg ctgtgcgccc tgctggcccc cggcggcgcc tacgtgctgg acgacagcga  2460
cggcctgggc cgcgagttcg acggcatcgg cgccgtgagc ggcggcggcg ccaccagccg  2520
cctgctggtg aactaccccg agccctaccg cagccagatc ctggactacc tgttcaagcc  2580
caacttcggc gccagcctgc acatcctgaa ggtggagatc ggcggcgacg gccagaccac  2640
cgacggcacc gagcccagcc acatgcacta cgccctggac gagaactact tccgcggcta  2700
cgagtggtgg ctgatgaagg aggccaagaa gcgcaacccc aacatcaccc tgatcggcct  2760
gccctggagc ttcccccggct ggctgggcaa gggcttcgac tggccctacg tgaacctgca  2820
gctgaccgcc tactacgtgg tgacctggat cgtgggcgcc aagcgctacc acgacctgga  2880
catcgactac atcggcatct ggaacgagcg cagctacaac gccaactaca tcaagatcct  2940
gcgcaagatg ctgaactacc agggcctgca gcgcgtgaag atcatcgcca gcgacaacct  3000
gtgggagagc atcagcgcca gcatgctgct ggacgccgag ctgttcaagg tggtggacgt  3060
gatcggcgcc cactaccccg gcacccacag cgccaaggac gccaagctga ccggcaagaa  3120
gctgtggagc agcgaggact tcagcaccct gaacagcgac atgggcgccg gctgctgggg  3180
ccgcatcctg aaccagaact acatcaacgg ctacatgacc agcaccatcg cctggaacct  3240
ggtggccagc tactacgagc agctgcccta cggccgctgc ggcctgatga ccgcccagga  3300
gccctggagc ggccactacg tggtggagag ccccgtgtgg gtgagcgccc acaccaccca  3360
gttcacccag cccggctggt actacctgaa gaccgtgggc cacctggaga agggcggcag  3420
ctacgtggcc ctgaccgacg gcctgggcaa cctgaccatc atcatcgaga ccatgagcca  3480
caagcacagc aagtgcatcc gcccccttcct gccctacttc aacgtgagcc agcagttcgc  3540
caccttcgtg ctgaagggca gcttcagcga gatccccgag ctgcaggtgt ggtacaccaa  3600
gctgggcaag accagcgagc gcttcctgtt caagcagctg gacagcctgt ggctgctgga  3660
cagcgacggc agcttcaccc tgagcctgca cgaggacgag ctgttcaccc tgaccaccct  3720
gaccaccggc cgcaagggca gctacccccct gcccccccaag agccagccct tccccagcac  3780
ctacaaggac gacttcaacg tggactaccc cttcttcagc gaggccccca acttcgccga  3840
ccagaccggc gtgttcgagt acttcaccaa catcgaggac cccggcgagc accacttcac  3900
cctgcgccag gtgctgaacc agcgccccat cacctgggcc gccgacgcca gcaacaccat  3960
cagcatcatc ggcgactaca actggaccaa cctgaccatc aagtgcgacg tgtacatcga  4020
gacccccgac accggcggcg tgttcatcgc cggccgcgtg aacaagggcg gcatcctgat  4080
ccgcagcgcc cgcggcatct tcttctggat cttcgccaac ggcagctacc gcgtgaccgg  4140
cgacctggcc ggctggatca tctacgccct gggccgcgtg gaggtgaccg ccaagaagtg  4200
gtacaccctg accctgacca tcaagggcca cttcaccagc ggcatgctga acgacaagag  4260
cctgtggacc gacatccccg tgaacttccc caagaacggc tgggccgcca tcggcaccca  4320
cagcttcgag ttcgcccagt tcgacaactt cctggtggag gccacccgct gacaattgtt  4380
aattaagttt aaaccctcga ggccgcaagc aataaaatat ctttattttc attacatctg  4440
tgtgttggtt ttttgtgttg tacactgaat tccctgcagg ttggccactc cctctctgcg  4500
cgctcgctcg ctcactgagg ccgcccgggc aaagcccggg cgtcgggcga cctttggtcg  4560
cccggcctca gtgagcgagc gagcgcgcag agagggagtg gccaactcca tcactagggg  4620
ttcct                                                              4625
```

```
SEQ ID NO: 89          moltype = DNA  length = 4606
FEATURE                Location/Qualifiers
misc_feature           1..4606
                       note = Synthetic polynucleotide
source                 1..4606
                       mol_type = other DNA
                       organism = synthetic construct
SEQUENCE: 89
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg agggcggagt  300
tagggcggag ccaatcagcg tgcgccgttc cgaaagttgc cttttatggc tgggcggaga  360
atgggcggtg aacgccgatg attatataag gacgcgccgg gtgtggcaca gctagttccg  420
tcgcagccgg gatttgggtc gcggttcttg tttgtggatc cctgtgatcg tcacttggta  480
agtcactgac tgtctatgcc tgggaaaggg tgggcaggag atggggcagt gcaggaaaag  540
```

```
tggcactatg aaccctcctg gtggcgaggg gaggggggtg gtcctcgaac gccttgcaga  600
actggcctgg atacagagtg gaccggctgg ccccatctgg aagacttcga gatacactgt  660
tgtcttactg cgctcaacag tgtatctcga agtcttccaa atggtgccag ccatcgcagc  720
ggggtgcagg aaatgggggc agcccccctt tttggctatc cttccacgtg ttcttttttg  780
tatcttttgt gtttcctaga aaacatctca gtcaccaccg cagccctagg aatgcatcta  840
gacaattgta ctaaccttct tctctttcct ctcctgacag tccggaaagc caccatgtac  900
gccctgttcc tgctggccag cctgctgggc gccgccctgg ccggccccgt gctgggcctg  960
aaggagtgca cccgcggcag cgccgtgtgg tgccagaacg tgaagaccgc cagcgactgc  1020
ggcgccgtga agcactgcct gcagaccgtg tggaacaagc ccaccgtgaa gagcctgccc  1080
tgcgacatct gcaaggacgt ggtgaccgcc gccggcgaca tgctgaagga caacgccacc  1140
gaggaggaga tcctggtgta cctggagaag acctgcgact ggctgcccaa gcccaacatg  1200
agcgccagct gcaaggagat cgtggacagc tacctgcccg tgatcctgga catcatcaag  1260
ggcgagatga gccgccccgg cgaggtgtgc agcgccctga acctgtgcga gagcctgcag  1320
aagcacctgg ccgagctgaa ccaccagaag cagctggaga gcaacaagat ccccgagctg  1380
gacatgaccg aggtggtggc ccccttcatg gccaacatcc ccctgctgct gtacccccag  1440
gacggccccc gcagcaagcc ccagcccaag gacaacggcg acgtgtgcca ggactgcatc  1500
cagatggtga ccgacatcca gaccgccgtg cgcaccaaca gcaccttcgt gcaggccctg  1560
gtggagcacg tgaaggagga gtgcgaccgc ctgggccccg gcatggccga catctgcaag  1620
aactacatca gccagtacag cgagatcgcc atccagatga tgatgcacat gcagcccaag  1680
gagatctgcg ccctggtggg cttctgcgac gaggtgaagg agatgcccat gcagaccctg  1740
gtgcccgcca aggtggccag caagaacgtg atccccgccc tggagctggt ggagcccatc  1800
aagaagcacg aggtgcccgc caagagcgac gtgtactgcg aggtgtgcga gttcctggtg  1860
aaggaggtga ccaagctgat cgacaacaac aagaccgaga aggagatcct ggacgccttc  1920
gacaagatgt gcagcaagct gcccaagagc ctgagcgagg agtgccagga ggtggtggac  1980
acctacggca gcagcatcct gagcatcctg ctggaggagg tgagccccga gctggtgtgc  2040
agcatgctgc acctgtgcag cggcacccgc ctgcccgccc tgaccgtgca cgtgacccag  2100
cccaaggacg gcggcttctg cgaggtgtgc aagaagctgg tgggctacct ggaccgcaac  2160
ctggagaaga acagcaccaa gcaggagatc ctggccgccc tggagaaggg ctgcagcttc  2220
ctgcccgacc cctaccagaa gcagtgcgac cagttcgtgg ccgagtacga gcccgtgctg  2280
atcgagatcc tggtggaggt gatggacccc agcttcgtgt gcctgaagat cggcgcctgc  2340
cccagcgccc acaagcccct gctgggcacc gagaagtgca tctggggccc cagctactgg  2400
tgccagaaca ccgagaccgc cgcccagtgc aacgccgtgg agcactgcaa gcgccacgtg  2460
tggaacagaa gaaagagagg aagtggagag ggcagaggaa gtcttctgac atgcggagac  2520
gtggaagaga atcccggccc tatggaattc agcagcccca gcagagagga atgccccaag  2580
cctctgagcc gggtgtcaat catggccgga tctctgacag gactgctgct gcttcaggcc  2640
gtgtcttggg cttctggcgc tagaccttgc atccccaaga gcttcggcta cagcagcgtc  2700
gtgtgcgtgt gcaatgccac ctactgcgac agcttcgacc ctcctacctt tcctgctctg  2760
ggcaccttca gcagatacga gagcaccaga tccggcagac ggatggaact gagcatggga  2820
cccatccagg ccaatcacac aggcactggc ctgctgctga cactgcagcc tgagcagaaa  2880
ttccagaaag tgaaaggctt cggcggagcc atgacagatg ccgccgctct gaatatcctg  2940
gctctgtctc caccagctca gaacctgctg ctcaagagct acttcagcga ggaaggcatc  3000
ggctacaaca tcatcagagt gcccatggcc agctgcgact tcagcatcag gacctacacc  3060
tacgccgaca cacccgacga tttccagctg cacaacttca gcctgcctga agaggacacc  3120
aagctgaaga tccctctgat ccacagagcc ctgcagctgg cacaaagacc cgtgtcactg  3180
ctggcctctc catggacatc tcccacctgg ctgaaaacaa atggcgccgt gaatggcaag  3240
ggcagcctga aaggccaacc tggcgacatc taccaccaga cctgggccag atacttcgtg  3300
aagttcctgg acgcctatgc cgagcacaag ctgcagtttt gggccgtgac agccgagaac  3360
gaaccttctg ctggactgct gagcggctac ccctttcagt gcctgggctt tacacccgag  3420
caccagcggg actttatcgc ccgtgatctg ggacccacac tggccaatag cacccaccat  3480
aatgtgcggc tgctgatgct ggacgaccag agactgcttc tgccccactg ggctaaagtg  3540
gtgctgacag atcctgaggc cgccaaatac gtgcacggaa tcgccgtgca ctggtatctg  3600
gactttctgg cccctgccaa ggccacactg ggagagacac acagactgtt ccccaacacc  3660
atgctgttcg ccagcgaagc ctgtgtgggc agcaagtttt gggaacagag cgtgcggctc  3720
ggcagctggg atagaggcat gcagtacagc cacagcatca tcaccaacct gctgtaccac  3780
gtcgtcggct ggaccgactg gaatctggcc ctgaatcctg aaggcggccc taactgggtc  3840
cgaaacttcg tggacagccc catcatcgtg gacatcacca aggacacctt ctacaagcag  3900
cccatgttct accacctggg acacttcagc aagttcatcc ccgagggctc tcagcgcgtt  3960
ggactggtgg cttcccagaa gaacgatctg gacgccgtgg ctctgatgca ccctgatgga  4020
tctgctgtgg tggtggtcct gaaccgcagc agcaaagatg tgcccctgac catcaaggat  4080
cccgccgtgg gattcctgga aacaatcagc cctggctact ccatccacac ctacctgtgg  4140
cgtagacagt gacaattgtt aattaagttt aaaccctcga ggccgcaagc cgcatcgata  4200
ccgtcgacta gagctcgctg atcagcctcg actgtgcctt ctagttgcca gccatctgtt  4260
gtttgcccct cccccgtgcc ttccttgacc ctggaaggtg ccactcccac tgtcctttcc  4320
taataaaatg aggaaattgc atcgcattgt ctgagtaggt gtcattctat tctggggggt  4380
ggggtggggc aggacagcaa gggggaggat tgggaagaca atagcaggca tgctggggat  4440
gtacactgaa ttccctgcag gttggccact ccctctctgc gcgctcgctc gctcactgag  4500
gccgcccggg caaagcccgg gcgtcgggcg acctttggtc gcccggcctc agtgagcgag  4560
cgagcgcgca gagagggagt ggccaactcc atcactaggg gttcct                4606
```

```
SEQ ID NO: 90          moltype = DNA  length = 10870
FEATURE                Location/Qualifiers
misc_feature           1..10870
                       note = Nucleotide sequence of first strand of PR006A vector
source                 1..10870
                       mol_type = other DNA
                       organism = synthetic construct
SEQUENCE: 90
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
```

-continued

```
gccaactcca tcactagggg ttcctgctag ctctgggtat ttaagcccga gtgagcacgc  180
agggtctcca ttttgaagcg ggaggttacg cgttcgtcga ctactagtgg gtaccagagc  240
tccctaggtt ctagaaccgg tgacgtctcc catggtgaag cttggatctg aattcggtac  300
ctagttatta atagtaatca attacggggt cattagttca tagcccatat atggagttcc  360
gcgttacata acttacggta aatggcccgc ctggctgacc gcccaacgac ccccgcccat  420
tgacgtcaat aatgacgtat gttcccatag taacgccaat agggactttc cattgacgtc  480
aatgggtgga gtatttacgg taaactgccc acttggcagt acatcaagtg tatcatatgc  540
caagtacgcc ccctattgac gtcaatgacg gtaaatggcc cgcctggcat tatgcccagt  600
acatgacctt atgggacttt cctacttggc agtacatcta cgtattagtc atcgctatta  660
ccatggtcga ggtgagcccc acgttctgct tcactctccc catctccccc ccctccccac  720
ccccaatttt gtatttattt atttttaat tattttgtgc agcgatgggg gcgggggggg  780
gggggggcg cgcgccaggc ggggcggggc ggggcgaggg gcggggcggg gcgaggcgga  840
gaggtgcggc ggcagccaat cagagcggcg cgctccgaaa gtttcctttt atggcgaggc  900
ggcggcggcg gcggccctat aaaaagcgaa gcgcgcggcg ggcgggagtc gctgcgcgct  960
gccttcgccc cgtgccccgc tccgccgccg cctcgcgccg cccgccccgg ctctgactga  1020
ccgcgttact cccacaggtg agcgggcggg acggcccttc tcctccgggc tgtaattagc  1080
gcttggttta atgacggctt gtttcttttc tgtggctgcg tgaaagcctt gaggggctcc  1140
gggagctaga gcctctgcta accatgttca tgccttcttc tttttcctac agctcctggg  1200
caacgtgctg gttattgtgc tgtctcatca ttttggcaaa gaattcctcg aagatccgaa  1260
gggaaagtct tccacgactg tgggatccgt tcgaagatat caccggttga gccaccatgt  1320
ggaccctggt gagctgggtg gccctgaccg ccggcctggt ggccggcacc cgctgccccg  1380
acggccagtt ctgccccgtg gcctgctgcc tggaccccgg cggcgccagc tacagctgct  1440
gccgcccct gctggacaag tggcccacca ccctgagccg ccacctgggc ggcccctgcc  1500
aggtggacgc ccactgcagc gccggccaca gctgcatctt caccgtgagc ggcaccagca  1560
gctgctgccc cttccccgag gccgtggcct gcggcgacgg ccaccactgc tgcccccgcg  1620
gcttccactg cagcgccgac ggccgcagct gcttccagcg cagcggcaac aacagcgtgg  1680
gcgccatcca gtgccccgac agccagttcg agtgccccga cttcagcacc tgctgcgtga  1740
tggtggacgg cagctggggc tgctgcccca tgccccaggc cagctgctgc gaggaccgcg  1800
tgcactgctg cccccacggc gccttctgcg acctggtgca cacccgctgc atcaccccca  1860
ccggcaccca ccccctggcc aagaagctgc ccgcccagcg caccaaccgc gccgtggccc  1920
tgagcagcag cgtgatgtgc cccgacgccc gcagccgctg ccccgacggc agcacctgct  1980
gcgagctgcc cagcggcaag tacggctgct gccccatgcc caacgccacc tgctgcagcg  2040
accacctgca ctgctgcccc caggacaccg tgtgcgacct gatccagagc aagtgcctga  2100
gcaaggagaa cgccaccacc gacctgctga ccaagctgcc cgcccacacc gtgggcgacg  2160
tgaagtgcga catggaggtg agctgccccg acggctacac ctgctgccgc ctgcagagcg  2220
gcgcctgggg ctgctgcccc ttcacccagg ccgtgtgctg cgaggaccac atccactgct  2280
gccccgccgg cttcacctgc gacacccaga agggcacctg cgagcagggc ccccaccagg  2340
tgccctggat ggagaaggcc cccgcccacc tgagcctgcc cgacccccag gccctgaagc  2400
gcgacgtgcc ctgcgacaac gtgagcagct gccccagcag cgacacctgc tgccagctga  2460
ccagcggcga gtggggctgc tgccccatcc ccgaggccgt gtgctgcagc gaccaccagc  2520
actgctgccc ccagggctac acctgcgtgg ccgagggcca gtgccagcgc ggcagcgaga  2580
tcgtggccgg cctggagaag atgcccgccc gccgcgccag cctgagccac ccccgcgaca  2640
tcggctgcga ccagcacacc agctgccccg tgggccagac ctgctgcccc agcctgggcg  2700
gcagctgggc ctgctgccag ctgccccacg ccgtgtgctg cgaggaccgc cagcactgct  2760
gccccgccgg ctacacctgc aacgtgaagg cccgcagctg cgagaaggag gtggtgagcg  2820
cccagcccgc caccttcctg gcccgcagcc cccacgtggg cgtgaaggac gtggagtgcg  2880
gcgagggcca cttctgccac gacaaccaga cctgctgccg cgacaaccgc cagggctggg  2940
cctgctgccc ctaccgccag ggcgtgtgct gcgccgaccg ccgccactgc tgccccgccg  3000
gcttccgctg cgccgcccgc ggcaccaagt gcctgcgccg cgaggccccc cgctgggacg  3060
ccccctgcg cgaccccgcc ctgcgccagc tgctgtgaca attgttaatt aagtttaaac  3120
cctcgaggcc gcaagcttat cgataatcaa cctctggatt acaaaatttg tgaaagattg  3180
actggtattc ttaactatgt tgctcctttt acgctatgtg gatacgctgc tttaatgcct  3240
ttgtatcatg ctattgcttc ccgtatggct ttcattttct cctccttgta taaatcctgg  3300
ttgctgtctc tttatgagga gttgtggccc gttgtcaggc aacgtggcgt ggtgtgcact  3360
gtgtttgctg acgcaacccc cactggttgg ggcattgcca ccacctgtca gctcctttcc  3420
gggactttcg ctttccccct ccctattgcc acggcggaac tcatcgccgc ctgccttgcc  3480
cgctgctgga caggggctcg gctgttgggc actgacaatt ccgtggtgtt gtcggggaaa  3540
tcatcgtcct ttccttggct gctcgcctgt gttgccacct ggattctgcg cgggacgtcc  3600
ttctgctacg tcccttcggc cctcaatcca gcggaccttc cttcccgcgg cctgctgccg  3660
gctctgcggc ctcttccgcg tcttcgcctt cgccctcaga cgagtcggat ctccctttgg  3720
gccgcctccc cgcatcgata ccgtcgacta gagctcgctg atcagcctcg actgtgcctt  3780
ctagttgcca gccatctgtt gtttgcccct cccccgtgcc ttccttgacc ctggaaggtg  3840
ccactcccac tgtcctttcc taataaaatg aggaaattgc atcgcattgt ctgagtaggt  3900
gtcattctat tctggggggt ggggtggggc aggacagcaa gggggaggat tgggaagaca  3960
atagcaggca tgctggggag agatccacga taacaaacag ctttttttggg gcccacatgt  4020
acactgaatt ccctgcaggt tggccactcc ctctctgcgc gctcgctcgc tcactgaggc  4080
cgcccgggca aagcccgggc gtcgggcgac ctttggtcgc ccggcctcag tgagcgagcg  4140
agcgcgcaga gagggagtgg ccaactccat cactaggggt tcctgcggcc gctcgtacgg  4200
tctcgaggaa ttcctgcagg ataacttgcc aacctcattc taaaatgtat atagaagccc  4260
aaaagacaat aacaaaaata ttcttgtaga acaaaatggg aaagaatgtt ccactaaata  4320
tcaagattta gagcaaagca tgagatgtgt ggggatagac agtgaggctg ataaaataga  4380
gtagagctca gaaacagacc cattgatata tgtaagtgac ctatgaaaaa aatatggcat  4440
tttacaatgg gaaaatgatg gtcttttttct tttttagaaa aacagggaaa tatatttata  4500
tgtaaaaaat aaaagggaac ccatatgtca taccatacac acaaaaaaat tccagtgaat  4560
tataagtcta aatggagaag gcaaaacttt aaatctttta gaaaataata tagaagcatg  4620
cagaccagcc tggccaacat gatgaaaccc tctctactaa taataaaatc agtagaacta  4680
ctcaggacta ctttgagtgg gaagtccttt tctatgaaga cttctttggc caaaattagg  4740
ctctaaatgc aaggagatag tgcatcatgc ctggctgcac ttactgataa atgatgttat  4800
caccatcttt aaccaaatgc acaggaacaa gttatggtac tgatgtgctg gattgagaag  4860
```

```
gagctctact tccttgacag gacacatttg tatcaactta aaaaagcaga tttttgccag  4920
cagaactatt cattcagagg taggaaactt agaatagatg atgtcactga ttagcatggc  4980
ttccccatct ccacagctgc ttcccaccca ggttgcccac agttgagttt gtccagtgct  5040
cagggctgcc cactctcagt aagaagcccc acaccagccc ctctccaaat atgttggctg  5100
ttccttccat taaagtgacc ccactttaga gcagcaagtg gatttctgtt tcttacagtt  5160
caggaaggag gagtcagctg tgagaacctg gagcctgaga tgcttctaag tcccactgct  5220
actggggtca gggaagccag actccagcat cagcagtcag gagcactaag cccttgccaa  5280
catcctgttt ctcagagaaa ctgcttccat tataatggtt gtcctttttt aagctatcaa  5340
gccaaacaac cagtgtctac cattattctc atcacctgaa gccaagggtt ctagcaaaag  5400
tcaagctgtc ttgtaatggt tgatgtgcct ccagcttctg tcttcagtca ctccactctt  5460
agcctgctct gaatcaactc tgaccacagt tccctggagc cctgccacc tgctgcccct  5520
gccaccttct ccatctgcag tgctgtgcag ccttctgcac tcttgcagag ctaataggtg  5580
gagacttgaa ggaagaggag gaaagtttct cataatagcc ttgctgcaag ctcaaatggg  5640
aggtgggcac tgtgcccagg agccttggag caaaggctgt gcccaacctc tgactgcatc  5700
caggtttggt cttgacagag ataagaagcc ctggcttttg gagccaaaat ctaggtcaga  5760
cttaggcagg attctcaaag tttatcagca gaacatgagg cagaagaccc tttctgctcc  5820
agcttcttca ggctcaacct tcatcagaat agatagaaag agaggctgtg agggttctta  5880
aaacagaagc aaatctgact cagagaataa acaacctcct agtaaactac agcttagaca  5940
gagcatctgg tggtgagtgt gctcagtgtc ctactcaact gtctggtatc agccctcatg  6000
aggacttctc ttctttccct catagacctc catctctgtt ttccttagcc tgcagaaatc  6060
tggatggcta ttcacagaat gcctgtgctt tcagagttgc attttttctc tggtattctg  6120
gttcaagcat ttgaaggtag gaaaggttct ccaagtgcaa gaaagccagc cctgagcctc  6180
aactgcctgg ctagtgtggt cagtaggatg caaaggctgt tgaatgccac aaggccaaac  6240
tttaacctgt gtaccacaag cctagcagca gaggcagctc tgctcactgg aactctctgt  6300
cttctttctc ctgagccttt tcttttcctg agtttctag ctctcctcaa ccttacctct  6360
gccctaccca ggacaaaccc aagagccact gtttctgtga tgtcctctcc agccctaatt  6420
aggcatcatg acttcagcct gaccttccat gctcagaagc agtgctaatc cacttcagat  6480
gagctgctct atgcaacaca ggcagagcct acaaaccttt gcaccagagc cctccacata  6540
tcagtgtttg ttcatactca cttcaacagc aaatgtgact gctgagatta agattttaca  6600
caagatggtc tgtaatttca cagttagttt tatcccatta ggtatgaaag aattagcata  6660
attcccctta aacatgaatg aatcttagat tttttaataa atagttttgg aagtaaagac  6720
agagacatca ggagcacaag gaatagcctg agaggacaaa cagaacaaga aagagtctgg  6780
aaatacacag gatgttcttg gcctcctcaa agcaagtgca agcagatagt accagcagcc  6840
ccaggctatc agagcccagt gaagagaagt accatgaaag ccacagctct aaccaccctg  6900
ttccagagtg acagacagtc cccaagacaa gccagcctga gccagagaga gaactgcaag  6960
agaaagtttc taatttaggt tctgttagat tcagacaagt gcaggtcatc ctctctccac  7020
agctactcac ctctccagcc taacaaagcc tgcagtccac actccaaccc tggtgtctca  7080
cctcctagcc tctcccaaca tcctgctctc tgaccatctt ctgcatctct catctcacca  7140
tctcccactg tctacagcct actcttgcaa ctaccatctc atttctgac atcctgtcta  7200
catcttctgc catactctgc catctaccat accacctctt accatctacc acaccatctt  7260
ttatctccat ccctctcaga agcctccaag ctgaatcctg ctttatgtgt tcatctcagc  7320
ccctgcatgg aaagctgacc ccagaggcag aactattccc agagagcttg gccaagaaaa  7380
acaaaactac cagcctggcc aggctcagga gtagtaagct gcagtgtctg ttgtgttcta  7440
gcttcaacag ctgcaggagt tccactctca aatgctccac atttctcaca tcctcctgat  7500
tctggtcact acccatcttc aaagaacaga atatctcaca tcagcatact gtgaaggact  7560
agtcatgggt gcagctgctc agagctgcaa agtcattctg gatggtggag agcttacaaa  7620
catttcatga tgctcccccc gctctgatgg ctggagccca atccctacac agactcctgc  7680
tgtatgtgtt ttcctttcac tctgagccac agccagaggg caggcattca gtctcctctt  7740
caggctgggg ctggggcact gagaactcac ccaacacctt gctctcactc cttctgcaaa  7800
acaagaaaga gctttgtgct gcagtagcca tgaagaatga aaggaaggct ttaactaaaa  7860
aatgtcagag attattttca accccttact gtggatcacc agcaaggagg aaacacaaca  7920
cagagacatt ttttcccctc aaattatcaa aagaatcact gcatttgtta aagagagcaa  7980
ctgaatcagg aagcagagtt ttgaacatat cagaagttag gaatctgcat cagagacaaa  8040
tgcagtcatg gttgtttgct gcataccagc cctaatcatt agaagcctca tggacttcaa  8100
acatcattcc ctctgacaag atgctctagc ctaactccat gagataaaat aaatctgcct  8160
ttcagagcca aagaagagtc caccagcttc ttctcagtgt gaacaagagc tccagtcagg  8220
ttagtcagtc cagtgcagta gaggagacca gtctgcatcc tctaatttc aaaggcaaga  8280
agatttgttt accctggaca ccaggcacaa gtgaggtcac agagctctta gatatgcagt  8340
cctcatgagt gaggagacta aagcgcatgc catcaagact tcagtgtaga gaaaacctcc  8400
aaaaaagcct cctcactact tctggaatag ctcagaggcc gaggcggcct cggcctctgc  8460
ataaataaaa aaaattagtc agccatgggg cggagaatgg gcggaactgg gcggagttag  8520
gggcgggatg ggcggagtta ggggcgggac tatggttgct gactaattga gatgcatgct  8580
ttgcatactt ctgcctgctg gggagcctgg ggactttcca cacctggttg ctgactaatt  8640
gagatgcatg ctttgcatac ttctgcctgc tggggagcct ggggactttc cacaccctaa  8700
ctgacacaca ttccacagct gcattaatga atcggccaac gcgcggggag aggcggtttg  8760
cgtattgggc gctcttccgc ttcctcgctc actgactcgc tgcgctcggt cgttcggctg  8820
cggcgagcgg tatcagctca ctcaaaggcg gtaatacggt tatccacaga atcaggggat  8880
aacgcaggaa agaacatgtg agcaaaaggc cagcaaaagg ccaggaaccg taaaaaggcc  8940
gcgttgctgg cgtttttcca taggctccgc ccccctgacg agcatcacaa aaatcgacgc  9000
tcaagtcaga ggtggcgaaa cccgacagga ctataaagat accaggcgtt tccccctgga  9060
agctccctcg tgcgctctcc tgttccgacc ctgccgctta ccggatacct gtccgccttt  9120
ctcccttcgg gaagcgtggc gctttctcat agctcacgct gtaggtatct cagttcggtg  9180
taggtcgttc gctccaagct gggctgtgtg cacgaacccc ccgttcagcc cgaccgctgc  9240
gccttatccg gtaactatcg tcttgagtcc aacccggtaa gacacgactt atcgccactg  9300
gcagcagcca ctggtaacag gattagcaga gcgaggtatg taggcggtgc tacagagttc  9360
ttgaagtggt ggcctaacta cggctacact agaagaacag tatttggtat ctgcgctctg  9420
ctgaagccag ttaccttcgg aaaaagagtt ggtagctctt gatccggcaa acaaaccacc  9480
gctggtagcg gtggtttttt tgtttgcaag cagcagatta cgcgcagaaa aaaggatct  9540
caagaagatc ctttgatctt ttctacgggg tctgacgctc agtggaacga aaactcacgt  9600
```

```
taagggattt tggtcatgag attatcaaaa aggatcttca cctagatcct tttaaattaa  9660
aaatgaagtt ttaaatcaat ctaaagtata tatgagtaaa cttggtctga cagttaccaa  9720
tgcttaatca gtgaggcacc tatctcagcg atctgtctat ttcgttcatc catagttgcc  9780
tgactcctgc aaaccacgtt gtgtctcaaa atctctgatg ttacattgca caagataaaa  9840
atatatcatc atgaacaata aaactgtctg cttacataaa cagtaataca aggggtgtta  9900
tgagccatat tcaacgggaa acgtcttgct cgaggccgcg attaaattcc aacatggatg  9960
ctgatttata tgggtataaa tgggctcgcg ataatgtcgg gcaatcaggt gcgacaatct  10020
atcgattgta tgggaagccc gatgcgccag agttgtttct gaaacatggc aaaggtagcg  10080
ttgccaatga tgttacagat gagatggtca gactaaactg gctgacggaa tttatgcctc  10140
ttccgaccat caagcatttt atccgtactc ctgatgatgc atggttactc accactgcga  10200
tccccgggaa aacagcattc caggtattag aagaatatcc tgattcaggt gaaaatattg  10260
ttgatgcgct ggcagtgttc ctgcgccggt tgcattcgat tcctgtttgt aattgtcctt  10320
ttaacagcga tcgcgtattt cgtctcgctc aggcgcaatc acgaatgaat aacggtttgg  10380
ttgatgcgag tgattttgat gacgagcgta atggctggcc tgttgaacaa gtctggaaag  10440
aaatgcataa gcttttgcca ttctcaccgg attcagtcgt cactcatggt gatttctcac  10500
ttgataacct tatttttgac gaggggaaat taataggttg tattgatgtt ggacgagtcg  10560
gaatcgcaga ccgataccag gatcttgcca tcctatggaa ctgcctcggt gagttttctc  10620
cttcattaca gaaacggctt tttcaaaaat atggtattga taatcctgat atgaataaat  10680
tgcagtttca tttgatgctc gatgagtttt tctaagggcg gcctgccacc atacccacgc  10740
cgaaacaagc gctcatgagc ccgaagtggc gagcccgatc ttccccatcg gtgatgtcgg  10800
cgatataggc gccagcaacc gcacctgtgg cgccggtgat gagggcgcgc caagtcgacg  10860
tccggcagtc                                                         10870

SEQ ID NO: 91          moltype = DNA  length = 10870
FEATURE                Location/Qualifiers
misc_feature           1..10870
                       note = Nucleotide sequence of second strand of PR006A vector
source                 1..10870
                       mol_type = other DNA
                       organism = synthetic construct
SEQUENCE: 91
gactgccgga cgtcgacttg gcgcgccctc atcaccggcg ccacaggtgc ggttgctggc  60
gcctatatcg ccgacatcac cgatggggaa gatcgggctc gccacttcgg gctcatgagc  120
gcttgtttcg gcgtgggtat ggtggcaggc cgcccttaga aaaactcatc gagcatcaaa  180
tgaaactgca atttattcat atcaggatta tcaataccat atttttgaaa aagccgtttc  240
tgtaatgaag gagaaaactc accgaggcag ttccatagga tggcaagatc ctggtatcgg  300
tctgcgattc cgactcgtcc aacatcaata caacctatta atttcccctc gtcaaaaata  360
aggttatcaa gtgagaaatc accatgagtg acgactgaat ccggtgagaa tggcaaaagc  420
ttatgcattt ctttccagac ttgttcaaca ggccagccat tacgctcgtc atcaaaatca  480
ctcgcatcaa ccaaaccgtt attcattcgt gattgcgcct gagcgagacg aaatacgcga  540
tcgctgttaa aaggacaatt acaaacagga atcgaatgca accggcgcag gaacactgcc  600
agcgcatcaa caatattttc acctgaatca ggatattctt ctaatacctg gaatgctgtt  660
ttcccgggga tcgcagtggt gagtaaccat gcatcatcag gagtacggat aaaatgcttg  720
atggtcggaa gaggcataaa ttccgtcagc cagtttagtc tgaccatctc atctgtaaca  780
tcattggcaa cgctaccttt gccatgtttc agaaacaact ctggcgcatc gggcttccca  840
tacaatcgat agattgtcgc acctgattgc ccgacattat cgcgagccca tttataccca  900
tataaatcag catccatgtt ggaatttaat cgcggcctcg agcaagacgt ttcccgttga  960
atatggctca taacacccct tgtattactg tttatgtaag cagacagttt tattgttcat  1020
gatgatatat ttttatcttg tgcaatgtaa catcagagat tttgagacac aacgtggttt  1080
gcaggagtca ggcaactatg gatgaacgaa atagacagat cgctgagata ggtgcctcac  1140
tgattaagca ttggtaactg tcagaccaag tttactcata tatactttag attgatttaa  1200
aacttcattt ttaatttaaa aggatctagg tgaagatcct ttttgataat ctcatgacca  1260
aaatccctta acgtgagttt tcgttccact gagcgtcaga ccccgtagaa aagatcaaag  1320
gatcttcttg agatcctttt tttctgcgcg taatctgctg cttgcaaaca aaaaaaccac  1380
cgctaccagc ggtggtttgt ttgccggatc aagagctacc aactcttttt ccgaaggtaa  1440
ctggcttcag cagagcgcag ataccaaata ctgttcttct agtgtagccg tagttaggcc  1500
accacttcaa gaactctgta gcaccgccta catacctcgc tctgctaatc ctgttaccag  1560
tggctgctgc cagtggcgat aagtcgtgtc ttaccgggtt ggactcaaga cgatagttac  1620
cggataaggc gcagcggtcg ggctgaacgg ggggttcgtg cacacagccc agcttggagc  1680
gaacgaccta caccgaactg agatacctac agcgtgagct atgagaaagc gccacgcttc  1740
ccgaagggag aaaggcggac aggtatccgg taagcggcag ggtcggaaca ggagagcgca  1800
cgagggagct tccaggggga aacgcctggt atctttatag tcctgtcggg tttcgccacc  1860
tctgacttga gcgtcgattt ttgtgatgct cgtcaggggg gcggagccta tggaaaaacg  1920
ccagcaacgc ggccttttta cggttcctgg ccttttgctg gccttttgct cacatgttct  1980
ttcctgcgtt atcccctgat tctgtggata accgtattac cgcctttgag tgagctgata  2040
ccgctcgccg cagccgaacg accgagcgca gcgagtcagt gagcgaggaa gcggaagagc  2100
gcccaatacg caaaccgcct ctccccgcgc gttggccgat tcattaatgc agctgtggaa  2160
tgtgtgtcag ttagggtgtg gaaagtcccc aggctcccca gcaggcagaa gtatgcaaag  2220
catgcatctc aattagtcag caaccaggtg tggaaagtcc ccaggctccc cagcaggcag  2280
aagtatgcaa agcatgcatc tcaattagtc agcaaccata gtcccgcccc taactccgcc  2340
catcccgccc ctaactccgc ccagttccgc ccattctccg ccccatggct gactaatttt  2400
ttttatttat gcagaggccg aggccgcctc ggcctctgag ctattccaga agtagtgagg  2460
aggctttttt ggaggtttc tctacactga agtcttgatg gcatgcgctt tagtctcctc  2520
actcatgagg actgcatatc taagagctct gtgacctcac ttgtgcctgg tgtccagggt  2580
aaacaaatct tcttgccttt gaaaattaga ggatgcagac tggtctcctc tactgcactg  2640
gactgactaa cctgactgga gctcttgttc acactgagaa gaagctggtg gactcttctt  2700
tggctctgaa aggcagattt attttatctc atggagttag gctagagcat cttgtcagag  2760
ggaatgatgt ttgaagtcca tgaggcttct aatgattagg gctggtatgc agcaaacaac  2820
catgactgca tttgtctctg atgcagattc ctaacttctg atatgttcaa aactctgctt  2880
```

```
cctgattcag ttgctctctt taacaaatgc agtgattctt ttgataattt gaggggaaaa  2940
aatgtctctg tgttgtgttt cctccttgct ggtgatccac agtaaggggt tgaaaataat  3000
ctctgacatt ttttagttaa agccttcctt tcattcttca tggctactgc agcacaaagc  3060
tctttcttgt tttgcagaag gagtgagagc aaggtgttgg gtgagttctc agtgccccag  3120
ccccagcctg aagaggagac tgaatgcctg ccctctggct gtggctcaga gtgaaaggaa  3180
aacacataca gcaggagtct gtgtagggat tgggctccag ccatcagagc gggggggagca  3240
tcatgaaatg tttgtaagct ctccaccatc cagaatgact ttgcagctct gagcagctgc  3300
acccatgact agtccttcac agtatgctga tgtgagatat tctgttcttt gaagatgggt  3360
agtgaccaga atcaggagga tgtgagaaat gtggagcatt tgagagtgga actcctgcag  3420
ctgttgaagc tagaacacaa cagacactgc agcttactac tcctgagcct ggccaggctg  3480
gtagttttgt ttttcttggc caagctctct gggaatagtt ctgcctctgg ggtcagcttt  3540
ccatgcaggg gctgagatga acacataaag caggattcag cttggaggct tctgagaggg  3600
atggagataa aagatggtgt ggtagatggt aagaggtggt atggtagatg gcagagtatg  3660
gcagaagatg tagacaggat gtcagaaaat gagatggtag ttgcaagagt aggctgtaga  3720
cagtgggaga tggtgagatg agagatgcag aagatggtca gagagcagga tgttgggaga  3780
ggctaggagg tgagacacca gggttggagt gtggactgca ggctttgtta ggctggagag  3840
gtgagtagct gtggagagag gatgacctgc acttgtctga atctaacaga acctaaatta  3900
gaaactttct cttgcagttc tctctctggc tcaggctggc ttgtcttggg gactgtctgt  3960
cactctggaa cagggtggtt agagctgtgg ctttcatggt acttctcttc actgggctct  4020
gatagcctgg ggctgctggt actatctgct tgcacttgct ttgaggaggc caagaacatc  4080
ctgtgtattt ccagactctt tcttgttctg tttgtcctct caggctattc cttgtgctcc  4140
tgatgtctct gtctttactt ccaaaactat ttattaaaaa atctaagatt cattcatgtt  4200
taaggggaat tatgctaatt ctttcatacc taatgggata aaactaactg tgaaattaca  4260
gaccatcttg tgtaaaatct taatctcagc agtcacattt gctgttgaag tgagtatgaa  4320
caaacactga tatgtggagg gctctggtgc aaaggtttgt aggctctgcc tgtgttgcat  4380
agagcagctc atctgaagtg gattagcact gcttctgagc atggaaggtc aggctgaagt  4440
catgatgcct aattagggct ggagaggaca tcacagaaac agtggctctt gggtttgtcc  4500
tgggtagggc agaggtaagg ttgaggagag ctagaaaact caggaaaaga aaaggctcag  4560
gagaaagaag acagagagtt ccagtgagca gagctgcctc tgctgctagg cttgtggtac  4620
acaggttaaa gtttggcctt gtggcattca acagcctttg catcctactg accacactag  4680
ccaggcagtt gaggctcagg gctggctttc ttgcacttgg agaacctttc ctaccttcaa  4740
atgcttgaac cagaatacca gagaaaaaat gcaactctga aagcacaggc attctgtgaa  4800
tagccatcca gatttctgca ggctaaggaa aacagagatg gaggtctatg agggaaagaa  4860
gagaagtcct catgagggct gataccagac agttgagtag gacactgagc acactcacca  4920
ccagatgctc tgtctaagct gtagtttact aggaggttgt ttattctctg agtcagattt  4980
gcttctgttt taagaaccct cacagcctct ctttctatct attctgatga aggttgagcc  5040
tgaagaagct ggagcagaaa gggtcttctg cctcatgttc tgctgataaa ctttgagaat  5100
cctgcctaag tctgacctag attttggctc caaaagccag ggcttcttat ctctgtcaag  5160
accaaacctg gatgcagtca gaggttgggc acagcctttg ctccaaggct cctgggcaca  5220
gtgcccacct cccatttgag cttgcagcaa ggctattatg agaaactttc ctcctcttcc  5280
ttcaagtctc cacctattag ctctgcaaga gtgcagaagg ctgcacagca ctgcagatgg  5340
agaaggtggc aggggcagca ggtggcaggg gctccaggga actgtggtca gagttgattc  5400
agagcaggct aagagtggag tgactgaaga cagaagctgg aggcacatca accattacaa  5460
gacagcttga cttttgctag aacccttggc ttcaggtgat gagaataatg gtagacactg  5520
gttgtttggc ttgatagctt aaaaaaggac aaccattata atggaagcag tttctctgag  5580
aaacaggatg ttggcaaggg cttagtgctc ctgactgctg atgctggagt ctggcttccc  5640
tgaccccagt agcagtggga cttagaagca tctcaggctc caggttctca cagctgactc  5700
ctccttcctg aactgtaaga aacagaaatc cacttgctgc tctaaagtgg ggtcacttta  5760
atggaaggaa cagccaacat atttggagag gggctggtgt ggggcttctt actgagagtg  5820
ggcagccctg agcactggac aaactcaact gtgggcaacc tgggtgggaa gcagctgtgg  5880
agatggggaa gccatgctaa tcagtgacat catctattct aagtttccta cctctgaatg  5940
aatagttctg ctggcaaaaa tctgcttttt taagttgata caaatgtgtc ctgtcaagga  6000
agtagagctc cttctcaatc cagcacatca gtaccataac ttgttcctgt gcatttggtt  6060
aaagatggtg ataacatcat ttatcagtaa gtgcagccag gcatgatgca ctatctcctt  6120
gcatttagag cctaattttg gccaaagaag tcttcataga aaaggacttc ccactcaaag  6180
tagtcctgag tagttctact gattttatta ttagtagaga gggtttcatc atgttggcca  6240
ggctggtctg catgcttcta tattattttc taaaagattt aaagttttgc cttctccatt  6300
tagacttata attcactgga atttttttgt gtgtatggta tgacatatgg gttccctttt  6360
attttttaca tataaatata tttccctgtt tttctaaaaa agaaaaagac catcattttc  6420
ccattgtaaa atgccatatt tttttcatag gtcacttaca tatatcaatg ggtctgtttc  6480
tgagctctac tctattttat cagcctcact gtctatcccc acacatctca tgctttgctc  6540
taaatcttga tatttagtgg aacattcttt cccattttgt tctacaagaa tatttttgtt  6600
attgtctttt gggcttctat atacatttta gaatgaggtt ggcaagttat cctgcaggaa  6660
ttcctcgaga ccgtacgagc ggccgcagga accccctagtg atggagttgg ccactccctc  6720
tctgcgcgct cgctcgctca ctgaggccgg gcgaccaaag gtcgcccgac gcccgggctt  6780
tgcccgggcg gcctcagtga gcgagcgagc gcgcagagag ggagtggcca acctgcaggg  6840
aattcagtgt acatgtgggc cccaaaaaag ctgtttgtta tcgtggatct ctccccagca  6900
tgcctgctat tgtcttccca atcctccccc ttgctgtcct gccccacccc accccccaga  6960
atagaatgac acctactcag acaatgcgat gcaatttcct cattttatta ggaaaggaca  7020
gtgggagtgg caccttccag ggtcaaggaa ggcacggggg aggggcaaac aacagatggc  7080
tggcaactag aaggcacagt cgaggctgat cagcgagctc tagtcgacgg tatcgatgcg  7140
gggaggcggc ccaaagggag atccgactcg tctgagggcg aaggcgaaga cgcggaagag  7200
gccgcagagc cggcagcagg ccgcgggaag gaaggtccgc tggattgagg gccgaaggga  7260
cgtagcagaa ggacgtcccg cgcagaatcc aggtggcaac acaggcgagc agccaaggaa  7320
aggacgatga tttccccgac aacaccacgg aattgtcagt gcccaacagc cgagcccctg  7380
tccagcagcg ggcaaggcag gcggcgatga gttccgccgt ggcaataggg agggggaaag  7440
cgaaagtccc ggaaaggagc tgacaggtgg tggcaatgcc ccaaccagtg ggggttgcgt  7500
cagcaaacac agtgcacacc acgccacgtt gcctgacaac gggccacaac tcctcataaa  7560
gagacagcaa ccaggattta tacaaggagg agaaaatgaa agccatacgg gaagcaatag  7620
```

-continued

```
catgatacaa aggcattaaa gcagcgtatc cacatagcgt aaaaggagca acatagttaa  7680
gaataccagt caatctttca caaattttgt aatccagagg ttgattatcg ataagcttgc  7740
ggcctcgagg gtttaaactt aattaacaat tgtcacagca gctggcgcag ggcggggtcg  7800
cgcagggggg cgtcccagcg gggggcctcg cggcgcaggc acttggtgcc gcgggcggcg  7860
cagcggaagc cggcggggca gcagtggcgg cggtcggcgc agcacacgcc ctggcggtag  7920
gggcagcagg cccagccctg gcggttgtcg cggcagcagg tctggttgtc gtggcagaag  7980
tggccctcgc cgcactccac gtccttcacg cccacgtggg ggctgcgggc caggaaggtg  8040
gcgggctggg cgctcaccac ctccttctcg cagctgcggg ccttcacgtt gcaggtgtag  8100
ccggcggggc agcagtgctg gcggtcctcg cagcacacgg cgtggggcag ctggcagcag  8160
gcccagctgc cgcccaggct ggggcagcag gtctggccca cggggcagct ggtgtgctgg  8220
tcgcagccga tgtcgcgggg gtggctcagg ctggcgcggc gggcgggcat cttctccagg  8280
ccggccacga tctcgctgcc gcgctggcac tggccctcgg ccacgcaggt gtagccctgg  8340
gggcagcagt gctggtggtc gctgcagcac acggcctcgg ggatggggca gcagccccac  8400
tcgccgctgg tcagctggca gcaggtgtcg ctgctggggc agctgctcac gttgtcgcag  8460
ggcacgtcgc gcttcagggc ctgggggtcg ggcaggctca ggtgggcggg ggccttctcc  8520
atccagggca cctggtgggg gccctgctcg caggtgccct tctgggtgtc gcaggtgaag  8580
ccggcggggc agcagtggat gtggtcctcg cagcacacgg cctgggtgaa ggggcagcag  8640
ccccaggcgc cgctctgcag gcggcagcag gtgtagccgt cggggcagct cacctccatg  8700
tcgcacttca cgtcgcccac ggtgtgggcg ggcagcttgg tcagcaggtc ggtggtggcg  8760
ttctccttgc tcaggcactt gctctggatc aggtcgcaca cggtgtcctg gggcagcag  8820
tgcaggtggt cgctgcagca ggtggcgttg ggcatggggc agcagccgta cttgccgctg  8880
ggcagctcgc agcaggtgct gccgtcgggg cagcggctgc gggcgtcggg gcacatcacg  8940
ctgctgctca gggccacggc gcggttggtg cgctgggcgg gcagcttctt ggccaggggg  9000
tgggtgccgg tgggggtgat gcagcgggtg tgcaccaggt cgcagaaggc gccgtggggg  9060
cagcagtgca cgcggtcctc gcagcagctg gcctggggca tggggcagca gccccagctg  9120
ccgtccacca tcacgcagca ggtgctgaag tcggggcact cgaactggct gtcggggcac  9180
tggatggcgc ccacgctgtt gttgccgctg cgctggaagc agctgcggcc gtcggcgctg  9240
cagtggaagc cgcgggggca gcagtggtgg ccgtcgccgc aggccacggc ctcggggaag  9300
gggcagcagc tgctggtgcc gctcacggtg aagatgcagc tgtggccggc gctgcagtgg  9360
gcgtccacct ggcaggggcc gcccaggtgg cggctcaggg tggtgggcca cttgtccagc  9420
agggggcggc agcagctgta gctggcgccg ccggggtcca ggcagcaggc cacggggcag  9480
aactggccgt cggggcagcg ggtgccggcc accaggccgg cggtcagggc cacccagctc  9540
accagggtcc acatggtggc tcaaccggtg atatcttcga acggatccca cagtcgtgga  9600
agactttccc ttcggatctt cgaggaattc tttgccaaaa tgatgagaca gcacaataac  9660
cagcacgttg cccaggagct gtaggaaaaa gaagaaggca tgaacatggt tagcagaggc  9720
tctagctccc ggagcccctc aaggctttca cgcagccaca gaaaagaaac aagccgtcat  9780
taaaccaagc gctaattaca gcccggagga gaagggccgt cccgcccgct cacctgtggg  9840
agtaacgcgg tcagtcagag ccggggcggg cggcgcgagg cggcggcgga gcggggcacg  9900
gggcgaaggc agcgcgcagc gactcccgcc cgccgcgcgc ttcgcttttt atagggccgc  9960
cgccgccgcc gcctcgccat aaaaggaaac tttcggagcg cgccgctctg attggctgcc  10020
gccgcacctc tccgcctcgc cccgccccgc ccctcgcccc gccccgcccc gcctggcgcg  10080
cgcccccccc cccccccgc ccccatcgct gcacaaaata attaaaaaat aaataaatac  10140
aaaattgggg gtggggaggg gggggagatg gggagagtga agcagaacgt ggggctcacc  10200
tcgaccatgg taatagcgat gactaatacg tagatgtact gccaagtagg aaagtcccat  10260
aaggtcatgt actgggcata atgccaggcg ggccatttac cgtcattgac gtcaataggg  10320
ggcgtacttg gcatatgata cacttgatgt actgccaagt gggcagttta ccgtaaatac  10380
tccacccatt gacgtcaatg gaaagtccct attggcgtta ctatgggaac atacgtcatt  10440
attgacgtca atgggcgggg gtcgttgggc ggtcagccag gcgggccatt taccgtaagt  10500
tatgtaacgc ggaactccat atatgggcta tgaactaatg accccgtaat tgattactat  10560
taataactag gtaccgaatt cagatccaag cttcaccatg ggagacgtca ccggttctag  10620
aacctaggga gctctggtac ccactagtag tcgacgaacg cgtaacctcc cgcttcaaaa  10680
tggagaccct gcgtgctcac tcgggcttaa atacccagag ctagcaggaa cccctagtga  10740
tggagttggc cactccctct ctgcgcgctc gctcgctcac tgaggccgcc cgggcaaagc  10800
ccgggcgtcg ggcgaccttt ggtcgcccgg cctcagtgag cgagcgagcg cgcagagagg  10860
gagtggccaa                                                        10870
```

GENE THERAPIES FOR LYSOSOMAL DISORDERS

CROSS-REFERENCE TO RELATED APPLICATIONS

This application is a division of U.S. patent application Ser. No. 16/846,065, filed Apr. 10, 2020, which claims priority to U.S. Provisional Patent Application No. 62/988,665, filed on Mar. 12, 2020, U.S. Provisional Patent Application No. 62/960,471, filed on Jan. 13, 2020, U.S. Provisional Patent Application No. 62/954,089, filed on Dec. 27, 2019, U.S. Provisional Patent Application No. 62/934,450, filed on Nov. 12, 2019 and U.S. Provisional Patent Application No. 62/831,846, filed on Apr. 10, 2019. The disclosure of each of these applications is incorporated herein by reference in its entirety.

REFERENCE TO AN ELECTRONIC SEQUENCE LISTING

The contents of the electronic sequence listing (PRVL_010_06US_SeqList_ST26.xml; Size: 535,200 bytes; and Date of Creation: Apr. 25, 2024) are herein incorporated by reference in their entirety.

FIELD

The disclosure relates to the field of gene therapy and methods of using same.

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegaly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease. Several therapeutics exist that address the peripheral disease and the principal clinical manifestations in hematopoietic bone marrow and viscera, including enzyme replacement therapies as described below, chaperone-like small molecule drugs that bind to defective Gcase and improve stability, and substrate reduction therapy that block the production of substrate that accumulate in Gaucher disease leading to symptoms and findings. However, other aspects of Gaucher disease (particularly those affecting the skeleton and brain) appear refractory to treatment.

Progranulin (PGRN) is an additional protein linked to lysosomal function. PGRN is encoded by the GRN gene. GRN haploinsufficiency in humans leads to an approximately 90% risk of developing FTD-GRN (fronto-temporal dementia with GRN mutation), a neurodegenerative disease characterized by impairment of executive function, changes in behavior, and language difficulties, accompanied by atrophy of the frontal and temporal lobes. No disease-modifying therapies are available for patients with FTD.

SUMMARY

Provided herein is a method for treating a subject having or suspected of having fronto-temporal dementia with a GRN mutation, the method comprising administering to the subject a recombinant adeno-associated virus (rAAV) comprising: (i) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (ii) an AAV9 capsid protein. In some embodiments, the rAAV is administered to a subject at a dose ranging from about $1\times10^{13}$ vector genomes (vg) to about $7\times10^{14}$ vg. In some embodiments, the rAAV is administered via an injection into the cisterna magna.

In some embodiments, the promoter operably linked to a transgene insert encoding a PGRN protein is a chicken beta actin (CBA) promoter. In some embodiments, the rAAV vector further comprises a cytomegalovirus (CMV) enhancer. In some embodiments, the rAAV vector further comprises a Woodchuck Hepatitis Virus Posttranscriptional Regulatory Element (WPRE). In some embodiments, the rAAV vector further comprises a Bovine Growth Hormone polyA signal tail. In some embodiments, the nucleic acid comprises two adeno-associated virus inverted terminal repeats (ITR) sequences flanking the expression construct. In some embodiments, each ITR sequence is a wild-type AAV2 ITR sequence. In some embodiments, the rAAV vector further comprises a TRY region between the 5' ITR and the expression construct, wherein the TRY region comprises SEQ ID NO: 28.

Provided herein is a method for treating a subject having or suspected of having fronto-temporal dementia with a GRN mutation, the method comprising administering to the subject a rAAV comprising: (i) a rAAV vector comprising a nucleic acid comprising, in 5' to 3' order: (a) an AAV2 ITR; (b) a CMV enhancer; (c) a CBA promoter; (d) a transgene insert encoding a PGRN protein, wherein the transgene insert comprises the nucleotide sequence of SEQ ID NO: 68; (e) a WPRE; (f) a Bovine Growth Hormone polyA signal tail; and (g) an AAV2 ITR; and (ii) an AAV9 capsid protein. In some embodiments, the rAAV is administered to a subject at a dose ranging from about $1\times10^{13}$ vg to about $7\times10^{14}$ vg. In some embodiments, the rAAV is administered via an injection into the cisterna magna.

In some embodiments, the rAAV is administered in a formulation comprising about 20 mM Tris, pH 8.0, about 1 mM $MgCl_2$, about 200 mM NaCl, and about 0.001% w/v poloxamer 188.

Provided herein is a pharmaceutical composition comprising (i) a rAAV comprising: (a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (b) an AAV9 capsid protein; and (ii) about 20 mM Tris, pH 8.0, (iii) about 1 mM $MgCl_2$, (iv) about 200 mM NaCl, and (v) about 0.001% w/v poloxamer 188.

Provided herein is a rAAV comprising: (a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (b) an AAV9 capsid protein, for use in a method of treating fronto-temporal dementia with a GRN mutation in a subject.

Provided herein is a method of quantifying a PGRN protein level in a cerebrospinal fluid (CSF) sample, the method comprising: (1) diluting the CSF sample in a master mix containing dithiothreitol (DTT) and sample buffer; (2)

loading the diluted CSF sample, an anti-progranulin antibody, a secondary antibody that detects the anti-progranulin antibody, luminol and peroxide into wells of a capillary cartridge; (3) loading the capillary cartridge into an automated Western blot immunoassay instrument; (4) using the automated Western blot immunoassay instrument to calculate signal intensity, peak area, and signal-to-noise ratio; and (5) quantifying a progranulin protein level in the CSF sample as the peak area of immunoreactivity to the anti-progranulin antibody.

BRIEF DESCRIPTION OF THE DRAWINGS

FIG. 36A shows data for overexpression of TREM2. FIG. 36B shows data for overexpression of GBA1 from the same construct.

FIG. 52D: Neurons were lysed, and the Triton-X insoluble protein fraction was isolated and analyzed on the Protein Simple Western Jess system with an anti-TDP-43 antibody (#12892-AP-1). A band corresponding to TDP-43 was detected, and the area under the curve was quantified for each band and normalized to the total protein concentration of the insoluble fraction. The y-axis depicts the amount of insoluble TDP-43 as a percent of excipient treated levels normalized separately for each FTD-GRN cell line (n=3; mean±SEM). FIG. 52D shows that PR006 treatment decreased insoluble TDP-43, a hallmark of FTD-GRN pathology, in FTD-GRN neuronal cultures. FIG. 52F: Quantification of nuclear TDP-43 signal from immunofluorescence images of iPSC-derived neurons treated with PR006A. The TDP-43 signal intensity per nucleus in excipient or PR006A treated FTD-GRN neurons was determined; the y-axis depicts the TDP-43 signal intensity per nucleus as a percent of the TDP-43 signal intensity per nucleus of excipient treated Control neurons (n=145-306 cells; mean±SEM). TDP-43 was measured using an anti-TDP-43 antibody (#12892-AP-1) and nuclear area was determined by DAPI stain. FIG. 52F shows that PR006 treatment increased nuclear TDP-43 expression levels in FTD-GRN neuronal cultures to near wild-type control levels. Statistics were determined using an unpaired t-test, =p<0.01, *=p<0.001.

FIG. 53A: Presence of vector genomes was assessed in the cerebral cortex and spinal cord, and biodistribution is shown as vector genomes per μg of gDNA on a log scale (n=8-10/group; mean±SEM). Vector genome presence was quantified by qPCR using a vector reference standard curve. Dashed line (at 50 vector genomes/μg gDNA) represents the threshold for positive vector presence. FIG. 53B: PR006A-encoded GRN RNA expression was assessed by quantitative RT-PCR (qRT-PCR) in the cerebral cortex (n=8-10/group; mean±SEM). The number of GRN copies (specific to our codon optimized PR006A sequence) was normalized to 1 μg of total RNA and is shown on a log scale. FIG. 53C: Progranulin protein levels were measured using a human-specific progranulin ELISA in the brain and spinal cord (n=8-10/group; mean±SEM). Tissue progranulin levels were normalized to total protein concentration. The lower limit of quantitation (LLOQ) is indicated by a dashed gray line. For tissue ELISA assays, LLOQ (ng/mg) values are determined by dividing the assay LLOQ (ng/mL) by the total protein concentration average from all samples. A simple line corresponding to the treatment group legend color on the x-axis without error bars indicates that all animals in that group were 0. Statistical analysis was conducted using ANOVA followed by Dunnett's test to compare to the excipient treated Grn KO mouse group; *=p<0.05, =p<0.01, *=p<0.001. vg=vector genomes; LLOQ=lower limit of quantitation; SC=spinal cord.

FIG. 53D: Presence of vector genomes was assessed, and biodistribution is shown as vector genomes per μg of gDNA on a log scale (n=8-10/group; mean±SEM). Vector genome presence was quantified by qPCR using a vector reference standard curve. Dashed line (at 50 vector genomes/μg gDNA) represents the threshold for positive vector presence. FIG. 53E: Progranulin protein levels were measured using an ELISA (n=8-10/group; mean±SEM). Tissue progranulin levels were normalized to total protein concentration. A simple line corresponding to the treatment group legend color on the x-axis without error bars indicates that all animals in that group were 0. Statistical analysis was conducted using ANOVA followed by Dunnett's test to compare to the excipient treated Grn KO mouse group; *=p<0.05, ***=p<0.001. vg=vector genomes.

FIG. 53G: Lipofuscin accumulation (autofluorescent lipofuscin granules) was semi-quantitatively scored in H&E-stained sections in different brain regions by a blinded board-certified pathologist according to the following grading scheme: 0=no lipofuscin observed; 1=very small granules of lipofuscin (<2 μm) scattered throughout region; 2=increased density of small granule accumulation, and/or development of larger granules (>2-3 μm); 3=multifocal regions with a high density of lipofuscin granules visible from a low objective power; 4=widespread lipofuscin accumulation.

Lipofuscin severity scores in the cerebral cortex, hippocampus, and thalamus/hypothalamus brain regions is shown (n=8-10/group). FIG. 53H: IHC analysis of ubiquitin was performed and quantified in the cerebral cortex, hippocampus, and thalamus. The size of above-threshold immunoreactive objects (immunoreactive object size [μm2] is shown for ubiquitin (n=8-10/group; mean±SEM). Statistics were determined by ANOVA followed by Dunnett's test to compare to the excipient treated Grn KO mouse group, *=p<0.05, =p<0.01, *=p<0.001. vg=vector genomes; WT=wildtype.

FIG. 53I: Gene expression (mRNA levels) of Tnf and Cd68 was measured by qRT-PCR in the somatosensory cortex (mean±SEM; n=8-10/group). Gene expression was normalized to the housekeeping gene Ppib. FIG. 53J-FIG. 53K: IHC analysis of Iba1 (FIG. 53J) and GFAP (FIG. 53K) was performed and quantified in fixed brain sections in the cerebral cortex, hippocampus, and thalamus. The percent of the area of interest that is covered by above-threshold objects (immunoreactive area [%]) is shown (mean±SEM; n=8-10/group). Statistics were determined using ANOVA with Dunnett's adjustment comparing each group to the excipient treated Grn KO mouse group, *=p<0.05, ***=p<0.001. vg=vector genomes; WT=wildtype.

FIG. 53L: Cellular Component: Vacuole (GO: 0005773), FIG. 53M: Lysosome, and FIG. 53N: Complement System (HALLMARK pathway) (median±range; n=8-10/group). Statistical analysis was conducted using ANOVA followed by Dunnett's test to compare to the excipient-treated Grn KO mouse group while controlling for the family-wise Type I error rate, ***=p<0.001. GSVA=gene set variation analysis; vg=vector genomes; WT=wildtype.

FIG. 59A: Presence of vector genomes was assessed in the cerebral cortex and spinal cord (mean±SEM; n=4/group). Biodistribution is shown as vector genomes per 1 μg of gDNA on a log scale. Vector genome presence was quantified by qPCR using a vector reference standard curve. Dashed line (at 50 vector genomes/μg gDNA) represents the threshold for positive vector presence. FIG. 59B-FIG. 59C: Progranulin protein levels were measured using an ELISA in CNS tissues (brain and spinal cord (FIG. 59B)), and CSF (FIG. 59C) (mean±SEM; n=4/group). Tissue progranulin levels were normalized to total protein concentration, and CSF levels of progranulin were normalized to fluid volume. The lower limit of quantitation (LLOQ) is indicated by a dashed gray line. For tissue ELISA assays, LLOQ (ng/mg) values were determined by dividing the assay LLOQ (ng/mL) by the total protein concentration average from all samples. A simple red line on the x-axis without error bars indicates that all animals in that group were 0. Statistical analyses were performed using Kruskal-Wallis; *=p<0.05, =p<0.01, *=p<0.001. vg=vector genomes; LLOQ=lower limit of quantitation; SC=spinal cord.

FIG. 59D: Representative lipofuscin images from the thalamus/hypothalamus region of brain sections. White arrowheads indicate examples of lipofuscin accumulation. A summary of lipofuscin severity scores in the cerebral cortex, hippocampus, and thalamus/hypothalamus of H&E-stained slides from brain sections that were evaluated for autofluorescent lipofuscin granules is provided. Lipofuscin accumulation was semi-quantitatively scored by a blinded board-certified pathologist according to the following grading scheme: 0=no lipofuscin observed; 1=very small granules of lipofuscin (<2 μm) scattered throughout region; 2=increased density of small granule accumulation, and/or development of larger granules (>2-3 μm); 3=multifocal regions with a high density of lipofuscin granules visible from a low objective power; 4=widespread lipofuscin accumulation. FIG. 59E: IHC analysis of ubiquitin (n=4/group) was performed and quantified in the cerebral cortex, hippocampus, and thalamus. The positive cell density (cells/mm$^2$) for each region is shown (mean±SEM). Statistics were determined using a t-test, *=p<0.05, **=p<0.01. vg=vector genomes.

FIG. 59F: Gene expression of Tnf and Cd68 was measured by qRT-PCR in the somatosensory cortex (mean±SEM; n=4/group). Gene expression was normalized to the housekeeping gene Ppib. (FIG. 59G) Protein expression of the proinflammatory cytokine TNFα was measured in the cerebral cortex using a Mesoscale Discovery mouse pro-inflammatory cytokine assay (mean±SEM; n=4/group). Cerebral cortices were homogenized, and protein expression levels were normalized to total protein concentration of tissue lysates. FIG. 59H-FIG. 59I: IHC analysis of Iba1 (FIG. 59H) and GFAP (FIG. 59I) was performed and quantified in fixed brain sections. A compilation of the positive cell density (cells/mm$^2$) from the three brain regions analyzed (cerebral cortex, hippocampus, and thalamus) is shown (mean±SEM; n=3-4/group). Statistical analyses were performed using a t-test, *=p<0.05. vg=vector genomes.

FIG. 62A: Presence of vector genomes was assessed in the liver, heart, lung, kidney, spleen, and gonads (mean±SEM; n=4/group). Biodistribution is shown as vector genomes per μg of gDNA on a log scale. Vector genome presence was quantified by qPCR using a vector reference standard. FIG. 62B: Progranulin protein levels were measured using an ELISA (mean±SEM; n=4/group). Tissue progranulin levels were normalized to total protein concentration. A simple red line on the x-axis without error bars indicates that all animals in that group were 0. Statistical analyses were performed using Kruskal-Wallis; *=p<0.05, =p<0.01, *=p<0.001. vg=vector genomes.

DETAILED DESCRIPTION

Figure 1:
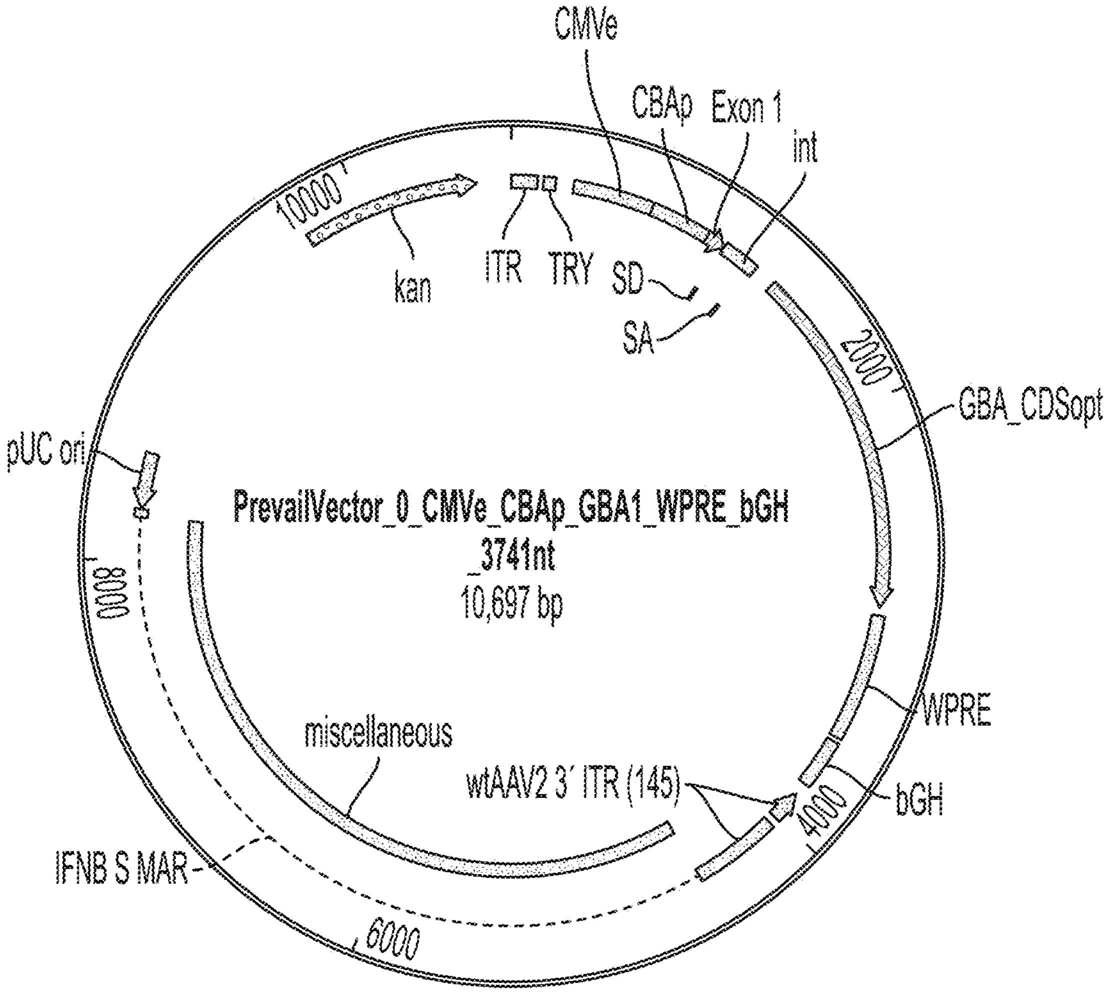
FIG. 1 is a schematic depicting one embodiment of a vector comprising an expression construct encoding Gcase (e.g., GBA1 or a portion thereof).
Figure 2:
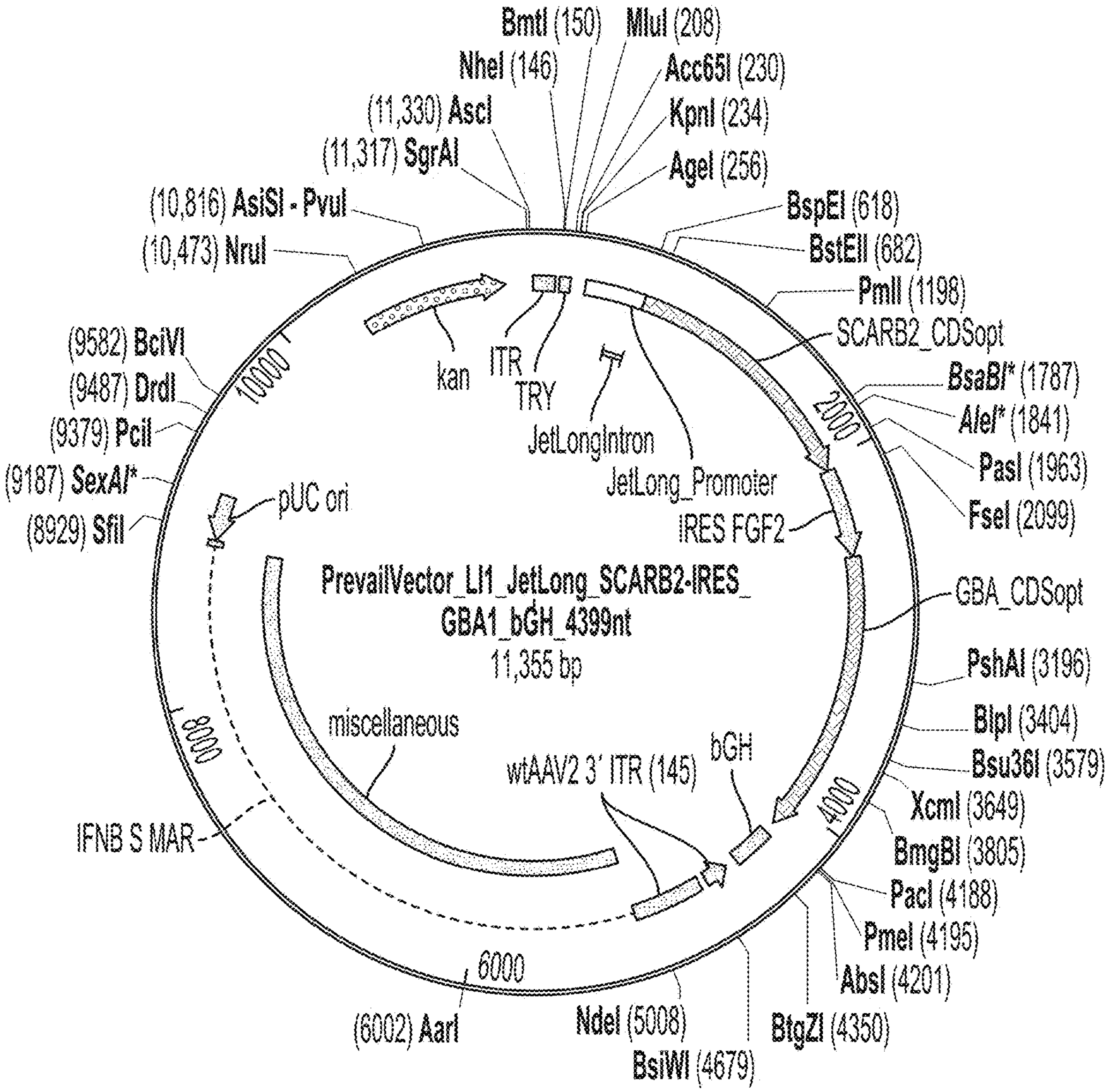
FIG. 2 is a schematic depicting one embodiment of a vector comprising an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
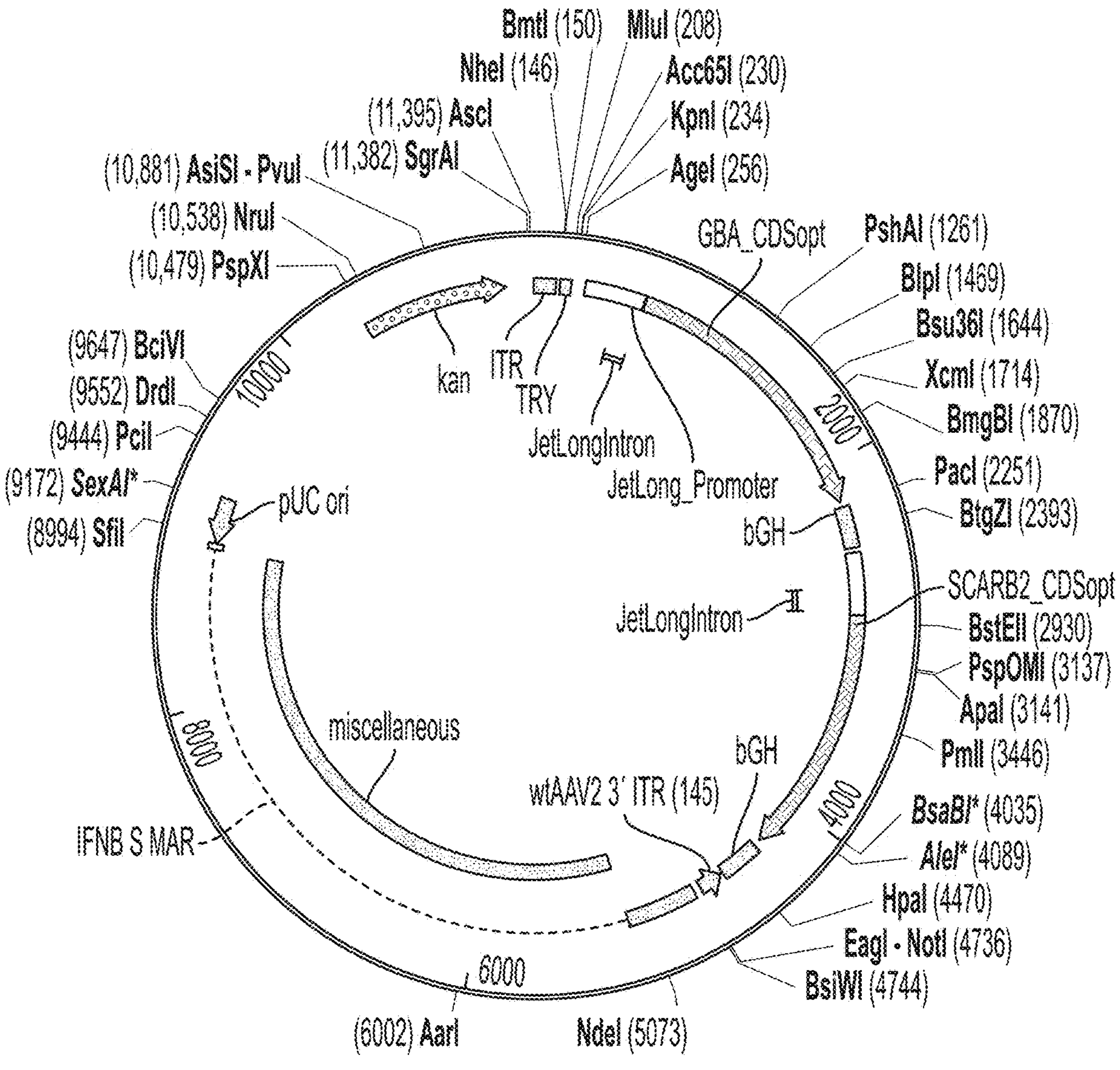
FIG. 3 is a schematic depicting one embodiment of a vector comprising an expression construct encoding Gcase (e.g., GBA1 or a portion thereof) and LIMP2 (SCARB2) or a portion thereof. Expression of the coding sequences of Gcase and LIMP2 are each driven by a separate promoter.

The disclosure is based, in part, on compositions and methods for expression of combinations of certain gene products (e.g., gene products associated with CNS disease) in a subject. A gene product can be a protein, a fragment (e.g., portion) of a protein, an interfering nucleic acid that inhibits a CNS disease-associated gene, etc. In some embodiments, a gene product is a protein or a protein fragment encoded by a CNS disease-associated gene. In some embodiments, a gene product is an interfering nucleic acid (e.g., shRNA, siRNA, miRNA, amiRNA, etc.) that inhibits a CNS disease-associated gene.

A CNS disease-associated gene refers to a gene encoding a gene product that is genetically, biochemically or functionally associated with a CNS disease, such as FTD (frontotemporal dementia) or PD (Parkinson's disease). For example, individuals having a pathogenic mutation in the GRN gene (which encodes the protein PGRN) have an increased risk of developing FTD compared to individuals that do not have a mutation in GRN. Similarly, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SNCA (which encodes α-Syn) is a PD-associated gene. In some embodiments, an expression cassette described herein encodes a wild-type or non-mutant form of a CNS disease-associated gene (or coding sequence thereof). Examples of CNS disease-associated genes are listed in Table 1.

TABLE 1

Examples of CNS disease-associated genes

| Name | Gene | Function | NCBI Accession No. |
|---|---|---|---|
| Lysosome membrane protein 2 | SCARB2/LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |
| Non-lysosomal Glucosylceramidase | GBA2 | catalyzes the conversion of glucosylceramide to free glucose and ceramide | NP_065995.1 (Isoform 1), NP_001317589.1 (Isoform 2) |
| Galactosylceramidase | GALC | removes galactose from ceramide derivatives | EAW81359.1 (Isoform CRA_a), EAW81360.1 (Isoform CRA_b), EAW81362.1 (Isoform CRA_c) |
| Sphingomyelin phosphodiesterase 1 | SMPDI | converts sphingomyelin to ceramide | EAW68726.1 (Isoform CRA_a), EAW68727.1 (Isoform CRA_b), EAW68728.1 (Isoform CRA_c), EAW68729.1 (Isoform CRA_d) |
| Cathepsin B | CTSB | thiol protease believed to participate in intracellular degradation and | AAC37547.1, AAH95408.1, AAH10240.1 |

TABLE 1-continued

| Examples of CNS disease-associated genes | | | |
|---|---|---|---|
| Name | Gene | Function | NCBI Accession No. |
| | | turnover of proteins; also implicated in tumor invasion and metastasis | |
| RAB7, member RAS oncogene family-like 1 | RAB7L1 | regulates vesicular transport | AAH02585.1 |
| Vacuolar protein sorting-associated protein 35 | VPS35 | component of retromer cargo-selective complex | NP_060676.2 |
| GTP cyclohydrolase 1 | GCH1 | responsible for hydrolysis of guanosine triphosphate to form 7.8-dihydroneopterin triphosphate | AAH25415.1 |
| Interleukin 34 | IL34 | increases growth or survival of monocytes; elicits activity by binding the Colony stimulating factor 1 receptor | AAH29804.1 |
| Triggering receptor expressed on myeloid cells 2 | TREM2 | forms a receptor signaling complex with the TYRO protein tyrosine kinase binding protein; functions in immune response and may be involved in chronic inflammation | AAF69824.1 |
| Progranulin | PGRN | plays a role in development, inflammation, cell proliferation and protein homeostasis | NP_002087.1 |

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk and/or risk of Gaucher disease (e.g., neuronopathic Gaucher disease, such as Type 2 Gaucher disease or Type 3 Gaucher disease). The disclosure is based, in part, on expression constructs (e.g., vectors) encoding one or more genes, for example Gcase, GBA2, prosaposin, progranulin (PGRN), LIMP2, GALC, CTSB, SMPD1, GCH1, RAB7, VPS35, IL-34, TREM2, TMEM106B, or a combination of any of the foregoing (or portions thereof), associated with central nervous system (CNS) diseases, for example Gaucher disease, PD, etc. In some embodiments, combinations of gene products described herein act together (e.g., synergistically) to reduce one or more signs and symptoms of a CNS disease when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase protein.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2 protein.

In some aspects, the disclosure provides an isolated nucleic acid comprising an expression construct encoding GBA2 protein (e.g., the gene product of GBA2 gene). In some embodiments, the isolated nucleic acid comprises a GBA2-encoding sequence that has been codon optimized (e.g., codon optimized for expression in mammalian cells, for example human cells). In some embodiments, the nucleic acid sequence encoding the GBA2 encodes a protein comprising an amino acid sequence as set forth in SEQ ID NO: 30 (e.g., as set forth in NCBI Reference Sequence NP_065995.1). In some embodiments, the isolated nucleic acid comprises the sequence set forth in SEQ ID NO: 31. In some embodiments the expression construct comprises adeno-associated virus (AAV) inverted terminal repeats (ITRs), for example AAV ITRs flanking the nucleic acid sequence encoding the GBA2 protein.

In some aspects, the disclosure provides an isolated nucleic acid comprising an expression construct encoding GALC protein (e.g., the gene product of GALC gene). In some embodiments, the isolated nucleic acid comprises a GALC-encoding sequence that has been codon optimized (e.g., codon optimized for expression in mammalian cells, for example human cells). In some embodiments, the nucleic acid sequence encoding the GALC encodes a protein comprising an amino acid sequence as set forth in SEQ ID NO: 33 (e.g., as set forth in NCBI Reference Sequence NP_000144.2). In some embodiments, the isolated nucleic acid comprises the sequence set forth in SEQ ID NO: 34. In some embodiments the expression construct comprises adeno-associated virus (AAV) inverted terminal repeats (ITRs), for example AAV ITRs flanking the nucleic acid sequence encoding the GALC protein.

In some aspects, the disclosure provides an isolated nucleic acid comprising an expression construct encoding CTSB protein (e.g., the gene product of CTSB gene). In some embodiments, the isolated nucleic acid comprises a CTSB-encoding sequence that has been codon optimized (e.g., codon optimized for expression in mammalian cells, for example human cells). In some embodiments, the nucleic acid sequence encoding the CTSB encodes a protein comprising an amino acid sequence as set forth in SEQ ID NO: 35 (e.g., as set forth in NCBI Reference Sequence NP_001899.1). In some embodiments, the isolated nucleic acid comprises the sequence set forth in SEQ ID NO: 36. In some embodiments the expression construct comprises adeno-associated virus (AAV) inverted terminal repeats (ITRs), for example AAV ITRs flanking the nucleic acid sequence encoding the CTSB protein.

In some aspects, the disclosure provides an isolated nucleic acid comprising an expression construct encoding SMPD1 protein (e.g., the gene product of SMPD1 gene). In some embodiments, the isolated nucleic acid comprises a SMPD1-encoding sequence that has been codon optimized (e.g., codon optimized for expression in mammalian cells, for example human cells). In some embodiments, the nucleic acid sequence encoding the SMPD1 encodes a protein comprising an amino acid sequence as set forth in SEQ ID NO: 37 (e.g., as set forth in NCBI Reference Sequence NP_000534.3). In some embodiments, the isolated nucleic acid comprises the sequence set forth in SEQ ID NO: 38. In some embodiments the expression construct comprises adeno-associated virus (AAV) inverted terminal repeats (ITRs), for example AAV ITRs flanking the nucleic acid sequence encoding the SMPD1 protein.

In some aspects, the disclosure provides an isolated nucleic acid comprising an expression construct encoding GCH1 protein (e.g., the gene product of GCH1 gene). In some embodiments, the isolated nucleic acid comprises a GCH1-encoding sequence that has been codon optimized (e.g., codon optimized for expression in mammalian cells, for example human cells). In some embodiments, the nucleic acid sequence encoding the GCH1 encodes a protein comprising an amino acid sequence as set forth in SEQ ID NO: 45 (e.g., as set forth in NCBI Reference Sequence NP_000534.3). In some embodiments, the isolated nucleic acid comprises the sequence set forth in SEQ ID NO: 46. In some embodiments the expression construct comprises adeno-associated virus (AAV) inverted terminal repeats (ITRs), for example AAV ITRs flanking the nucleic acid sequence encoding the GCH1 protein.

In some aspects, the disclosure provides an isolated nucleic acid comprising an expression construct encoding RAB7L protein (e.g., the gene product of RAB7L gene). In some embodiments, the isolated nucleic acid comprises a RAB7L-encoding sequence that has been codon optimized (e.g., codon optimized for expression in mammalian cells, for example human cells). In some embodiments, the nucleic acid sequence encoding the RAB7L encodes a protein comprising an amino acid sequence as set forth in SEQ ID NO: 47 (e.g., as set forth in NCBI Reference Sequence NP_003920.1). In some embodiments, the isolated nucleic acid comprises the sequence set forth in SEQ ID NO: 48. In some embodiments the expression construct comprises adeno-associated virus (AAV) inverted terminal repeats (ITRs), for example AAV ITRs flanking the nucleic acid sequence encoding the RAB7L protein.

In some aspects, the disclosure provides an isolated nucleic acid comprising an expression construct encoding VPS35 protein (e.g., the gene product of VPS35 gene). In some embodiments, the isolated nucleic acid comprises a VPS35-encoding sequence that has been codon optimized (e.g., codon optimized for expression in mammalian cells, for example human cells). In some embodiments, the nucleic acid sequence encoding the VPS35 encodes a protein comprising an amino acid sequence as set forth in SEQ ID NO: 49 (e.g., as set forth in NCBI Reference Sequence NP_060676.2). In some embodiments, the isolated nucleic acid comprises the sequence set forth in SEQ ID NO: 50. In some embodiments the expression construct comprises adeno-associated virus (AAV) inverted terminal repeats (ITRs), for example AAV ITRs flanking the nucleic acid sequence encoding the VPS35 protein.

In some aspects, the disclosure provides an isolated nucleic acid comprising an expression construct encoding IL-34 protein (e.g., the gene product of IL34 gene). In some embodiments, the isolated nucleic acid comprises a IL-34-encoding sequence that has been codon optimized (e.g., codon optimized for expression in mammalian cells, for example human cells). In some embodiments, the nucleic acid sequence encoding the IL-34 encodes a protein comprising an amino acid sequence as set forth in SEQ ID NO: 55 (e.g., as set forth in NCBI Reference Sequence NP_689669.2). In some embodiments, the isolated nucleic acid comprises the sequence set forth in SEQ ID NO: 56. In some embodiments the expression construct comprises adeno-associated virus (AAV) inverted terminal repeats (ITRs), for example AAV ITRs flanking the nucleic acid sequence encoding the IL-34 protein.

In some aspects, the disclosure provides an isolated nucleic acid comprising an expression construct encoding TREM2 protein (e.g., the gene product of TREMgene). In some embodiments, the isolated nucleic acid comprises a TREM2-encoding sequence that has been codon optimized (e.g., codon optimized for expression in mammalian cells, for example human cells). In some embodiments, the nucleic acid sequence encoding the TREM2 encodes a protein comprising an amino acid sequence as set forth in SEQ ID NO: 57 (e.g., as set forth in NCBI Reference Sequence NP_061838.1). In some embodiments, the isolated nucleic acid comprises the sequence set forth in SEQ ID NO: 58. In some embodiments the expression construct comprises adeno-associated virus (AAV) inverted terminal repeats (ITRs), for example AAV ITRs flanking the nucleic acid sequence encoding the TREM2 protein.

In some aspects, the disclosure provides an isolated nucleic acid comprising an expression construct encoding TMEM106B protein (e.g., the gene product of TMEM106B gene). In some embodiments, the isolated nucleic acid comprises a TMEM106B-encoding sequence that has been codon optimized (e.g., codon optimized for expression in mammalian cells, for example human cells). In some embodiments, the nucleic acid sequence encoding the TMEM106B encodes a protein comprising an amino acid sequence as set forth in SEQ ID NO: 63 (e.g., as set forth in NCBI Reference Sequence NP_060844.2). In some embodiments, the isolated nucleic acid comprises the sequence set forth in SEQ ID NO: 64. In some embodiments the expression construct comprises adeno-associated virus (AAV) inverted terminal repeats (ITRs), for example AAV ITRs flanking the nucleic acid sequence encoding the TMEM106B protein.

In some aspects, the disclosure provides an isolated nucleic acid comprising an expression construct encoding progranulin (e.g., the gene product of PGRN gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the progranulin (PGRN) encodes a protein comprising an amino acid sequence as set forth in SEQ ID NO: 67 (e.g., as set forth in NCBI Reference Sequence NP_002078.1). In some embodiments, the isolated nucleic acid comprises the sequence set forth in SEQ ID NO: 68. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product is a Gcase protein and a second gene product is selected from GBA2, prosaposin, progranulin, LIMP2, GALC, CTSB, SMPD1, GCH1, RAB7, VPS35, IL-34, TREM2, and TMEM106B.

In some embodiments, an expression construct encodes (e.g., alone or in addition to another gene product) an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an interfering nucleic acid inhibits expression of TMEM106B. In some embodiments, an interfering nucleic acid that targets TMEM106B comprises a sequence set forth in SEQ ID NO: 64 or 65. In some embodiments, an interfering nucleic acid that targets TMEM106B binds to (e.g., hybridizes with) a sequence set forth in SEQ ID NO: 64 or 65.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of, or encodes a peptide having, the sequence set forth in any one of SEQ ID NOs: 1-91.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector or a Baculovirus vector. In some embodiments, an rAAV vector is single-stranded (e.g., single-stranded DNA).

In some embodiments, the disclosure provides a host cell comprising an isolated nucleic acid as described by the disclosure or a vector as described by the disclosure.

In some embodiments, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having or suspected of having a central nervous system (CNS) disease, the method comprising administering to the subject a composition (e.g., a composition comprising an isolated nucleic acid or a vector or a rAAV) as described by the disclosure. In some embodiments, the CNS disease is a neurodegenerative disease, such as a neurodegenerative disease listed in Table 12. In some embodiments, the CNS disease is a synucleinopathy, such as a synucleinopathy listed in Table 13. In some embodiments, the CNS disease is a tauopathy, such as a tauopathy listed in Table 14. In some embodiments, the CNS disease is a lysosomal storage disease, such as a lysosomal storage disease listed in Table 15. In some embodiments, the lysosomal storage disease is neuronopathic Gaucher disease, such as Type 2 Gaucher disease or Type 3 Gaucher disease.

In some embodiments, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, the disclosure provides a method for treating a subject having or suspected of having frontotemporal dementia (FTD), FTD with GRN mutation, FTD with tau mutation, FTD with C9orf72 mutation, ceroid lipofuscinosis, Parkinson's disease, Alzheimer's disease, corticobasal degeneration, motor neuron disease, or Gaucher disease, the method comprising administering to the subject an rAAV encoding Progranulin (PGRN), wherein the PGRN is encoded by the nucleic acid sequence in SEQ ID NO:68; and wherein the rAAV comprises a capsid protein having an AAV9 serotype.

In some embodiments, the disclosure provides a method for treating a subject having or suspected of having FTD with a GRN mutation, the method comprising administering to the subject an rAAV encoding Progranulin (PGRN), wherein the PGRN is encoded by the nucleic acid sequence in SEQ ID NO:68; and wherein the rAAV comprises a capsid protein having an AAV9 serotype. In some embodiments, the rAAV is administered to a subject at a dose of about $3.5\times10^{13}$ vector genomes (vg), about $7.0\times10^{13}$ vg, or about $1.4\times10^{14}$ vg. In some embodiments, the rAAV is administered via an injection into the cisterna magna.

In some embodiments, a composition comprises a nucleic acid (e.g., an rAAV genome, for example encapsidated by AAV capsid proteins) that encodes two or more gene products (e.g., CNS disease-associated gene products), for example 2, 3, 4, 5, or more gene products described in this application. In some embodiments, a composition comprises two or more (e.g., 2, 3, 4, 5, or more) different nucleic acids (e.g., two or more rAAV genomes, for example separately encapsidated by AAV capsid proteins), each encoding one or more different gene products. In some embodiments, two or more different compositions are administered to a subject, each composition comprising one or more nucleic acids encoding different gene products. In some embodiments, different gene products are operably linked to the same promoter type (e.g., the same promoter). In some embodiments, different gene products are operably linked to different promoters.

Isolated Nucleic Acids and Vectors

An isolated nucleic acid may be DNA or RNA. The disclosure provides, in some aspects, isolated nucleic acids (e.g., rAAV vectors) comprising an expression construct encoding one or more PD-associated genes, for example a Gcase (e.g., the gene product of GBA1 gene) or a portion thereof. Gcase, also referred to as β-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NP_000148.2 (SEQ ID NO: 14). In some embodiments, an isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, an isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, an isolated nucleic acid comprises the sequence set forth in SEQ ID NO: 19. In some embodiments the isolated nucleic acid comprises a SCARB2-encoding sequence that has been codon optimized.

Aspects of the disclosure relate to an isolated nucleic acid comprising an expression construct encoding GBA2 protein (e.g., the gene product of GBA2 gene). GBA2 protein refers to non-lysosomal glucosylceramidase. In humans, GBA2 gene is located on chromosome 9. In some embodiments, the GBA2 gene encodes a peptide that is represented by NCBI Reference Sequence NP_065995.1 (SEQ ID NO: 30). In some embodiments, an isolated nucleic acid comprises the sequence set forth in SEQ ID NO: 31. In some embodiments the isolated nucleic acid comprises a GBA2-encoding sequence that has been codon optimized.

Aspects of the disclosure relate to an isolated nucleic acid comprising an expression construct encoding GALC protein (e.g., the gene product of GALC gene). GALC protein refers to galactosylceramidase (or galactocerebrosidase), which is an enzyme that hydrolyzes galactose ester bonds of galactocerebroside, galactosylsphingosine, lactosylceramide, and monogalactosyldiglyceride. In humans, GALC gene is located on chromosome 14. In some embodiments, the GALC gene encodes a peptide that is represented by NCBI Reference Sequence NP_000144.2 (SEQ ID NO: 33). In some embodiments, an isolated nucleic acid comprises the sequence set forth in SEQ ID NO: 34. In some embodiments the isolated nucleic acid comprises a GALC-encoding sequence that has been codon optimized.

Aspects of the disclosure relate to an isolated nucleic acid comprising an expression construct encoding CTSB protein (e.g., the gene product of CTSB gene). CTSB protein refers to cathepsin B, which is a lysosomal cysteine protease that plays an important role in intracellular proteolysis. In humans, CTSB gene is located on chromosome 8. In some embodiments, the CTSB gene encodes a peptide that is represented by NCBI Reference Sequence NP_001899.1 (SEQ ID NO: 35). In some embodiments, an isolated nucleic acid comprises the sequence set forth in SEQ ID NO: 36. In some embodiments the isolated nucleic acid comprises a CTSB-encoding sequence that has been codon optimized.

Aspects of the disclosure relate to an isolated nucleic acid comprising an expression construct encoding SMPD1 protein (e.g., the gene product of SMPD1 gene). SMPD1 protein refers to sphingomyelin phosphodiesterase 1, which is a hydrolase enzyme that is involved in sphingolipid metabolism. In humans, SMPD1 gene is located on chromosome 11. In some embodiments, the SMPD1 gene encodes a peptide that is represented by NCBI Reference Sequence NP_000534.3 (SEQ ID NO: 37). In some embodiments, an isolated nucleic acid comprises the sequence set forth in SEQ ID NO: 38. In some embodiments the isolated nucleic acid comprises a SMPD1-encoding sequence that has been codon optimized.

Aspects of the disclosure relate to an isolated nucleic acid comprising an expression construct encoding GCH1 protein (e.g., the gene product of GCH1 gene). GCH1 protein refers to GTP cyclohydrolase 1, which is a hydrolase enzyme that is part of the folate and biopterin biosynthesis pathways. In humans, GCH1 gene is located on chromosome 14. In some embodiments, the GCH1 gene encodes a peptide that is represented by NCBI Reference Sequence NP_000152.1 (SEQ ID NO: 45). In some embodiments, an isolated nucleic acid comprises the sequence set forth in SEQ ID NO: 46. In some embodiments the isolated nucleic acid comprises a GCH1-encoding sequence that has been codon optimized.

Aspects of the disclosure relate to an isolated nucleic acid comprising an expression construct encoding RAB7L protein (e.g., the gene product of RAB7L gene). RAB7L protein refers to RAB7, member RAS oncogene family-like 1, which is a GTP binding protein. In humans, RAB7L gene is located on chromosome 1. In some embodiments, the RAB7L gene encodes a peptide that is represented by NCBI Reference Sequence NP_003920.1 (SEQ ID NO: 47). In some embodiments, an isolated nucleic acid comprises the sequence set forth in SEQ ID NO: 48. In some embodiments the isolated nucleic acid comprises a RAB7L-encoding sequence that has been codon optimized.

Aspects of the disclosure relate to an isolated nucleic acid comprising an expression construct encoding VPS35 protein (e.g., the gene product of VPS35 gene). VPS35 protein refers to vacuolar protein sorting-associated protein 35, which is part of a protein complex involved in retrograde transport of proteins from endosomes to the trans-Golgi network. In humans, VPS35 gene is located on chromosome 16. In some embodiments, the VPS35 gene encodes a peptide that is represented by NCBI Reference Sequence NP_060676.2 (SEQ ID NO: 49). In some embodiments, an isolated nucleic acid comprises the sequence set forth in SEQ ID NO: 50. In some embodiments the isolated nucleic acid comprises a VPS35-encoding sequence that has been codon optimized.

Aspects of the disclosure relate to an isolated nucleic acid comprising an expression construct encoding IL-34 protein (e.g., the gene product of IL34 gene). IL-34 protein refers to interleukin 34, which is a cytokine that increases growth and survival of monocytes. In humans, IL34 gene is located on chromosome 16. In some embodiments, the IL34 gene encodes a peptide that is represented by NCBI Reference Sequence NP_689669.2 (SEQ ID NO: 55). In some embodiments, an isolated nucleic acid comprises the sequence set forth in SEQ ID NO: 56. In some embodiments the isolated nucleic acid comprises a IL-34-encoding sequence that has been codon optimized.

Aspects of the disclosure relate to an isolated nucleic acid comprising an expression construct encoding TREM2 protein (e.g., the gene product of TREM2 gene). TREM2 protein refers to triggering receptor expressed on myeloid cells 2, which is an immunoglobulin superfamily receptor found on myeloid cells. In humans, TREM2 gene is located on chromosome 6. In some embodiments, the TREM2 gene encodes a peptide that is represented by NCBI Reference Sequence NP_061838.1 (SEQ ID NO: 57). In some embodiments, the isolated nucleic acid comprises the sequence set forth in SEQ ID NO: 58. In some embodiments an isolated nucleic acid comprises a TREM2-encoding sequence that has been codon optimized.

Aspects of the disclosure relate to an isolated nucleic acid comprising an expression construct encoding TMEM106B protein (e.g., the gene product of TMEM106B gene). TMEM106B protein refers to transmembrane protein 106B, which is a protein involved in dendrite morphogenesis and regulation of lysosomal trafficking. In humans, TMEM106B gene is located on chromosome 7. In some embodiments, the TMEM106B gene encodes a peptide that is represented by NCBI Reference Sequence NP_060844.2 (SEQ ID NO: 62). In some embodiments, an isolated nucleic acid comprises the sequence set forth in SEQ ID NO: 63. In some embodiments the isolated nucleic acid comprises a TMEM106B-encoding sequence that has been codon optimized.

Aspects of the disclosure relate to an isolated nucleic acid comprising an expression construct encoding progranulin protein (e.g., the gene product of PGRN gene). PGRN protein refers to progranulin, which is a protein involved in development, inflammation, cell proliferation and protein homeostasis. In humans, the PGRN gene is located on chromosome 17. In some embodiments, the PGRN gene encodes a peptide that is represented by NCBI Reference Sequence NP_002078.1 (SEQ ID NO: 67). In some embodiments, an isolated nucleic acid comprises the sequence set forth in SEQ ID NO: 68. In some embodiments the isolated nucleic acid comprises a PGRN-encoding sequence that has been codon optimized. In some embodiments, the nucleic acid further comprises a chicken 3-actin (CBA) promoter and a cytomegalovirus enhancer (CMVe).

In some aspects, the disclosure provides an automated Western blot immunoassay to quantify a PGRN protein level in a cerebrospinal fluid (CSF) sample. In some embodiments, the immunoassay is a capillary-based automated Western blot immunoassay platform, where all steps, such as protein separation, immunoprobing, washing, and detection by chemiluminescence, occur in a capillary cartridge. In some embodiments, a CSF sample is from a human or a non-human primate. In some aspects, the immunoassay allows detection of differences in PGRN protein levels in the presence of circulating antibody. In some aspects, the disclosure provides a method of quantifying a progranulin protein level in a CSF sample, the method comprising: (1) diluting the CSF sample (e.g., a 4-fold dilution); (2) loading the CSF sample; an anti-progranulin antibody; a secondary antibody that detects the anti-progranulin antibody, luminol, and peroxide into wells of a capillary cartridge; (3) loading the capillary cartridge into an automated Western blot immunoassay instrument; (4) using the automated Western blot immunoassay instrument to calculate one or more of: signal intensity, peak area, signal-to-noise ratio and total protein normalization parameters; and (5) quantifying a progranulin protein level in the CSF sample as the peak area of immunoreactivity to the anti-progranulin antibody. In some embodiments, the CSF sample is diluted in a master mix comprising dithiothreitol (DTT) and sample buffer. The master mix may further comprise other proprietary components. In some aspects, the anti-progranulin antibody detects human progranulin. In some embodiments, a progranulin protein level is quantified from the calculated parameters using software that controls the automated Western blot immunoassay instrument. In some embodiments, the software is Compass software for Simple Western™ (ProteinSimple, San Jose, CA).

In some embodiments, the disclosure provides a method of quantifying a progranulin protein level in a cerebrospinal fluid (CSF) sample, the method comprising: (1) diluting the CSF sample (e.g., a 4-fold dilution) in a master mix containing dithiothreitol (DTT) and sample buffer; (2) loading the diluted CSF sample, an anti-progranulin antibody; a secondary antibody that detects the anti-progranulin antibody, luminol, and peroxide into wells of a capillary cartridge; (3) loading the capillary cartridge into an automated Western blot immunoassay instrument; (4) using the automated Western blot immunoassay instrument to calculate signal intensity, peak area, and signal-to-noise ratio; and (5) quantifying a progranulin protein level in the CSF sample as the peak area of immunoreactivity to the anti-progranulin antibody.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, an isolated nucleic acid or vector (e.g., rAAV vector) described by the disclosure comprises or consists of a sequence set forth in any one of SEQ ID NOs: 1-91. In some embodiments, an isolated nucleic acid or vector (e.g., rAAV vector) described by the disclosure comprises or consists of a sequence that is complementary (e.g., the complement of) a sequence set forth in any one of SEQ ID NOs: 1-91. In some embodiments, an isolated nucleic acid or vector (e.g., rAAV vector) described by the disclosure comprises or consists of a sequence that is a reverse complement of a sequence set forth in any one of SEQ ID NOs: 1-91. In some embodiments, an isolated nucleic acid or vector (e.g., rAAV vector) described by the disclosure comprises or consists of a portion of a sequence set forth in any one of SEQ ID NOs: 1-91. A portion may comprise at least 25%, 50%, 60%, 70%, 80%, 90%, 95%, or 99% of a sequence set forth in any one of SEQ ID NOs: 1-91. In some embodiments, a nucleic acid sequence described by the disclosure is a nucleic acid sense strand (e.g., 5' to 3' strand), or in the context of a viral sequences a plus (+) strand. In some embodiments, a nucleic acid sequence described by the disclosure is a nucleic acid antisense strand (e.g., 3' to 5' strand), or in the context of viral sequences a minus (−) strand.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by another gene listed in Table 1, for example the SCARB2/LIMP2 gene or the PSAP gene. However, the skilled artisan recognizes that the order of expression of a first gene product (e.g., Gcase) and a second gene product (e.g., LIMP2, etc.) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornoe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34 (Database issue):D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, shRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein) or TMEM106B (e.g., the gene encoding TMEM106B protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA or TMEM106B). In some embodiments, an inhibitory nucleic acid is an artificial miRNA (amiRNA) that includes a miR-155 scaffold and a SNCA or TMEM106B targeting sequence.

The skilled artisan recognizes that when referring to nucleic acid sequences comprising or encoding inhibitory nucleic acids (e.g., dsRNA, siRNA, miRNA, amiRNA, etc.) any one or more thymidine (T) nucleotides or uridine (U) nucleotides in a sequence provided herein may be replaced with any other nucleotide suitable for base pairing (e.g., via a Watson-Crick base pair) with an adenosine nucleotide. For example, T may be replaced with U, and U may be replaced with T.

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, an rAAV vector is single-stranded (e.g., single-stranded DNA). In some embodiments, the vector is a recombinant AAV (rAAV) vector. In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Figure 20:
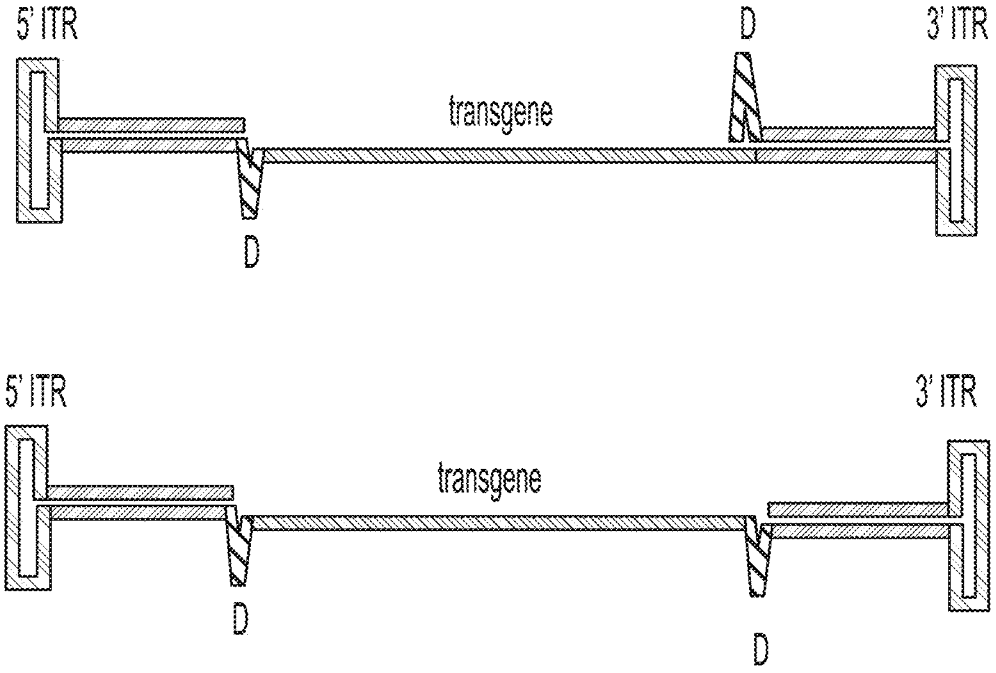
FIG. 20 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).
Figure 21:
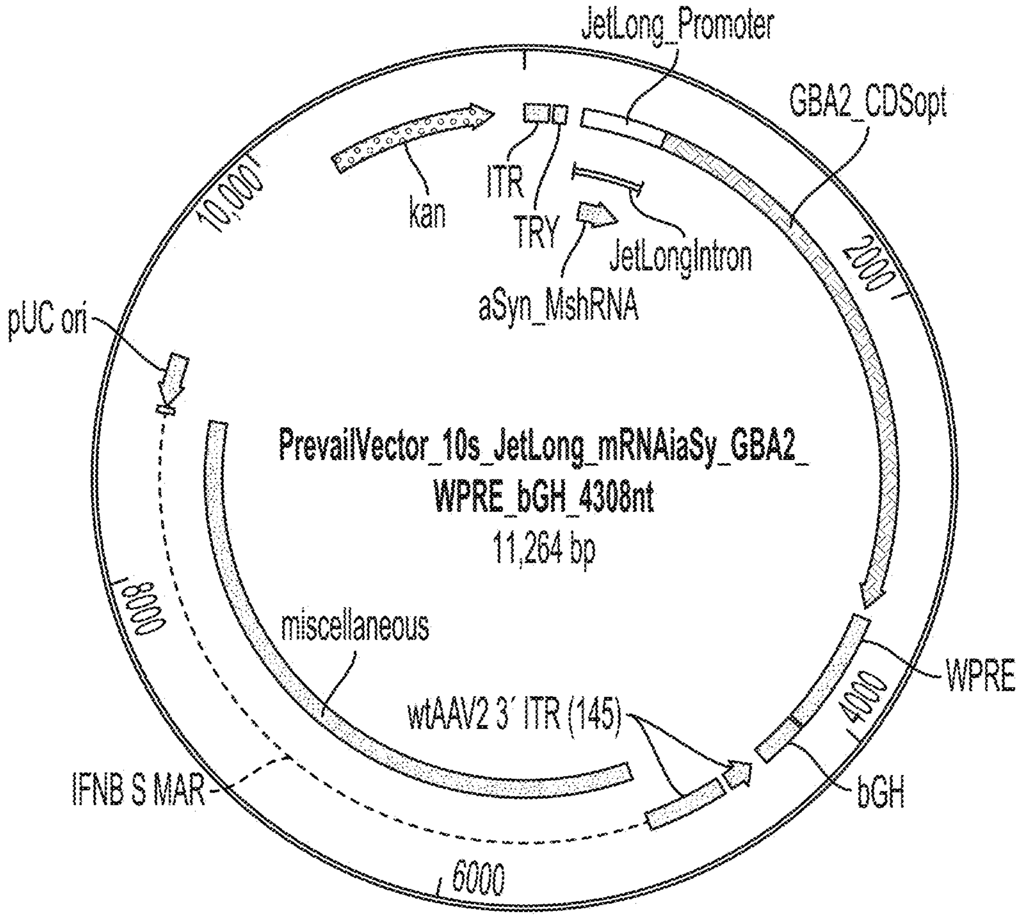
FIG. 21 a schematic depicting one embodiment of a vector comprising an expression construct encoding GBA2 or a portion thereof, and an interfering RNA for α-Syn.
Figure 22:
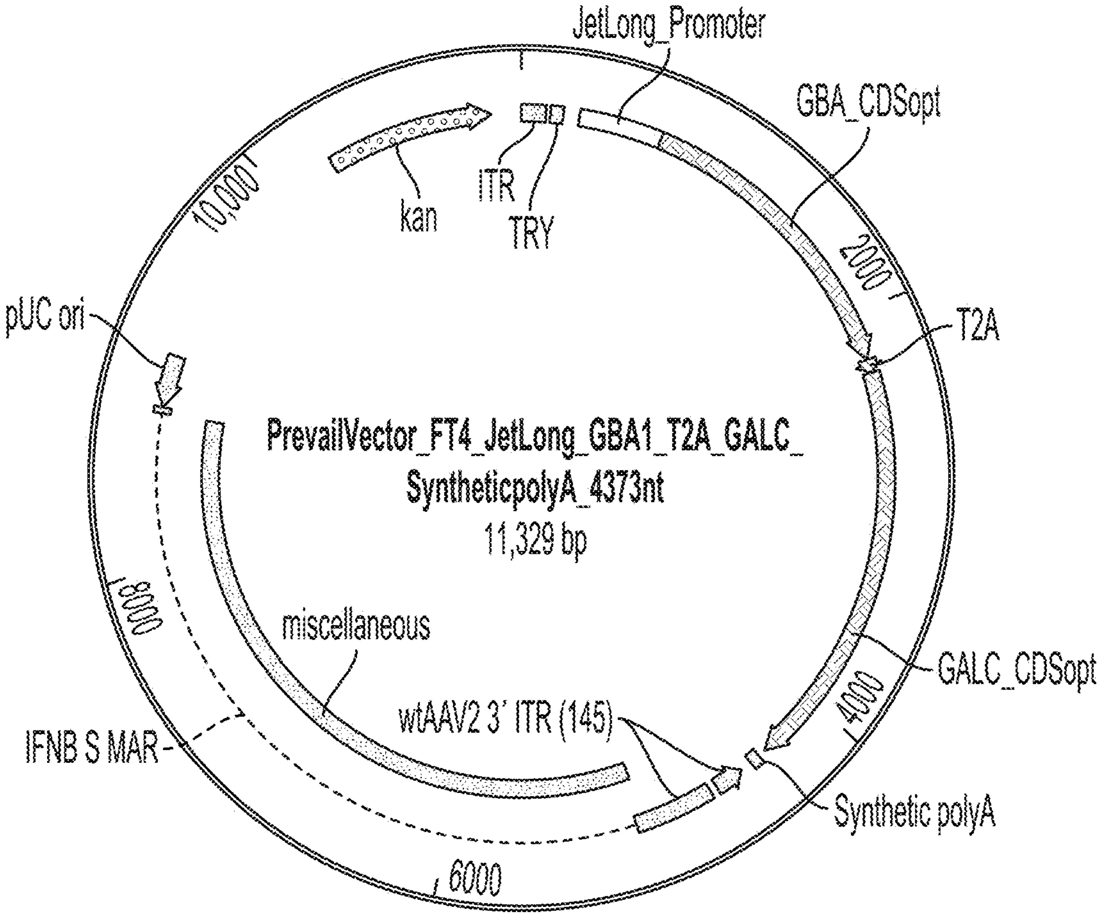
FIG. 22 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 23:
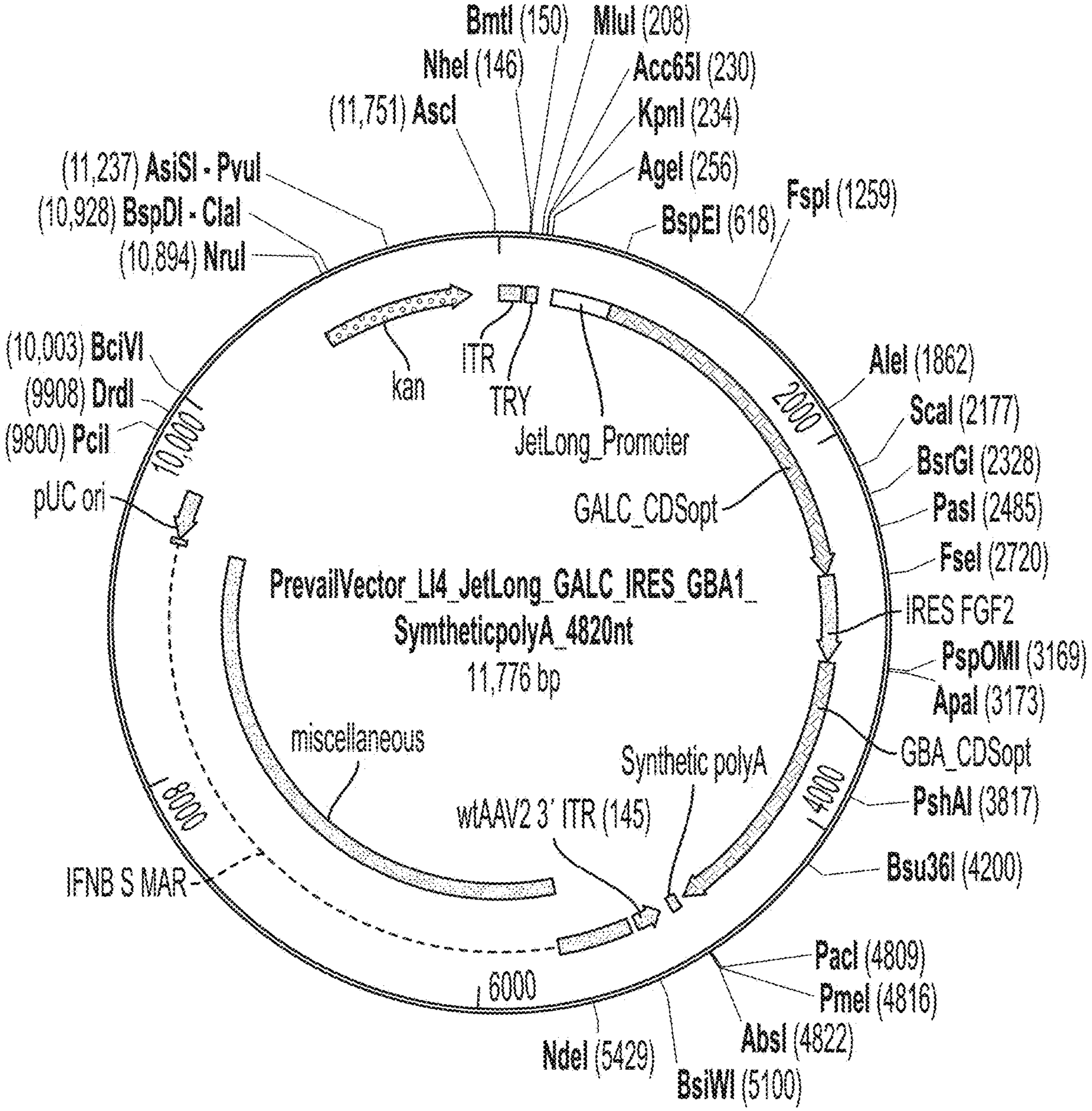
FIG. 23 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 24:
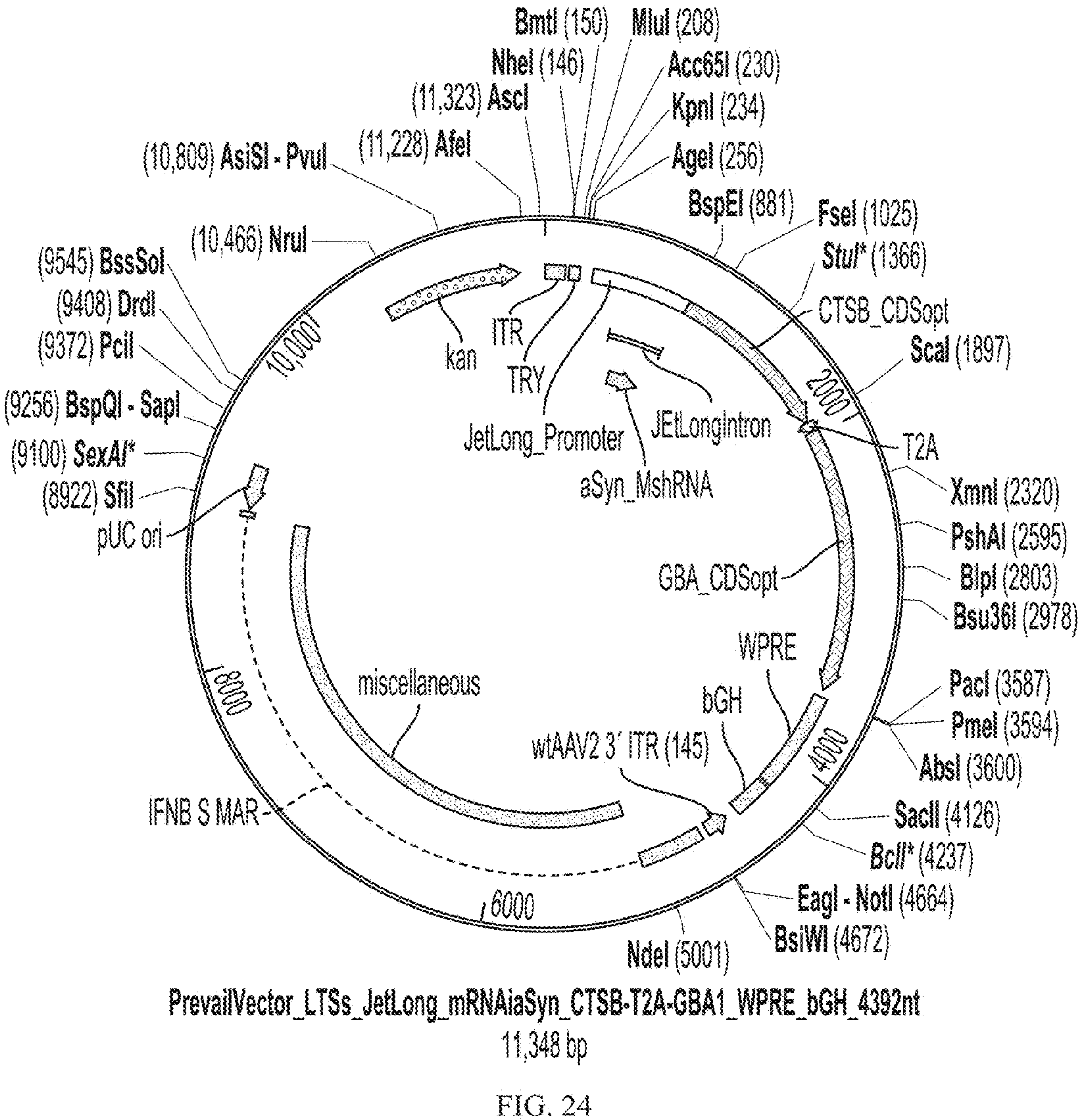
FIG. 24 is a schematic depicting one embodiment of a vector comprising an expression construct encoding Gcase (e.g., GBA1 or a portion thereof), Cathepsin B (e.g., CTSB or a portion thereof), and an interfering RNA for α-Syn. Expression of the coding sequences of Gcase and Cathepsin B are separated by a T2A self-cleaving peptide sequence.
Figure 25:
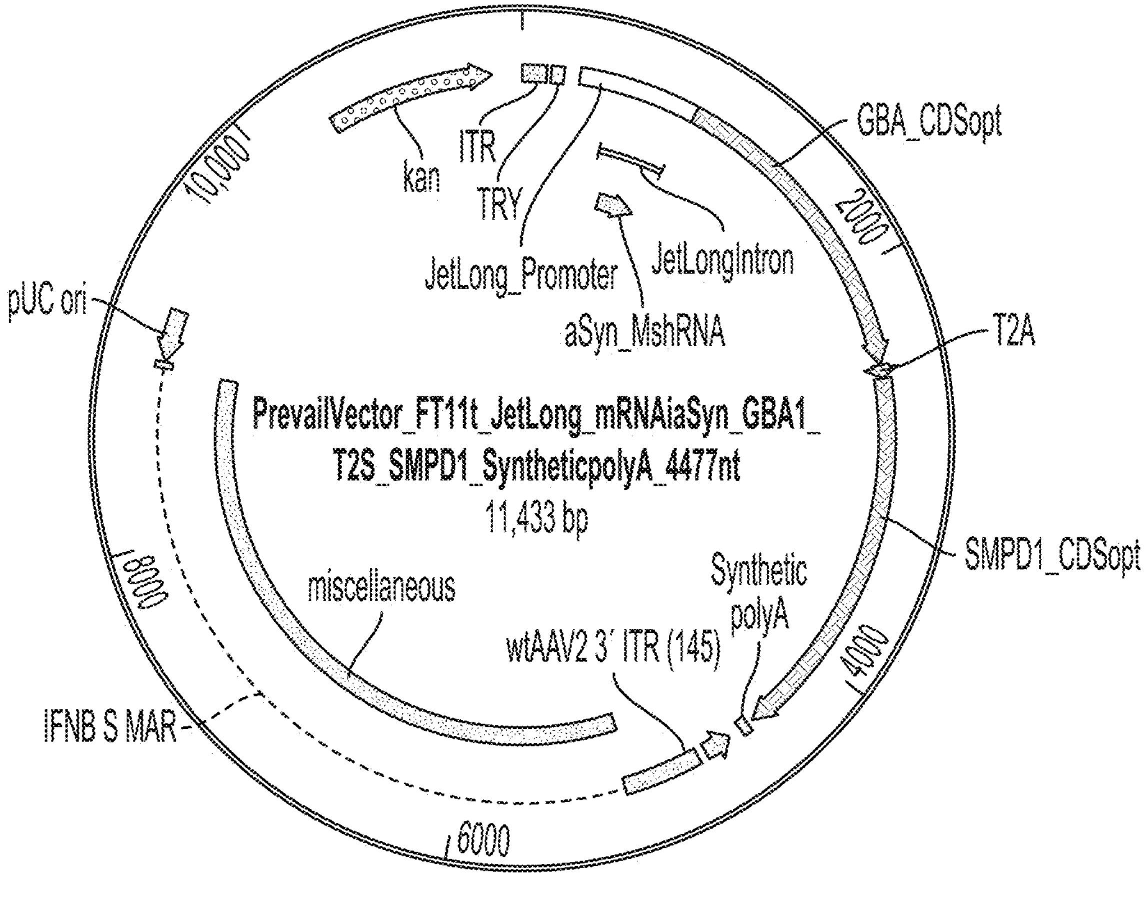
FIG. 25 is a schematic depicting one embodiment of a vector comprising an expression construct encoding Gcase (e.g., GBA1 or a portion thereof), Sphingomyelin phosphodiesterase 1 (e.g., SMPD1 a portion thereof, and an interfering RNA for α-Syn.
Figure 26:
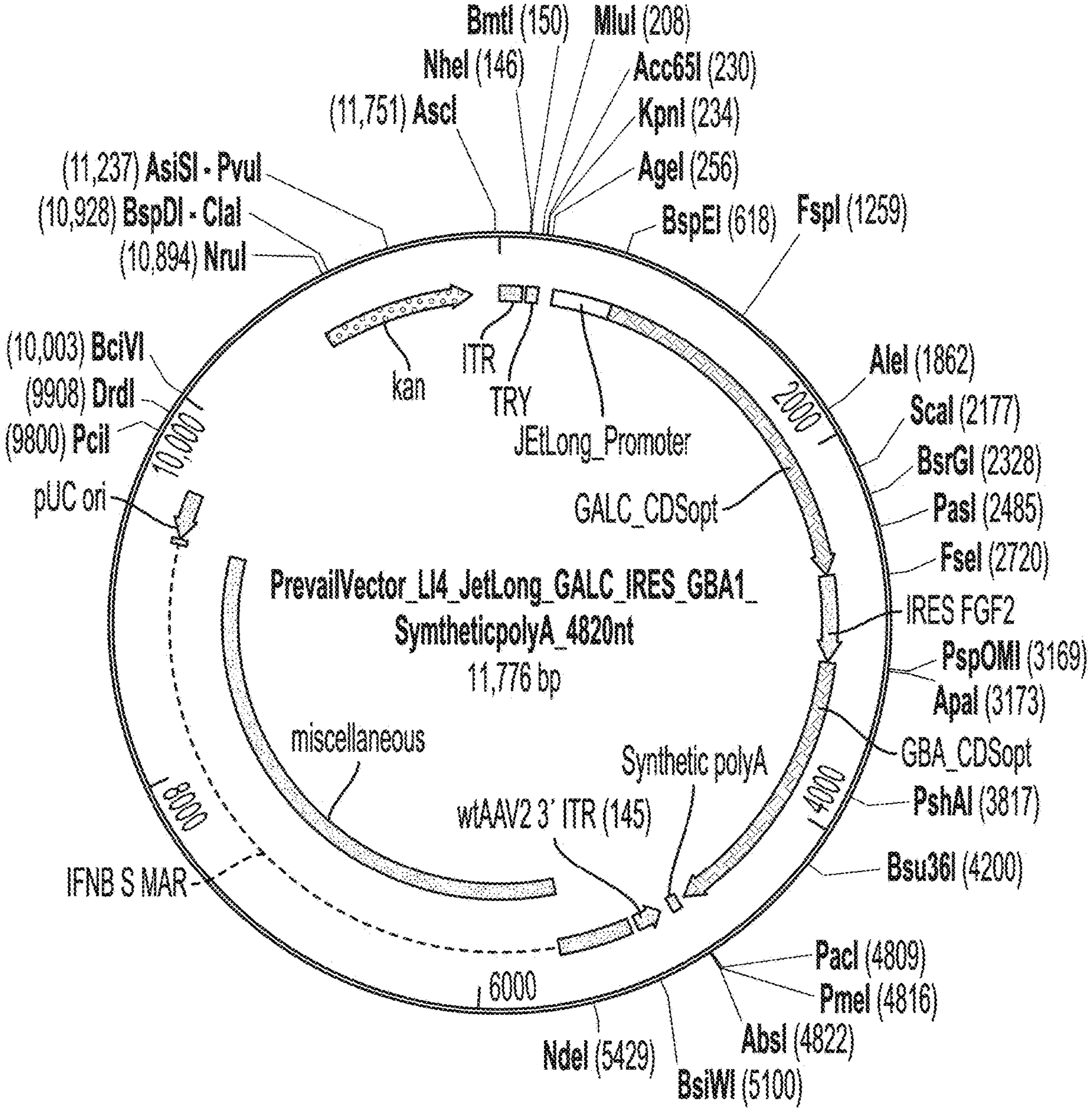
FIG. 26 is a schematic depicting one embodiment of a vector comprising an expression construct encoding Gcase (e.g., GBA1 or a portion thereof) and Galactosylceramidase (e.g., GALC or a portion thereof). The coding sequences of Gcase and Galactosylceramidase are separated by an internal ribosomal entry site (IRES).
Figure 27:
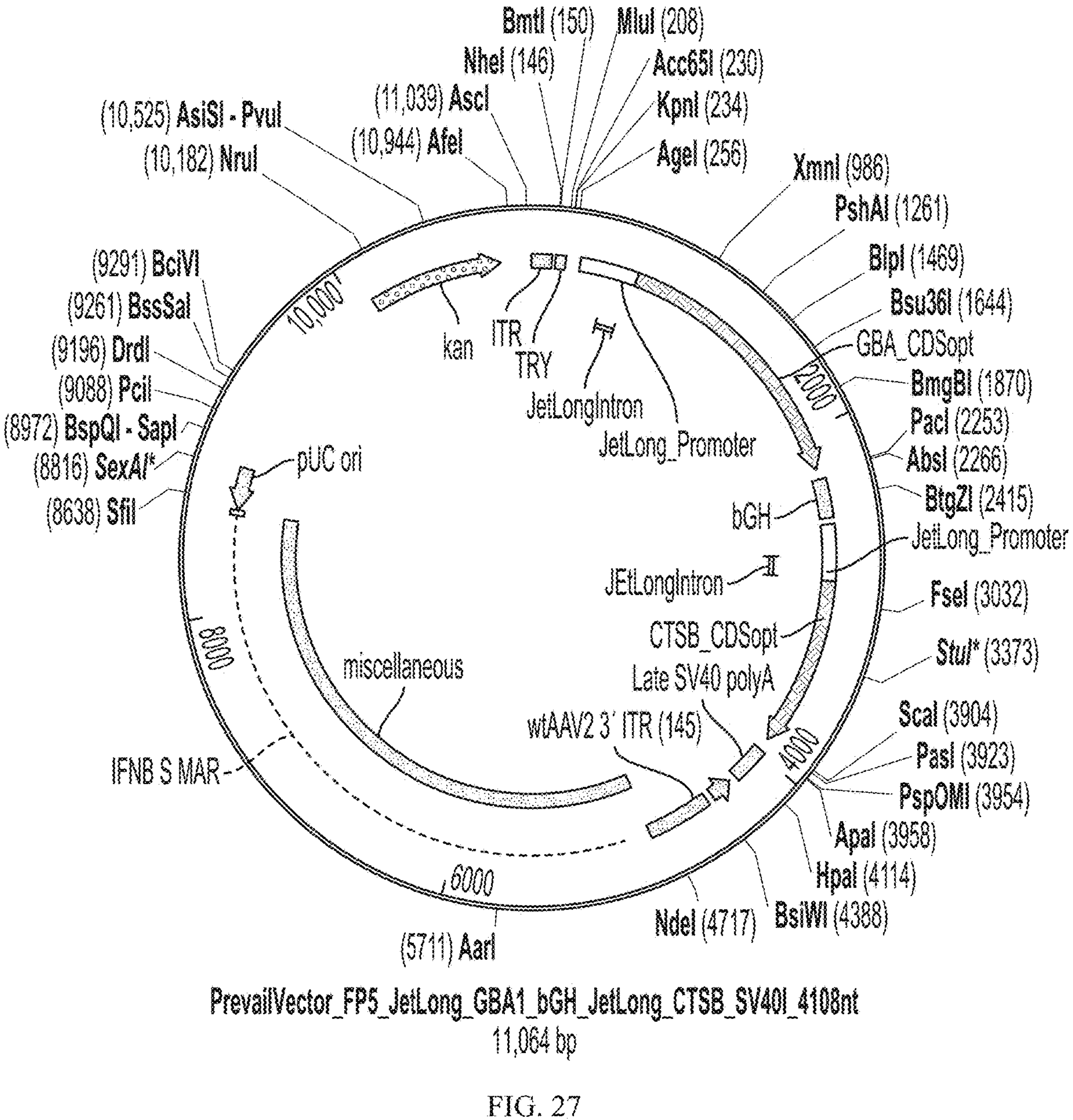
FIG. 27 is a schematic depicting one embodiment of a vector comprising an expression construct encoding Gcase (e.g., GBA1 or a portion thereof) and Cathepsin B (e.g., CTSB or a portion thereof). Expression of the coding sequences of Gcase and Cathepsin B are each driven by a separate promoter.
Figure 28:
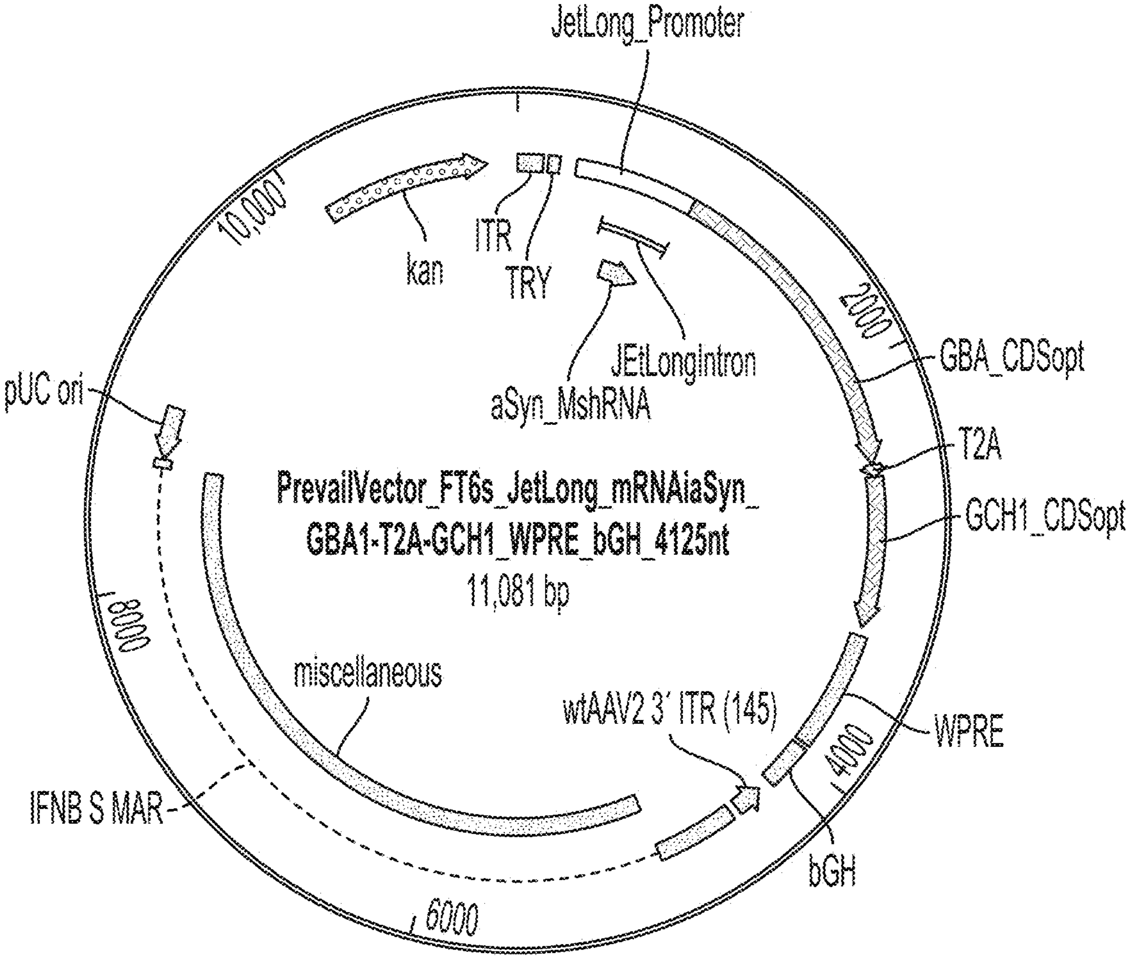
FIG. 28 is a schematic depicting one embodiment of a vector comprising an expression construct encoding Gcase (e.g., GBA1 or a portion thereof), GCH1 (e.g., GCH1 or a portion thereof), and an interfering RNA for α-Syn. The coding sequences of Gcase and GCH1 are separated by an T2A self-cleaving peptide sequence
Figure 29:
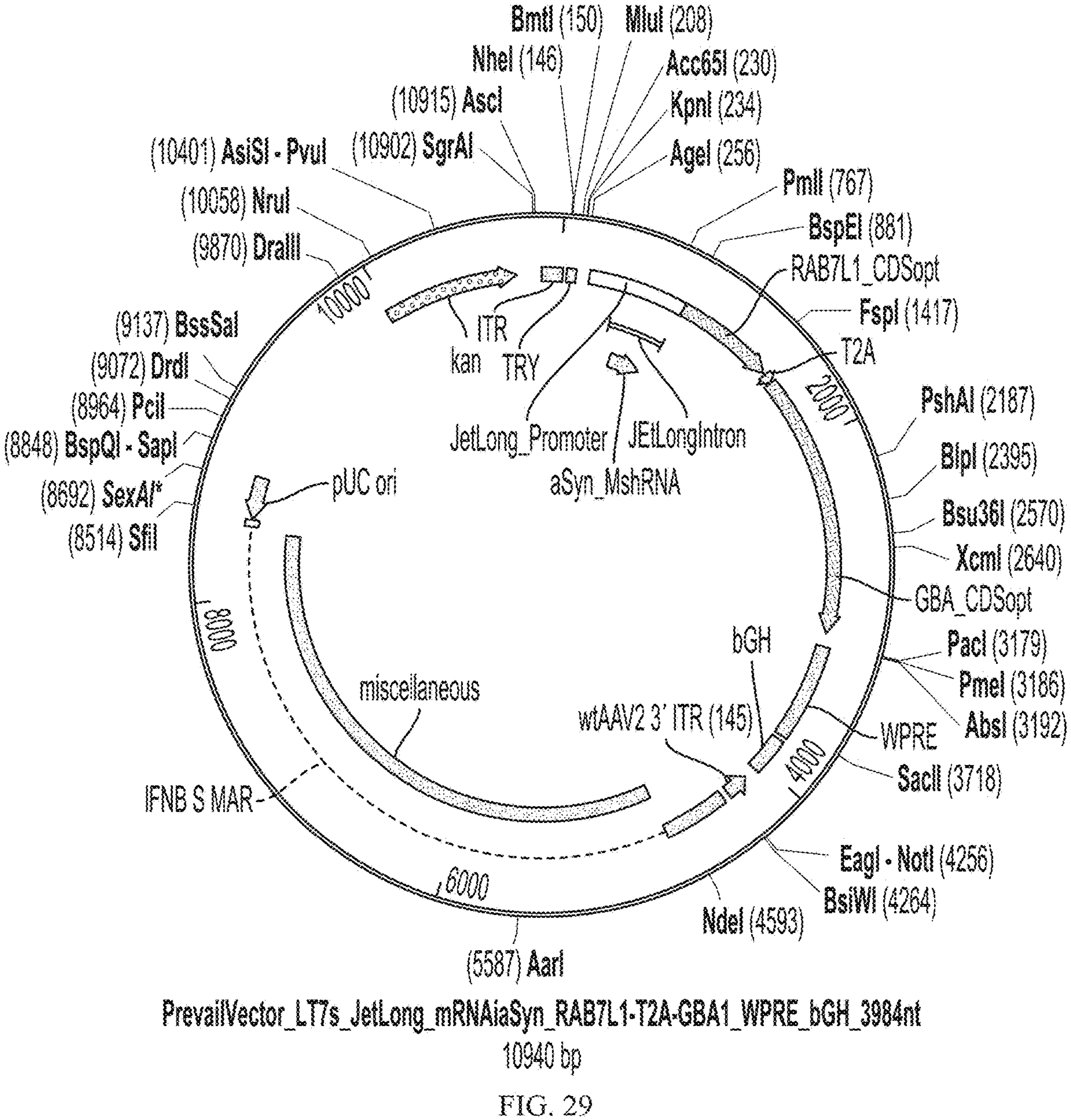
FIG. 29 is a schematic depicting one embodiment of a vector comprising an expression construct encoding Gcase (e.g., GBA1 or a portion thereof), RAB7L1 (e.g., RAB7L1 or a portion thereof), and an interfering RNA for α-Syn. The coding sequences of Gcase and RAB7L1 are separated by an T2A self-cleaving peptide sequence.
Figure 30:
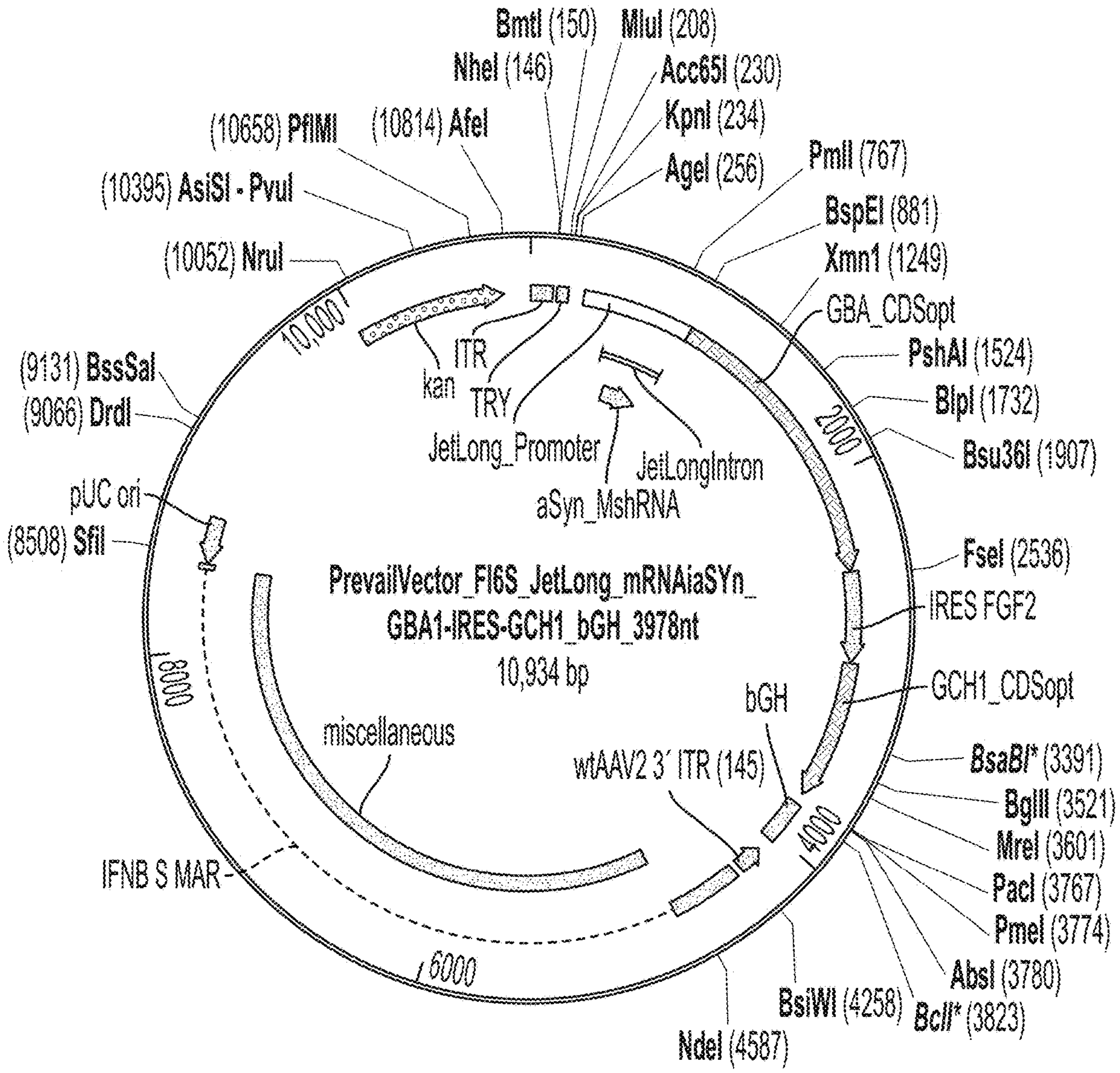
FIG. 30 is a schematic depicting one embodiment of a vector comprising an expression construct encoding Gcase (e.g., GBA1 or a portion thereof), GCH1 (e.g., GCH1 or a portion thereof), and an interfering RNA for α-Syn. Expression of the coding sequences of Gcase and GCH1 are an internal ribosomal entry site (IRES).
Figure 31:
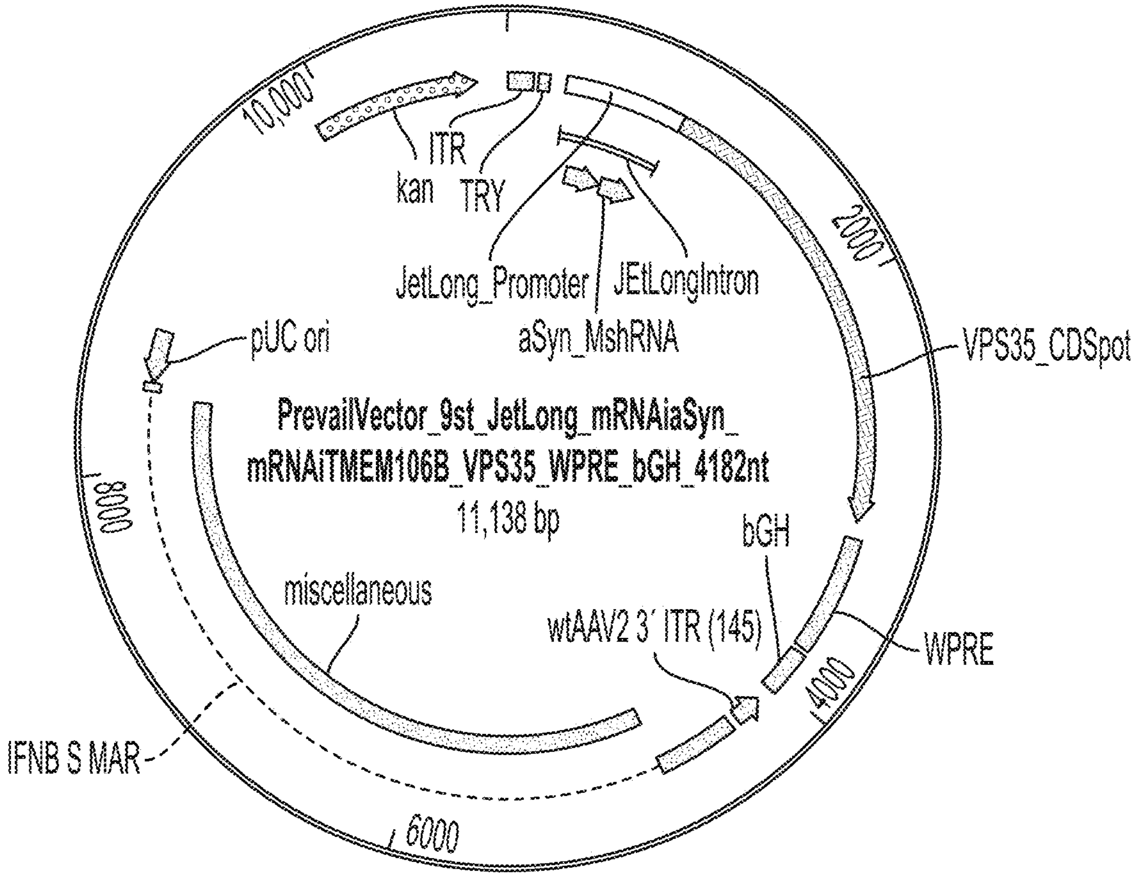
FIG. 31 is a schematic depicting one embodiment of a vector comprising an expression construct encoding VPS35 (e.g., VPS35 or a portion thereof) and interfering RNAs for α-Syn and TMEM106B.
Figure 32:
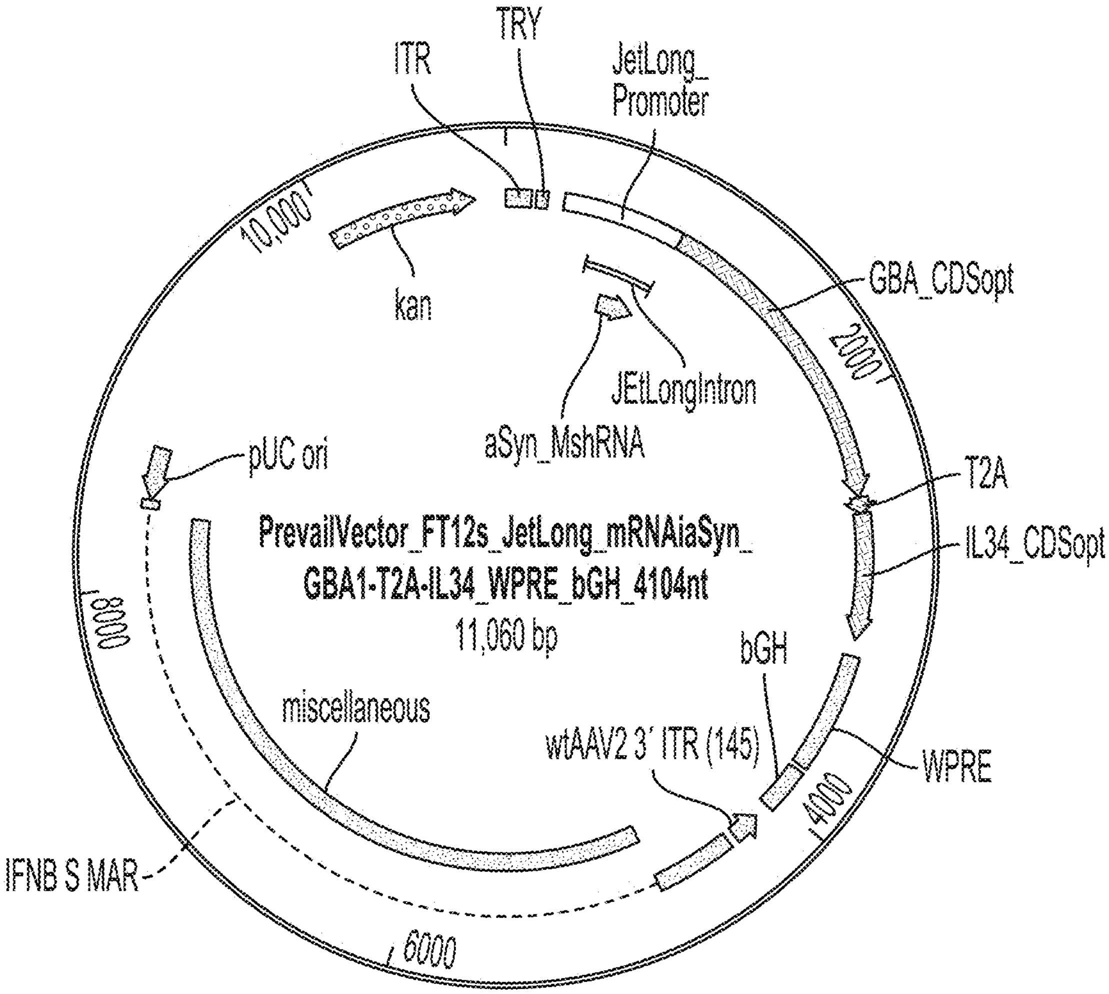
FIG. 32 is a schematic depicting one embodiment of a vector comprising an expression construct encoding Gcase (e.g., GBA1 or a portion thereof), IL-34 (e.g., IL34 or a portion thereof), and an interfering RNA for α-Syn. The coding sequences of Gcase and IL-34 are separated by T2A self-cleaving peptide sequence.
Figure 33:
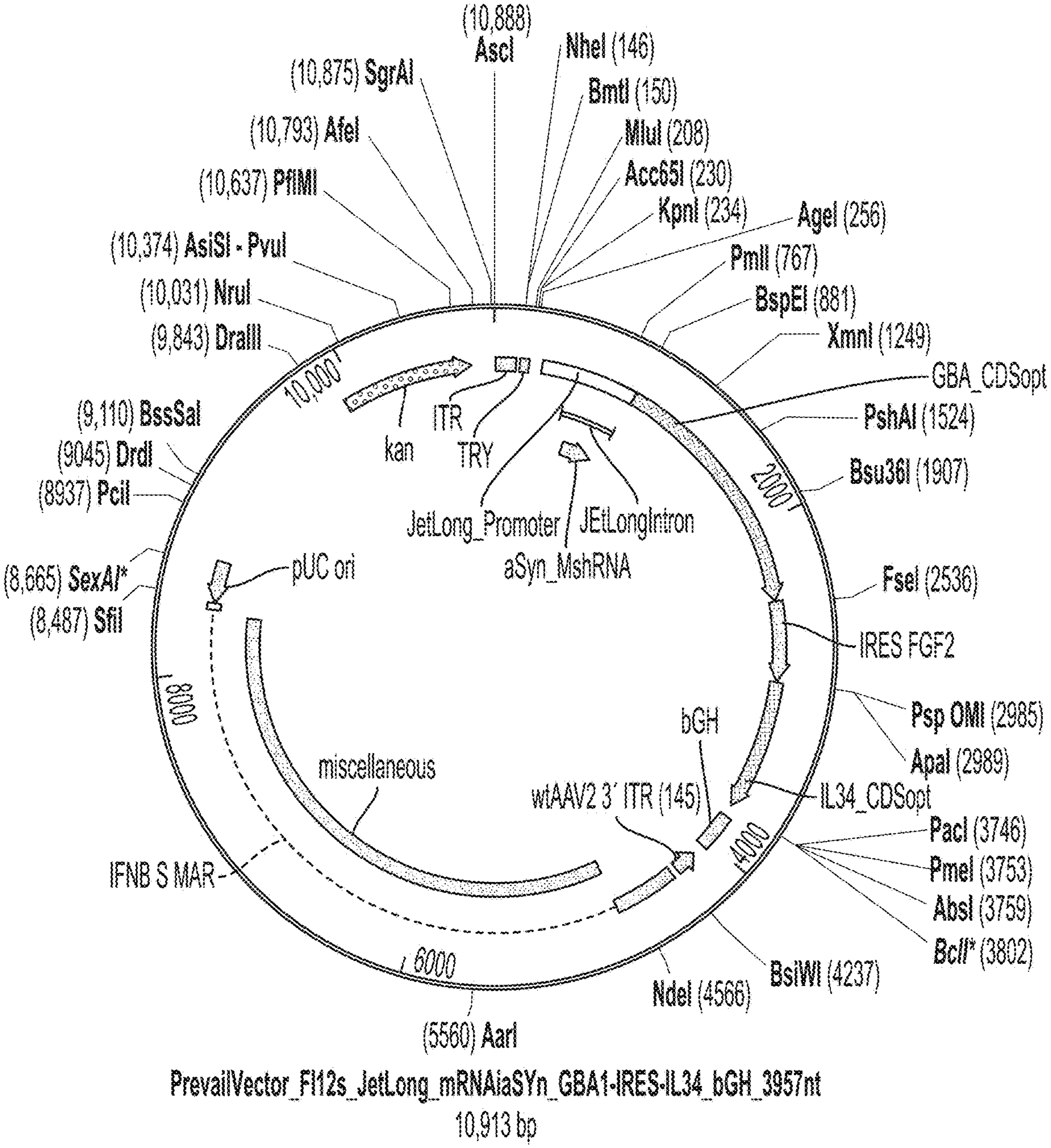
FIG. 33 is a schematic depicting one embodiment of a vector comprising an expression construct encoding Gcase (e.g., GBA1 or a portion thereof) and IL-34 (e.g., IL34 or a portion thereof). The coding sequences of Gcase and IL-34 are separated by an internal ribosomal entry site (IRES).
Figure 34:
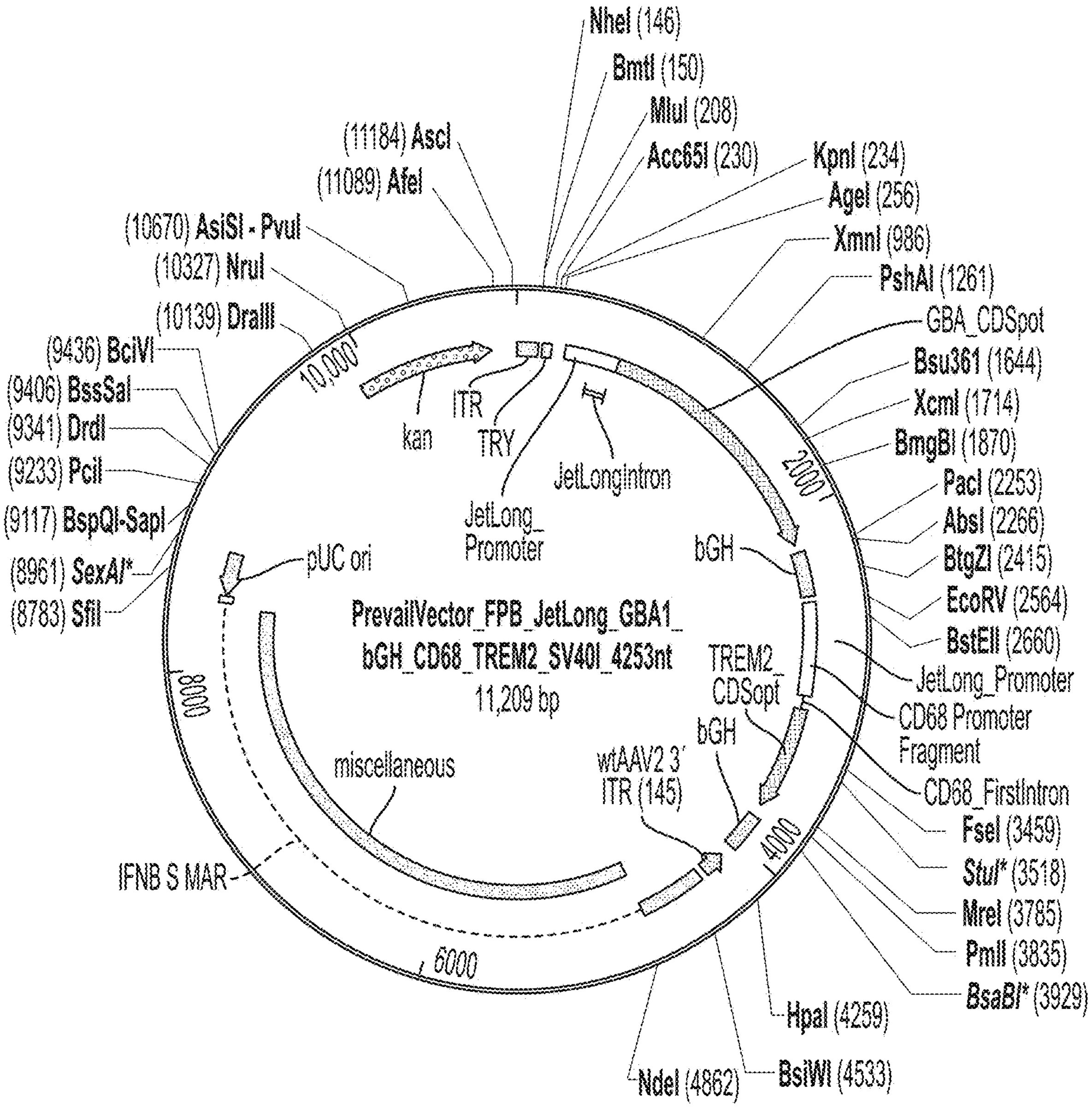
FIG. 34 is a schematic depicting one embodiment of a vector comprising an expression construct encoding Gcase (e.g., GBA1 or a portion thereof) and TREM2 (e.g., TREM2 or a portion thereof). Expression of the coding sequences of Gcase and TREM2 are each driven by a separate promoter.
Figure 35:
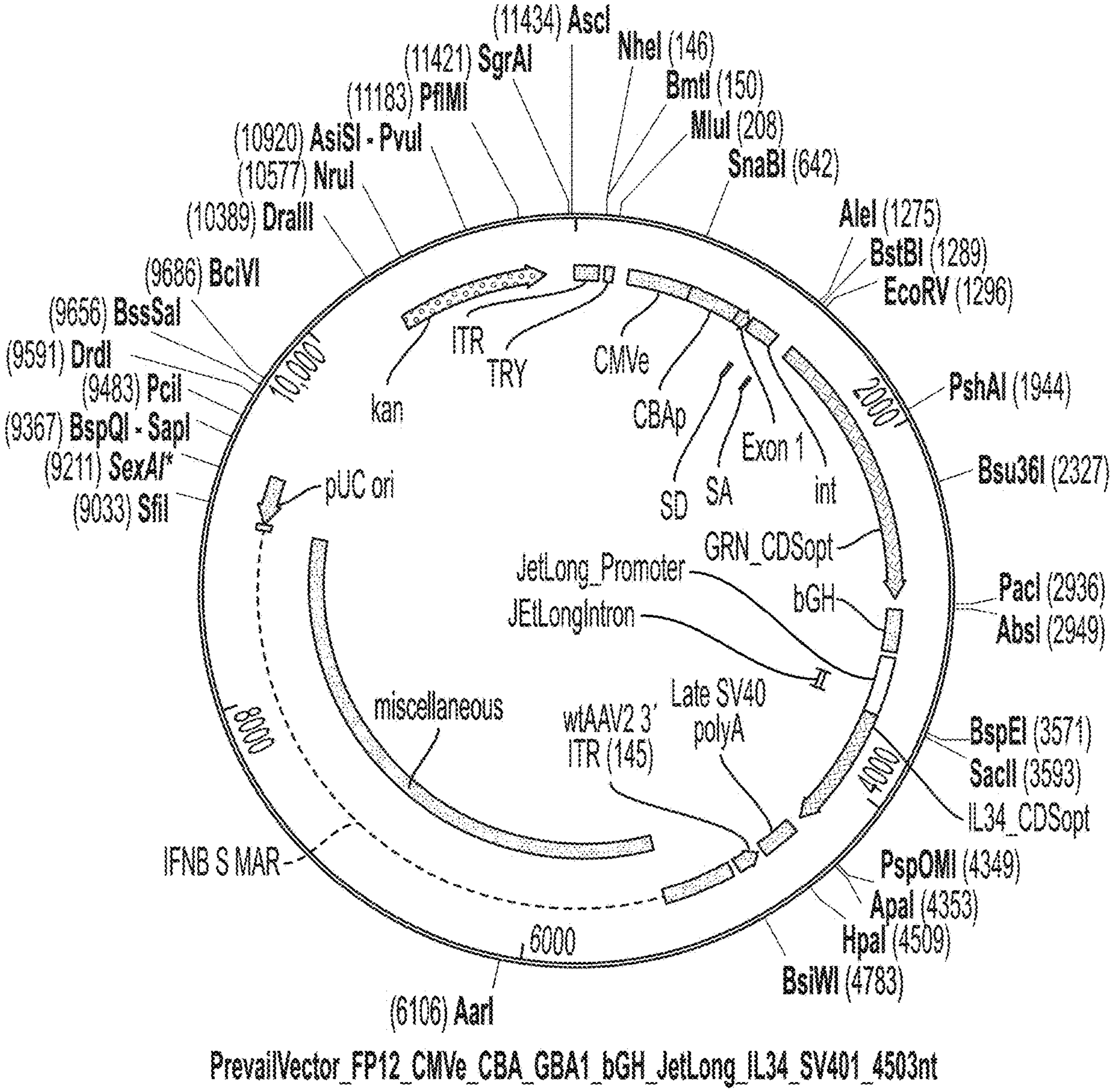
FIG. 35 is a schematic depicting one embodiment of a vector comprising an expression construct encoding Gcase (e.g., GBA1 or a portion thereof) and IL-34 (e.g., IL34 or a portion thereof). Expression of the coding sequences of Gcase and IL-34 are each driven by a separate promoter.

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 20. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region (FIG. 20). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *JMol GenetMed* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type “D” sequence (e.g., SEQ ID NO: 27). In some embodiments, a modified “D” sequence comprises the sequence set forth in SEQ ID NO: 26, also referred to as an “S” sequence as described in Wang et al. (1995) *J Mol Biol* 250(5):573-80.

An isolated nucleic acid or rAAV vector as described by the disclosure may further comprise a “TRY” sequence, for example as set forth in SEQ ID NO: 28 or as described by Francois et al., (2005) *J. Virol.* 79(17):11082-11094. In some embodiments, a TRY sequence is positioned between an ITR (e.g. a 5' ITR) and an expression construct (e.g. a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term “rAAVs” generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived. In some embodiments, an AAV capsid protein variant is an AAV1RX capsid protein, for example as described by Albright et al. *Mol Ther.* 2018 Feb. 7; 26(2):510-523. In some embodiments, a capsid protein variant is an AAV TM6 capsid protein, for example as described by Rosario et al. *Mol Ther Methods Clin Dev.* 2016; 3: 16026.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989)*J Virol.* 63(9):3822-8 and Wright (2009) *Hum Gene Ther.* 20(7): 698-706. In some embodiments, an rAAV comprises a capsid protein that specifically or preferentially targets myeloid cells, for example microglial cells.

Figure 64:
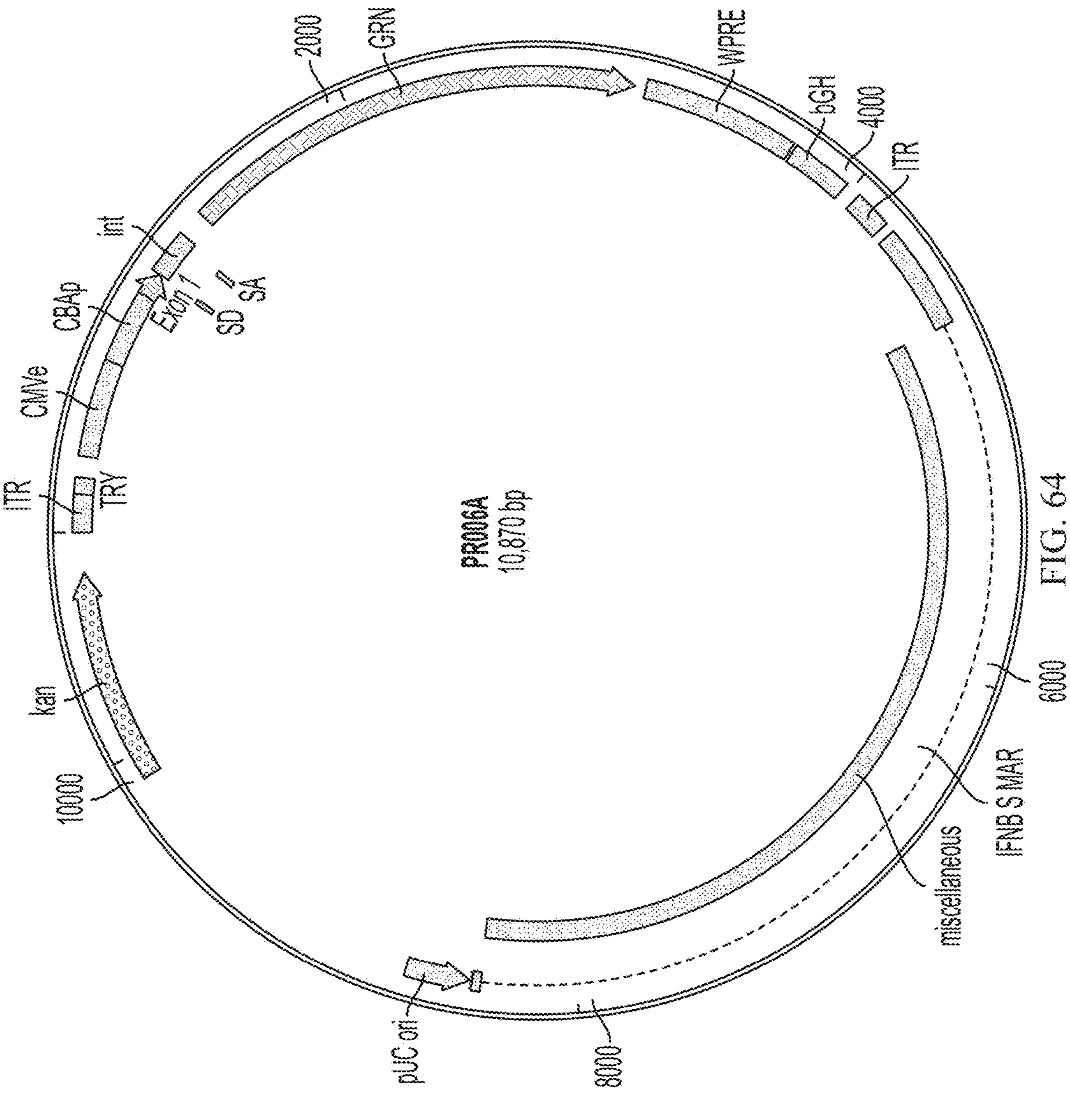
FIG. 64 is a schematic depicting one embodiment of a recombinant adeno-associated virus vector (PR006A) comprising an expression construct encoding human progranulin. "bp" refers to "base pairs". "kan" refers to a gene that confers resistance to kanamycin. "GRN" refers to "progranulin". "ITR" refers to an adeno-associated virus inverted terminal repeat sequence. "TRY" refers to a sequence comprising three transcriptional regulatory activation sites: TATA, RBS, and YY1. "CBAp" refers to a chicken 3-actin promoter. "CMVe" refers to a cytomegalovirus enhancer. "WPRE" refers to a woodchuck hepatitis virus post-transcriptional regulatory element. "bGH" refers to a bovine Growth Hormone polyA signal tail. "int" refers to an intron. The nucleotide sequences of the two strands of PR006A are provided in SEQ ID NOs: 90 and 91.

In some embodiments, the disclosure provides an rAAV referred to as “PR006A”. PR006A is a rAAV that delivers a functional human GRN gene, leading to increased expression of functional human PGRN. The PR006A vector insert comprises the chicken j-actin (CBA) promoter element, comprising 4 parts: the cytomegalovirus (CMV) enhancer, CBA promoter, exon 1, and intron (int) to constitutively express a codon-optimized coding sequence of human GRN (SEQ ID NO:68). The 3' region also contains a woodchuck hepatitis virus post-transcriptional regulatory element (WPRE) followed by a bovine growth hormone polyadenylation signal tail. Three well described transcriptional regulatory activation sites are included at the 5' end of the promoter region: TATA, RBS, and YY1 (see, e.g., Francois et al., (2005) *J. Virol.* 79(17):11082-11094). The flanking inverted terminal repeats (ITRs) allow for the correct packaging of the intervening sequences. The backbone contains the gene to confer resistance to kanamycin as well as a stuffer sequence to prevent reverse packaging. A schematic depicting the rAAV vector is shown in FIG. 64. SEQ ID NO 90 provides the nucleotide sequence of the first strand (in 5' to 3' order) of the PR006A vector shown in FIG. 64. SEQ ID NO 91 provides the nucleotide sequence of the second strand (in 5' to 3' order) of the PR006A vector shown in FIG. 64. PR006A comprises AAV9 capsid proteins.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) Hum Gene Ther 13(16):1935-43, Smith et al. (2009) Mol Ther 17(11): 1888-1896, U.S. Pat. Nos. 8,945,918, 9,879,282, and International PCT Publication WO 2017/184879. However, an rAAV can be produced using any suitable method (e.g., using recombinant rep and cap genes). In some embodiments, an rAAV as disclosed herein is produced in HEK293 (human embryonic kidney) cells.

Pharmaceutical Compositions

In some aspects, the disclosure provides pharmaceutical compositions comprising an isolated nucleic acid or rAAV as described herein and a pharmaceutically acceptable carrier. As used herein, the term “pharmaceutically acceptable” refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term “pharmaceutically acceptable carrier” means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

In some embodiments, the disclosure provides a PR006A finished drug product comprising the PR006A rAAV described above presented in aqueous solution. In some embodiments, the final formulation buffer comprises about 20 mM Tris [pH 8.0], about 1 mM $MgCl_2$, about 200 mM NaCl, and about 0.001% [w/v] poloxamer 188. In some embodiments, the finished drug product and the final formulation buffer are suitable for intra-cisterna magna (ICM) injection.

Methods

Aspects of the disclosure relate to compositions for expression of one or more CNS disease-associated gene products in a subject to treat CNS-associated diseases. The one or more CNS disease-associated gene products may be encoded by one or more isolated nucleic acids or rAAV vectors. In some embodiments, a subject is administered a single vector (e.g., isolated nucleic acid, rAAV, etc.) encoding one or more (1, 2, 3, 4, 5, or more) gene products. In some embodiments, a subject is administered a plurality (e.g., 2, 3, 4, 5, or more) vectors (e.g., isolated nucleic acids, rAAVs, etc.), where each vector encodes a different CNS disease-associated gene product.

A CNS-associated disease may be a neurodegenerative disease, synucleinopathy, tauopathy, or a lysosomal storage disease. Examples of neurodegenerative diseases and their associated genes are listed in Table 12.

A "synucleinopathy" refers to a disease or disorder characterized by the accumulation of alpha-Synuclein (the gene product of SNCA) in a subject (e.g., relative to a healthy subject, for example a subject not having a synucleinopathy). Examples of synucleinopathies and their associated genes are listed in Table 13.

A "tauopathy" refers to a disease or disorder characterized by accumulation of abnormal Tau protein in a subject (e.g., relative to a healthy subject not having a tauopathy). Examples of tauopathies and their associated genes are listed in Table 14.

A "lysosomal storage disease" refers to a disease characterized by abnormal build-up of toxic cellular products in lysosomes of a subject. Examples of lysosomal storage diseases and their associated genes are listed in Table 15.

As used herein "treat" or "treating" refers to (a) preventing or delaying onset of a CNS disease; (b) reducing severity of a CNS disease; (c) reducing or preventing development of symptoms characteristic of a CNS disease; (d) and/or preventing worsening of symptoms characteristic of a CNS disease. Symptoms of CNS disease may include, for example, motor dysfunction (e.g., shaking, rigidity, slowness of movement, difficulty with walking, paralysis), cognitive dysfunction (e.g., dementia, depression, anxiety, psychosis), difficulty with memory, emotional and behavioral dysfunction.

The disclosure is based, in part, on compositions for expression of combinations of PD-associated gene products in a subject that act together (e.g., synergistically) to treat Parkinson's disease.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

The disclosure is based, in part, on compositions for expression of one or more CNS-disease associated gene products in a subject to treat Gaucher disease. In some embodiments, the Gaucher disease is a neuronopathic Gaucher disease, for example Type 2 Gaucher disease or Type 3 Gaucher disease. In some embodiments, a subject having Gaucher disease does not have PD or PD symptoms.

Accordingly, in some aspects, the disclosure provides a method for treating a subject having or suspected of having neuronopathic Gaucher disease, the method comprising administering to the subject a composition (e.g., a composition comprising an isolated nucleic acid or a vector or a rAAV) as described by the disclosure.

The disclosure is based, in part, on compositions for expression of one or more CNS-disease associated gene products in a subject to treat Alzheimer's disease or frontotemporal dementia (FTD). In some embodiments, the subject does not have Alzheimer's disease. In some embodiments, the subject has FTD and does not have Alzheimer's disease. In some embodiments, the subject has FTD with GRN (progranulin) mutation. In some embodiments, the subject has FTD with GRN mutation, and the subject is heterozygous for a GRN mutation (e.g., a pathogenic GRN mutation). In some embodiments, a GRN mutation is a null mutation (e.g., a nonsense, a frameshift, or a splice site mutations, or a complete or partial (exonic) gene deletion). In some embodiments, a GRN mutation is a pathogenic mutation with proven functional deleterious effect. In some embodiments, a GRN mutation is a missense pathogenic mutation. In some embodiments, a GRN mutation is listed in the Molgen FTD database (molgen.ua.ac.be). In some embodiments, a GRN mutation produces a low plasma PGRN level (<70 ng/mL) in a subject.

In some embodiments, the subject has FTD, FTD with GRN mutation, FTD with tau mutation, FTD with C9orf72 mutation, neuronal ceroid lipofuscinosis, Parkinson's disease, Alzheimer's disease, corticobasal degeneration, motor neuron disease, or Gaucher disease.

In some embodiments, the subject has symptomatic FTD (e.g., behavioral-variant FTD (bvFTD), primary progressive aphasia (PPA)-FTD, FTD with corticobasal syndrome, or a combination of syndromes).

Accordingly, in some aspects, the disclosure provides a method for treating a subject having or suspected of having FTD with GRN mutation, the method comprising administering to the subject a composition (e.g., a composition comprising an isolated nucleic acid or a vector or a rAAV) as described by the disclosure.

In some embodiments, a subject having Alzheimer's disease or FTD (e.g. FTD with GRN mutation) is administered an rAAV encoding Progranulin (PGRN) or a portion thereof. In some embodiments, a subject having Alzheimer's disease or FTD (e.g. FTD with GRN mutation) is administered an rAAV encoding PGRN or a portion thereof, wherein the PGRN protein is encoded by a codon-optimized nucleic acid sequence or the nucleic acid sequence in SEQ ID NO:68. In some embodiments, the PGRN protein comprises the amino acid sequence in SEQ ID NO:67 or a portion thereof. In some embodiments, the rAAV encoding PGRN comprises a capsid protein having an AAV9 serotype.

In some embodiments, a composition comprising an rAAV encoding PGRN for treating FTD (e.g. FTD with GRN mutation) is administered to a subject at a dose ranging from about $1\times10^{12}$ vector genomes (vg) to about $1\times10^{15}$ vg, or from about $1\times10^{13}$ vg to about $7\times10^{14}$ vg, or from about $1\times10^{13}$ vg to about $5\times10^{14}$ vg, or from about $2\times10^{13}$ vg to about $2\times10^{14}$ vg, or from about $3\times10^{13}$ vg to about $2\times10^{14}$ vg, or from about $3.5\times10^{13}$ vg to about $1.4\times10^{14}$ vg. In some embodiments, a composition comprising an rAAV encoding PGRN for treating FTD (e.g. FTD with GRN mutation) is administered to a subject at a dose of about $2\times10^{13}$ vg, about $3\times10^{13}$ vg, about $4\times10^{13}$ vg, about $5\times10^{13}$ vg, about $6\times10^{13}$ vg, about $7\times10^{13}$ vg, about $8\times10^{13}$ vg, about $9\times10^{13}$ vg, about $1\times10^{14}$ vg, or about $2\times10^{14}$ vg.

In some aspects, the disclosure provides a method for treating a subject having or suspected of having FTD (e.g. FTD with GRN mutation), the method comprising administering to the subject a composition comprising an rAAV encoding PGRN, wherein the composition is administered at a dose of about $3.5\times10^{13}$ vector genomes (vg), about $7.0\times10^{13}$ vg, or about $1.4\times10^{14}$ vg.

In some aspects, the disclosure provides a method for treating a subject having or suspected of having FTD (e.g. FTD with GRN mutation), the method comprising administering to the subject a composition comprising an rAAV encoding PGRN, wherein the composition is administered at a dose of about $1\times10^{14}$ vector genomes (vg), about $2.0\times10^{14}$ vg, or about $4.0\times10^{14}$ vg.

In some embodiments, a composition comprising an rAAV encoding PGRN for treating FTD (e.g. FTD with GRN mutation) to a subject as a single dose, and the composition is not administered to the subject subsequently.

In some embodiments, the composition comprising the rAAV is delivered via a single suboccipital injection into the cisterna magna. In some embodiments, the injection into the cisterna magna is performed under radiographic guidance.

In some embodiments, the disclosure provides a method for treating a symptom of a subject having or suspected of having FTD with GRN mutation, the method comprising administering to the subject a composition comprising an rAAV encoding the sequence for functional Progranulin (PGRN) protein, wherein the PGRN protein is encoded by a codon-optimized nucleic acid sequence or the nucleic acid sequence in SEQ ID NO:68. In some embodiments, a symptom of FTD with GRN mutation may be a personality change, impairment of executive function, disinhibition, apathy, slow speech production, misuse of grammar, multimodal agnosia, semantic aphasia, or impaired word comprehension. In some embodiments, the rAAV encoding PGRN comprises a capsid protein having an AAV9 serotype.

In some embodiments, the disclosure provides a method for reducing lipofuscin accumulation in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for reducing ubiquitin accumulation in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for reducing gene expression and/or protein expression of TNFα and/or CD68 in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for increasing the maturation of cathepsin D in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for increasing the level of nuclear TDP-43 (transactive response DNA binding protein 43 kDa) protein in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some embodiments, the disclosure provides a method for reducing a level of neurofilament light chain (NFL) in blood or CSF of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some embodiments, the rAAV encoding PGRN comprises a capsid protein having an AAV9 serotype.

A subject is typically a mammal, preferably a human. In some embodiments, a subject is between the ages of 1 month old and 10 years old (e.g., 1 month, 2 months, 3 months, 4, months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 3, years, 4 years, 5 years, 6 years, 7 years, 8 years, 9 years, 10 years, or any age therebetween). In some embodiments, a subject is between 2 years old and 20 years old. In some embodiments, a subject is between 30 years old and 100 years old. In some embodiments, a subject is older than 55 years old.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, a composition is administered to a subject by intra-cisterna magna (ICM) injection. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

In some embodiments, a subject is administered an immunosuppressant prior to (e.g., between 1 month and 1 minute prior to) or at the same time as a composition as described herein. In some embodiments, the immunosuppressant is a corticosteroid (e.g., prednisone, budesonide, etc.), an mTOR inhibitor (e.g., sirolimus, everolimus, etc.), an antibody (e.g., adalimumab, etanercept, natalizumab, etc.), or methotrexate.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection. In some embodiments, a rAAV as described herein is administered to a subject at a dose ranging from about $1\times10^{10}$ vector genomes (vg) to about $1\times10^{17}$ vg by intravenous injection. In some embodiments, a rAAV as described herein is administered to a subject at a dose ranging from about $1\times10^{10}$ vg to about $1\times10^{16}$ vg by injection into the cisterna magna.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of expression constructs described by the disclosure are shown in FIGS. 1-8, 21-35, 39, 41-51 and 64 and in Table 2 below.

TABLE 2

| Name | Promoter 1 | shRNA | CDS1 | PolyA 1 |
|---|---|---|---|---|
| CMVe_CBAp_GBA1_WPRE_bGH | CBA | | GBA1 | WPRE-bGH |
| LT1s_JetLong_mRNAiaSYn_SCARB2-T2A-GBA1_bGH | JetLong | aSyn | SCARB2 | bGH |
| LI1_JetLong_SCARB2-IRES-GBA1_bGH | JetLong | | SCARB2 | bGH |
| FP1_JetLong_GBA1_bGH_JetLong_SCARB2_SV40L | JetLong | | GBA1 | bGH |
| PrevailVector_LT2s_JetLong_mRNAiaSYn_PSAP-T2A-GBA1_bGH_4353nt | JetLong | aSyn | PSAP | bGH |
| PrevailVector_LI2_JetLong_PSAP_TRES_GBA1_SymtheticpolyA_4337nt | JetLong | — | PSAP | Synthetic pA |
| PrevailVector_10s_JetLong_mRNAiaSy_GBA2_WPRE_bGH_4308nt | JetLong | aSyn | GBA2 | WPRE_bGH |
| PrevailVector_FT4_JetLong_GBA1_T2A_GALC_SyntheticpolyA_4373nt | JetLong | — | GBA1 | Synthetic pA |
| PrevailVector_LT4_JetLong_GALC_T2A_GBA1_SyntheticpolyA_4373nt | JetLong | — | GALC | Synthetic pA |
| PrevailVector_LT5s_JetLong_mRNAiaSyn_CTSB-T2A-GBA1_WPRE_bGH_4392nt | JetLong | aSyn | CTSB | WPRE_bGH |
| Prevail_Vector_FT11t_JetLong_mRNAiaSyn_GBA1_T2S_SMPD1_SyntheticpolyA_4477nt | JetLong | aSyn | GBA1 | Synthetic pA |
| PrevailVector_LI4_JetLong_GALC_TRES_GBA1_SymtheticpolyA_4820nt | JetLong | — | GALC | Synthetic pA |
| PrevailVector_FP5_JetLong_GBA1_bGH_JetLong_CTSB_SV40l_4108nt | JetLong | — | GBA1 | bGH |
| PrevailVector_FT6s_JetLong_mRNAiaSyn_GBA1-T2A-GCH1_WPRE_bGH_4125nt | JetLong | aSyn | GBA1 | WPRE_bGH |
| PrevailVector_LT7s_JetLong_mRNAiaSyn_RAB7L1-T2A-GBA1_WPRE_bGH_3984nt | JetLong | aSyn | RAB7L1 | WPRE_bGH |
| PrevailVector_FI6s_JetLong_mRNAiaSYn_GBA1-IRES-GCH1_bGH_3978nt | JetLong | aSyn | GBA1 | bGH |
| PrevailVector_9st_JetLong_mRNAiaSyn_mRNAiTMEM106B_VPS35_WPRE_bGH_4182nt | JetLong | aSyn & TMEM106B | VPS35 | WPRE_bGH |

TABLE 2-continued

| | | | | |
|---|---|---|---|---|
| PrevailVector_FT12s_JetLong_mRNAiaSyn_GBA1-T2A-IL34_WPRE_bGH_4104nt | JetLong | aSyn | GBA1 | WPRE_bGH |
| PrevailVector_FI12s_JetLong_mRNAiaSYn_GBA1-IRES-IL34_bGH_3957nt | JetLong | aSyn | GBA1 | bGH |
| PrevailVector_FP8_JetLong_GBA1_bGH_CD68_TREM2_SV40l_4253nt | JetLong | — | GBA1 | bGH |
| PrevailVector_FP12_CMVe_CBA_GBA1_bGH_JetLong_IL34_SV40l_4503nt | CBA | | GBA1 | bGH |

| Name | Bicis-tronic element | Pro-moter 2 | CDS2 | PolyA2 | Length between ITRs |
|---|---|---|---|---|---|
| CMVe_CBAp_GBA1_WPRE_bGH | | | | | 3741 |
| LT1s_JetLong_mRNAiaSYn_SCARB2-T2A-GBA1_bGH | T2A | | GBA1 | | 4215 |
| LI1_JetLong_SCARB2-IRES-GBA1_bGH | IRES | | GBA1 | | 4399 |
| FP1_JetLong_GBA1_bGH_JetLong_SCARB2_SV40L | | JetLong | SCARB2 | SV40L | 4464 |
| PrevailVector_LT2s_JetLong_mRNAiaSYn_PSAP-T2A-GBA1_bGH_4353nt | T2A | — | GBA1 | — | 4353 |
| PrevailVector_LI2_JetLong_PSAP_TRES_GBA1_SymtheticpolyA_4337nt | IRES | — | GBA1 | — | 4337 |
| PrevailVector_10s_JetLong_mRNAiaSy_GBA2_WPRE_bGH_4308nt | — | — | — | — | 4308 |
| PrevailVector_FT4_JetLong_GBA1_T2A_GALC_SyntheticpolyA_4373nt | T2A | — | GALC | — | 4373 |
| PrevailVector_LT4_JetLong_GALC_T2A_GBA1_SyntheticpolyA_4373nt | T2A | — | GBA1 | — | 4373 |
| PrevailVector_LT5s_JetLong_mRNAiaSyn_CTSB-T2A-GBA1_WPRE_bGH_4392nt | T2A | — | GBA1 | — | 4392 |
| Prevail_Vector_FT11t_JetLong_mRNAiaSyn_GBA1_T2S_SMPD1_SyntheticpolyA_4477nt | T2A | — | SMPD1 | — | 4477 |
| PrevailVector_LI4_JetLong_GALC_TRES_GBA1_SymtheticpolyA_4820nt | IRES | — | GBA1 | — | 4820 |
| PrevailVector_FP5_JetLong_GBA1_bGH_JetLong_CTSB_SV40l_4108nt | — | JetLong | CTSB | SV40L | 4108 |
| PrevailVector_FT6s_JetLong_mRNAiaSyn_GBA1-T2A-GCH1_WPRE_bGH_4125nt | T2A | — | GCH1 | — | 4125 |
| PrevailVector_LT7s_JetLong_mRNAiaSyn_RAB7L1-T2A-GBA1_WPRE_bGH_3984nt | T2A | — | GBA1 | — | 3984 |
| PrevailVector_FI6s_JetLong_mRNAiaSYn_GBA1-IRES-GCH1_bGH_3978nt | IRES | — | GCH1 | — | 3978 |
| PrevailVector_9st_JetLong_mRNAiaSyn_mRNAiTMEM106B_VPS35_WPRE_bGH_4182nt | — | — | — | — | 4182 |
| PrevailVector_FT12s_JetLong_mRNAiaSyn_GBA1-T2A-IL34_WPRE_bGH_4104nt | T2A | — | IL34 | — | 4104 |
| PrevailVector_FI12s_JetLong_mRNAiaSYn_GBA1-IRES-IL34_bGH_3957nt | IRES | — | IL34 | — | 3957 |
| PrevailVector_FP8_JetLong_GBA1_bGH_CD68_TREM2_SV40l_4253nt | — | CD68 | TREM2 | SV40L | 4253 |
| PrevailVector_FP12_CMVe_CBA_GBA1_bGH_JetLong_IL34_SV40l_4503nt | | JetLong | IL34 | SV40L | 4503 |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GlcCer and GlcSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-aSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. ModelMech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 μL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1 gene.

The rAAV-GBA1 vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV-GBA1 vector product contains the "D" domain nucleotide sequence shown in FIG. 7 (inset box, top sequence). A variant vector harboring a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting a rAAV-GBA1 vector is shown in FIG. 8. The rAAV-GBA1 vector is packaged into an rAAV using AAV9 serotype capsid proteins.

rAAV-GBA1 is administered to a subject as a single dose via a fluoroscopy guided sub-occipital injection into the cisterna magna (intracisternal magna; ICM). One embodiment of a rAAV-GBA1 dosing regimen study is as follows:

A single dose of rAAV-GBA1 is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV-GBA1 vector and a rAAV-GBA1 S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

Figure 7:
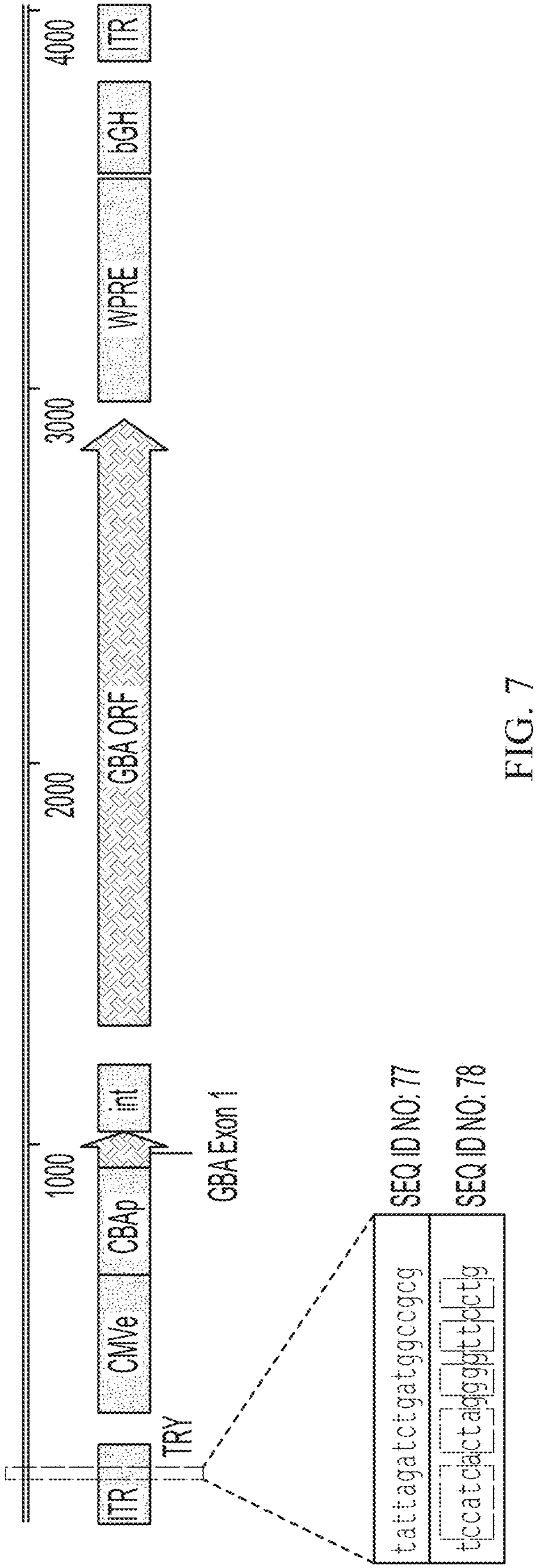
FIG. 7 is a schematic depicting one embodiment of a vector comprising an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, a rAAV vector comprises a mutant "D" domain (e.g., an "S" domain, with the nucleotide changes shown on the bottom line).
Figure 8:
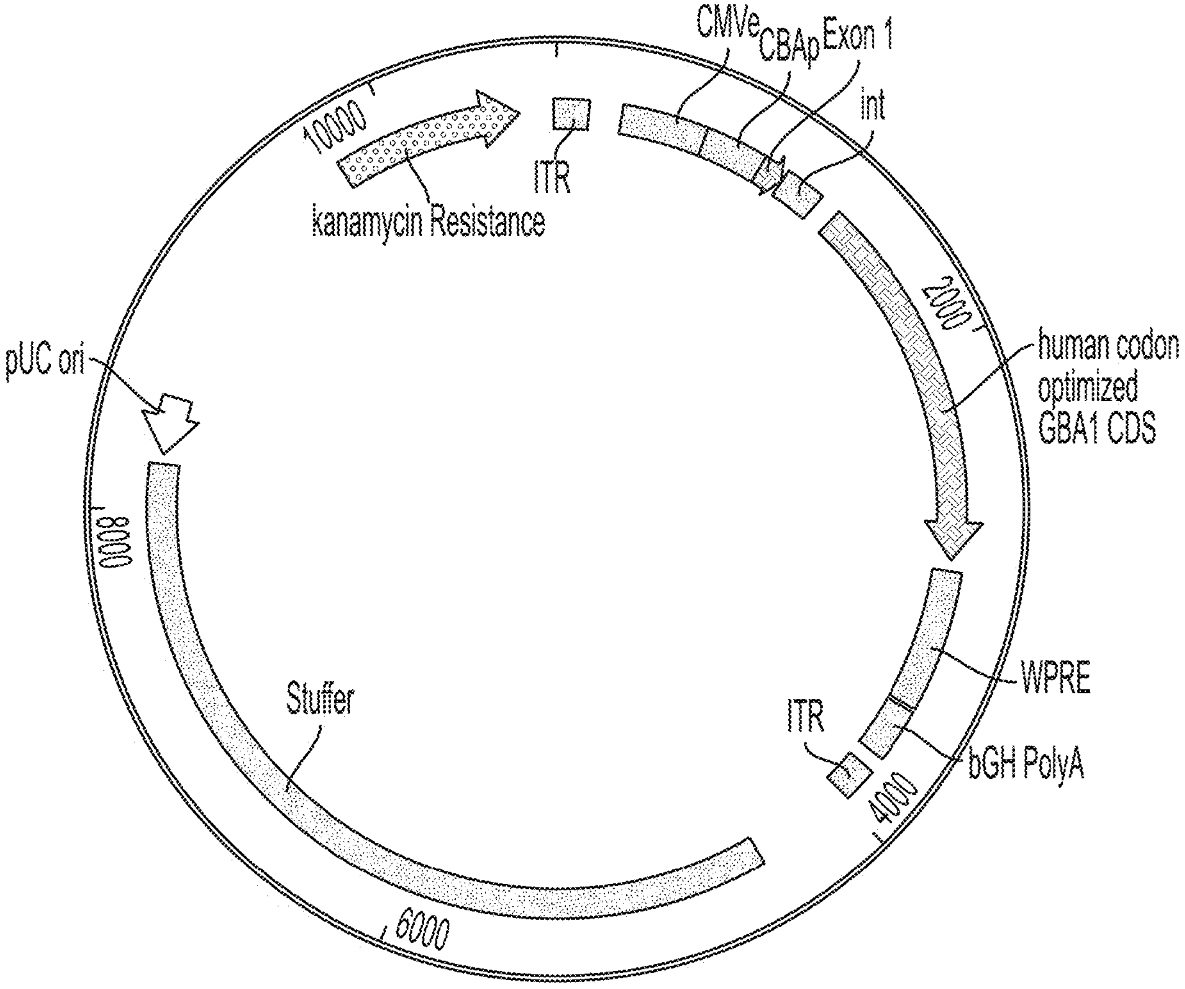
FIG. 8 is a schematic depicting one embodiment of the vector described in FIG. 6

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector rAAV-GBA1, which harbors an intact "D" domain, a second vector form with a mutant D domain (termed an "S" domain herein) was also evaluated. Both rAAV-GBA1 and the variant express the same transgene. While both vectors produced virus that was efficacious in vivo as detailed below, rAAV-GBA1, which contains a wild-type "D" domain, was selected for further development.

Figure 9:
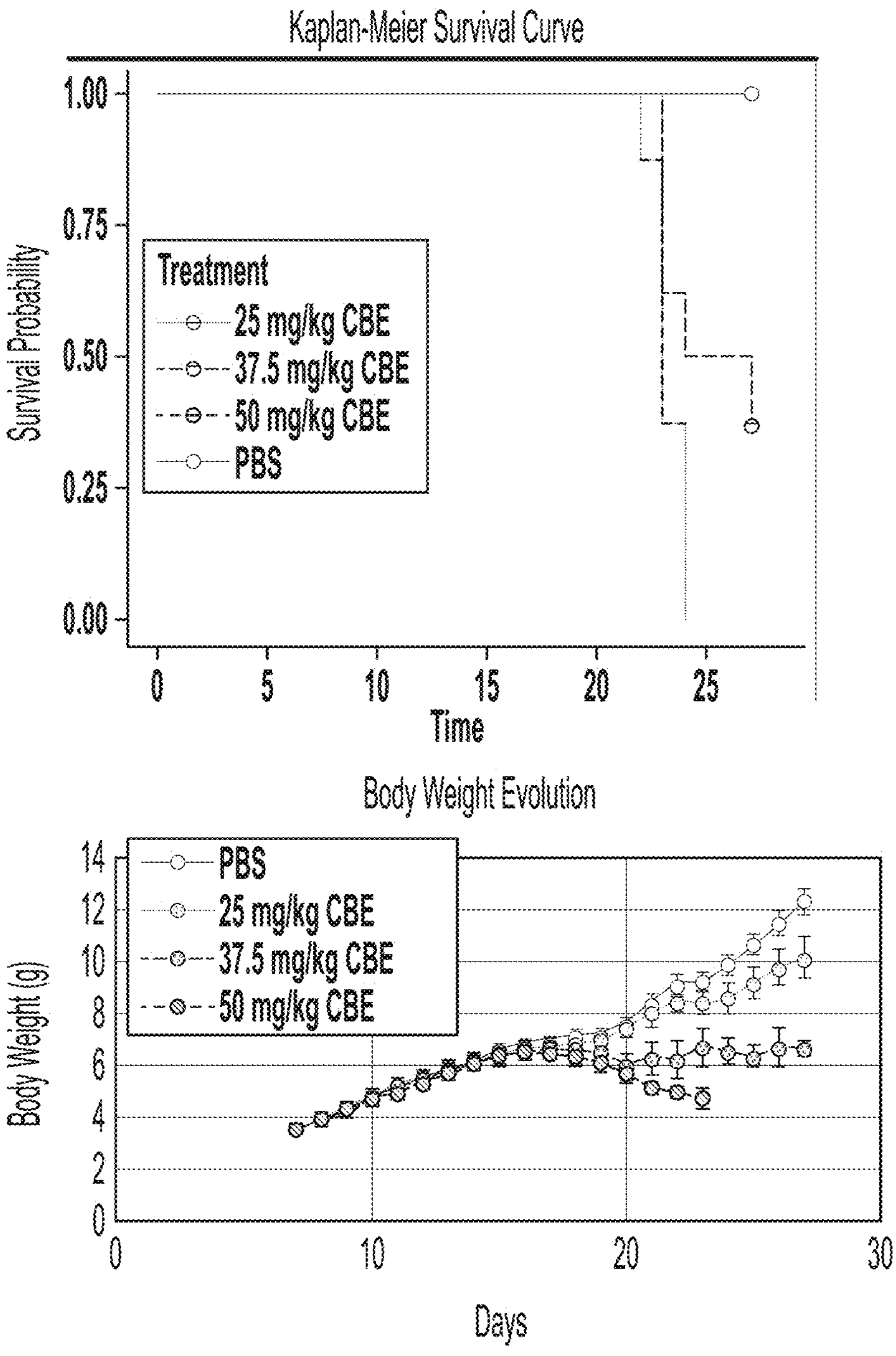
FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *p<0.05; p<0.01; *p<0.001, nominal p-values for treatment groups by linear regression.
Figure 9:
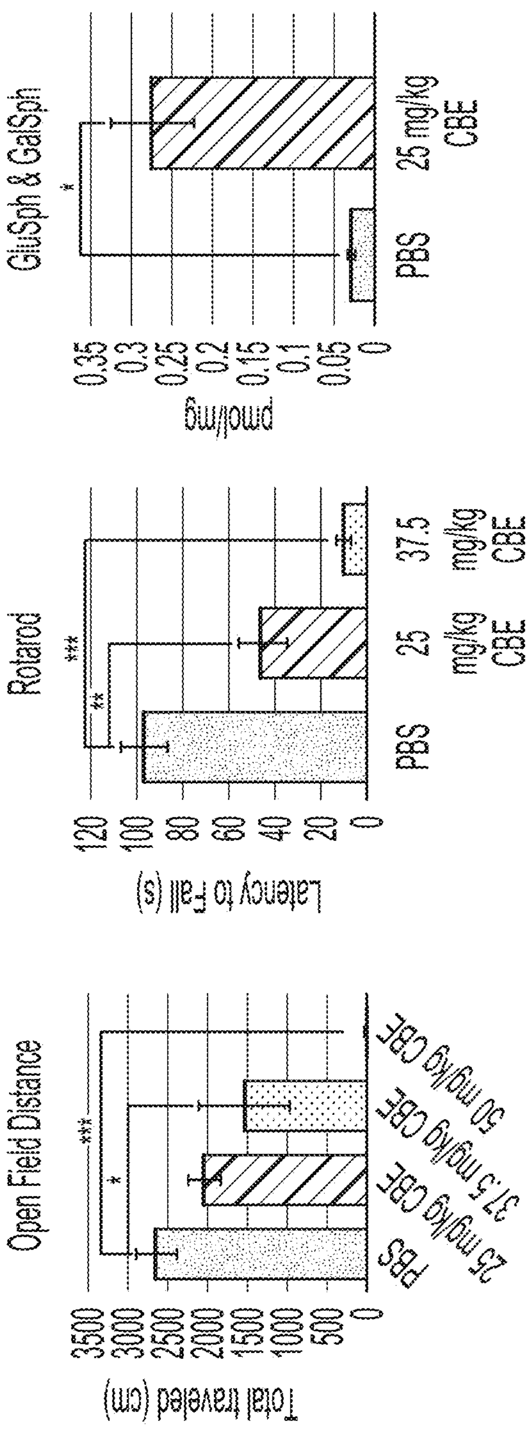

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Figure 10:
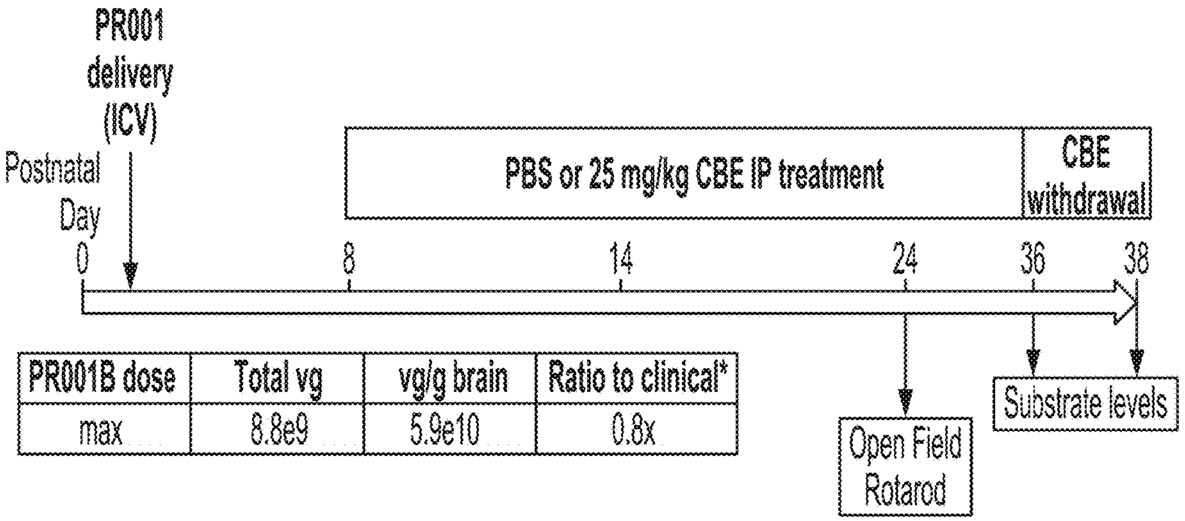
FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Based on the study described above, the 25 mg/kg CBE dose was selected since it produced behavioral deficits without impacting survival. To achieve widespread GBA1 distribution throughout the brain and transgene expression during CBE treatment, rAAV-GBA1 or excipient was delivered by intracerebroventricular (ICV) injection at postnatal day 3 (P3) followed by daily IP CBE or PBS treatment initiated at P8 (FIG. 10).

Figure 11:
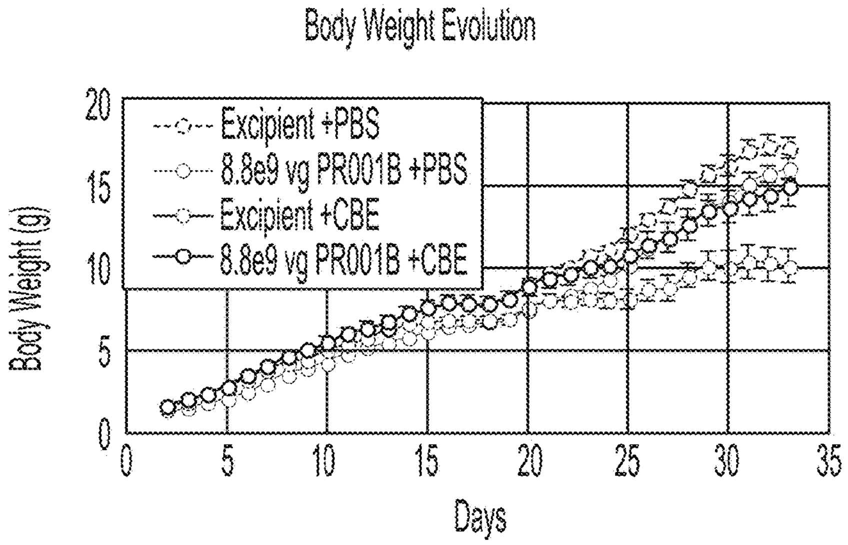
FIG. 11 shows representative data for in-life assessment of maximal rAAV dose in a CBE mouse model. At P3, mice were treated with either excipient or 8.8e9 vg rAAV-GBA1 via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day3). All treatment groups (excipient+PBS n=8, rAAV-GBA1+PBS n=7, excipient+CBE n=8, and variant+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *p<0.05; ***p<0.001, nominal p-values for treatment groups by linear regression in the CBE-treated animals.
Figure 11:
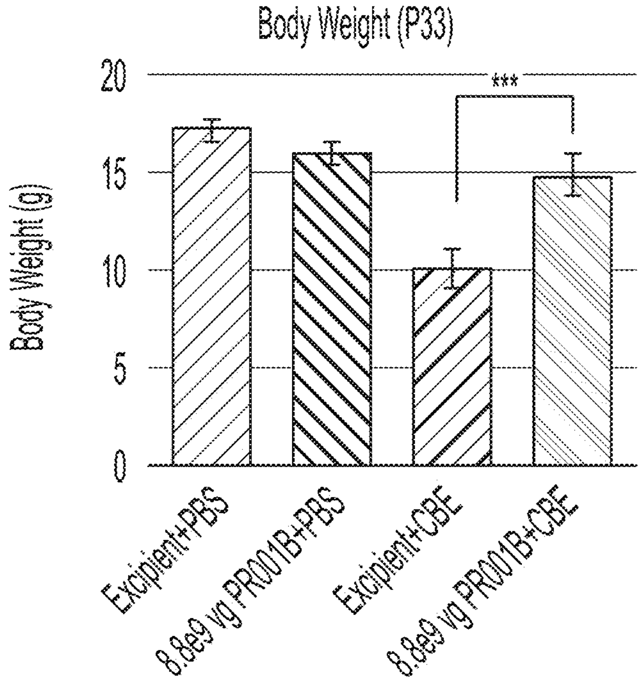
Figure 11:
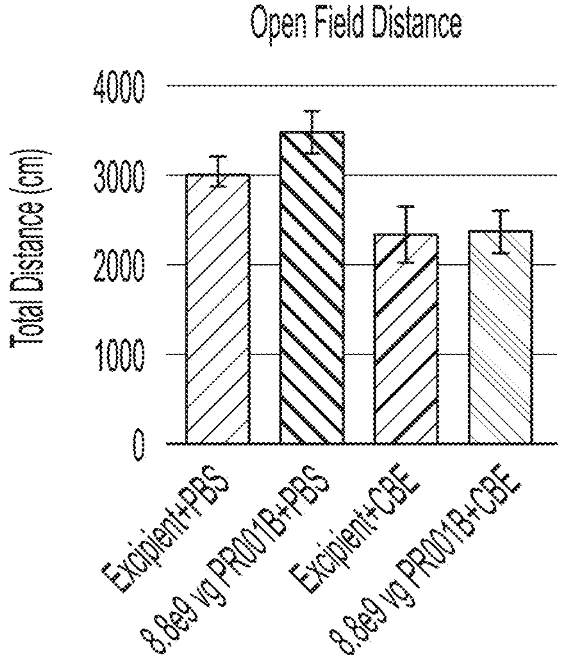
Figure 11:
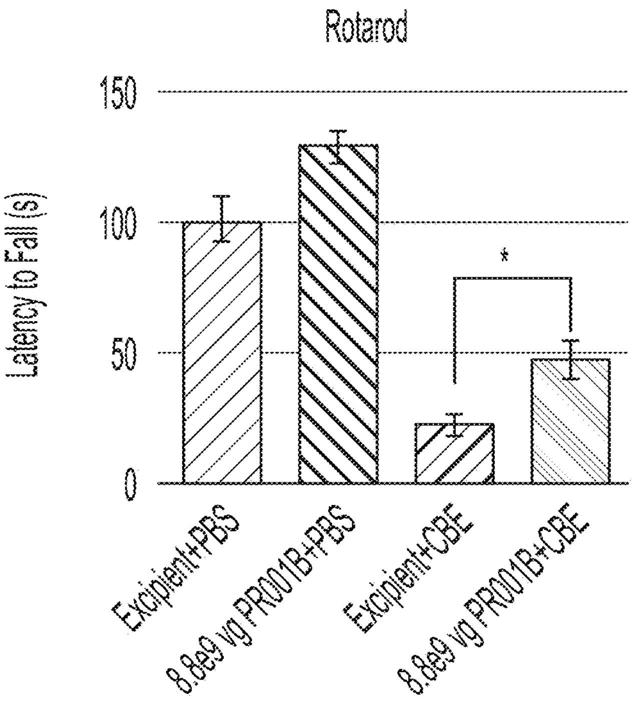

CBE-treated mice that received rAAV-GBA1 performed statistically significantly better on the rotarod than those that received excipient (FIG. 11). Mice in the variant treatment group did not differ from excipient treated mice in terms of other behavioral measures, such as the total distance traveled during testing (FIG. 11).

Figure 12:
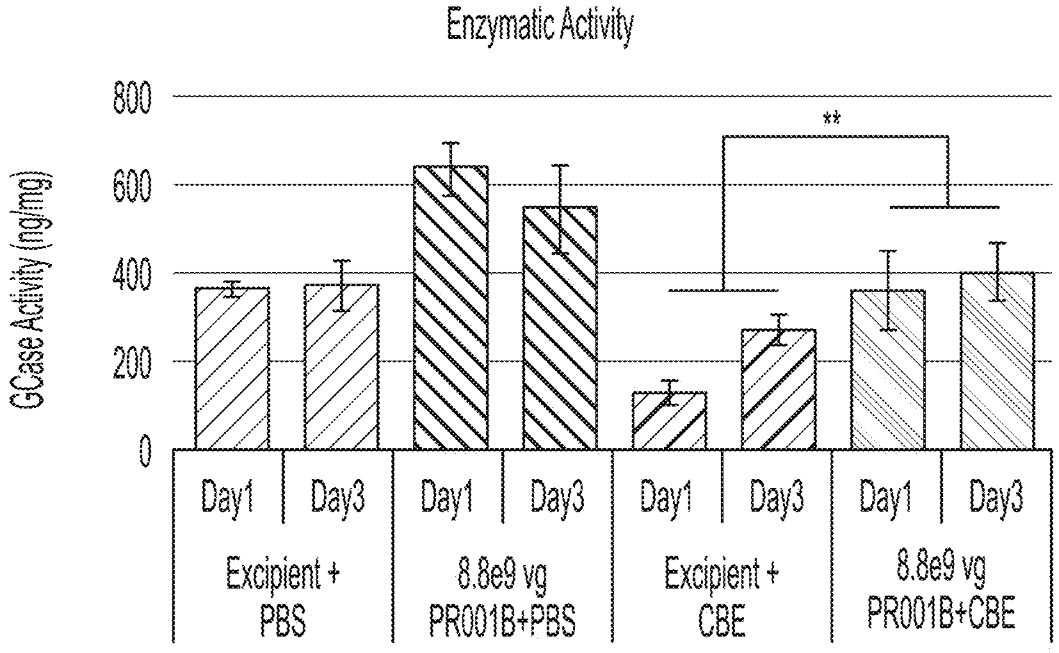
FIG. 12 shows representative data for biochemical assessment of maximal rAAV dose in a CBE mouse model. The cortex of all treatment groups (excipient+PBS n=8, variant+PBS n=7, excipient+CBE n=7, and variant+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 μg of genomic DNA. Means are presented. Error bars are SEM. (*)p<0.1; p<0.01; *p<0.001, nominal p-values for treatment groups by linear regression in the CBE-treated animals, with collection days and gender corrected for as covariates.
Figure 12:
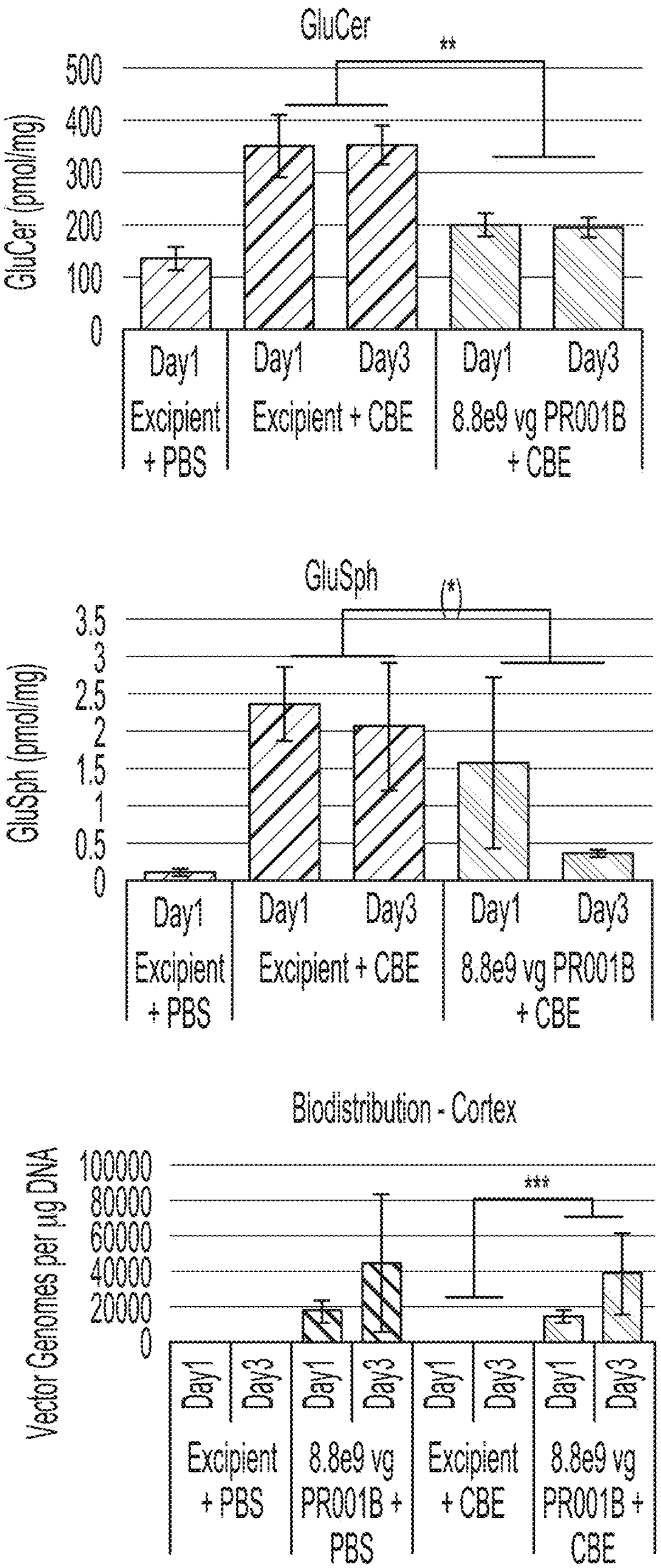

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with rAAV-GBA1, while CBE treatment reduced GCase activity. Additionally, mice that received both CBE and rAAV-GBA1 had GCase activity levels that were similar to the PBS-treated group, indicating that delivery of rAAV-GBA1 is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV-GBA1 treatment significantly reduced substrate accumulation.

Figure 13:
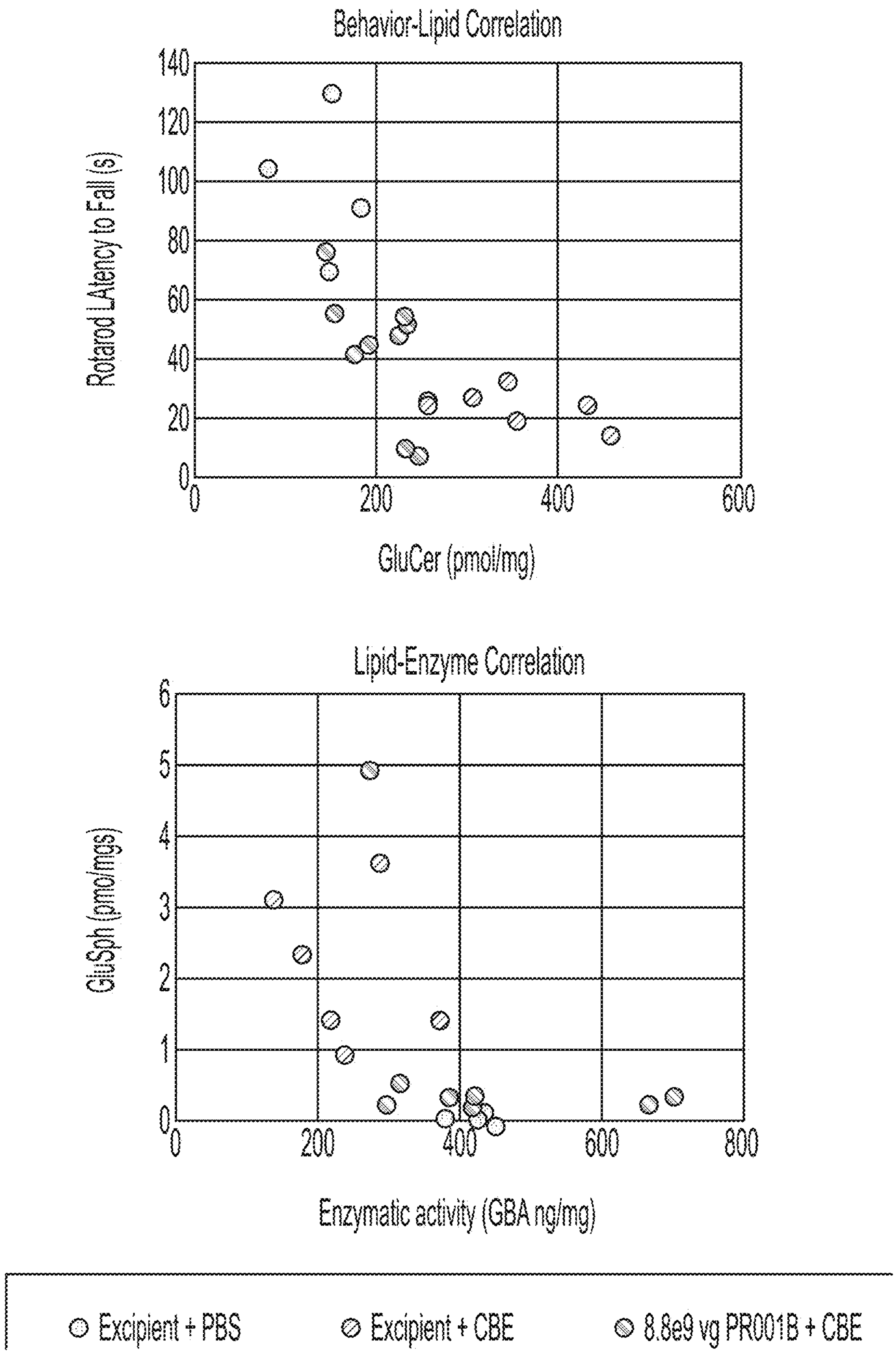
FIG. 13 shows representative data for behavioral and biochemical correlations in a CBE mouse model after administration of excipient+PBS, excipient+CBE, and variant+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).
Figure 14:
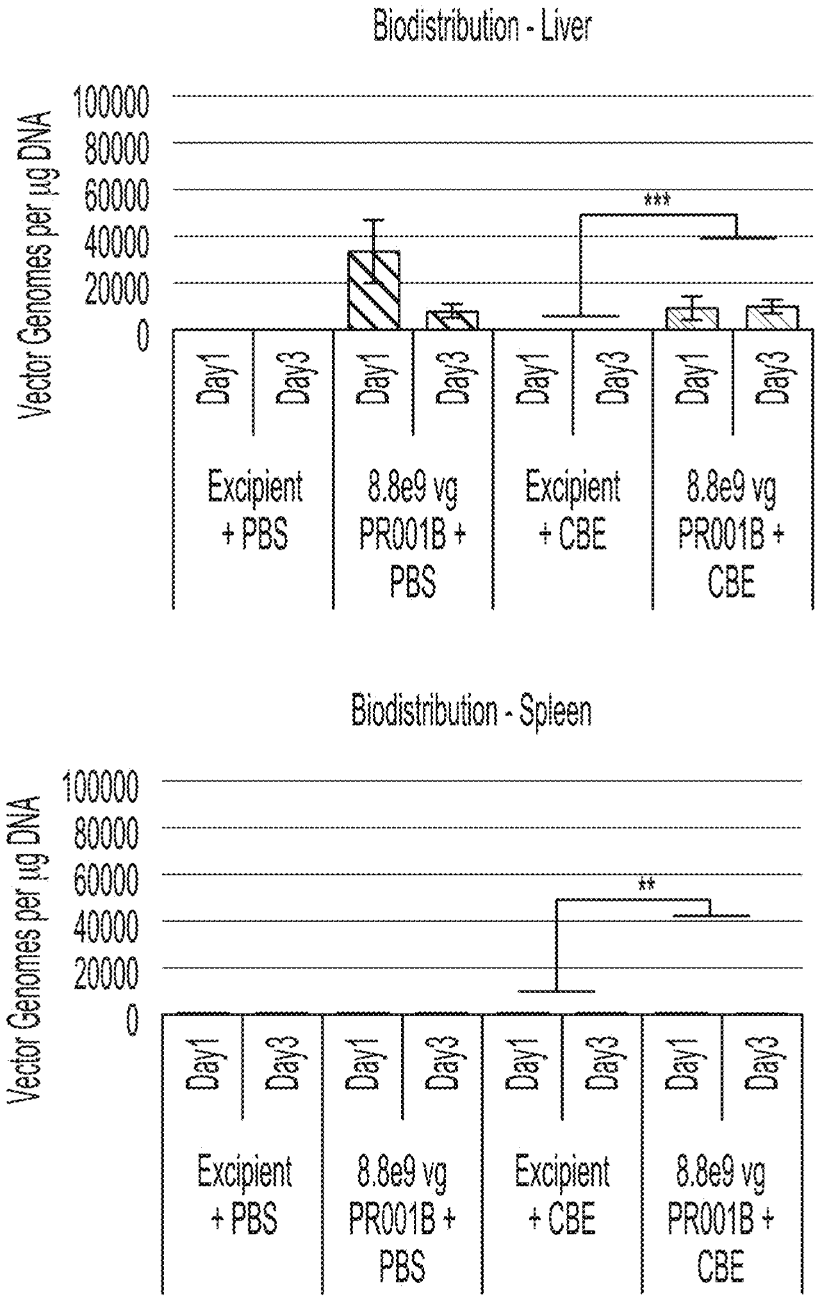
FIG. 14 shows representative data for biodistribution of variant in a CBE mouse model. Presence of vector genomes was assessed in the liver, spleen, kidney, and gonads for all treatment groups (excipient+PBS n=8, variant+PBS n=7, excipient+CBE n=7, and variant+CBE n=9). Biodistribution is shown as vector genomes per 1 μg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.
Figure 14:
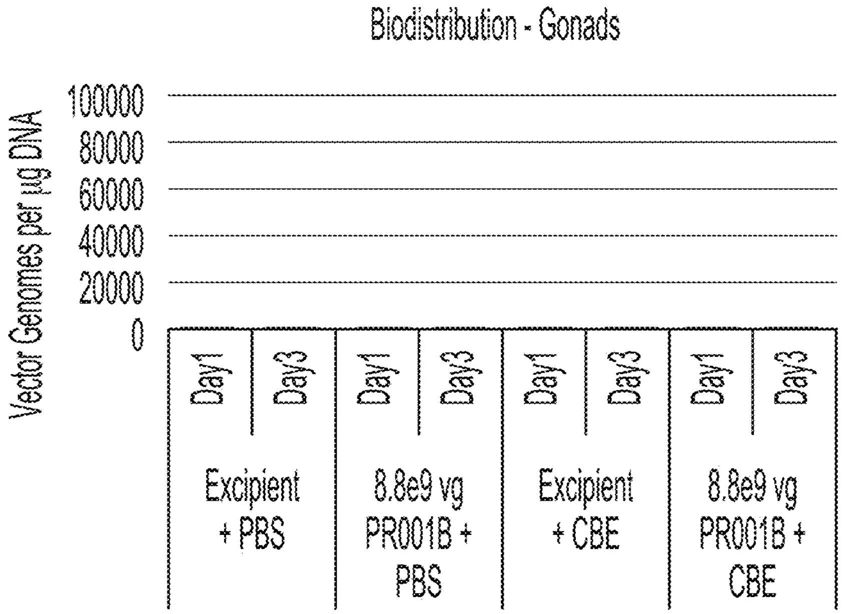
Figure 14:
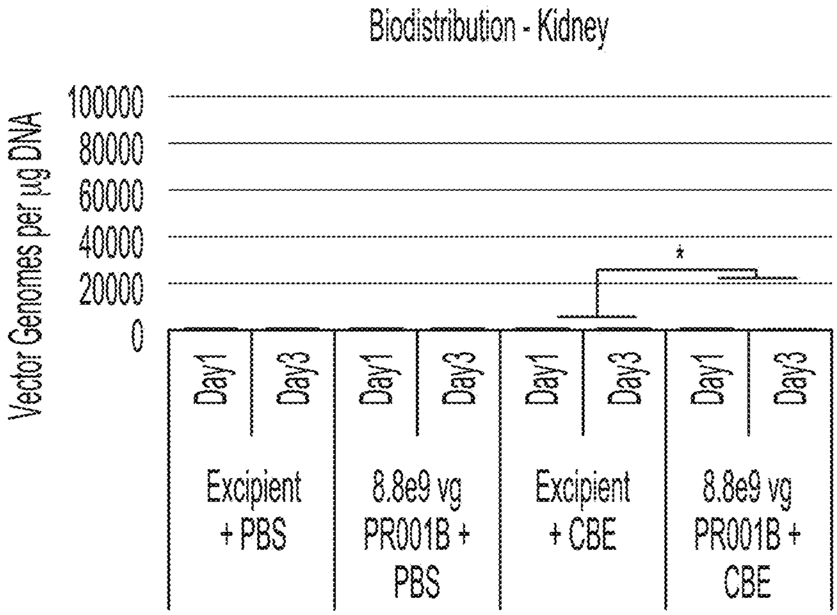

Lipid levels were negatively correlated with both GCase activity and performance on the Rotarod across treatment groups. The increased GCase activity after rAAV-GBA1 administration was associated with substrate reduction and enhanced motor function (FIG. 13). As shown in FIG. 14, preliminary biodistribution was assessed by vector genome presence, as measured by qPCR (with >100 vector genomes per 1 μg genomic DNA defined as positive). Mice that received rAAV-GBA1, both with and without CBE, were positive for rAAV-GBA1 vector genomes in the cortex, indicating that ICV delivery results in rAAV-GBA1 delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of rAAV-GBA1 in the CBE model. Using the 25 mg/kg CBE dose model, excipient or rAAV-GBA1 was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV-GBA1 doses was assessed, resulting in the following five groups, with 10 mice (5M/5F) per group:

Excipient ICV+PBS IP

Excipient ICV+25 mg/kg CBE IP 3.2e9 vg (2.13e10 vg/g brain) rAAV-GBA1 ICV+25 mg/kg CBE IP 1.0e10 vg (6.67e10 vg/g brain) rAAV-GBA1 ICV+25 mg/kg CBE IP 3.2e10 vg (2.13e11 vg/g brain) rAAV-GBA1 ICV+25 mg/kg CBE IP.

Figure 15:
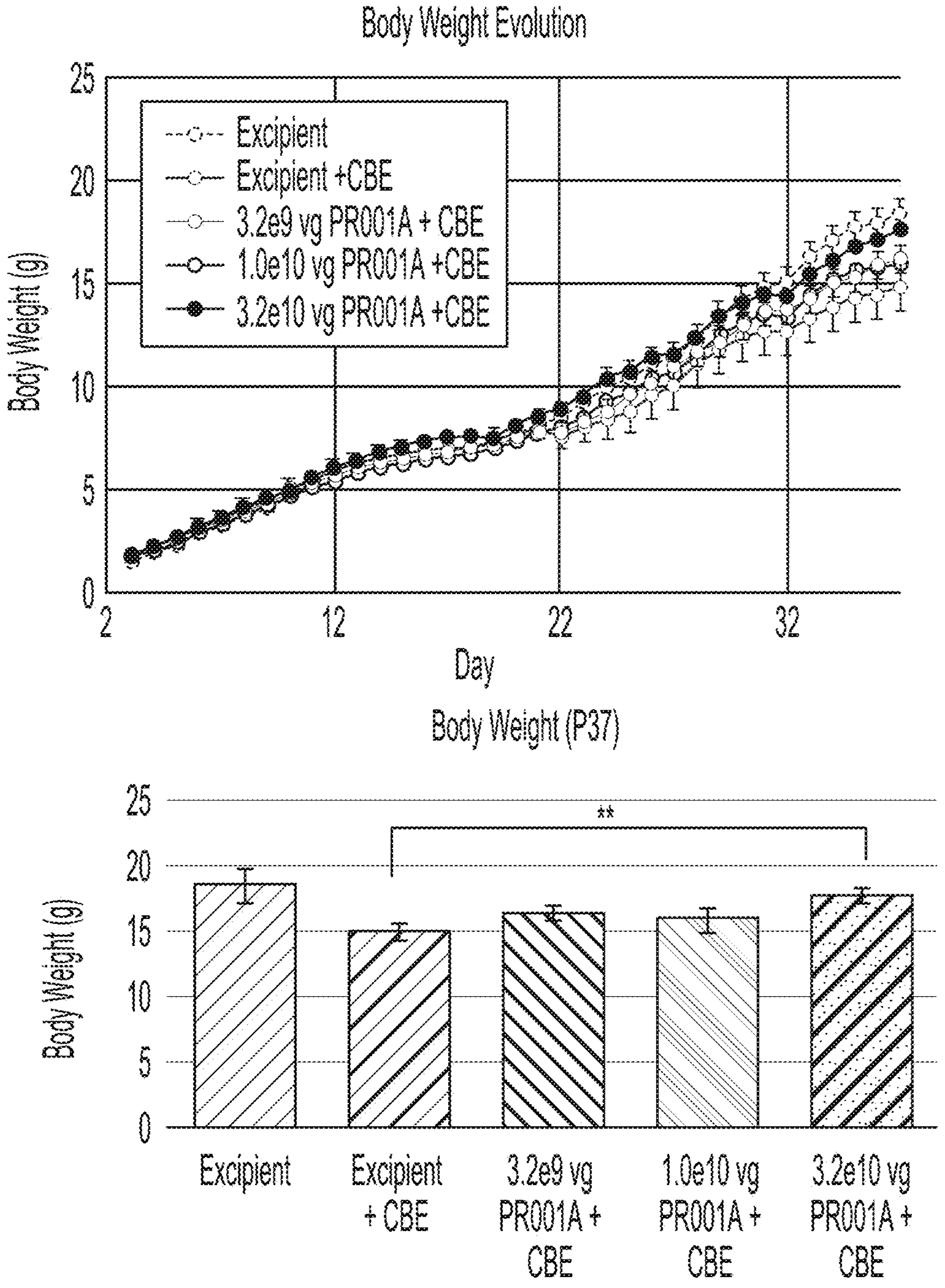
FIG. 15 shows representative data for in-life assessment of rAAV dose ranging in a CBE mouse model. Mice received excipient or one of three different doses of rAAV-GBA1 by ICV delivery at P3: 3.2e9 vg, 1.0e10 vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7. Means are presented. Error bars are SEM; * p<0.05; **p<0.01 for nominal p-values by linear regression in the CBE-treated groups, with gender corrected for as a covariate.
Figure 15:
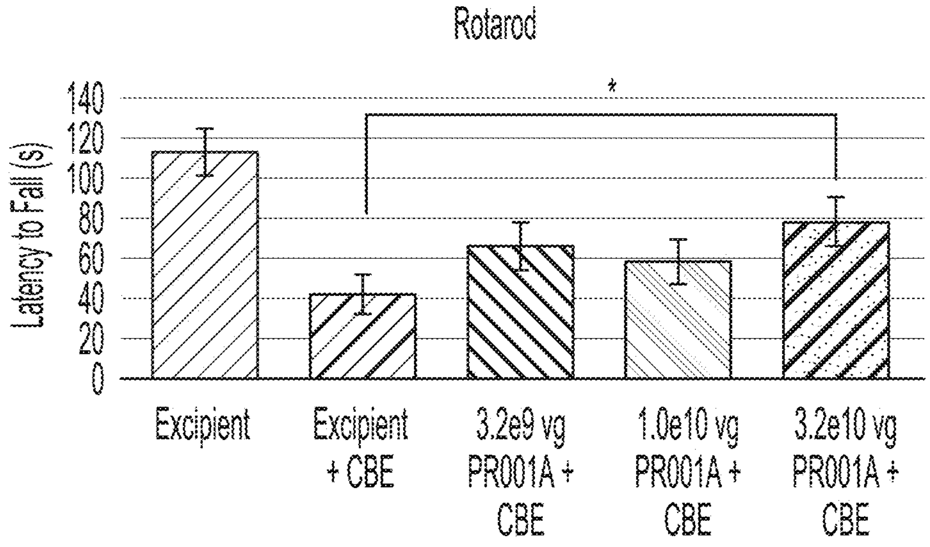
Figure 15:
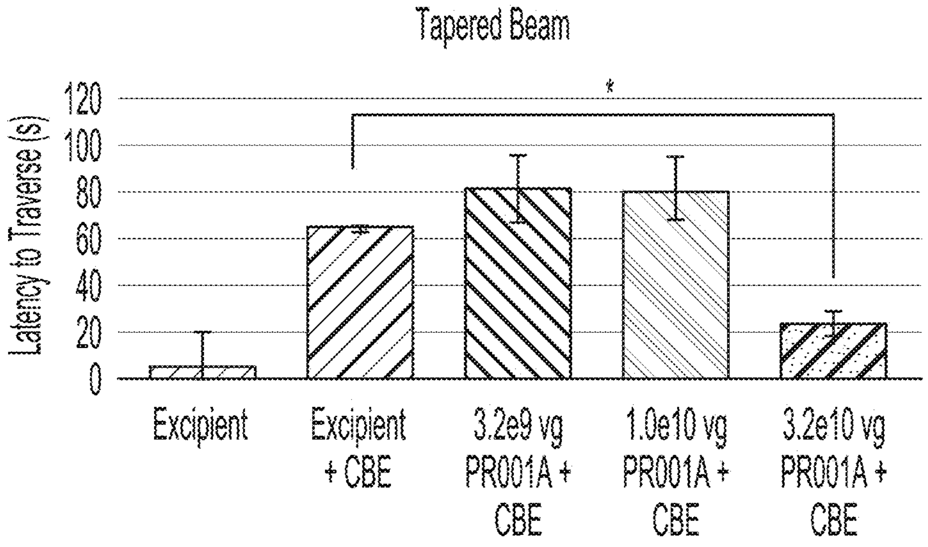

The highest dose of rAAV-GBA1 rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-GBA1-treated groups (Excipient+PBS: 0; Excipient+25 mg/kg CBE: 1; 3.2e9 vg rAAV-GBA1+25 mg/kg CBE: 4; 1.0e10 vg rAAV-GBA1+25 mg/kg CBE: 0; 3.2e10 vg rAAV-GBA1+25 mg/kg CBE: 3).

Figure 16:
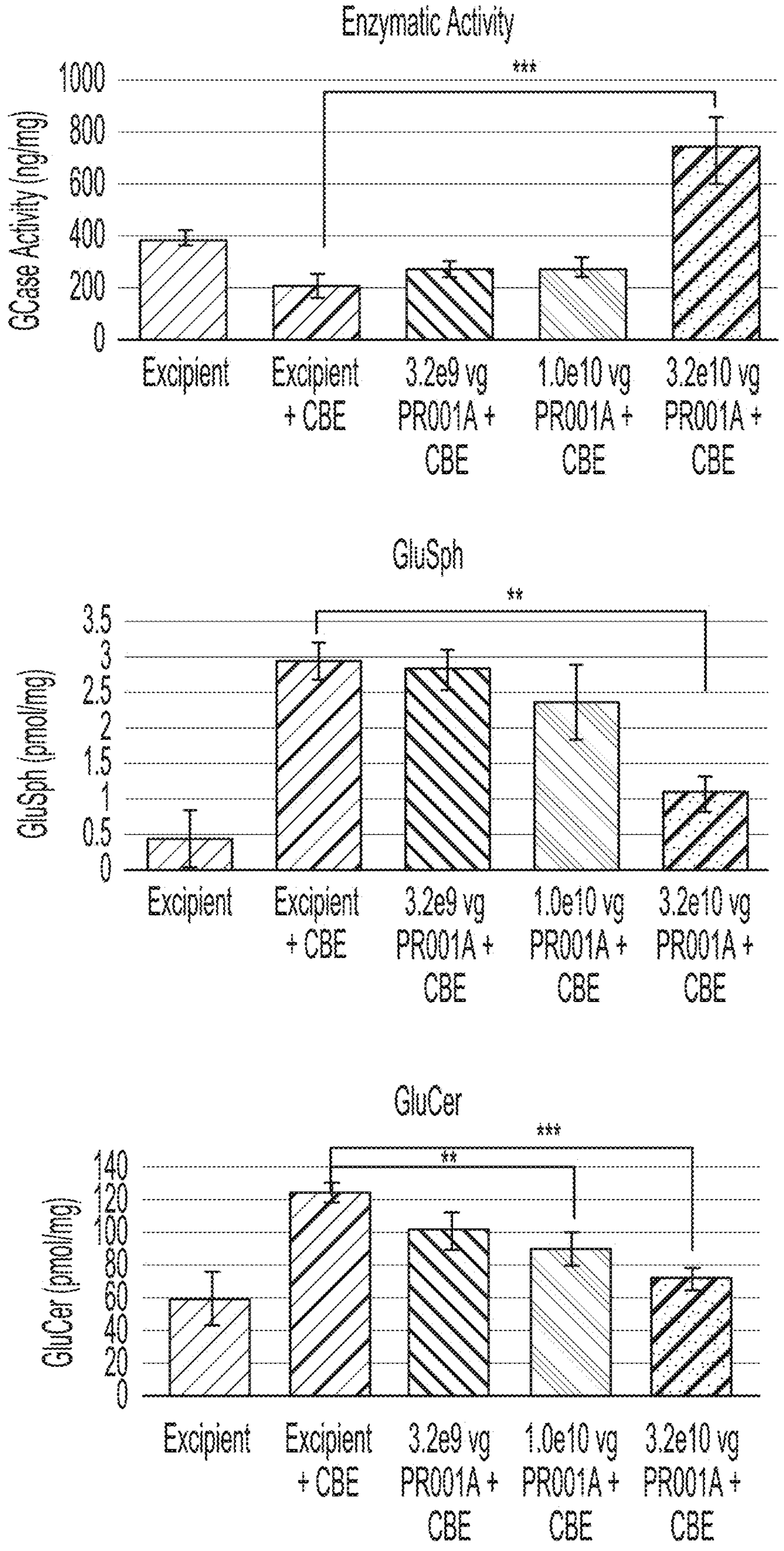
FIG. 16 shows representative data for biochemical assessment of rAAV dose ranging in a CBE mouse model. The cortex of all treatment groups (excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 μg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.
Figure 16:
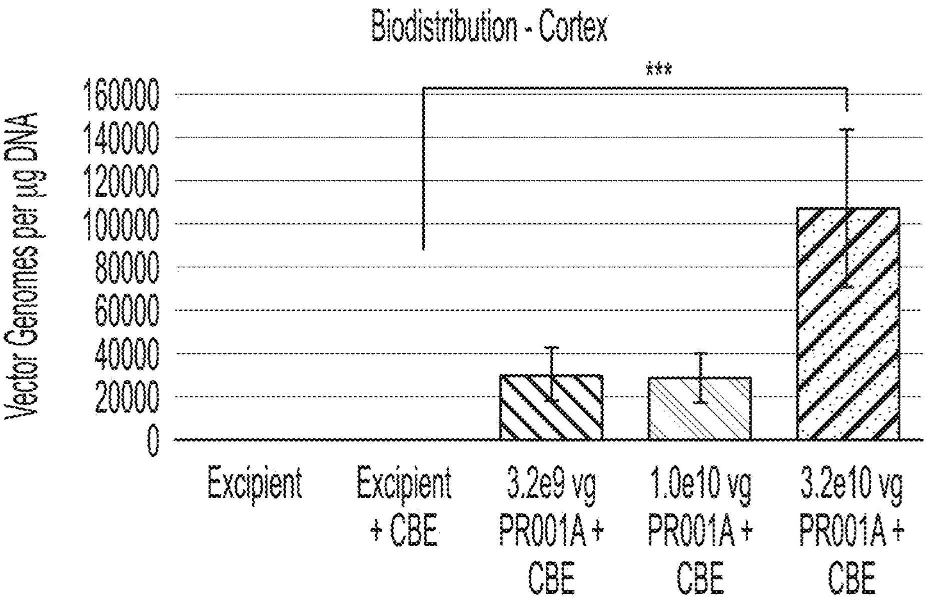
Figure 16:
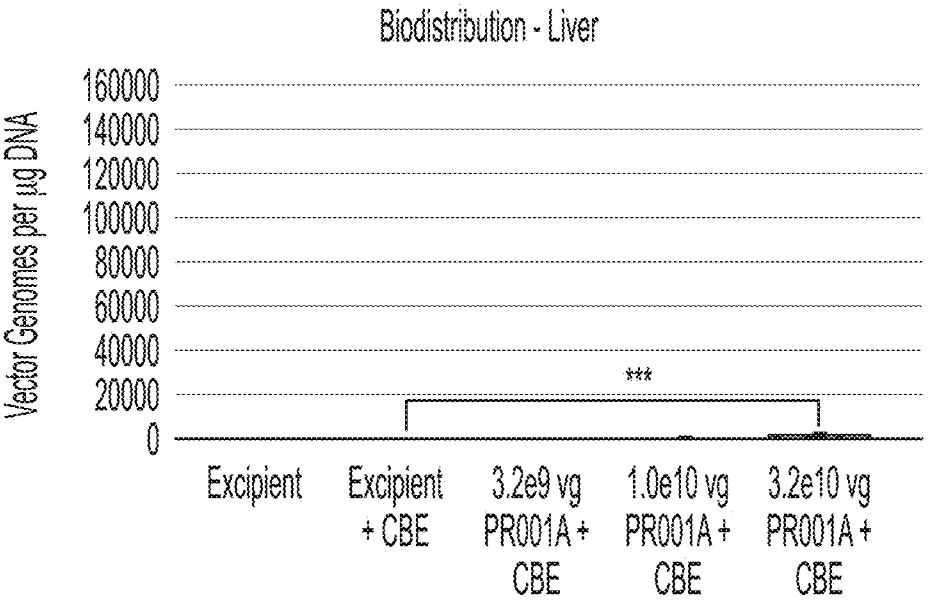

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV-GBA1 dose showed a statistically significant increase in GCase activity compared to CBE treatment. CBE-treated mice also had accumulation of GluCer and GluSph, both of which were rescued by administering a high dose of rAAV-GBA1.

In addition to the established chemical CBE model, rAAV-GBA1 is also evaluated in the 4L/PS-NA genetic model, which is homozygous for the V394L GD mutation in Gba1 and is also partially deficient in saposins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 μl of maximal titer virus was delivered by ICV at P23, with a final dose of 2.4e10 vg (6.0e10 vg/g brain). With 6 mice per group, the treatment groups were:

WT+Excipient ICV

4L/PS-NA+Excipient ICV

4L/PS-NA+2.4e10 vg (6.0e10 vg/g brain) rAAV-GBA1 ICV

Figure 17:
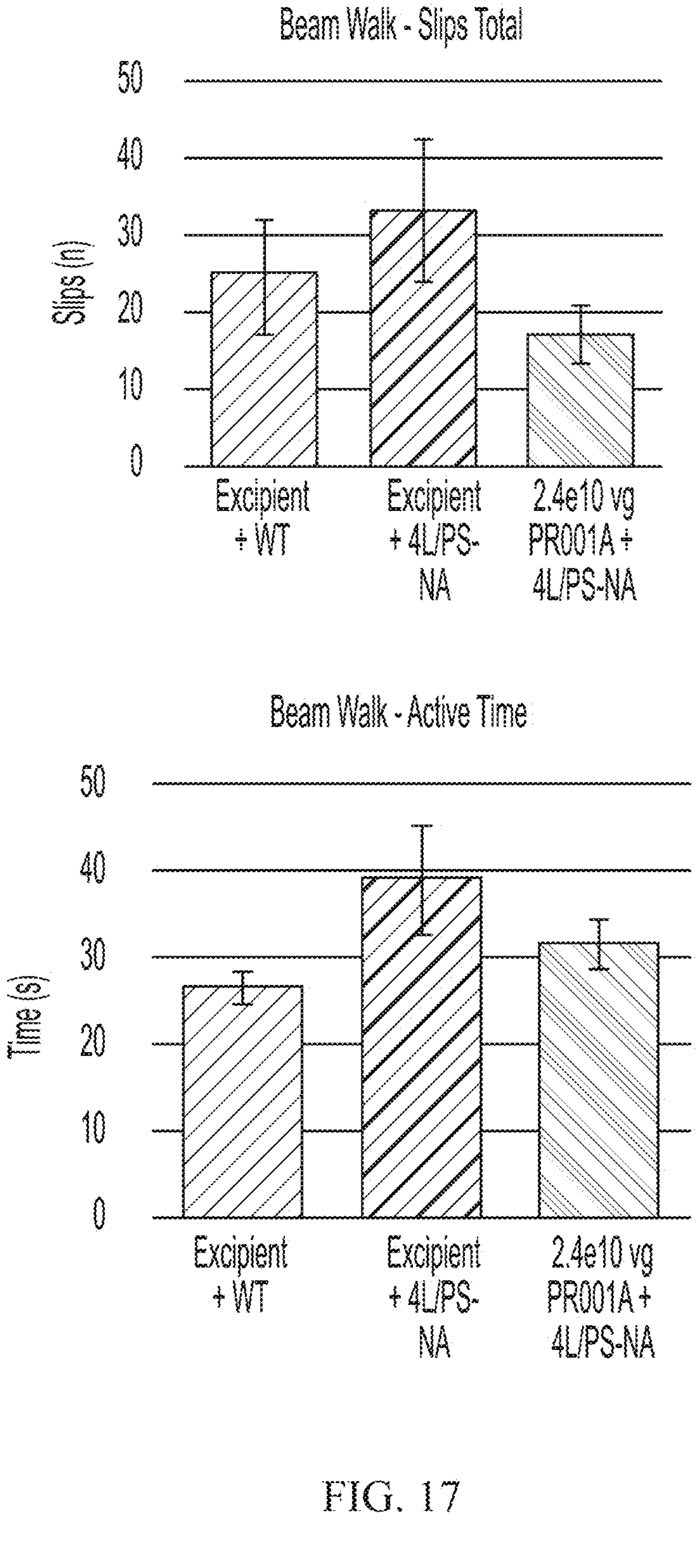
FIG. 17 shows representative data for tapered beam analysis in maximal dose rAAV-GBA1 in a genetic mouse model. Motor performance of the treatment groups (WT+excipient, n=5), 4L/PS-NA+excipient (n=6), and 4L/PS-NA+rAAV-GBA1 (n=5)) was assayed by Beam Walk 4 weeks post rAAV-GBA1 administration. The total slips and active time are shown as total over 5 trials on different beams. Speed and slips per speed are shown as the average over 5 trials on different beams. Means are presented. Error bars are SEM.
Figure 17:
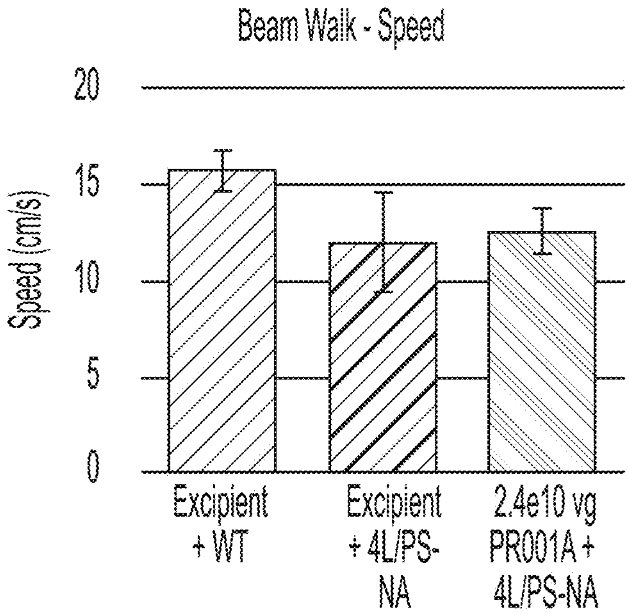
Figure 17:
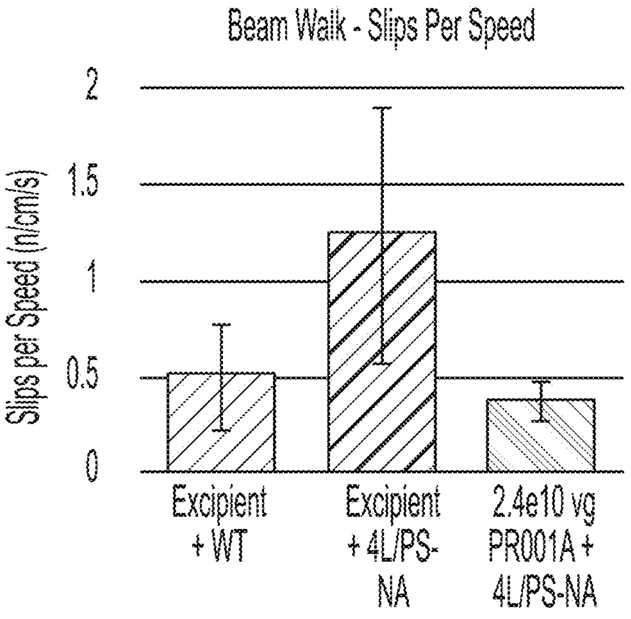

Motor performance by the beam walk test was assessed 4 weeks post-rAAV-GBA1 delivery. The group of mutant mice that received rAAV-GBA1 showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV-GBA1 are currently being tested using the CBE model, corresponding to 0.03×, 0.1×, and 1× the proposed phase 1 high clinical dose. Each group includes 10 mice (5M/5F) per group:

Excipient ICV

Excipient ICV+25 mg/kg CBE IP 3.2e8 vg (2.13e9 vg/g brain) rAAV-GBA1 ICV+25 mg/kg CBE IP 1.0e9 vg (6.67e9 vg/g brain) rAAV-GBA1 ICV+25 mg/kg CBE IP 1.0e10 vg (6.67e10 vg/g brain) rAAV-GBA1 ICV+25 mg/kg CBE IP.

In addition to motor phenotypes, lipid levels and GCase activity are assessed in the cortex. Time course of treatments and analyses are also performed.

A larger dose ranging study was initiated to evaluate efficacy and safety data. 10 4L/PS-NA mice (5M/5F per group) were injected with 10 μl of rAAV-GBA1. Using an allometric brain weight calculation, the doses correlate to 0.15×, 1.5×, 4.4×, and 14.5× the proposed phase 1 high clinical dose. The injection groups consist of:

WT+Excipient ICV

4L/PS-NA+Excipient ICV

4L/PS-NA+4.3e9 vg (11.e10 vg/g brain) rAAV-GBA1 ICV

4L/PS-NA+4.3e10 vg (11.e11 vg/g/brain) rAAV-GBA1 ICV

4L/PS-NA+1.3e11 vg (3.2e11 vg/g brain) rAAV-GBA1 ICV

4L/PS-NA+4.3e11 vg (11.e12 vg/g brain) rAAV-GBA1 ICV.

Figure 18:
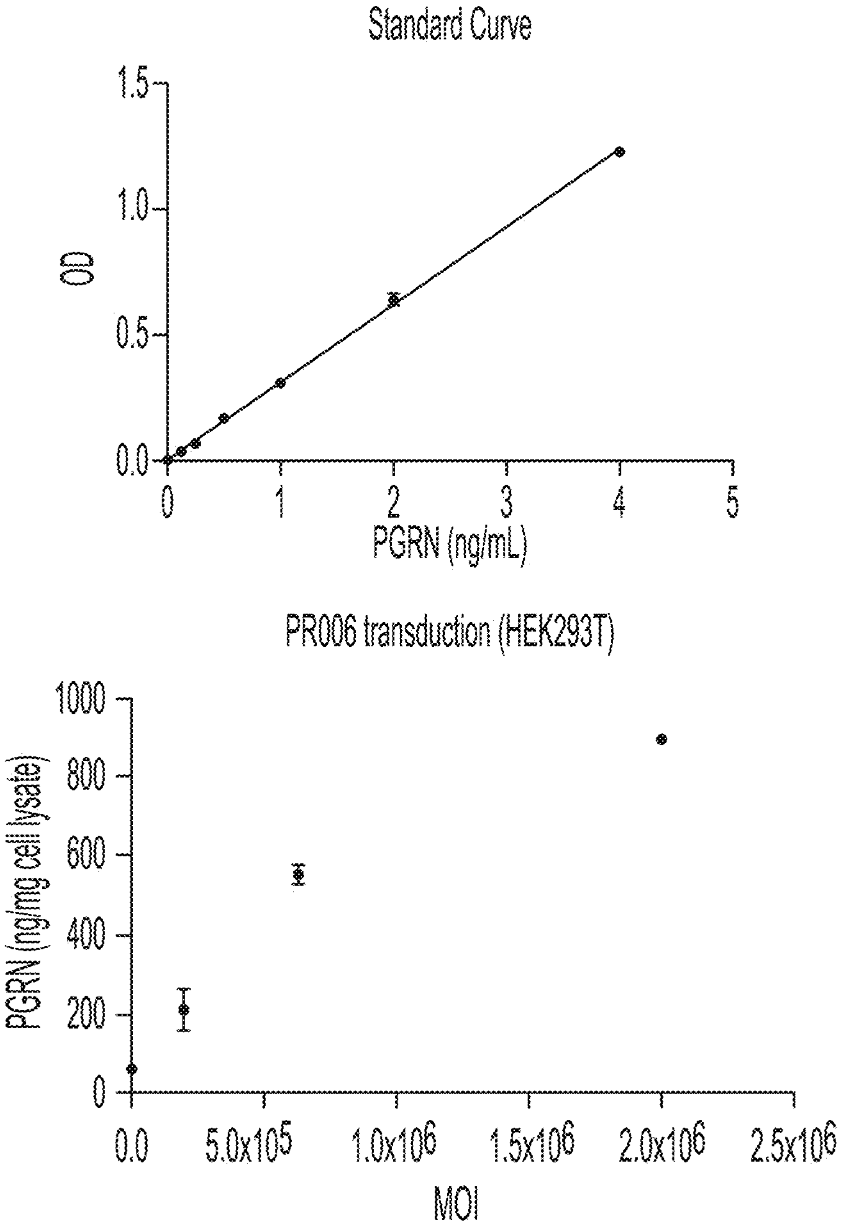
FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

Example 9: In Vitro Analysis of rAAV Vectors rAAV constructs were tested in vitro and in vivo. FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

Figure 19:
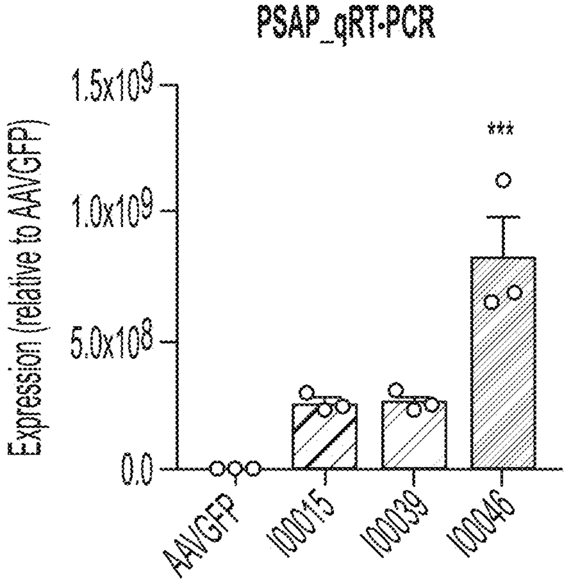
FIG. 19 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to mock transfected cells.
Figure 19:
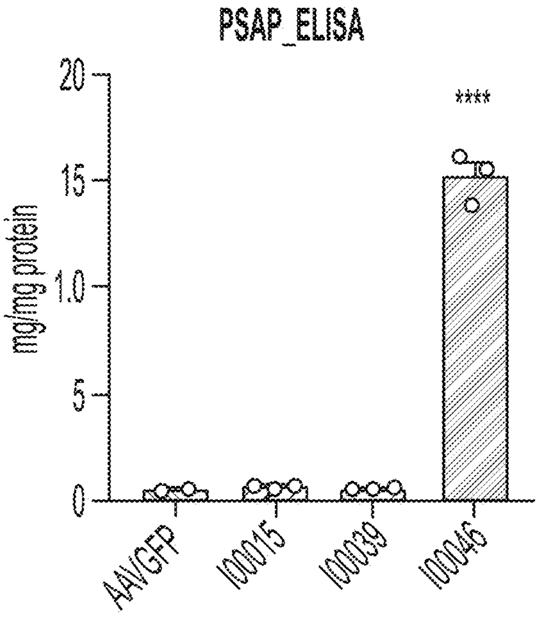
Figure 19:
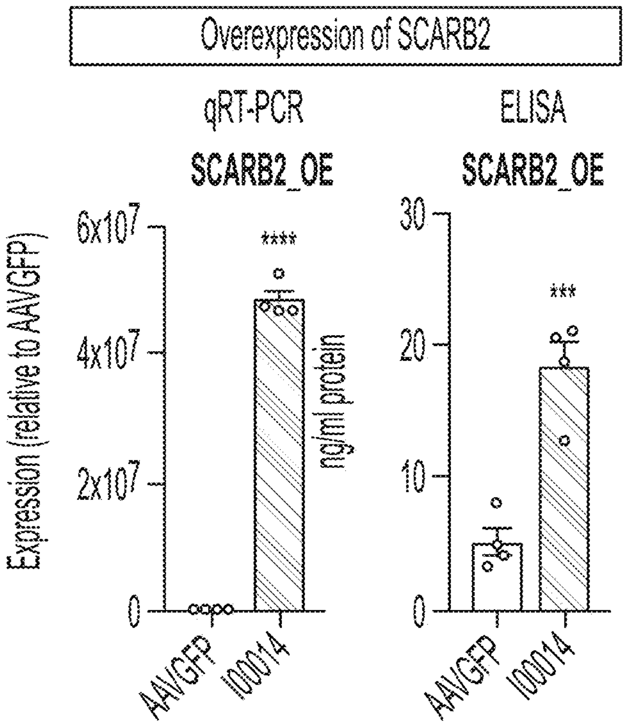
Figure 19:
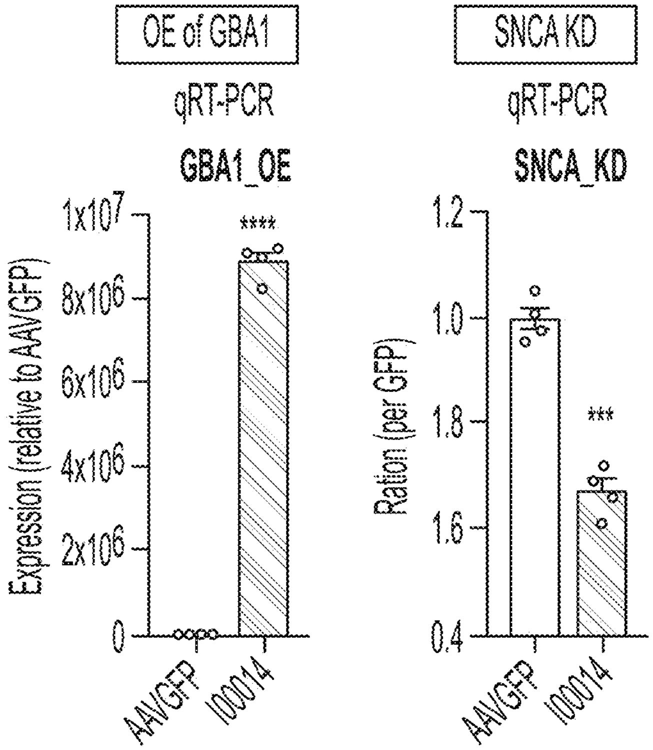

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 3. "Opt" refers to a nucleic acid sequence codon optimized for expression in mammalian cells (e.g., human cells). FIG. 19 shows representative data indicating that transfection of HEK293 cells with each of the constructs resulted in overexpression of the corresponding gene product compared to mock transfected cells.

Figure 36A:
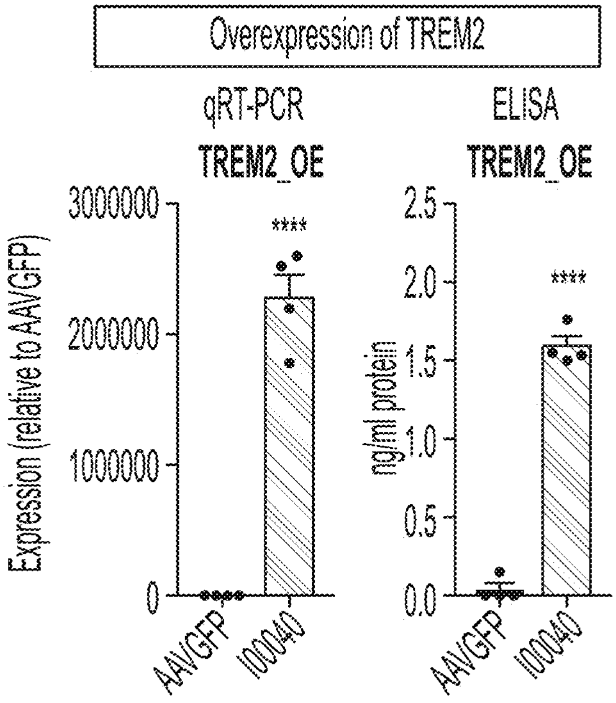
FIG. 36A-FIG. 36B show representative data for overexpression of TREM2 and GBA1 in HEK293 cells relative to control transduced cells, as measured by qPCR and ELISA.
Figure 36B:
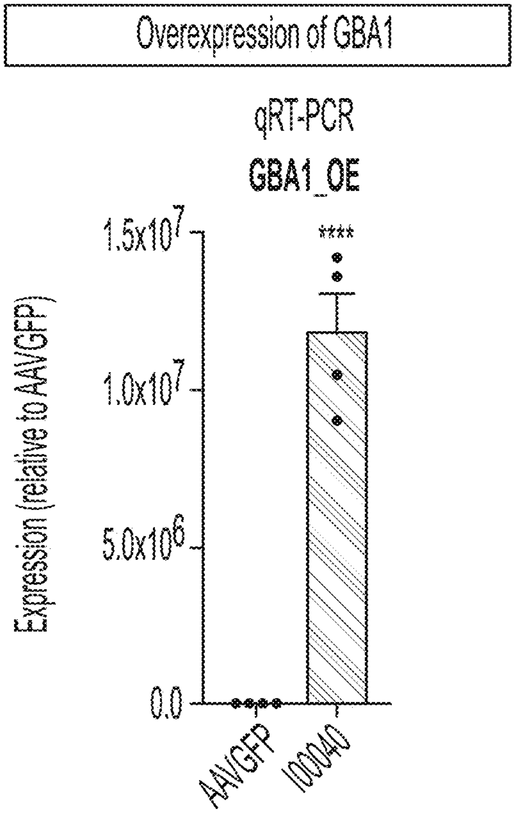

A pilot study was performed to assess in vitro activity of rAAV vectors encoding TREM2, alone or in combination with one or more inhibitory RNAs. Vectors tested include those shown in Table 3. "Opt" refers to a nucleic acid sequence codon optimized for expression in mammalian cells (e.g., human cells). FIGS. 36A-36B show representative data indicating that transfection of HEK293 cells with each of the constructs resulted in overexpression of the corresponding gene product compared to mock transfected cells.

TABLE 3

| ID | Promoter | Inhibitory RNA | Promoter | Transgene |
|---|---|---|---|---|
| I00015 | JL_intronic | SNCA | JetLong | Opt-PSAP_GBA1 |
| I00039 | — | — | JetLong | Opt-PSAP-GRN |
| I00046 | — | — | CBA | Opt-PSAP |
| I00014 | JetLong | SNCA | JetLong | Opt-SCARB2_GBA1 |
| I00040 | | | JL, CD68 | opt-GBA1, TREM2 |

Example 10: Testing of SNCA and TMEM106B shRNA Constructs

HEK293 Cells

Human embryonic kidney 293 cell line (HEK293) were used in this study (#85120602, Sigma-Aldrich). HEK293 cells were maintained in culture media (D-MEM [#11995065, Thermo Fisher Scientific] supplemented with 10% fetal bovine serum [FBS] [#10082147, Thermo Fisher Scientific]) containing 100 units/ml penicillin and 100 μg/ml streptomycin (#15140122, Thermo Fisher Scientific).

Plasmid Transfection

Plasmid transfection was performed using Lipofectamine 2000 transfection reagent (#11668019, Thermo Fisher Scientific) according to the manufacture's instruction. Briefly, HEK293 cells (#12022001, Sigma-Aldrich) were plated at the density of $3\times10^5$ cells/ml in culture media without antibiotics. On the following day, the plasmid and Lipofectamine 2000 reagent were combined in Opti-MEM solution (#31985062, Thermo Fisher Scientific). After 5 minutes, the mixtures were added into the HEK293 culture. After 72 hours, the cells were harvested for RNA or protein extraction, or subjected to the imaging analyses. For imaging analyses, the plates were pre-coated with 0.01% poly-L-Lysine solution (P8920, Sigma-Aldrich) before the plating of cells.

Gene Expression Analysis by Quantitative Real-Time PCR (qRT-PCR)

Relative gene expression levels were determined by quantitative real-time PCR (qRT-PCR) using Power SYBR Green Cells-to-CT Kit (#4402955, Thermo Fisher Scientific) according to the manufacturer's instruction. The candidate plasmids were transiently transfected into HEK293 cells plated on 48-well plates ($7.5\times10^4$ cells/well) using Lipofectamine 2000 transfection reagent (0.5 μg plasmid and 1.5 μl reagent in 50 μl Opti-MEM solution). After 72 hours, RNA was extracted from the cells and used for reverse transcription to synthesize cDNA according to the manufacturer's instruction. For quantitative PCR analysis, 2-5 μl of cDNA products were amplified in duplicates using gene specific primer pairs (250 nM final concentration) with Power SYBR Green PCR Master Mix (#4367659, Thermo Fisher Scientific). The primer sequences for SNCA, TMEM106B, and GAPDH genes were: 5'-AAG AGG GTG TTC TCT ATG TAG GC-3' (SEQ ID NO: 71), 5'-GCT CCT CCA ACA TTT GTC ACT T-3' (SEQ ID NO: 72) for SNCA, 5'-ACA CAG TAC CTA CCG TTA TAG CA-3' (SEQ ID NO: 73), 5'-TGT TGT CAC AGT AAC TTG CAT CA-3' (SEQ ID NO: 74) for TMEM106B, and 5'-CTG GGC TAC ACT GAG CAC C-3' (SEQ ID NO: 75), 5'-AAG TGG TCG TTG AGG GCA ATG-3' (SEQ ID NO: 76) for GAPDH. Quantitative PCR was performed in a QuantStudio 3 Real-Time PCR system (Thermo Fisher Scientific). Expression levels were normalized by the housekeeping gene GAPDH and calculated using the comparative CT method.

Fluorescence Imaging Analysis

EGFP reporter plasmids, which contain 3'-UTR of human SNCA gene at downstream of EGFP coding region, were used for the validation of SNCA and TMEM106B knockdown plasmids. EGFP reporter plasmids and candidate knockdown plasmids were simultaneously transfected into HEK293 cells plated on poly-L-Lysine coated 96-well plates ($3.0\times10^4$ cells/well) using Lipofectamine 2000 transfection reagent (0.04 μg reporter plasmid, 0.06 μg knockdown plasmid and 0.3 μl reagent in 10 μl Opti-MEM solution). After 72 hours, the fluorescent intensities of EGFP signal were measured at excitation 488 nm/emission 512 nm using Varioskan LUX multimode reader (Thermo Fisher Scientific). Cells were fixed with 4% PFA at RT for 10 minutes, and incubated with D-PBS containing 40 μg/ml 7-aminoactinomycin D (7-AAD) for 30 min at RT. After washing with D-PBS, the fluorescent intensities of 7-AAD signal were measured at excitation 546 nm/emission 647 nm using Varioskan reader to quantify cell number. Normalized EGFP signal per 7-AAD signal levels were compared with the control knockdown samples.

Enzyme-Linked Immunosorbent Assay (ELISA)

α-Synuclein reporter plasmids, which contain 3'-UTR of human SNCA gene or TMEM106B gene downstream of SNCA coding region, were used for the validation of knockdown plasmids at the protein level. Levels of α-synuclein protein were determined by ELISA (#KHB0061, Thermo Fisher Scientific) using the lysates extracted from HEK293 cells. The candidate plasmids were transiently transfected into HEK293 cells plated on 48-well plates ($7.5\times10^4$ cells/ well) using Lipofectamine 2000 transfection reagent (0.1 μg reporter plasmid, 0.15 μg knockdown plasmid and 0.75 μl reagent in 25 μl Opti-MEM solution). After 72 hours, cells were lysed in radioimmunoprecipitation assay (RIPA) buffer (#89900, Thermo Fisher Scientific) supplemented with protease inhibitor cocktail (#P8340, Sigma-Aldrich), and sonicated for a few seconds. After incubation on ice for 30 min, the lysates were centrifuged at 20,000×g at 4° C. for 15 min, and the supernatant was collected. Protein levels were quantified. Plates were read in a Varioskan plate reader at 450 nm, and concentrations were calculated using SoftMax Pro 5 software. Measured protein concentrations were normalized to total protein concentration determined with a bicinchoninic acid assay (#23225, Thermo Fisher Scientific).

Figure 37:
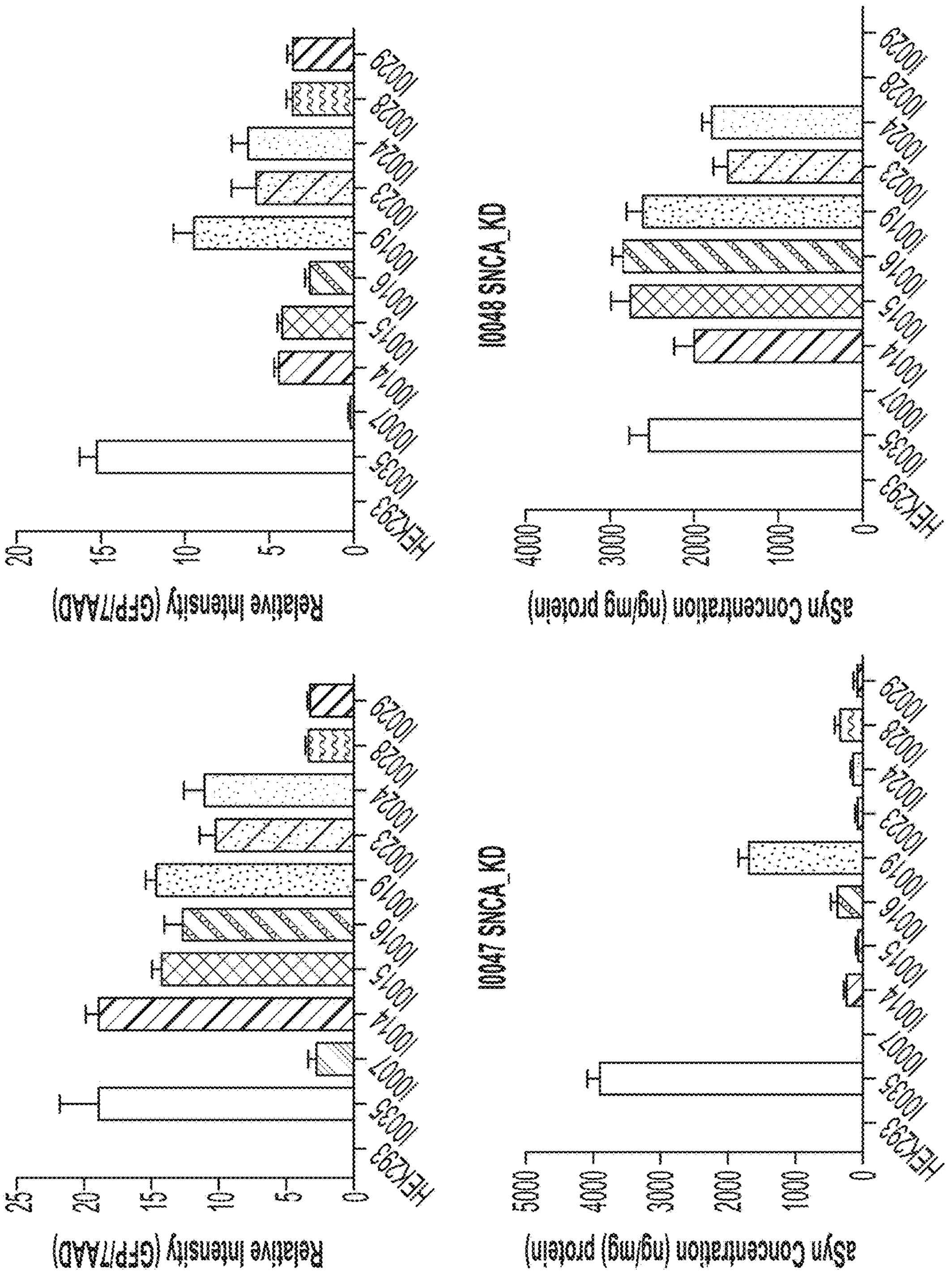
FIG. 37 shows representative data indicating successful silencing of SNCA in vitro by GFP reporter assay (top) and α-Syn assay (bottom).
Figure 38:
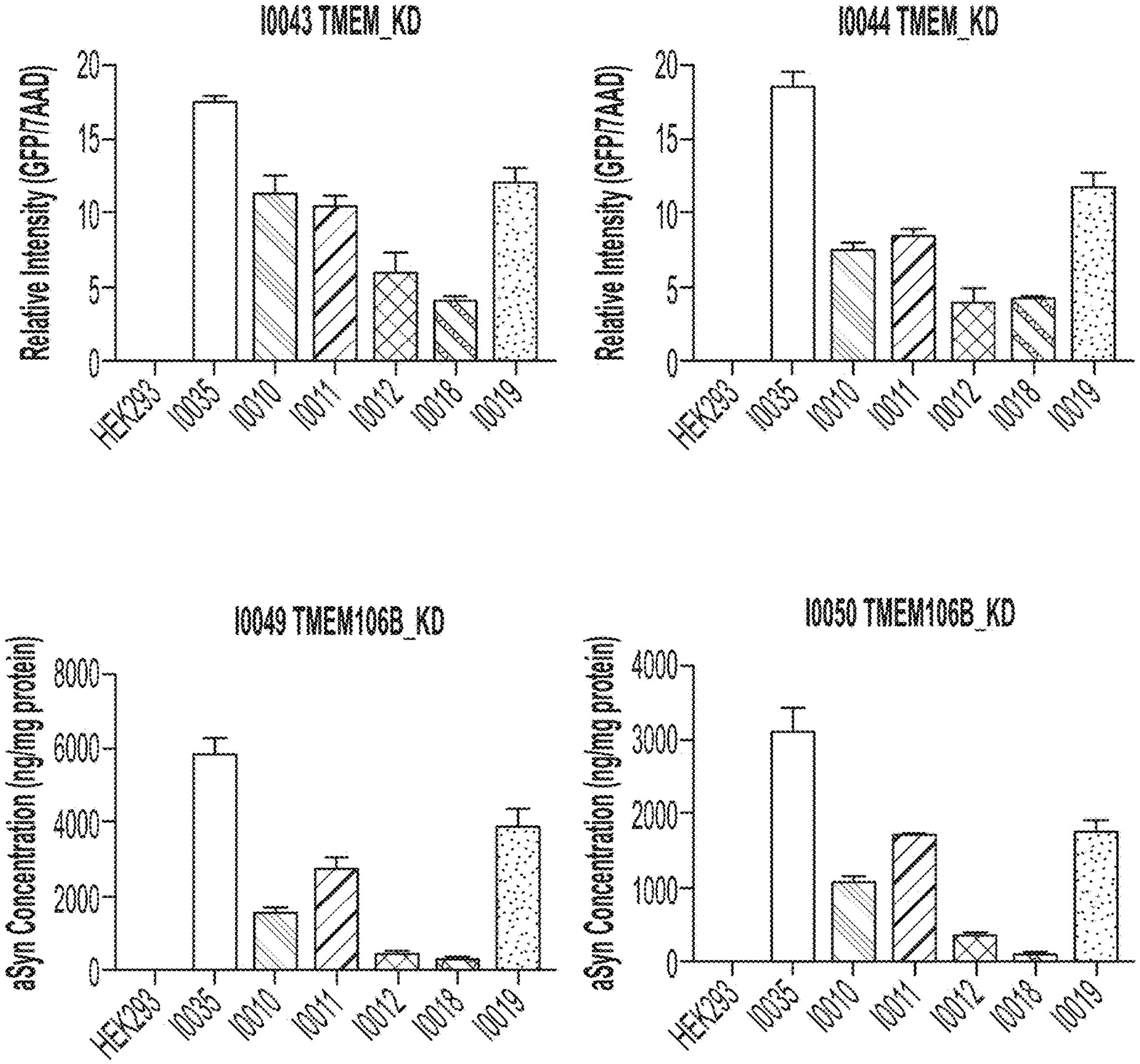
FIG. 38 shows representative data indicating successful silencing of TMEM106B in vitro by GFP reporter assay (top) and α-Syn assay (bottom).

FIG. 37 and Table 4 show representative data indicating successful silencing of SNCA in vitro by GFP reporter assay (top) and α-Syn assay (bottom). FIG. 38 and Table 5 show representative data indicating successful silencing of TMEM106B in vitro by GFP reporter assay (top) and α-Syn assay (bottom).

TABLE 4

| ID | Promoter | Knockdown | Promoter | Overexpress |
|---|---|---|---|---|
| I00007 | CMV_intronic | SNCA_mi | CMV | opt-GBA1 |
| I00008 | H1 | SNCA_sh | CMV | opt-GBA1 |
| I00009 | H1 | SNCA_Pubsh4 | CMV | opt-GBA1 |
| I00014 | JL_intronic | SNCA_mi | JetLong | opt-SCARB2_GBA |
| I00015 | JL_intronic | SNCA_mi | JetLong | opt-PSAP_GBA |
| I00016 | JL_intronic | SNCA_mi | JetLong | opt-CTSB_GBA |
| I00019 | JL_intronic | SNCA_TMEM_mi | JetLong | opt-VPS35 |
| I00023 | JL_intronic | SNCA_mi | JetLong | opt-GBA1_IL34 |
| I00024 | JL_intronic | SNCA_mi | JetLong | opt-GBA2 |
| I00028 | intronic | SNCA_Broadsh | CMV | opt-GBA1 |
| I00029 | intronic | SNCA_Pubsh4 | CMV | opt-GBA1 |

TABLE 5

| ID | Promoter | Knockdown | Promoter | Overexpress |
|---|---|---|---|---|
| I00010 | H1 | TMEM_Pubsh | CMV | opt-GRN |
| I00011 | JL_intronic | TMEM_mi | JetLong | opt-GBA1_GRN |
| I00012 | H1 | TMEM_sh | CMV | opt-GRN |
| I00019 | JL_intronic | SNCA_TMEM_mi | JetLong | opt-VPS35 |

Example 11: ITR "D" Sequence Placement and Cell Transduction

Figure 40:
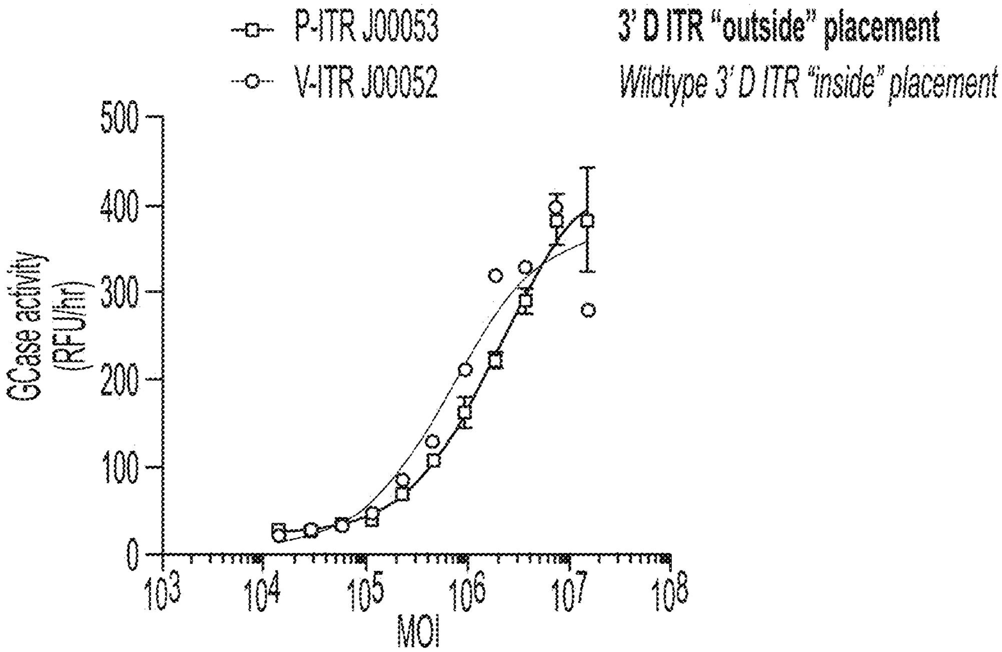
FIG. 40 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.
Figure 41:
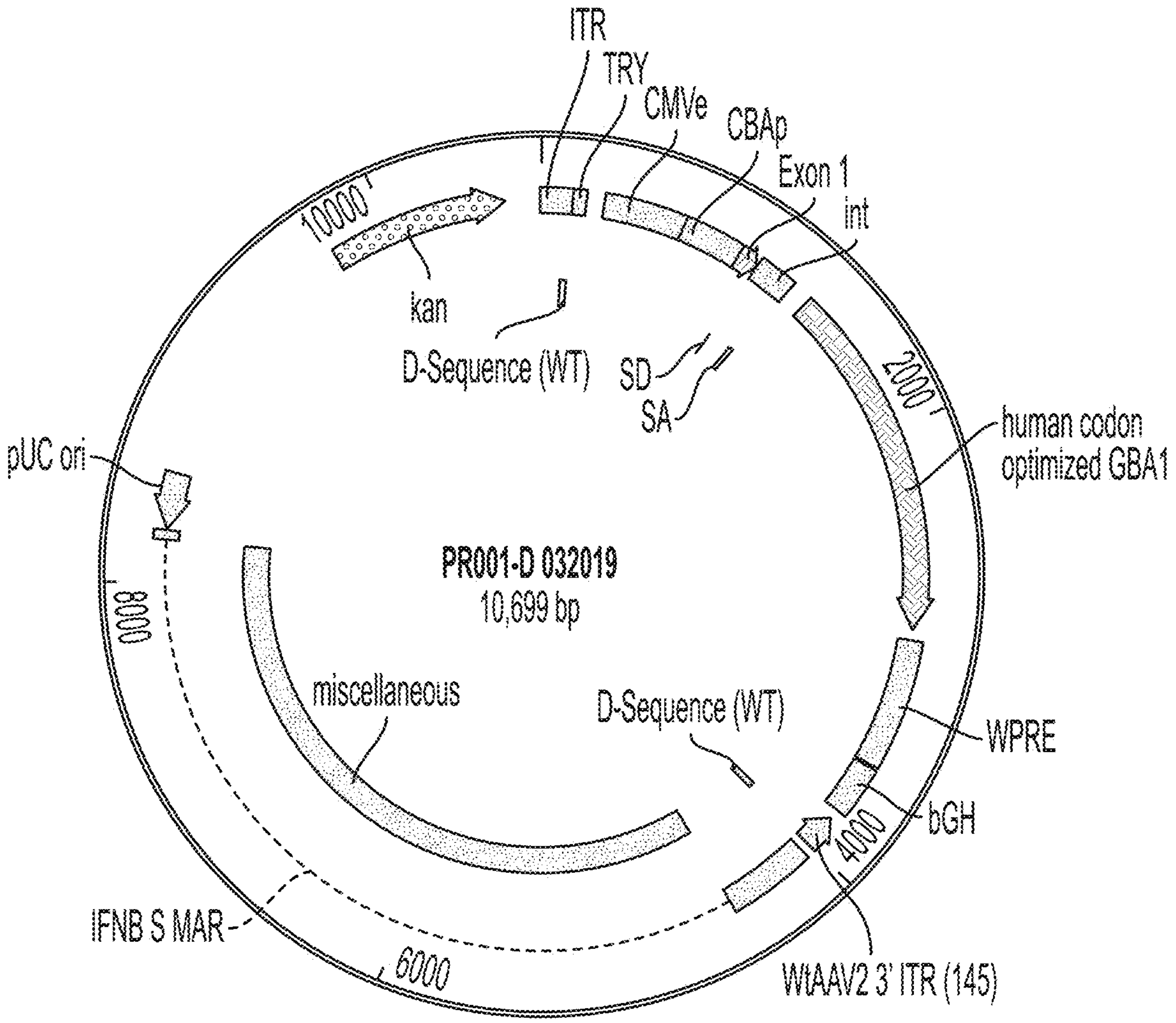
FIG. 41 is a schematic depicting one embodiment of a vector comprising an expression construct encoding Gcase (e.g., GBA1 or a portion thereof).
Figure 42:
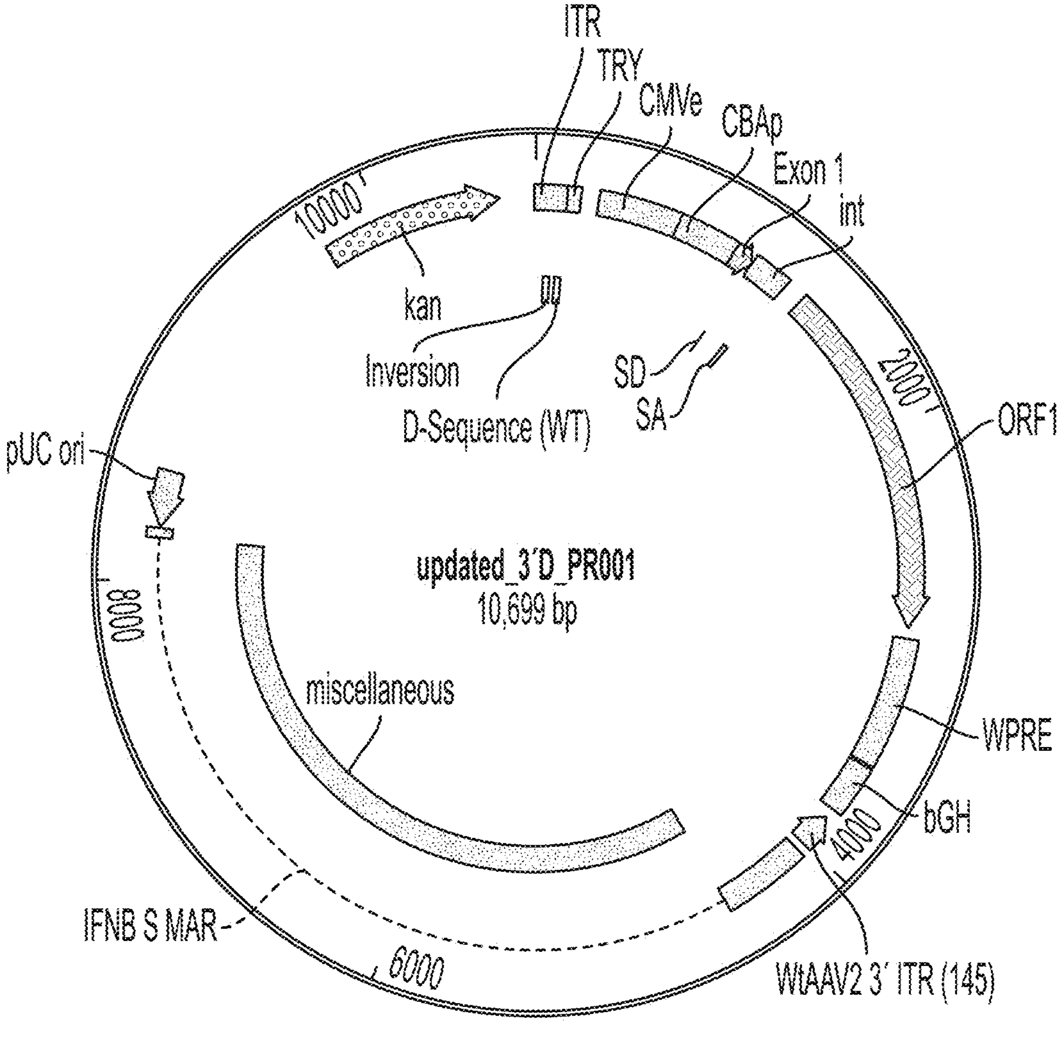
FIG. 42 is a schematic depicting one embodiment of a vector comprising an expression construct encoding Gcase (e.g., GBA1 or a portion thereof).
Figure 43:
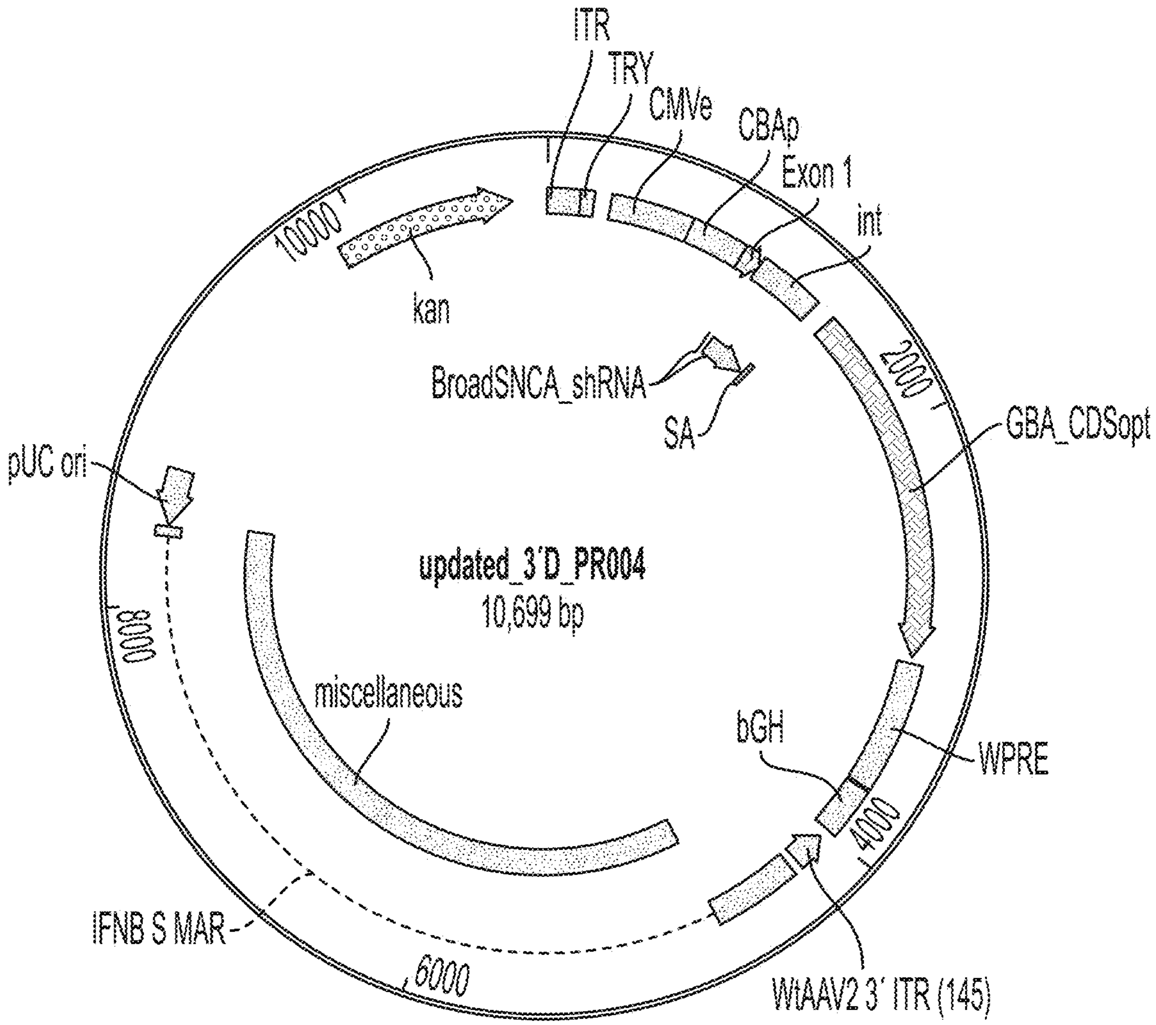
FIG. 43 is a schematic depicting one embodiment of a vector comprising an expression construct encoding Gcase (e.g., GBA1 or a portion thereof) and an interfering RNA for α-Syn.
Figure 44:
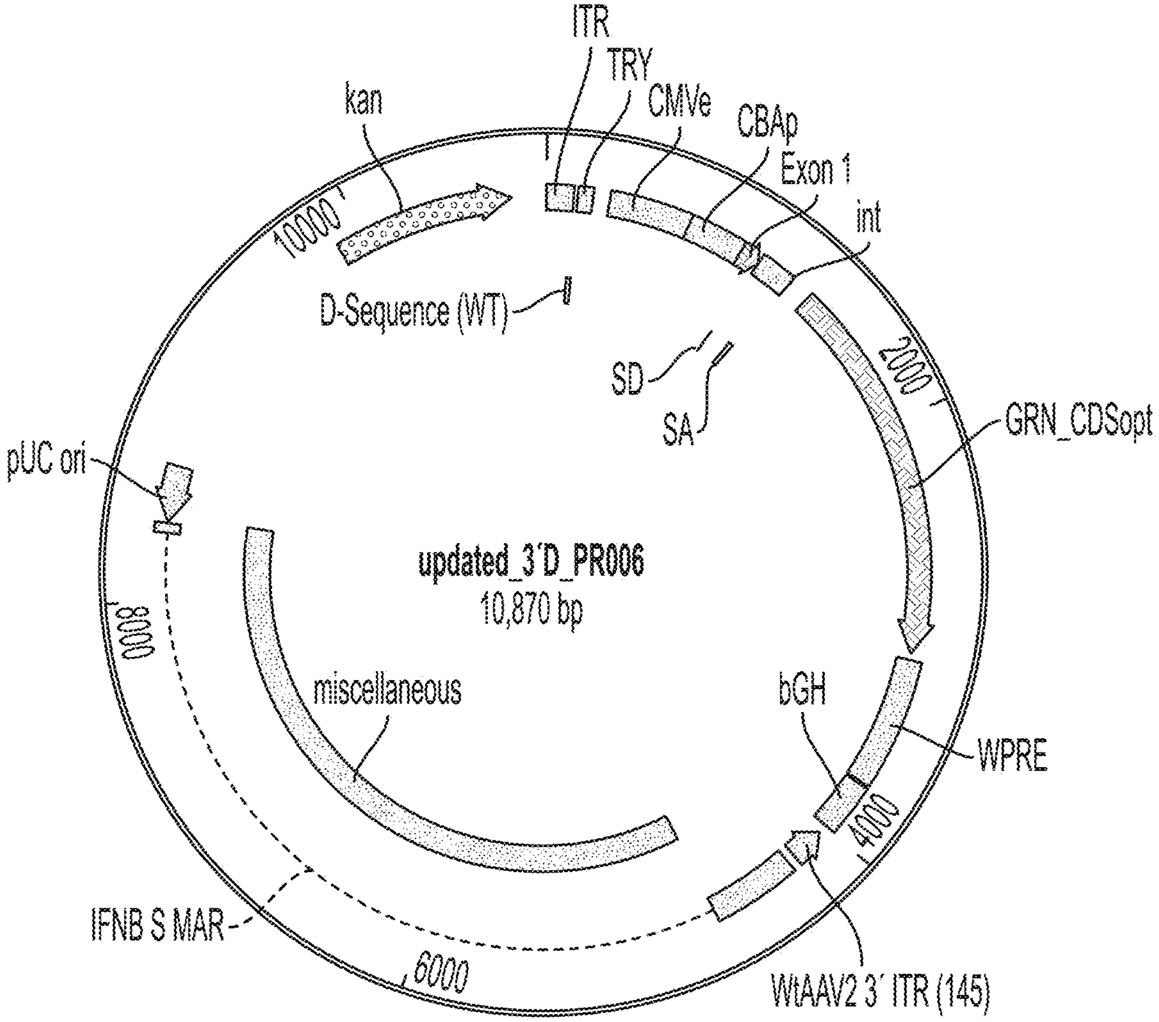
FIG. 44 is a schematic depicting one embodiment of a vector comprising an expression construct encoding PGRN.
Figure 45:
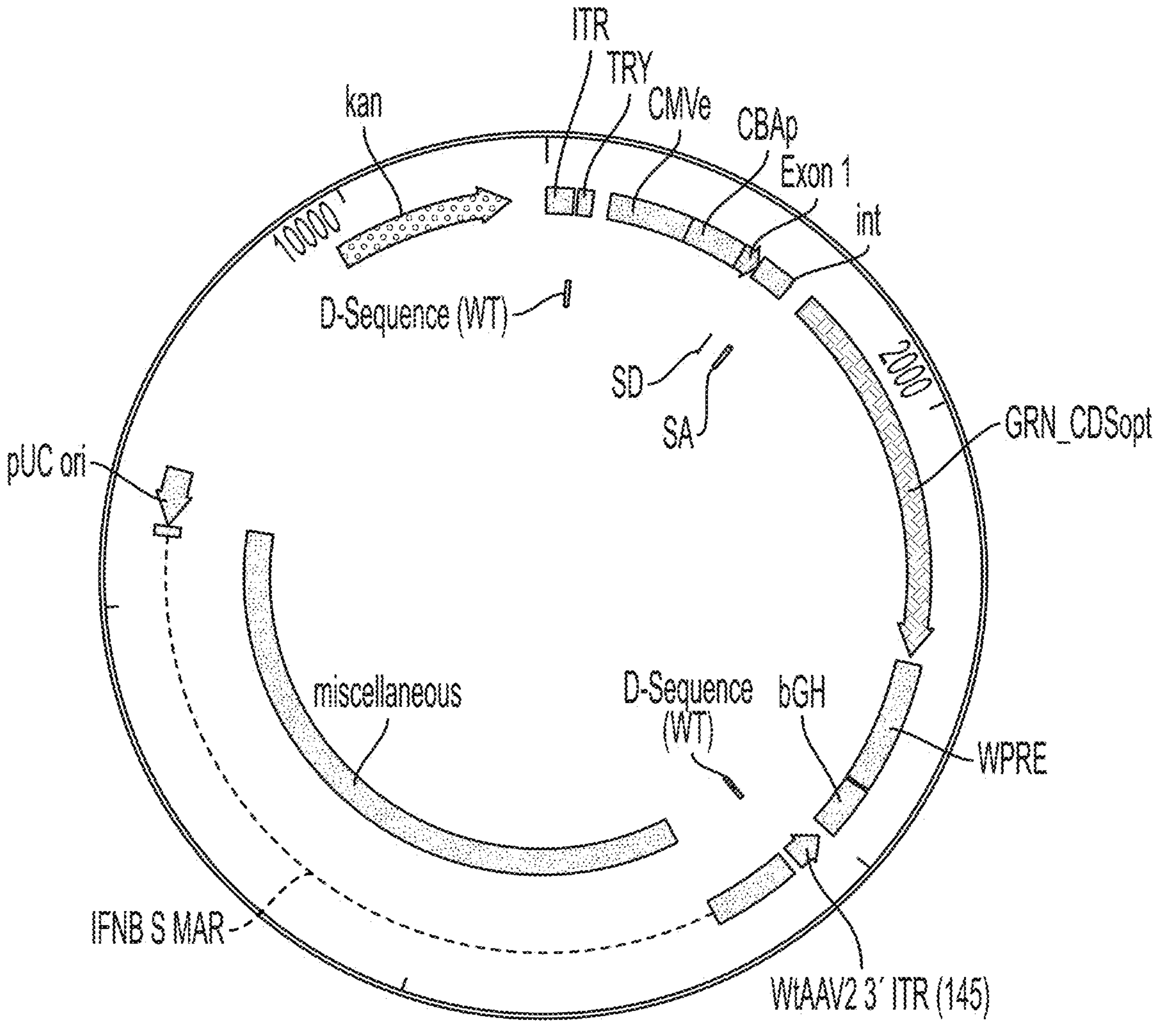
FIG. 45 is a schematic depicting one embodiment of a vector comprising an expression construct encoding PGRN.
Figure 46:
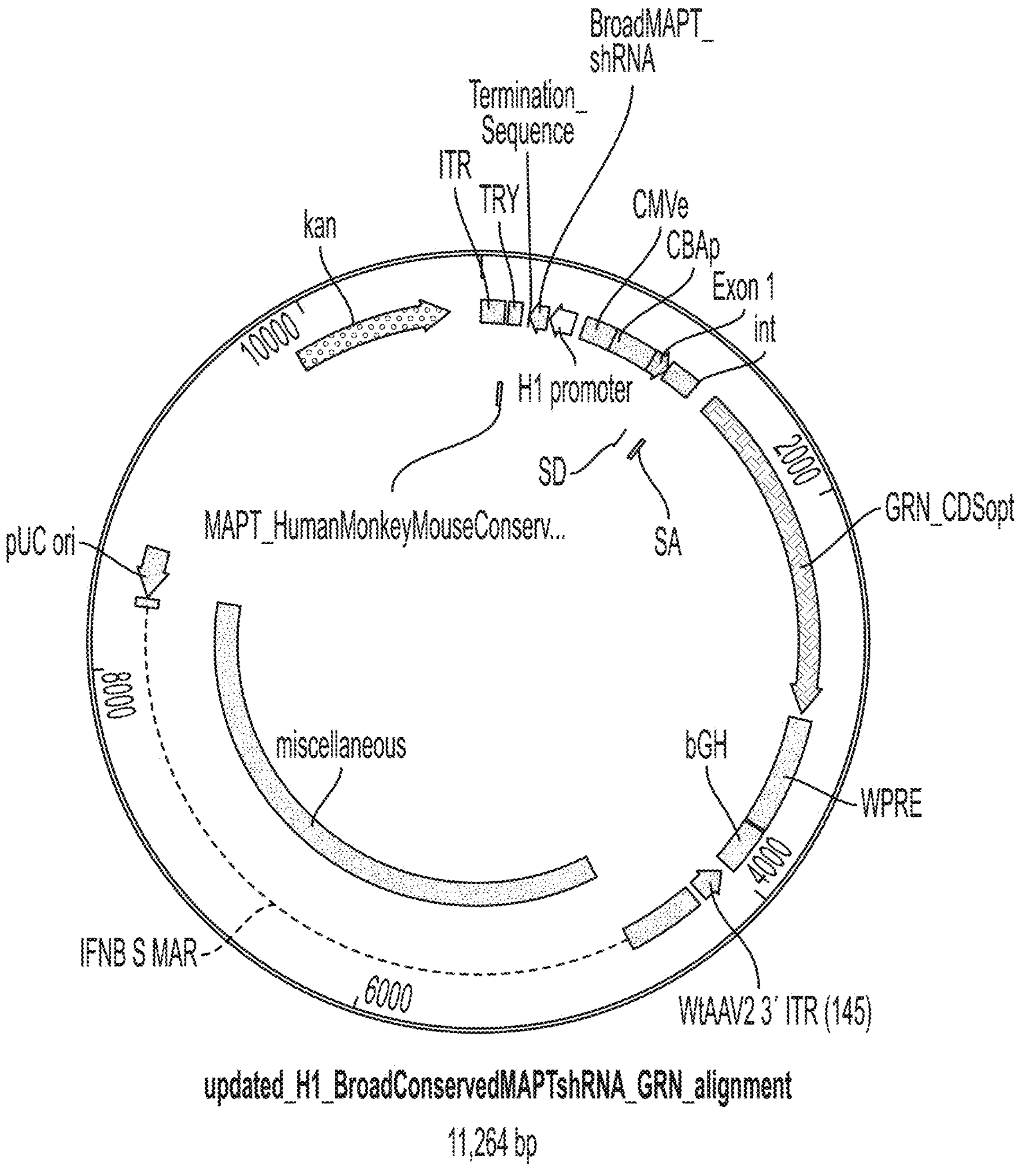
FIG. 46 is a schematic depicting one embodiment of a vector comprising an expression construct encoding PGRN and an interfering RNA for microtubule-associated protein tau (MAPT).
Figure 47:
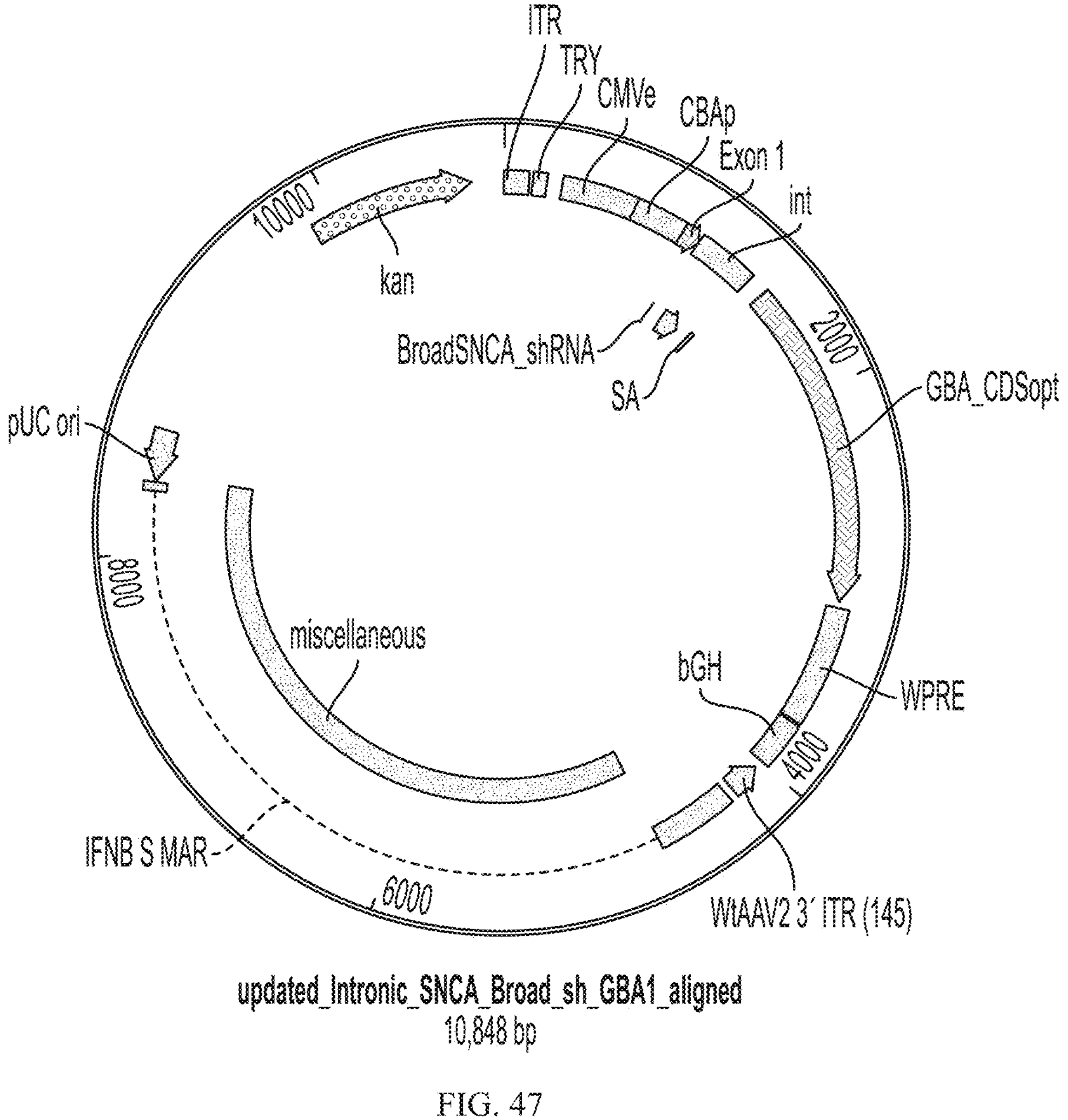
FIG. 47 is a schematic depicting one embodiment of a vector comprising an expression construct encoding Gcase (e.g., GBA1 or a portion thereof) and an interfering RNA for α-Syn.
Figure 48:
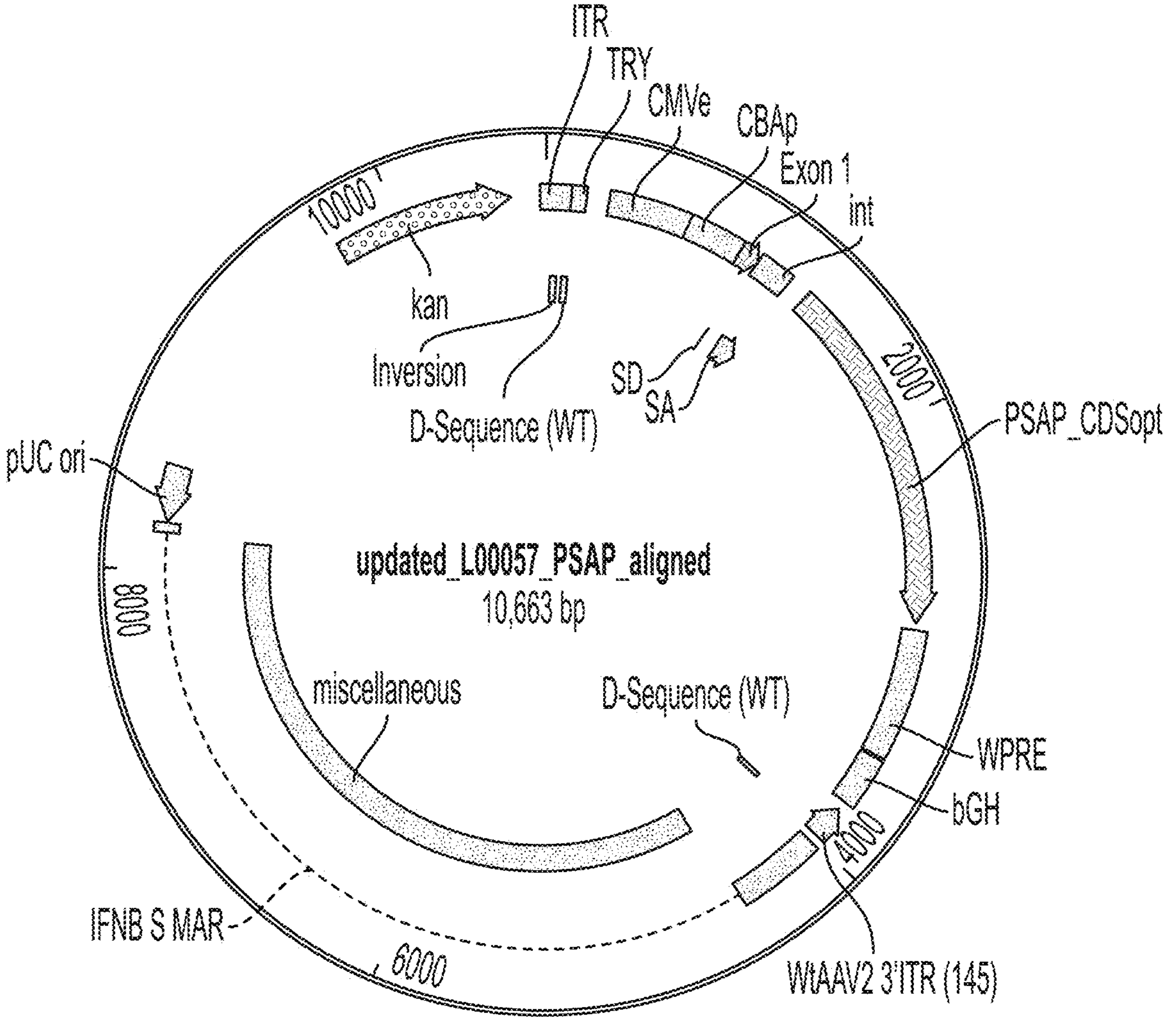
FIG. 48 is a schematic depicting one embodiment of a vector comprising an expression construct encoding PSAP.
Figure 49:
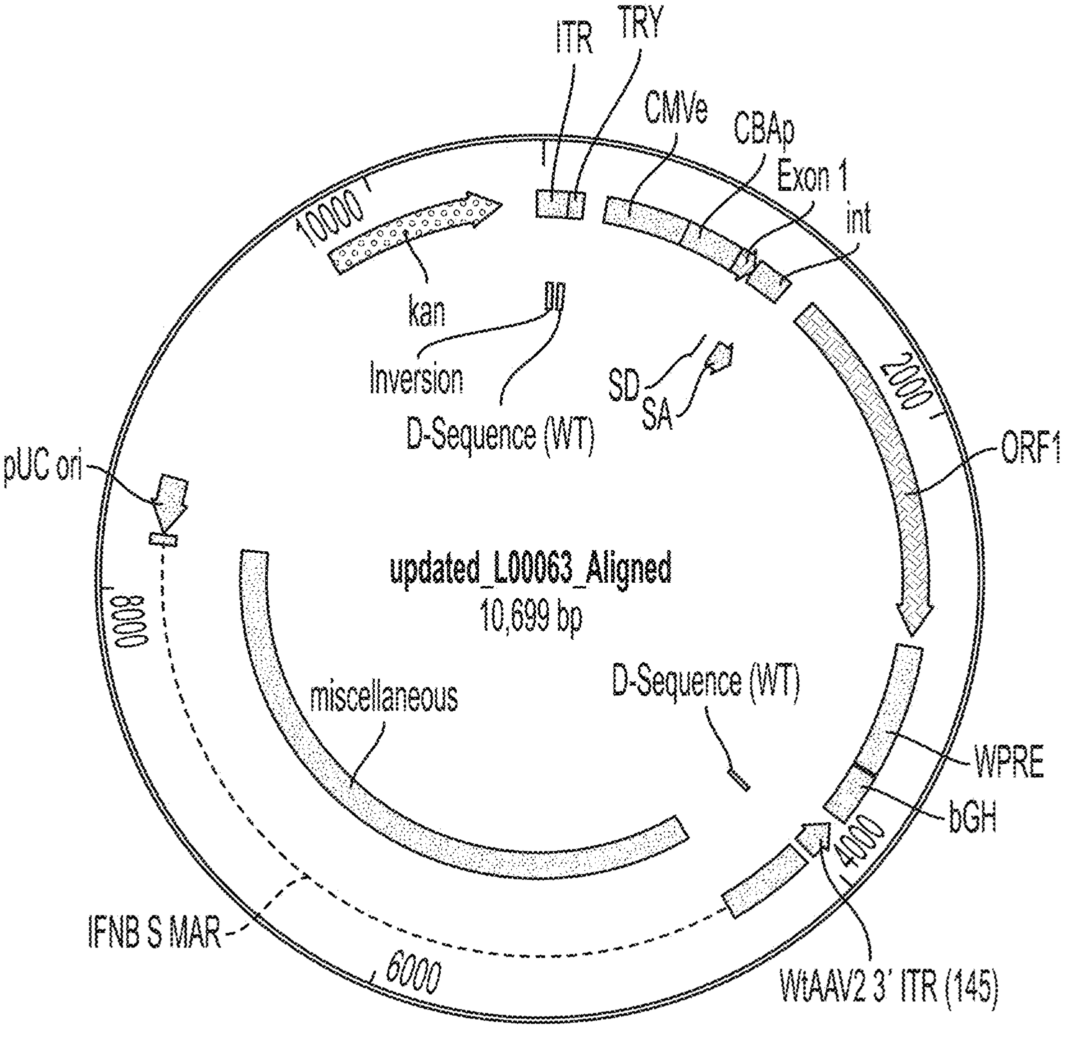
FIG. 49 is a schematic depicting one embodiment of a vector comprising an expression construct encoding Gcase (e.g., GBA1 or a portion thereof).
Figure 50:
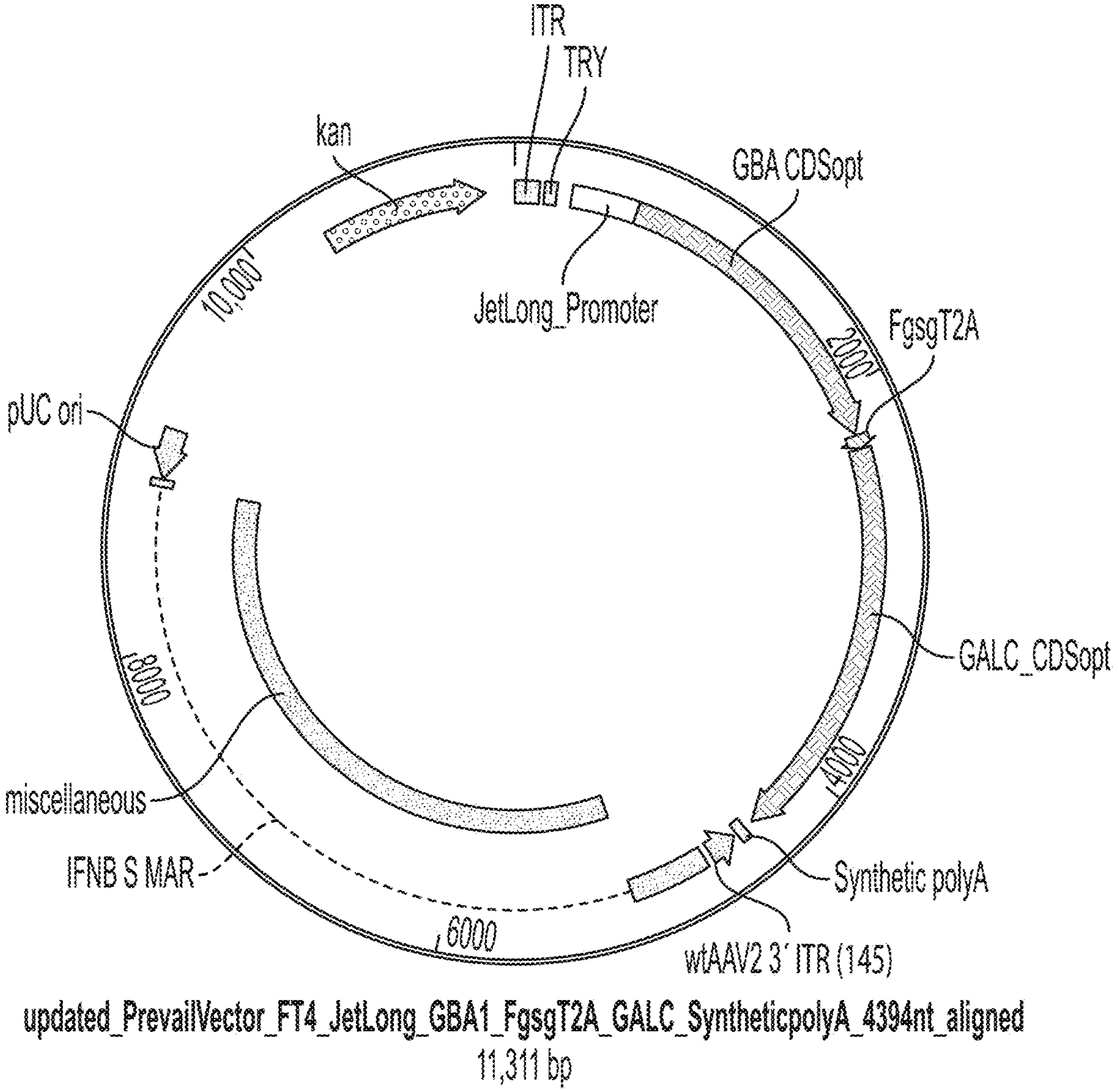
FIG. 50 is a schematic depicting one embodiment of a vector comprising an expression construct encoding Gcase (e.g., GBA1 or a portion thereof) and Galactosylceramidase (e.g., GALC or a portion thereof).
Figure 51:
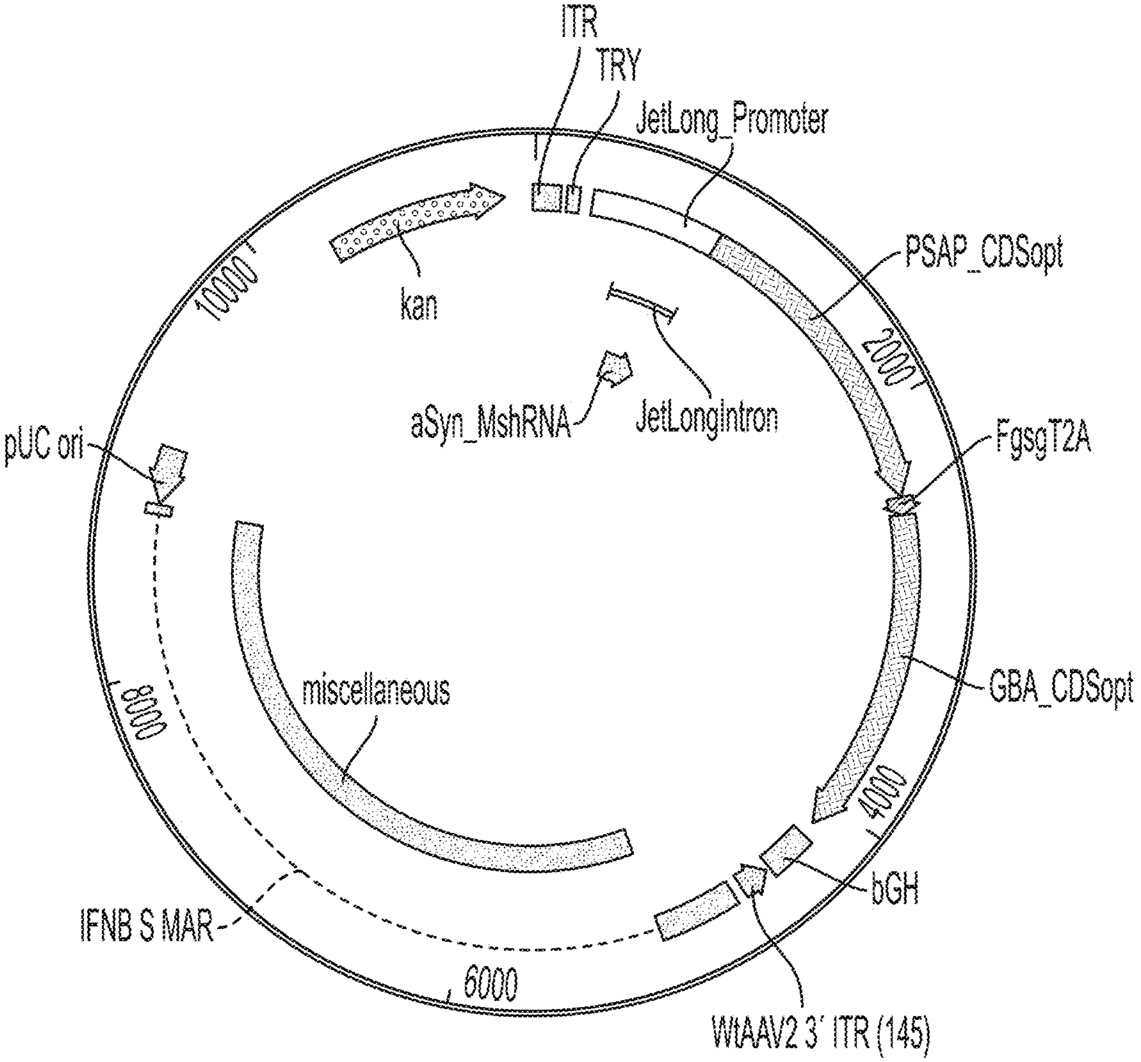
FIG. 51 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.

The effect of placement of ITR "D" sequence on cell transduction of rAAV vectors was investigated. HEK293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 20. Surprisingly, data indicate that rAAVs having the "D" sequence located in the "outside" position retain the ability to be packaged and transduce cells efficiently (FIG. 40).

Example 12: In Vitro Testing of Progranulin rAAVs

Figure 39:
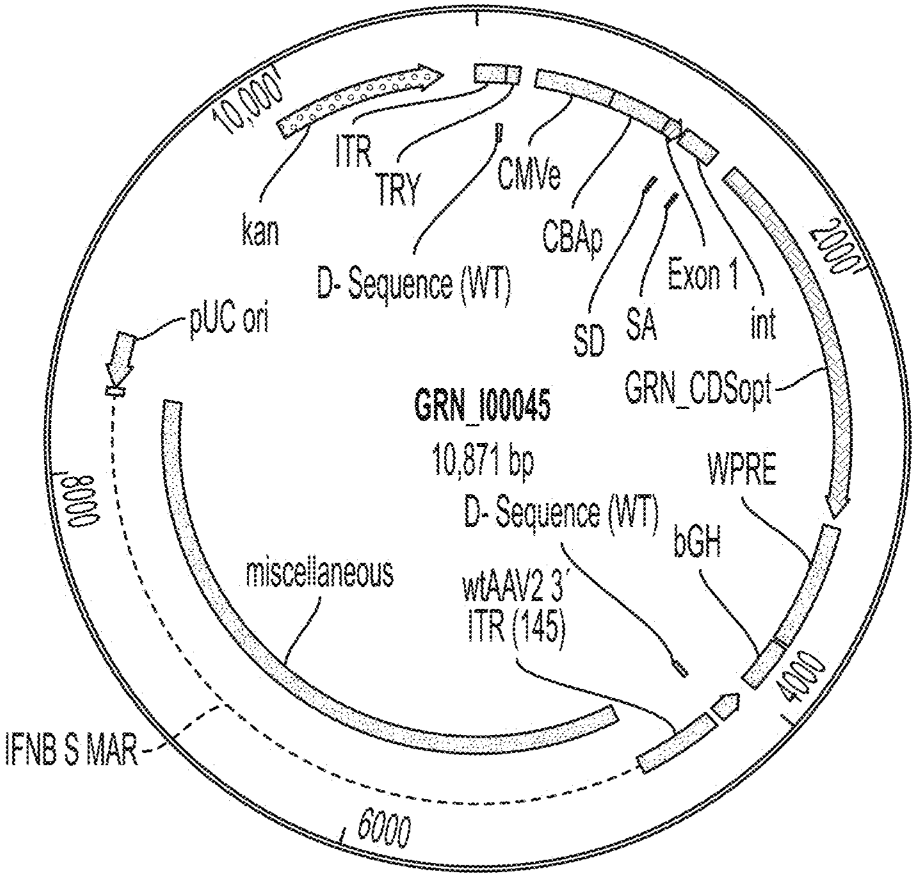
FIG. 39 is a schematic depicting one embodiment of a vector comprising an expression construct encoding PGRN.

FIG. 39 is a schematic depicting one embodiment of a vector comprising an expression construct encoding PGRN. Progranulin is overexpressed in the CNS of rodents deficient in GRN, either heterozygous or homozygous for GRN deletion, by injection of an rAAV vector encoding PGRN (e.g., codon-optimized PGRN), either by intraparenchymal or intrathecal injection such as into the cisterna magna.

Mice are injected at 2 months or 6 months of age, and aged to 6 months or 12 months and analyzed for one or more of the following: expression level of GRN at the RNA and protein levels, behavioral assays (e.g., improved movement), survival assays (e.g., improved survival), microglia and inflammatory markers, gliosis, neuronal loss, Lipofuscinosis, and/or Lysosomal marker accumulation rescue, such as LAMP1. Assays on PGRN-deficient mice are described, for example by Arrant et al. (2017) *Brain* 140: 1477-1465; Arrant et al. (2018) *J. Neuroscience* 38(9):2341-2358; and Amado et al. (2018) doi:https://doi.org/10.1101/30869; the entire contents of which are incorporated herein by reference.

Example 13: In Vitro and In Vivo Testing of Progranulin rAAV

In vitro and in vivo assays were performed to analyze the effects of an rAAV construct (PR006 (also referred to as PR006A); see FIG. 64) encoding progranulin (PGRN) protein. PR006 comprises a capsid having an AAV9 serotype.

In Vitro Nonclinical Studies

Progranulin Expression Derived from PR006A in HEK293T Cells

Figure 60:
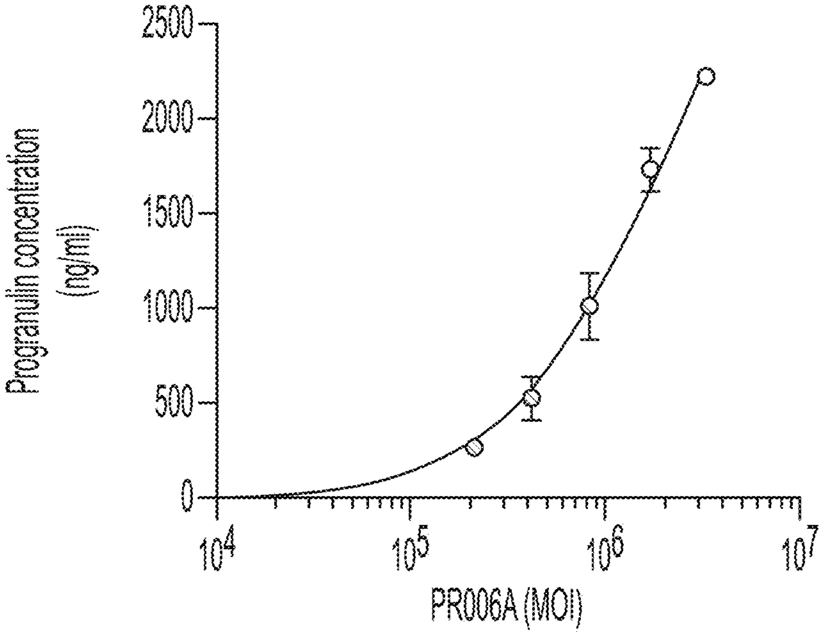
FIG. 60 is a graph depicting a dose-response curve of HEK293T cells transduced with PR006A (n=2; mean±SEM). An equal number of cells were transduced with varying amounts of PR006A. After 72 hours, progranulin protein levels in the cell media were measured using an ELISA assay.

The ability of PR006A to induce progranulin protein production in a cellular context was investigated. HEK293T cells were transduced with PR006A over a range of multiplicities of infection (MOI) ranging from $2.1\times10^5$ to $3.3\times10^6$ vector genomes (vg)/cell. PR006A transduction resulted in a robust, dose-dependent increase in progranulin protein expression and secretion into the cell media (FIG. 60). Substantially lower progranulin protein levels, reflecting the expression derived from the endogenous human GRN gene, were detected in a negative control group treated with excipient (the intended clinical vehicle) alone.

Efficacy in FTD-GRN iPSC-Derived Neurons

An assay was performed to analyze the efficacy of the rAAV construct in vitro in human FTD-GRN (Frontotemporal dementia with GRN mutation) neuronal cultures. Cell lines were obtained from the National Institute of Neurological Disorders and Stroke (NINDS) Human Cell and Data Repository (NHCDR): Materials ND50015 (FTD-GRN, M1L), ND50060 (FTD-GRN, R493X) and ND38555 (control, wild-type) (see Table 6).

TABLE 6

Summary of iPSC cell line characteristics

| Cell Line | NINDS Cell Line ID # | Clinical Diagnosis of FTD? | GRN mutation | Age | Gender | Source Cell/ Reprogramming Method |
|---|---|---|---|---|---|---|
| FTD-GRN #1 | ND50015 | Yes | MIL | 54 | F | Fibroblast/Episomal plasmids |
| FTD-GRN #2 | ND50060 | At risk (sibling affected at 62 yrs) | R493X | 60 | M | Fibroblast/Episomal plasmids |
| Control | ND38555 | No | N/A | 48 | F | Fibroblast/Retroviral plasmids |

To establish a cellular model that is pathologically relevant to FTD-GRN, iPSCs from each line were differentiated into neuronal cells using a two-step protocol. In the first step, iPSCs were differentiated into proliferating neuronal stem cell (NSC) lines, which lacked expression of pluripotency markers (i.e., Oct4 and SSEA1) and gained expression of neuronal stem cell markers (i.e., SOX2, Nestin, SOX1, and PAX6), as detected by immunofluorescence labeling.

Figure 52A:
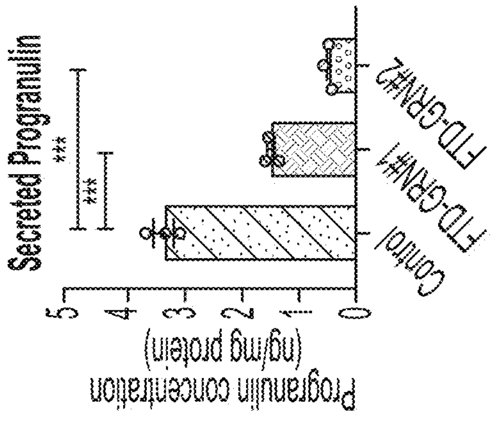
FIG. 52A shows that iPSC-derived neuronal stem cell (NSC) lines from patients with FTD-GRN mutations secreted less progranulin than NSC lines derived from healthy control subjects. Statistics were determined using an unpaired t-test; *=$p<0.05$, =$p<0.01$, *=$p<0.001$. Data is presented as mean±SEM.

Control and FTD-GRN NSC lines were seeded at an equal density, and 48 hours later, progranulin expression was measured by an enzyme-linked immunosorbent assay (ELISA) in cell lysates (intracellular progranulin) (FIG. 52E) and cell media (secreted progranulin) (FIG. 52A). Progranulin expression was normalized to total protein concentration to account for differences in cell number (n=3; mean±SEM). The NSC lines with heterozygous GRN mutations had significantly lower intracellular and secreted progranulin levels compared to Control NSCs, with FTD-GRN NSCs expressing ~25-50% of endogenous progranulin levels. This suggested that this FTD-GRN cell model recapitulates the clinical progranulin deficiency observed in FTD-GRN patients, who express one third to one half of normal progranulin levels in the plasma (Finch et al., *Brain* 132, 583-591 (2009); Ghidoni et al., *Neurology* 71, 1235-1239, (2008); Sleegers et al., *Ann Neurol* 65, 603-609 (2009)).

Figure 52B:
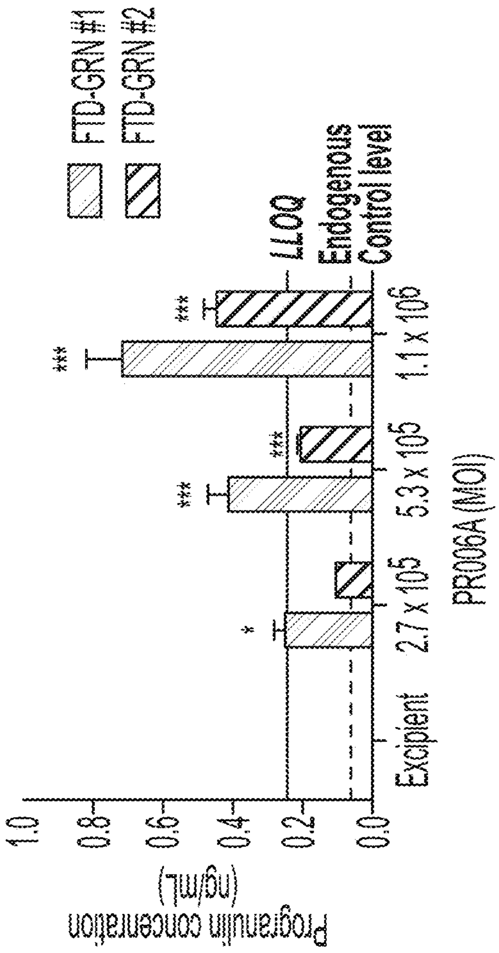
FIG. 52B shows results from dose-ranging PR006A transduction in FTD-GRN mutation carrier neuronal cultures. NSCs were seeded at an equal density and differentiated into neurons. On day 7, neurons were transduced with excipient or the indicated amounts of PR006A for 72 hours. Secreted progranulin expression was measured from the cell media by ELISA and normalized to volume (n=3-4; mean±SEM). Black dashed line represents endogenous levels of secreted progranulin from Control neurons (excipient-treated). Secreted progranulin was not detectable in excipient-treated FTD-GRN neurons. Statistics were determined using ANOVA followed by Tukey HSD and statistical comparison of each condition to excipient-treated Control neurons is indicated on the graph, *=$p<0.05$, ***=$p<0.001$. LLOQ=lower limit of quantitation; MOI=multiplicity of infection.
Figure 52C:
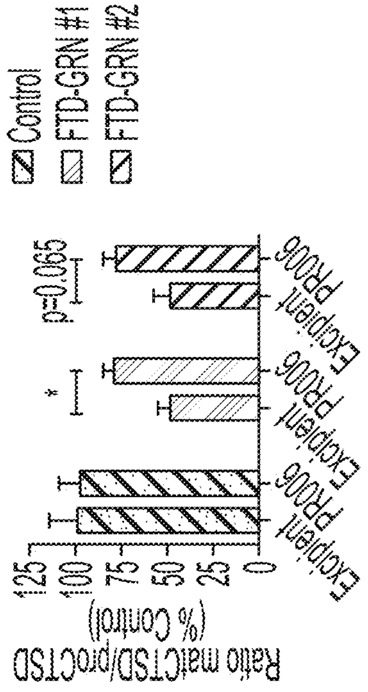
FIG. 52C shows that PR006 treatment of neuronal cultures rescued the defective maturation of a key lysosomal protease, cathepsin D, in FTD-GRN neuronal cultures. NSCs were seeded at equal concentrations and differentiated into neurons. On day 7, neurons were transduced with excipient or PR006A at an MOI of $5.3\times10^5$ for 72 hours. Neurons were lysed, and lysates were analyzed on the Protein Simple Western Jess system with an anti-cathepsin D (CTSD) primary antibody. Bands corresponding to both the mature cathepsin D (matCTSD) and pro-cathepsin D (proCTSD) were detected, and the area under the curve was quantified for each band and normalized to an internal total protein normalization signal. The matCTSD/proCTSD ratio in excipient or PR006A treated FTD-GRN neurons was determined; the y-axis depicts the matCTSD/proCTSD ratio as a percent of the ratio of excipient-treated Control neurons (n=3; mean±SEM). Statistics were determined using a paired t-test, *=$p<0.05$.
Figure 52D:
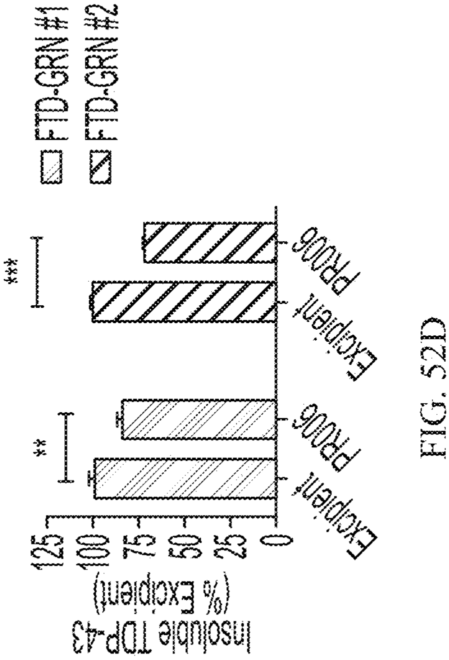
FIG. 52D and FIG. 52F show that PR006A reduces TDP-43 pathology in FTD-GRN neuronal cultures. NSCs were seeded at equal concentrations and differentiated into neurons. On day 7, neurons were transduced with excipient or PR006A at an MOI of $5.3\times10^5$ and collected 21 days after transduction.
Figure 52F:
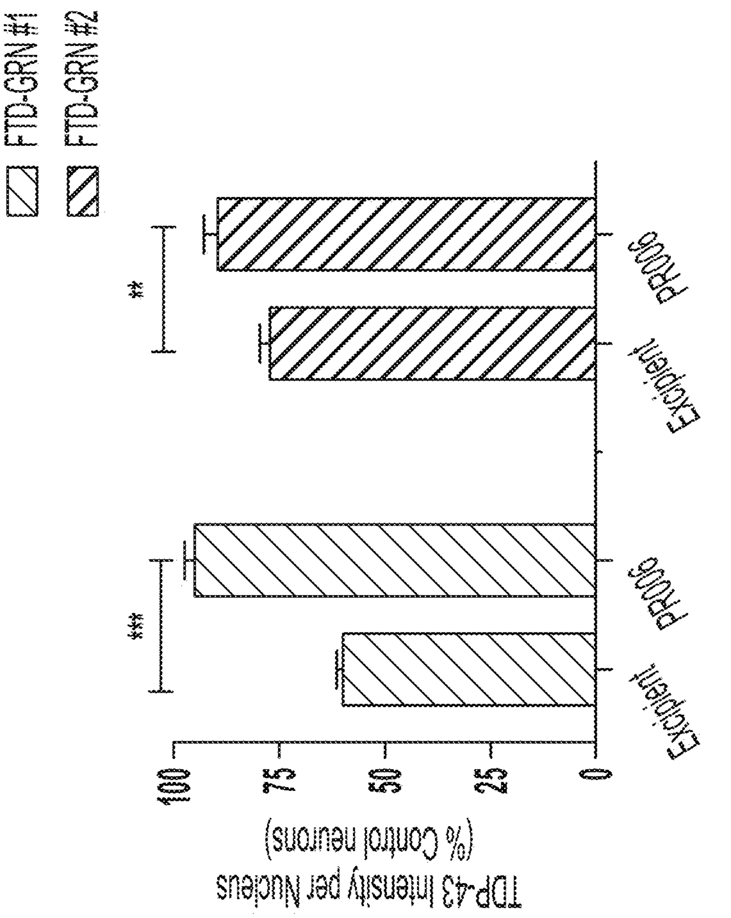
Figure 52E:
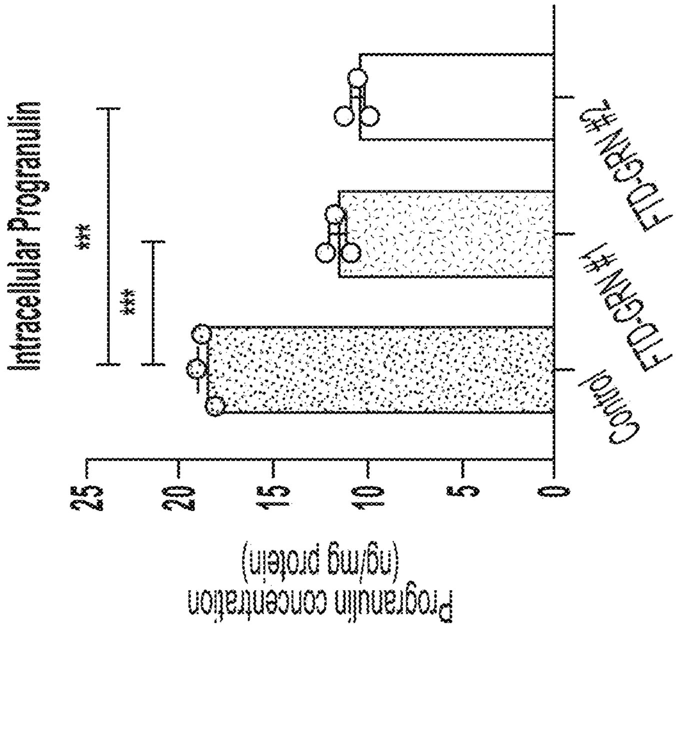
FIG. 52E shows that iPSC-derived NSC lines from patients with FTD-GRN mutations expressed less progranulin than NSC lines derived from healthy control subjects. Statistics were determined using an unpaired t-test; *=p<0.05, =p<0.01, *=p<0.001. Data is presented as mean±SEM.
Figure 52G:
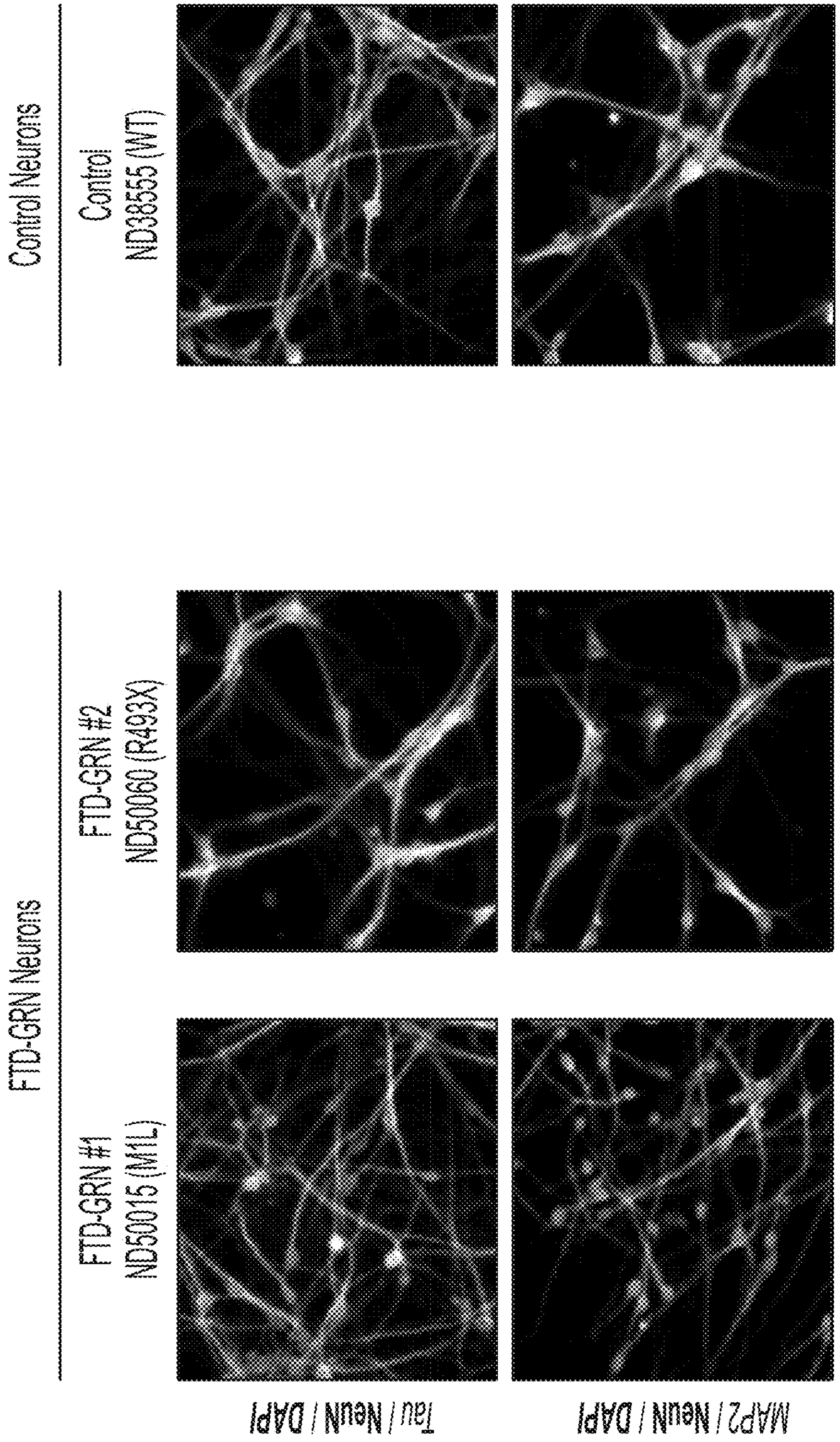
FIG. 52G is a series of images showing that neuronal stem cell (NSC) lines from human FTD-GRN and human control cell lines were successfully differentiated into neuronal cultures. Control and FTD-GRN NSC lines (FTD-GRN #1 and FTD-GRN #2) were differentiated into neurons after a period of 7 days, as indicated by cell morphology and immunofluorescence staining for neuronal markers (NeuN [red]; MAP2 or Tau as labeled at left [green]). DAPI (blue) was used to stain the nucleus.

NSCs from all cell lines were differentiated into neuronal cultures. After establishing that the iPSC-derived NSCs exhibit reduced progranulin expression, the lines were differentiated into neurons to generate a clinically representative cell type for nonclinical efficacy studies of PR006A. NSCs were seeded into neuronal differentiation media, terminally differentiated into postmitotic neurons for a period of 7 days, and then assessed for expression of neuronal markers (i.e., MAP2, NeuN, Tau, Tuj 1, NF—H) by immunofluorescence (FIG. 52G). Both Control and FTD-GRN iPSC-derived NSC lines efficiently differentiated into neurons using this protocol.

FTD-GRN iPSC-derived neuronal cultures were used to evaluate the efficacy of PR006A in vitro. FTD-GRN neurons were treated with excipient or PR006A at MOIs of $2.7\times10^{5}$, $5.3\times10^{5}$, or $1.1\times10^{6}$ vg/cell. PR006 transduction resulted in a robust, dose-dependent expression of secreted progranulin, as measured by ELISA, in all cell lines (FIG. 52B). Excipient-treated Control and FTD-GRN neurons were assessed for endogenous progranulin levels. Control neurons expressed endogenous secreted progranulin, while no secreted progranulin was detected in FTD-GRN neurons (FIG. 52B). Linear regression analysis confirmed a significant correlation between PR006A dose and progranulin levels across both FTD-GRN cell lines ($p=3.5\times10^{13}$). These results demonstrate that treatment with PR006A results in elevated secretion of progranulin in the FTD-GRN neuronal model.

Progranulin is known to stimulate maturation of the lysosomal protease cathepsin D (CTSD), whose loss of function has also been implicated in lysosomal storage disorders and neurodegeneration. CTSD is expressed as an inactive full-length pro-protein (proCTSD) that undergoes proteolytic processing into an enzymatically active mature protease (matCTSD). Progranulin has been reported to act as a molecular chaperone that binds to proCTSD to enhance its maturation into the matCTSD protease. In FTD-GRN neuronal cultures, PR006 transduction rescued the defective maturation of cathepsin D (FIG. 52C). Control, FTD-GRN #1, and FTD-GRN #2 neurons were transduced with PR006A or excipient. An MOI of $5.3\times10^{5}$ PR006A was used for efficacy experiments since it restored progranulin levels to at least 2-fold those of Control cells (FIG. 52B). To evaluate efficacy, proCTSD and matCTSD expression levels were measured in cell lysates using the automated a Simple Western™ (Jess) platform (FIG. 52C). Excipient-treated FTD-GRN neurons had a lower ratio of matCTSD to proCTSD as compared to excipient-treated Control neurons; PR006A treatment significantly increased the ratio in both FTD-GRN neuronal lines (FIG. 52C). In Control neurons, the ratio of matCTSD to proCTSD was not significantly altered by PR006A treatment. These findings demonstrate that PR006A restores a lysosomal function-related phenotype in FTD-GRN neurons.

In normal neurons, TDP-43 (transactive response DNA binding protein 43 kDa) protein is localized in the nucleus. In post-mortem brains of FTD-GRN patients, aggregation of TDP-43 in the cytoplasm of neurons is observed, and nuclear accumulation of TDP-43 is reduced. FTD neurons have decreased nuclear TDP-43, leading to aggregation and downstream toxicity in neurons. Since Grn KO mice do not fully recapitulate this TDP-43 pathology, induced pluripotent stem cell (iPSC)-derived neurons are a valuable FTD-GRN model to study TDP-43 biology. Decreased accumulation of TDP-43 in the nucleus, and increased accumulation of insoluble TDP-43, have been reported in iPSC-derived neurons from patients with FTD-GRN, relative to control neurons that do not carry a GRN mutation, as described by Valdez et al. (*Human Molecular Genetics* 26, 4861-4872 (2017)). PR006A transduction of neuronal cultures from both FTD-GRN mutation carrier lines reversed TDP-43 abnormalities, resulting in decreased insoluble TDP-43 (measured using the Simple Western™ (Jess) platform (FIG. 52D)) and increased nuclear localization of TDP-43 (measured using immunofluorescence (FIG. 52F)).

To summarize, PR006 transduction restored defective maturation in the lysosomal enzyme, cathepsin D, and improved abnormal TDP-43 pathology in FTD-GRN neurons.

In Vivo Nonclinical Studies

Efficacy and Biodistribution in Aged Grn Knockout Mice

PR006A efficacy in vivo and the maximal dose PR006A were evaluated in the Grn knockout (KO) mouse model. In the Grn KO mouse model used in these studies (B6(Cg)-$Grn^{tm1.1Aidi}$/J (Jackson Laboratory, Bar Harbor, ME), exons 1-4 are deleted from the target progranulin (Grn) gene (Yin et al., *J Exp Med* 207, 117-128 (2010)). These animals have a complete loss of progranulin, display age-dependent phenotypes including lysosomal alterations, neuronal lipofuscin accumulation, ubiquitin accumulation, microgliosis, and neuroinflammation, and are therefore widely used to model FTD-GRN. All attempts were made to eliminate bias from the study; mice were assigned to treatment groups that were balanced for gender and body weight, and a blinded assessment of experimental endpoints was conducted by qualified personnel.

In the initial studies, PR006A was delivered to aged Grn KO mice at a dose of $9.7\times10^{10}$ vg ($2.4\times10^{11}$ vg/g brain), which was the highest achievable dose at the time of the study due to injection volume constraints and the physical titer of the virus lot used for the study. Aged mice were used since many of the FTD-GRN-related phenotypes, including CNS inflammation and microgliosis, develop in an age dependent manner, with the most pronounced manifestation of phenotypes occurring between 12-24 months of age.

Figure 61:
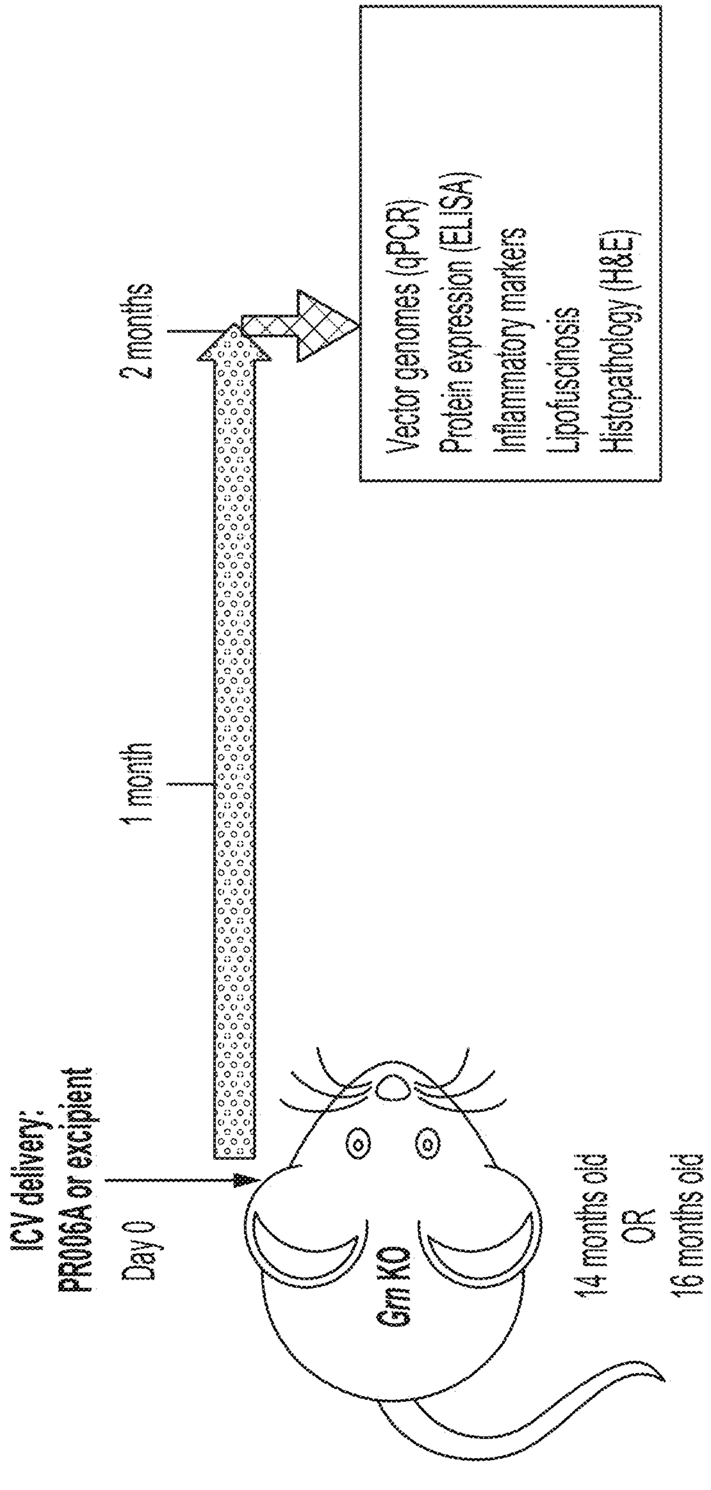
FIG. 61 is a diagram of a study design for maximal dose PR006A in an aged FTD-GRN mouse model. 10 μl excipient (control) or PR006A at a dose of $9.7\times10^{10}$ vg ($2.4\times10^{11}$ vg/g brain) was delivered by ICV injection to two cohorts of Grn KO mice: (1) 16 months old at time of injection (n=4-5/group; PRV-2018-027) and (2) 14 months old at time of injection (n=1/excipient-treated group; n=3/PR006A-treated group; PRV-2019-002). The animals were sacrificed two months post-injection. CNS and peripheral tissues were collected to analyze PR006A biodistribution (qPCR), progranulin protein expression (ELISA), and histopathology (H&E). Expression of proinflammatory markers, lipofuscin accumulation, and ubiquitin accumulation were assessed in the brain.

In the studies with aged Grn KO mice, PR006A was administered by single intracerebroventricular (ICV) injection. 10 μl excipient (the intended clinical vehicle; 20 mM Tris pH 8.0, 200 mM NaCl, and 1 mM $MgCl_2$+0.001% Pluronic F68) or $9.7\times10^{10}$ vg PR006A ($2.4\times10^{11}$ vg/g brain [based on an adult mouse brain weight of 400 mg]) was delivered by ICV injection into two cohorts of aged Grn KO mice: (1) 16-months-old at time of injection (n=4/group; PRV-2018-027; FIG. 61) and (2) 14-months-old at time of injection (planned n=3/group; PRV-2019-002; FIG. 61). The animals were sacrificed two months post-injection.

In study PRV-2018-027, a single dose of PR006A was delivered to 16-month-old mice with the following treatment groups:

| Model | ICV | ICV dose | N |
|---|---|---|---|
| Grn KO | Excipient | N/A | 4 (2 M/2 F) |
| Grn KO | PR006A | $9.7\times10^{10}$ vg ($2.4\times10^{11}$ vg/g brain) | 5 (3 M/2 F) |

Due to unforeseen study deviations (errors in genotyping and premature loss of animals), study PRV-2019-002 (14-month-old cohort) enrolled only 1 mouse in the excipient-treated group instead of the planned n=3. The low sample number made statistical analysis impossible, and therefore this study is excluded from further discussion here. However, the findings from the study were comparable to those from study PRV-2018-027.

Figure 59A:
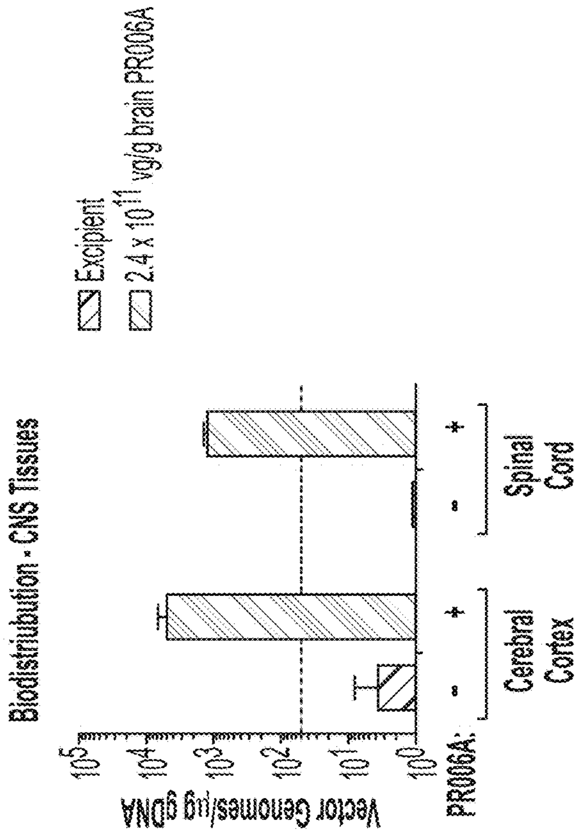
FIG. 59A-FIG. 59C are a series of bar graphs depicting the results of experiments analyzing biodistribution and progranulin expression in the CNS in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue).
Figure 59B:
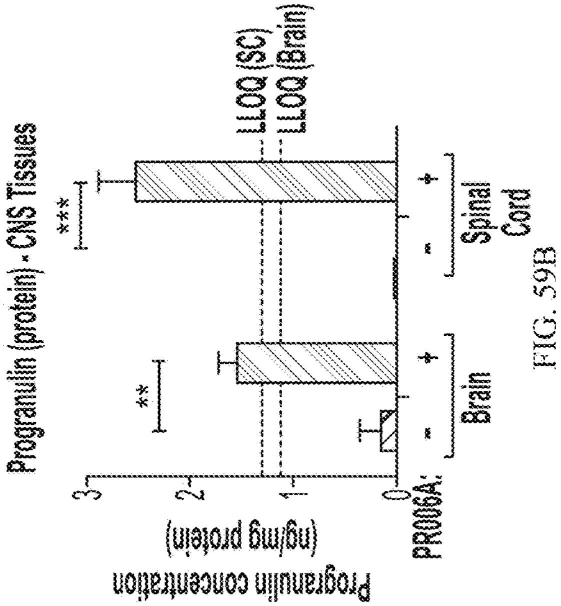
Figure 59C:
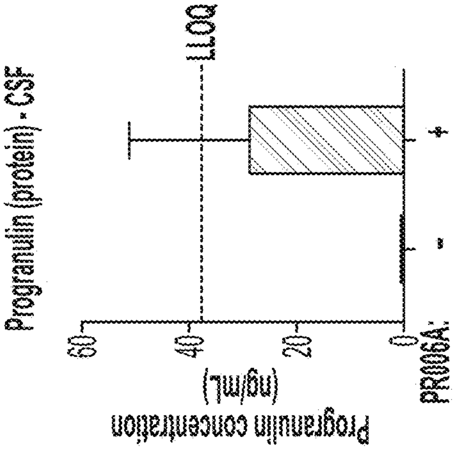

Biodistribution and Progranulin Expression: Biodistribution was determined by measuring vector genome presence using a qPCR assay that meets the current U.S. Food and Drug Administration Center for Biologics Evaluation and Research (CBER)/Office of Tissues and Advanced Therapies (OTAT) standards for PCR sensitivity (with >50 vector genomes per 1 μg genomic DNA defined as positive). All mice that received PR006A were positive for vector genomes in the cerebral cortex and spinal cord, indicating that ICV administration successfully results in PR006A transduction in the brain and CNS (FIG. 59A). ICV PR006A resulted in significant levels of human progranulin protein in the CNS (brain, spinal cord) of the Grn KO mice, whereas, as expected, human progranulin was not detectable in the mice that received excipient (FIG. 59B). Since progranulin is primarily a secreted protein, expression in the CSF can be considered a surrogate of protein production within the brain and represents a potential translational endpoint for FTD-GRN patients who have decreased CSF progranulin levels. We were able to detect human progranulin in the CSF of PR006A-treated mice, but because of the small sample volume and the technical limitations of obtaining sufficient volume of CSF in mice, the measurements of CSF progranulin level were below the lower limit of quantitation (LLOQ) of the assay (FIG. 59C).

Figure 62B:
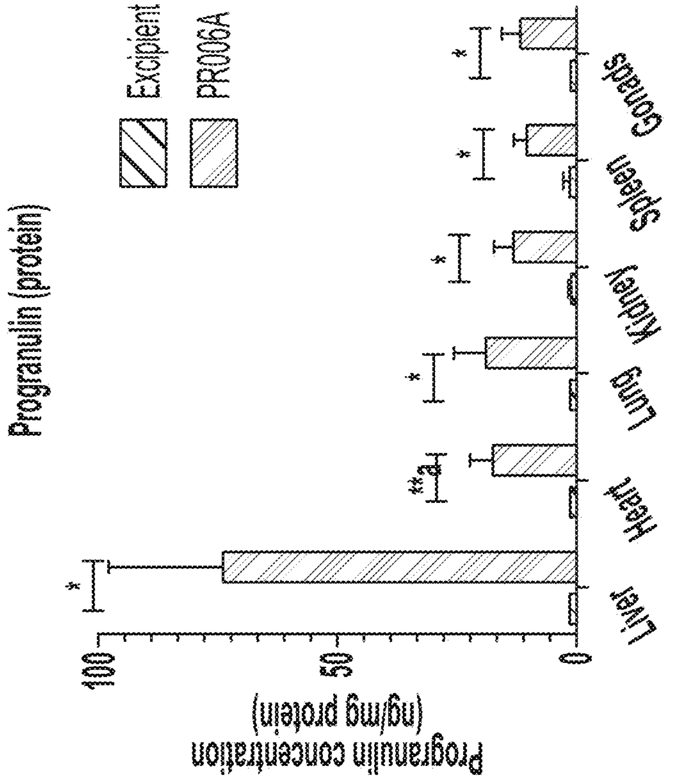
FIG. 62A-FIG. 62B are bar graphs showing results for peripheral tissue biodistribution and progranulin expression in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue).
Figure 62A:
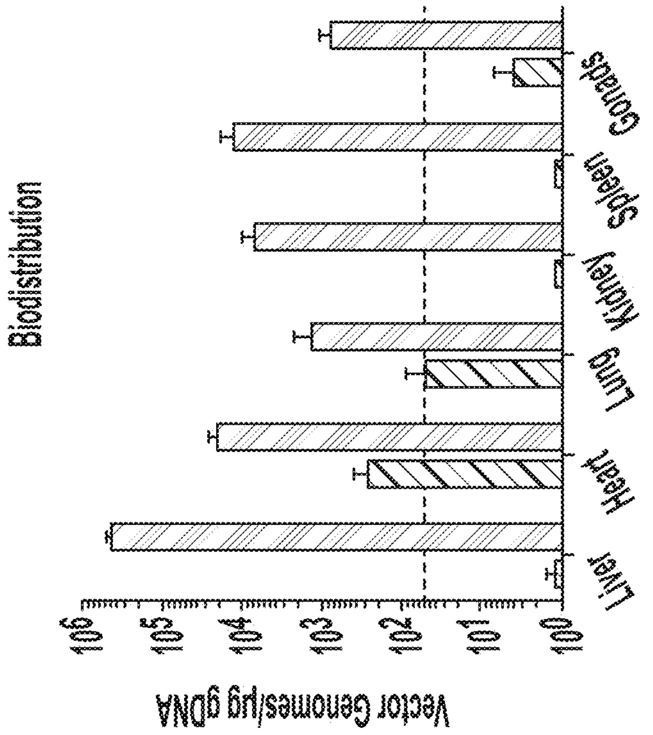

ICV administration also resulted in broad vector genome presence and progranulin protein levels in peripheral tissues, including liver, heart, lung, kidney, spleen, and gonads (FIG. 62A-FIG. 62B). In addition, significant levels of human progranulin were detectable in plasma of the PR006A-treated Grn KO mice. As expected, human progranulin was not detected in the excipient treated Grn KO mice.

Figure 59D:
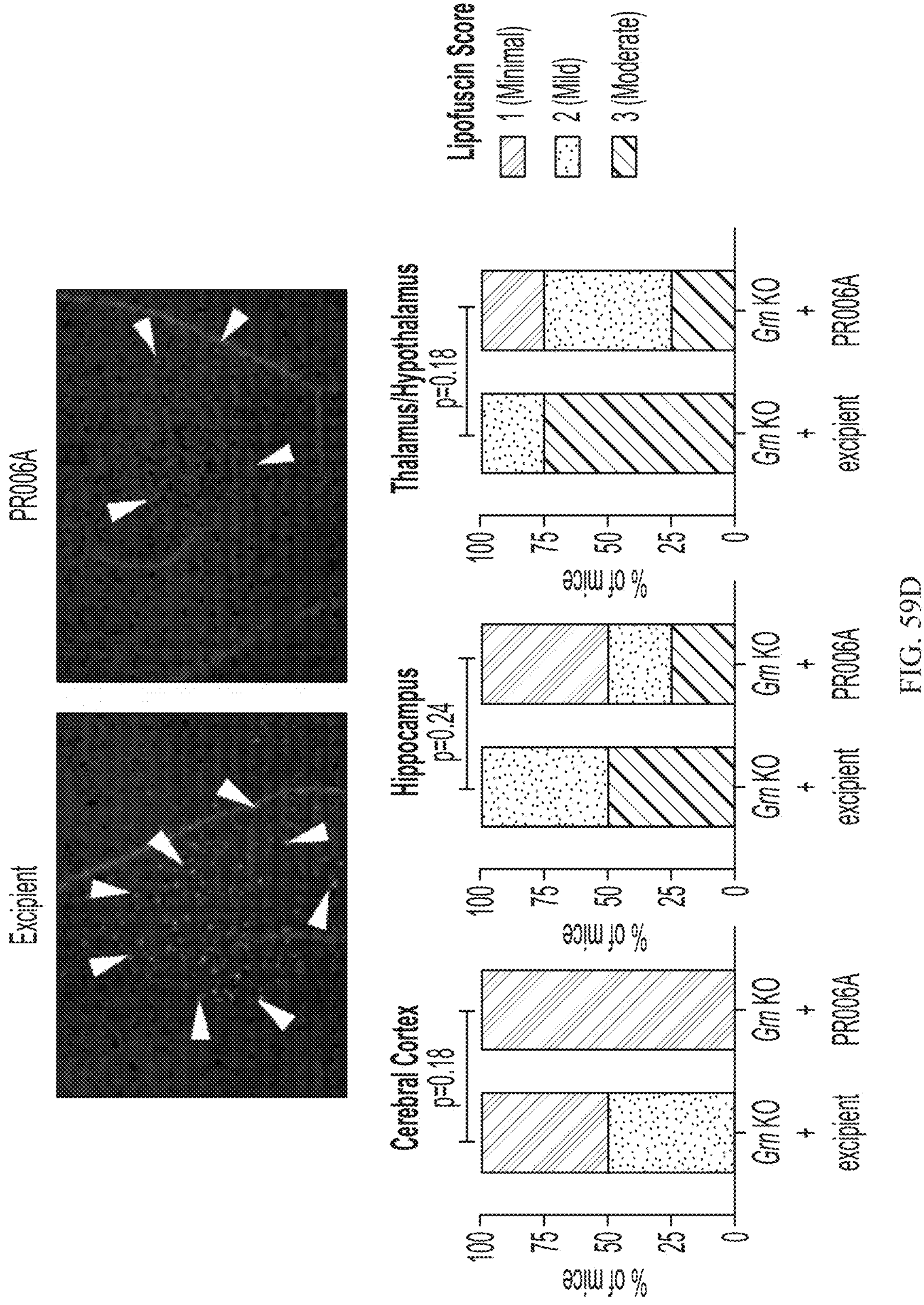
FIG. 59D-FIG. 59E are a series of bar graphs and images depicting the results of experiments showing reduced lysosomal and neuropathology defects in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue). Lipofuscinosis was analyzed by scoring of H&E-stained brain sections by a pathologist.
Figure 59G:
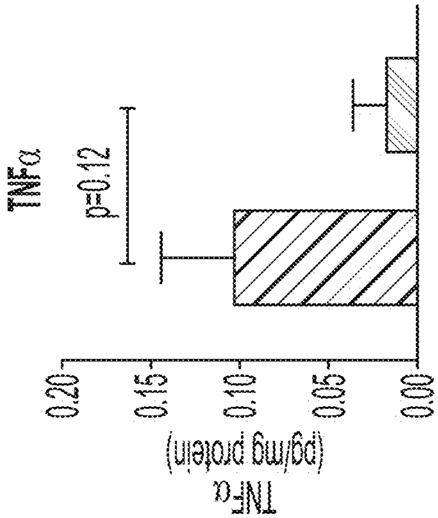
FIG. 59F-FIG. 59I are a series of bar graphs depicting the results of experiments showing decreased neuroinflammation markers in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue).
Figure 59F:
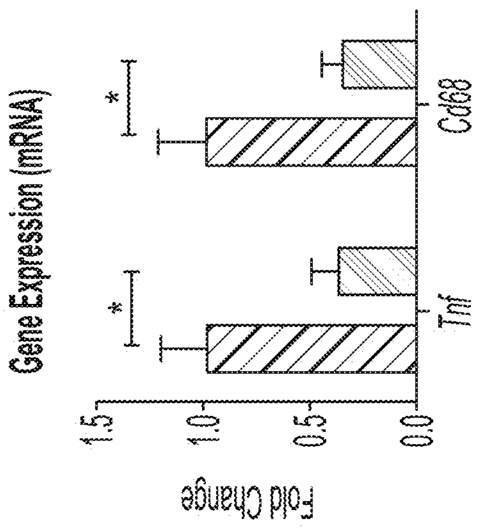
Figure 59E:
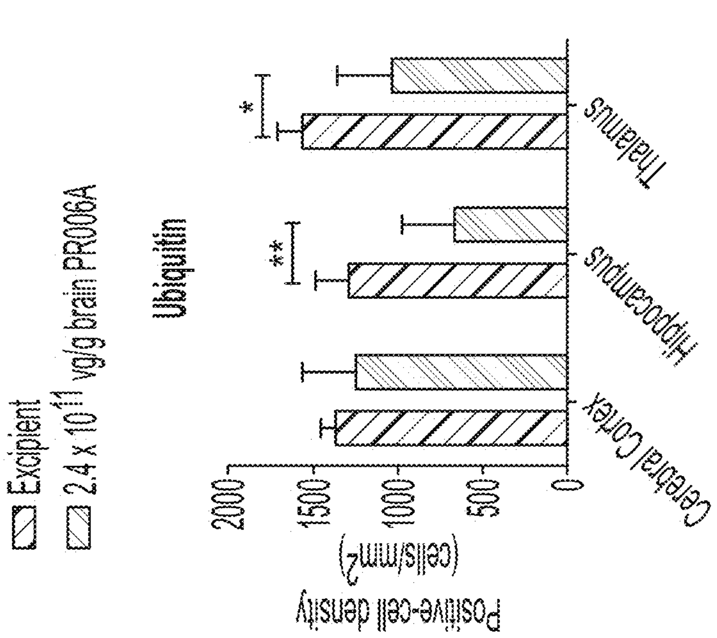

Lipofuscin Accumulation: Accumulation of neuronal lipofuscin, an electron-dense, autofluorescent material that accumulates progressively over time in lysosomes of post-mitotic cells and is an indicator of lysosomal dysfunction, is a hallmark age-dependent phenotype of Grn KO mice. Lipofuscin accumulation was assessed using two independent methods in adjacent brain sections: (1) in a more clinical approach, lipofuscin accumulation in the brain was scored by a blinded pathologist on a scale of 0 (no lipofuscin observed) to 4 (widespread lipofuscin accumulation) and (2) in a more quantitative approach, lipofuscin autofluorescence was detected by immunohistochemistry (IHC) and automatically quantified. Grn KO mice exhibited substantial lipofuscinosis throughout the brain, and ICV PR006A treatment reduced the lipofuscin score severity in the cerebral cortex, hippocampus, and thalamus (FIG. 59D). Quantitation of lipofuscin accumulation from IHC images also detected decreased lipofuscinosis with PR006A treatment in all three brain regions. Since ubiquitin-positive inclusions are a defining pathological feature of FTD-GRN patients that also accumulate in the Grn KO mouse model in an age-dependent manner, IHC was performed and quantified in the brain regions of interest (cerebral cortex, hippocampus, thalamus) to assess ubiquitin accumulation. PR006A treatment significantly reduced ubiquitin accumulation in Grn KO mice (FIG. 59E). These findings suggest that PR006A improves lysosomal dysfunction in the Grn KO mouse model of FTD-GRN.

Figure 59H:
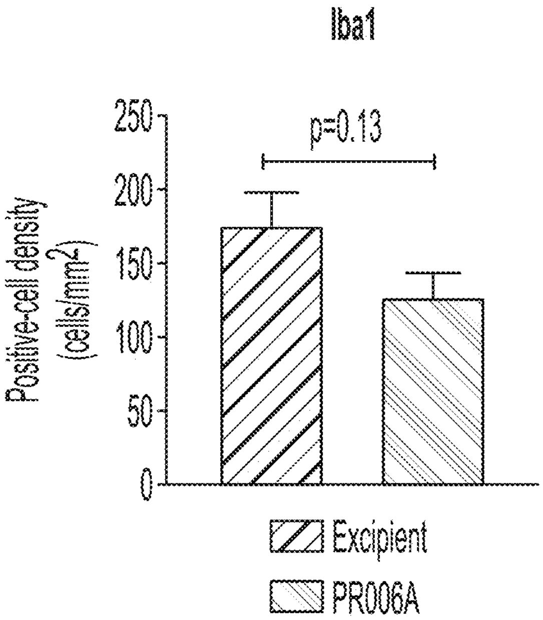
Figure 59I:
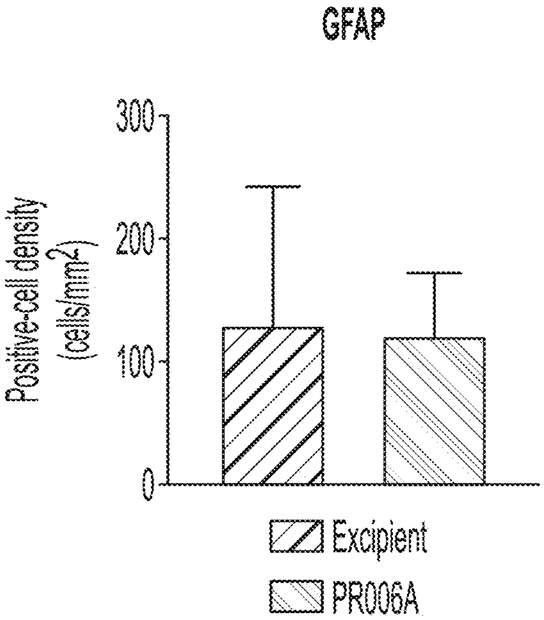

Neuroinflammation: Chronic CNS inflammation is a pathological feature in the brain of patients with FTD-GRN that is recapitulated in Grn KO mice in an age-dependent manner. Progranulin has anti-inflammatory effects in mouse models of FTD-GRN, and loss of progranulin leads to upregulation of proinflammatory cytokines, including TNFα. In this study, treatment with PR006A suppressed inflammatory marker levels in aged Grn KO mice. ICV PR006A decreased gene expression of the proinflammatory cytokine Tnf (TNFα) and Cd68 (CD68), a marker of microglia, in the cerebral cortex (FIG. 59F). TNFα protein levels were also decreased in cerebral cortex samples from PR006A-treated Grn KO mice using the Mesoscale Discovery mouse pro-inflammatory cytokine assay (FIG. 59G). To further evaluate neuroinflammation, immunohistochemistry (IHC) was performed for Iba1, a marker of microgliosis, and GFAP, a marker of astrocytosis, and quantified in the brain regions of interest (cerebral cortex, hippocampus, thalamus). PR006A treatment resulted in a trend towards decreased microgliosis (Iba1) but did not affect astrocytosis (GFAP) in Grn KO mice (FIG. 59H; FIG. 59I). Taken together, these results indicate that PR006A treatment reduces neuroinflammation in the aged Grn KO mouse model of FTD-GRN.

Histopathology: thorough histopathological analysis by a blinded board-certified pathologist of hematoxylin and eosin (H&E) staining of the brain, thoracic spinal cord, liver, heart, spleen, lung, and kidney of all mice from these studies revealed no adverse events related to PR006A treatment. Administration of PR006A to Grn KO mice resulted in a decreased incidence and/or severity of findings that are characteristic of the model, including a reduction in frequency and/or severity scores of neuronal necrosis in the medulla and pons. Additionally, there was a reduction in both the incidence and severity of axonal degeneration in the thoracic spinal cord with PR006A treatment. These findings are discussed in detail in the Toxicology section below.

Conclusion: ICV PR006A at a dose of $9.7\times10^{10}$ vg ($2.4\times10^{11}$ vg/g brain) resulted in broad vector genome presence throughout the brain and peripheral tissues in aged Grn KO mice. PR006A treatment increased global progranulin expression. In addition, PR006A reduced accumulation of lipofuscin and ubiquitin in the brain, pathologies known to occur in both the Grn KO mouse model and patients with FTD-GRN. PR006A also reduced the expression of proinflammatory cytokines and immune cell activation in the cerebral cortex, phenotypes that are indicative of chronic CNS inflammation.

Dose-Ranging Efficacy in Adult Grn Knockout Mice

Figure 63:
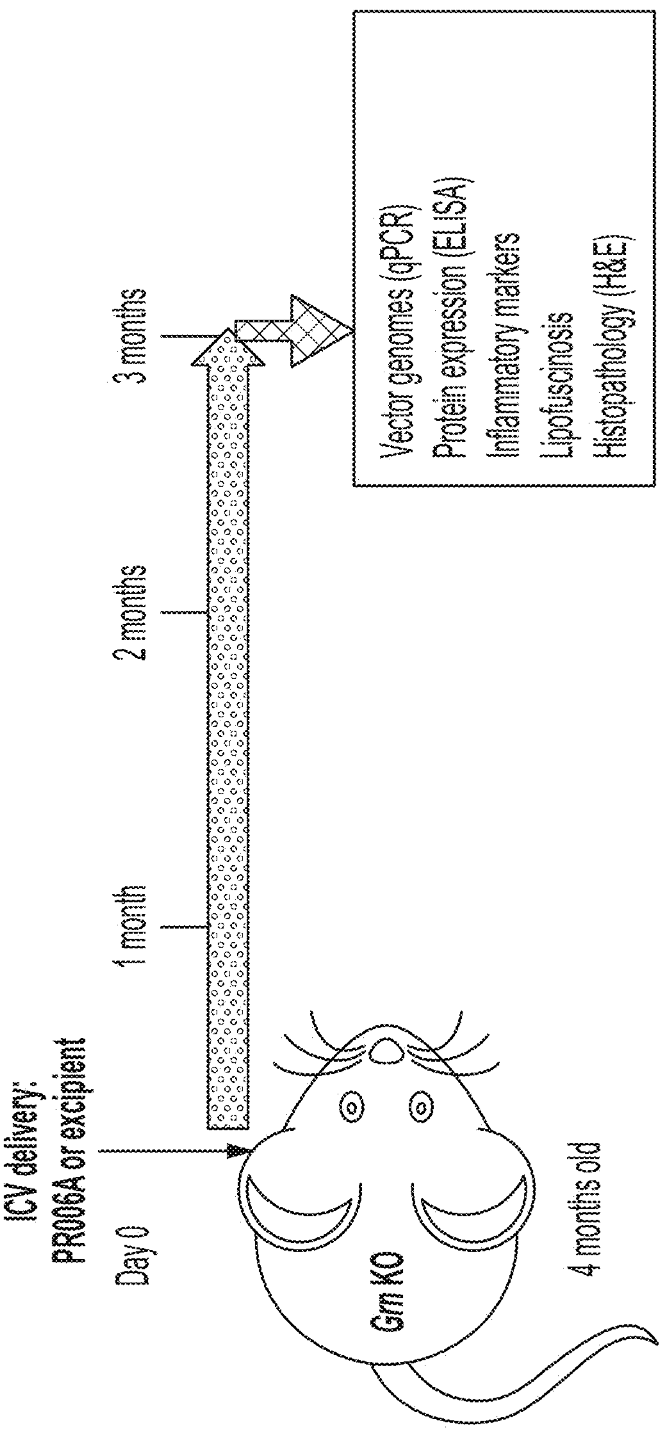
FIG. 63 is a diagram of a study design for dose-ranging PR006A in an adult FTD-GRN mouse model 10 μl excipient (control) or PR006A at dose of $1.1\times10^{9}$ vg ($2.7\times10^{9}$ vg/g brain), $1.1\times10^{10}$ vg ($2.7\times10^{10}$ vg/g brain), or $1.1\times10^{11}$ vg ($2.7\times10^{11}$ vg/g brain) PR006A was delivered by ICV injection into 4-month-old Grn KO mice (n=10/group). The animals were sacrificed three months post-injection, when the mice were 7 months old. CNS and peripheral tissues were collected to analyze PR006A biodistribution (qPCR), progranulin protein expression (ELISA), and histopathology (H&E). Expression of proinflammatory markers, lipofuscin accumulation, ubiquitin accumulation, and global gene expression changes were assessed in the brain.

To further assess efficacious doses of PR006A, a larger, dose-ranging study in adult Grn KO mice was performed. In PRV-2019-004, 10 μl excipient (the intended clinical vehicle; 20 mM Tris pH 8.0, 200 mM NaCl, and 1 mM $MgCl_2$+0.001% Pluronic F68) or PR006A was delivered via ICV to 4-month-old animals. These adult mice were used instead of the aged Grn KO mice because the latter were not available in sufficient numbers for conducting a dose-ranging study. While the adult Grn KO mice have a milder phenotype than aged mice, they still exhibit lysosomal defects and neuroinflammatory changes and therefore are suitable for evaluating the efficacious dose range of PR006A. In order to assess PR006A efficacy over a broad range of viral doses, PR006A was administered at $1.1\times10^{11}$ vg ($2.7\times10^{11}$ vg/g brain), the highest achievable dose at the time of the study due to injection volume constraints and the physical titer of the virus lot used for the study, a middle dose of $1.1\times10^{10}$ vg ($2.7\times10^{10}$ vg/g brain), or a low dose of $1.1\times10^{9}$ vg ($2.7\times10^{9}$ vg/g brain), with a full log difference spanning each dose. The details of the experimental design are given in FIG. 63.

Three doses of PR006A were assessed, with 10 mice (4M/6F) per group:

| Model | ICV | ICV dose | N |
|---|---|---|---|
| Grn KO | Excipient | N/A | 10 (4 M/6 F) |
| Grn KO | PR006A | $1.1\times10^{9}$ vg ($2.7\times10^{9}$ vg/g brain) | 10 (4 M/6 F) |
| Grn KO | PR006A | $1.1\times10^{10}$ vg ($2.7\times10^{10}$ vg/g brain) | 10 (4 M/6 F) |
| Grn KO | PR006A | $1.1\times10^{11}$ vg ($2.7\times10^{11}$ vg/g brain) | 10 (4 M/6 F) |

Age-matched mice of the same background strain as the Grn KO mice with wildtype (WT) Grn alleles (7-month old C57BL/6J) served as controls for select efficacy endpoints in this study.

| Model | ICV | ICV dose | N |
|---|---|---|---|
| WT (C57BL/6J) | N/A | N/A | 10 (5 M/5 F) |

Figure 53A:
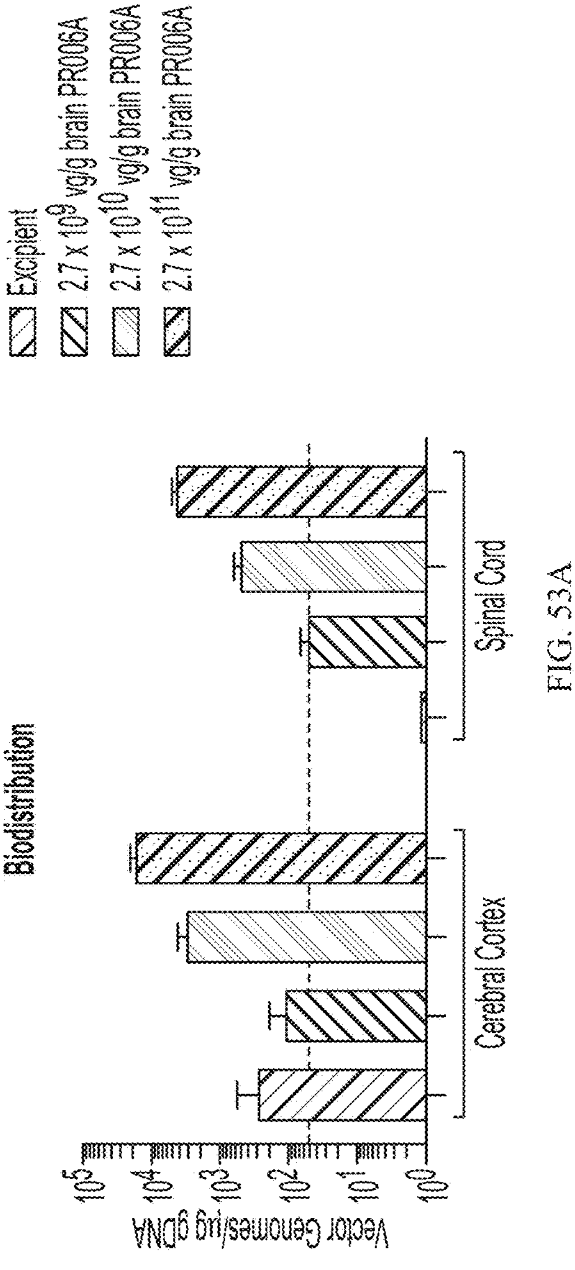
FIG. 53A-FIG. 53C are a series of bar graphs depicting the results of experiments analyzing biodistribution and progranulin expression in the CNS in adult dose-ranging PR006A FTD-GRN mouse model study. 4-month-old Grn KO mice were given PR006A or excipient by ICV administration. They were sacrificed 3 months after the treatment with excipient (red) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) (blue) for biochemical endpoints in the CNS.
Figure 53B:
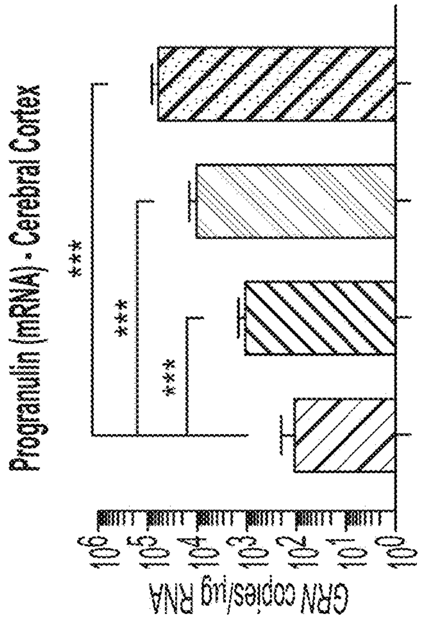
Figure 53C:
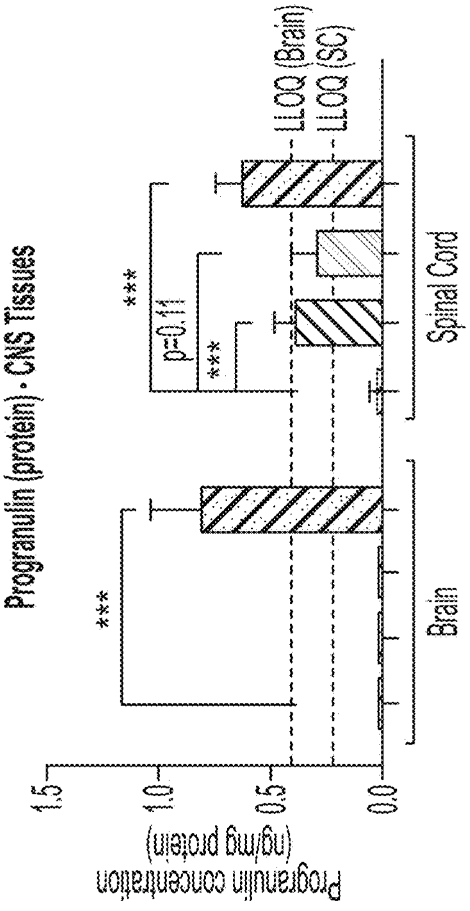

Biodistribution and Progranulin Expression: Biodistribution was determined by measuring vector genome presence using a qPCR assay that meets the current U.S. Food and Drug Administration CBER/OTAT standards for PCR sensitivity (with >50 vector genomes per g genomic DNA defined as positive). Mice that received PR006A were positive for vector genomes in the cerebral cortex and spinal cord in a dose-dependent manner, indicating that ICV administration successfully results in PR006A transduction in the CNS (FIG. 53A). qRT-PCR analysis of PR006A-encoded GRN revealed that ICV dosing of PR006A resulted in a dose-dependent induction of human GRN mRNA expression in the cerebral cortex (FIG. 53B). PR006A treatment increased levels of human progranulin protein in the brain and spinal cord (FIG. 53C). In brain tissue, human progranulin levels were detected and quantified at the highest PR006A dose; at lower doses, progranulin levels were below the assay limit of detection due to the high background in brain. However, based on the log-fold difference between doses, proportional estimation of expected progranulin levels at the lower doses would be well below the lower limit of quantitation (LLOQ) of the assay in brain tissue. The level of endogenous mouse progranulin was measured in age and strain-matched mice with wildtype (WT) Grn alleles; in both the cerebral cortex and spinal cord, the levels of human progranulin in PR006A-treated Grn KO mice did not exceed the level of endogenous progranulin in WT mice at any dose. Since different detection assays employing non-species-cross-reactive anti-progranulin antibodies were used to measure human and mouse progranulin, the absolute numbers cannot be compared with accuracy.

Figure 53D:
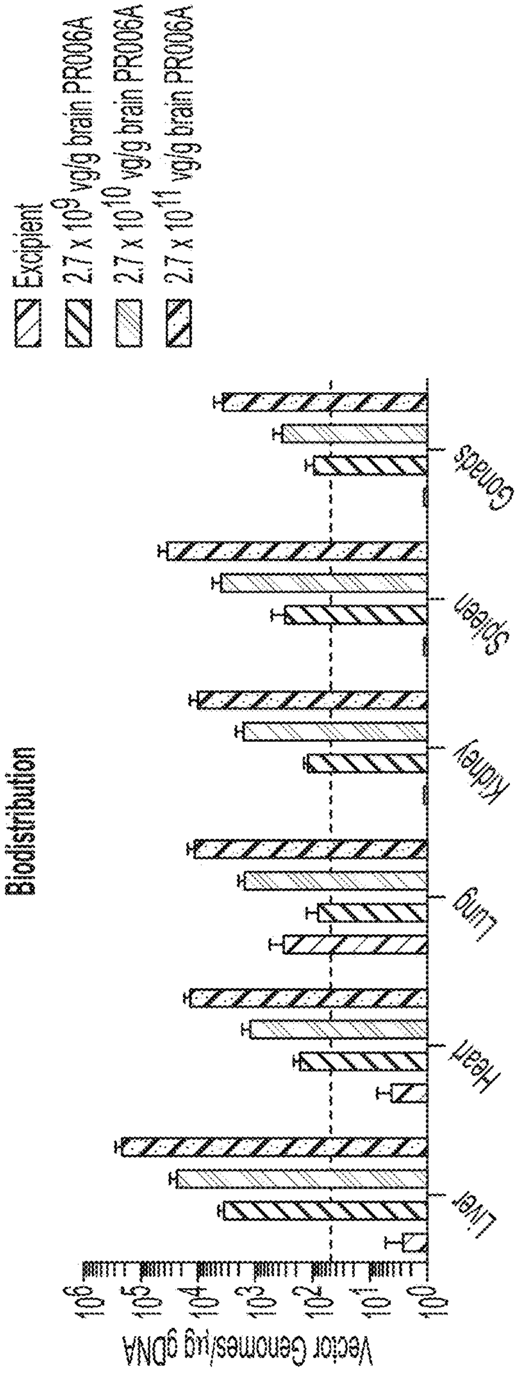
FIG. 53D-FIG. 53E are a series of bar graphs depicting the results of experiments analyzing peripheral tissue biodistribution and progranulin expression in adult dose-ranging PR006A FTD-GRN mouse model study. 4-month-old Grn KO mice were given PR006A or excipient by ICV administration. They were sacrificed 3 months after the treatment with excipient (red) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) (blue) for biochemical endpoints in the liver, heart, lung, kidney, spleen, and gonads.
Figure 53E:
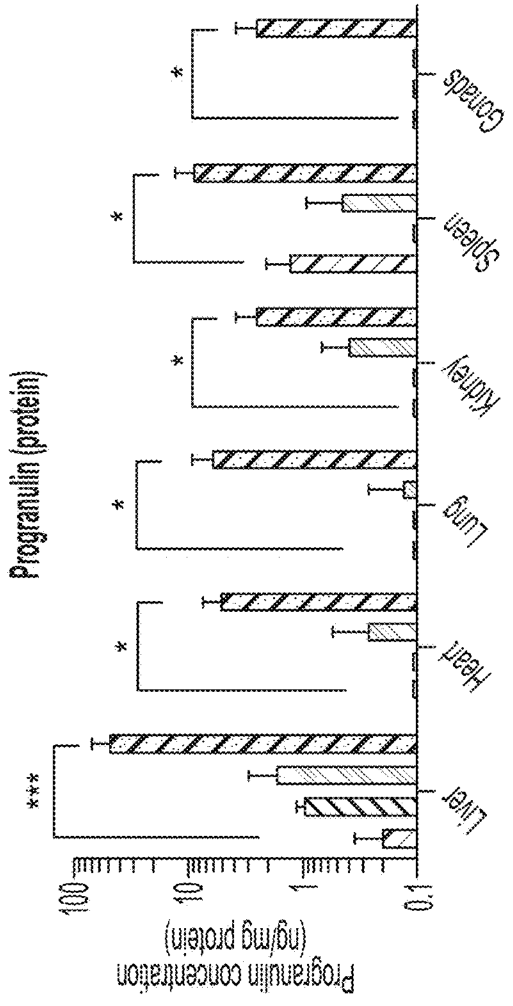

PR006A administration also resulted in broad vector genome presence and progranulin protein levels in peripheral tissues, including liver, heart, lung, kidney, spleen, and gonads (FIG. 53D; FIG. 53E).

Figure 53F:
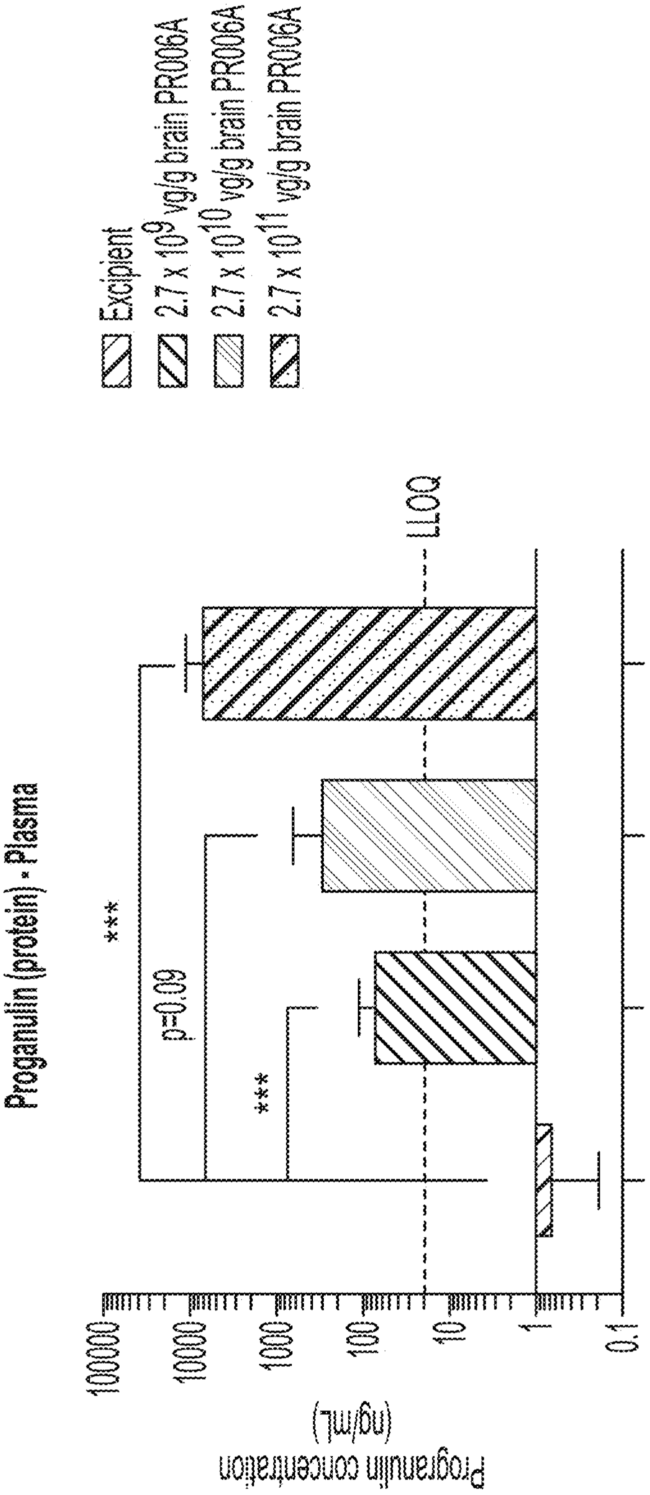
FIG. 53F is a bar graph depicting the results of experiments analyzing progranulin levels in the plasma in the adult dose-ranging PR006A FTD-GRN mouse model study. 4-month-old Grn KO mice were given PR006A or excipient by ICV administration. They were sacrificed 3 months after the treatment with excipient (red) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) (blue) for biochemical endpoints in the plasma. Progranulin protein levels were measured using a human-specific progranulin ELISA in plasma (n=8-10/group; mean±SEM). Plasma levels are shown on a log scale. The lower limit of quantitation (LLOQ) is indicated by a dashed gray line. Statistical analysis was conducted using ANOVA followed by Dunnett's test to compare to the excipient treated Grn KO mouse group; *=p<0.05, =p<0.01, *=p<0.001. LLOQ=lower limit of quantitation. vg=vector genomes.

In plasma, significant levels of human progranulin were detected in PR006A-treated Grn KO mice at all dose levels (FIG. 53F). In line with expectations, human progranulin was not detected in the excipient treated Grn KO mice. The levels of human progranulin in animals treated with the mid-dose of PR006A were in the same range as levels of mouse progranulin measured in mice with WT Grn alleles. Since different detection assays, employing non-species-cross-reactive anti-progranulin antibodies, were used to measure human and mouse progranulin, the absolute numbers cannot be compared with accuracy.

Figure 53G:
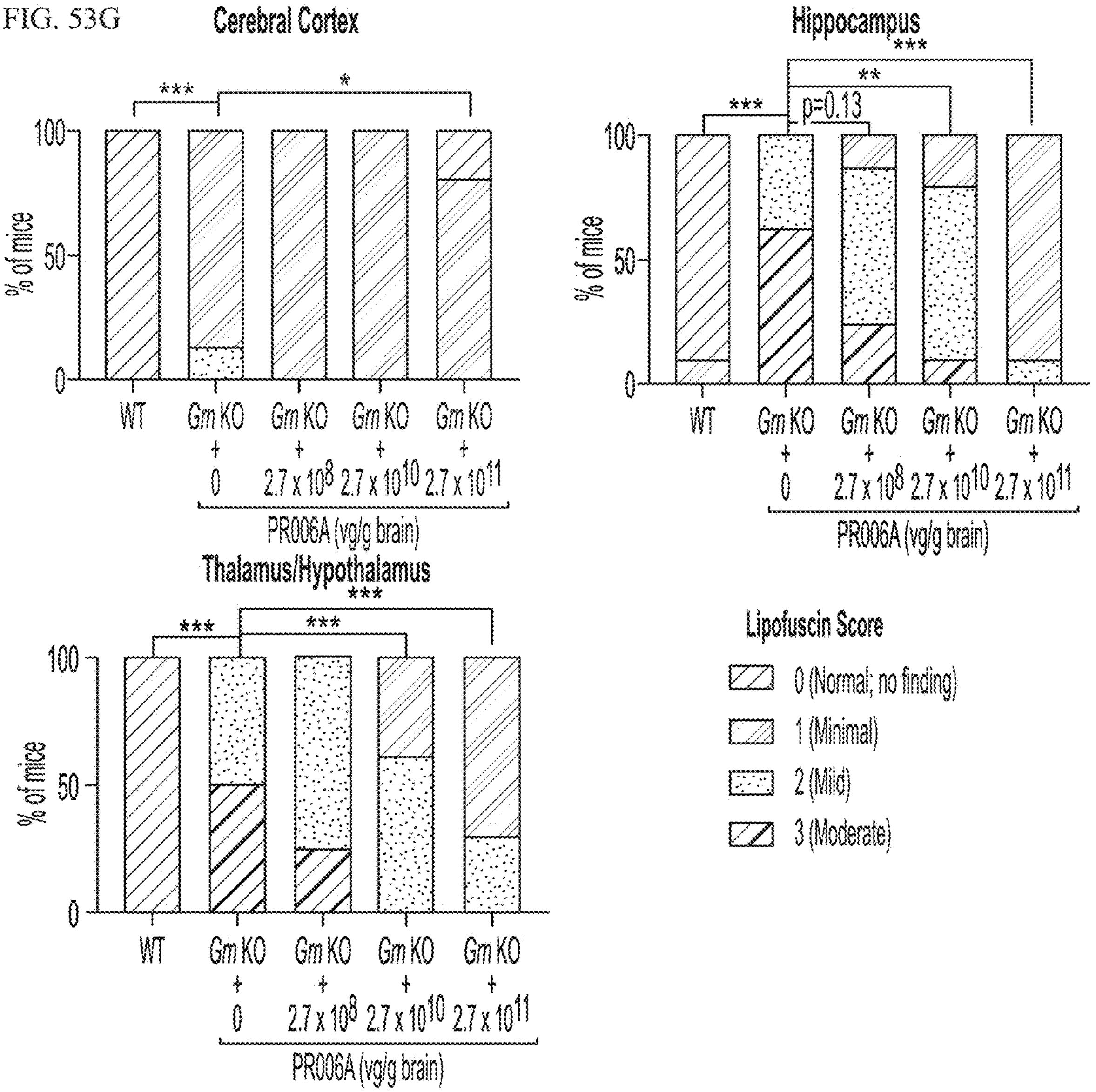
FIG. 53G-FIG. 53H are a series of bar graphs depicting the results of experiments showing reduced lysosomal and neuropathology defects in adult dose-ranging PR006A FTD-GRN adult mouse model study. 4-month-old Grn KO mice were given PR006A or excipient by ICV administration. They were sacrificed for analysis 3 months after the treatment with excipient (red) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) (blue). Lipofuscinosis was analyzed by two independent methods: (1) scoring of H&E-stained brain sections by a pathologist, and (2) quantification of lipofuscin autofluorescence from IHC sections.
Figure 53H:
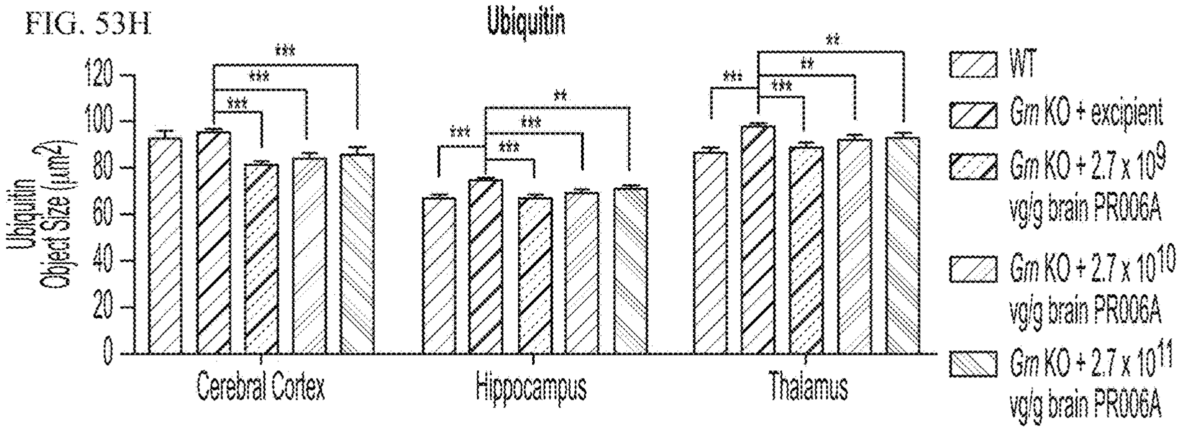

Lipofuscin Accumulation: Lipofuscin accumulation was assessed using two independent methods in adjacent brain sections: (1) in a more clinical approach, lipofuscin accumulation in the brain was scored by a blinded pathologist on a scale of 0 (no lipofuscin observed) to 4 (widespread lipofuscin accumulation) and (2) in a more quantitative approach, lipofuscin autofluorescence was detected by IHC and automatically quantified. Grn KO mice exhibited lipofuscinosis throughout the brain, whereas WT mice did not have detectable lipofuscin in the brain (FIG. 53G). ICV administration of PR006A led to a dose-dependent reduction in the severity scores of intracellular lipofuscin accumulation in the brains of Grn KO mice (FIG. 53G). PR006A efficacy with respect to a reduction in lipofuscinosis could be most readily quantified in brain regions that display the most robust lipofuscinosis phenotype in the Grn KO mouse model of FTD-GRN, including the hippocampus and thalamus. In addition to lipofuscin scoring by a pathologist, IHC performed in brain regions of interest (i.e., cerebral cortex, hippocampus, thalamus) to quantitatively assess lipofuscinosis detected a dose-dependent reduction in the amount of lipofuscin accumulation in the cerebral cortex and thalamic brain regions, with significant decreases occurring at the middle and high PR006A doses. IHC was also performed to assess ubiquitin accumulation in the brain, an additional FTD-GRN-related pathology that occurs in Grn KO mice. Compared to WT mice, Grn KO mice exhibited an increase in ubiquitin throughout the brain (FIG. 53H). PR006A significantly reduced ubiquitin immunoreactive object size to near WT levels at all three doses (FIG. 53H).

Figures 53I, 53J, 53K:
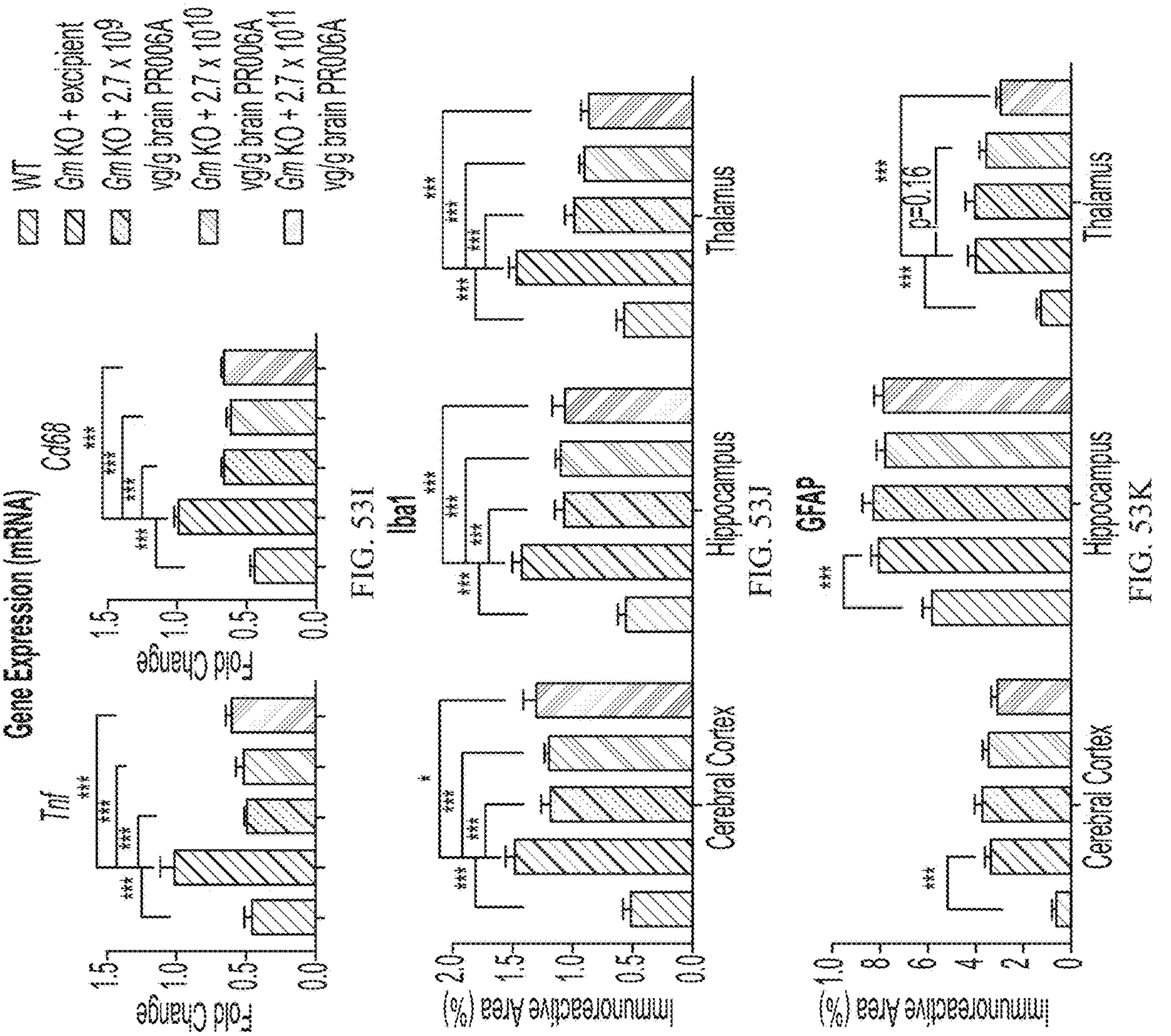
FIG. 53I-FIG. 53K are a series of bar graphs depicting the results of experiments showing decreased neuroinflammatory markers in adult dose-ranging PR006A FTD-GRN mouse model study. 4-month-old Grn KO mice were given PR006A or excipient by ICV administration. They were sacrificed for analysis 3 months after the treatment with excipient (red) or PR006A at dose of $1.1\times10^{9}$ vg ($2.7\times10^{9}$ vg/g brain), $1.1\times10^{10}$ vg ($2.7\times10^{10}$ vg/g brain), or $1.1\times10^{11}$ vg ($2.7\times10^{11}$ vg/g brain) (blue).

Neuroinflammation: Treatment with PR006A suppressed inflammatory marker levels in the brain of adult Grn KO mice. ICV PR006A decreased gene expression of the proinflammatory cytokine Tnf(TNFα) and Cd68 (CD68), a marker of microglia, in the cortex over a range of doses, from $2.7\times10^{9}$ vg/g brain to $2.7\times10^{11}$ vg/g brain (FIG. 53I). In line with published data, we observed an increase in the gene expression of these neuroinflammatory markers in excipient-treated Grn KO mice compared to age-matched mice with wildtype Grn alleles (FIG. 53I). In contrast to the observations in 18-month-old aged Grn KO mice from PRV-2018-027 and reports of TNFα abnormalities in the literature, there was no robust increase in cerebral cortex TNFα protein levels in the 7-month-old adult excipient-treated Grn KO mice; additionally, no significant changes were observed with PR006A in Grn KO mice. These findings are consistent with previously published findings that robust neuroinflammatory phenotypes do not occur in the Grn KO mouse model until 12-24 months of age. Immunohistochemistry (IHC) was performed and quantified in the brain regions of interest (cerebral cortex, hippocampus, and thalamus) to further evaluate neuronal inflammation by staining for Iba1, a marker of microgliosis, and GFAP, a marker of astrocytosis. There was a significant increase in microgliosis (Iba1) and astrocytosis (GFAP) throughout the brain in Grn KO mice compared to WT mice (FIG. 53J-FIG. 53K). PR006A treatment significantly reduced microgliosis (Iba1) at all three doses (FIG. 53J). A trend toward decreased astrocytosis (GFAP) was observed at the middle PR006A dose and a significant decrease in astrocytosis (GFAP) was observed at the high PR006A dose in the thalamus brain region (FIG. 53K).

Figure 53L:
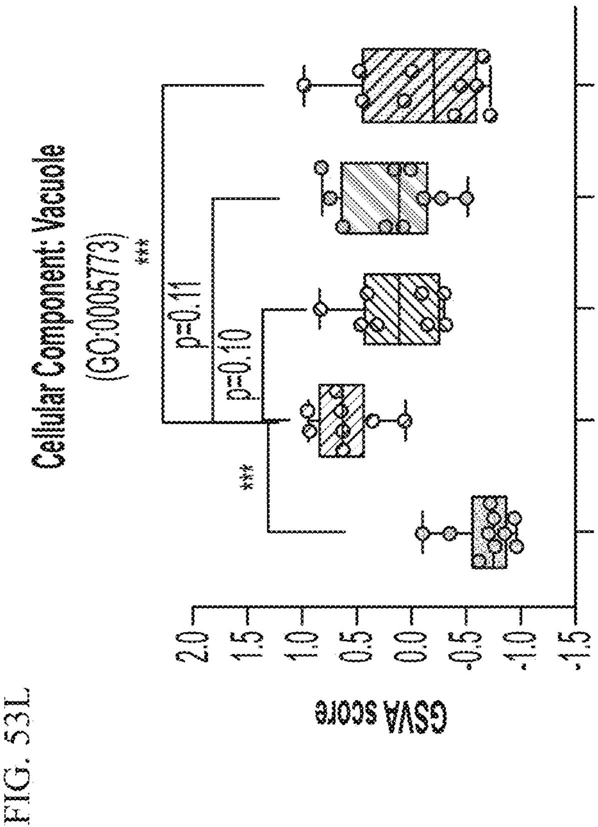
FIG. 53L-FIG. 53N are a series of bar graphs depicting the results of experiments showing decreased gene expression of lysosomal and immune pathways in adult dose-ranging PR006A FTD-GRN mouse model study. 4-month-old Grn KO mice were given PR006A or excipient by ICV administration. They were sacrificed for analysis 3 months after the treatment with excipient (red) or PR006A at dose of $1.1\times10^{9}$ vg ($2.7\times10^{9}$ vg/g brain), $1.1\times10^{10}$ vg ($2.7\times10^{10}$ vg/g brain), or $1.1\times10^{11}$ vg ($2.7\times10^{11}$ vg/g brain) (blue). RNA sequencing was performed in cerebral cortex samples from in ICV-treated Grn KO mice and from age-matched WT C57BL/6J mice (gray). Gene Set Variation Analysis (GSVA) methodology was used to compare mRNA expression levels of previously published gene signatures that are dysregulated in excipient treated Grn KO mice compared to WT mice. Data shown are the GSVA activity scores for curated gene sets from two published studies and one HALLMARK pathway.
Figure 53M:
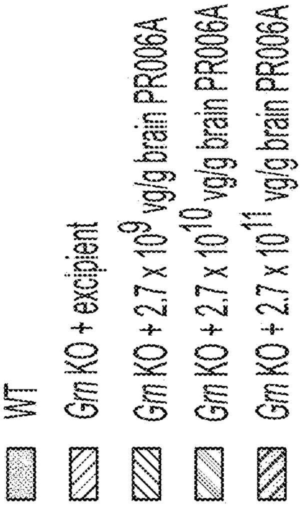
Figure 53M:
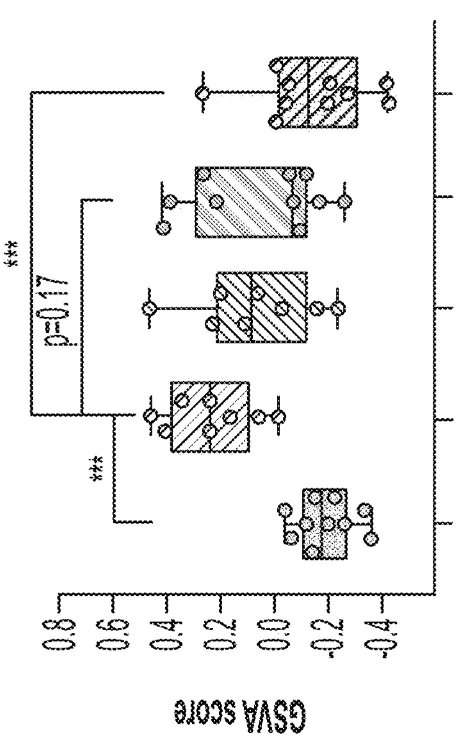
Figure 53N:
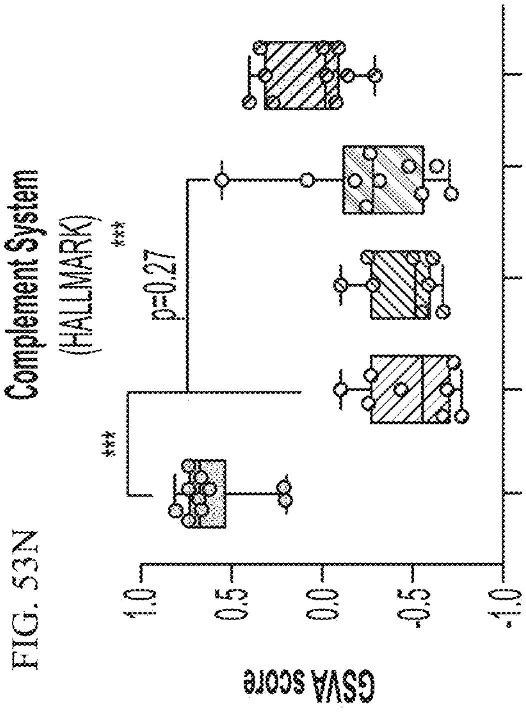

While many of the Grn KO mouse model phenotypes occur late in life, studies have reported that Grn KO mice exhibit widespread gene expression changes as early as 4 months of age, including changes in lysosomal- and immune-related pathways. Therefore, in addition to the targeted qRT-PCR analysis described above, a transcriptomics approach to evaluate changes in mRNA levels, which can be assessed globally with sensitive, high throughput technologies (RNA sequencing), and require minimal sample material, was employed. We performed RNA sequencing on cerebral cortices and used Gene Set Variation Analysis (GSVA) (Hanzelmann et al., *BMC Bioinformatics* 14, 7 (2013)) to determine which gene expression pathways are altered in the 7-month old excipient-treated Grn KO mice, as compared to age-matched WT mice of the same strain. We confirmed deficiencies in lysosomal- and immune-related pathways in mice lacking Grn, as reported in previously published studies. Significant changes were reported in a subset of the GO TERM (GO: 0005773) "Vacuole" genes (contains 4 genes reported to be dysregulated in Grn KO mice described by Lui et al (*Cell* 165, 921-935 (2016))), the "Lysosomal Genes" set (a subset of 25 μlysosomal-related genes shown to be dysregulated in Grn KO mice described by Evers et al (*Cell Reports* 20, 2565-2574 (2017))), and the "Complement" gene set from Gene Set Enrichment Analysis HALLMARK database (contains genes encoding components of the complement system, part of the innate immune system). We then measured and compared activity levels of these gene sets with PR006A treatment (FIG. 53L-FIG. 53N). Treatment with PR006A dose-dependently reversed the gene set deficiencies observed in the Grn KO mice.

Histopathology: A thorough histopathological analysis performed by a blinded board-certified pathologist on hematoxylin and eosin (H&E) staining of the brain, thoracic spinal cord, liver, heart, spleen, lung, kidney, and gonads of all mice from these studies found no evidence of toxicity related to PR006A treatment. The details of the toxicity analysis are provided in the section below.

Conclusion: ICV PR006A at doses ranging from $2.7\times10^{9}$ vg/g brain to $2.7\times10^{11}$ vg/g brain resulted in broad vector genome presence throughout the brain and peripheral tissues in a dose-dependent manner. PR006A treatment also led to production of progranulin mRNA and protein in the CNS. A clear dose-response relationship between PR006A and decreased lipofuscinosis, a readout of lysosomal dysfunction, was observed throughout multiple brain regions. A robust and statistically significant reduction of lipofuscinosis was observed at the middle and highest dose level of PR006A. All PR006A doses reduced ubiquitin accumulation in the brain. Starting at the lowest dose of $2.7\times10^{9}$ vg/g brain, PR006A reduced the expression of proinflammatory markers in the brain at the RNA and protein level.

Summary: In Vivo Nonclinical Studies

PR006A effectively transduced Grn KO mice, resulting in a robust, dose-dependent biodistribution of the transgene and production of progranulin mRNA and protein in the CNS. PR006A dose-dependently reversed gene expression abnormalities in lysosomal and neuroinflammatory pathways. PR006A reduced many of the phenotypes that occur in the brain of this FTD-GRN mouse model, including lipofuscinosis, ubiquitin accumulation, and microgliosis. In the dose-ranging study, the lowest dose of $2.7\times10^{9}$ vg/g brain PR006A significantly suppressed the expression of inflammatory markers in the cerebral cortex. The middle dose of $2.7\times10^{10}$ vg/g brain PR006A improved both lysosomal defects (e.g., lipofuscinosis) and neuroinflammation, in a robust and statistically significant way. The high dose of $2.7\times10^{11}$ vg/g brain PR006A further increased progranulin expression with no evidence of toxicity.

TABLE 7

| Summary of Biodistribution | | | | | | | | | |
|---|---|---|---|---|---|---|---|---|---|
| Study | Dose | Cerebral Cortex | Spinal Cord | Liver | Spleen | Heart | Kidney | Lung | Gonads |
| PRV-2018-027 | $9.7 \times 10^{10}$ vg PR006A | + | + | + | + | + | + | + | + |
| PRV-2019-004 | $1.1 \times 10^{9}$ vg PR006A | + | + | + | + | + | + | + | + |
| | $1.1 \times 10^{10}$ vg PR006A | + | + | + | + | + | + | + | + |
| | $1.1 \times 10^{11}$ vg PR006A | + | + | + | + | + | + | + | + |

Positive biodistribution is defined as >50 vg/μg genomic DNA.

Safety Pharmacology

Throughout these studies, there were no adverse events that can be attributed to the test article. Safety findings from in-life and histopathological analyses of the animals in PRV-2018-027, PRV-2019-002, and PRV-2019-004 are discussed in the section below.

Single-Dose Toxicity

A series of nonclinical studies with PR006A were conducted investigating safety endpoints in mice and monkeys. Three of the studies were performed in a Grn KO mouse model, where endpoints included neuropathological evaluations and assessed both protective activity as well as potential toxicity resulting from PR006A administration via intracerebroventricular (ICV) injection; ICM administration is more technically difficult in mice. These mouse models are representative of FTD-GRN in which patients have a mutation in the GRN gene resulting in reduced progranulin levels. In cynomolgus monkeys, neuropathology was also performed as part of a pilot study in which PR006A was injected into the cisterna magna (ICM). A GLP study was conducted in cynomolgus monkeys in which PR006A was delivered to the ICM, and monkeys were sacrificed at Day 7, Day 30, or Day 183. The GLP study incorporated a comprehensive list of clinical endpoints in addition to anatomical pathology evaluations on a full list of tissues. To support single-dose administration in the clinic, the following single-dose studies were conducted.

Maximal Dose PR006A in an Aged FTD-GRN Mouse Model (PRV-2018-027 and PRV-2019-002)

As part of these efficacy studies in Grn KO mice, neuropathological evaluations were conducted in mice treated ICV with either excipient or PR006A. Grn KO mice have a complete loss of progranulin and are widely used as models of FTD-GRN due to their age-dependent phenotypes, which include lysosomal alterations, neuronal lipofuscin accumulation, microgliosis, and neuroinflammation. Aspects of the pharmacology portions of the study are summarized in the sections above whereas toxicological-related endpoints assessed in this study are summarized below. Two studies of PR006A were conducted in the aged Grn KO mouse model. In the first study (PRV-2018-027), 9 mixed gender Grn KO mice 16 months of age received ICV administration of either PR006A or excipient. Animals were sacrificed 9 weeks post-administration. A single PR006A dose group was included in this study: 10 μl of undiluted virus, for a total dose of $9.7 \times 10^{10}$ vg ($2.4 \times 10^{11}$ vg/g brain), and the control group was treated with 10 μl of excipient.

TABLE 8

| Study Design PRV-2018-027 | | | | | | |
|---|---|---|---|---|---|---|
| Model | Treatment | RoA (Dose Volume) | PR006A Dose (vg/g brain) | Total PR006A Dose (vg) | Number of Mice | Post-Treatment Necropsy |
| Grn KO | Excipient | ICV (10 μl) | 0 | 0 | 4 (2 M/2 F) | 9 weeks |
| Grn KO | PR006A | ICV (10 μl) | $2.4 \times 10^{11}$ | $9.7 \times 10^{10}$ | 5 (3 M/2 F) | 9 weeks |

ROA: route of administration

Various post-mortem endpoints, such as biodistribution, lysosomal alterations, and inflammatory markers, were evaluated as part of this study protocol (see section above). Animals were also checked for survival twice per day, and body weight was measured once per day. After euthanasia at 2-months post-treatment, target tissues were harvested, drop fixed in chilled 4% paraformaldehyde, and stored at 4° C. The tissues from the 8 animals that completed the study were trimmed, processed, and embedded in paraffin blocks. They were then sectioned at ~5 μm, stained with hematoxylin and eosin (H&E) and examined by a board-certified veterinary pathologist.

During this study, 1 mouse died prematurely from the treatment group; no abnormalities were recorded for the deceased animal during necropsy, and therefore there is no known cause of death. No other deaths or abnormalities were observed. All treatment groups tracked similarly in terms of body weights, with no significant differences present.

On histopathological examination, there were no PR006A-related adverse findings. There was widespread lipofuscin accumulation in the brain, consistent with expected findings in a Grn KO mouse. In PR006A-treated animals, there was a reduction in the score severity for lipofuscin accumulation in all regions of the brain. Morphologic changes also appeared to demonstrate a slight reduction in frequency and/or severity scores, particularly with respect to neuronal necrosis in the medulla and pons, with PR006A treatment. However, these trends in the morphologic changes were not as consistent as that of the lipofuscin scores.

In the thoracic spinal cord, there was axonal degeneration and, very rarely (1 out of 4 animals in each group), minimal neuronal necrosis observed. There was a minor reduction in both the incidence and severity of axonal degeneration in the animals treated with PR006A.

The following findings, which are presumably associated with the Grn homozygous knockout mouse, appeared to have a reduced incidence and/or severity in the animals treated with PR006A: dilated tubules in the medulla of the kidney, glomerulopathy in the kidney, and foreign material in the lung (characterized as linear, acellular, dark pink structures, usually within airways and frequently associated with foreign body giant cells and/or macrophages). A larger cohort of animals would be necessary for more definitive conclusions.

All other histopathologic findings observed were considered incidental and/or were of similar incidence and severity in excipient- and test article-treated animals and, therefore, were considered unrelated to administration of PR006A.

In the second study (PRV-2019-002), 5 mixed gender Grn KO mice 14 months of age received ICV administration of either PR006A or excipient. Animals were sacrificed 8 weeks post-administration. A single PR006A dose group was included in this study: 10 μl of undiluted virus, for a total dose of $9.7\times10^{10}$ vg ($2.4\times10^{11}$ vg/g brain), and the control group was treated with 10 μl of excipient.

TABLE 9

Study Design PRV-2019-002

| Model | Treatment | RoA (Dose Volume) | PR006A Dose (vg/g brain) | Total PR006A Dose (vg) | Number of Mice | Post-Treatment Necropsy |
|---|---|---|---|---|---|---|
| Grn KO | Excipient | ICV (10 μl) | 0 | 0 | 2 (0 M/2 F)* | 8 weeks |
| Grn KO | PR006A | ICV (10 μl) | $2.4\times10^{11}$ | $9.7\times10^{10}$ | 3 (1 M/2 F) | 8 weeks |

*Genotype results at the end of the study confirmed that n = 1 animal from the excipient group to be Grn heterozygous KO instead of the expected Grn homozygous KO.

The animals were analyzed in an identical manner to study PRV-2018-027. Animals were checked for survival twice per day, and body weight was measured once per day. After euthanasia at 2-months post-treatment, target tissues were harvested, drop fixed in chilled 4% paraformaldehyde, and stored at 4° C., until evaluation.

In the CNS, findings consistent with those previously observed in the Grn KO mouse were observed in the brain (Yin et al., *JExp Med* 207(1):117-128 (2010)). Specifically, there was a widespread increase in lipofuscin accumulation throughout the brain. Rarely minimal neuronal necrosis was also observed (in the single untreated early death animal and in one Excipient animal).

Due to the low sample numbers it was not possible to demonstrate a consistent trend in the findings related to treatment. There was no consistent difference in response between the Test Article (PR006A) and Excipient.

For non-CNS tissues, findings that were considered to be consistent with the phenotype of the Grn KO mouse were observed in the kidney (tubular dilation and infiltrates of mononuclear inflammatory cells) and liver (vacuolation of Kupffer cells/sinusoidal lining cells, and Kupffer cell microgranulomas) (Yin et al., *JExp Med* 207(1):117-128 (2010)).

There was a finding of "glomerulopathy" observed in all animals that underwent surgery and were enrolled in the study. While published reports of this finding as a change associated with standard, unchallenged, Grn knockout mice were not found, one study has demonstrated progranulin-deficient mice treated with a diet that induces hyperhomocysteinemia, develop glomerular basement membrane thickening and podocyte foot process effacement (Fu et al., *Hypertension* 69(2):259-266 (2017)).

All other findings were consistent with those commonly observed in laboratory mice. Due to the low sample number, no conclusive difference related to treatment could be shown.

Dose-Ranging PR006A in an Adult FTD-GRN Mouse Model (PRV-2019-004)

To further assess the safety of PR006A, a larger, dose-ranging study in adult Grn KO mice was performed. A total of 40 mixed-gender mice were divided into 4 groups and administered either excipient or one of three doses of PR006A by a single unilateral ICV injection into the left hemisphere; all animals, regardless of treatment group, received a total dose volume of 10 μl. Mice were treated at 4 months of age and euthanized 3 months post-treatment. An additional wildtype (WT) control group, which included untreated C57BL/6J mice (the same background strain) aged to approximately 7 months, were also euthanized and subjected to a similar necropsy.

The study was conducted according to the study design below:

TABLE 10

| Study Design PRV-2019-004 | | | | | | | |
|---|---|---|---|---|---|---|---|
| Group | Model | Treat-ment | RoA (Dose Volume) | Dose of PR006A (vg/g brain) | Total PR006A Dose (vg) | Number of Mice | Post-Treatment Necropsy |
| 1 | Grn KO | Excipient | ICV (10 μl) | 0 | 0 | 10 (4 M/6 F) | Week 13 |
| 2 | Grn KO | PR006A | ICV (10 μl) | $2.7 \times 10^{11}$ | $1.1 \times 10^{11}$ | 10 (4 M/6 F) | Week 13 |
| 3 | Grn KO | PR006A | ICV (10 μl) | $2.7 \times 10^{10}$ | $1.1 \times 10^{10}$ | 10 (4 M/6 F) | Week 13 |
| 4 | Grn KO | PR006A | ICV (10 μl) | $2.7 \times 10^{9}$ | $1.1 \times 10^{9}$ | 10 (4 M/6 F) | Week 13 |
| N/A | WT (C57BL/6J) | None | N/A | 0 | 0 | 10 (5 M/5 F) | N/A |

During the study, animals were checked for survival twice a day and weighed once a week. Mice were euthanized 3 months post-treatment, and various post-mortem evaluations were conducted to assess efficacy of PR006A (see section above). In addition, sections stained for H&E from brain, thoracic spinal cord, liver, heart, spleen, lung, kidney, and gonads were evaluated by a board-certified pathologist.

On histopathological examination, there were no adverse PR006A-related findings in any of the mice regardless of treatment group.

There were findings consistent with the Grn KO mouse model phenotype, such as accumulation of intracellular lipofuscin in various regions of the brain: cerebral cortex, cerebral nuclei, hippocampus, thalamus/hypothalamus, cerebellum and brainstem (particularly the pons and medulla). Clear evidence of morphologic changes on the H&E stained sections (vacuolation of neurons and gliosis) was not observed. Accumulation of lipofuscin pigment can precede easily detectable morphologic changes and, therefore, serves as an adequate biomarker of efficacy. While all Grn homozygous KO groups demonstrated lipofuscin accumulation, there were differences in the severity of this finding across treatment groups. The frequency of higher scores for lipofuscin accumulation was greatest for the group of animals treated with excipient (Group 1). Of those animals treated with PR006A, the frequency of higher scores were observed in Group 4 (low dose PR006A; $2.7\times10^{9}$ vg/g brain), followed by Group 3 (middle dose PR006A; $2.7\times10^{10}$ vg/g brain). The lowest severity scores were observed with in Group 2 (high dose PR006A; $2.7\times10^{11}$ vg/g brain). These findings demonstrate a dose-dependent reduction in the severity scores of intracellular lipofuscin accumulation in the brains of Grn homozygous knock-out mice. All other histopathologic findings were considered incidental and/or were of similar incidence and severity in excipient and test article-treated animals and, therefore, were considered unrelated to administration of PR006A.

GLP Single-Dose Study in Monkeys (PRV-2018-028)

Study Design

The purpose of this GLP study was to evaluate the toxicity and biodistribution of the test article, PR006A, when administered once via ICM injection in cynomolgus monkeys with a 6-day, 29-day, or 182-day post-administration observation period; animals were sacrificed at study Day 7, Day 30, or Day 183. The study was designed to evaluate 2 dose levels: the highest dose is the maximum feasible dose achievable with 1.2 mL volume (the highest volume there was experience in administering) of undiluted PR006A, and a lower dose that is equivalent to one log unit lower than the high dose. The doses equate to a low dose of $4.8\times10^{11}$ vg and a high dose of $4.8\times10^{12}$ vg; with a brain weight estimate of 74 g in a cynomolgus monkey, the NHP species used in this study, this translates to approximately $6.5\times10^{9}$ vg/g brain and $6.5\times10^{10}$ vg/g brain. The study also includes a control arm in which animals receive 1.2 ml of excipient only (20 mM Tris pH 8.0, 200 mM NaCl, and 1 mM $MgCl_2$+0.001% [w/v] Pluronic F68). This study utilized both male and female cynomolgus macaques. The Day 7 group included 1 female at the highest dose and was designed as a sentinel for early toxicity; the remaining two timepoints (Day 30 and Day 183) included 2 males and 1 female at each dose. In addition to samples from multiple brain regions, peripheral tissue samples were collected for qPCR analysis. All samples that were positive with qPCR were analyzed for transgene expression. A tabulated summary of this study's design is provided in Table 11.

TABLE 11

| Overview of the GLP NHP Study PRV-2018-028 | |
|---|---|
| Purpose | Assess the tolerance and biodistribution of PR006A in NHPs |
| Regulatory Compliance | GLP |
| Test Article | PR006A |
| Total No. of Animals | 19 cynomolgus monkeys |
| Weight (age) | 2-5 kg (25-50 months) |
| Study Design | Group Assignments: |

TABLE 11-continued

Overview of the GLP NHP Study PRV-2018-028

| | Group | Dose (vg/g brain) | Number of Animals: Necropsy (Day 7) | Number of Animals: Necropsy (Day 30) | Number of Animals: Necropsy (Day 183) |
|---|---|---|---|---|---|
| | 1 | 0 | 0 | 2 M/1 F | 2 M/1 F |
| | 2 | $6.5 \times 10^{9}$ | 0 | 2 M/1 F | 2 M/1 F |
| | 3 | $6.5 \times 10^{10}$ | 1 F | 2 M/1 F | 2 M/1 F |

| | | | |
|---|---|---|---|
| Dosing Route and Frequency | Intra-cisterna magna using a polypropylene 1-3 cc syringe and spinal needle (Pencan 25 G × 2.5 cm BBraun); single slow bolus delivered at a maximum rate of 0.5 cc/min | | |
| Formulations | Dosing solution provided at concentration of $4.01 \times 10^{12}$ vg/mL | | |
| Clinical Signs | Daily (including food consumption); Detailed Observations weekly | | |
| Body weights | Weekly | | |
| Neurological, Ophthalmic, ECG Examinations | Once pre-dose and during Weeks 2 and 26 | | |
| Clinical Pathology | All groups hematology, clinical chemistry, coagulation parameters | | |
| Hematology | red blood cell count | mean corpuscular volume | |
| | hemoglobin | platelet count | |
| | hematocrit | white blood cell count | |
| | mean corpuscular | absolute neutrophil count | |
| | hemoglobin | absolute lymphocyte count | |
| | mean corpuscular | absolute monocyte count | |
| | hemoglobin concentration | absolute reticulocyte count | |
| | absolute eosinophil count | differential blood cell count | |
| | absolute basophil count | blood smear | |
| Clinical Chemistry | glucose | alanine aminotransferase | |
| | urea nitrogen | alkaline phosphatase | |
| | creatinine | gamma glutamyltransferase | |
| | total protein | aspartate aminotransferase | |
| | albumin | calcium | |
| | globulin | inorganic phosphorus | |
| | albumin/globulin ratio | sodium | |
| | cholesterol | potassium | |
| | total bilirubin | chloride | |
| | creatine kinase | triglycerides | |
| Coagulation | prothrombin time | | |
| | fibrinogen | | |
| | activated partial thromboplastin time | | |
| Vector Shedding (urine/feces) | At sacrifice | | |
| Necropsy | Day 7, Day 30, Day 183 | | |
| Tissue Preservation for Histopathology | The following tissues from each animal will be collected in 10% neutral-buffered formalin (unless otherwise indicated) or recorded as missing, if applicable. | | |
| Tissue Preservation, continued | Adrenal[a] | Injection site | Prostate[a] |
| | Aorta | (overlying skin) | Rectum |
| | Bone, femur with | Jejunum | Salivary gland |
| | bone marrow | Kidney[a] | Sciatic nerve |
| | Bone, sternum | Lesions | Seminal vesicle[a] |
| | with bone | Liver[a] | Skin/subcutis |
| | marrow | Lung with large | Spinal cord |
| | Brain[a] | bronchi | (cervical, |
| | Cecum | Lymph node | thoracic, lumbar) |
| | Cervix | (mandibular) | Spleen[a] |
| | Colon | Lymph node | Stomach |
| | Duodenum | (mesenteric) | Testis[a] |
| | Epididymis[a] | Mammary gland | Thymus[a] |
| | Esophagus | Muscle, biceps | Thyroid with |
| | Eye[b] | femoris | parathyroid[a] |
| | Gall bladder | Optic nerve | Tongue |
| | GALT (Peyer's | Ovary[a] | Trachea |
| | Patch) | Oviducts | Urinary bladder |
| | Heart[a] | Pancreas | Uterus[a] |
| | Ileum | Pituitary gland[a] | Vagina |
| Histopathology | All groups-all tissues | | |
| Biodistribution | The following tissues/biofluids will be analyzed for biodistribution by qPCR: | | |
| | Frontal cortex | Liver | |
| | Hippocampus | DRG (cervical) | |

TABLE 11-continued

| Overview of the GLP NHP Study PRV-2018-028 | | |
|---|---|---|
| | Ventral mesencephalon | DRG (thoracic) |
| | Periventricular gray | DRG (lumbar) |
| | Putamen | Spinal cord (thoracic) |
| | Testis | Spinal cord (lumbar) |
| | Ovary | Spinal cord (cervical) |
| | Kidney | Spleen |
| | Stomach (pyloric) | Heart (apex) |
| | Blood | CSF |
| | Lung | |
| Transgene Expression | All samples that are positive for qPCR will be evaluated for progranulin expression | |

Abbreviations:
F, female;
ICM; intra-cisterna magna;
M, male;
MgCl2; magnesium chloride;
NaCl, sodium chloride;
vg, vector genome(s);
DRG, dorsal root ganglia;
GALT, gut-associated lymphoid tissue.

TABLE 11A

| Group Assignments | | | | |
|---|---|---|---|---|
| | Dose | Number of Animals | | |
| Group | (vg/g brain) | Necropsy (Day 7) | Necropsy (Day 30) | Necropsy (Day 183) |
| 1 | 0 | 0 | 2 M/1 F | 2 M/1 F |
| 2 | 6.5 x 109 | 0 | 2 M/1 F | 2 M/1 F |
| 3 | 6.5x 1010 | 1 F | 2 M/1 F | 2 M/1 F |

Cynomolgus NHPs were assessed by multiple in-life observations and measurements, including mortality/morbidity (daily), clinical observations (daily), body weight (baseline and weekly thereafter), visual inspection of food consumption (daily), neurological observations (baseline and during Week 2 and 26), indirect ophthalmoscopy (baseline and during Weeks 2 and 26), and electrocardiographic (ECG) measurement (baseline and during Weeks 2 and 26).

Analysis of neutralizing antibodies (nAb) to the AAV9 capsid was performed at baseline and at sacrifice on Days 7, 30, or 183. Clinical pathology consisting of hematology, coagulation, clinical chemistry, and urinalysis was performed twice at baseline (blood tests; once for urinalysis) and once during Weeks 1 and 13 of the dosing phase.

Animals were euthanized and tissues harvested on Day 7, Day 30, or Day 183. The tissues outlined in Table 11, if present, were collected from all animals, weighed (if applicable), and divided into replicates. One replicate was preserved in 10% neutral-buffered formalin (except when special fixatives are required for optimum fixation) for histopathological evaluation (all animals). Additional replicates were collected for qPCR and transgene expression analysis.

Safety and Toxicology

There were no unscheduled deaths, and all animals survived until the scheduled necropsy. There were no adverse PR006A-related clinical observations, body weight changes, ophthalmic observations, or physical or neurological examination findings; gross macroscopic examination at necropsy showed no drug-related abnormalities in any of the cohorts. In addition, there were no PR006A-related changes in PR interval, QRS duration, QT interval, corrected QT (QTc) interval, or heart rate observed in males or combined sexes administered $6.5\times10^{9}$ or $6.5\times10^{10}$ vg/g brain. No abnormal ECG waveforms or arrhythmias were observed during the qualitative assessment of the ECGs.

Biodistribution

Figure 54A:
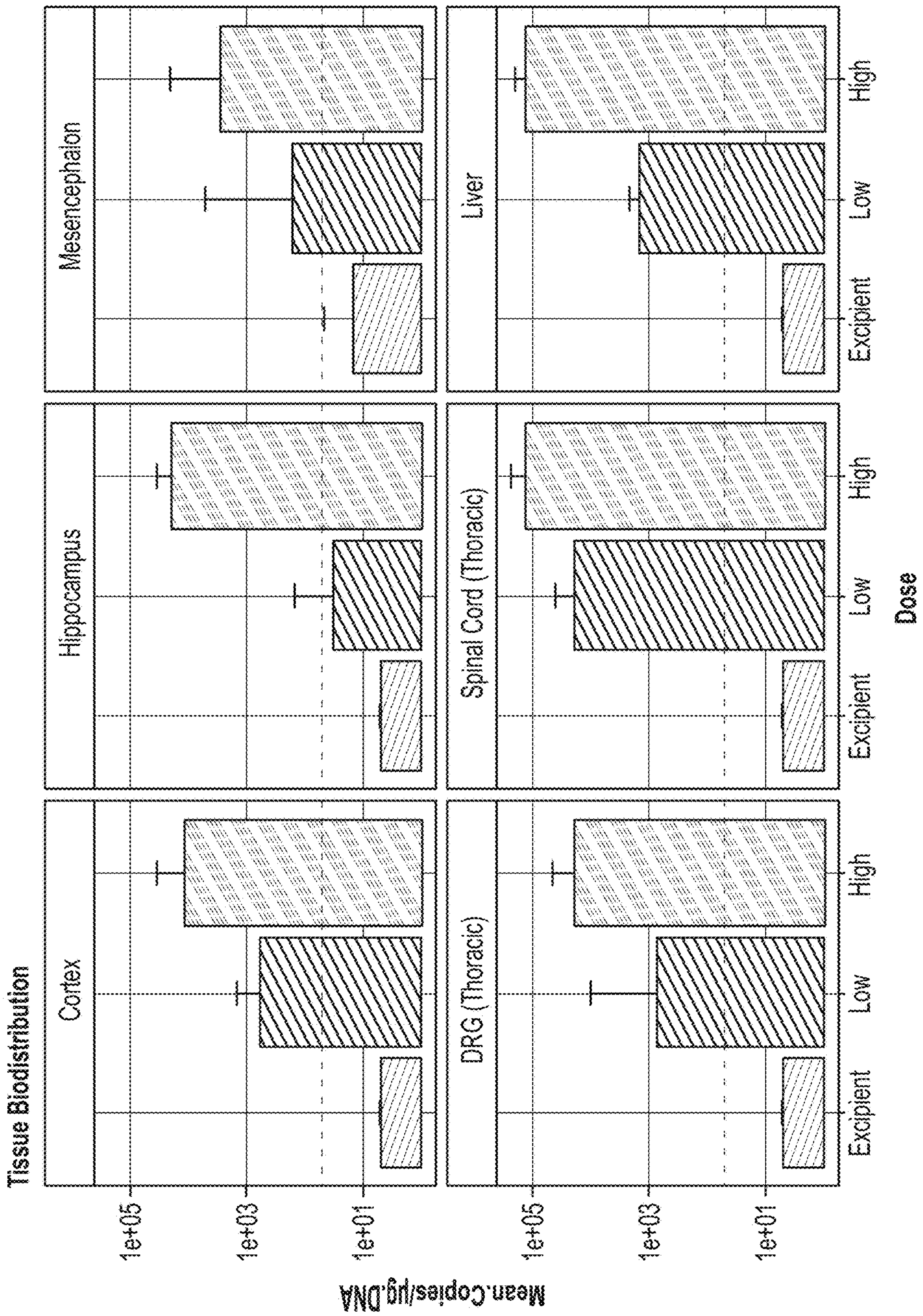
FIG. 54A is a series of bar graphs depicting the results of experiments analyzing biodistribution of PR006A transgene quantified by qPCR. Transgene levels were analyzed using qPCR methodologies in NHPs 182 days after ICM injection of either excipient, low dose of PR006A ($6.5\times10^{9}$ vg/g brain), or high dose of PR006A ($6.5\times10^{10}$ vg/g brain). Each bar represents the average±SEM of 3 animals per group; the yellow line indicates the lower limit of quantitation at 50 vg/μg DNA.

Biodistribution analysis of the PR006A transgene was performed using a qPCR-based assay. At Day 183 in the high dose group ($6.5\times10^{10}$ vg/g brain), there was widespread transduction throughout the CNS and periphery, with all tissues examined positive for vector presence with a cutoff of 50 vg/μg DNA, the lower limit of quantitation for the qPCR assay. Data from select representative regions from Day 183 are shown in FIG. 54A; Day 30 data is not shown. At Day 30 in the high dose group ($6.5\times10^{10}$ vg/g brain), all CNS tissues examined were positive for transduction, with the exception of the putamen. Tissues from animals treated with the low dose ($6.5\times10^{9}$ vg/g brain) were positive in the CNS at Day 183, but only the spleen and liver were positive from the peripheral tissues. In addition, the one female NHP treated with the high dose of PR006A was positive in the ovaries at Day 7, and males treated with the high dose were positive in the testes at Day 30 and Day 183. PR006A transduction was most robust in liver and tissues of the nervous system, and consistently lower in the other peripheral organs examined. In the brain, vector transduction stabilized at Day 183 when compared to Day 30, demonstrating a robust and durable transduction of the transgene.

Figure 54B:
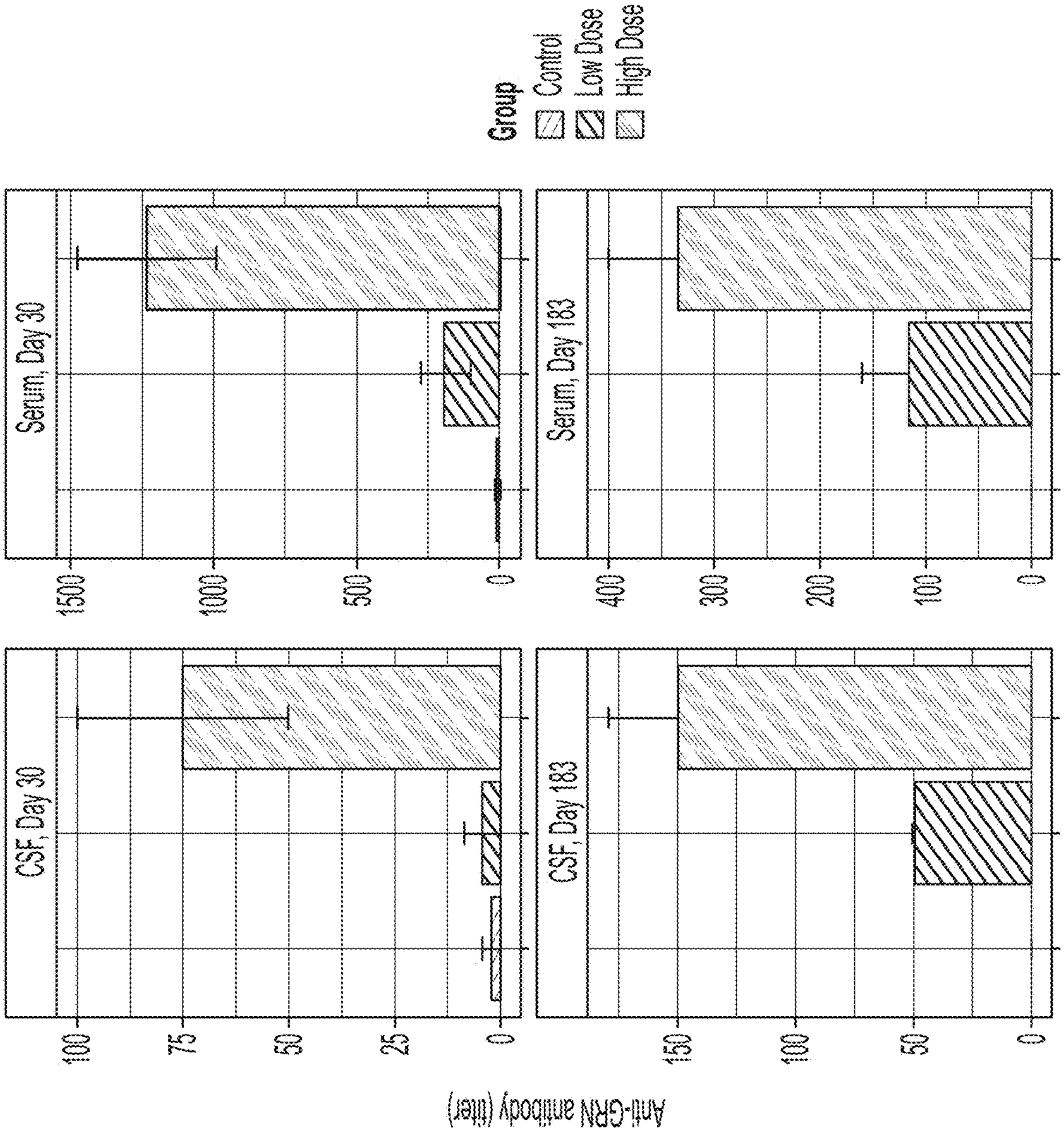
FIG. 54B is a series of bar graphs depicting the results of experiments analyzing levels of anti-drug antibody to human progranulin. Antibodies to progranulin in NHP serum and CSF samples at Day 29 and Day 182 post-treatment with either excipient, a low dose of PR006A ($6.5\times10^{9}$ vg/g brain), or a high dose of PR006A ($6.5\times10^{10}$ vg/g brain). Data represents the mean SEM.

In the NHPs receiving ICM administration of PR006A, there was a significant allogeneic immune response to the transgene product, progranulin, with anti-progranulin antibodies detected in serum and CSF samples collected at Day 30 and Day 183 post-treatment; the immune response indicates that the human progranulin protein was expressed in the NHPs. The antidrug antibody (ADA) levels were determined using established immune assay technologies. The data are illustrated in FIG. 54B.

Figure 54C:
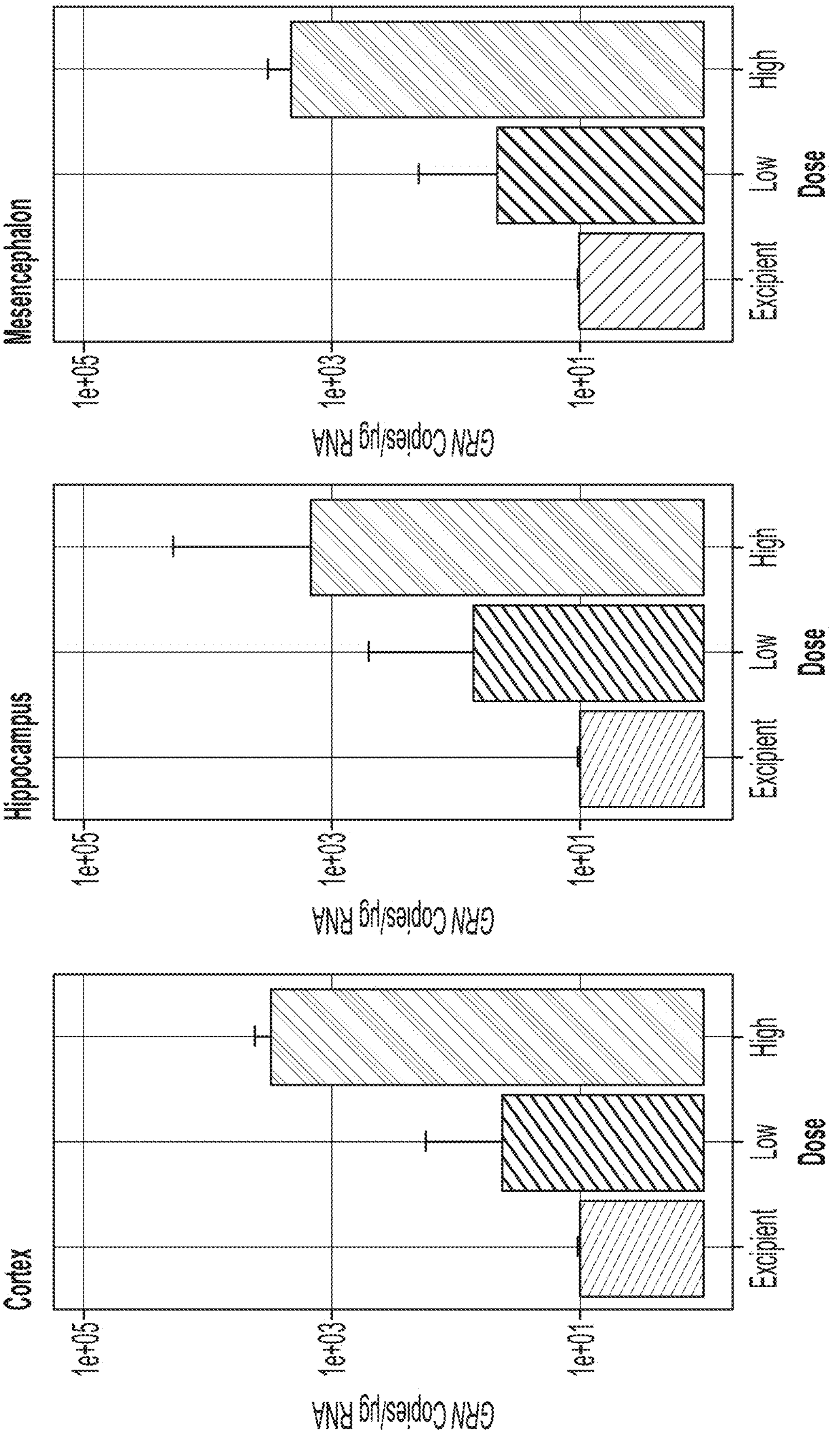
FIG. 54C is a series of bar graphs depicting the results of experiments analyzing expression of PR006A transgene (GRN). GRN expression levels were determined in NHP cortex, hippocampus and ventral mesencephalon collected on Day 183 using RT-qPCR. Data is presented as mean±SEM.

Expression of PR006A (GRN) was measured at the mRNA level using a RT-qPCR-based assay, and at the protein level using a Simple Western™ (Jess) analysis. Concomitant with levels of PR006A transduction, expression of the transgene was observed by mRNA measurements using RT-qPCR in select brain regions (FIG. 54C), liver, gonads, spinal cord and DRG collected on Day 183.

Expression of the transgene was measurable in brain and liver at both doses of PR006A, and the expression levels were both dose-dependent and durable. In gonads, expression was measurable in the males at the high dose only; at both doses in the females, expression was measurable at Day 7 and Day 30, but not at Day 183.

Figure 54D:
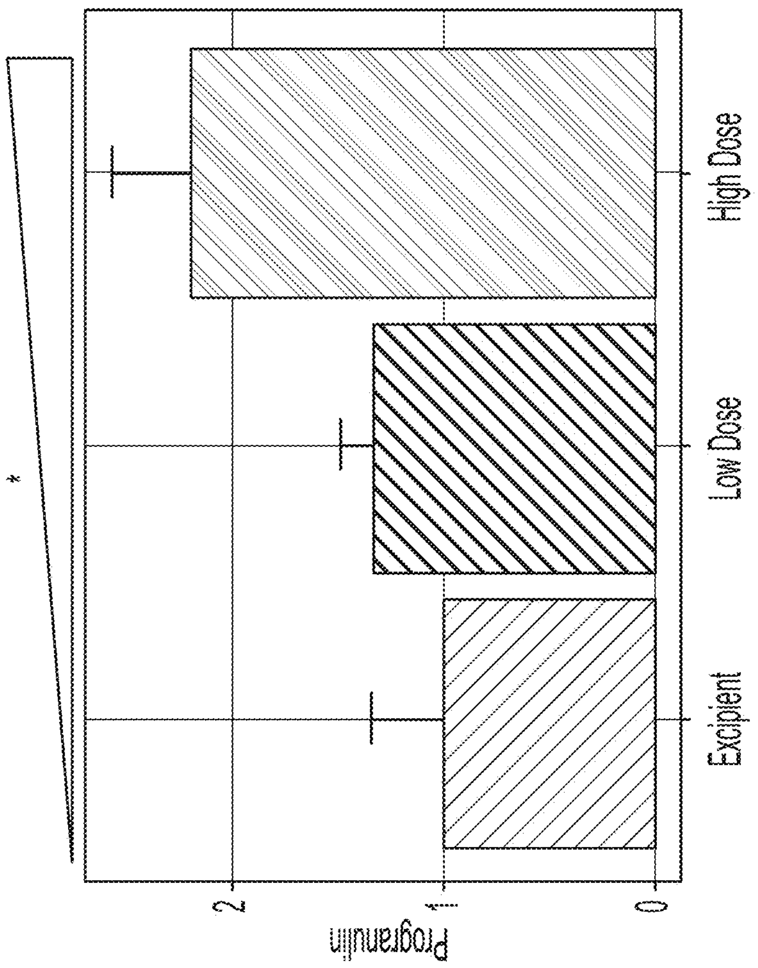
FIG. 54D is a bar graph depicting the results of experiments analyzing progranulin levels in the CSF quantified by Simple Western™ (Jess) platform. Progranulin levels were determined in NHP CSF samples that were collected at Day 183, determined by a Simple Western™ (Jess) analysis. CSF samples from NHPs treated with excipient, low dose of PR006A ($6.5\times10^{9}$ vg/g brain weight) or high dose of PR006A ($6.5\times10^{10}$ vg/g brain weight). Data presented is mean±SEM; P-value: *p<0.05, by one-way dose dependence response analysis using William's trend test.

To confirm that human progranulin was produced in the treated NHPs, protein levels in CSF were evaluated on a Simple Western™ (Jess) platform. Details of the method are provided in Example 14. The method was qualified by measuring progranulin levels in CSF samples from FTD-GRN patients and establishing that they were approximately half of the levels measured in CSF samples from healthy human controls and from FTD patients without a GRN mutation. Results from the CSF indicate that levels of progranulin are elevated in a dose-dependent manner in animals treated with both the low and high doses of PR006A (FIG. 54D). These results indicate that the effective and broad transduction of PR006A in NHPs following ICM administration leads to increased levels of progranulin.

Progranulin protein measurements focused on CSF because the Simple Western™ (Jess) assay is not suitable to measure progranulin levels in brain tissue due to the high level of nonspecific background bands. The assays currently available do not reliably measure levels of transgene-derived human progranulin in NHP tissues due to the high levels of nonspecific background. CSF levels are generally believed to reflect relevant brain concentrations, and they are of particular value as translational biomarkers to clinical studies.

SUMMARY

There have been no adverse safety findings or toxicity concerns in any of the nonclinical studies, including a small pilot non-GLP study in NHPs and a GLP study in NHPs through Day 183, that preclude the initiation of a clinical study. The pathology findings in the GLP study were consistently minimal in severity with a low number of affected cells across both dose groups. There were no other in-life or post-mortem PR006A-related adverse findings.

Phase ½ Trial in Human Subjects with FTD-GRN

Human subjects (n=15) will be enrolled in an open-label trial of the PR006 recombinant AAV. The subject inclusion criteria comprise: 30-80 years old (inclusive), has a pathogenic GR mutation, is at a symptomatic disease stage, and has stable use of background medications prior to investigational product dosing. Each subject will receive the investigational product as a single ICM (intra-cisterna magna) injection. The trial will include a 3-month biomarker readout, a 12-month clinical readout and a 5-year safety and clinical follow-up. The trial will analyze: (1) safety and tolerability: (2) key biomarkers, including: progranulin, NfL (neurofilament light chain), and volumetric MRI (magnetic resonance imaging); and (3) Efficacy: CDR plus NACC FTLD (Clinical Dementia Rating plus National Alzheimer's Coordinating Center Frontal Temporal Lobar Dementia); measures of behavior, cognition, language, function, and QoL (quality of life).

TABLE 12

Examples of neurodegenerative diseases

Figure 4:
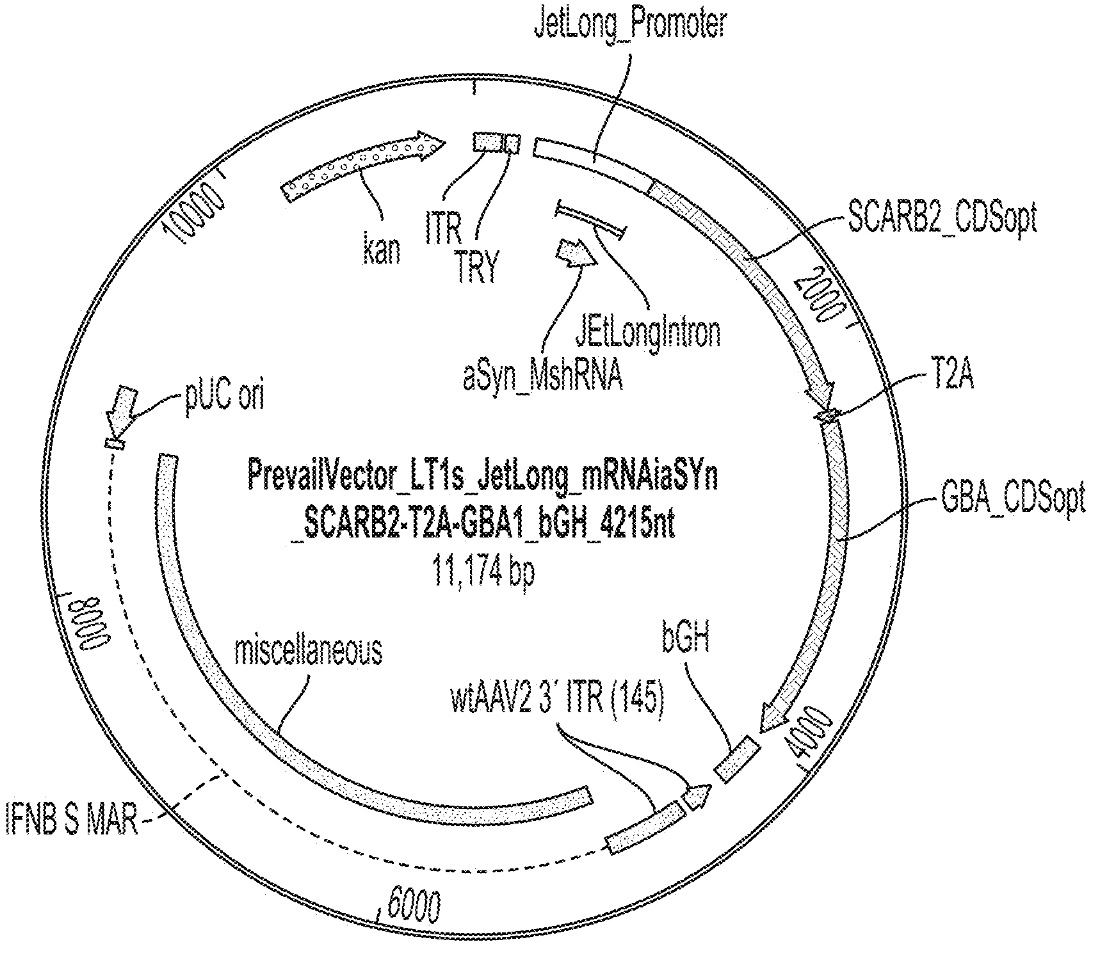
FIG. 4 is a schematic depicting one embodiment of a vector comprising an expression construct encoding Gcase (e.g., GBA1 or a portion thereof), LIMP2 (SCARB2) or a portion thereof, and an interfering RNA for α-Syn.
Figure 5:
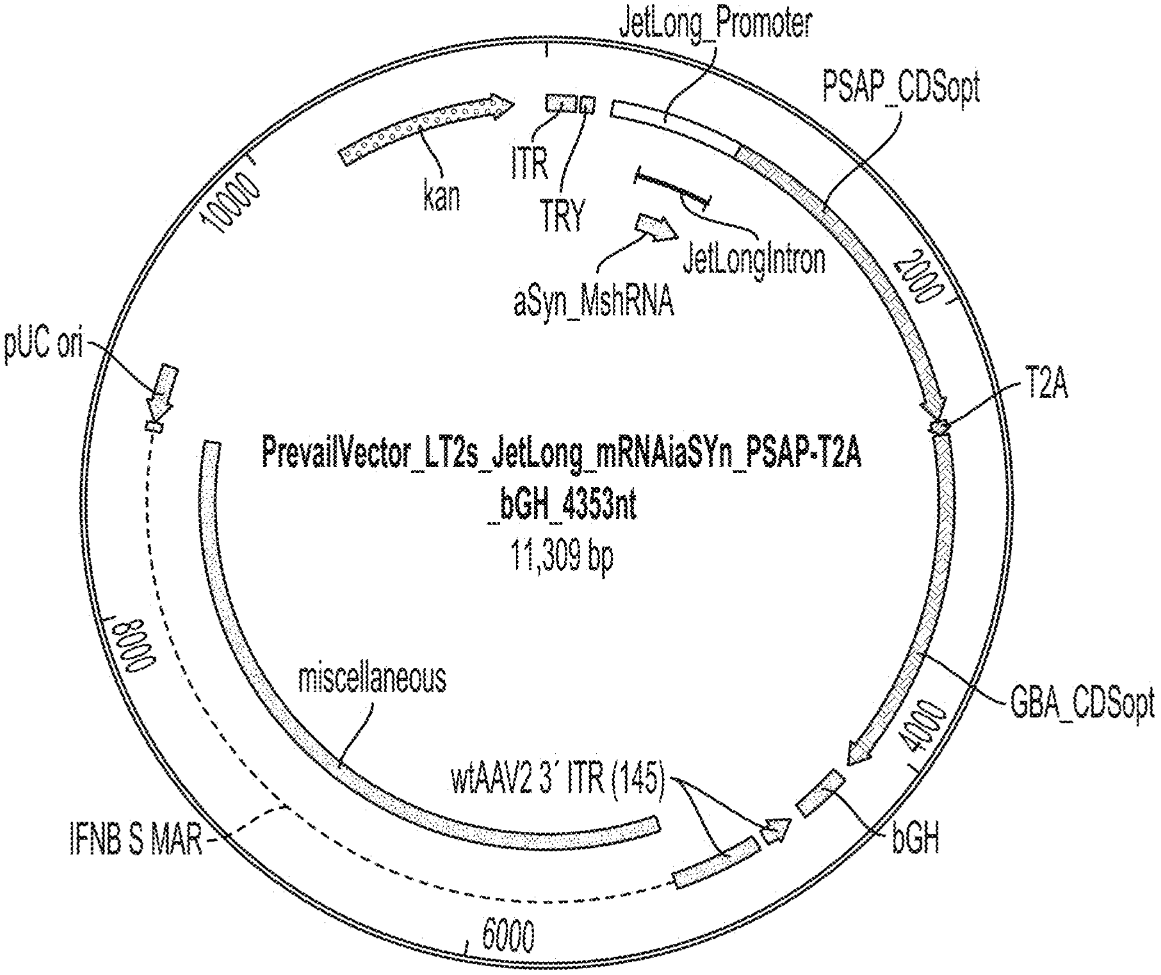
FIG. 5 is a schematic depicting one embodiment of a vector comprising an expression construct encoding Gcase (e.g., GBA1 or a portion thereof), Prosaposin (e.g., PSAP or a portion thereof), and an interfering RNA for α-Syn.
Figure 6:
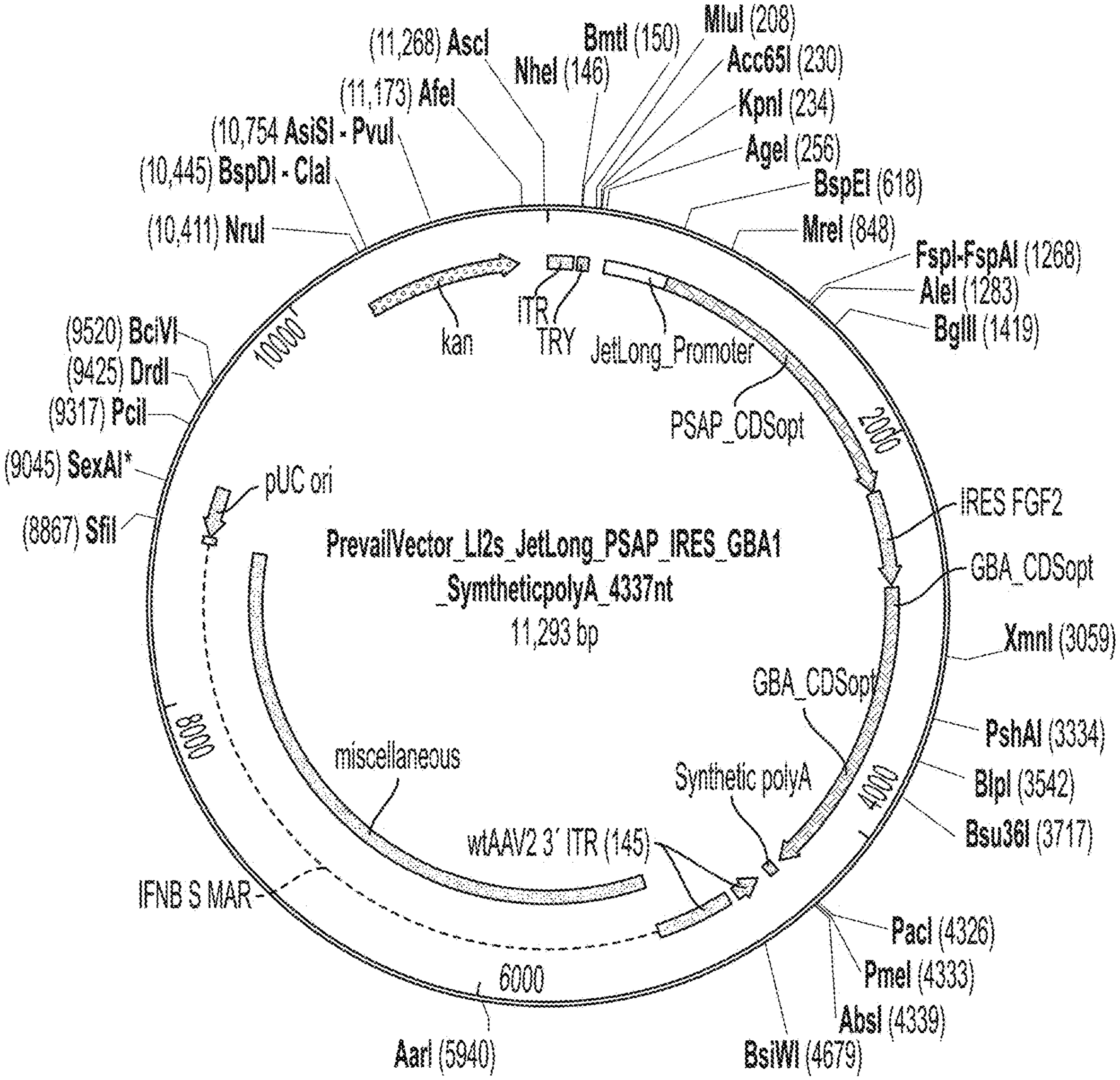
FIG. 6 is a schematic depicting one embodiment of a vector comprising an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

| Disease | Associated genes |
|---|---|
| Alzheimer's disease | APP, PSEN1, PSEN2, APOE |
| Parkinson's disease | LRRK2, PARK7, PINK1, PRKN, SNCA, GBA, UCHL1, ATP13A2, VPS35 |
| Huntington's disease | HTT |
| Amyotrophic lateral sclerosis | ALS2, ANG, ATXN2, C9orf72, CHCHD10, CHMP2B, DCTN1, ERBB4, FIG4, FUS, HNRNPA1, MATR3, NEFH, OPTN, PFN1, PRPH, SETX, SIGMAR1, SMN1, SOD1, SPG11, SQSTM1, TARDBP, TBK1, TRPM7, TUBA4A, UBQLN2, VAPB, VCP |
| Batten disease (Neuronal ceroid lipofunscinosis) | PPT1, TPP1, CLN3, CLN5, CLN6, MFSD8, CLN8, CTSD, DNAJC5, CTSF, ATP13A2, GRN, KCTD7 |
| Friedreich's ataxia | FXN |
| Lewy body disease | APOE, GBA, SNCA, SNCB |
| Spinal muscular atrophy | SMN1, SMN2 |
| Multiple sclerosis | CYP2781, HLA-DRB1, IL2RA, IL7R, TNFRSF1A |
| Prion disease (Creutzfeldt-Jakob disease, Fatal familial insomnia, Gertsmann-Straussler-Scheinker syndrome, Variably protease-sensitive prionopathy) | PRNP |

TABLE 13

Examples of synucleinopathies

| Disease | Associated genes |
|---|---|
| Parkinson's disease | LRRK2, PARK7, PINK1, PRKN, SNCA, GBA, UCHL1, ATP13A2, VPS35 |
| Dementia with Lewy bodies | APOE, GBA, SNCA, SNCB |
| Multiple system atrophy | COQ2, SNCA |

TABLE 14

Examples of tauopathies

| Disease | Associated genes |
|---|---|
| Alzheimer's disease | APP, PSEN1, PSEN2, APOE |
| Primary age-related tauopathy | MAPT |
| Progressive supranuclear palsy | MAPT |
| Corticobasal degeneration | MAPT, GRN, C9orf72, VCP, CHMP2B, TARDBP, FUS |
| Frontotemporal dementia with parkinsonism-17 | MAPT |
| Subacute sclerosing panencephalitis | SCN1A |
| Lytico-Bodig disease | |
| Gangioglioma, gangliocytoma | |
| Meningioangiomatosis | |
| Postencephalitic parkinsonism | |
| Chronic traumatic encephalopathy | |

TABLE 15

Examples of lysosomal storage diseases

| Disease | Associated genes |
|---|---|
| Niemann-Pick disease | NPC1, NPC2, SMPD1 |
| Fabry disease | GLA |
| Krabbe disease | GALC |
| Gaucher disease | GBA |
| Tach-Sachs disease | HEXA |
| Metachromatic leukodystrophy | ARSA, PSAP |
| Farber disease | ASAH1 |
| Galactosialidosis | CTSA |

TABLE 15-continued

Examples of lysosomal storage diseases

| Disease | Associated genes |
|---|---|
| Schindler disease | NAGA |
| GM1 gangliosidosis | GLB1 |
| GM2 gangliosidosis | GM2A |
| Sandhoff disease | HEXB |
| Lysosomal acid lipase deficiency | LIPA |
| Multiple sulfatase deficiency | SUMF1 |
| Mucopolysaccharidosis Type I | IDUA |
| Mucopolysaccharidosis Type II | IDS |
| Mucopolysaccharidosis Type III | GNS, HGSNAT, NAGLU, SGSH |
| Mucopolysaccharidosis Type IV | GALNS, GLB1 |
| Mucopolysaccharidosis Type VI | ARSB |
| Mucopolysaccharidosis Type VII | GUSB |
| Mucopolysaccharidosis Type IX | HYAL1 |
| Mucolipidosis Type II | GNPTAB |
| Mucolipidosis Type III alpha/beta | GNPTAB |
| Mucolipidosis Type III gamma | GNPTG |
| Mucolipidosis Type IV | MCOLN1 |
| Neuronal ceroid lipofuscinosis | PPT1, TPP1, CLN3, CLN5, CLN6, MFSD8, CLN8, CTSD, DNAJC5, CTSF, ATP13A2, GRN, KCTD7 |
| Alpha-mannosidosis | MAN2B1 |
| Beta-mannosidosis | MANBA |
| Aspartylglucosaminuria | AGA |
| Fucosidosis | FUCA1 |

Example 14: Automated Western Assay for Detection of Progranulin in Cerebrospinal Fluid The purpose of this experiment was to quantify the protein levels of progranulin (PGRN) in cerebrospinal fluid (CSF) using the ProteinSimple (San Jose, CA) Automated Western platform Jess. This test method may be used to analyze non-human primate (NHP) CSF samples. To determine the expression levels of human progranulin protein, the transgene product of PR006A, CSF samples from non-human primate subjects were analyzed on a Simple Western™ (Jess) platform using an antibody that specifically detects human progranulin protein. The Simple Western™ platform is a capillary-based automated Western blot immunoassay platform, where all steps, including protein separation, immunoprobing, washing, and detection by chemiluminescence occur in a capillary cartridge. Samples (at 4-fold dilution) and primary antibody to human progranulin (Adipogen PG-359-7, at 10-fold dilution), in addition to secondary antibodies and all buffers manufactured by ProteinSimple, were loaded onto a customized cartridge which was run on the Jess platform. Semi-quantitative data analysis occurred automatically after each run was completed, where parameters such as signal intensity, peak area, and signal-to-noise ratio were calculated using the Jess instrument. For each individual sample, the level of progranulin was measured as the peak area of immunoreactivity to the antibody. All analyses were performed with blinded samples.

The assay described here was performed on CSF samples from a non-human primate animal study. CSF samples were tested for presence and levels of progranulin protein to study efficacy of gene therapy using an rAAV construct (PR006; see FIG. 64) encoding progranulin (PGRN) protein. In this study, either the excipient or PR006 were delivered at low dose of PR006 ($1.8\times10^{10}$ vg/g brain weight) or high dose of PR006 ($1.8\times10^{11}$ vg/g brain weight) by intra-cisterna magna (ICM) injection into NHP animals. Each group consisted of 3 animals. Nine NHP animals were sacrificed at day 180 post-infection (Table 16), and CSF samples were analyzed using the Jess-based assay.

TABLE 16

NHP animal summary with grouping and dosing

| Group | Dose of PR006 (vg/g brain weight) | Number of animals Necropsy (Day 180) |
|---|---|---|
| 1 | 0 | 2 M/1 F |
| 2 | $1.8\times10^{10}$ | 2 M/1 F |
| 3 | $1.8\times10^{11}$ | 2 M/1 F |

TABLE 17

Materials for automated Western assay

| Material Description | Manufacturer | Item Number |
|---|---|---|
| 12-230 kDa Jess Separation Module, 25 capillary cartridges | ProteinSimple | SM-W004 |
| EZ Standard Pack 1, 12-230 kDa | ProteinSimple | PS-ST01EZ-8 |
| Anti-mouse detection module for Jess | ProteinSimple | DM-002 |
| Progranulin monoclonal antibody (human), clone PG359-7 (primary antibody) | Adipogen | AG-20A-0052-C100 |

Note:
all reagents should be allowed to warm to room temperature prior to opening vials.

The following procedures were followed in performing this method:

Preparation of Stock Solutions:

1. Prepare 400 mM DTT solution by adding 40 μL of water to clear tube in the separation module EZ Standard Pack. Mix gently.
2. To prepare master mix, add 20 μL of 10× sample buffer and 20 μL of 400 mM DTT into the EZ pink master mix tube. Mix gently.
3. To prepare the biotinylated ladder, Pipette 20 μL of water into the EZ clear biotinylated ladder tube with pink pellet. Mix gently.
4. Prepare luminol and peroxide mix by adding equal amounts of each. For one run, add 200 μL of luminol to 200 μL of peroxide.
5. Prepare primary antibody dilution (10 fold-dilution) by mixing 25 μL of primary antibody and 225 μL of antibody diluent 2.

Preparation of Samples:

1. Samples are diluted in 0.1× sample buffer. Prepare 0.1× sample buffer by adding 10 μL of 10× sample buffer into 990 μL of water.
2. Dilute samples as necessary. For example, NHP CSF samples were diluted 4-fold prior to addition of master mix. Add 5 μL of NHP CSF to 15L 0.1× sample buffer.
3. Prepare samples by adding 1× of master mix to 4× of sample. To run technical duplicates, prepare a total of 15 μL of sample plus master mix per sample. For example, add 3 μL of master mix to 12 μL of diluted sample. Mix gently.
4. Boil samples at 95° C. for 5 minutes.
5. Spin down samples briefly using desktop mini-centrifuge. Vortex before loading the sample.

Load Reagents and Samples into Cartridge:

1. Pipette all samples according to cartridge map.
   a. Pipette 15 μL of luminol+peroxide mix to each well in lane E.
   b. Pipette 10 μL of streptavidin to first well in lane D.
   c. Pipette 10 μL of secondary antibody to remaining 24 wells in lane D.
   d. Pipette 10 μL of antibody dilution to first well in lane C.
   e. Pipette 10 μL of primary antibody dilution to remaining 24 wells in lane C.
   f. Pipette 10 μL of antibody diluent to all wells in lane B.
   g. Pipette 10 μL of prepared EZ ladder to first well in lane A.
   h. Pipette 5 μL of sample and master mix solution to duplicate lanes in lane A.
2. Spin cartridge at room temperature at 2500RPM for 5 minutes.

Load Capillaries and Cartridge into Instrument:

1. Load capillaries into slot. Make sure light turns blue.
2. Load spun cartridge into instrument.
3. Press start button after blue light stops blinking at the instrument.

The assay system suitability was considered acceptable if CV (coefficient of variance) percentage for duplicates was ≤30%.

Before the assay was used to detect progranulin in NHP CSF samples, the assay was tested as follows. Qualification of Jess assays included assessment of dilution linearity, selectivity and specificity. Normal CSF samples from BioIVT were used to determine dilution linearity of Jess assay. CSF samples from fronto-temporal dementia (FTD) patients with PGRN mutation (obtained from National Centralized Repository for Alzheimer's Disease and Related Dementias (NCRAD; Indianapolis, Indiana)) were used to determine selectivity and specificity of Jess assay.

TABLE 18

Results summary

| | Elements | Acceptance Criteria | Results |
|---|---|---|---|
| Dilution Linearity | Investigate endogenous PGRN levels in naïve CSF samples (BioIVT). Conduct an analysis of blank sample in the matrix. Minimal required dilution (MRD) is determined by diluting a neat matrix in 2-fold serial dilution. If endogenous levels of PGRN are too low in matrix, dilutions will be performed using spiked matrix. | The MRD is defined as the lowest dilution required where a linear raw signal or concentration is observed. Within the linear range, the corrected observed concentrations should be ±30% of the MRD. | Pass All tested matrices passed by having a linear dilution range with ±30% of the MRD (see Results and Discussion section, Dilution Linearity. |
| Selectivity and Specificity | Investigate PGRN levels in FTD patient CSF samples. | The MRD is defined through Dilution Linearity test. | Pass All tested matrices passed by having a % CV of technical replicate with 20% (see Results and Discussion section, Selectivity and Specificity. |

Results and Discussion

Dilution Linearity

Dilution linearity of PGRN protein detected by Jess was tested in CSF samples from commercially available (BioIVT) normal individuals. Endogenous levels of PGRN in CSF samples were measured to determine dilution linearity. Two individuals were tested in 2-fold serial dilution that ranges from 2 to 64 fold dilution.

Table 19 reported the peak area of PGRN protein at 58 kDa detected by Jess and the 00 differences of each dilution from 16-fold dilution. Results within the linearity range are in bold font (within 100±30% difference). Dilution linearity was established to be within 4 to 16 fold dilution.

TABLE 19

Dilution linearity in CSF samples

| | CSF #1 | | CSF #2 | |
|---|---|---|---|---|
| Dilution factor | 58 kDa Peak Area (Dilution Adjusted) | % Difference | 58 kDa Peak Area (Dilution Adjusted) | % Difference |
| 1:2 | 3915099 | −41.2 | 6392991 | −38.8 |
| 1:4 | 6040885 | −9.2 | 8020821 | −23.2 |
| 1:8 | 5773987 | −13.3 | 12615004 | 20.8 |
| 1:16 | 6656474 | 0.0 | 10446186 | 0.0 |
| 1:32 | 8911479 | 33.9 | 11782404 | 12.8 |
| 1:64 | 12056943 | 81.1 | 6795118 | −35.0 |

In summary, all of the tested matrices had an acceptable linear range that passed the acceptance criteria of a % difference that is 0±30%, though the size of the range and amount of dilution varied between matrices. Sample linearity MRD was established to be 4-fold dilution. Dilution linearity was established to be within 4- to 16-fold dilution. A summary of the MIRD and linear dilution range that passes acceptance criteria for CSF is depicted in Table 20.

TABLE 20

| MRD and linear dilution range of the CSF | | |
|---|---|---|
| Tissue | Linearity MRD | Linear Dilution Range |
| CSF | 1:4 | 1:4-1:16 |

Selectivity and Specificity

Selectivity and specificity of PGRN protein detected by Jess were tested in CSF samples from the PR006 FTD patient samples from NCRAD. Three groups (group A, B, and C) of CSF samples were collected form heterozygous FTD patients (group A), familial non-carrier (group B or C), and normal individuals (group B or C). Six samples were analyzed for each group. The groups of samples are listed in Table 16 FTD Patient CSF sample information.

Figure 55:
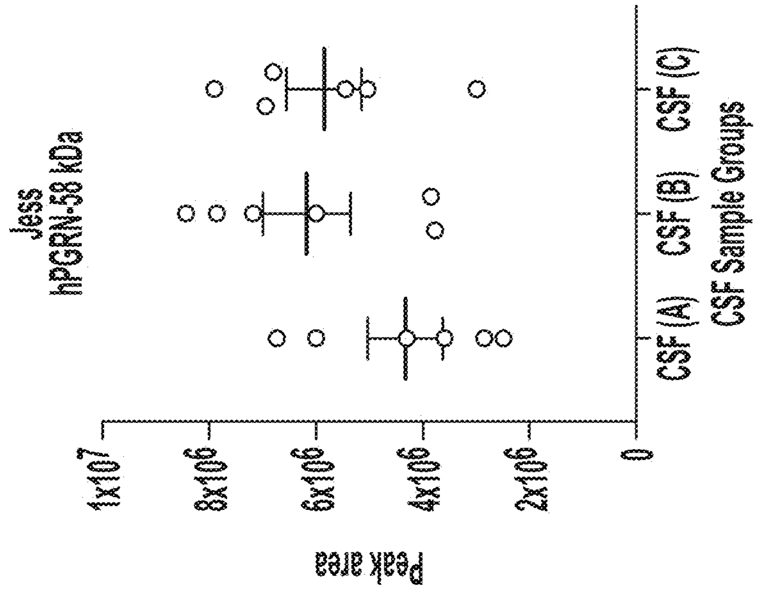
FIG. 55 is a graph showing selectivity and specificity results for the automated Western Jess assay. Progranulin protein levels in FTD patient CSF samples were detected at 58 kDa by Jess. Group (A): heterozygous FTD patients and groups (B) and (C): familial non-carrier or normal individuals. Data are presented as mean±standard error of the mean (SEM). SEM values are shown as vertical error bars.
Figure 57:
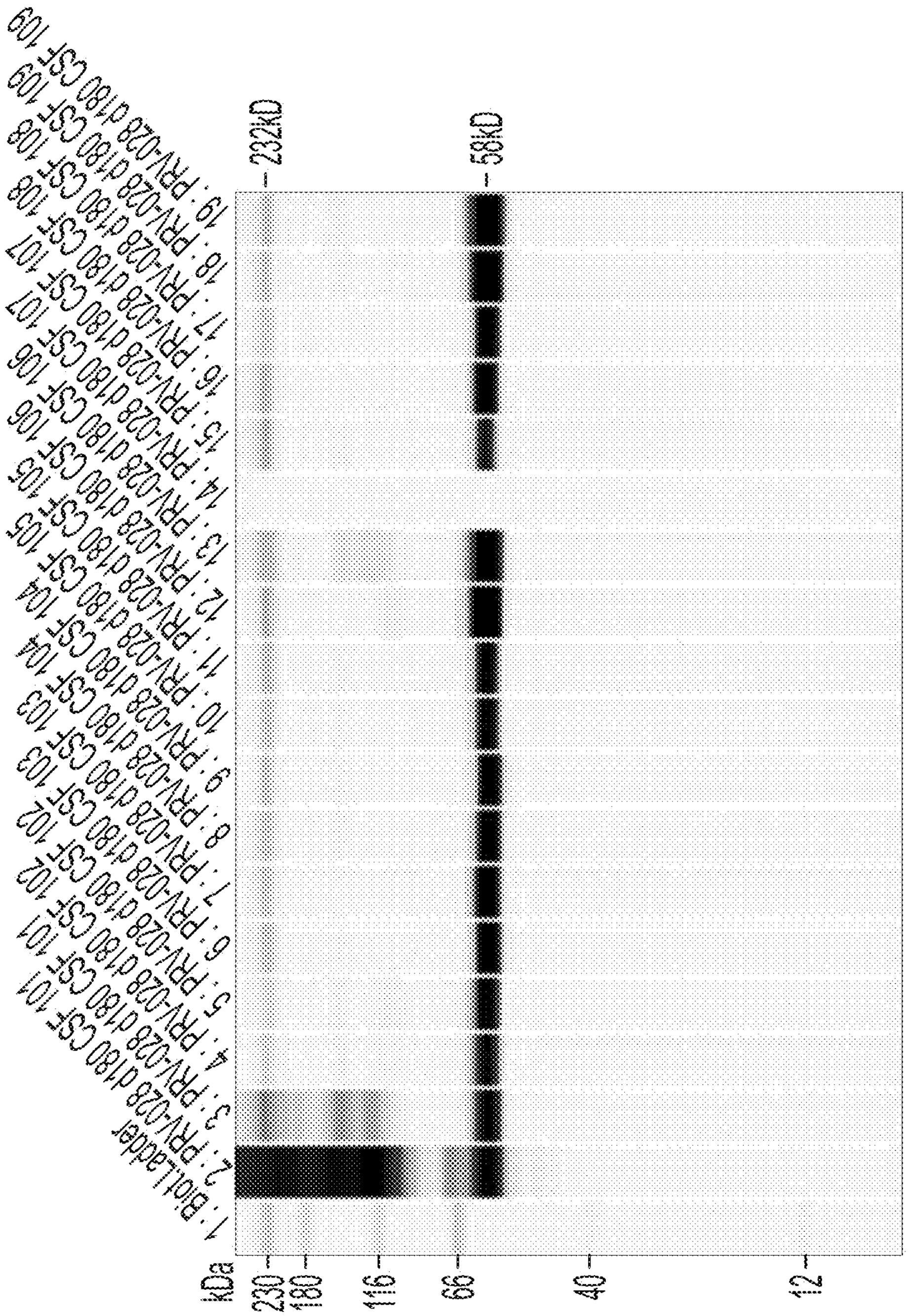
FIG. 57 is a gel image of each CSF sample run in duplicate on the Jess automated Western platform. Samples were analyzed at a 4-fold dilution using the primary antibody Adipogen PG-359-7. The first lane is the molecular weight standards, and on the right is the band identification used to calculate the immunoreactivities reported in Example 14.
Figure 58B:
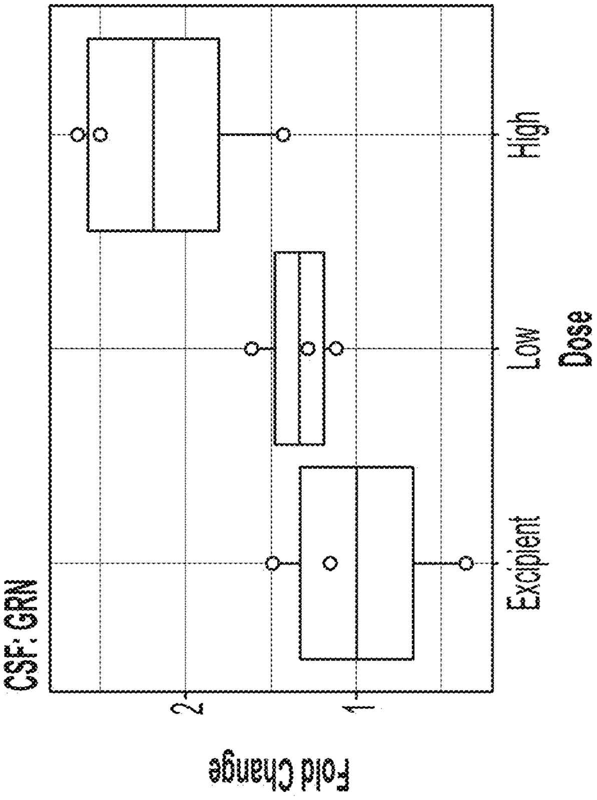
FIG. 58A-FIG. 58B are a series of plots showing the measurement of human PGRN expression levels. Human PGRN expression levels were determined in non-human primate (NHP) CSF samples that were collected at Day 180, using a Simple Western™ (Jess) analysis. CSF from NHPs treated with excipient ("Excipient"), low dose of PR006A ($6.5\times10^{9}$ vg/g brain weight; "low") or high dose of PR006 ($6.5\times10^{10}$ vg/g brain weight; "high") were analyzed. The data is expressed as average immunoreactivity peak area (FIG. 58A), or fold change over excipient-treated animals (FIG. 58B). Each dot represents a single CSF sample from one NHP (mean of the technical duplicate) and the box represents the mean value +/− standard error of the three individual NHPs.
Figure 58A:
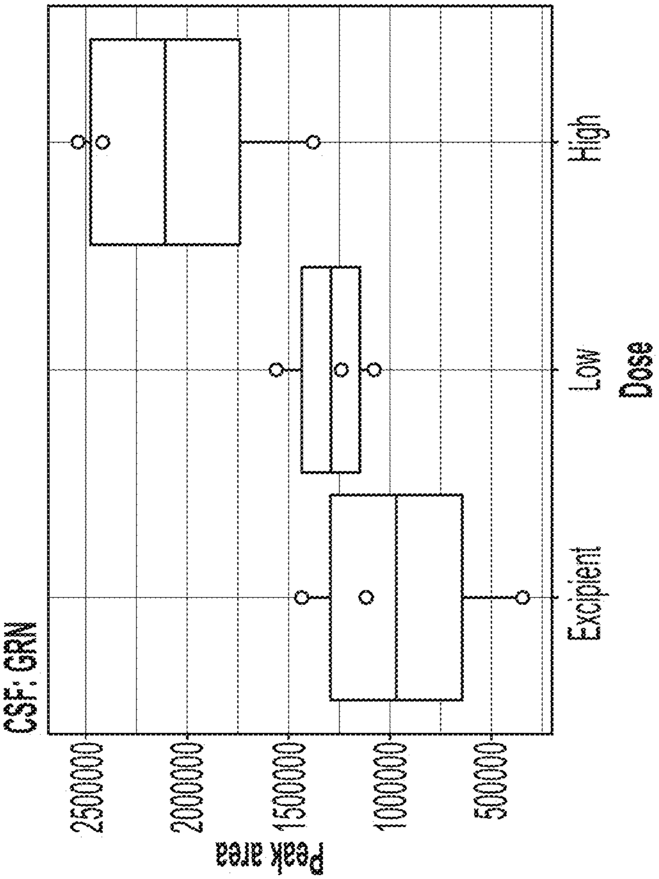

CSF samples were 4-fold diluted in 0.1× sample buffer provided by ProteinSimple and tested in technical duplicates. Samples duplicates with result % CV more than 20% were re-analyzed. Results with % CV less than 20% were reported in Table 22. Table 22 reported the peak area of PGRN protein at 58 kDa detected by Jess and the % CV between duplicates. Results showed about two fold higher of PGRN levels in group B and C as compared to group A, which indicates the selectivity and specificity of Jess assay in determine PGRN levels for CSF samples (FIG. 55).

TABLE 21

| FTD patient CSF sample information | | | | | | | |
|---|---|---|---|---|---|---|---|
| Barcode | Alternate MRN | Visit | Kit Number | Specimen Type | Box Name | Position | Group |
| 0003355598 | ST-20000108 | Cycle 2-CSF | 257282 | CSF | 27488 CSF | 1 | C |
| 0004777338 | ST-20000118 | Cycle 2-CSF | 267633 | CSF | 27488 CSF | 2 | C |
| 0004777329 | ST-20000306 | Cycle 1-CSF | 260551 | CSF | 27488 CSF | 3 | A |
| 0004777326 | ST-20000328 | Cycle 2-CSF | 260544 | CSF | 27488 CSF | 4 | C |
| 0004777335 | ST-20000386 | Cycle 1-CSF | 267110 | CSF | 27488 CSF | 5 | A |
| 0004777345 | ST-20000590 | Cycle 2-CSF | 267859 | CSF | 27488 CSF | 6 | B |
| 0004777332 | ST-20000621 | Cycle 1-CSF | 266413 | CSF | 27488 CSF | 7 | B |
| 0004628923 | ST-20000757 | Cycle 1-CSF | 269817 | CSF | 27488 CSF | 8 | B |
| 0004695103 | ST-20001142 | Cycle 1-CSF | 308149 | CSF | 27488 CSF | 9 | A |
| 0004074629 | ST-20000107 | Cycle 2-CSF | 258212 | CSF | 27488 CSF | 10 | C |
| 0003358475 | ST-20000110 | Cycle 2-CSF | 258210 | CSF | 27488 CSF | 11 | C |
| 0003358463 | ST-20000274 | Cycle 2-CSF | 257292 | CSF | 27488 CSF | 12 | A |
| 0004788828 | ST-20000309 | Cycle 2-CSF | 303093 | CSF | 27488 CSF | 13 | C |
| 0003358781 | ST-20000615 | Cycle 1-CSF | 257278 | CSF | 27488 CSF | 14 | B |
| 0003358793 | ST-20000616 | Cycle 1-CSF | 257305 | CSF | 27488 CSF | 15 | A |
| 0004777321 | ST-20000637 | Cycle 1-CSF | 257307 | CSF | 27488 CSF | 16 | B |
| 0004777341 | ST-20000768 | Cycle 1-CSF | 267857 | CSF | 27488 CSF | 17 | B |
| 0004695106 | ST-20001165 | Cycle 1-CSF | 317396 | CSF | 27488 CSF | 18 | A |

TABLE 22

| Selectivity and specificity results | | | |
|---|---|---|---|
| Groups | Sample Barcode | 58 kD Peak Area (Dilution Adjusted) | % CV |
| Group (A) | 0004777329 | 2838645 | 5.08 |
| Heterozygous | 0004777335 | 4293344 | 1.20 |
| FTD patients | 0004695103 | 6738165 | 1.08 |
| | 0003358463 | 3594249 | 11.10 |
| | 0003358793 | 5992434 | 2.49 |
| | 0004695106 | 2472462 | 10.40 |
| Group (B) | 0004777345 | 3836185 | 11.18 |
| Normal or | 0004777332 | 6006224 | 3.05 |
| familial non- | 0004628923 | 3758940 | 1.44 |
| carrier | 0003358781 | 7860294 | 17.08 |
| | 0004777321 | 7187172 | 0.69 |
| | 0004777341 | 8450410 | 0.50 |
| Group (C) | 0003355598 | 2981005 | 1.70 |
| Normal or | 0004777338 | 6803428 | 0.18 |
| familial non- | 0004777326 | 5030695 | 3.56 |
| carrier | 0004074629 | 5448863 | 3.47 |
| | 0003358475 | 7892529 | 1.17 |
| | 0004788828 | 6944800 | 1.85 |

Figure 56:
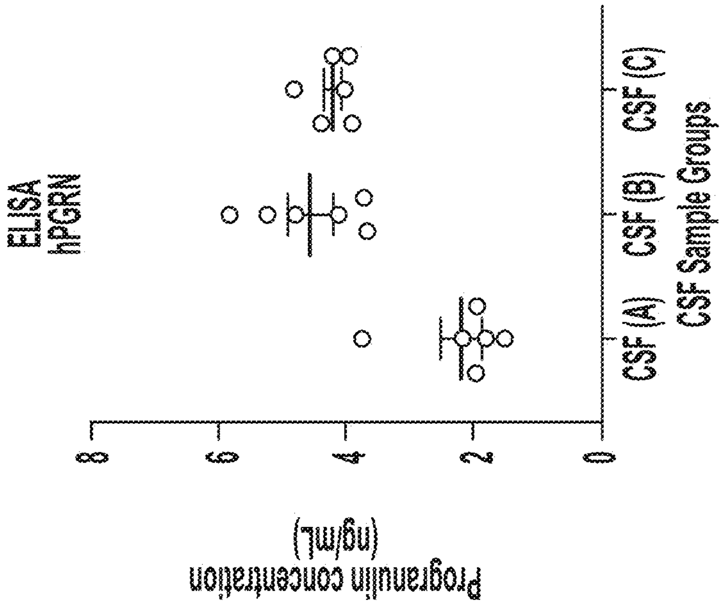
FIG. 56 is a graph showing Progranulin levels in FTD patient CSF samples detected by ELISA. Group (A): heterozygous FTD patients and groups (B) and (C): familial non-carrier or normal individuals. Data are presented as mean±standard error of the mean (SEM). SEM values are shown as vertical error bars.

CSF samples from FTD patient study (Table 21) were also analyzed with a human PGRN ELISA kit (Adipogen, AG-45A-0018YEK-KI01). Results from ELISA (FIG. 56) showed similar trends of PGRN levels between groups as Jess and demonstrated the Jess assay is suitable to use for the assessment of PGRN levels in CSF samples.

In conclusion, this ProteinSimple Automated Western Jess assay was determined to be suitable to use for the assessment of PGRN levels in NUP CSF samples.

Jess data for NHP CSF samples is shown in Table 23. Each sample represents the average across two technical replicates. The peak area for 58 kD band in the sample lane is reported. Data is presented as mean peak area of technical replicate and dilution folds adjusted.

TABLE 23

Jess data for NHP CSF samples

| Sample ID | Dose Group | Peak area (58 kD) |
|---|---|---|
| PRV-028 d180 CSF 101 | Low dose | 4944754 |
| PRV-028 d180 CSF 102 | Control | 4449066 |
| PRV-028 d180 CSF 103 | Low dose | 6222881 |
| PRV-028 d180 CSF 104 | High dose | 5499901 |
| PRV-028 d180 CSF 105 | Low dose | 4293853 |
| PRV-028 d180 CSF 106 | High dose | 10149400 |
| PRV-028 d180 CSF 107 | Control | 1360173 |
| PRV-028 d180 CSF 108 | Control | 5742081 |
| PRV-028 d180 CSF 109 | High dose | 9658597 |

The goal of this assay was to confirm the level of progranulin (PGRN) protein expression levels following the transduction of PR006 in tissue regions of interest for the NHP study. This was done using an automated Western platform, in which progranulin protein was detected using a monoclonal antibody. Progranulin expression was measurable in CSF in both control and PR006-treated NHP; the assay does not differentiate between endogenous progranulin protein and PR006A-induced progranulin protein.

This Application incorporates by reference the contents of the following documents in their entirety: International PCT Application Publication No. WO 2019/070893; International PCT Application Publication No. WO 2019/070891; U.S. Provisional Application Ser. No. 62/567,296, filed Oct. 3, 2017, entitled "GENE THERAPIES FOR LYSOSOMAL DISORDERS"; 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2017, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

Each of the U.S. patents, U.S. patent application publications, U.S. patent applications, foreign patents, foreign patent applications and non-patent publications referred to in this application is incorporated herein by reference, in its entirety.

SEQUENCES

In some embodiments, an expression cassette encoding one or more gene products (e.g., a first, second and/or third gene product) comprises or consists of (or encodes a peptide having) a sequence set forth in any one of SEQ ID NOs: 1-91. In some embodiments, a gene product is encoded by a portion (e.g., fragment) of any one of SEQ ID NOs: 1-91.

NUMBERED EMBODIMENTS

Notwithstanding the appended claims, the disclosure sets forth the following numbered embodiments:

1. An isolated nucleic acid comprising an expression construct encoding a Gcase protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the Gcase protein is encoded by a codon-optimized nucleic acid sequence.
2. The isolated nucleic acid of embodiment 1, wherein the Gcase protein comprises the amino acid sequence set forth in SEQ ID NO: 14 or a portion thereof.
3. The isolated nucleic acid of embodiment 1 or 2, wherein the Gcase protein is encoded by a codon-optimized nucleic acid sequence, optionally the nucleic acid sequence set forth in SEQ ID NO: 15.
4. The isolated nucleic acid of any one of embodiments 1 to 3, wherein the modified "D" region is a "D" sequence located on the outside of the ITR relative to the expression construct.
5. The isolated nucleic acid of any one of embodiments 1 to 4, wherein the ITR comprising the modified "D" sequence is a 3' ITR.
6. The isolated nucleic acid of any one of embodiments 1 to 5, further comprising a TRY sequence, optionally wherein the TRY sequence is set forth in SEQ ID NO: 28.
7. An isolated nucleic acid comprising an expression construct encoding a prosaposin protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the prosaposin protein is encoded by a codon-optimized nucleic acid sequence.
8. The isolated nucleic acid of embodiment 7, wherein the prosaposin protein comprises the amino acid sequence set forth in SEQ ID NO: 16 or a portion thereof.
9. The isolated nucleic acid of embodiment 7 or 8, wherein the prosaposin protein is encoded by a codon-optimized nucleic acid sequence, optionally the nucleic acid sequence set forth in SEQ ID NO: 17.
10. The isolated nucleic acid of any one of embodiments 7 to 9, wherein the modified "D" region is a "D" sequence located on the outside of the ITR relative to the expression construct.
11. The isolated nucleic acid of any one of embodiments 7 to 10, wherein the ITR comprising the modified "D" sequence is a 3' ITR.
12. The isolated nucleic acid of any one of embodiments 7 to 11, further comprising a TRY sequence, optionally wherein the TRY sequence is set forth in SEQ ID NO: 28.
13. An isolated nucleic acid comprising an expression construct encoding a SCARB2 protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the SCARB2 protein is encoded by a codon-optimized nucleic acid sequence.
14. The isolated nucleic acid of embodiment 13, wherein the SCARB2 protein comprises the amino acid sequence set forth in SEQ ID NO: 18 or a portion thereof.
15. The isolated nucleic acid of embodiment 13 or 14, wherein the SCARB2 protein is encoded by a codon-optimized nucleic acid sequence or the nucleic acid sequence set forth in SEQ ID NO: 19.
16. The isolated nucleic acid of any one of embodiments 13 to 15, wherein the modified "D" region is a "D" sequence located on the outside of the ITR relative to the expression construct.
17. The isolated nucleic acid of any one of embodiments 13 to 16, wherein the ITR comprising the modified "D" sequence is a 3' ITR.
18. The isolated nucleic acid of any one of embodiments 13 to 17, further comprising a TRY sequence, optionally wherein the TRY sequence is set forth in SEQ ID NO: 28.
19. An isolated nucleic acid comprising an expression construct encoding a GBA2 protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the GBA2 protein is encoded by a codon-optimized nucleic acid sequence.
20. The isolated nucleic acid of embodiment 19, wherein the GBA2 protein comprises the amino acid sequence set forth in SEQ ID NO: 30 or a portion thereof.

21. The isolated nucleic acid of embodiment 19 or 20, wherein the GBA2 protein is encoded by a codon-optimized nucleic acid sequence or the nucleic acid sequence set forth in SEQ ID NO: 31.

22. The isolated nucleic acid of any one of embodiments 19 to 21, wherein the modified "D" region is a "D" sequence located on the outside of the ITR relative to the expression construct.

23. The isolated nucleic acid of any one of embodiments 19 to 22, wherein the ITR comprising the modified "D" sequence is a 3' ITR.

24. The isolated nucleic acid of any one of embodiments 19 to 23, further comprising a TRY sequence, optionally wherein the TRY sequence is set forth in SEQ ID NO: 28.

25. An isolated nucleic acid comprising an expression construct encoding a GALC protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the GALC protein is encoded by a codon-optimized nucleic acid sequence.

26. The isolated nucleic acid of embodiment 25, wherein the GALC protein comprises the amino acid sequence set forth in SEQ ID NO: 33 or a portion thereof.

27. The isolated nucleic acid of embodiment 25 or 26, wherein the GALC protein is encoded by a codon-optimized nucleic acid sequence or the nucleic acid sequence set forth in SEQ ID NO: 34.

28. The isolated nucleic acid of any one of embodiments 25 to 27, wherein the modified "D" region is a "D" sequence located on the outside of the ITR relative to the expression construct.

29. The isolated nucleic acid of any one of embodiments 25 to 28, wherein the ITR comprising the modified "D" sequence is a 3' ITR.

30. The isolated nucleic acid of any one of embodiments 25 to 29, further comprising a TRY sequence, optionally wherein the TRY sequence is set forth in SEQ ID NO: 28.

31. An isolated nucleic acid comprising an expression construct encoding a CTSB protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the CTSB protein is encoded by a codon-optimized nucleic acid sequence.

32. The isolated nucleic acid of embodiment 31, wherein the CTSB protein comprises the amino acid sequence set forth in SEQ ID NO: 30 or a portion thereof.

33. The isolated nucleic acid of embodiment 31 or 32, wherein the CTSB protein is encoded by a codon-optimized nucleic acid sequence or the nucleic acid sequence set forth in SEQ ID NO: 36.

34. The isolated nucleic acid of any one of embodiments 31 to 33, wherein the modified "D" region is a "D" sequence located on the outside of the ITR relative to the expression construct.

35. The isolated nucleic acid of any one of embodiments 31 to 34, wherein the ITR comprising the modified "D" sequence is a 3' ITR.

36. The isolated nucleic acid of any one of embodiments 31 to 35, further comprising a TRY sequence, optionally wherein the TRY sequence is set forth in SEQ ID NO: 28.

37. An isolated nucleic acid comprising an expression construct encoding a SMPD1 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the SMPD1 protein is encoded by a codon-optimized nucleic acid sequence.

38. The isolated nucleic acid of embodiment 37, wherein the SMPD1 protein comprises the amino acid sequence set forth in SEQ ID NO: 37 or a portion thereof.

39. The isolated nucleic acid of embodiment 37 or 38, wherein the SMPD1 protein is encoded by a codon-optimized nucleic acid sequence or the nucleic acid sequence set forth in SEQ ID NO: 38.

40. The isolated nucleic acid of any one of embodiments 37 to 39, wherein the modified "D" region is a "D" sequence located on the outside of the ITR relative to the expression construct.

41. The isolated nucleic acid of any one of embodiments 37 to 40, wherein the ITR comprising the modified "D" sequence is a 3' ITR.

42. The isolated nucleic acid of any one of embodiments 37 to 41, further comprising a TRY sequence, optionally wherein the TRY sequence is set forth in SEQ ID NO: 28.

43. An isolated nucleic acid comprising an expression construct encoding a GCH1 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the GCH1 protein is encoded by a codon-optimized nucleic acid sequence.

44. The isolated nucleic acid of embodiment 43, wherein the GCH1 protein comprises the amino acid sequence set forth in SEQ ID NO: 45 or a portion thereof.

45. The isolated nucleic acid of embodiment 43 or 44, wherein the GCH1 protein is encoded by a codon-optimized nucleic acid sequence or the nucleic acid sequence set forth in SEQ ID NO: 46.

46. The isolated nucleic acid of any one of embodiments 43 to 45, wherein the modified "D" region is a "D" sequence located on the outside of the ITR relative to the expression construct.

47. The isolated nucleic acid of any one of embodiments 43 to 46, wherein the ITR comprising the modified "D" sequence is a 3' ITR.

48. The isolated nucleic acid of any one of embodiments 43 to 47, further comprising a TRY sequence, optionally wherein the TRY sequence is set forth in SEQ ID NO: 28.

49. An isolated nucleic acid comprising an expression construct encoding a RAB7L protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the RAB7L protein is encoded by a codon-optimized nucleic acid sequence.

50. The isolated nucleic acid of embodiment 49, wherein the RAB7L protein comprises the amino acid sequence set forth in SEQ ID NO: 47 or a portion thereof.

51. The isolated nucleic acid of embodiment 49 or 50, wherein the RAB7L protein is encoded by a codon-optimized nucleic acid sequence or the nucleic acid sequence set forth in SEQ ID NO: 48.

52. The isolated nucleic acid of any one of embodiments 49 to 51, wherein the modified "D" region is a "D" sequence located on the outside of the ITR relative to the expression construct.

53. The isolated nucleic acid of any one of embodiments 49 to 52, wherein the ITR comprising the modified "D" sequence is a 3' ITR.

54. The isolated nucleic acid of any one of embodiments 49 to 53, further comprising a TRY sequence, optionally wherein the TRY sequence is set forth in SEQ ID NO: 28.

55. An isolated nucleic acid comprising an expression construct encoding a VPS35 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the VPS35 protein is encoded by a codon-optimized nucleic acid sequence.

56. The isolated nucleic acid of embodiment 55, wherein the VPS35 protein comprises the amino acid sequence set forth in SEQ ID NO: 49 or a portion thereof.

57. The isolated nucleic acid of embodiment 55 or 56, wherein the VPS35 protein is encoded by a codon-optimized nucleic acid sequence or the nucleic acid sequence set forth in SEQ ID NO: 50.

58. The isolated nucleic acid of any one of embodiments 55 to 57, wherein the modified "D" region is a "D" sequence located on the outside of the ITR relative to the expression construct.

59. The isolated nucleic acid of any one of embodiments 55 to 58, wherein the ITR comprising the modified "D" sequence is a 3' ITR.

60. The isolated nucleic acid of any one of embodiments 55 to 59, further comprising a TRY sequence, optionally wherein the TRY sequence is set forth in SEQ ID NO: 28.

61. An isolated nucleic acid comprising an expression construct encoding a IL-34 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the IL-34 protein is encoded by a codon-optimized nucleic acid sequence.

62. The isolated nucleic acid of embodiment 61, wherein the IL-34 protein comprises the amino acid sequence set forth in SEQ ID NO: 55 or a portion thereof.

63. The isolated nucleic acid of embodiment 61 or 62, wherein the IL-34 protein is encoded by a codon-optimized nucleic acid sequence or the nucleic acid sequence set forth in SEQ ID NO: 56.

64. The isolated nucleic acid of any one of embodiments 61 to 63, wherein the modified "D" region is a "D" sequence located on the outside of the ITR relative to the expression construct.

65. The isolated nucleic acid of any one of embodiments 61 to 64, wherein the ITR comprising the modified "D" sequence is a 3' ITR.

66. The isolated nucleic acid of any one of embodiments 61 to 65, further comprising a TRY sequence, optionally wherein the TRY sequence is set forth in SEQ ID NO: 28.

67. An isolated nucleic acid comprising an expression construct encoding a TREM2 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the TREM2 protein is encoded by a codon-optimized nucleic acid sequence.

68. The isolated nucleic acid of embodiment 67, wherein the TREM2 protein comprises the amino acid sequence set forth in SEQ ID NO: 57 or a portion thereof.

69. The isolated nucleic acid of embodiment 67 or 68, wherein the TREM2 protein is encoded by a codon-optimized nucleic acid sequence or the nucleic acid sequence set forth in SEQ ID NO: 58.

70. The isolated nucleic acid of any one of embodiments 67 to 69, wherein the modified "D" region is a "D" sequence located on the outside of the ITR relative to the expression construct.

71. The isolated nucleic acid of any one of embodiments 67 to 70, wherein the ITR comprising the modified "D" sequence is a 3' ITR.

72. The isolated nucleic acid of any one of embodiments 67 to 71, further comprising a TRY sequence, optionally wherein the TRY sequence is set forth in SEQ ID NO: 28.

73. An isolated nucleic acid comprising an expression construct encoding a TMEM106B protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the TMEM106B protein is encoded by a codon-optimized nucleic acid sequence.

74. The isolated nucleic acid of embodiment 73, wherein the TMEM106B protein comprises the amino acid sequence set forth in SEQ ID NO: 63 or a portion thereof.

75. The isolated nucleic acid of embodiment 73 or 74, wherein the TMEM106B protein is encoded by a codon-optimized nucleic acid sequence or the nucleic acid sequence set forth in SEQ ID NO: 64.

76. The isolated nucleic acid of any one of embodiments 73 to 75, wherein the modified "D" region is a "D" sequence located on the outside of the ITR relative to the expression construct.

77. The isolated nucleic acid of any one of embodiments 73 to 76, wherein the ITR comprising the modified "D" sequence is a 3' ITR.

78. The isolated nucleic acid of any one of embodiments 73 to 77, further comprising a TRY sequence, optionally wherein the TRY sequence is set forth in SEQ ID NO: 28.

79. An isolated nucleic acid comprising an expression construct encoding a Progranulin (PGRN) protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the PGRN protein is encoded by a codon-optimized nucleic acid sequence.

80. The isolated nucleic acid of embodiment 79, wherein the PGRN protein comprises the amino acid sequence set forth in SEQ ID NO: 67 or a portion thereof.

81. The isolated nucleic acid of embodiment 79 or 80, wherein the PGRN protein is encoded by a codon-optimized nucleic acid sequence or the nucleic acid sequence set forth in SEQ ID NO: 68.

82. The isolated nucleic acid of any one of embodiments 79 to 81, wherein the modified "D" region is a "D" sequence located on the outside of the ITR relative to the expression construct.

83. The isolated nucleic acid of any one of embodiments 79 to 82, wherein the ITR comprising the modified "D" sequence is a 3' ITR.

84. The isolated nucleic acid of any one of embodiments 79 to 83, further comprising a TRY sequence, optionally wherein the TRY sequence is set forth in SEQ ID NO: 28.

85. An isolated nucleic acid comprising an expression construct encoding a first gene product and a second gene product, wherein each gene product independently is selected from the gene products, or portions thereof, set forth in Table 1.

86. The isolated nucleic acid of embodiment 85, wherein the first gene product is a Gcase protein, or a portion thereof.

87. The isolated nucleic acid of embodiment 85 or 86, wherein the second gene product is LIMP2 or a portion thereof, or Prosaposin or a portion thereof.

88. The isolated nucleic acid of any one of embodiments 85 to 87, further encoding an interfering nucleic acid (e.g., shRNA, miRNA, dsRNA, etc.), optionally wherein the interfering nucleic acid inhibits expression of α-Syn or TMEM106B.

89. The isolated nucleic acid of any one of embodiments 85 to 88, further comprising one or more promoters, optionally wherein each of the one or more promoters is independently a chicken-beta actin (CBA) promoter, a CAG promoter, a CD68 promoter, or a JeT promoter.

90. The isolated nucleic acid of any one of embodiments 85 to 89, further comprising an internal ribosomal entry site (IRES), optionally wherein the IRES is located between the first gene product and the second gene product.

91. The isolated nucleic acid of any one of embodiments 85 to 90, further comprising a self-cleaving peptide coding sequence, optionally wherein the self-cleaving peptide is T2A.

92. The isolated nucleic acid of any one of embodiments 85 to 91, wherein the expression construct comprises two adeno-associated virus (AAV) inverted terminal repeat (ITR) sequences flanking the first gene product and the second gene product, optionally wherein one of the ITR sequences lacks a functional terminal resolution site.

93. The isolated nucleic acid of embodiment 92, wherein at least one of the ITRs comprises a modified "D" region relative to a wild-type AAV2 ITR (SEQ ID NO: 29).

94. The isolated nucleic acid of embodiment 93, wherein the modified "D" region is a "D" sequence located on the outside of the ITR relative to the expression construct.

95. The isolated nucleic acid of embodiment 93 or 94, wherein the ITR comprising the modified "D" sequence is a 3' ITR.

96. The isolated nucleic acid of any one of embodiments 85 to 95, further comprising a TRY sequence, optionally wherein the TRY sequence is set forth in SEQ ID NO: 28.

97. An isolated nucleic acid having the sequence set forth in any one of SEQ ID NOs: 1 to 91.

98. A vector comprising the isolated nucleic acid of any one of embodiments 1 to 97.

99. The vector of embodiment 98, wherein the vector is a plasmid.

100. The vector of embodiment 98, wherein the vector is a viral vector, optionally wherein the viral vector is a recombinant AAV (rAAV) vector or a Baculovirus vector.

101. A composition comprising the isolated nucleic acid of any one of embodiments 1 to 97 or the vector of any one of embodiments 98 to 100.

102. A host cell comprising the isolated nucleic acid of any one of embodiments 1 to 97 or the vector of any one of embodiments 98 to 100.

103. A recombinant adeno-associated virus (rAAV) comprising:

(i) a capsid protein; and (ii) the isolated nucleic acid of any one of embodiments 1 to 97, or the vector of any one of embodiments 98 to 100.

104. The rAAV of embodiment 103, wherein the capsid protein is capable of crossing the blood-brain barrier, optionally wherein the capsid protein is an AAV9 capsid protein or an AAVrh.10 capsid protein.

105. The rAAV of embodiment 103 or 104, wherein the rAAV transduces neuronal cells and non-neuronal cells of the central nervous system (CNS).

106. A method for treating a subject having or suspected of having Parkinson's disease, the method comprising administering to the subject an isolated nucleic acid of any one of embodiments 1 to 97, the vector of any one of embodiments 98 to 100, the composition of embodiment 101, or the rAAV of any one of embodiments 103 to 105.

107. The method of embodiment 106, wherein the administration comprises direct injection to the CNS of the subject, optionally wherein the direct injection is intracerebral injection, intraparenchymal injection, intrathecal injection, intra-cisterna magna injection or any combination thereof.

108. The method of embodiment 107, wherein the direct injection to the CNS of the subject comprises convection enhanced delivery (CED).

109. The method of any one of embodiments 106 to 108, wherein the administration comprises peripheral injection, optionally wherein the peripheral injection is intravenous injection.

110. A method for treating a subject having or suspected of having fronto-temporal dementia with a GRN mutation, the method comprising administering to the subject a recombinant adeno-associated virus (rAAV) comprising:

(i) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (ii) an AAV9 capsid protein.

111. The method of embodiment 110, wherein the rAAV is administered to the subject at a dose ranging from about $1\times10^{13}$ vector genomes (vg) to about $7\times10^{14}$ vg.

112. The method of embodiment 110 or 111, wherein the rAAV is administered via an injection into the cisterna magna.

113. The method of any one of embodiments 110-112, wherein the promoter is a chicken beta actin (CBA) promoter.

114. The method of any one of embodiments 110-113, wherein the rAAV vector further comprises a cytomegalovirus (CMV) enhancer.

115. The method of any one of embodiments 110-114, wherein the rAAV vector further comprises a Woodchuck Hepatitis Virus Posttranscriptional Regulatory Element (WPRE).

116. The method of any one of embodiments 110-115, wherein the rAAV vector further comprises a Bovine Growth Hormone polyA signal tail.

117. The method of any one of embodiments 110-116, wherein the nucleic acid comprises two adeno-associated virus inverted terminal repeats (ITR) sequences flanking the expression construct.

118. The method of embodiment 117, wherein each ITR sequence is a wild-type AAV2 ITR sequence.

119. The method of any one of embodiments 110-118, wherein the rAAV vector further comprises a TRY region between the 5' ITR and the expression construct, wherein the TRY region comprises SEQ ID NO: 28.

120. A method for treating a subject having or suspected of having fronto-temporal dementia with a GRN mutation, the method comprising administering to the subject a rAAV comprising:

(i) a rAAV vector comprising a nucleic acid comprising, in 5' to 3' order:
(a) an AAV2 ITR;
(b) a CMV enhancer;
(c) a CBA promoter;
(d) a transgene insert encoding a PGRN protein, wherein the transgene insert comprises the nucleotide sequence of SEQ ID NO: 68;
(e) a WPRE;
(f) a Bovine Growth Hormone polyA signal tail; and
(g) an AAV2 ITR; and
(ii) an AAV9 capsid protein.

121. The method of embodiment 120, wherein the rAAV is administered to the subject at a dose ranging from about $1\times10^{13}$ vg to about $7\times10^{14}$ vg.

122. The method of embodiment 120 or 121, wherein the rAAV is administered via an injection into the cisterna magna.

123. The method of any one of embodiments 110-122, wherein the rAAV is administered in a formulation comprising about 20 mM Tris, pH 8.0, about 1 mM $MgCl_2$, about 200 mM NaCl, and about 0.001% w/v poloxamer 188.

124. A pharmaceutical composition comprising
(i) a rAAV comprising:
(a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and
(b) an AAV9 capsid protein; and
(ii) about 20 mM Tris, pH 8.0,
(iii) about 1 mM $MgCl_2$,
(iv) about 200 mM NaCl, and
(v) about 0.001% w/v poloxamer 188.

125. A rAAV comprising:
(a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and
(b) an AAV9 capsid protein, for use in a method of treating fronto-temporal dementia with a GRN mutation in a subject.

126. A method of quantifying a PGRN protein level in a cerebrospinal fluid (CSF) sample, the method comprising:
(1) diluting the CSF sample in a master mix containing dithiothreitol (DTT) and sample buffer;
(2) loading the diluted CSF sample, an anti-progranulin antibody, a secondary antibody that detects the anti-progranulin antibody, luminol and peroxide into wells of a capillary cartridge;
(3) loading the capillary cartridge into an automated Western blot immunoassay instrument;
(4) using the automated Western blot immunoassay instrument to calculate signal intensity, peak area, and signal-to-noise ratio; and
(5) quantifying a progranulin protein level in the CSF sample as the peak area of immunoreactivity to the anti-progranulin antibody.

What is claimed is:

1. A pharmaceutical composition comprising:

(i) a recombinant adeno-associated virus (rAAV) comprising:

(a) a rAAV vector comprising a nucleic acid comprising an expression construct comprising a promoter operably linked to a transgene insert encoding a progranulin (PGRN) protein, wherein the transgene insert comprises the nucleotide sequence of SEQ ID NO: 68; and (b) an adeno-associated virus (AAV) 9 capsid protein;

(ii) about 20 mM Tris, pH 8.0, (iii) about 1 mM $MgCl_2$, (iv) about 200 mM NaCl, and (v) about 0.001% w/v poloxamer 188.

2. The pharmaceutical composition of claim 1, wherein the promoter is a chicken beta actin (CBA) promoter.

3. The pharmaceutical composition of claim 1, wherein the rAAV vector further comprises a cytomegalovirus (CMV) enhancer.

4. The pharmaceutical composition of claim 1, wherein the rAAV vector further comprises a Woodchuck Hepatitis Virus Posttranscriptional Regulatory Element (WPRE).

5. The pharmaceutical composition of claim 1, wherein the rAAV vector further comprises a Bovine Growth Hormone polyA signal tail.

6. The pharmaceutical composition of claim 1, wherein the nucleic acid comprises two adeno-associated virus inverted terminal repeat (ITR) sequences flanking the expression construct, wherein the first ITR sequence is a 5' ITR, and the second ITR sequence is a 3' ITR.

7. The pharmaceutical composition of claim 6, wherein each of the two ITR sequences is a wild-type AAV2 ITR sequence.

8. The pharmaceutical composition of claim 6, wherein the rAAV vector further comprises a TRY region between the 5' ITR and the expression construct, wherein the TRY region comprises SEQ ID NO: 28.

9. A pharmaceutical composition comprising:

(i) a recombinant adeno-associated virus (rAAV) comprising:

(a) a rAAV vector comprising a nucleic acid comprising, in 5' to 3' order:

an AAV2 inverted terminal repeat (ITR);

a cytomegalovirus (CMV) enhancer;

a chicken beta actin (CBA) promoter;

a transgene insert encoding a progranulin (PGRN) protein, wherein the transgene insert comprises the nucleotide sequence of SEQ ID NO: 68;

a Woodchuck Hepatitis Virus Posttranscriptional Regulatory Element (WPRE);

a Bovine Growth Hormone polyA signal tail; and an AAV2 ITR; and (b) an adeno-associated virus (AAV) 9 capsid protein;

(ii) about 20 mM Tris, pH 8.0, (iii) about 1 mM $MgCl_2$, (iv) about 200 mM NaCl, and (v) about 0.001% w/v poloxamer 188.

* * * * *